US012637473B2

(12) United States Patent
Wang et al.

(10) Patent No.: US 12,637,473 B2
(45) **Date of Patent: *May 26, 2026**

(54) MDM2 PROTEIN DEGRADERS

(71) Applicant: THE REGENTS OF THE UNIVERSITY OF MICHIGAN, Ann Arbor, MI (US)

(72) Inventors: Shaomeng Wang, Superior Township, MI (US); Yangbing Li, Ann Arbor, MI (US); Jiuling Yang, Ypsilanti, MI (US); Angelo Aguilar, Ann Arbor, MI (US); Bing Zhou, Ann Arbor, MI (US); Jiantao Hu, Ann Arbor, MI (US); Fuming Xu, Ann Arbor, MI (US); Rohan Rej, Ann Arbor, MI (US); Xin Han, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1116 days.

This patent is subject to a terminal disclaimer.

(21) Appl. No.: 17/462,355

(22) Filed: Aug. 31, 2021

(65) Prior Publication Data

US 2022/0411432 A1 Dec. 29, 2022

Related U.S. Application Data

(62) Division of application No. 16/091,541, filed as application No. PCT/US2017/026274 on Apr. 6, 2017, now Pat. No. 11,192,898.

(60) Provisional application No. 62/409,571, filed on Oct. 18, 2016, provisional application No. 62/393,874, filed on Sep. 13, 2016, provisional application No. 62/318,974, filed on Apr. 6, 2016.

(51) Int. Cl.

*C07D 487/10* (2006.01)
*A61P 35/00* (2006.01)
*C07D 401/04* (2006.01)
*C07D 401/14* (2006.01)
*C07D 417/14* (2006.01)

(52) U.S. Cl.

CPC ............ *C07D 487/10* (2013.01); *A61P 35/00* (2018.01); *C07D 401/04* (2013.01); *C07D 401/14* (2013.01); *C07D 417/14* (2013.01)

(58) Field of Classification Search

CPC .. C07D 417/14; C07D 401/14; C07D 401/04; C07D 487/10; A61P 35/00

See application file for complete search history.

(56) References Cited

U.S. PATENT DOCUMENTS

| | | | | |
|---|---|---|---|---|
| 8,044,042 | B2 | 10/2011 | Adachi et al. | |
| 8,114,995 | B2 | 2/2012 | Hansen et al. | |
| 8,476,260 | B2 | 7/2013 | Miyoshi et al. | |
| 8,557,984 | B2 | 10/2013 | Bouillot et al. | |
| 8,580,957 | B2 | 11/2013 | Demont et al. | |
| 11,046,703 | B2 * | 6/2021 | Wang .................. | C07D 487/10 |
| 11,192,898 | B2 * | 12/2021 | Wang .................. | C07D 401/14 |
| 2003/0096841 | A1 | 5/2003 | Robarge et al. | |
| 2010/0286127 | A1 | 11/2010 | Miyoshi et al. | |
| 2011/0118283 | A1 | 5/2011 | Ding et al. | |
| 2012/0059002 | A1 | 3/2012 | Hansen et al. | |
| 2012/0157428 | A1 | 6/2012 | Albrecht et al. | |
| 2012/0202799 | A1 | 8/2012 | Crowe et al. | |
| 2012/0208800 | A1 | 8/2012 | Chung et al. | |
| 2012/0252781 | A1 | 10/2012 | Bailey et al. | |
| 2012/0264738 | A1 | 10/2012 | Sugimoto et al. | |
| 2012/0273468 | A1 | 11/2012 | Arjakine et al. | |
| 2013/0079335 | A1 | 3/2013 | Bailey | |
| 2013/0184264 | A1 | 7/2013 | Bradner et al. | |
| 2013/0245089 | A1 | 9/2013 | Glenn et al. | |
| 2013/0252331 | A1 | 9/2013 | Bradner et al. | |
| 2013/0281399 | A1 | 10/2013 | McLure et al. | |
| 2013/0281450 | A1 | 10/2013 | Pratt et al. | |
| 2013/0331382 | A1 | 12/2013 | Hubbard et al. | |
| 2014/0005169 | A1 | 1/2014 | Albrecht et al. | |
| 2014/0011862 | A1 | 1/2014 | Bradner et al. | |
| 2014/0213575 | A1 | 7/2014 | Schmees et al. | |
| 2014/0256706 | A1 | 9/2014 | Wang et al. | |
| 2015/0246923 | A1 | 9/2015 | Wang et al. | |
| 2015/0291562 | A1 | 10/2015 | Crew et al. | |
| 2015/0291611 | A1 | 10/2015 | Gollner et al. | |
| 2016/0058872 | A1 | 3/2016 | Crew et al. | |

FOREIGN PATENT DOCUMENTS

| | | | |
|---|---|---|---|
| CA | 2265645 | A1 | 3/1998 |
| JP | 2013-510828 | A | 3/2013 |
| JP | 2015-510906 | A | 4/2015 |

(Continued)

OTHER PUBLICATIONS

Konopleva, Leukemia, 2020, vol. 4:2858-2874. (Year: 2020).*
Wang, Pharmacological Reviews, 414-453, 2024. (Year: 2024).*
"Crystallization", Kirk-Othmer Encyclopedia of Chemical Technology, vol. 8, pp. 95-147, John Wiley & Sons, Inc. (2002).
Berstein, Polymorphism in Molecular Crystals, pp. 115-118, International Union of Crystallography; 1st Edition (Jul. 15, 2002).
Braga et al., Making crystals from crystals: a green route to crystal engineering and polymorphism, Chem. Commun. (Camb.), (29):3635-45 (2005).
Davidovich et al., Detection of polymorphism by powder x-ray diffraction: Interference by preferred orientation, American Pharmaceutical Review, 7(1):10, 12, 25, 16, 100 (2004).
Dean, "10.11.2 Powder Diffraction", pp. 10.24-10.26, Analytical Chemistry Handbook, McGraw-Hill, Inc. (1995).

(Continued)

*Primary Examiner* — D Margaret M Seaman
(74) *Attorney, Agent, or Firm* — MARSHALL, GERSTEIN & BORUN LLP

(57) ABSTRACT

The present disclosure provides compounds represented by Formula I-A:

$$A^1\text{-}L^1\text{-}B^1 \qquad \text{I-A}$$

Figure 1:
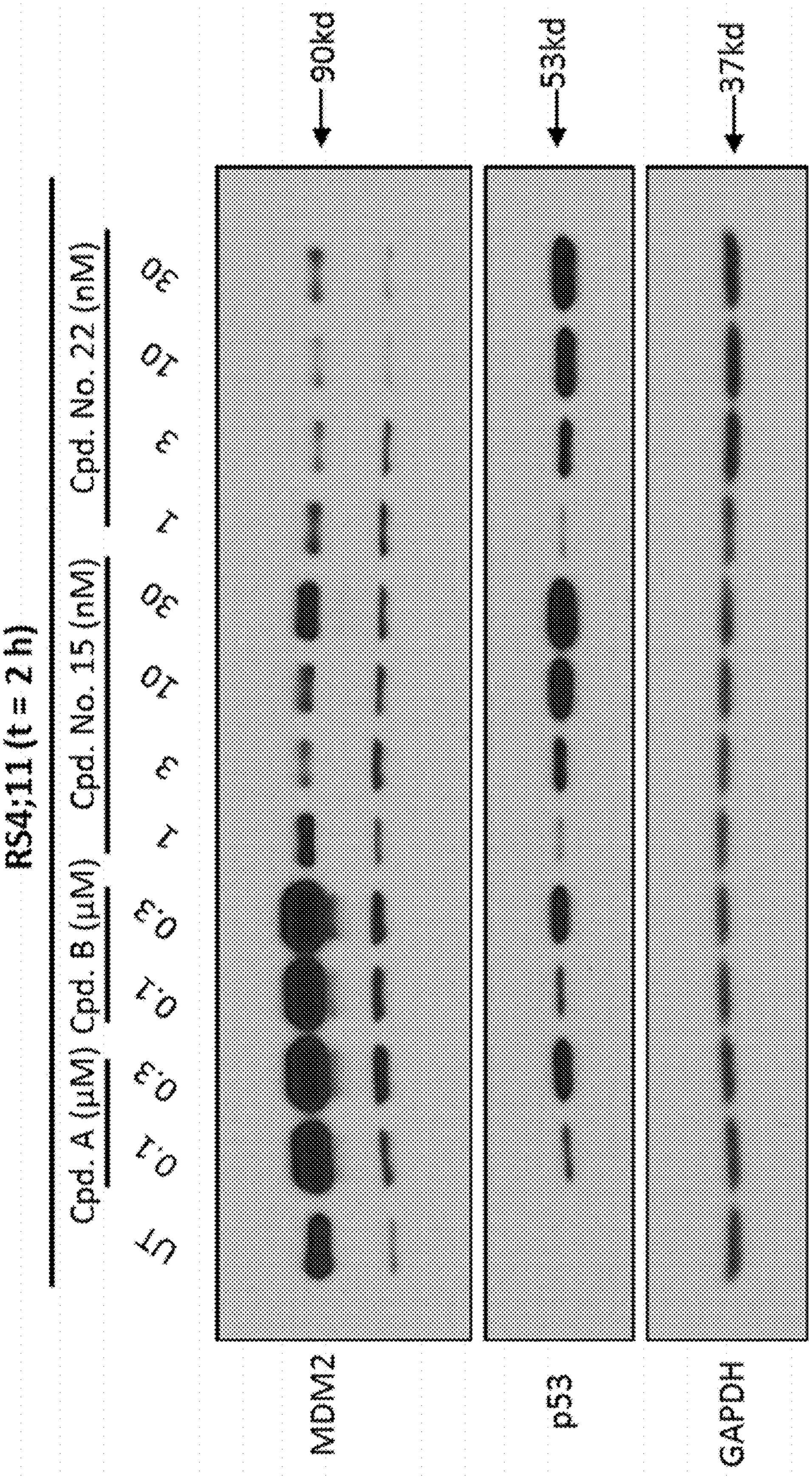

and the pharmaceutically acceptable salts, hydrates, and solvates thereof, wherein $A^1$, $B^1$, and $L^1$ are as defined as set forth in the specification. The present disclosure also provides compounds of Formula I-A for use to treat a condition or disorder responsive to degradation of MDM2 protein such as cancer.

13 Claims, 8 Drawing Sheets

(56) References Cited

FOREIGN PATENT DOCUMENTS

| | | | | |
|---|---|---|---|---|
| RU | 2013145310 | A | | 4/2015 |
| WO | WO-98/11111 | A1 | | 3/1998 |
| WO | WO-02/059106 | A1 | | 8/2002 |
| WO | 2006/091646 | | * | 8/2006 |
| WO | WO-2006/091646 | A2 | | 8/2006 |
| WO | WO-2006/129623 | A1 | | 12/2006 |
| WO | WO-2008/036168 | A2 | | 3/2008 |
| WO | WO-2008/092231 | A1 | | 8/2008 |
| WO | WO-2009/084693 | A1 | | 7/2009 |
| WO | WO-2009/158404 | A1 | | 12/2009 |
| WO | WO-2010/123975 | A1 | | 10/2010 |
| WO | 2011/060049 | | * | 5/2011 |
| WO | WO-2011/054843 | A1 | | 5/2011 |
| WO | WO-2011/054844 | A1 | | 5/2011 |
| WO | WO-2011/054845 | A1 | | 5/2011 |
| WO | WO-2011/054846 | A1 | | 5/2011 |
| WO | WO-2011/054848 | A1 | | 5/2011 |
| WO | WO-2011/054864 | A1 | | 5/2011 |
| WO | WO-2011/060049 | A2 | | 5/2011 |
| WO | WO-2011/067185 | A1 | | 6/2011 |
| WO | WO-2011/143651 | A1 | | 11/2011 |
| WO | WO-2011/143660 | A2 | | 11/2011 |
| WO | WO-2011/143669 | A2 | | 11/2011 |
| WO | WO-2011/153509 | A1 | | 12/2011 |
| WO | WO-2011/161031 | A1 | | 12/2011 |
| WO | WO-2012/075383 | | | 6/2012 |
| WO | WO-2012/075456 | A1 | | 6/2012 |
| WO | WO-2012/116170 | A1 | | 8/2012 |
| WO | WO-2012/151512 | A2 | | 11/2012 |
| WO | WO-2012/155066 | A2 | | 11/2012 |
| WO | WO-2012/174487 | | | 12/2012 |
| WO | WO-2013/024104 | | | 2/2013 |
| WO | WO-2013/027168 | | | 2/2013 |
| WO | WO-2013/030150 | A1 | | 3/2013 |
| WO | WO-2013/033268 | | | 3/2013 |
| WO | WO-2013/097601 | A1 | | 7/2013 |
| WO | WO-2013/158644 | A2 | | 10/2013 |
| WO | WO-2014/134201 | A1 | | 9/2014 |
| WO | WO-2014/164596 | A1 | | 10/2014 |
| WO | WO-2015131005 | A1 | | 9/2015 |
| WO | WO-2015/161032 | A1 | | 10/2015 |
| WO | WO-2016/028391 | A2 | | 2/2016 |

OTHER PUBLICATIONS

Delmore, J.E., et al., "BET Bromodomain Inhibition as a Therapeutic Strategy to Target c-Myc.," *Cell*, vol. 146, No. 6 (2011), pp. 904-917.

International Search Report for Patent Application No. PCT/US2017/026274, dated Sep. 8, 2017.

Ivanisevic et al., Uses of x-ray powder diffraction in the pharmaceutical industry, IN: Gad (ed.), Pharmaceutical Sciences Encyclopedia: Drug Discovery, Development, and Manufacturing, John Wiley & Sons, pp. 1-42 (2010).

Jain et al., Polymorphism in Pharmacy, Indian Drugs, 23(6):315-329 (1986).

Jordan, Tamoxifen: A most unlikely pioneering medicine, Nature Rev., vol. 2, pp. 205-213 (Mar. 2003).

Lai, A. C., et al., "Modular PROTAC Design for the Degradation of Oncogenic BCR-ABL" (2016) *Angewandte Chemie International Edition*, vol. 55, No. 2, pp. 807-810.

Ruchelman et al., Isosteric analogs of lenalidomide and pomalidomide: synthesis and biological activity, Bioorg. Med. Chem. Lett., 23(1):360-5 (2013).

Seal, J., et al., "Identification of a Novel Series of BET Family Bromodomain Inhibitors: Binding Mode and Profile of I-BET151 (GSK1210151A)," *Bioorganic & Medicinal Chemistry Letters*, vol. 22, No. 8 (2012), pp. 2968-2972.

Seddon, Pseydopolymorph: A Polemic, Crystal Growth & Design, 4(6):1087 (2004).

Various Chapters by Grant, Morris and Guillory in Brittain (ed.), Polymorphism in Pharamceutical Solids, pp. 1-2, 125-181 and 183-226 Marcel Dekker, Inc., (1999).

Vippagunta et al., Crystalline solids, Adv. Drug Deli. Rev., 48(1):3-26 (May 2001).

Yu et al., Physical characterization of polymorphic drugs: an integrated characterization strategy, PSTT, 1(3):118-127 (1998).

* cited by examiner

MDM2 PROTEIN DEGRADERS

BACKGROUND OF THE INVENTION

Field of the Invention

The present disclosure provides MDM2 protein degraders and therapeutic methods of treating conditions and diseases wherein degradation of MDM2 provides a benefit

Background

The p53 tumor suppressor is a principal mediator of growth arrest, senescence, and apoptosis in response to a broad array of cellular damage. Rapid induction of high p53 protein levels by various stress types prevents inappropriate propagation of cells carrying potentially mutagenic, damaged DNA. p53 can kill cells via a dual transcription-dependent and -independent function in the nucleus and at the mitochondria. It has been demonstrated that cellular p53 protein levels are the single most important determinant of its function. In normal unstressed cells, p53 is a very unstable protein with a half-life ranging from 5 to 30 min, which is present at very low cellular levels owing to continuous degradation largely mediated by MDM2. Conversely, a hallmark of many cellular stress pathways such as DNA damage, hypoxia, telomere shortening, and oncogene activation is the rapid stabilization of p53 via a block of its degradation. MDM2 has emerged as the principal cellular antagonist of p53 by limiting the p53 tumor suppressor function. Moll and Petrenko, *Molecular Cancer Research* 1:1001-1008 (2003).

MDM2 is transcriptionally activated by p53 and MDM2, in turn, inhibits p53 activity by at least three mechanisms. Wu et al., *Genes Dev.* 7:1126 (1993). First, MDM2 protein directly binds to the p53 transactivation domain and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation.

Small-molecule inhibitors that target the p53-MDM2 interaction have therapeutic potential for treating cancer and other diseases. Chene, *Nat. Rev. Cancer* 3:102 (2003) and Vassilev et al., *Science* 303:844 (2004). Antagonists of the p53-MDM2 interaction are described in U.S. Pat. Nos. 7,759,383; 7,737,174; 8,518,984; 8,680,132; 8,629,141; 6,617,346; 6,734,302; 7,132,421; 7,425,638; 7,579,368; 7,060,713; 7,553,833; 6,916,833; 7,495,007; 7,638,548; 7,576,082; 7,625,895; and 7,083,983; and U.S. Patent Application Publication Nos. 2005/0288287; 2009/0143364; 2009/0312310; 2006/0211718; 2010/0048593; 2005/0227932; 2008/0261917; 2009/0227542; 2008/0171723; 2006/0211757; 2005/0137137; 2002/0132977; and 2009/0030181.

Phthalimide-based drugs, e.g., thalidomide or lenalidomide, bind to protein-degradation machinery, e.g., cereblon (CRBN; part of an ubiquitin E3 ligase complex). This may promote the recruitment of two transcription factors (IKZF1 and IKZF3) that are essential to disease progression, resulting in drug-induced ubiquitylation and degradation by the proteasome. See, e.g., Ito et al., *Science* 327:1345-1350 (2010) and Winter et al., *Science* 345:1376-1381 (2015).

A high-affinity VHL ligand, see Bondeson et al., *Nat. Chem. Biol.* 11:611-617 (2015), may recruit a target protein to an E3 ubiquitin ligase, resulting in drug induced ubiquitination and degradation. See, e.g., van Hagen et al, *Nucleic Acids Research* 38: 1922-1931 (2010); Buckley et al, *J. Am. Chem. Soc.* 734:4465-4468 (2012); Buckley et al., *Angew, Chem. Int. Ed. Engl.* 57:11463-11467 (2012); Lipkowitz and Weissman, *Nat Rev Cancer* 11:629-643 (2011); and Zengerle et al., *ACS Chem. Biol.* 76:1770-1777 (2015).

There is an ongoing need for new agents, e.g., small molecules, for treating cancer and other diseases responsive to the disruption or prevention of the MDM2-p53 interaction.

BRIEF SUMMARY OF THE INVENTION

In one aspect, the present disclosure provides heterobifunctional compounds represented by any one of Formulae I-A, I-III, or VII-XII, below, and the pharmaceutically acceptable salts and solvates thereof, collectively referred to as "Compounds of the Disclosure." Compounds of the Disclosure are MDM2 protein degraders and thus are useful in treating diseases or conditions wherein inhibition and/or degradation of MDM2 provides a benefit.

In another aspect, the present disclosure provides synthetic intermediates represented by Formula IV-VI, below, and the pharmaceutically acceptable salts and solvates thereof, collectively referred to as "Intermediates of the Disclosure." Intermediates of the Disclosure can be used to prepare MDM2 protein degraders having Formulae I-A, I-III, or VII-XII.

In another aspect, the present disclosure provides methods of treating a condition or disease by administering a therapeutically effective amount of a Compound of the Disclosure to an individual, e.g., a human, in need thereof. The disease or condition of interest is treatable by degradation of MDM2 proteins, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, the Compounds of the Disclosure reduce the proliferation of unwanted cells by inducing apoptosis in those cells.

In another aspect, the present disclosure provides a method of degrading MDM2 proteins in an individual, comprising administering to the individual an effective amount of at least one Compound of the Disclosure.

In another embodiment, the present disclosure provides a method of reducing MDM2 protein within a cell of an individual, e.g., a patient in need thereof, the method comprising administering a Compound of the Disclosure to the individual.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating diseases or conditions wherein degradation of MDM2 proteins provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in treatment of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF DRAWINGS

FIG. 1 is an illustration showing that Cpd. No. 15 and Cpd. No. 22 induce MDM2 degradation and p53 activation of in the RS4; 11 cell line.

Figure 2:
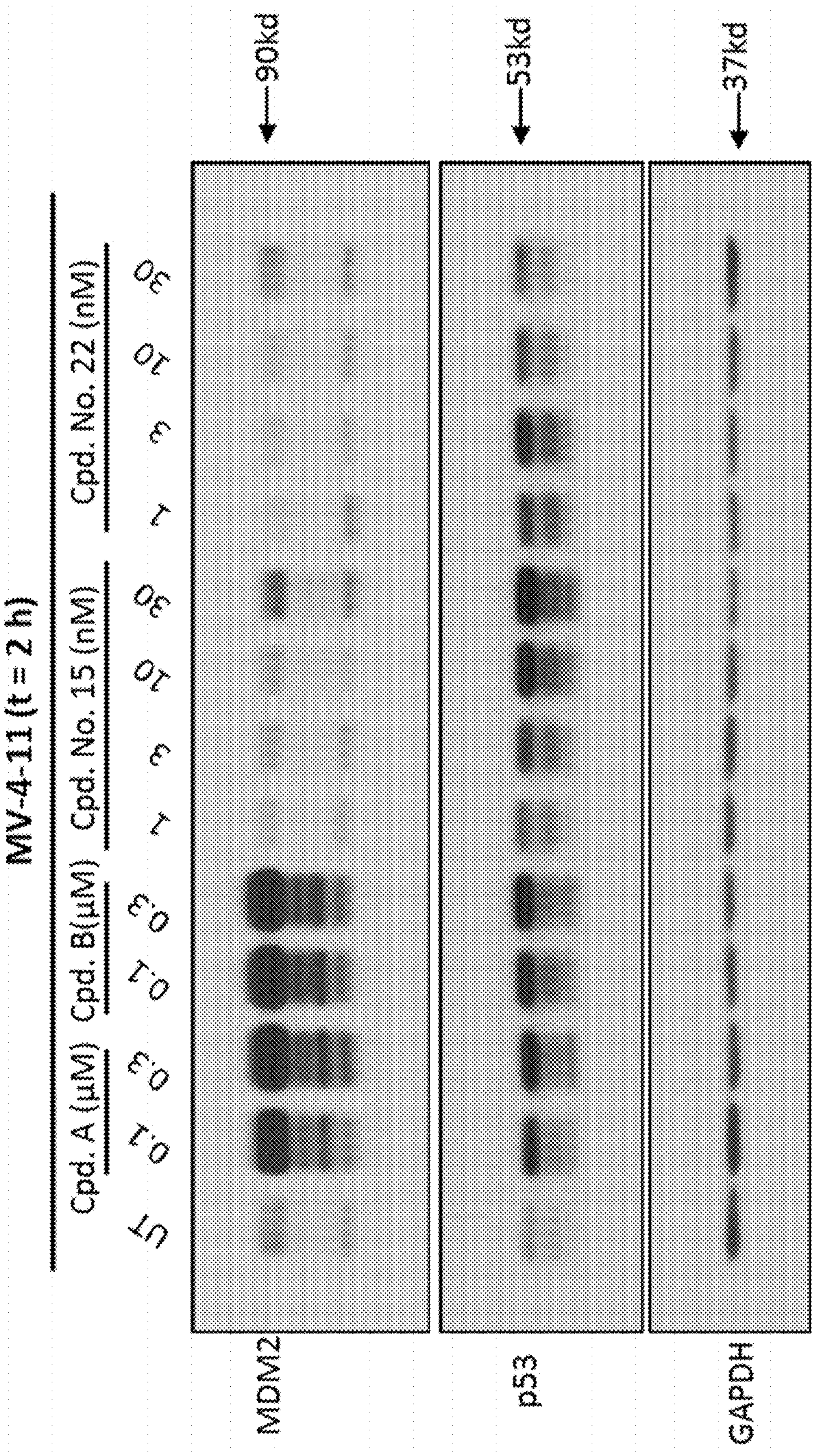

FIG. 2 is an illustration showing that Cpd. No. 15 and Cpd. No. 22 induce MDM2 degradation and p53 activation in the MV-4-11 cell line.

Figure 3:
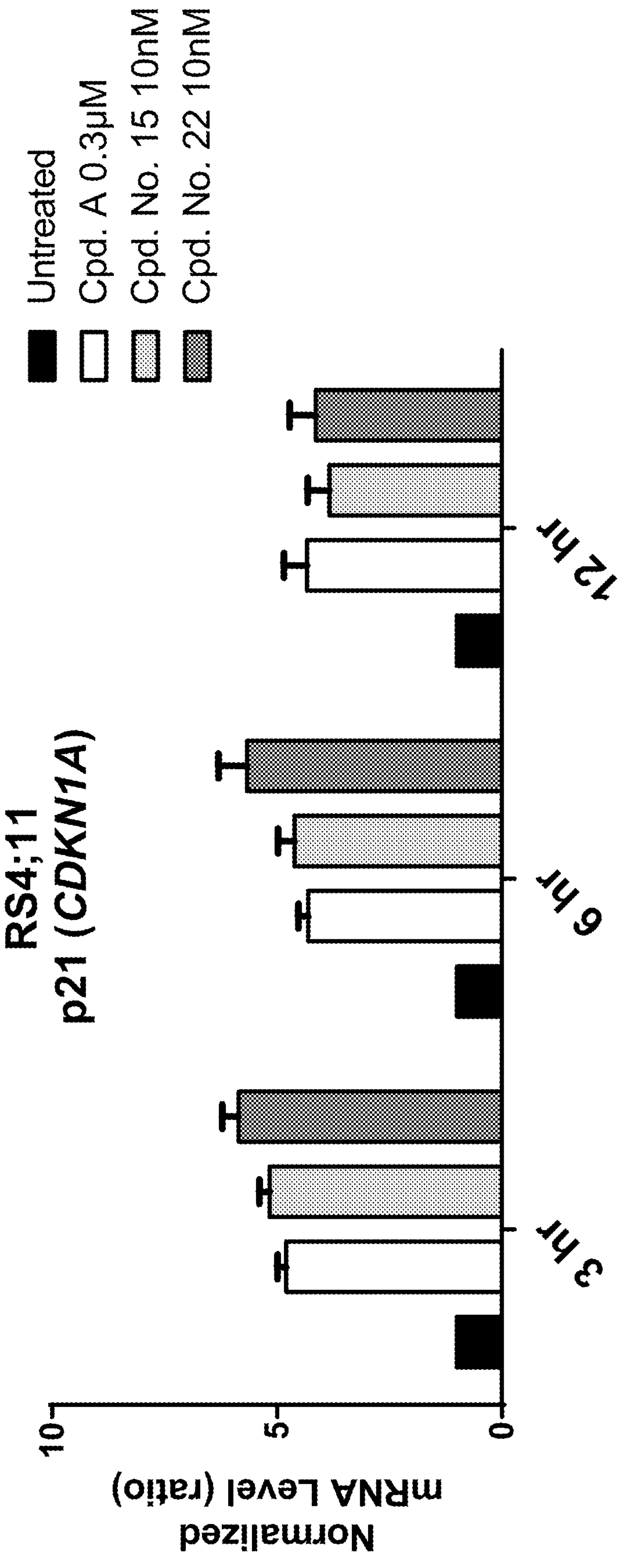

FIG. 3. is a bar chart showing that Cpd. No. 15 and Cpd. No. 22 activate mRNA levels of p21, a representative p53 target gene.

Figure 4:
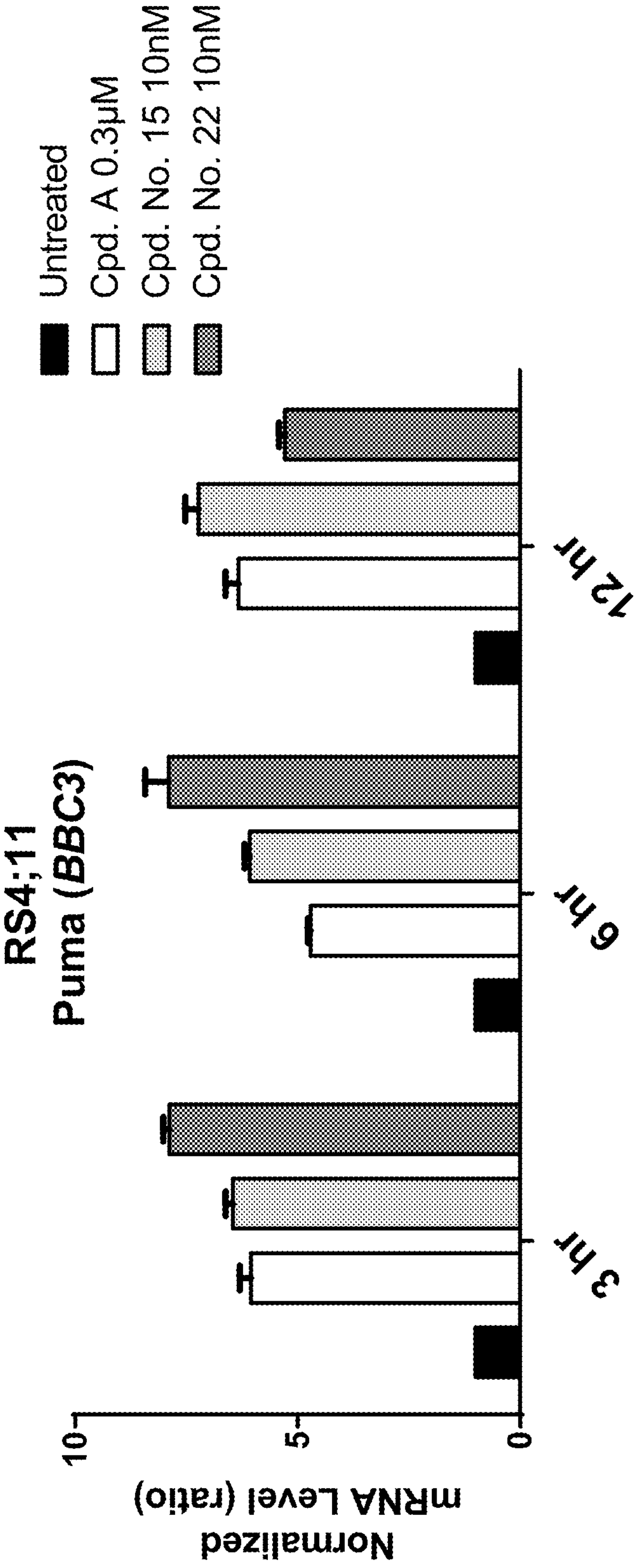

FIG. 4. is a bar chart showing that Cpd. No. 15 and Cpd. No. 22 activate mRNA levels of PUMA, a representative p53 target gene.

Figure 5:
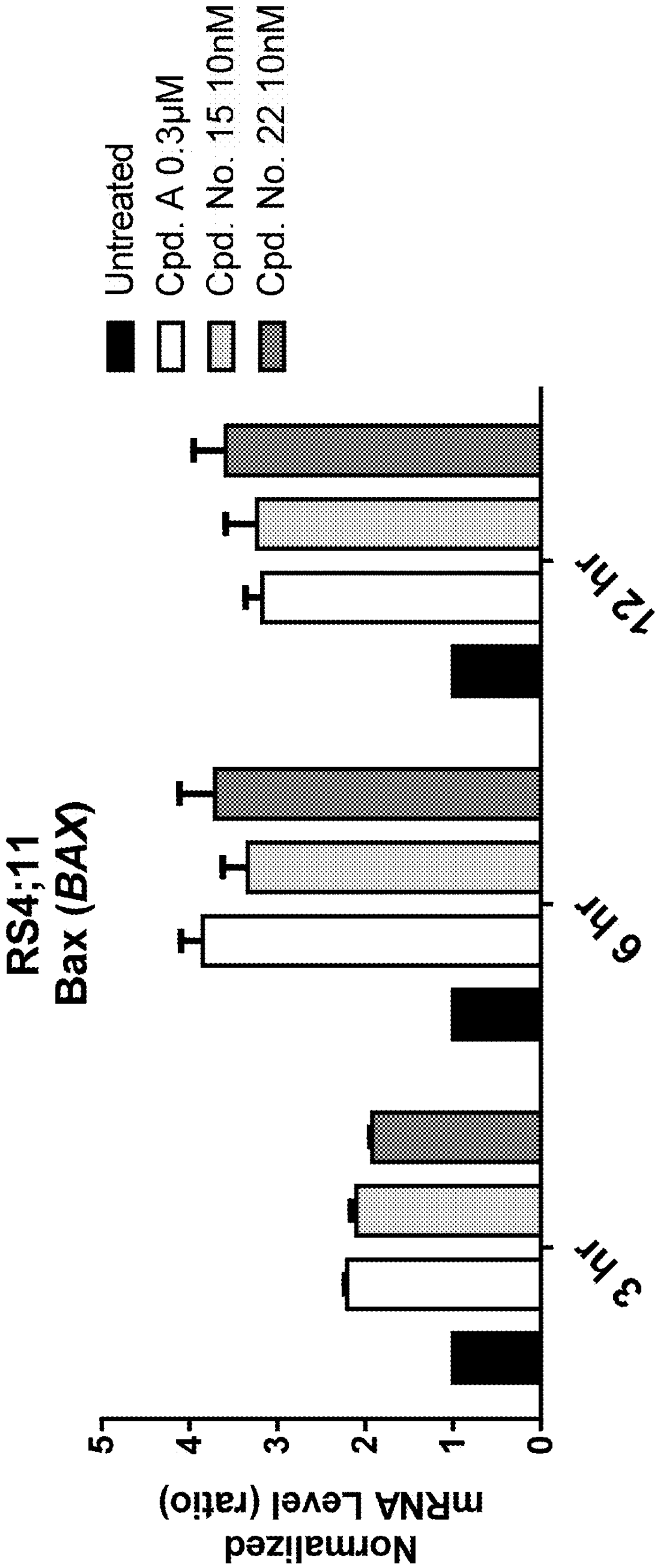

FIG. 5. is a bar chart showing that Cpd. No. 15 and Cpd. No. 22 activate mRNA levels of BAN a representative p53 target gene.

Figure 6:
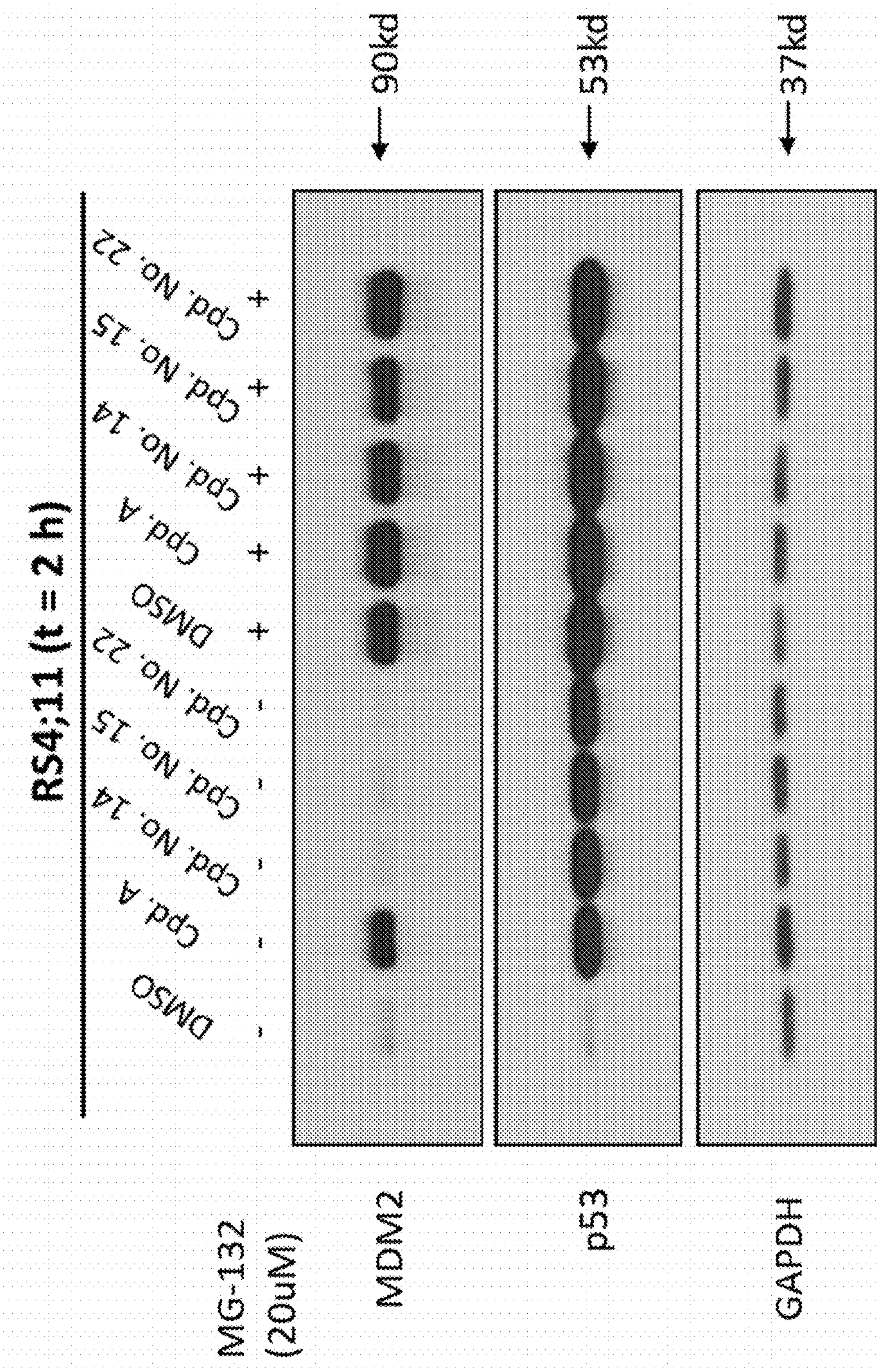

FIG. 6 is an illustration showing that MDM2 degradation by Cpd. No. 14, Cpd. No. 15, and Cpd. No. 22 is proteasome-dependent.

Figure 7:
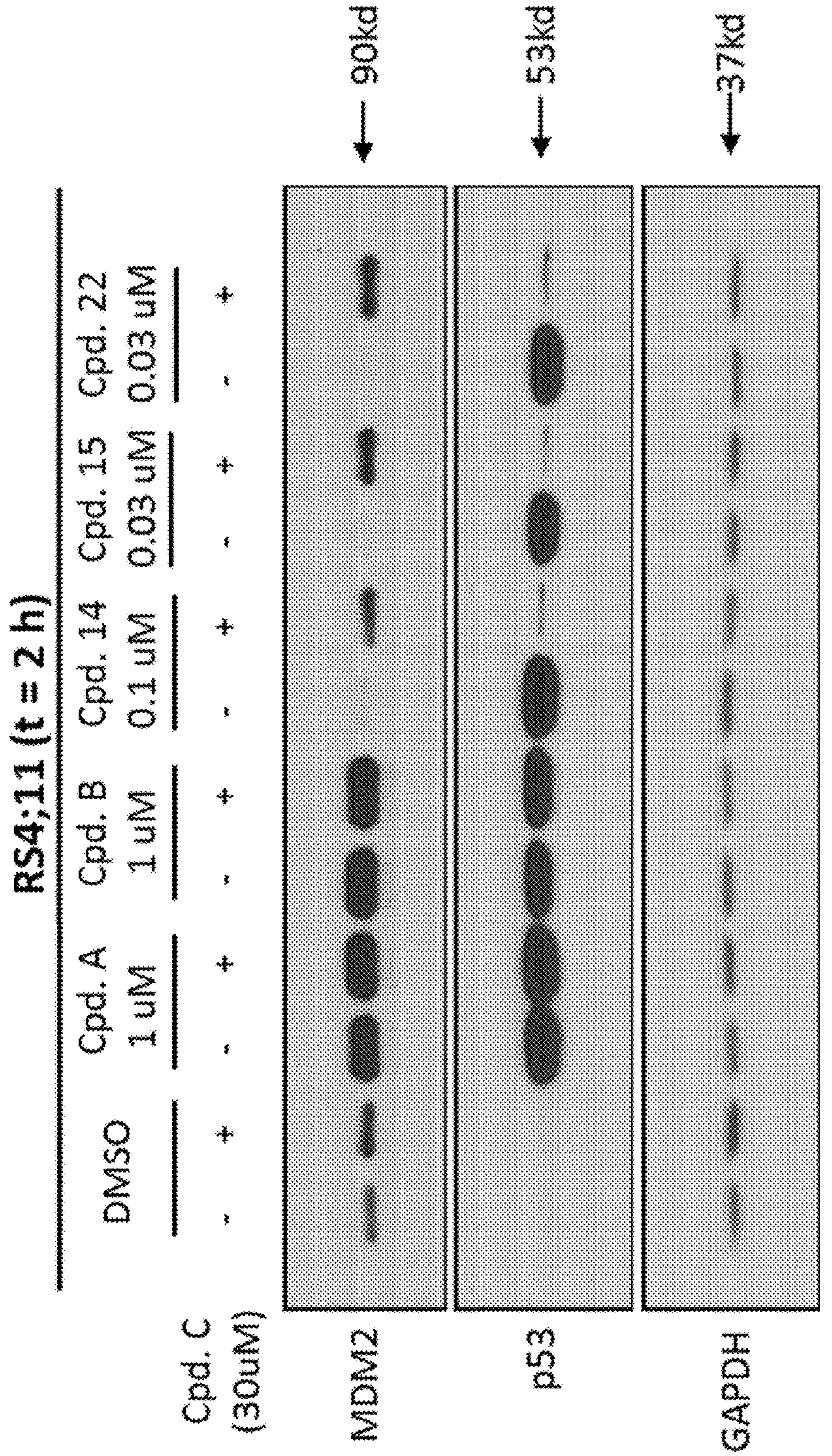

FIG. 7 is an illustration showing that MDM2 degradation by Cpd. No. 14, Cpd. No. 15, and Cpd. No. 22 is cereblon (CRBN)-dependent.

Figure 8:
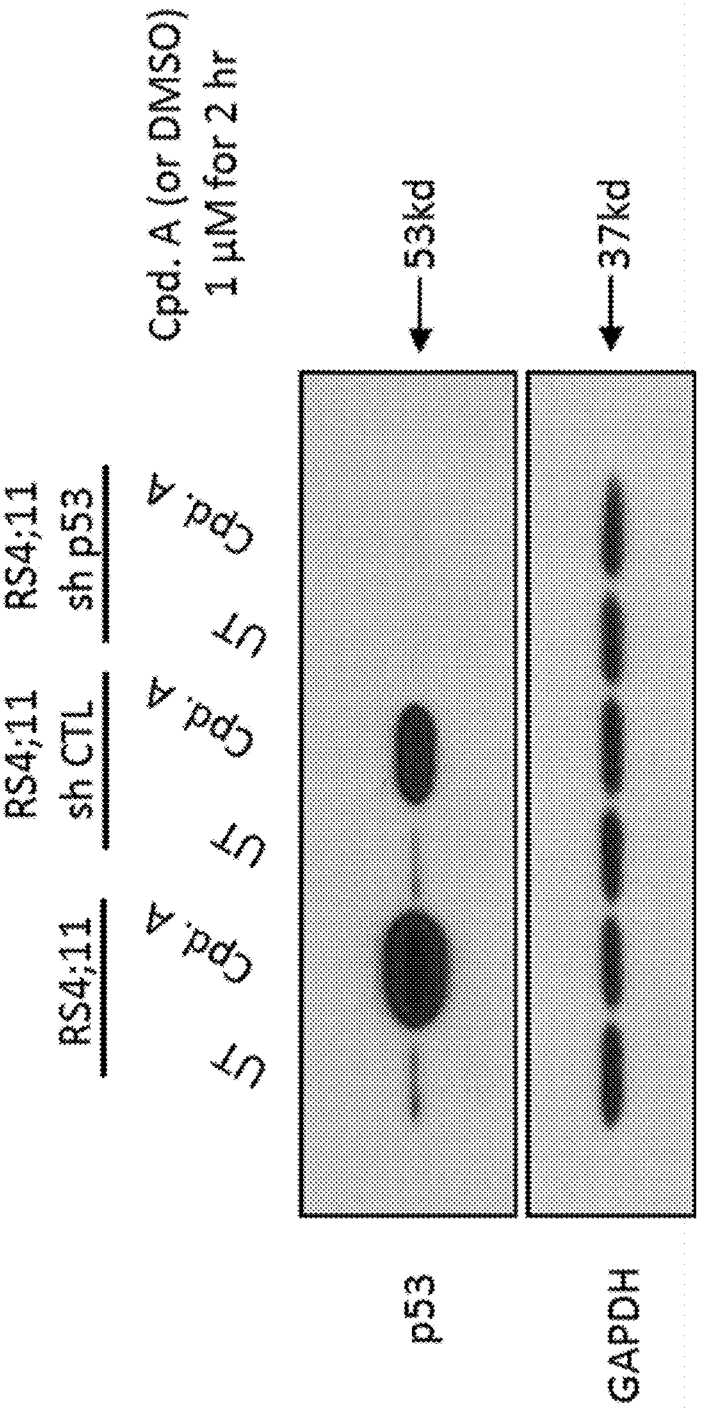

FIG. 8 is an illustration showing that cell growth inhibitory activity is p53-dependent.

DETAILED DESCRIPTION OF THE INVENTION

Compounds of the Disclosure are heterobifunctional compounds that promote MDM2 degradation.

In one embodiment, Compounds of the Disclosure are compounds represented by Formula I-A:

$A^1$-$L^1$-$B^1$ I-A and the pharmaceutically acceptable salts or solvates thereof, wherein:

$A^1$ is a monovalent radical of a MDM2 inhibitor;

$L^1$ is a linker; and $B^1$ is monovalent radical of a ligand for an E3 ubiquitin ligase protein.

In another embodiment, Compounds of the Disclosure are compounds represented by Formula I-A, and the pharmaceutically acceptable salts or solvates thereof, wherein:

$A^1$ is:

A-17

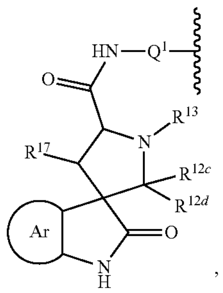

, $R^{12c}$ and $R^{12d}$ are independently selected from the group consisting of hydrogen and optionally substituted $C_{1-8}$ alkyl; or $R^{12c}$ and $R^{12d}$ taken together with the carbon atom to which they are attached form a 4- to 8-membered optionally substituted cycloalkyl or a 4- to 8-membered optionally substituted heterocyclo;

$R^{13}$ is selected from the group consisting of hydrogen, optionally substituted $C_{1-6}$ alkyl, and heteroalkyl;

$R^{17}$ is selected from the group consisting of optionally substituted aryl and optionally substituted heteroaryl;

$Q^1$ is selected from the group consisting of alkylenyl, arylenyl, e.g., phenylenyl, heteroarylenyl, cycloalkylenyl, and heterocyclenyl; and

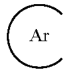

is a fused optionally substituted phenyl, fused optionally substituted thienyl, fused optionally substituted pyridyl, or fused optionally substituted pyrimidyl group.

In another embodiment, Compounds of the Disclosure are compounds represented by Formula I-A, and the pharmaceutically acceptable salts or solvates thereof, wherein:

$A^1$ is:

A-18

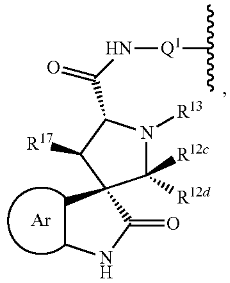

,

-continued
A-19
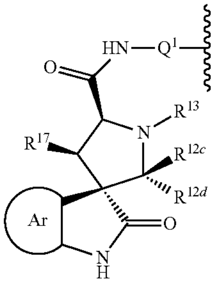
,
A-20
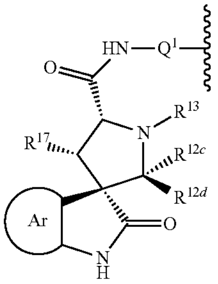
,
A-21
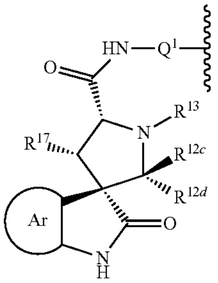
,
A-22
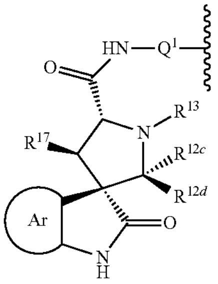
,
A-23
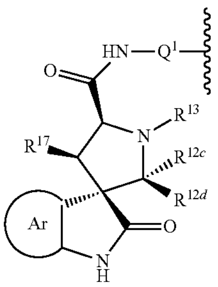
,
-continued
A-24
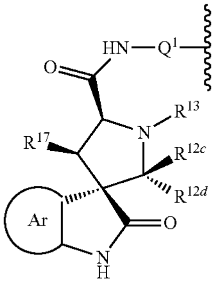
,
A-25
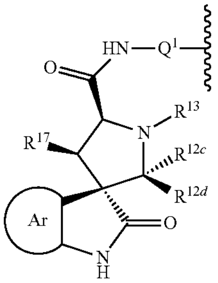
,
A-26
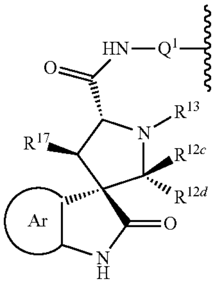
,
A-27
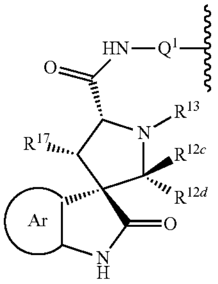
,
A-28
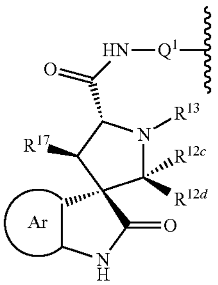
, -continued

A-29

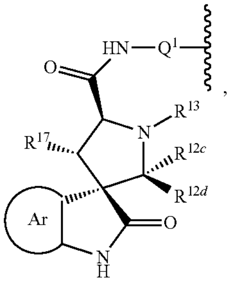

A-30

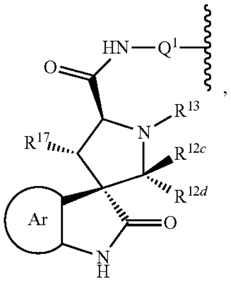

A-31

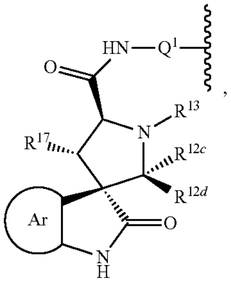

A-32

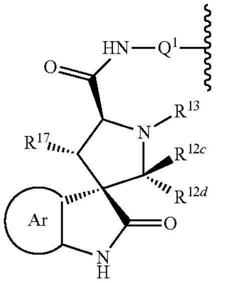

or

A-33

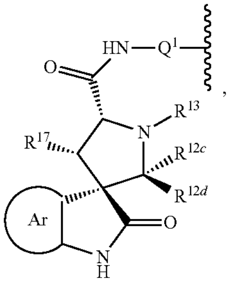

and $R^{12c}$, $R^{12d}$, $R^{13}$, $R^{17}$, $Q^1$, and

are as defined in connection with A-17.

In another embodiment, Compounds of the Disclosure are compounds represented by Formula I-A, and the pharmaceutically acceptable salts or solvates thereof, wherein:

$A^1$ is:

A-34

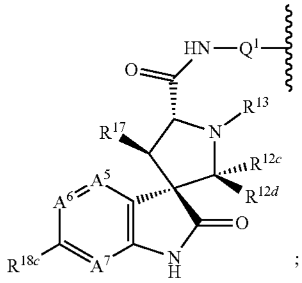

;

$A^5$ is selected from the group consisting of —C($R^{18a}$)═ and —N═;

$A^6$ is selected from the group consisting of —C($R^{18b}$)═ and —N═;

$A^7$ is selected from the group consisting of —C($R^{18d}$)═ and —N═;

$R^{18a}$, $R^{18b}$, $R^{18c}$, and $R^{18d}$ are each independently selected from the group consisting of hydrogen, halo, $C_{1-4}$ alkyl, haloalkyl, alkoxy, and haloalkoxy; and $R^{12c}$, $R^{12d}$, $R^{13}$, $R^{17}$, and $Q^1$ are as defined in connection with A-17.

In another embodiment, Compounds of the Disclosure are compounds represented by Formula I-A, and the pharmaceutically acceptable salts or solvates thereof, wherein $A^1$ is A-34, $A^5$ is —N═, $A^6$ is —C($R^{18b}$)═, and $A^7$ is —C($R^{18d}$)═.

In another embodiment, Compounds of the Disclosure are compounds represented by Formula I-A, and the pharmaceutically acceptable salts or solvates thereof, wherein $A^1$ is A-34, $A^5$ is C($R^{18a}$)═, $A^6$ is —N═, and $A^7$ is —C($R^{18d}$)═.

In another embodiment, Compounds of the Disclosure are compounds represented by Formula I-A, and the pharmaceutically acceptable salts or solvates thereof, wherein $A^1$ is A-34, $A^5$ is —C($R^{18a}$)═, $A^6$ is —C($R^{18b}$)═, and $A^7$ is —N═.

In another embodiment, Compounds of the Disclosure are compounds represented by Formula I-A, and the pharmaceutically acceptable salts or solvates thereof, wherein $A^1$ is A-34, $A^5$ is —C($R^{18a}$)═, $A^6$ is —N═, and $A^7$ is —N═.

In another embodiment, Compounds of the Disclosure are compounds represented by Formula I-A, and the pharmaceutically acceptable salts or solvates thereof, wherein:

$A^1$ is:

A-35

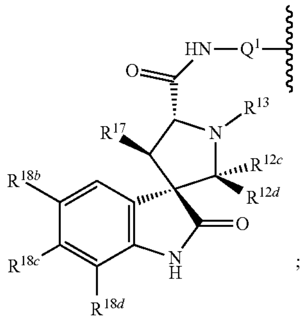

;

$R^{18b}$, $R^{18c}$, and $R^{18d}$ are as defined in connection with A-34; and $R^{12c}$, $R^{12d}$, $R^{13}$, $R^{17}$, and $Q^1$ are as defined in connection with A-17.

In another embodiment, Compounds of the Disclosure are compounds represented by Formula I-A, and the pharmaceutically acceptable salts or solvates thereof, wherein:

$A^1$ is:

A-36

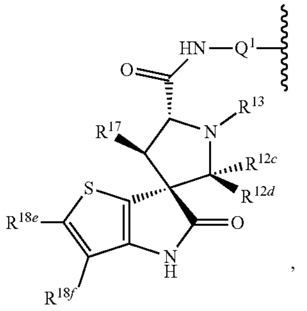

$R^{18e}$ and $R^{18d}$ are independently selected from the group consisting of hydrogen, halo, $C_{1-4}$ alkyl, haloalkyl, alkoxy, and haloalkoxy; and $R^{12c}$, $R^{12d}$, $R^{13}$, $R^{17}$, and $Q^1$ are as defined in connection with A-17.

In another embodiment, Compounds of the Disclosure are compounds represented by Formula I-A, and the pharmaceutically acceptable salts or solvates thereof, wherein:

$A^1$ is:

A-37

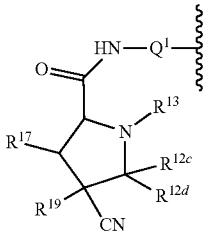

$R^{19}$ is selected from the group consisting optionally substituted aryl and optionally substituted heteroaryl; and $R^{12c}$, $R^{12d}$, $R^{13}$, $R^{17}$, and $Q^1$ are as defined in connection with A-17.

In another embodiment, Compounds of the Disclosure are compounds represented by Formula I-A, and the pharmaceutically acceptable salts or solvates thereof, wherein:

$A^1$ is:

A-38

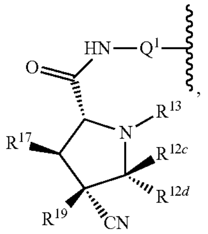

-continued

A-39

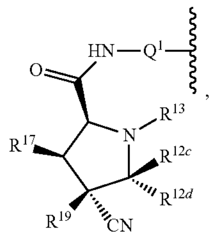

A-40

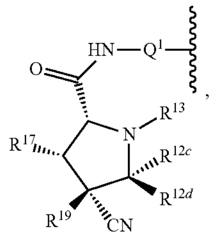

A-41

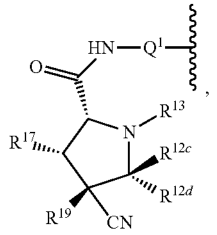

A-42

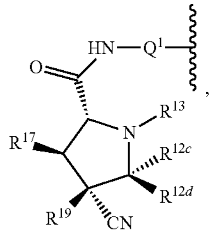

A-43

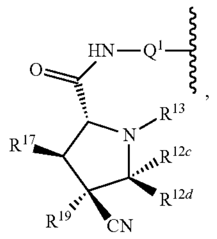

A-44

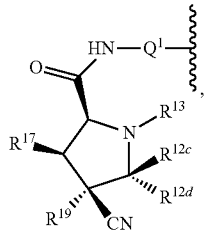

-continued

A-45

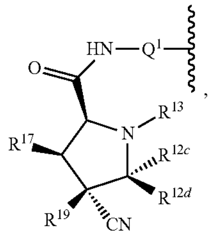
,

A-46

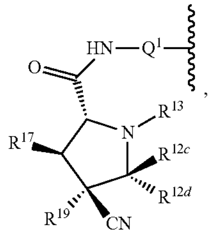
,

A-47

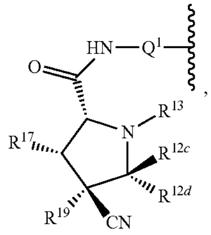
,

A-48

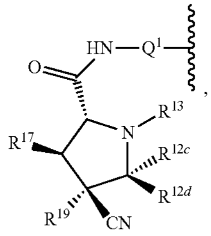
,

A-49

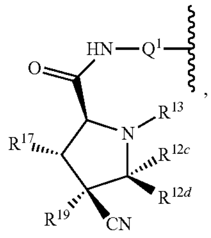
,

A-50

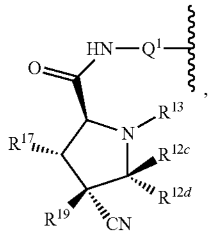
,

-continued

A-51

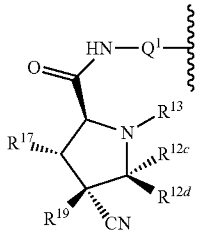
,

A-52

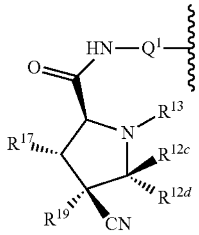
or

A-53

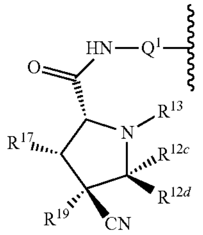
, wherein $R^{12c}$, $R^{12d}$, $R^{13}$, $R^{17}$, $R^{19}$, and $Q^1$ are as defined in connection with A-37.

In another embodiment, Compounds of the Disclosure are compounds represented by Formula I-A, and the pharmaceutically acceptable salts or solvates thereof, wherein:

$A^1$ is:

A-54

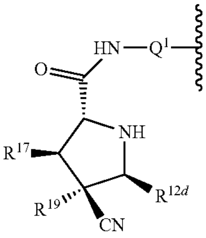
;

and $R^{12d}$, $R^{17}$, $R^{19}$, and $Q^1$ are as defined in connection with A-37.

In another embodiment, Compounds of the Disclosure are compounds represented by Formula I-A, and the pharmaceutically acceptable salts or solvates thereof, wherein: $A^1$ is:

A-55

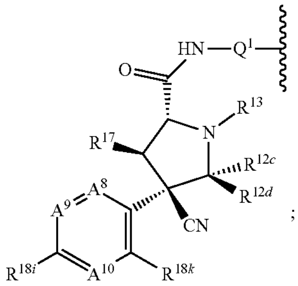

;

$A^8$ is selected from the group consisting of —C($R^{18g}$)═ and —N═;

$A^9$ is selected from the group consisting of —C($R^{18h}$)═ and —N═;

$A^{10}$ is selected from the group consisting of —C($R^{18j}$)═ and —N═;

$R^{18g}$, $R^{18h}$, $R^{18l}$, $R^{18j}$, and $R^{18k}$ are each independently selected from the group consisting of hydrogen, halo, $C_{1-4}$ alkyl, haloalkyl, alkoxy, and haloalkoxy; and $R^{12c}$, $R^{12d}$, $R^{13}$, $R^{17}$, and $Q^1$ are as defined in connection with A-37.

In another embodiment, Compounds of the Disclosure are compounds represented by Formula I-A, and the pharmaceutically acceptable salts or solvates thereof, wherein $A^1$ is A-55, $A^8$ is —N═, $A^9$ is —C($R^{18h}$)═, and $A^{10}$ is —C($R^{18j}$)═.

In another embodiment, Compounds of the Disclosure are compounds represented by Formula I-A, and the pharmaceutically acceptable salts or solvates thereof, wherein $A^1$ is A-55, $A^8$ is C($R^{18g}$)═, $A^9$ is —N═, and $A^{10}$ is —C($R^{18j}$)═.

In another embodiment, Compounds of the Disclosure are compounds represented by Formula I-A, and the pharmaceutically acceptable salts or solvates thereof, wherein $A^1$ is A-55, $A^8$ is —C($R^{18g}$)═, $A^9$ is —C($R^{18h}$)═, and $A^{10}$ is —N═.

In another embodiment, Compounds of the Disclosure are compounds represented by Formula I-A, and the pharmaceutically acceptable salts or solvates thereof, wherein $A^1$ is A-55, $A^8$ is —C($R^{18g}$)═, $A^9$ is —N═, and $A^{10}$ is —N═.

In another embodiment, Compounds of the Disclosure are compounds represented by Formula I-A, and the pharmaceutically acceptable salts or solvates thereof, wherein:

$A^1$ is:

A-56

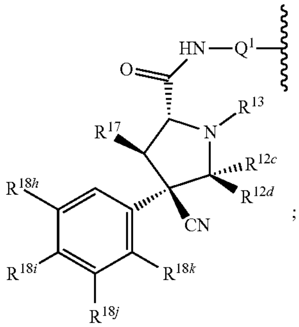

;

and $R^{12c}$, $R^{12d}$, $R^{13}$, $R^{17}$, $R^{18h}$, $R^{18l}$, $R^{18j}$, $R^{18k}$, and $Q^1$ are as defined in connection with A-55.

In another embodiment, Compounds of the Disclosure are compounds represented by Formula I-A, and the pharmaceutically acceptable salts or solvates thereof, wherein:

$A^1$ is:

A-57

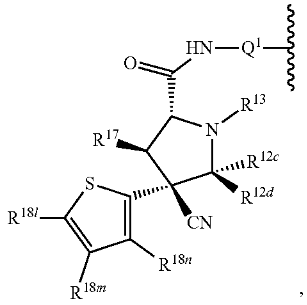

, $R^{18l}$, $R^{18m}$, and $R^{18n}$ are each independently selected from the group consisting of hydrogen, halo, $C_{1-4}$ alkyl, haloalkyl, alkoxy, and haloalkoxy; and $R^{12c}$, $R^{12d}$, $R^{13}$, $R^{17}$, and $Q^1$ are as defined in connection with A-37.

In another embodiment, Compounds of the Disclosure are compounds represented by Formula I-A, and the pharmaceutically acceptable salts or solvates thereof, wherein:

$A^1$ is:

A-58

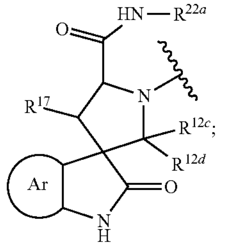

and $R^{22a}$ is selected from the group consisting of optionally substituted cycloalkyl, optionally substituted heterocyclo, optionally substituted aryl, and optionally substituted heteroaryl; and $R^{12c}$, $R^{12d}$, $R^{17}$, and

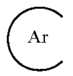

is as defined in connection with A-17.

In another embodiment, Compounds of the Disclosure are compounds represented by Formula I-A, and the pharmaceutically acceptable salts or solvates thereof, wherein:

$A^1$ is:
A-59
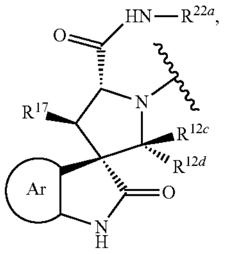
A-60
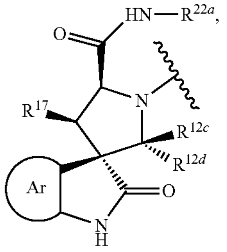
A-61
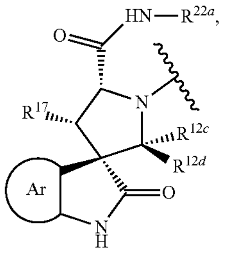
A-62
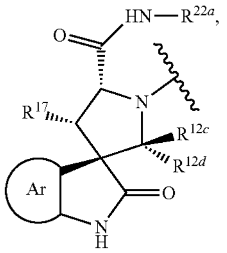
A-63
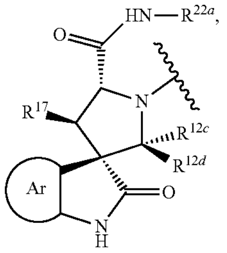
A-64
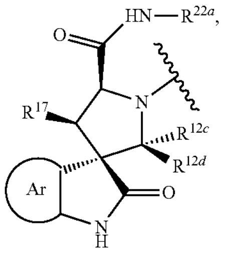
-continued
A-65
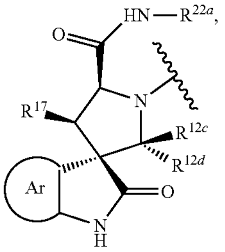
A-66
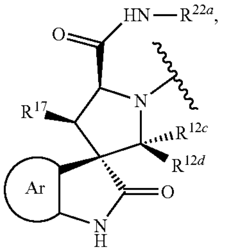
A-67
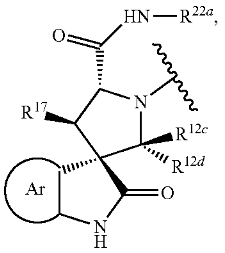
A-68
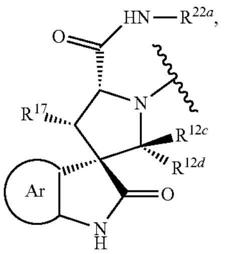
A-69
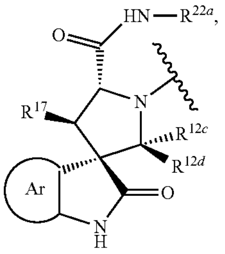
A-70
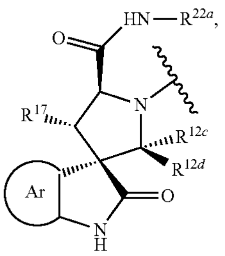

-continued

A-71

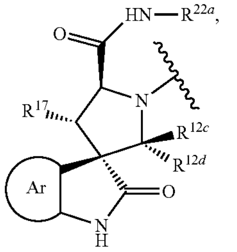

A-72

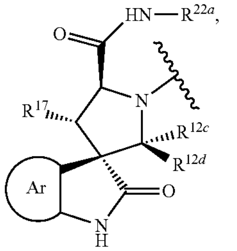

A-73

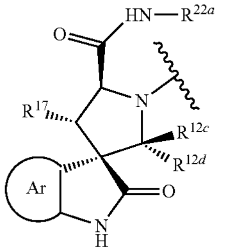

or

A-74

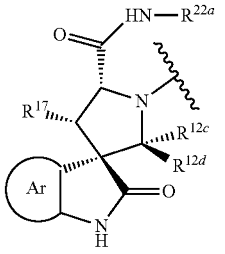

wherein $R^{12c}$, $R^{12d}$, $R^{17}$, $R^{22a}$, and

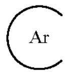

is as defined in connection with A-58.

In another embodiment, Compounds of the Disclosure are compounds represented by Formula I-A, and the pharmaceutically acceptable salts or solvates thereof, wherein:

$A^1$ is:

A-75

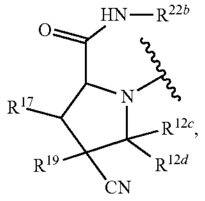

$R^{22b}$ is selected from the group consisting of optionally substituted cycloalkyl, optionally substituted heterocyclo, optionally substituted aryl, and optionally substituted heteroaryl; and $R^{12c}$, $R^{12d}$, $R^{17}$, and $R^{19}$ are as defined in connection with A-37.

In another embodiment, Compounds of the Disclosure are compounds represented by Formula I-A, and the pharmaceutically acceptable salts or solvates thereof, wherein:

$A^1$ is:

A-76

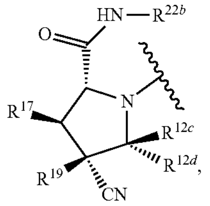

A-77

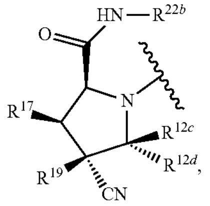

A-78

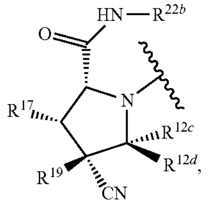

A-79

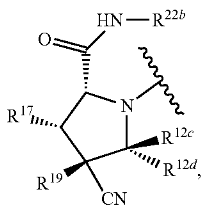

A-80

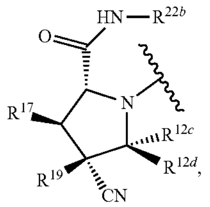

-continued
A-81
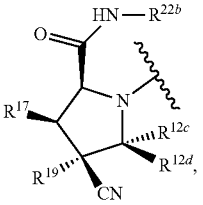
A-82
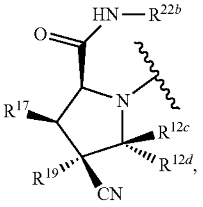
A-83
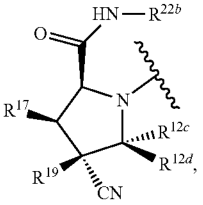
A-84
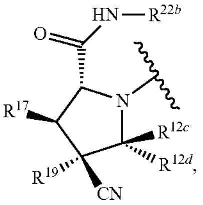
A-85
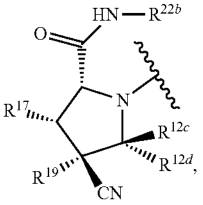
A-86
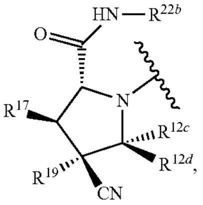
A-87
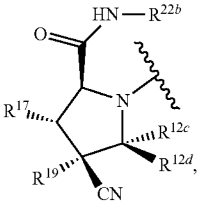
-continued
A-88
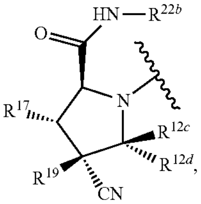
A-89
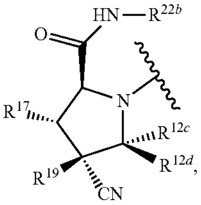
A-90
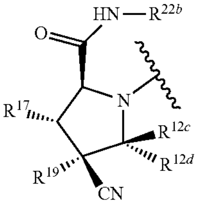
or
A-91
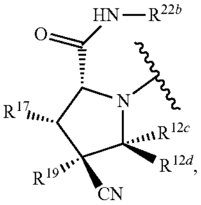
$R^{12c}$, $R^{12d}$, $R^{17}$, $R^{19}$, and $R^{22b}$ are as defined in connection with A-75.
In another embodiment, Compounds of the Disclosure are compounds represented by Formula I-A, and the pharmaceutically acceptable salts or solvates thereof, wherein:
$A^1$ is:
A-92
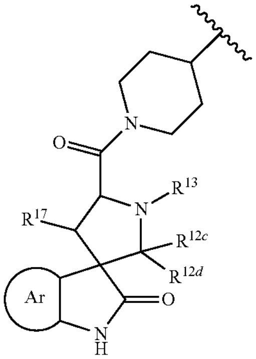
, and $R^{12c}$, $R^{12d}$, $R^{13}$, $R^{17}$, and

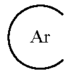

are as defined in connection with A-17.

In another embodiment, Compounds of the Disclosure are compounds represented by Formula I-A, and the pharmaceutically acceptable salts or solvates thereof, wherein:

$A^1$ is:

A-93

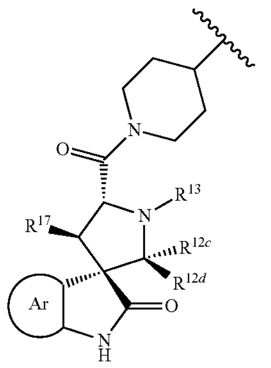

and $R^{12c}$, $R^{12d}$, $R^{13}$, $R^{17}$, and

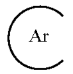

are as defined in connection with A-17.

In another embodiment, Compounds of the Disclosure are compounds represented by Formula I-A, and the pharmaceutically acceptable salts or solvates thereof, wherein $A^1$ is any one or more of A-17, A-18, A-19, A-20, A-21, A-22, A-23, A-24, A-25, A-26, A-27, A-28, A-29, A-30, A-31, A-32, A-33, A-34, A-35, A-46, A-37, A-38, A-39, A-40, A-41, A-42, A-43, A-44, A-45, A-46, A-47, A-48, A-49, A-50, A-51, A-52, A-53, A-54, A-55, A-56, A-57, A-58, A-59, A-60, A-61, A-62, A-63, A-64, A-65, A-66, A-67, A-68, A-69, A-70, A-71, A-72, A-73, A-74, A-75, A-76, A-77, A-78, A-79, A-80, A-81, A-82, A-83, A-84, A-85, A-86, A-87, A-88, A-89, A-90, A-91, A-92, or A-93, i.e., $A^1$ is any one or more of A-17 to A-93.

In another embodiment, Compounds of the Disclosure are compounds represented by Formula I-A, and the pharmaceutically acceptable salts or solvates thereof, wherein $A^1$ is selected from the group consisting of A-28, A-48, A-69, A-86, and A-93.

In another embodiment, Compounds of the Disclosure are compounds represented by Formula I-A, and the pharmaceutically acceptable salts or solvates thereof, wherein $A^1$ is selected from the group consisting of A-28, A-48, A-69, and A-86.

In another embodiment, Compounds of the Disclosure are compounds represented by Formula I-A, and the pharmaceutically acceptable salts or solvates thereof, wherein $A^1$ is selected from the group consisting of A-28 and A-48.

In another embodiment, Compounds of the Disclosure are compounds represented by Formula I-A, and the pharmaceutically acceptable salts or solvates thereof, wherein $A^1$ is selected from the group consisting of A-69 and A-86.

In another embodiment, Compounds of the Disclosure are compounds represented by Formula I-A, and the pharmaceutically acceptable salts or solvates thereof, wherein $A^1$ is selected from the group consisting of A-1 to A-16 (below).

In another embodiment, Compounds of the Disclosure are compounds represented by Formula I-A, and the pharmaceutically acceptable salts or solvates thereof, wherein $A^1$ is selected from the group consisting of A-1 to A-93.

In another embodiment, Compounds of the Disclosure are compounds represented by Formula I-A, and the pharmaceutically acceptable salts or solvates thereof, wherein $A^1$ is selected from the group consisting of A-1 to A-91.

In another embodiment, Compounds of the Disclosure are compounds represented by Formula I-A, and the pharmaceutically acceptable salts or solvates thereof, wherein $A^1$ is selected from the group consisting of A-92 and A-93.

In another embodiment, Compounds of the Disclosure are compounds represented by Formula I-A, and the pharmaceutically acceptable salts or solvates thereof, wherein $A^1$ is selected from the group consisting of A-17 to A-93.

In another embodiment, Compounds of the Disclosure are compounds represented by Formula I-A, and the pharmaceutically acceptable salts or solvates thereof, wherein $A^1$ is selected from the group consisting of A-17 to A-91.

In another embodiment, Compounds of the Disclosure are compounds represented by Formula I-A, and the pharmaceutically acceptable salts or solvates thereof, wherein $A^1$ is selected from the group consisting of A-17 to A-36.

In another embodiment, Compounds of the Disclosure are compounds represented by Formula I-A, and the pharmaceutically acceptable salts or solvates thereof, wherein $A^1$ is selected from the group consisting of A-37 to A-57.

In another embodiment, Compounds of the Disclosure are compounds represented by Formula I-A, and the pharmaceutically acceptable salts or solvates thereof, wherein $A^1$ is selected from the group consisting of A-58 to A-91.

In another embodiment, Compounds of the Disclosure are compounds represented by Formula I-A, and the pharmaceutically acceptable salts or solvates thereof, wherein $A^1$ is selected from the group consisting of A-10, A-11, A-15, A-28, A-48, A-69, A-86, A-93, A-98, A-99, and A-101.

In another embodiment, Compounds of the Disclosure are compounds represented by Formula I-A, and the pharmaceutically acceptable salts or solvates thereof, wherein $A^1$ is selected from the group consisting of A-35, A-56, A-99, A-100, and A-101.

In another embodiment, Compounds of the Disclosure are compounds represented by Formula I-A, and the pharmaceutically acceptable salts or solvates thereof, wherein:

$A^1$ is any one or more of A-17 to A-93; and $R^{17}$ is optionally substituted aryl. In another embodiment, the optional substituents are fluoro or chloro.

In another embodiment, Compounds of the Disclosure are compounds represented by Formula I-A, and the pharmaceutically acceptable salts or solvates thereof, wherein:

$A^1$ is:

A-94

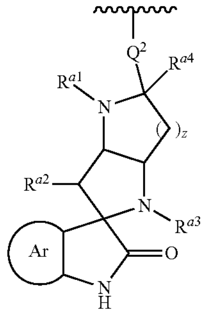

$R^{a1}$ is selected from the group consisting of hydrogen and optionally substituted $C_{1-6}$ alkyl;

$R^{a2}$ is selected from the group consisting of optionally substituted aryl and optionally substituted heteroaryl;

$R^{a3}$ is selected from the group consisting of hydrogen, optionally substituted $C_{1-6}$ alkyl, and aralkyl $R^{a4}$ is selected from the group consisting of hydrogen and optionally substituted $C_{1-6}$ alkyl;

$Q^2$ is selected from the group consisting of alkylenyl, arylenyl, e.g., phenylenyl, heteroarylenyl, cycloalkylenyl, and heterocyclenyl;

z is 1, 2, or 3; and

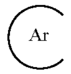

is a fused optionally substituted phenyl, fused optionally substituted thienyl, fused optionally substituted pyridyl, or fused optionally substituted pyrimidyl group.

In another embodiment, Compounds of the Disclosure are compounds represented by Formula I-A, and the pharmaceutically acceptable salts or solvates thereof, wherein:

$A^1$ is:

A-95

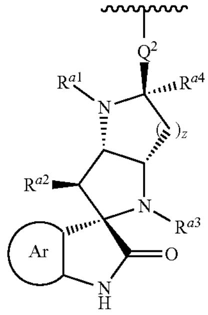

and $R^{a1}$, $R^{a2}$, $R^{a3}$, $R^{a4}$, $Q^2$, z and

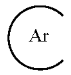

are as defined in connection with A-94.

In another embodiment, Compounds of the Disclosure are compounds represented by Formula I-A, and the pharmaceutically acceptable salts or solvates thereof, wherein:

$A^1$ is:

A-96

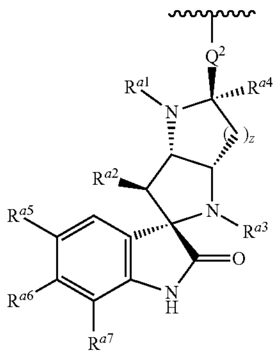

$R^{a5}$, $R^{a6}$, and $R^{a7}$ are each independently selected from the group consisting of hydrogen and halo, e.g., fluoro or chloro; and $R^{a1}$, $R^{a2}$, $R^{a3}$, $R^{a4}$, $Q^2$, and z are as defined in connection with A-94.

In another embodiment, Compounds of the Disclosure are compounds represented by Formula I-A, and the pharmaceutically acceptable salts or solvates thereof, wherein:

$A^1$ is:

A-97

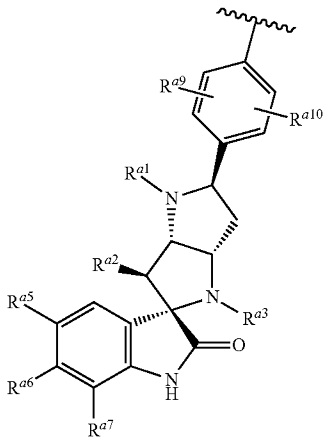

$R^{a9}$ and $R^{a10}$ are independently selected from the group consisting of hydrogen, halo, $C_{1-4}$ alkyl, haloalkyl, alkoxy, and haloalkoxy; and $R^{a1}$, $R^{a2}$, $R^{a3}$, $R^{a5}$, $R^{a6}$, and $R^{a7}$ are as defined in connection with A-94.

In another embodiment, Compounds of the Disclosure are compounds represented by Formula I-A, and the pharmaceutically acceptable salts or solvates thereof, wherein:

$A^1$ is:

A-98

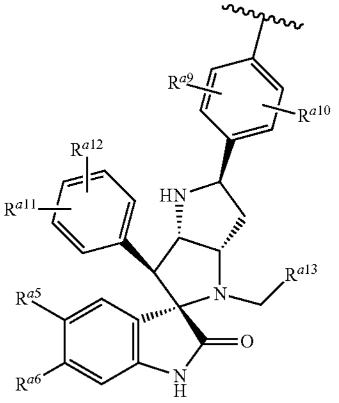

$R^{a5}$, $R^{a6}$, $R^{a11}$, and $R^{a12}$ are each independently selected from the group consisting of hydrogen and halo;

$R^{a9}$ and $R^{a10}$ are independently selected from the group consisting of hydrogen, halo, $C_{1-4}$ alkyl, haloalkyl, alkoxy, and haloalkoxy; and $R^{a13}$ is selected from the group consisting of hydrogen, $C_{1-4}$ alkyl, and $C_{3-8}$ cycloalkyl.

In another embodiment, Compounds of the Disclosure are compounds represented by Formula I-A, and the pharmaceutically acceptable salts or solvates thereof, wherein:

$A^1$ is:

A-99

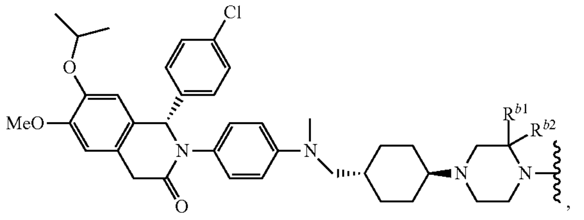

$R^{b1}$ and $R^{b2}$ are each hydrogen; or $R^{b1}$ and $R^{b2}$ taken together form a carbonyl, i.e., —C(═O)—, group.

In another embodiment, Compounds of the Disclosure are compounds represented by Formula I-A, and the pharmaceutically acceptable salts or solvates thereof, wherein:

$A^1$ is:

A-100

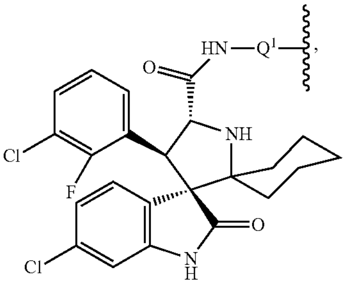

wherein $Q^1$ is selected from the group consisting of alkylenyl, phenylenyl, heteroarylenyl, cycloalkylenyl, and heterocyclenyl.

In another embodiment, Compounds of the Disclosure are compounds represented by Formula I-A, and the pharmaceutically acceptable salts or solvates thereof, wherein:

$A^1$ is:

A-101

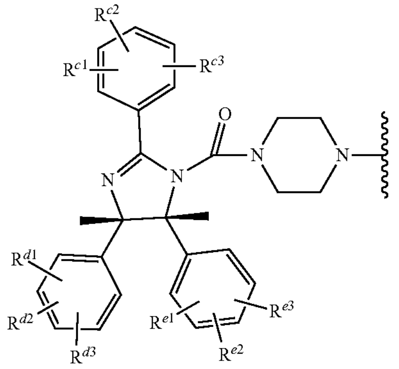

$R^{c1}$, $R^{c2}$, $R^{c3}$, $R^{d1}$, $R^{d2}$, $R^{d3}$, $R^{e1}$, $R^{e2}$, and $R^{e3}$ are each independently selected from the group consisting of hydrogen, halo, $C_{1-6}$ alkyl, haloalkyl, alkoxy, and haloalkoxy.

In another embodiment, Compounds of the Disclosure are compounds represented by Formula I-A, and the pharmaceutically acceptable salts or solvates thereof, wherein:

$A^1$ is any one or more of A-17 to A-93; and $R^{17}$ is optionally substituted heteroaryl. In another embodiment, the optional substituents are fluoro or chloro.

In another embodiment, Compounds of the Disclosure are compounds represented by Formula I-A, and the pharmaceutically acceptable salts or solvates thereof, wherein:

$A^1$ is any one or more of A-94 to A-97; and $R^{a2}$ is optionally substituted heteroaryl. In another embodiment, the optional substituents are fluoro or chloro.

In another embodiment, Compounds of the Disclosure are compounds represented by Formula I-A, and the pharmaceutically acceptable salts or solvates thereof, wherein:

$A^1$ is any one or more of A-17 to A-93;

$R^{17}$ is.

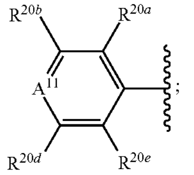

$A^{11}$ is selected from the group consisting of —C($R^{20c}$)═ and —N═; and $R^{20a}$, $R^{20b}$, $R^{20c}$, $R^{20d}$, and $R^{20e}$ are each independently selected from the group consisting of hydrogen, halo, $C_{1-4}$ alkyl, haloalkyl, alkoxy, and haloalkoxy. In another embodiment, $A^{11}$ is —C($R^{20c}$)═. In another embodiment, $A^{11}$ is —N═.

In another embodiment, Compounds of the Disclosure are compounds represented by Formula I-A, and the pharmaceutically acceptable salts or solvates thereof, wherein:

$A^1$ is any one or more of A-94 to A-97;

$R^{a2}$ is:

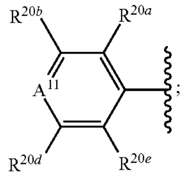

$A^{11}$ is selected from the group consisting of —C($R^{20c}$)= and —N=; and $R^{20a}$, $R^{20b}$, $R^{20c}$, $R^{20d}$, and $R^{20e}$ are each independently selected from the group consisting of hydrogen, halo, $C_{1-4}$ alkyl, haloalkyl, alkoxy, and haloalkoxy. In another embodiment, $A^{11}$ is —C($R^{20c}$)=. In another embodiment, $A^{11}$ is —N=.

In another embodiment, Compounds of the Disclosure are compounds represented by Formula I-A, and the pharmaceutically acceptable salts or solvates thereof, wherein:

$A^1$ is any one or more of A-17 to A-93;

$R^{12c}$ is hydrogen; and $R^{12d}$ is $C_{1-8}$ alkyl.

In another embodiment, Compounds of the Disclosure are compounds represented by Formula I-A, and the pharmaceutically acceptable salts or solvates thereof, wherein:

$A^1$ is any one or more of A-17 to A-93; and $R^{12c}$ and $R^{12d}$ are independently selected from $C_{1-8}$ alkyl, e.g., $R^{12c}$ is methyl and $R^{12d}$ is ethyl, $R^{12c}$ is methyl and $R^{12d}$ is methyl, $R^{12c}$ is ethyl and $R^{12d}$ is ethyl, $R^{12c}$ is propyl and $R^{12d}$ is propyl.

In another embodiment, Compounds of the Disclosure are compounds represented by Formula I-A, and the pharmaceutically acceptable salts or solvates thereof, wherein:

$A^1$ is any one or more of A-17 to A-93; and $R^{12c}$ and $R^{12d}$ taken together with the carbon atom to which they are attached form a 4- to 8-membered optionally substituted cycloalkyl, e.g., $R^{12c}$ and $R^{12d}$ taken together represent

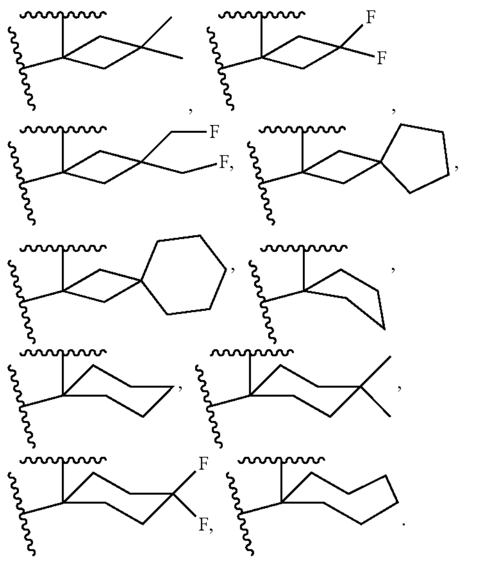

In another embodiment, Compounds of the Disclosure are compounds represented by Formula I-A, and the pharmaceutically acceptable salts or solvates thereof, wherein:

$A^1$ is any one or more of A-17 to A-93; and $R^{12c}$ and $R^{12d}$ taken together with the carbon atom to which they are attached form a 4- to 8-membered optionally substituted heterocyclo, e.g., $R^{12c}$ and $R^{12d}$ taken together represent

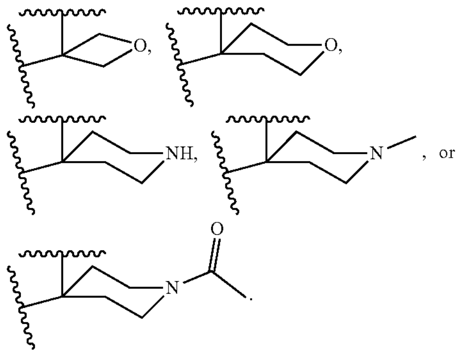

In another embodiment, Compounds of the Disclosure are compounds represented by Formula I-A, and the pharmaceutically acceptable salts or solvates thereof, wherein:

$A^1$ is any one or more of A-17 to A-57, A-92, or A-93; and $R^{13}$ is hydrogen.

In another embodiment, Compounds of the Disclosure are compounds represented by Formula I-A, and the pharmaceutically acceptable salts or solvates thereof, wherein:

$A^1$ is any one or more of A-17 to A-57 or A-100; and $Q^1$ is alkylenyl.

In another embodiment, Compounds of the Disclosure are compounds represented by Formula I-A, and the pharmaceutically acceptable salts or solvates thereof, wherein:

$A^1$ is any one or more of A-17 to A-57 or A-100; and $Q^1$ is phenylenyl, e.g., $Q^1$ is

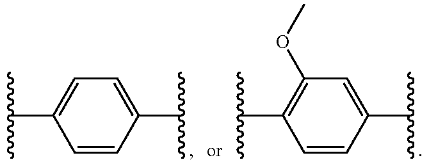

In another embodiment, Compounds of the Disclosure are compounds represented by Formula I-A, and the pharmaceutically acceptable salts or solvates thereof, wherein:

$A^1$ is any one or more of A-94 to A-97; and $Q^2$ is phenylenyl, e.g., $Q^2$ is

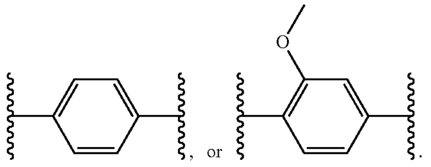

In another embodiment, Compounds of the Disclosure are compounds represented by Formula I-A, and the pharmaceutically acceptable salts or solvates thereof, wherein:

$A^1$ is any one or more of A-17 to A-57 or A-100; and $Q^1$ is heteroarylenyl, e.g., $Q^1$ is

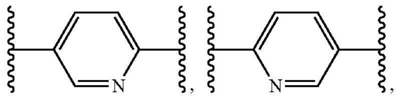

or

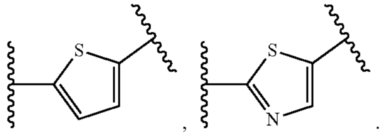

In another embodiment, Compounds of the Disclosure are compounds represented by Formula I-A, and the pharmaceutically acceptable salts or solvates thereof, wherein:

$A^1$ is any one or more of A-94 to A-97; and $Q^2$ is heteroarylenyl, e.g., $Q^2$ is

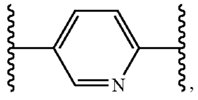

or

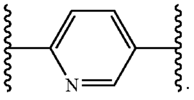

In another embodiment, Compounds of the Disclosure are compounds represented by Formula I-A, and the pharmaceutically acceptable salts or solvates thereof, wherein:

$A^1$ is any one or more of A-17 to A-57 or A-100; and $Q^1$ is cycloalkylenyl, e.g., $Q^1$ is

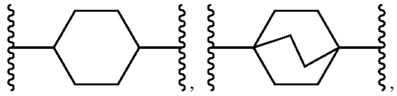

or

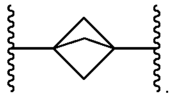

In another embodiment, Compounds of the Disclosure are compounds represented by Formula I-A, and the pharmaceutically acceptable salts or solvates thereof, wherein:

$A^1$ is any one or more of A-94 to A-96; and $Q^2$ is cycloalkylenyl, e.g., $Q^2$ is

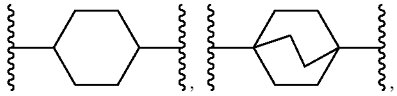

or

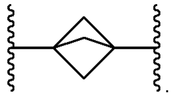

In another embodiment, Compounds of the Disclosure are compounds represented by Formula I-A, and the pharmaceutically acceptable salts or solvates thereof, wherein:

$A^1$ is any one or more of A-17 to A-57 or A-100; and $Q^1$ is heterocyclenyl, e.g., $Q^1$ is

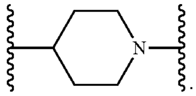 [SMILES: *C1CCN(*)CC1]

In another embodiment, Compounds of the Disclosure are compounds represented by Formula I-A, and the pharmaceutically acceptable salts or solvates thereof, wherein:

$A^1$ is any one or more of A-94 to A-96; and $Q^2$ is heterocyclenyl, e.g., $Q^2$ is

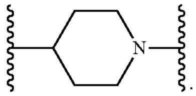

In another embodiment, Compounds of the Disclosure are compounds represented by Formula I-A, and the pharmaceutically acceptable salts or solvates thereof, wherein:

$A^1$ is any one or more of A-58 to A-74; and $R^{22a}$ is optionally substituted cycloalkyl, e.g., $R^{22a}$ is

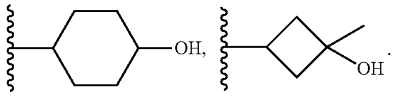

In another embodiment, Compounds of the Disclosure are compounds represented by Formula I-A, and the pharmaceutically acceptable salts or solvates thereof, wherein:

$A^1$ is any one or more of A-58 to A-74; and $R^{22a}$ is optionally substituted heterocyclo.

In another embodiment, Compounds of the Disclosure are compounds represented by Formula I-A, and the pharmaceutically acceptable salts or solvates thereof, wherein:

$A^1$ is any one or more of A-58 to A-74; and $R^{22a}$ is optionally substituted aryl, e.g., $R^{22a}$ is

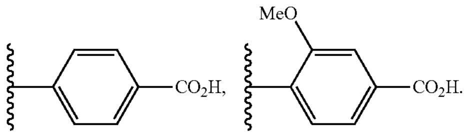 [SMILES: *c1ccc(C(=O)O)cc1 ; *c1ccc(C(=O)O)cc1OC]

In another embodiment, Compounds of the Disclosure are compounds represented by Formula I-A, and the pharmaceutically acceptable salts or solvates thereof, wherein:

$A^1$ is any one or more of A-58 to A-74; and $R^{22a}$ is optionally substituted heteroaryl, e.g., $R^{22a}$ is

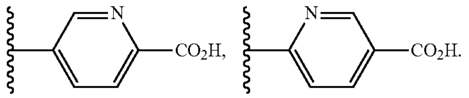 [SMILES: *c1ccc(C(=O)O)nc1 ; *c1ccc(C(=O)O)cn1]

In another embodiment, Compounds of the Disclosure are compounds represented by Formula I-A, and the pharmaceutically acceptable salts or solvates thereof, wherein:

$A^1$ is any one or more of A-75 to A-91; and $R^{22b}$ is optionally substituted cycloalkyl, e.g., $R^{22b}$ is

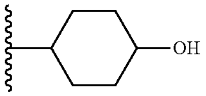
,
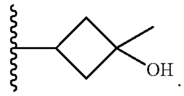
.

In another embodiment, Compounds of the Disclosure are compounds represented by Formula I-A, and the pharmaceutically acceptable salts or solvates thereof, wherein:

$A^1$ is any one or more of A-75 to A-91; and $R^{22b}$ is optionally substituted heterocyclo.

In another embodiment, Compounds of the Disclosure are compounds represented by Formula I-A, and the pharmaceutically acceptable salts or solvates thereof, wherein:

$A^1$ is any one or more of A-75 to A-91; and $R^{22b}$ is optionally substituted aryl, e.g., $R^{22b}$ is

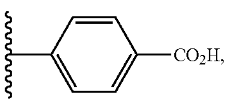
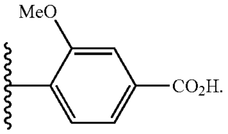

In another embodiment, Compounds of the Disclosure are compounds represented by Formula I-A, and the pharmaceutically acceptable salts or solvates thereof, wherein:

$A^1$ is any one or more of A-75 to A-91; and $R^{22b}$ is optionally substituted heteroaryl, e.g., $R^{22b}$ is

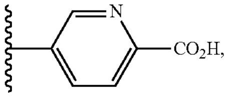
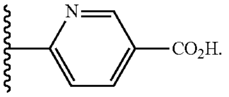

In another embodiment, Compounds of the Disclosure are compounds represented by Formula I-A, and the pharmaceutically acceptable salts or solvates thereof, wherein:

$L^1$ is —$X^1$-$L^1$-$Y^1$—;

$X^1$ is selected from the group consisting of —$N(R^{2a})$—,

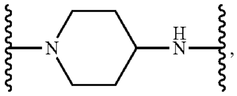
,
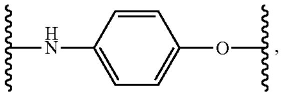
, and $X^2$; or $X^1$ is absent;

$X^2$ is selected from the group consisting of —N(H)C(═O)—, —C(═O)N(H)—, —C(═O)N(H)S$(O)_2$—, —N(H)C(═O)N(H)—, —N(H)C(═O)O—, —OC(═O)N(H)—, —C(═O)—, —$SO_2$—, —O—, —N(H)—, —$SO_2$N(H)—, —N(H)$SO_2$—, —$CH_2$—, —CH═CH—, and —C≡C—;

$L^2$ is selected from the group consisting of alkylenyl, heteroalkylenyl, -$A^4$-$(CH_2)_m$—W—$(CH_2)_n$— and —$(CH_2)_m$—W—$(CH_2)_u$—O—$(CH_2)_v$—; or $L^2$ is absent;

$A^4$ is selected from the group consisting of 5-membered heteroarylenyl and 6-membered heteroarylenyl; or $A^4$ is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

$Y^1$ is selected from the group consisting of —C≡C—, —CH═CH—, —$CH_2$—, —O—, —$N(R^{2b})$—, —C(═O)$N(R^{2c})$—, —$N(R^{2d})$C(═O)$CH_2$O—, and —$N(R^{2e})$C(═O)$CH_2$$N(R^{2f})$—; or $Y^1$ is absent;

wherein the carboxamide nitrogen atom of —$N(R^{2d})$C(═O)$CH_2$O— and —$N(R^{2e})$C(═O)$CH_2$$N(R^{2f})$—, and the carbon atom of —C(═O)$N(R^{2c})$— is attached to $L^2$; and $R^{2a}$, $R^{2b}$, $R^{2c}$, $R^{2d}$, $R^{2e}$, and $R^{2f}$ are each independently selected from the group consisting of hydrogen and $C_{1-4}$ alkyl.

In another embodiment, Compounds of the Disclosure are compounds represented by Formula I-A, and the pharmaceutically acceptable salts or solvates thereof, wherein:

$A^1$ is any one or more of A-17 to A-57 or A-100;

$L^1$ is —$X^1$-$L^1$-$Y^1$—;

$X^1$ is $X^2$; and $X^2$ is selected from the group consisting of —N(H)C(═O)—, —C(═O)N(H)—, —C(═O)N(H)S$(O)_2$—, —N(H)C(═O)N(H)—, —N(H)C(═O)O—, —OC(═O)N(H)—, —C(═O)—, —$SO_2$—, —O—, —N(H)—, —$SO_2$N(H)—, —N(H)$SO_2$—, —$CH_2$—, —CH═CH—, and —C≡C—. In another embodiment, $X^2$ is N(H)C(═O)—, —C(═O)N(H)—, or —C(═O)—. In another embodiment, $X^2$ is —N(H)C(═O)—. In another embodiment, $X^2$ is —C(═O)N(H)—. In another embodiment, $X^2$ is —N(H)C(═O)N(H)—. In another embodiment, $X^2$ is —N(H)C(═O)O—. In another embodiment, $X^2$ is —OC(═O)N(H)—. In another embodiment, $X^2$ is —C(═O)—. In another embodiment, $X^2$ is —$SO_2$—. In another embodiment, $X^2$ is —O—. In another embodiment, $X^2$ is —N(H)—. In another embodiment, $X^2$ is —$SO_2$N(H)—. In another embodiment, $X^2$ is —N(H)$SO_2$—. In another embodiment, $X^2$ is —$CH_2$—. In another embodiment, $X^2$ is —CH═CH—. In another embodiment, $X^2$ is —C≡C—.

In another embodiment, Compounds of the Disclosure are compounds represented by Formula I-A, and the pharmaceutically acceptable salts or solvates thereof, wherein:

$A^1$ is any one or more A-58 of A-91;

$L^1$ is —$X^1$-$L^1$-$Y^1$—;

$X^1$ is absent.

In another embodiment, Compounds of the Disclosure are compounds represented by Formula I-A, and the pharmaceutically acceptable salts or solvates thereof, wherein:

$A^1$ is A-92 or A-93;

$L^1$ is —$X^1$-$L^1$-$Y^1$—;

$X^1$ is $X^2$; and $X^2$ is selected from the group consisting of —N(H)C(═O)—, —C(═O)N(H)—, —C(═O)N(H)S$(O)_2$—, —N(H)C(═O)N(H)—, —N(H)C(═O)O—, —OC(═O)N(H)—, —C(═O)—, —$SO_2$—, —O—, —N(H)—, —$SO_2$N(H)—, —N(H)$SO_2$—, —$CH_2$—, —CH═CH—, and —C≡C—. In another embodiment, $X^2$ is N(H)C(═O)—, —C(═O)N(H)—, or —C(═O)—. In another embodiment, $X^2$ is —N(H)C(═O)—. In another embodiment, $X^2$ is —C(═O)N(H)—. In another embodiment, $X^2$ is —N(H)C(═O)N(H)—. In another embodiment, $X^2$ is —N(H)C(═O)O—. In another embodiment, $X^2$ is —OC(═O)N(H)—. In another embodiment, $X^2$ is —C(═O)—. In another embodiment, $X^2$ is —$SO_2$—. In another embodiment, $X^2$ is —O—. In another embodiment, $X^2$ is —N(H)—. In another embodiment, $X^2$ is —$SO_2$N(H)—. In another embodiment, $X^2$ is —N(H)$SO_2$—. In another embodiment, $X^2$ is —$CH_2$—. In another embodiment, $X^2$ is —CH═CH—. In another embodiment, $X^2$ is —C≡C—.

In another embodiment, Compounds of the Disclosure are compounds represented by Formula I-A, and the pharmaceutically acceptable salts or solvates thereof, wherein:

$A^1$ is A-94 to A-98;

$L^1$ is —$X^1$-$L^1$-$Y^1$—;

$X^1$ is $X^2$; and $X^2$ is selected from the group consisting of —N(H)C(═O)—, —C(═O)N(H)—, —C(═O)N(H)S(O)$_2$—, —N(H)C(═O)N(H)—, —N(H)C(═O)O—, —OC(═O)N(H)—, —C(═O)—, —$SO_2$—, —O—, —N(H)—, —$SO_2$N(H)—, —N(H)$SO_2$—, —$CH_2$—, —CH═CH—, and —C≡C—. In another embodiment, $X^2$ is N(H)C(═O)—, —C(═O)N(H)—, or —C(═O)—. In another embodiment, $X^2$ is —N(H)C(═O)—. In another embodiment, $X^2$ is —C(═O)N(H)—. In another embodiment, $X^2$ is —N(H)C(═O)N(H)—. In another embodiment, $X^2$ is —N(H)C(═O)O—. In another embodiment, $X^2$ is —OC(═O)N(H)—. In another embodiment, $X^2$ is —C(═O)—. In another embodiment, $X^2$ is —$SO_2$—. In another embodiment, $X^2$ is —O—. In another embodiment, $X^2$ is —N(H)—. In another embodiment, $X^2$ is —$SO_2$N(H)—. In another embodiment, $X^2$ is —N(H)$SO_2$—. In another embodiment, $X^2$ is —$CH_2$—. In another embodiment, $X^2$ is —CH═CH—. In another embodiment, $X^2$ is —C≡C—.

In another embodiment, Compounds of the Disclosure are compounds represented by Formula I-A, and the pharmaceutically acceptable salts or solvates thereof, wherein:

$A^1$ is A-99;

$L^1$ is —$X^1$-$L^1$-$Y^1$—;

$X^1$ is $X^2$; and $X^2$ is selected from the group consisting of —C(═O)N(H)—, —C(═O)—, —$SO_2$—, —$SO_2$N(H)—, —$CH_2$—, —CH═CH—, and —C≡C—. In another embodiment, $X^2$ is —C(═O)N(H)—, or —C(═O)—. In another embodiment, $X^2$ is —C(═O)—. In another embodiment, $X^2$ is —$SO_2$—. In another embodiment, $X^2$ is —N(H)—. In another embodiment, $X^2$ is —$SO_2$N(H)—. In another embodiment, $X^2$ is —$CH_2$—. In another embodiment, $X^2$ is —CH═CH—. In another embodiment, $X^2$ is —C≡C—.

In another embodiment, Compounds of the Disclosure are compounds represented by Formula VII:

VII

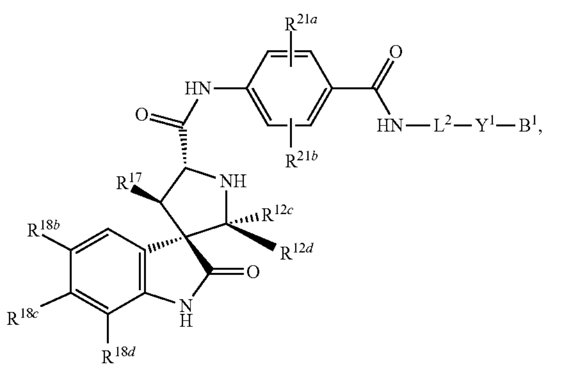

and the pharmaceutically acceptable salts or solvates thereof, wherein:

$R^{12c}$ and $R^{12d}$ taken together with the carbon atom to which they are attached form a 4- to 6-membered optionally substituted cycloalkyl;

$R^{17}$ is:

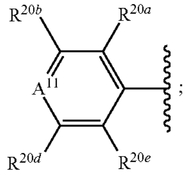

$A^{11}$ is —C($R^{20c}$)═;

$R^{20a}$, $R^{20b}$, and $R^{20c}$ are each hydrogen;

$R^{20d}$ and $R^{20e}$ are independently selected from the group consisting of hydrogen and halo, e.g., fluoro or chloro;

$R^{18b}$, $R^{18c}$, and $R^{18d}$ are each independently selected from the group consisting of hydrogen and halo, e.g., fluoro or chloro;

$R^{21a}$ and $R^{21b}$ are each independently selected from the group consisting of hydrogen, halo, $C_{1-4}$ alkyl, haloalkyl, alkoxy, and haloalkoxy;

$L^2$ is selected from the group consisting of alkylenyl, heteroalkylenyl, -$A^4$-$(CH_2)_m$—W—$(CH_2)_n$— and —$(CH_2)_m$—W—$(CH_2)_u$—O—$(CH_2)_v$—; or $L^2$ is absent;

$A^4$ is selected from the group consisting of 5-membered heteroarylenyl and 6-membered heteroarylenyl; or $A^4$ is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

$Y^1$ is selected from the group consisting of —C≡C—, —CH═CH—, —$CH_2$—, —O—, —N($R^{2b}$)—, —C(═O)N($R^{2c}$)—, —N($R^{2d}$)C(═O)$CH_2$O—, and —N($R^{2e}$)C(═O)$CH_2$N($R^{2f}$)—; or $Y^1$ is absent;

wherein the carboxamide nitrogen atom of —N($R^{2d}$)C(═O)$CH_2$O— and —N($R^{2e}$)C(═O)$CH_2$N($R^{2f}$)—, and the carbon atom of —C(═O)N($R^{2c}$)— is attached to $L^2$;

$R^{2b}$, $R^{2c}$, $R^{2d}$, $R^{2e}$, and $R^{2f}$ are each independently selected from the group consisting of hydrogen and $C_{1-4}$ alkyl; and $B^1$ is monovalent radical of a ligand for an E3 ubiquitin ligase protein.

In another embodiment, Compounds of the Disclosure are compounds represented by Formula VIII:

VIII

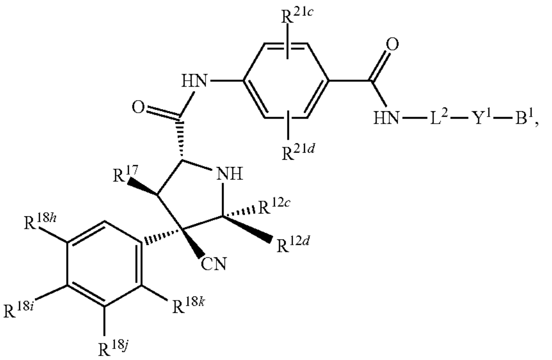

and the pharmaceutically acceptable salts or solvates thereof, wherein:

$R^{12c}$ and $R^{12d}$ are independently selected from the group consisting of hydrogen and optionally substituted $C_{1-8}$ alkyl; or $R^{12c}$ and $R^{12d}$ taken together with the carbon atom to which they are attached form a 4- to 6-membered optionally substituted cycloalkyl;

$R^{17}$ is:

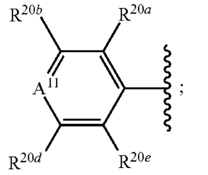

$A^{11}$ is —C($R^{20c}$)═;

$R^{20a}$, $R^{20b}$, and $R^{20c}$ are each hydrogen;

$R^{20d}$ and $R^{20e}$ are independently selected from the group consisting of hydrogen and halo, e.g., fluoro or chloro;

$R^{18h}$, $R^{18i}$, $R^{18j}$, and $R^{18k}$ are each independently selected from the group consisting of hydrogen and halo, e.g., fluoro or chloro;

$R^{21c}$ and $R^{21d}$ are each independently selected from the group consisting of hydrogen, halo, $C_{1-4}$ alkyl, haloalkyl, alkoxy, and haloalkoxy; $L^2$ is selected from the group consisting of alkylenyl, heteroalkylenyl, -$A^4$-$(CH_2)_m$—W—$(CH_2)_n$— and —$(CH_2)_m$—W—$(CH_2)_u$—O—$(CH_2)_v$—; or $L^2$ is absent;

$A^4$ is selected from the group consisting of 5-membered heteroarylenyl and 6-membered heteroarylenyl; or $A^4$ is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

$Y^1$ is selected from the group consisting of —C≡C—, —CH═CH—, —$CH_2$—, —O—, —N($R^{2b}$)—, —C(═O)N($R^{2c}$)—, —N($R^{2d}$)C(═O)$CH_2$O—, and —N($R^{2e}$)C(═O)$CH_2$N($R^{2f}$)—; or $Y^1$ is absent;

wherein the carboxamide nitrogen atom of —N($R^{2d}$)C(═O)$CH_2$O— and —N($R^{2e}$)C(═O)$CH_2$N($R^{2f}$)—, and the carbon atom of —C(═O)N($R^{2c}$)— is attached to $L^2$; and $R^{2b}$, $R^{2c}$, $R^{2d}$, $R^{2e}$, and $R^{2f}$ are each independently selected from the group consisting of hydrogen and $C_{1-4}$ alkyl; and $B^1$ is monovalent radical of a ligand for an E3 ubiquitin ligase protein.

In another embodiment, Compounds of the Disclosure are compounds represented by Formula IX:

IX

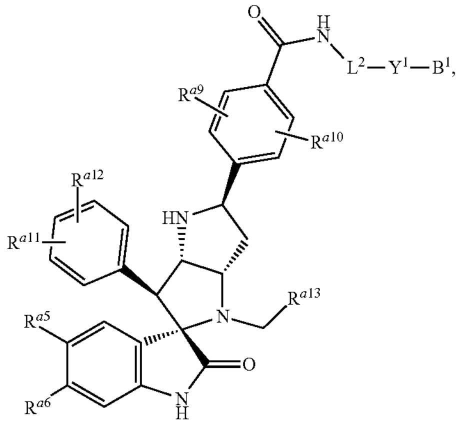

and the pharmaceutically acceptable salts or solvates thereof, wherein:

$R^{a5}$, $R^{a6}$, $R^{a11}$, and $R^{a12}$ are each independently selected from the group consisting of hydrogen and halo;

$R^{a9}$ and $R^{a10}$ are independently selected from the group consisting of hydrogen, halo, $C_{1-4}$ alkyl, haloalkyl, alkoxy, and haloalkoxy;

$R^{a13}$ is selected from the group consisting of hydrogen, $C_{1-4}$ alkyl, and $C_{3-8}$ cycloalkyl;

$L^2$ is selected from the group consisting of alkylenyl, heteroalkylenyl, -$A^4$-$(CH_2)_m$—W—$(CH_2)_n$— and —$(CH_2)_m$—W—$(CH_2)_u$—O—$(CH_2)_v$—; or $L^2$ is absent;

$A^4$ is selected from the group consisting of 5-membered heteroarylenyl and 6-membered heteroarylenyl; or $A^4$ is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

$Y^1$ is selected from the group consisting of $-C\equiv C-$, $-CH{=}CH-$, $-CH_2-$, $-O-$, $-N(R^{2b})-$, $-C({=}O)N(R^{2c})-$, $-N(R^{2d})C({=}O)CH_2O-$, and $-N(R^{2e})C({=}O)CH_2N(R^{2f})-$; or $Y^1$ is absent;

wherein the carboxamide nitrogen atom of $-N(R^{2d})C({=}O)CH_2O-$ and $-N(R^{2e})C({=}O)CH_2N(R^{2f})-$, and the carbon atom of $-C({=}O)N(R^{2c})-$ is attached to $L^2$;

$R^{2b}$, $R^{2c}$, $R^{2d}$, $R^{2e}$, and $R^{2f}$ are each independently selected from the group consisting of hydrogen and $C_{1-4}$ alkyl; and $B^1$ is monovalent radical of a ligand for an E3 ubiquitin ligase protein.

In another embodiment, Compounds of the Disclosure are compounds represented by Formula X:

X

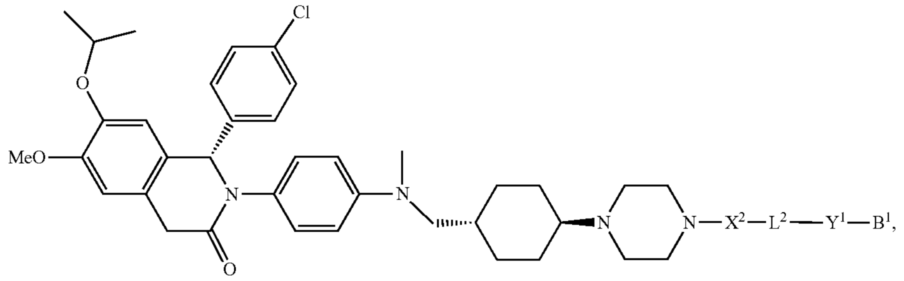

and the pharmaceutically acceptable salts or solvates thereof, wherein:

$X^2$ is selected from the group consisting of $-C({=}O)N(H)-$, $-C({=}O)-$, $-SO_2-$, $-SO_2N(H)-$, $-CH_2-$, $-CH{=}CH-$, and $-C\equiv C-$;

$L^2$ is selected from the group consisting of alkylenyl, heteroalkylenyl, $-A^4-(CH_2)_m-W-(CH_2)_n-$ and $-(CH_2)_m-W-(CH_2)_u-O-(CH_2)_v-$; or $L^2$ is absent;

$A^4$ is selected from the group consisting of 5-membered heteroarylenyl and 6-membered heteroarylenyl; or $A^4$ is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

$Y^1$ is selected from the group consisting of $-C\equiv C-$, $-CH{=}CH-$, $-CH_2-$, $-O-$, $-N(R^{2b})-$, $-C({=}O)N(R^{2c})-$, $-N(R^{2d})C({=}O)CH_2O-$, and $-N(R^{2e})C({=}O)CH_2N(R^{2f})-$; or $Y^1$ is absent;

wherein the carboxamide nitrogen atom of $-N(R^{2d})C({=}O)CH_2O-$ and $-N(R^{2e})C({=}O)CH_2N(R^{2f})-$, and the carbon atom of $-C({=}O)N(R^{2c})-$ is attached to $L^2$;

$R^{2b}$, $R^{2c}$, $R^{2d}$, $R^{2e}$, and $R^{2f}$ are each independently selected from the group consisting of hydrogen and $C_{1-4}$ alkyl; and $B^1$ is monovalent radical of a ligand for an E3 ubiquitin ligase protein.

In another embodiment, Compounds of the Disclosure are compounds represented by Formula XI:

XI

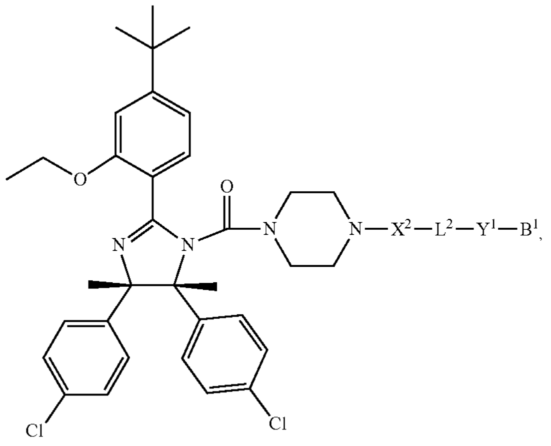

and the pharmaceutically acceptable salts or solvates thereof, wherein:

$X^2$ is selected from the group consisting of $-C({=}O)N(H)-$, $-C({=}O)-$, $-SO_2-$, $-SO_2N(H)-$, $-CH_2-$, $-CH{=}CH-$, and $-C\equiv C-$;

$L^2$ is selected from the group consisting of alkylenyl, heteroalkylenyl, $-A^4-(CH_2)_m-W-(CH_2)_n-$ and $-(CH_2)_m-W-(CH_2)_u-O-(CH_2)_v-$; or $L^2$ is absent;

$A^4$ is selected from the group consisting of 5-membered heteroarylenyl and 6-membered heteroarylenyl; or $A^4$ is absent;

W is selected from the group consisting of phenylenyl, 5-membered heteroarylenyl, 6-membered heteroarylenyl, heterocyclenyl, and cycloalkylenyl;

m is 0, 1, 2, 3, 4, 5, 6, or 7;

n is 0, 1, 2, 3, 4, 5, 6, 7, or 8;

u is 0, 1, 2, or 3;

v is 1, 2, 3, or 4;

$Y^1$ is selected from the group consisting of $-C\equiv C-$, $-CH{=}CH-$, $-CH_2-$, $-O-$, $-N(R^{2b})-$, $-C({=}O)N(R^{2c})-$, $-N(R^{2d})C({=}O)CH_2O-$, and $-N(R^{2e})C({=}O)CH_2N(R^{2f})-$; or $Y^1$ is absent;

wherein the carboxamide nitrogen atom of $-N(R^{2d})C({=}O)CH_2O-$ and $-N(R^{2e})C({=}O)CH_2N(R^{2f})-$, and the carbon atom of $-C({=}O)N(R^{2c})-$ is attached to $L^2$;

$R^{2b}$, $R^{2c}$, $R^{2d}$, $R^{2e}$, and $R^{2f}$ are each independently selected from the group consisting of hydrogen and $C_{1-4}$ alkyl; and $B^1$ is monovalent radical of a ligand for an E3 ubiquitin ligase protein.

In another embodiment, Compounds of the Disclosure are compounds represented by any one of Formula I-A or VII-XI and the pharmaceutically acceptable salts or solvates thereof, wherein:

$Y^1$ is selected from the group consisting of —C≡C—, —CH═CH—, —$CH_2$—, —O—, and —N($R^{2b}$)—; or $Y^1$ is absent.

In another embodiment, Compounds of the Disclosure are compounds represented by any one of Formula I-A or VII-XI and the pharmaceutically acceptable salts or solvates thereof, wherein $Y^1$ is —C≡C—. In another embodiment, $Y^1$ is —$CH_2$—. In another embodiment, $Y^1$ is —O—. In another embodiment, $Y^1$ is —N(H)—. In another embodiment, $Y^1$ is absent. In another embodiment, $Y^1$ is —CH═CH—.

In another embodiment, Compounds of the Disclosure are compounds represented by Formula I-A, and the pharmaceutically acceptable salts or solvates thereof, wherein:

$A^1$ is one or more of A-17 to A-98;

$Y^1$ is selected from the group consisting of —C≡C—, —CH═CH—, —$CH_2$—, —O—, and —N($R^{2b}$)—; or $Y^1$ is absent. In another embodiment, $Y^1$ is C≡C—. In another embodiment, $Y^1$ is —$CH_2$—. In another embodiment, $Y^1$ is —O—. In another embodiment, $Y^1$ is —N(H)—. In another embodiment, $Y^1$ is absent. In another embodiment, $Y^1$ is —CH═CH—.

In another embodiment, Compounds of the Disclosure are compounds represented by Formula I-A, and the pharmaceutically acceptable salts or solvates thereof, wherein:

$A^1$ is A-99;

$Y^1$ is selected from the group consisting of —C≡C—, —CH═CH—, —$CH_2$—, —O—, and —N($R^{2b}$)—; or $Y^1$ is absent. In another embodiment, $Y^1$ is —C≡C—. In another embodiment, $Y^1$ is —$CH_2$—. In another embodiment, $Y^1$ is —O—. In another embodiment, $Y^1$ is —N(H)—. In another embodiment, $Y^1$ is absent. In another embodiment, $Y^1$ is —CH═CH—.

In another embodiment, Compounds of the Disclosure are compounds represented by Formula I-A, and the pharmaceutically acceptable salts or solvates thereof, wherein:

$A^1$ is A-100;

$Y^1$ is selected from the group consisting of —C≡C—, —CH═CH—, —$CH_2$—, —O—, and —N($R^{2b}$)—; or $Y^1$ is absent. In another embodiment, $Y^1$ is —C≡C—. In another embodiment, $Y^1$ is —$CH_2$—. In another embodiment, $Y^1$ is —O—. In another embodiment, $Y^1$ is —N(H)—. In another embodiment, $Y^1$ is absent. In another embodiment, $Y^1$ is —CH═CH—.

In another embodiment, Compounds of the Disclosure are compounds represented by Formula I-A, and the pharmaceutically acceptable salts or solvates thereof, wherein:

$A^1$ is A-101;

$Y^1$ is selected from the group consisting of —C≡C—, —CH═CH—, —$CH_2$—, —O—, and —N($R^{2b}$)—; or $Y^1$ is absent. In another embodiment, $Y^1$ is —C≡C—. In another embodiment, $Y^1$ is —$CH_2$—. In another embodiment, $Y^1$ is —O—. In another embodiment, $Y^1$ is —N(H)—. In another embodiment, $Y^1$ is absent. In another embodiment, $Y^1$ is —CH═CH—.

In another embodiment, Compounds of the Disclosure are compounds represented by any one of Formula I-A or VII-XI, and the pharmaceutically acceptable salts or solvates thereof, wherein:

$B^1$ is selected from the group consisting of:

B-1a

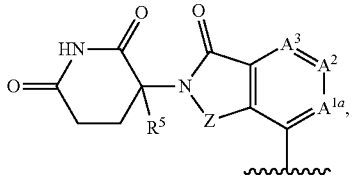

B-1b

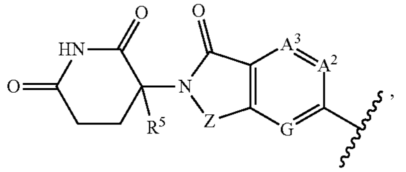

B-1c

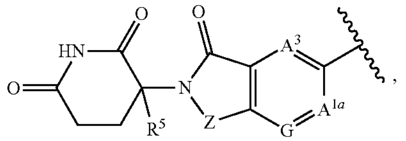

B-1d

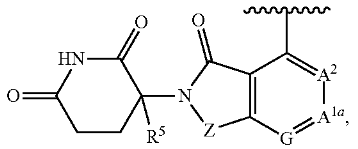

B-2

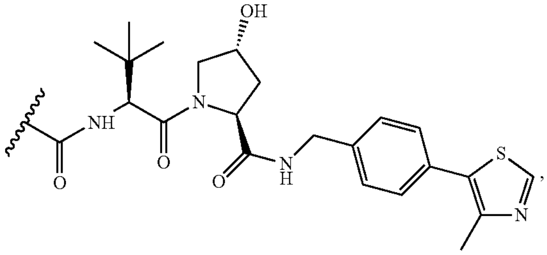

B-2a

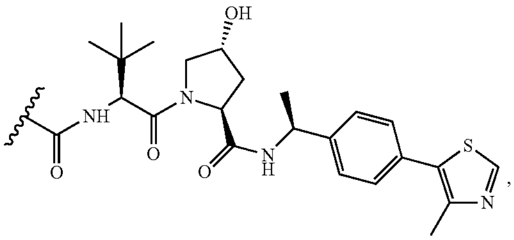

and

B-3

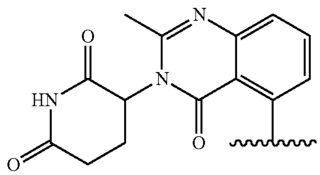

;

$A^{1a}$ is selected from the group consisting of —C($R^{16a}$)═ and —N═;

$A^2$ is selected from the group consisting of —C($R^{16b}$)═ and —N═;

$A^3$ is selected from the group consisting of —C($R^{16c}$)═ and —N═;

G is selected from the group consisting of —C($R^{16d}$)═ and —N═;

Z is selected from the group consisting of —$CH_2$ and —C(═O)—;

$R^5$ is selected from the group consisting of hydrogen, methyl, and fluoro;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl; and $R^{16c}$ is selected from the group consisting of hydrogen, halo, and $C_{1-4}$ alkyl; and $R^{16d}$ is selected from the group consisting of hydrogen, halo, and $C_{1-4}$ alkyl.

In another embodiment, Compounds of the Disclosure are compounds represented by any one of Formula I-A or VII-XI, and the pharmaceutically acceptable salts or solvates thereof, wherein $B^1$ is B-1a, B-1b, B-1c, or B-1d, and $R^5$ is partially or entirely enriched with an isotope of hydrogen, e.g., $R^5$ is about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% deuterium.

In another embodiment, Compounds of the Disclosure are compounds represented by any one of Formula I-A or VII-XI, and the pharmaceutically acceptable salts or solvates thereof, wherein $B^1$ is B-1a. In another embodiment, $B^1$ is B-1b. In another embodiment, $B^1$ is B-1c. In another embodiment, $B^1$ is B-1d. In another embodiment, $B^1$ is B-2. In another embodiment, $B^1$ is B-3. In another embodiment, $B^1$ is:

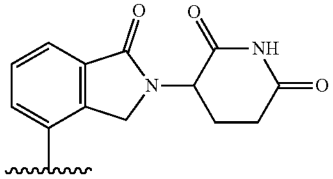

or

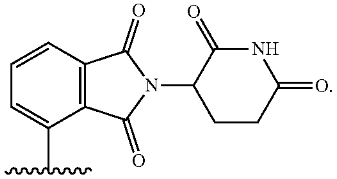

In another embodiment, $B^1$ is:

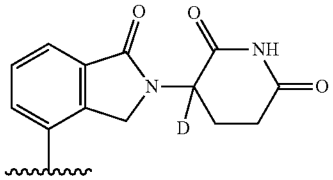

or

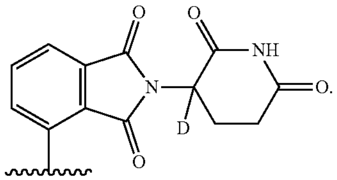

In another embodiment, $B^1$ is:

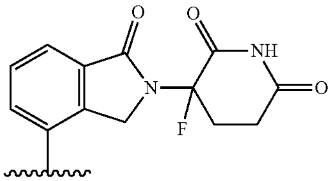

or

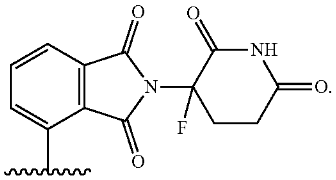

In another embodiment, Compounds of the Disclosure are compounds represented by Formulae I-A, and the pharmaceutically acceptable salts or solvates thereof, wherein $A^1$ is one or more of A-17 to A-93 and $B^1$ is B-1a, B-2, or B-3.

In another embodiment, Compounds of the Disclosure are compounds represented by Formula I-A, and the pharmaceutically acceptable salts or solvates thereof, wherein $A^1$ is any one or more of A-17 to A-98, and $B^1$ is B-1a. In another embodiment, $B^1$ is B-2. In another embodiment, $B^1$ is B-3. In another embodiment, $B^1$ is:

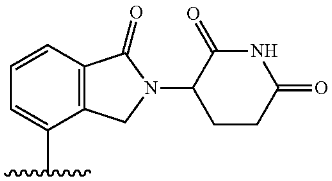

or

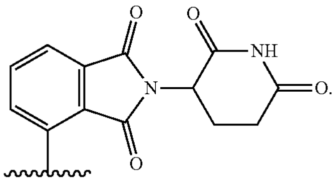

In another embodiment, $B^1$ is:

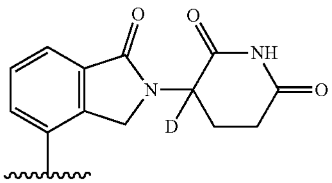

or

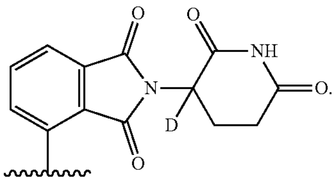

In another embodiment, $B^1$ is:

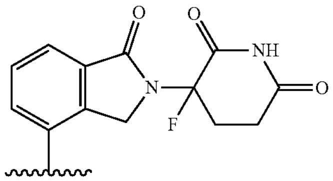

or

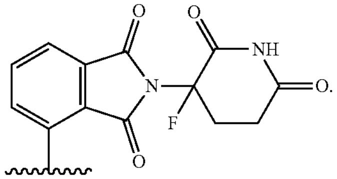

In another embodiment, Compounds of the Disclosure are compounds represented by any one of Formula I-A or VII-X, and the pharmaceutically acceptable salts or solvates thereof, wherein:

$B^1$ is B-2a:

B-2a

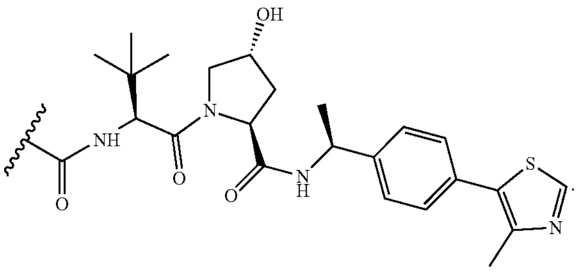

In another embodiment, Compounds of the Disclosure are compounds represented by any one of Formula I-A or VII-XI, and the pharmaceutically acceptable salts or solvates thereof, wherein:

$B^1$ is selected from the group consisting of

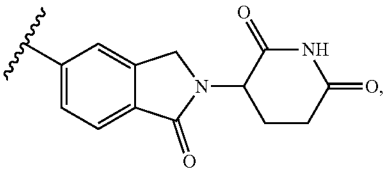

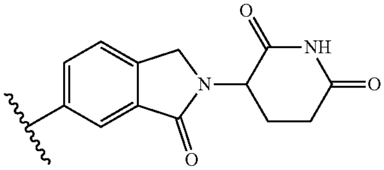

and

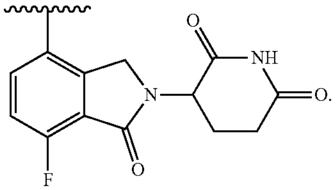

In another embodiment, Compounds of the Disclosure are compounds represented by Formula XII:

XII

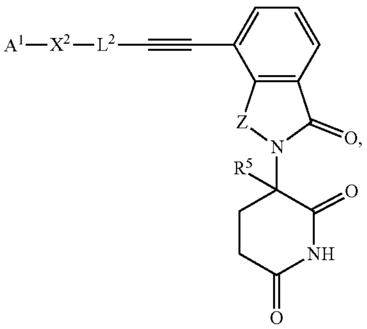

and the pharmaceutically acceptable salts or solvates thereof, wherein $A^1$ is any one or more of A-17 to A-101;

Z is selected from the group consisting of $—CH_2$ and —C(═O)—;

$R^5$ is selected from the group consisting of hydrogen, methyl, and fluoro;

$X^2$ is selected from the group consisting of —N(H)C(═O)—, —C(═O)N(H)—, $—C(═O)N(H)S(O)_2—$, —N(H)C(═O)N(H)—, —N(H)C(═O)O—, —OC(═O)N(H)—, —C(═O)—, $—SO_2—$, —O—, —N(H)—, $—SO_2N(H)—$, $—N(H)SO_2—$, $—CH_2—$, —CH═CH—, and —C≡C—; and $L^2$ is selected from the group consisting of alkylenyl and heteroalkylenyl; or $L^2$ is absent.

In another embodiment, Compounds of the Disclosure are compounds represented by Formula XII, and the pharmaceutically acceptable salts or solvates thereof, wherein $A^1$ is selected from the group consisting of A-10, A-11, A-15, A-28, A-48, A-69, A-86, A-93, A-98, A-99, and A-101.

In another embodiment, Compounds of the Disclosure are compounds represented by Formula XII, and the pharmaceutically acceptable salts or solvates thereof, wherein $A^1$ is selected from the group consisting of A-35, A-56, A-99, A-100, and A-101.

In another embodiment, Compounds of the Disclosure are compounds represented by Formula XII, and the pharmaceutically acceptable salts or solvates thereof, wherein $A^1$ is A-100.

In another embodiment, Compounds of the Disclosure are compounds represented by any one of Formulae I-A or VII-XII, and the pharmaceutically acceptable salts or solvates thereof, wherein $L^2$ is $—(CH_2)_m—W—(CH_2)_n—$. In another embodiment, W is phenylenyl. In another embodiment, W is 5-membered heteroarylenyl. In another embodiment. W is 6-membered heteroarylenyl. In another embodiment, W is heterocyclenyl. In another embodiment, W is cycloalkylenyl.

In another embodiment, Compounds of the Disclosure are compounds represented by any one of Formulae I-A or VII-XII, and the pharmaceutically acceptable salts or solvates thereof, wherein $L^2$ is $C_{1-12}$ alkylenyl. In another embodiment, $L^2$ is selected from the group consisting of $—CH_2—$, $—CH_2CH_2—$, $—CH_2CH_2CH_2—$, $—CH_2(CH_2)_2CH_2—$, $—CH_2(CH_2)_3CH_2—$, $—CH_2(CH_2)_4CH_2—$, $—CH_2(CH_2)_5CH_2—$, and $—CH_2(CH_2)_6CH_2—$. In another embodiment, $L^2$ is selected from the group consisting of $—CH_2—$, $—CH_2CH_2—$, $—CH_2CH_2CH_2—$, and $—CH_2(CH_2)_2CH_2—$. In another embodiment, $A^1$ is any one or more of A-17 to A-91. In another embodiment, $A^1$ is any one or more of A-58 to A-91.

In another embodiment, Compounds of the Disclosure are compounds represented by any one of Formulae I-A or VII-XI, and the pharmaceutically acceptable salts or solvates thereof, wherein $L^2$ is 3- to 20-membered heteroalkylenyl. In another embodiment, $L^2$ is selected from the group consisting of $—(CH_2)_oO—(CH_2CH_2O)_p—(CH_2)_q—$ and $—(CH_2)_rO—(CH_2)_s—O(CH_2)_t—$; wherein: o is 2 or 3; p is 0, 1, 2, 3, 4, 5, 6, or 7; q is 2 or 3; r is 2, 3, or 4; s is 3, 4, or 5; and t is 2 or 3. In another embodiment, $L^2$ is selected from the group consisting of $—CH_2CH_2OCH_2CH_2—$,
$—CH_2CH_2O(CH_2CH_2O)_2CH_2CH_2—$,
$—CH_2CH_2O(CH_2CH_2O)_3CH_2CH_2—$,
$—CH_2CH_2O(CH_2CH_2O)_4CH_2CH_2—$,
$—CH_2CH_2O(CH_2CH_2O)_6CH_2CH_2—$,
$—CH_2CH_2O(CH_2CH_2O)_6CH_2CH_2—$,
$—CH_2CH_2CH_2OCH_2CH_2OCH_2CH_2CH_2—$,
$—CH_2CH_2CH_2O(CH_2CH_2O)_2CH_2CH_2CH_2—$, and
$—CH_2CH_2CH_2O(CH_2)_4OCH_2CH_2CH_2—$. In another embodiment, $A^1$ is any one or more of A-17 to A-91. In another embodiment, $A^1$ is any one or more of A-58 to A-91.

In another embodiment, Compounds of the Disclosure are compounds represented by Formula I-A, and the pharmaceutically acceptable salts or solvates thereof, wherein:

$A^1$ is any one or more A-58 of A-91;
$L^1$ is $—X^1$-$L^1$-$Y^1—$;
$X^1$ is absent;
$L^2$ is selected from the group consisting of alkylenyl, heteroalkylenyl, and $-A^4$-$(CH_2)_m—W—(CH_2)_n—$; and
$A^4$ is absent.

In another embodiment, Compounds of the Disclosure are compounds represented by Formula I-A, and the pharmaceutically acceptable salts or solvates thereof, wherein:

$A^1$ is any one or more A-58 of A-91;
$L^1$ is $—X^1$-$L^1$-$Y^1—$;
$X^1$ is absent;
$L^2$ is selected from the group consisting of alkylenyl and heteroalkylenyl.

In another embodiment, Compounds of the Disclosure are compounds represented by any one of Formula I-A or VII-XI, and the pharmaceutically acceptable salts or solvates thereof, wherein $L^2$ is selected from the group consisting of:

$L^2$-1

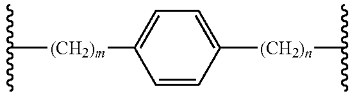

and $L^2$-2

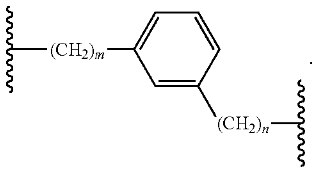

.

In another embodiment, $A^1$ is any one or more of A-17 to A-91. In another embodiment, m is 0. In another embodiment, n is 1, 2, 3, 4, or 5. In another embodiment, $L^2$ is $L^2$-1. In another embodiment, $L^2$ is $L^2$-2.

In another embodiment, Compounds of the Disclosure are compounds represented by any one of Formula I-A or VII-XI, and the pharmaceutically acceptable salts or solvates thereof, wherein $L^2$ is selected from the group consisting of:

$L^2$-3

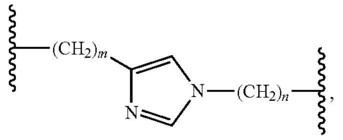

, $L^2$-4

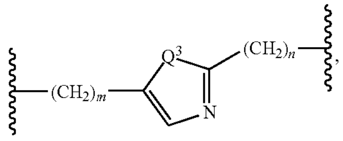

, $L^2$-5

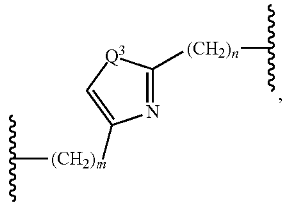

, $L^2$-6

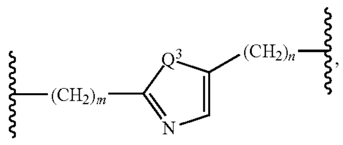

, $L^2$-7

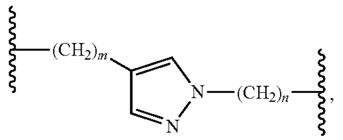

, $L^2$-8

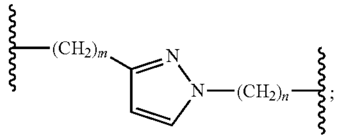

; and $L^2$-9

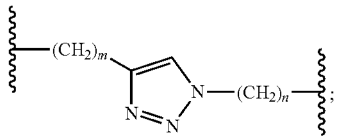

;

$Q^3$ is selected from the group consisting of —O—, —S—, and $—N(R^6)—$; and $R^6$ is selected from the group consisting of hydrogen and $C_{1-4}$ alkyl. In another embodiment, $A^1$ is any one or more of A-17 to A-91. In another embodiment, m is 0. In another embodiment, n is 1, 2, 3, 4, or 5. In another embodiment, n is 2, 3, or 4. In another embodiment, $L^2$ is $L^2$-3. In another embodiment, $L^2$ is $L^2$-4. In another embodiment, $L^2$ is $L^2$-5. In another embodiment, $L^2$ is $L^2$-6. In another embodiment, $L^2$ is $L^2$-7. In another embodiment, $L^2$ is $L^2$-8. In another embodiment, $L^2$ is $L^2$-9. In another embodiment, the $(CH_2)_n$ group is attached to $Y^1$. In another embodiment, the $(CH_2)_m$ group is attached to $Y^1$.

In another embodiment, Compounds of the Disclosure are compounds represented by any one of Formula I-A or VII-XI, and the pharmaceutically acceptable salts or solvates thereof, wherein $L^2$ is selected from the group consisting of:

$L^2$-10

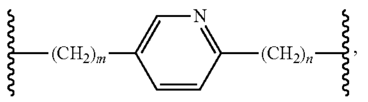

$L^2$-11

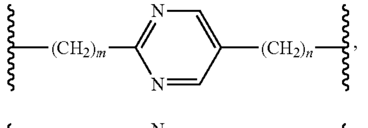

$L^2$-12

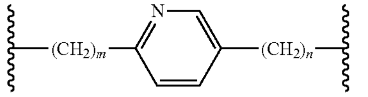

and $L^2$-13

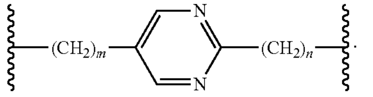

In another embodiment, $A^1$ is any one or more of A-17 to A-91. In another embodiment, m is 0. In another embodiment, n is 1, 2, 3, 4, or 5. In another embodiment, n is 2, 3, or 4. In another embodiment, $L^2$ is $L^2$-10. In another embodiment, $L^2$ is $L^2$-11. In another embodiment, $L^2$ is $L^2$-12. In another embodiment, $L^2$ is $L^2$-13.

In another embodiment, Compounds of the Disclosure are compounds represented by any one of Formula I-A or VII-XI, and the pharmaceutically acceptable salts or solvates thereof, wherein $L^2$ is selected from the group consisting of:

$L^2$-14

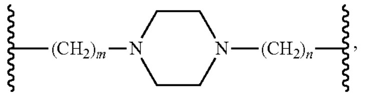

$L^2$-15

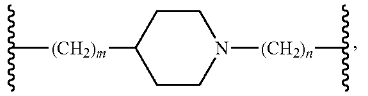

$L^2$-16

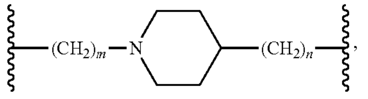

$L^2$-17

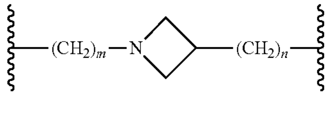

and $L^2$-18

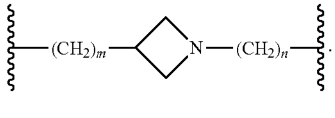

In another embodiment, $A^1$ is any one or more of A-17 to A-91. In another embodiment, m is 1, 2, or 3. In another embodiment, n is 0, 1, 2, 3, or 4. In another embodiment, n is 0, 1, or 2. In another embodiment, $L^2$ is $L^2$-14. In another embodiment, $L^2$ is $L^2$-15. In another embodiment, $L^2$ is $L^2$-16. In another embodiment, $L^2$ is $L^2$-17. In another embodiment, $L^2$ is $L^2$-18.

In another embodiment, Compounds of the Disclosure are compounds represented by any one of Formula I-A or VII-XI, and the pharmaceutically acceptable salts or solvates thereof, wherein $L^2$ is selected from the group consisting of $L^2$-16 and $L^2$-17. In another embodiment, m is 0, and n is 0 or 1. In another embodiment, m is 1, 2, or 3, and n is 0 or 1.

In another embodiment, Compounds of the Disclosure are compounds represented by any one of Formula I-A or VII-XI, and the pharmaceutically acceptable salts or solvates thereof, wherein $L^2$ is selected from the group consisting of:

$L^2$-19

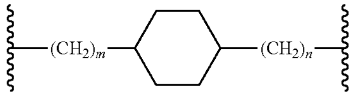

and $L^2$-20

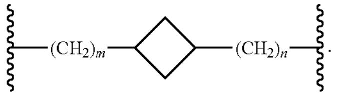

In another embodiment, $A^1$ is any one or more of A-17 to A-91. In another embodiment, m is 1, 2, or 3. In another embodiment, n is 0, 1, 2, 3, or 4. In another embodiment, n is 1 or 2. In another embodiment, $L^2$ is $L^2$-19. In another embodiment, $L^2$ is $L^2$-20.

In another embodiment, Compounds of the Disclosure are compounds represented by any one of Formula I-A or VII-XI, and the pharmaceutically acceptable salts or solvates thereof, wherein $L^2$ is selected from the group consisting of:

$L^2$-21

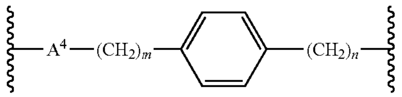

and $L^2$-22

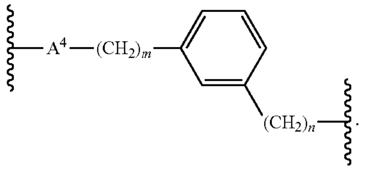

In another embodiment, $A^1$ is any one or more of A-17 to A-91. In another embodiment, m is 1, 2, or 3. In another embodiment, n is 1, 2, 3, 4, or 5. In another embodiment, $L^2$ is $L^2$-21. In another embodiment, $L^2$ is $L^2$-22. In another embodiment, $A^4$ is 5-membered heteroarylenyl. In another embodiment, $A^4$ is 6-membered heteroarylenyl.

In another embodiment, Compounds of the Disclosure are compounds represented by any one of Formula I-A or VII-XI, and the pharmaceutically acceptable salts or solvates thereof, wherein $L^2$ is selected from the group consisting of:

L2-23

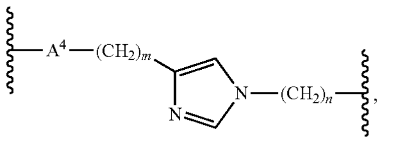

L2-24

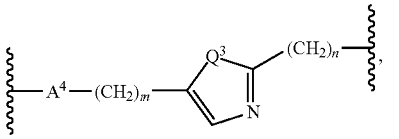

L2-25

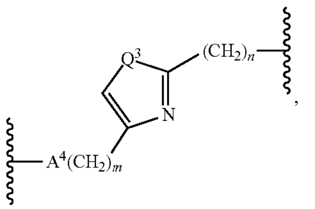

L2-26

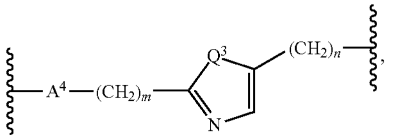

L2-27

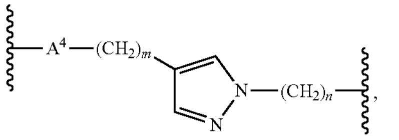

L2-28

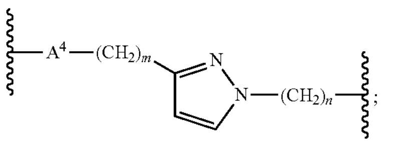

and

L2-29

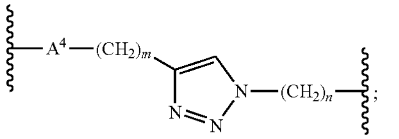

$Q^3$ is selected from the group consisting of —O—, —S—, and —$N(R^6)$—; and $R^6$ is selected from the group consisting of hydrogen and $C_{1-4}$ alkyl. In another embodiment, m is 1, 2, or 3. In another embodiment, $A^1$ is any one or more of A-17 to A-91. In another embodiment, n is 1, 2, 3, or 4. In another embodiment, n is 2, 3, or 4. In another embodiment, $L^2$ is $L^2$-23. In another embodiment, $L^2$ is $L^2$-24. In another embodiment, $L^2$ is $L^2$-25. In another embodiment, $L^2$ is $L^2$-26. In another embodiment, $L^2$ is $L^2$-27. In another embodiment, $L^2$ is $L^2$-28. In another embodiment, $L^2$ is $L^2$-29. In another embodiment, $A^4$ is 5-membered heteroarylenyl. In another embodiment, $A^4$ is 6-membered heteroarylenyl. In another embodiment, the $(CH_2)_n$ group is attached to $Y^1$. In another embodiment, the $(CH_2)_m$ group is attached to $Y^1$.

In another embodiment, Compounds of the Disclosure are compounds represented by any one of Formula I-A or VII-XI, and the pharmaceutically acceptable salts or solvates thereof, wherein $L^2$ is selected from the group consisting of:

L2-30

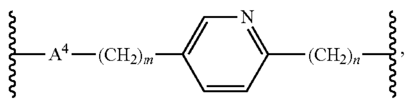

L2-31

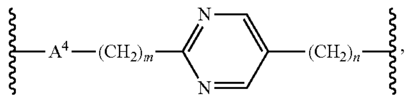

L2-32

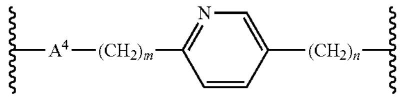

and

L2-33

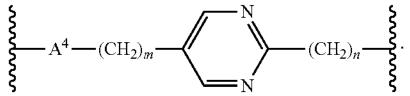

In another embodiment, $A^1$ is any one or more of A-17 to A-91. In another embodiment, m is 1, 2, or 3. In another embodiment, n is 1, 2, 3, or 4. In another embodiment, n is 2, 3, or 4. In another embodiment, $L^2$ is $L^2$-30. In another embodiment, $L^2$ is $L^2$-31. In another embodiment, $L^2$ is $L^2$-32. In another embodiment, $L^2$ is $L^2$-33. In another embodiment, $A^4$ is 5-membered heteroarylenyl. In another embodiment, $A^4$ is 6-membered heteroarylenyl.

In another embodiment, Compounds of the Disclosure are compounds represented by any one of Formula I-A or VII-XI, and the pharmaceutically acceptable salts or solvates thereof, wherein $L^2$ is selected from the group consisting of:

L2-34

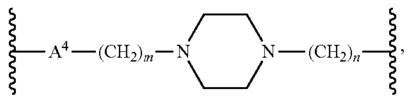

L2-35

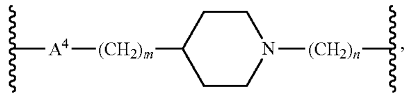

L2-36

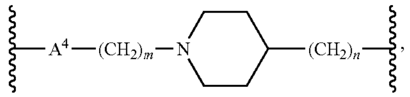

L2-37

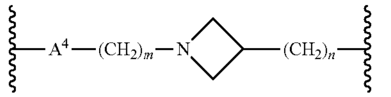

and

L2-38

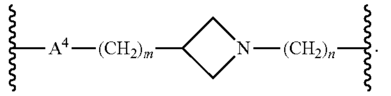

In another embodiment, $A^1$ is any one or more of A-17 to A-91. In another embodiment, m is 1, 2, or 3. In another embodiment, n is 0, 1, 2, 3, or 4. In another embodiment, n is 0, 1, or 2. In another embodiment, $L^2$ is $L^2$-34. In another embodiment, $L^2$ is $L^2$-35. In another embodiment, $L^2$ is $L^2$-36. In another embodiment, $L^2$ is $L^2$-37. In another embodiment, $L^2$ is $L^2$-38. In another embodiment, $A^4$ is 5-membered heteroarylenyl. In another embodiment, $A^4$ is 6-membered heteroarylenyl.

In another embodiment, Compounds of the Disclosure are compounds represented by any one of Formula I-A or VII-XI, and the pharmaceutically acceptable salts or solvates thereof, wherein $L^2$ is selected from the group consisting of:

$L^2$-39

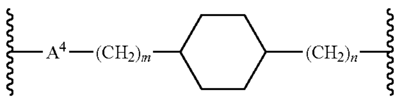

and $L^2$-40

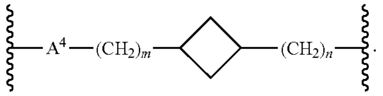

In another embodiment, $A^1$ is any one or more of A-17 to A-91. In another embodiment, m is 1, 2, or 3. In another embodiment, n is 0, 1, 2, 3, or 4. In another embodiment, n is 1 or 2. In another embodiment, $L^2$ is $L^2$-39. In another embodiment, $L^2$ is $L^2$-40. In another embodiment, $A^4$ is 5-membered heteroarylenyl. In another embodiment, $A^4$ is 6-membered heteroarylenyl.

In another embodiment, Compounds of the Disclosure are compounds represented by any one of Formula I-A or VII-XI, and the pharmaceutically acceptable salts or solvates thereof, wherein $L^1$ is —$X^1$-$L^2$-$Y^1$—; $X^1$ is X; $L^2$ is L; and $Y^1$ is Y, and X, L, and Y are as defined in connection with Formula I, below. In another embodiment, $A^1$ is any one or more of A-17 to A-91.

In another embodiment, Compounds of the Disclosure are compounds represented by Formula I-A, and the pharmaceutically acceptable salts or solvates thereof, wherein $A^1$ is A, and A is as defined in connection with Formula I, below.

In another embodiment, Compounds of the Disclosure are compounds represented by any one of Formula I-A or VII-XI, and the pharmaceutically acceptable salts or solvates thereof, wherein $B^1$ is B-1a. In another embodiment, $B^1$ is B-2. In another embodiment, $B^1$ is B-3. In another embodiment, $B^1$ is:

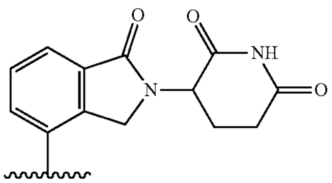

or

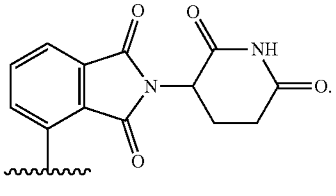

In another embodiment, Compounds of the Disclosure are compounds represented by Formula I-A, and the pharmaceutically acceptable salts or solvates thereof, wherein $A^1$ is any one or more of A-17 to A-91, and $B^1$ is B-1a. In another embodiment, $B^1$ is B-2. In another embodiment, $B^1$ is B-3. In another embodiment, $B^1$ is:

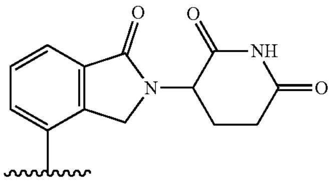

or

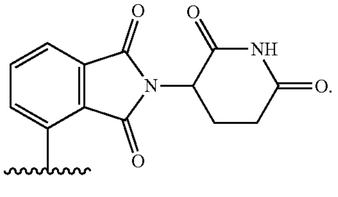

In another embodiment, Compounds of the Disclosure are compounds represented by Formula I-A, and the pharmaceutically acceptable salts or solvates thereof, wherein $A^1$ is a monovalent radical of a spiro-oxindole MDM2 inhibitor. In some embodiments, the spiro-oxindole MDM2 inhibitor is claimed and/or disclosed in U.S. Pat. Nos. 7,759,383; 7,737,174; 8,518,984; 8,680,132; or 8,629,141. In some embodiments, the spiro-oxindole MDM2 inhibitor is claimed and/or disclosed in US 2015/0291611, US 2016/0000764, or US 2016/0052938.

In another embodiment, Compounds of the Disclosure are compounds represented by Formula I-A, and the pharmaceutically acceptable salts or solvates thereof, wherein $A^1$ is a monovalent radical of a cis-imidazoline MDM2 inhibitor.

In another embodiment, Compounds of the Disclosure are compounds represented by Formula I-A, and the pharmaceutically acceptable salts or solvates thereof, wherein $A^1$ is a monovalent radical of a substituted piperidine MDM2 inhibitor.

In another embodiment, Compounds of the Disclosure are compounds represented by Formula I-A, and the pharmaceutically acceptable salts or solvates thereof, wherein $A^1$ is a monovalent radical of a spiroindolinone MDM2 inhibitor.

In another embodiment, Compounds of the Disclosure are compounds represented by Formula I-A, and the pharmaceutically acceptable salts or solvates thereof, wherein $A^1$ is a monovalent radical of an oxindole MDM2 inhibitor.

In another embodiment, Compounds of the Disclosure are compounds represented by Formula I-A, and the pharmaceutically acceptable salts or solvates thereof, wherein $A^1$ is a monovalent radical of a diphenyl-dihydro-imidazopyridinone MDM2 inhibitor.

In another embodiment, Compounds of the Disclosure are compounds represented by Formula I-A, and the pharmaceutically acceptable salts or solvates thereof, wherein $A^1$ is a monovalent radical of an imidazothiazole MDM2 inhibitor In another embodiment, Compounds of the Disclosure are compounds represented by Formula I-A, and the pharmaceutically acceptable salts or solvates thereof, wherein $A^1$ is a monovalent radical of a deazaflavin MDM2 inhibitor In another embodiment, Compounds of the Disclosure are compounds represented by Formula I-A, and the pharmaceutically acceptable salts or solvates thereof, wherein $A^1$ is a monovalent radical of a benzodiazapine MDM2 inhibitor.

In another embodiment, Compounds of the Disclosure are compounds represented by Formula I-A, and the pharmaceutically acceptable salts or solvates thereof, wherein $A^1$ is a monovalent radical of a isoindolin-1-one MDM2 inhibitor.

In another embodiment, Compounds of the Disclosure are compounds represented by Formula I-A, and the pharmaceutically acceptable salts or solvates thereof, $A^1$ is a monovalent radical of a boronic acid MDM2 inhibitor.

In another embodiment, Compounds of the Disclosure are compounds represented by Formula I-A, and the pharmaceutically acceptable salts or solvates thereof, wherein $A^1$ is a monovalent radical of a peptidic MDM2 inhibitor.

In another embodiment, Compounds of the Disclosure are compounds represented by Formula I:

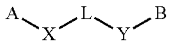

I and the pharmaceutically acceptable salts or solvates thereof, wherein:

A is selected from the group consisting of:

A-1

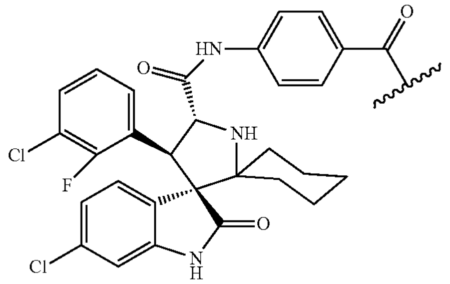

,

A-2

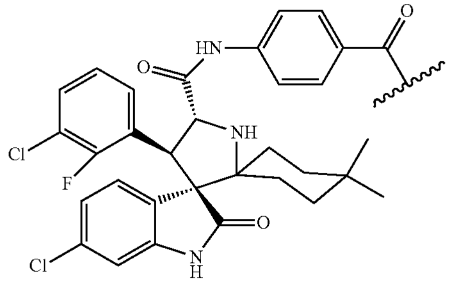

,

A-3

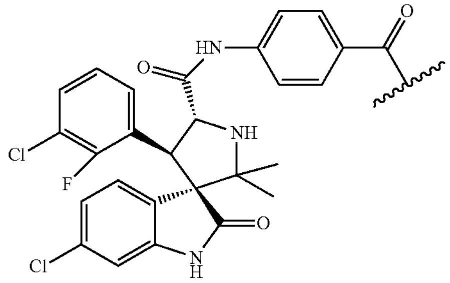

,

-continued

A-4

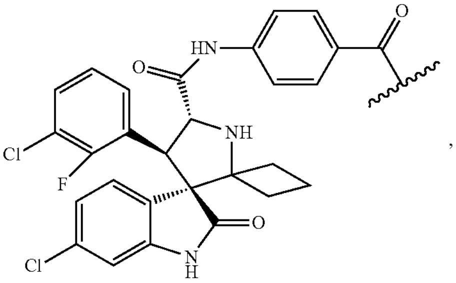

,

A-5

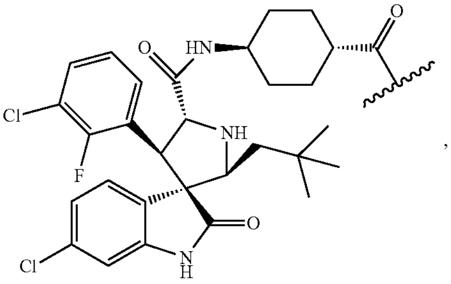

,

A-6

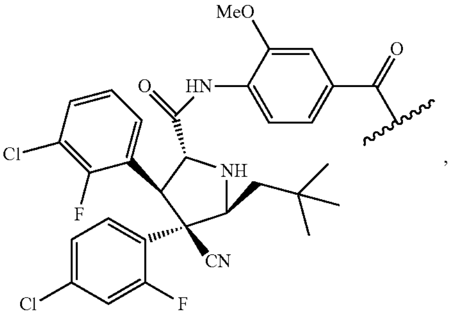

,

A-7

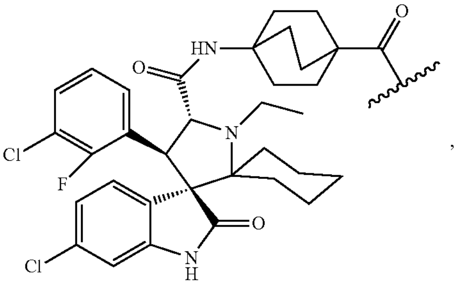

,

A-8

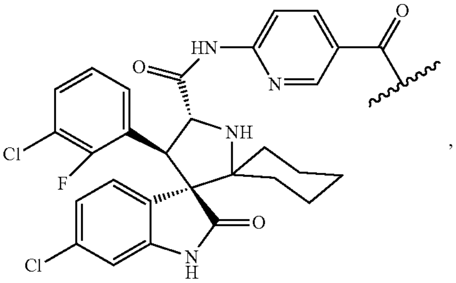

,

-continued
A-9
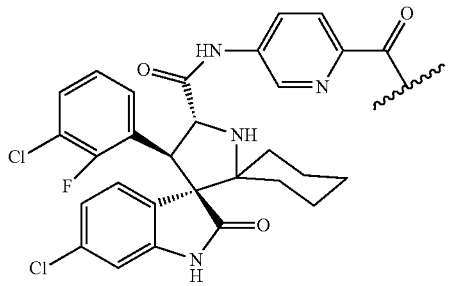
,
A10
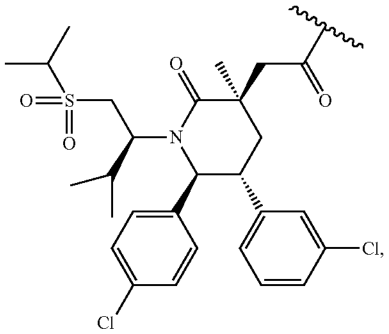
A-11
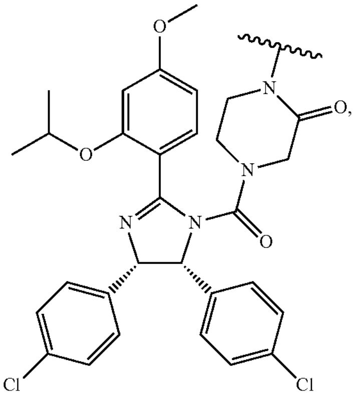
A-12
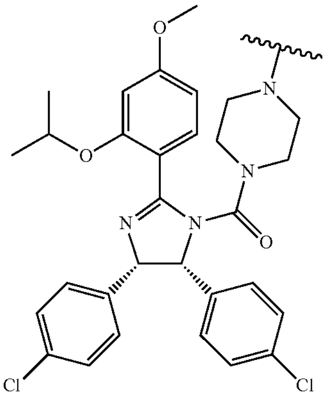
,
-continued
A-13
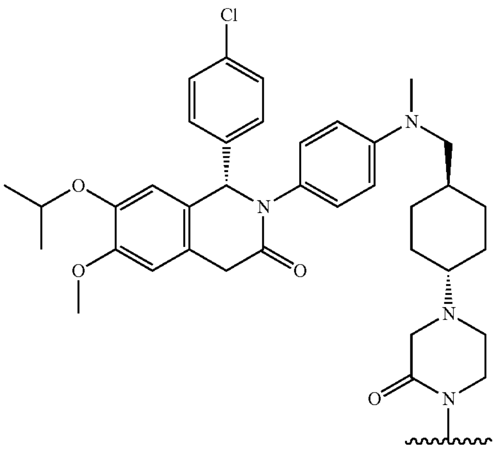
,
A-14
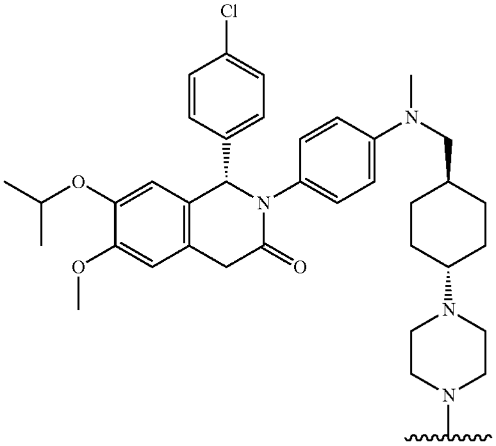
and
A-15
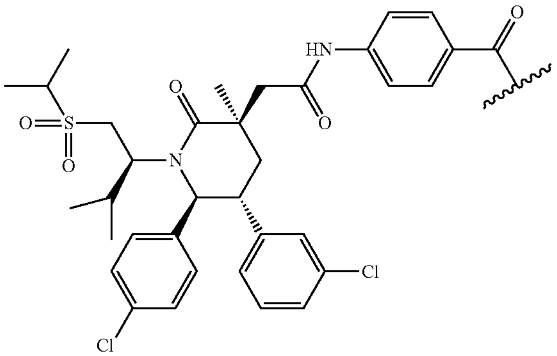
;
B is selected from the group consisting of:
B-1
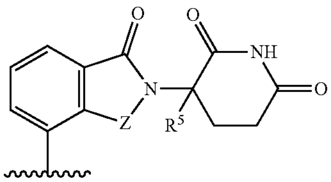
and -continued

B-2

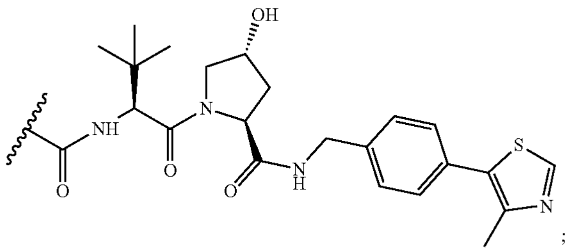

;

X is selected from the group consisting of —N($R^{2a}$)—,

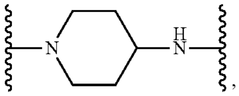

, and

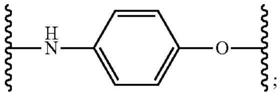

;

or

X is absent;

wherein the —N(H)— of

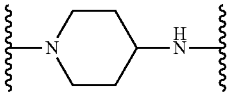

is attached to L and the —O— of

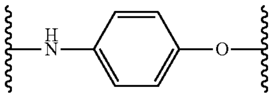

is attached to L;

L is selected from the group consisting of alkylenyl, heteroalkylenyl, and —$(CH_2)_m$—W—$(CH_2)_n$—;

W is selected from the group consisting of optionally substituted phenylenyl, optionally substituted 5-membered heteroarylenyl, and optionally substituted 6-membered heteroarylenyl;

m is 0, 1, 2, 3, 4, 5, 6, or 7;

n is 0, 1, 2, 3, 4, 5, 6, 7, or 8;

Y is selected from the group consisting of —C≡C—, —O—, —N($R^{2b}$)—, —C(═O)N($R^{2c}$)—, —N($R^{2d}$)C(═O)$CH_2$O—, and —N($R^{2e}$)C(═O)$CH_2$N($R^{2f}$)—; or Y is absent;

wherein the carboxamide nitrogen atom of —N($R^{2d}$)C(═O)$CH_2$O— and —N($R^{2e}$)C(═O)$CH_2$N($R^{2f}$)—, and the carbon atom of —C(═O)N($R^{2c}$)— is attached to L;

$R^{2a}$, $R^{2b}$, $R^{2c}$, $R^{2d}$, $R^{2e}$, and $R^{2f}$ are each independently selected from the group consisting of hydrogen and $C_{1-4}$ alkyl;

Z is selected from the group consisting of —$CH_2$ and —C(═O)—; and $R^5$ is selected from the group consisting of hydrogen, methyl, and fluoro, with the proviso that Y is absent when B is B-2.

In another embodiment, Compounds of the Disclosure are compounds represented by Formula II:

II

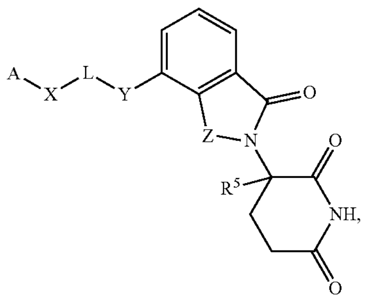

and the pharmaceutically acceptable salts or solvates thereof, wherein A, X, L, Y, Z and $R^5$ are as defined in connection with Formula I. In another embodiment, $R^5$ is hydrogen. In another embodiment, Z is —$CH_2$—. In another embodiment, Z is —C(═O)—.

In another embodiment, Compounds of the Disclosure are compounds represented by Formula II, and the pharmaceutically acceptable salts or solvates thereof, wherein Y is selected from the group consisting of —C≡C—, —O—, —N(H)—, —C(═O)N(H)—, —N(H)C(═O)$CH_2$O—, and —N(H)C(═O)$CH_2$N(H)—. In another embodiment, Y is selected from the group consisting of —C≡C—, —O—, and —N(H)—. In another embodiment, Y is selected from the group consisting of —C≡C— and —N(H)—.

In another embodiment, Compounds of the Disclosure are compounds represented by Formula II, and the pharmaceutically acceptable salts or solvates thereof, wherein Y is absent.

In another embodiment, Compounds of the Disclosure are compounds represented by Formula III:

III

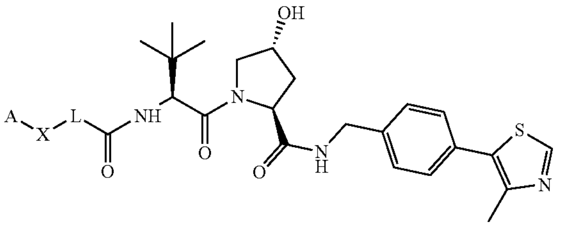

, and the pharmaceutically acceptable salts or solvates thereof, wherein A, X, and L are as defined in connection with Formula I.

In another embodiment, Compounds of the Disclosure are compounds represented by any one of Formulae I-A or I-III, and the pharmaceutically acceptable salts or solvates thereof, wherein X is selected from the group consisting of —N(H)—,

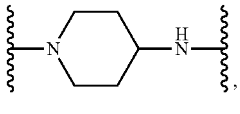

, and

-continued

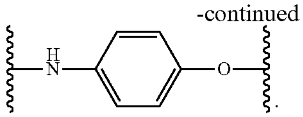

In another embodiment, Compounds of the Disclosure are compounds represented by any one of Formulae I-A or I-III, and the pharmaceutically acceptable salts or solvates thereof, wherein L is $C_{1-12}$ alkylenyl. In another embodiment, L is selected from the group consisting of $—CH_2—$, $—CH_2CH_2—$, $—CH_2CH_2CH_2—$, $—CH_2(CH_2)_2CH_2—$, $—CH_2(CH_2)_3CH_2—$, $—CH_2(CH_2)_4CH_2—$, $—CH_2(CH_2)_5CH_2—$, and $—CH_2(CH_2)_6CH_2—$.

In another embodiment, Compounds of the Disclosure are compounds represented by any one of Formulae I-A or I-III, and the pharmaceutically acceptable salts or solvates thereof, wherein L is 3- to 20-membered heteroalkylenyl. In another embodiment, L is selected from the group consisting of $—(CH_2)_oO—(CH_2CH_2O)_p—(CH_2)_q—$ and $—(CH_2)_rO—(CH_2)_s—O(CH_2)_t—$; wherein: o is 2 or 3; p is 0, 1, 2, 3, 4, 5, 6, or 7; q is 2 or 3; r is 2, 3, or 4; s is 3, 4, or 5; and t is 2 or 3. In another embodiment, L is selected from the group consisting of $—CH_2CH_2OCH_2CH_2—$, $—CH_2CH_2O(CH_2CH_2O)_2CH_2CH_2—$, $—CH_2CH_2O(CH_2CH_2O)_3CH_2CH_2—$, $—CH_2CH_2O(CH_2CH_2O)_4CH_2CH_2—$, $—CH_2CH_2O(CH_2CH_2O)_6CH_2CH_2—$, $—CH_2CH_2O(CH_2CH_2O)_6CH_2CH_2—$, $—CH_2CH_2CH_2OCH_2CH_2OCH_2CH_2CH_2—$, $—CH_2CH_2CH_2O(CH_2CH_2O)_2CH_2CH_2CH_2—$, and $—CH_2CH_2CH_2O(CH_2)_4OCH_2CH_2CH_2—$.

In another embodiment, Compounds of the Disclosure are compounds represented by any one of Formulae I-A or I-III, and the pharmaceutically acceptable salts or solvates thereof, wherein L is $—(CH_2)_m—W—(CH_2)_n—$. In another embodiment, W is phenylenyl. In another embodiment, W is 5-membered heteroarylenyl. In another embodiment, W is 6-membered heteroarylenyl.

In another embodiment, Compounds of the Disclosure are compounds represented by any one of Formulae I-A or I-III, and the pharmaceutically acceptable salts or solvates thereof, wherein L is selected from the group consisting of:

L-1

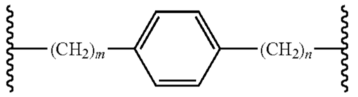

and

L-2

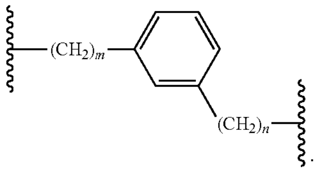

In another embodiment, Compounds of the Disclosure are compounds represented by any one of Formulae I-A or I-III, and the pharmaceutically acceptable salts or solvates thereof, wherein L is selected from the group consisting of:

L-3

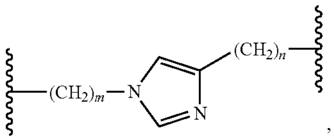

,

L-4

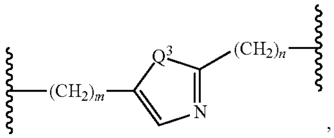

,

L-5

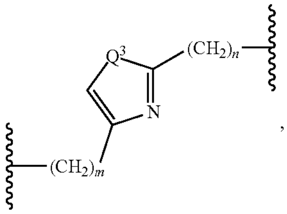

,

L-6

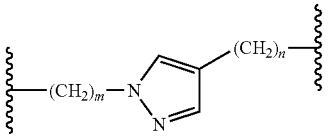

and

L-7

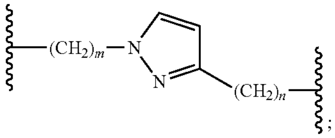

; and $Q^3$ is selected from the group consisting of —O—, —S—, and $—N(R^6)—$; and $R^6$ is selected from the group consisting of hydrogen and $C_{1-4}$ alkyl.

In another embodiment, Compounds of the Disclosure are compounds represented by any one of Formulae I-A or I-III, and the pharmaceutically acceptable salts or solvates thereof, wherein L is selected from the group consisting of:

L-8

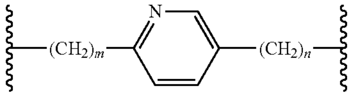

and

L-9

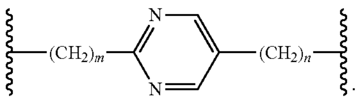

In another embodiment, Compounds of the Disclosure are compounds represented by any one of Formulae I-A or I-III, and the pharmaceutically acceptable salts or solvates thereof, wherein A is selected from the group consisting of A-1, A-2, A-3, A-4, A-5, A-6, A-7, A-8, and A-9. In another embodiment, A is A-1. In another embodiment, A is A-2. In another embodiment, A is A-3. In another embodiment, A is A-4. In another embodiment, A is A-5. In another embodiment, A is A-6. In another embodiment, A is A-7. In another embodiment, A is A-8. In another embodiment, A is A-9.

In another embodiment, Compounds of the Disclosure are compounds represented by any one of Formulae I-A or I-III, and the pharmaceutically acceptable salts or solvates thereof, wherein A is selected from the group consisting of A-10 and A-15.

In another embodiment, Compounds of the Disclosure are compounds represented by any one of Formulae I-A or I-III, and the pharmaceutically acceptable salts or solvates thereof, wherein A-11 and A-12.

In another embodiment, Compounds of the Disclosure are compounds represented by any one of Formulae I-A or I-III, and the pharmaceutically acceptable salts or solvates thereof, wherein A-13 and A-14.

In another embodiment, Compounds of the Disclosure are compounds represented by any one of Formulae I-A or I-III, and the pharmaceutically acceptable salts or solvates thereof, wherein A is:

A-16

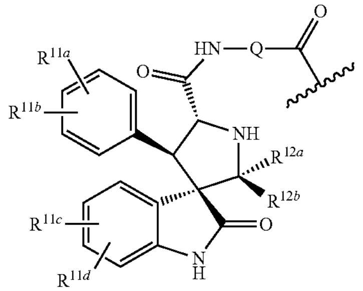

$R^{11a}$, $R^{11b}$, $R^{11c}$, and $R^{11d}$ are independently selected from the group consisting of hydrogen, chloro, and fluoro;

$R^{12a}$ and $R^{12b}$ are independently selected from the group consisting of hydrogen and $C_{1-6}$ alkyl; or $R^{12a}$ and $R^{12b}$ taken together with the carbon atom to which they are attached form a 4- to 8-membered optionally substituted cycloalkyl;

Q is selected from the group consisting of substituted phenylenyl, optionally substituted heteroarylenyl, and cycloalkylenyl.

In another embodiment, Compounds of the Disclosure are compounds represented by any one of Formulae I-A or I-III, and the pharmaceutically acceptable salts or solvates thereof, wherein A is A-16, $R^{12b}$ is $C_{1-6}$ alkyl, and $R^{12a}$ is hydrogen.

In another embodiment, Compounds of the Disclosure are compounds represented by any one of Formulae I-A or I-III, and the pharmaceutically acceptable salts or solvates thereof, wherein A is A-16 and $R^{12a}$ and $R^{12b}$ taken together with the carbon atom to which they are attached form a 4- to 6-membered optionally substituted cycloalkyl.

In another embodiment, Compounds of the Disclosure are compounds represented by any one of Formulae I-A or I-III, and the pharmaceutically acceptable salts or solvates thereof, wherein A is A-16 and Q is selected from the group consisting of:

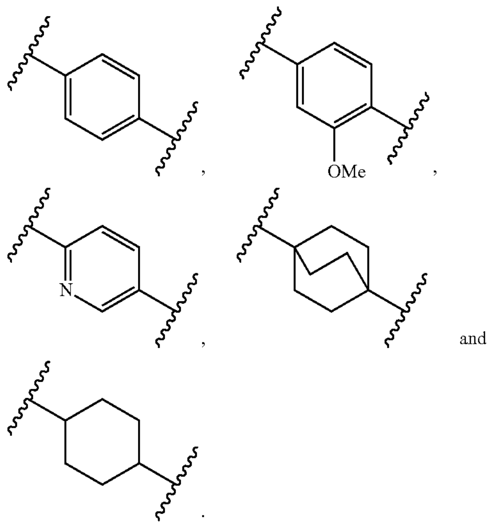

In another embodiment, Compounds of the Disclosure are any one or more of the compounds of Table 1, and the pharmaceutically acceptable salts and solvates thereof.

TABLE 1

| Cpd. No. | Structure |
|---|---|
| 1 | 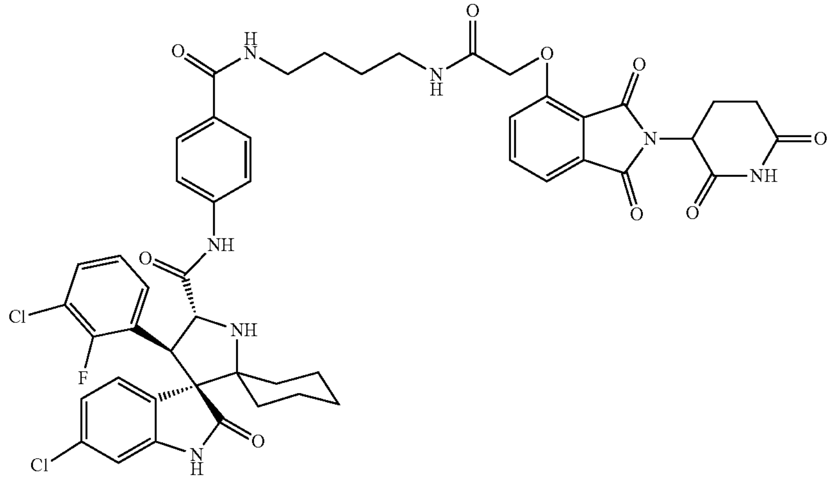 [SMILES: O=C(COc1cccc2c1C(=O)N(C1CCC(=O)NC1=O)C2=O)NCCCCNC(=O)c1ccc(NC(=O)[C@@H]2NC3(CCCCC3)[C@@]3(C(=O)Nc4cc(Cl)ccc43)[C@H]2c2cccc(Cl)c2F)cc1] |

TABLE 1-continued
| Cpd. No. | Structure |
|---|---|
| 2 | 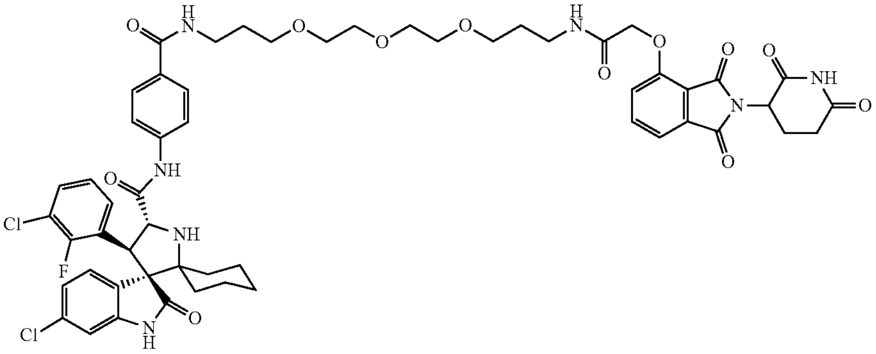 [SMILES: O=C(COc1cccc2c1C(=O)N(C1CCC(=O)NC1=O)C2=O)NCCCOCCOCCOCCCNC(=O)c1ccc(NC(=O)[C@@H]2NC3(CCCCC3)[C@@]3(C(=O)Nc4cc(Cl)ccc43)[C@H]2c2cccc(Cl)c2F)cc1] |
| 3 | 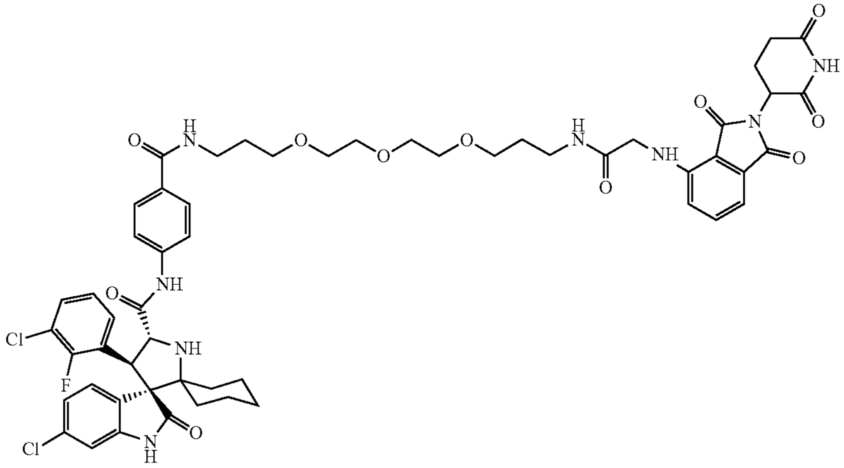 [SMILES: O=C(CNc1cccc2c1C(=O)N(C1CCC(=O)NC1=O)C2=O)NCCCOCCOCCOCCCNC(=O)c1ccc(NC(=O)[C@@H]2NC3(CCCCC3)[C@@]3(C(=O)Nc4cc(Cl)ccc43)[C@H]2c2cccc(Cl)c2F)cc1] |
| 4 | 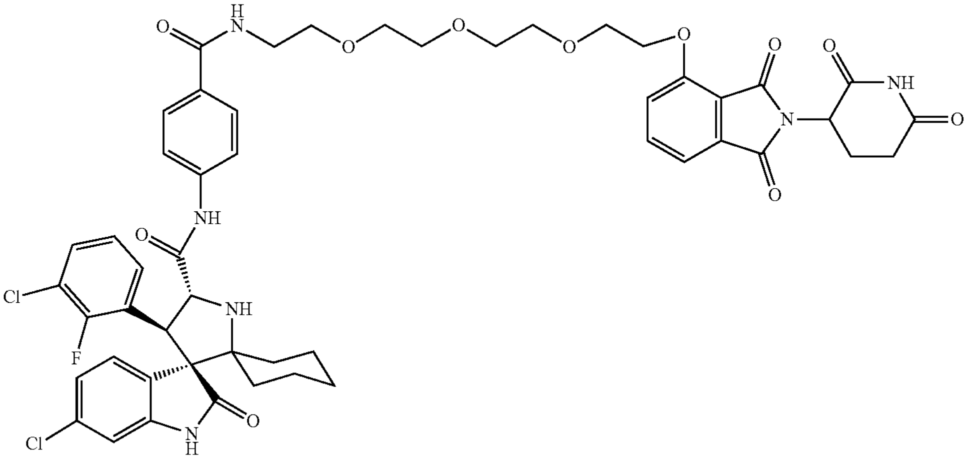 [SMILES: O=C1CCC(N2C(=O)c3cccc(OCCOCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |

TABLE 1-continued
| Cpd. No. | Structure |
|---|---|
| 5 | 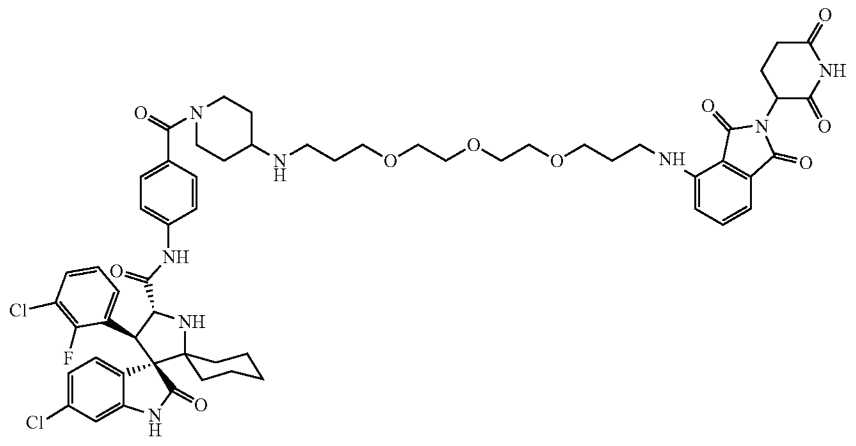 [SMILES: O=C1CCC(N2C(=O)c3cccc(NCCCOCCOCCOCCCNC4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)c3C2=O)C(=O)N1] |
| 6 | 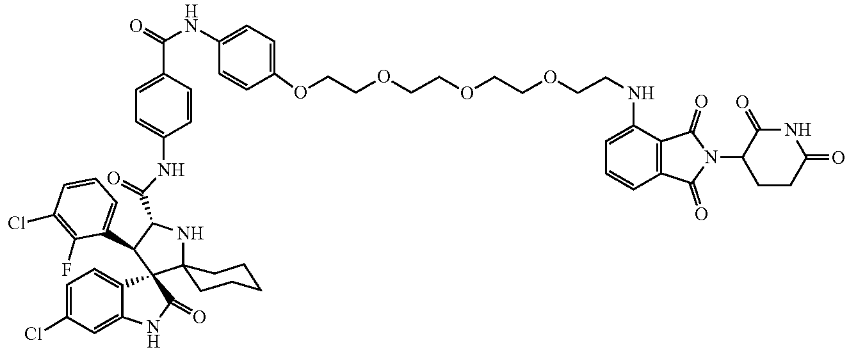 [SMILES: O=C1CCC(N2C(=O)c3cccc(NCCOCCOCCOCCOc4ccc(NC(=O)c5ccc(NC(=O)[C@@H]6NC7(CCCCC7)[C@@]7(C(=O)Nc8cc(Cl)ccc87)[C@H]6c6cccc(Cl)c6F)cc5)cc4)c3C2=O)C(=O)N1] |
| 7 | 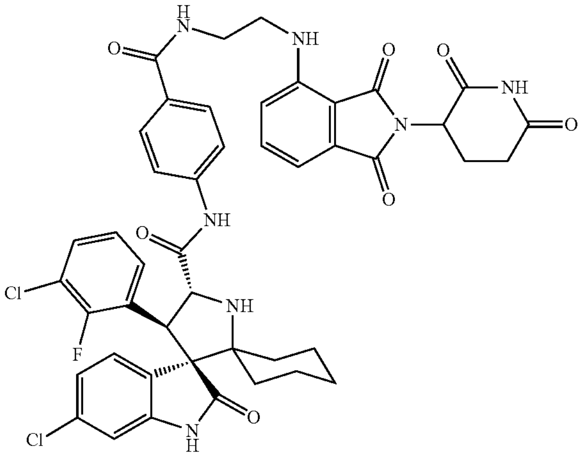 [SMILES: O=C1CCC(N2C(=O)c3cccc(NCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |

TABLE 1-continued
| Cpd. No. | Structure |
|---|---|
| 8 | 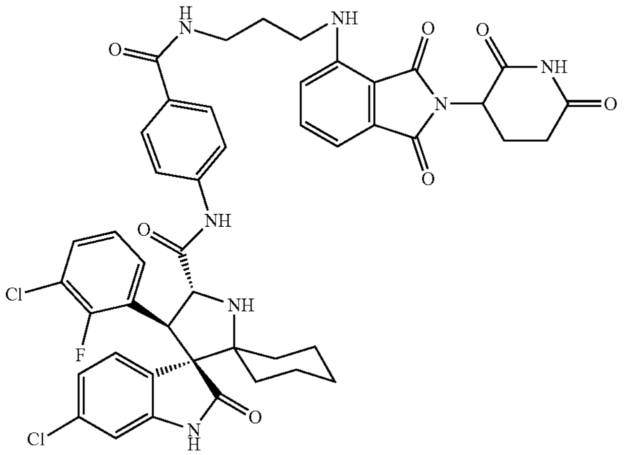 [SMILES: O=C1CCC(N2C(=O)c3cccc(NCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 9 | 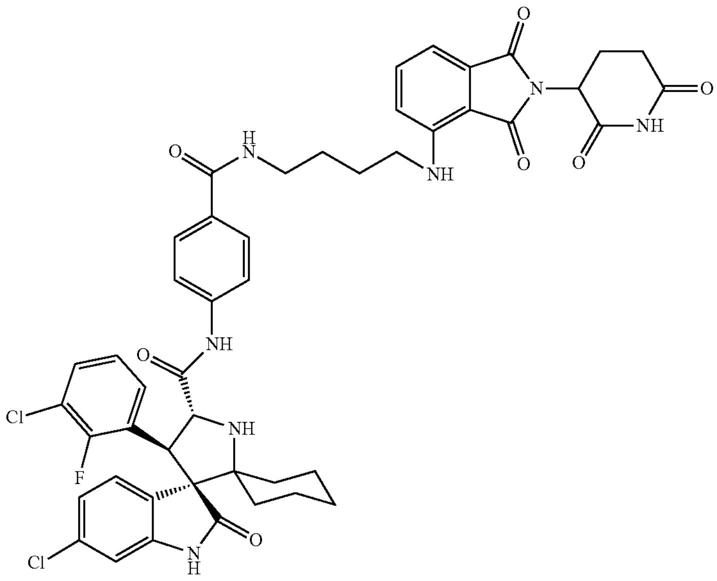 [SMILES: O=C1CCC(N2C(=O)c3cccc(NCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 10 | 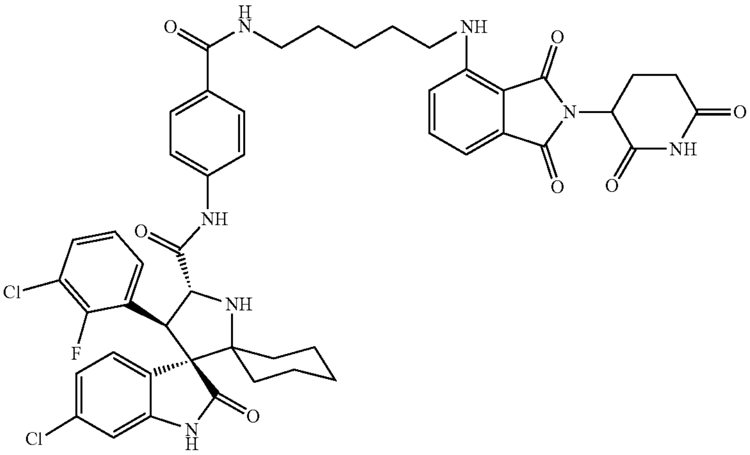 [SMILES: O=C1CCC(N2C(=O)c3cccc(NCCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |

TABLE 1-continued
| Cpd. No. | Structure |
|---|---|
| 11 | 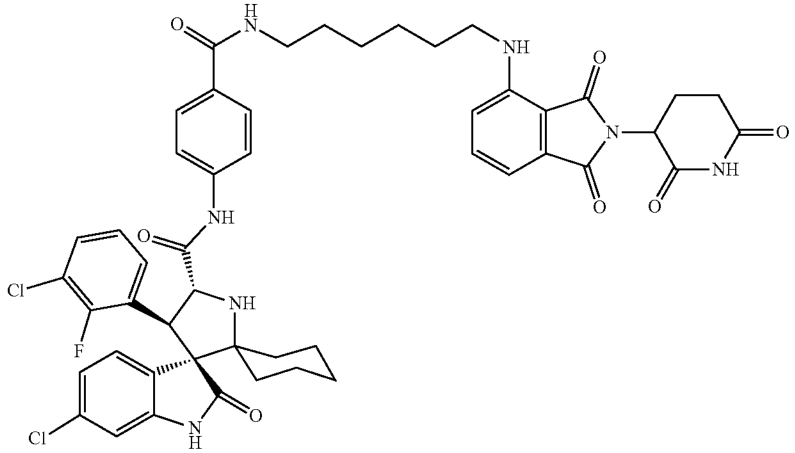 [SMILES: O=C1CCC(N2C(=O)c3cccc(NCCCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 12 | 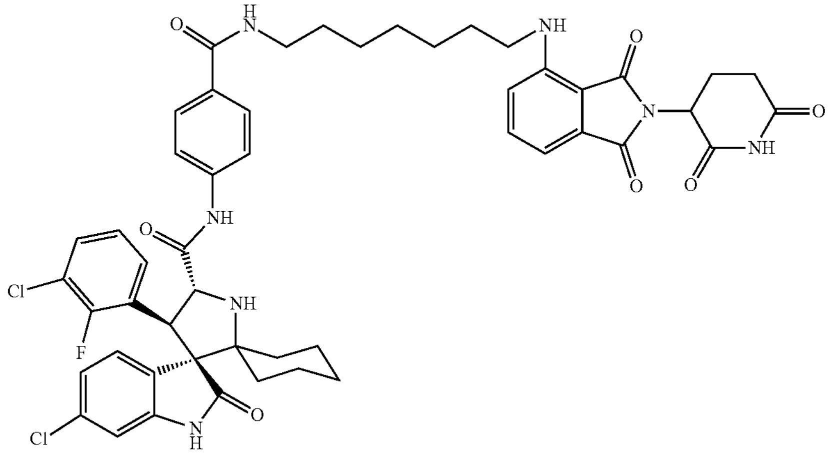 [SMILES: O=C1CCC(N2C(=O)c3cccc(NCCCCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 13 | 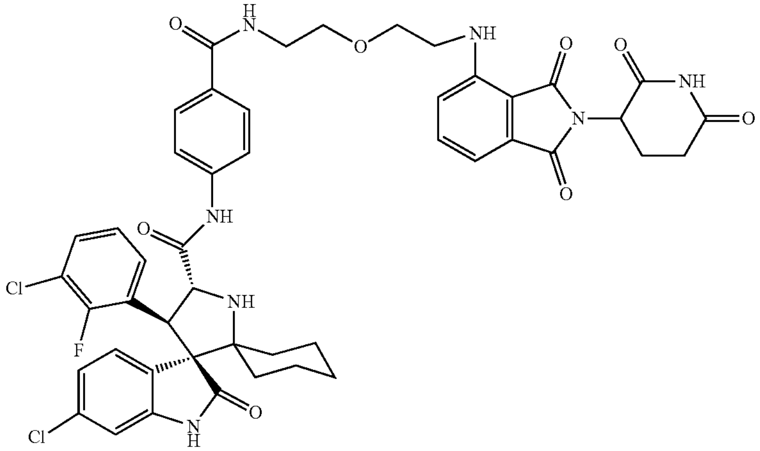 [SMILES: O=C1CCC(N2C(=O)c3cccc(NCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |

TABLE 1-continued
| Cpd. No. | Structure |
|---|---|
| 14 | 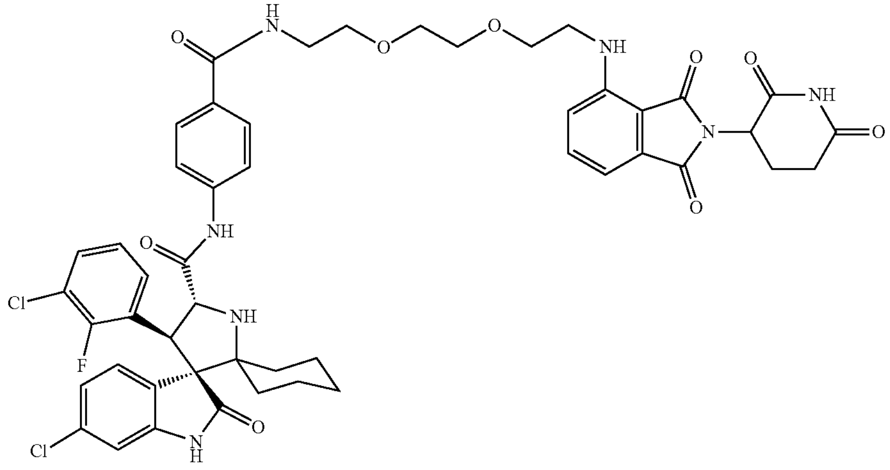 [SMILES: O=C1CCC(N2C(=O)c3cccc(NCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 15 | 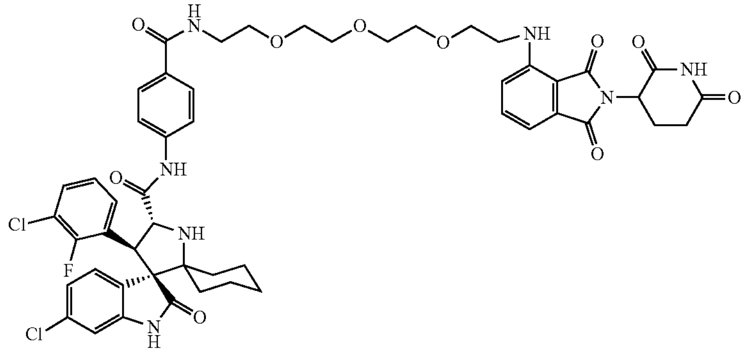 [SMILES: O=C1CCC(N2C(=O)c3cccc(NCCOCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 16 | 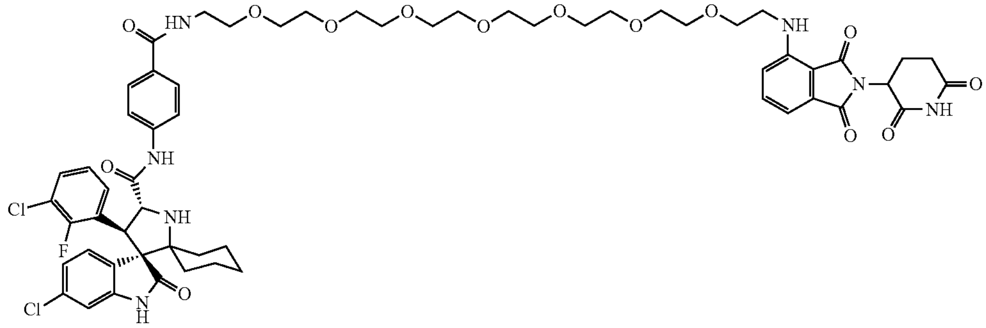 [SMILES: O=C1CCC(N2C(=O)c3cccc(NCCOCCOCCOCCOCCOCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 17 | 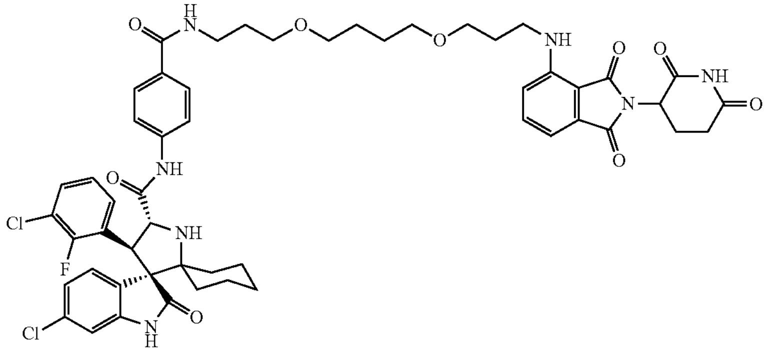 [SMILES: O=C1CCC(N2C(=O)c3cccc(NCCCOCCCCOCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |

TABLE 1-continued
| Cpd. No. | Structure |
|---|---|
| 18 | 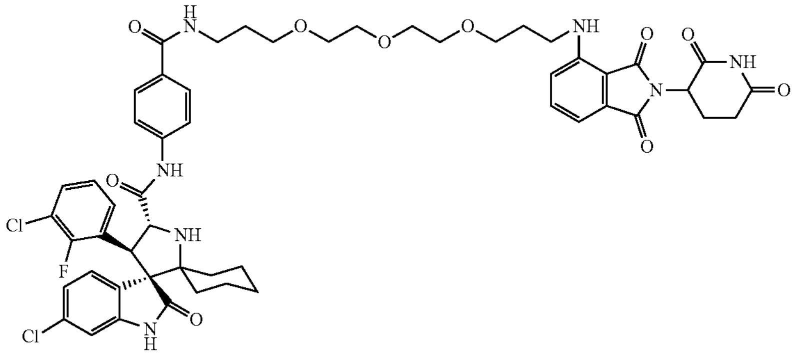 [SMILES: O=C1CCC(N2C(=O)c3cccc(NCCCOCCOCCOCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 19 | 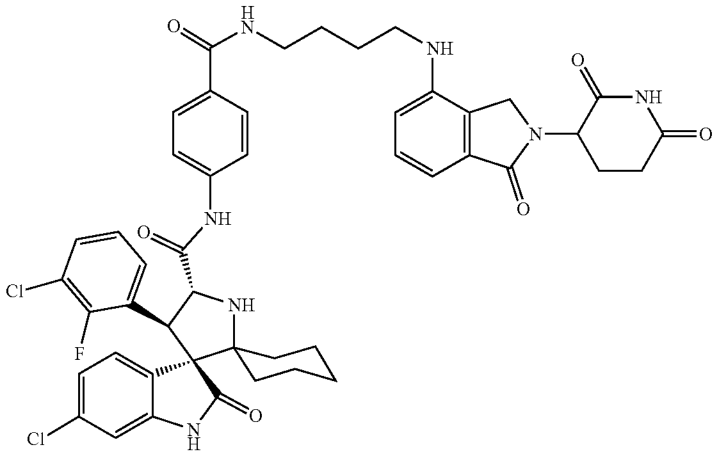 [SMILES: O=C1CCC(N2Cc3c(NCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 20 | 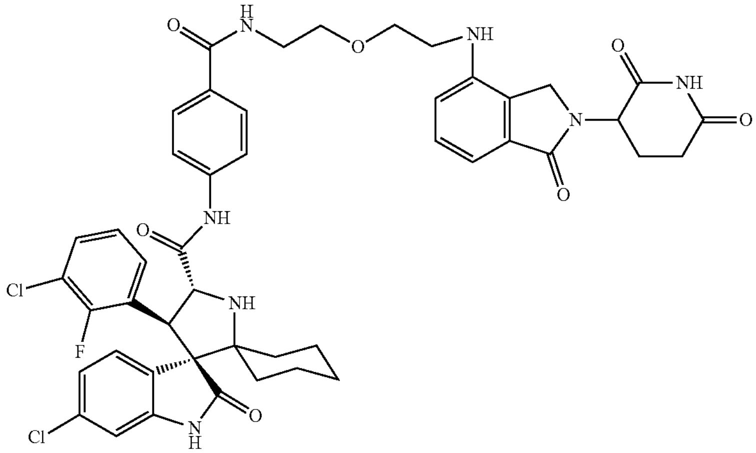 [SMILES: O=C1CCC(N2Cc3c(NCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |

TABLE 1-continued
| Cpd. No. | Structure |
|---|---|
| 21 | 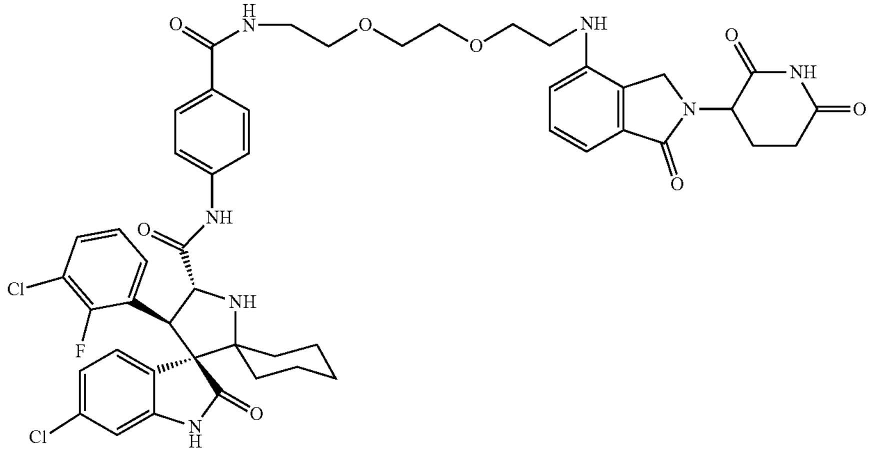 [SMILES: O=C1CCC(N2Cc3c(NCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 22 | 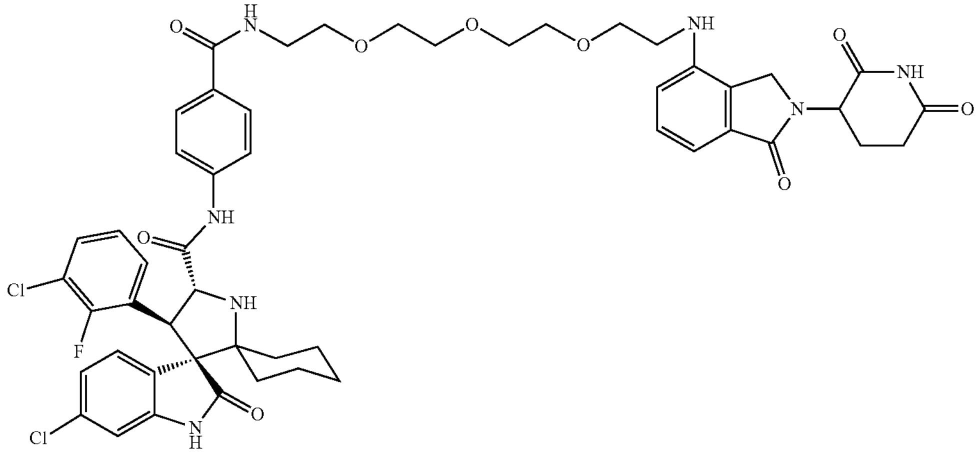 [SMILES: O=C1CCC(N2Cc3c(NCCOCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 23 | 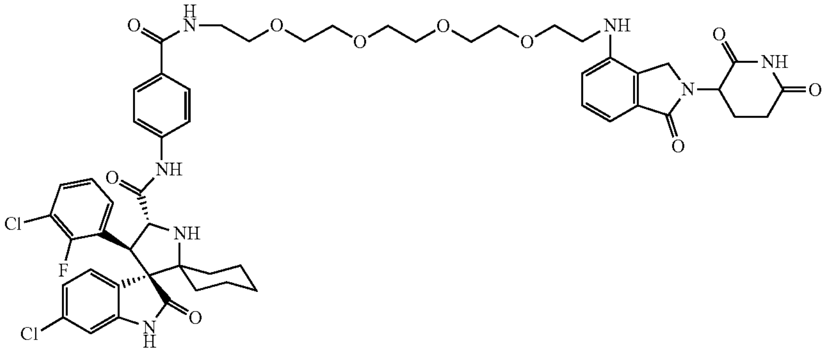 [SMILES: O=C1CCC(N2Cc3c(NCCOCCOCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |

TABLE 1-continued
| Cpd. No. | Structure |
|---|---|
| 24 | 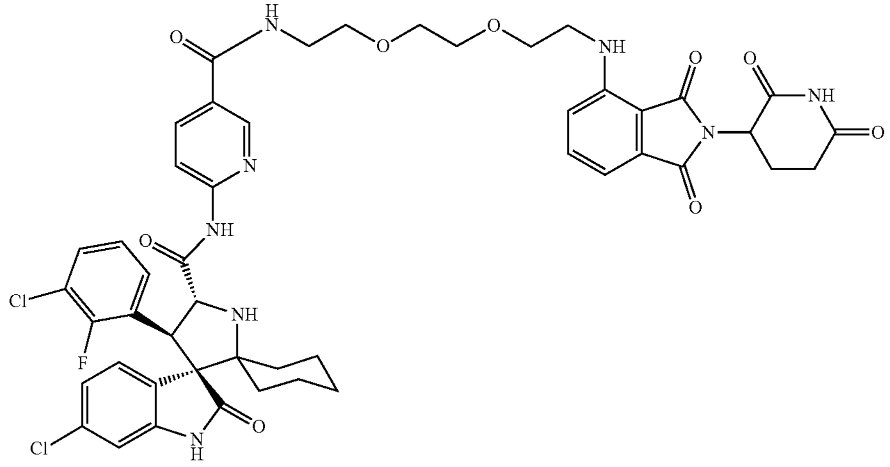 [SMILES: O=C1CCC(N2C(=O)c3cccc(NCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)nc4)c3C2=O)C(=O)N1] |
| 25 | 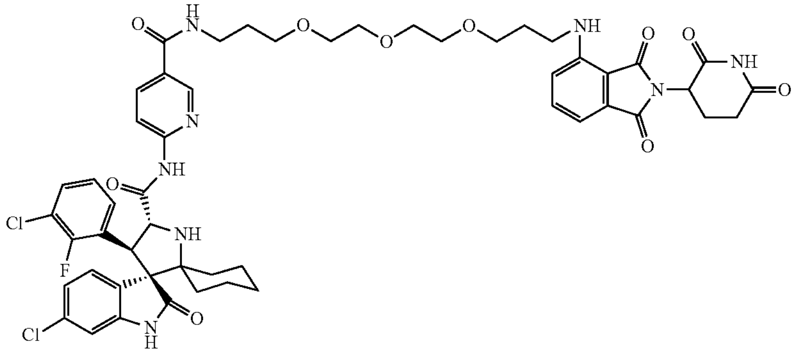 [SMILES: O=C1CCC(N2C(=O)c3cccc(NCCCOCCOCCOCCCNC(=O)c4ccc(NC(=O)[C@@H]5NC6(CCCCC6)[C@@]6(C(=O)Nc7cc(Cl)ccc76)[C@H]5c5cccc(Cl)c5F)nc4)c3C2=O)C(=O)N1] |
| 26 | 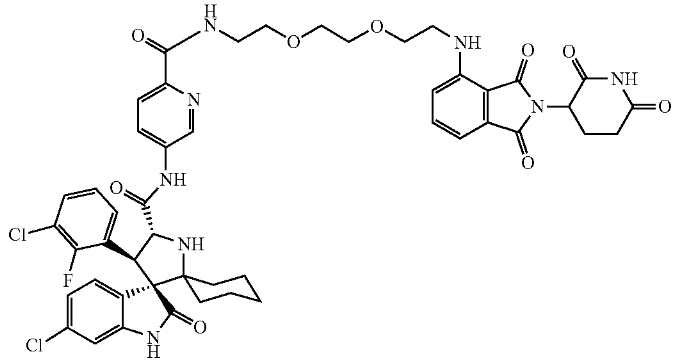 [SMILES: O=C1CCC(N2C(=O)c3cccc(NCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cn4)c3C2=O)C(=O)N1] |
| 27 | 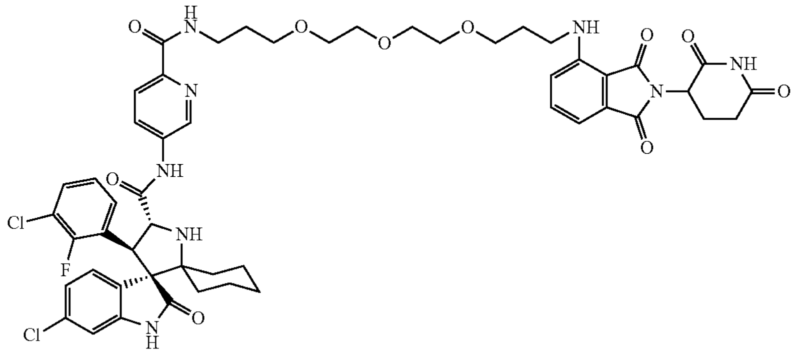 [SMILES: O=C1CCC(N2C(=O)c3cccc(NCCCOCCOCCOCCCNC(=O)c4ccc(NC(=O)[C@@H]5NC6(CCCCC6)[C@@]6(C(=O)Nc7cc(Cl)ccc76)[C@H]5c5cccc(Cl)c5F)cn4)c3C2=O)C(=O)N1] |

TABLE 1-continued
| Cpd. No. | Structure |
|---|---|
| 28 | 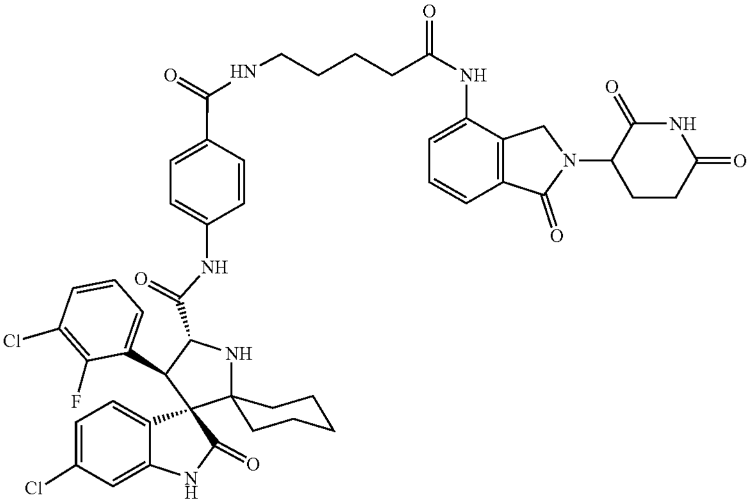 [SMILES: O=C1CCC(N2Cc3c(NC(=O)CCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 29 | 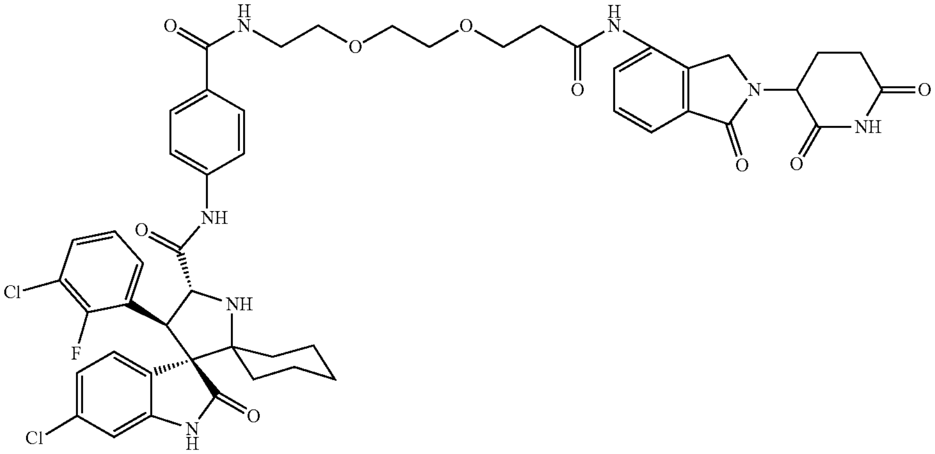 [SMILES: O=C1CCC(N2Cc3c(NC(=O)CCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 30 | 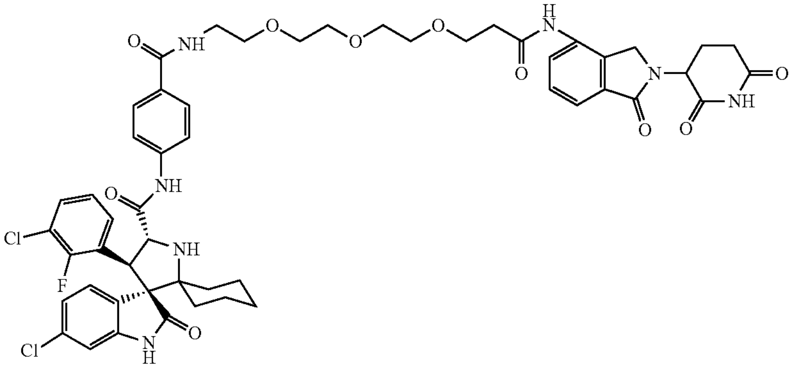 [SMILES: O=C1CCC(N2Cc3c(NC(=O)CCOCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |

TABLE 1-continued
| Cpd. No. | Structure |
| --- | --- |
| 31 | 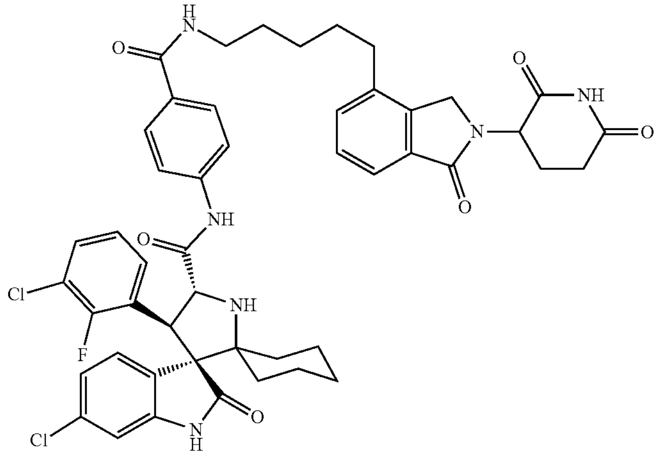 [SMILES: O=C1CCC(N2Cc3c(CCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 32 | 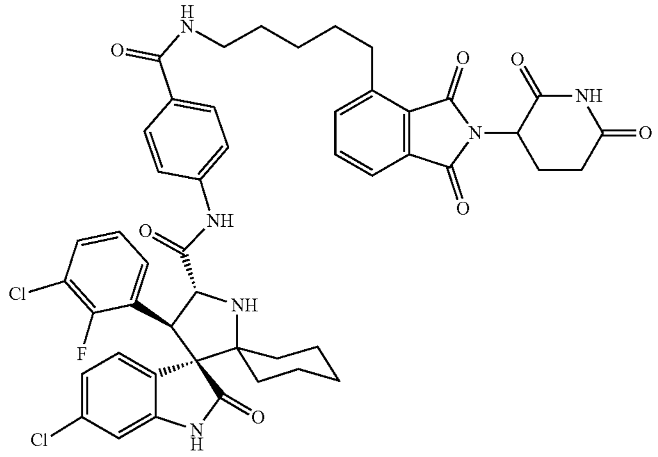 [SMILES: O=C1CCC(N2C(=O)c3cccc(CCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 33 | 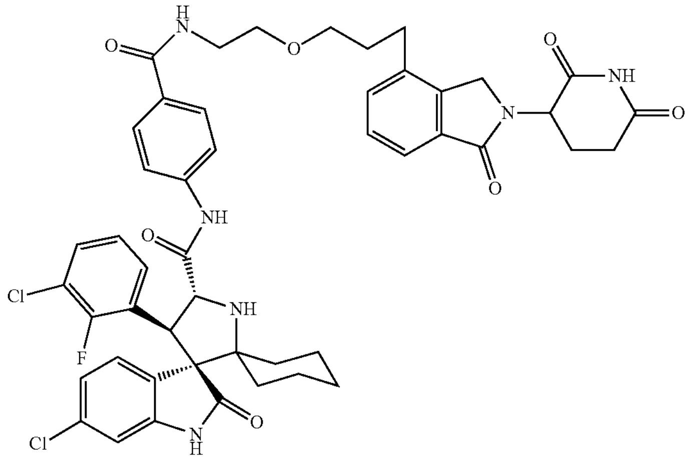 [SMILES: O=C1CCC(N2Cc3c(CCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |

TABLE 1-continued
| Cpd. No. | Structure |
|---|---|
| 34 | 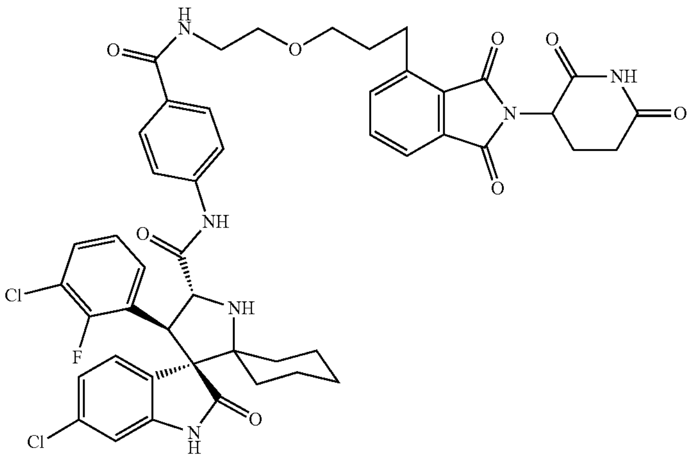 [SMILES: O=C1CCC(N2C(=O)c3cccc(CCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 35 | 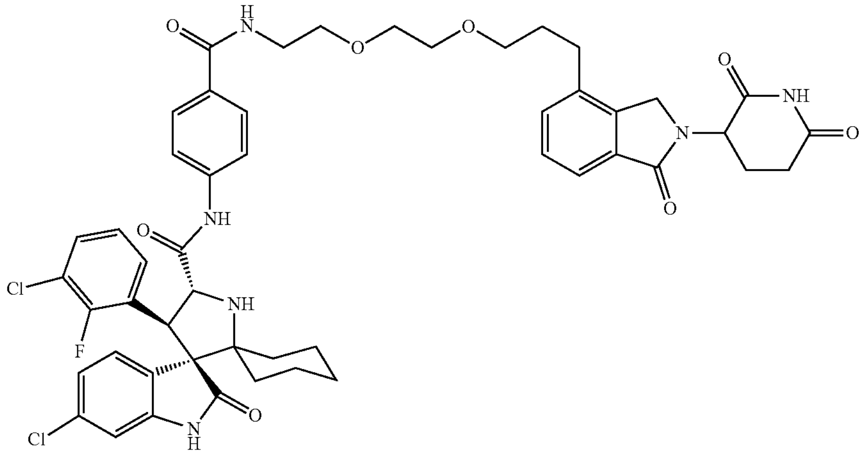 [SMILES: O=C1CCC(N2Cc3c(CCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 36 | 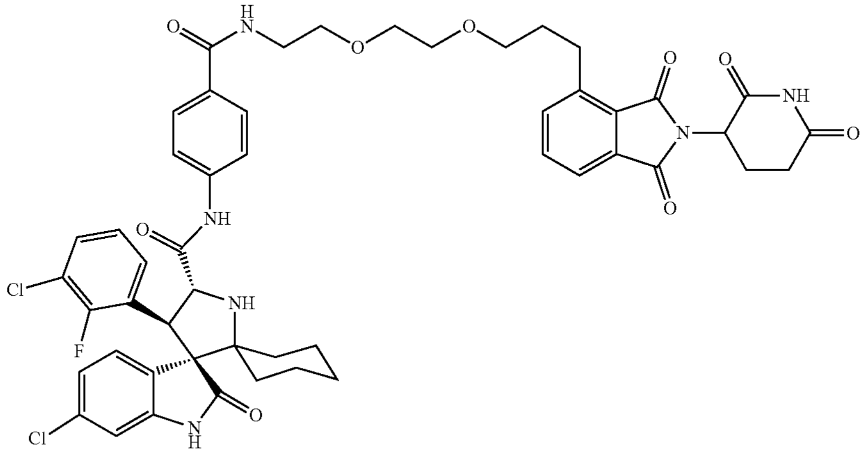 [SMILES: O=C1CCC(N2C(=O)c3cccc(CCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |

TABLE 1-continued
| Cpd. No. | Structure |
|---|---|
| 37 | 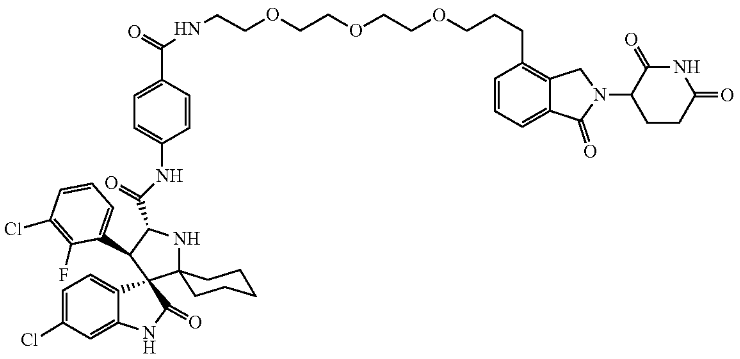 [SMILES: O=C1CCC(N2Cc3c(CCCOCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 38 | 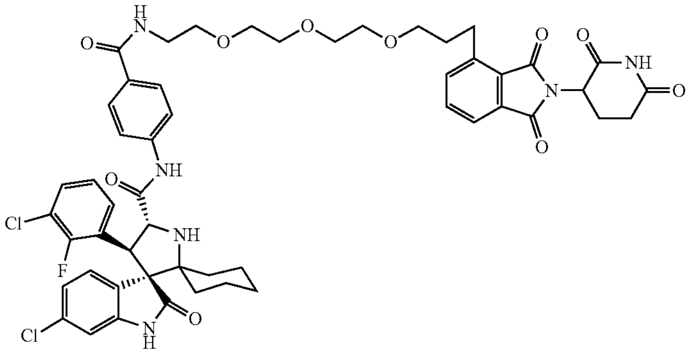 [SMILES: O=C1CCC(N2C(=O)c3cccc(CCCOCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)c3C2=O)C(=O)N1] |
| 39 | 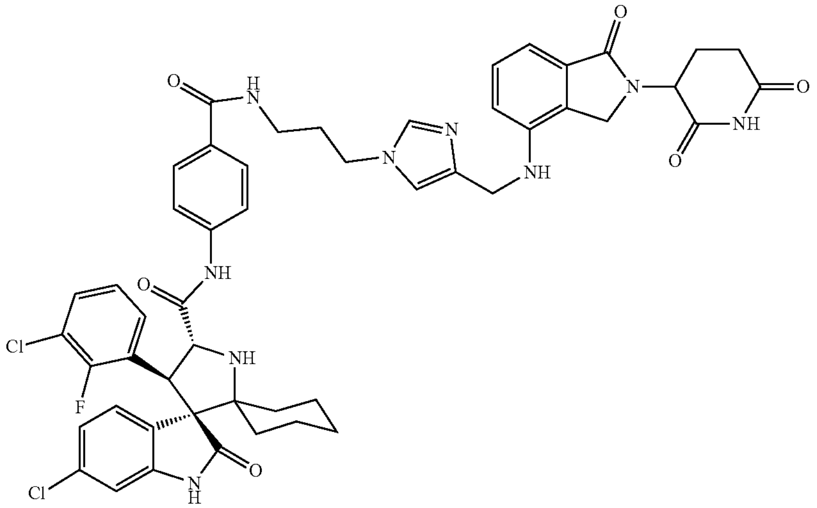 [SMILES: O=C1CCC(N2Cc3c(NCc4cn(CCCNC(=O)c5ccc(NC(=O)[C@@H]6NC7(CCCCC7)[C@@]7(C(=O)Nc8cc(Cl)ccc87)[C@H]6c6cccc(Cl)c6F)cc5)cn4)cccc3C2=O)C(=O)N1] |

TABLE 1-continued
| Cpd. No. | Structure |
|---|---|
| 40 | 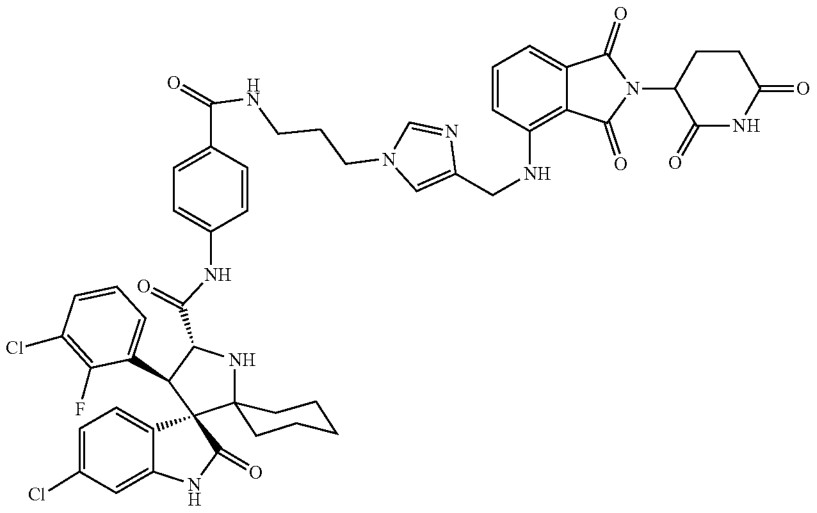 [SMILES: O=C1CCC(N2C(=O)c3cccc(NCc4cn(CCCNC(=O)c5ccc(NC(=O)[C@@H]6NC7(CCCCC7)[C@@]7(C(=O)Nc8cc(Cl)ccc87)[C@H]6c6cccc(Cl)c6F)cc5)cn4)c3C2=O)C(=O)N1] |
| 41 | 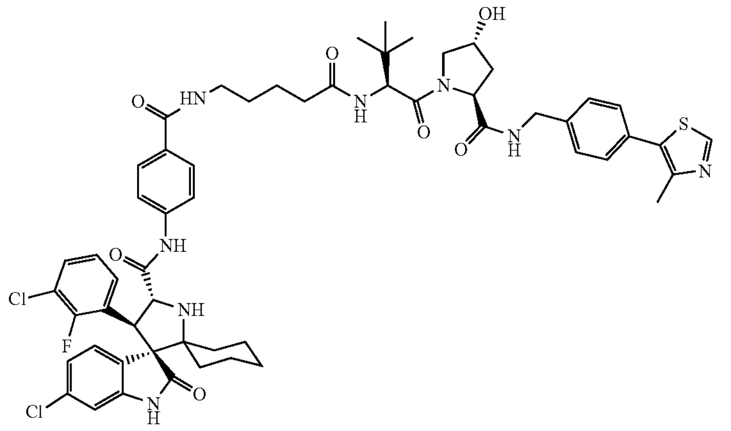 [SMILES: Cc1ncsc1-c1ccc(CNC(=O)[C@@H]2C[C@@H](O)CN2C(=O)[C@@H](NC(=O)CCCCNC(=O)c2ccc(NC(=O)[C@@H]3NC4(CCCCC4)[C@@]4(C(=O)Nc5cc(Cl)ccc54)[C@H]3c3cccc(Cl)c3F)cc2)C(C)(C)C)cc1] |
| 42 | 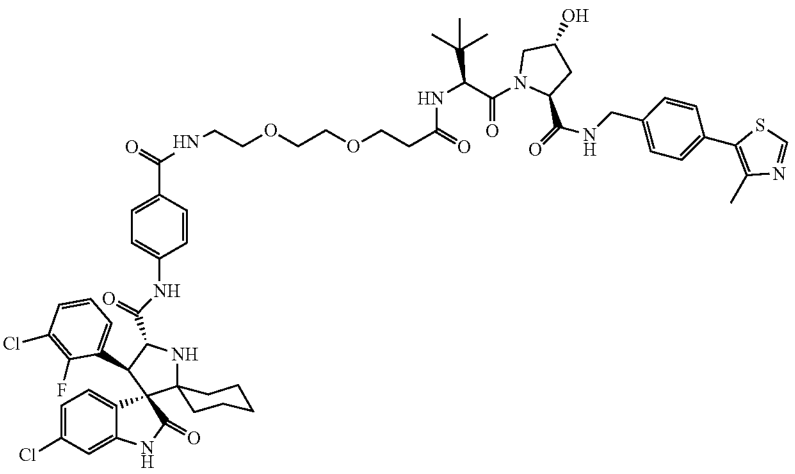 [SMILES: Cc1ncsc1-c1ccc(CNC(=O)[C@@H]2C[C@@H](O)CN2C(=O)[C@@H](NC(=O)CCOCCOCCNC(=O)c2ccc(NC(=O)[C@@H]3NC4(CCCCC4)[C@@]4(C(=O)Nc5cc(Cl)ccc54)[C@H]3c3cccc(Cl)c3F)cc2)C(C)(C)C)cc1] |

TABLE 1-continued
| Cpd. No. | Structure |
|---|---|
| 43 | 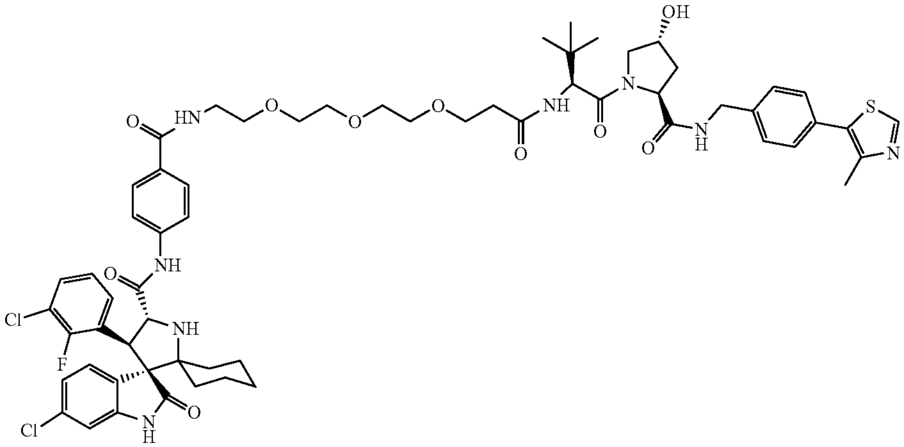 [SMILES: Cc1ncsc1-c1ccc(CNC(=O)[C@@H]2C[C@@H](O)CN2C(=O)[C@@H](NC(=O)CCOCCOCCOCCNC(=O)c2ccc(NC(=O)[C@@H]3NC4(CCCCC4)[C@@]4(C(=O)Nc5cc(Cl)ccc54)[C@H]3c3cccc(Cl)c3F)cc2)C(C)(C)C)cc1] |
| 44 | 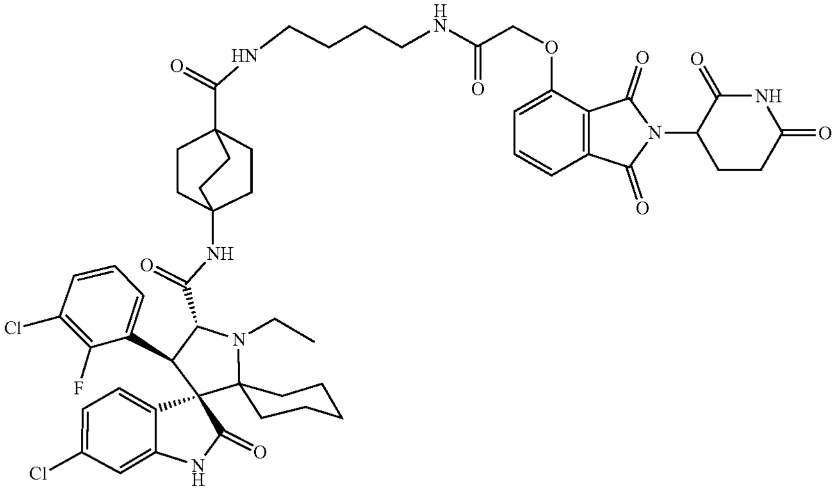 [SMILES: CCN1[C@@H](C(=O)NC23CCC(C(=O)NCCCCNC(=O)COc4cccc5c4C(=O)N(C4CCC(=O)NC4=O)C5=O)(CC2)CC3)[C@H](c2cccc(Cl)c2F)[C@]2(C(=O)Nc3cc(Cl)ccc32)C12CCCCC2] |
| 45 | 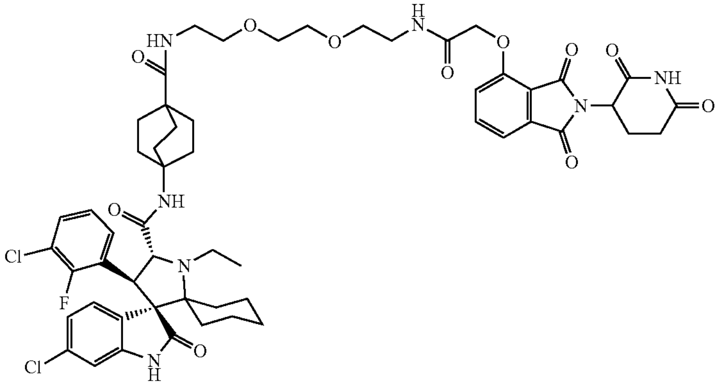 [SMILES: CCN1[C@@H](C(=O)NC23CCC(C(=O)NCCOCCOCCNC(=O)COc4cccc5c4C(=O)N(C4CCC(=O)NC4=O)C5=O)(CC2)CC3)[C@H](c2cccc(Cl)c2F)[C@]2(C(=O)Nc3cc(Cl)ccc32)C12CCCCC2] |

TABLE 1-continued
| Cpd. No. | Structure |
|---|---|
| 46 | 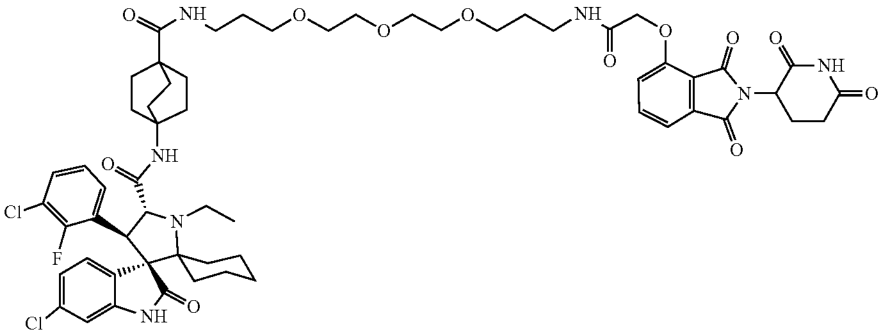 [SMILES: CCN1[C@@H](C(=O)NC23CCC(C(=O)NCCCOCCOCCOCCCNC(=O)COc4cccc5c4C(=O)N(C4CCC(=O)NC4=O)C5=O)(CC2)CC3)[C@H](c2cccc(Cl)c2F)[C@]2(C(=O)Nc3cc(Cl)ccc32)C12CCCCC2] |
| 47 | 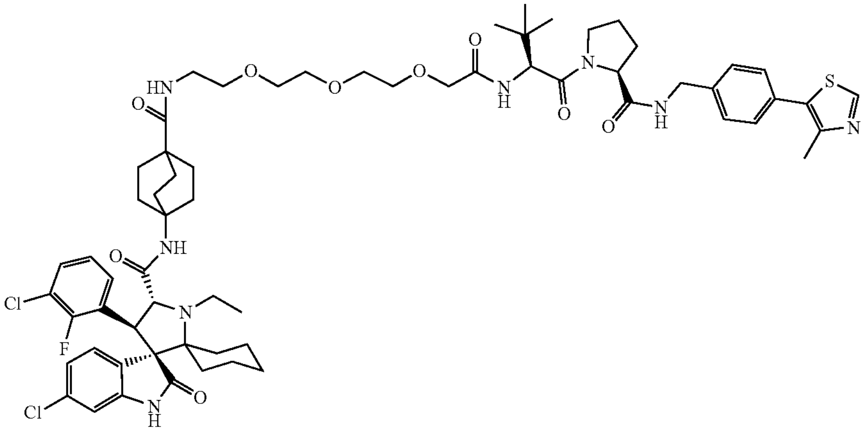 [SMILES: CCN1[C@@H](C(=O)NC23CCC(C(=O)NCCOCCOCCOCC(=O)N[C@H](C(=O)N4CCC[C@H]4C(=O)NCc4ccc(-c5scnc5C)cc4)C(C)(C)C)(CC2)CC3)[C@H](c2cccc(Cl)c2F)[C@]2(C(=O)Nc3cc(Cl)ccc32)C12CCCCC2] |
| 48 | 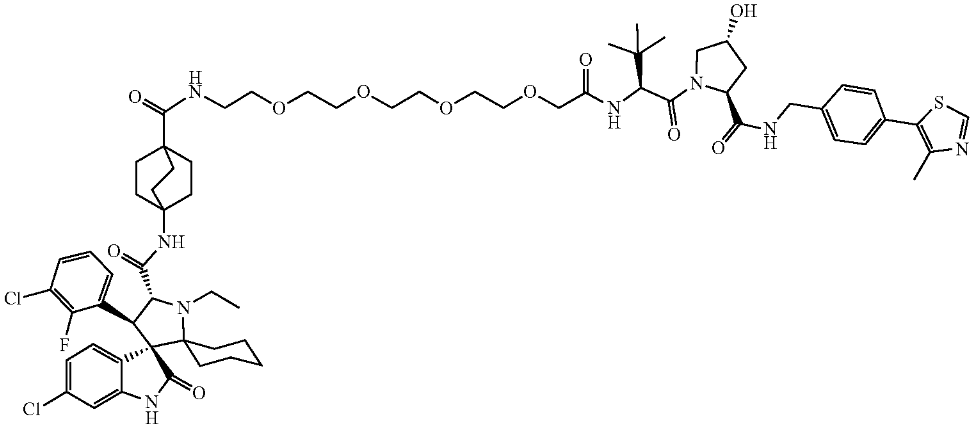 |
| 49 | 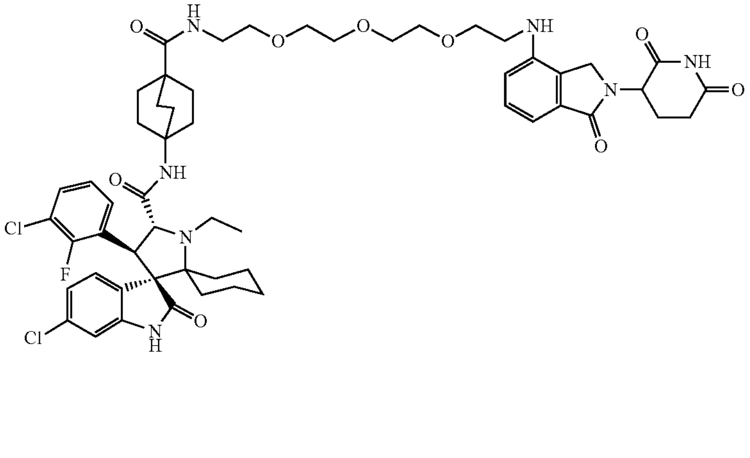 [SMILES: CCN1[C@@H](C(=O)NC23CCC(C(=O)NCCOCCOCCOCCNc4cccc5c4CN(C4CCC(=O)NC4=O)C5=O)(CC2)CC3)[C@H](c2cccc(Cl)c2F)[C@]2(C(=O)Nc3cc(Cl)ccc32)C12CCCCC2] |

TABLE 1-continued
| Cpd. No. | Structure |
|---|---|
| 50 | 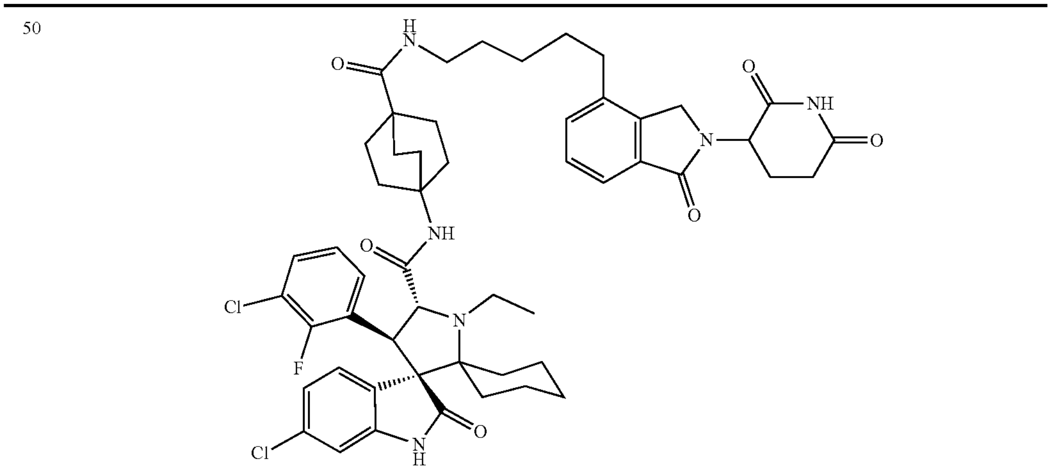 |
| 51 | 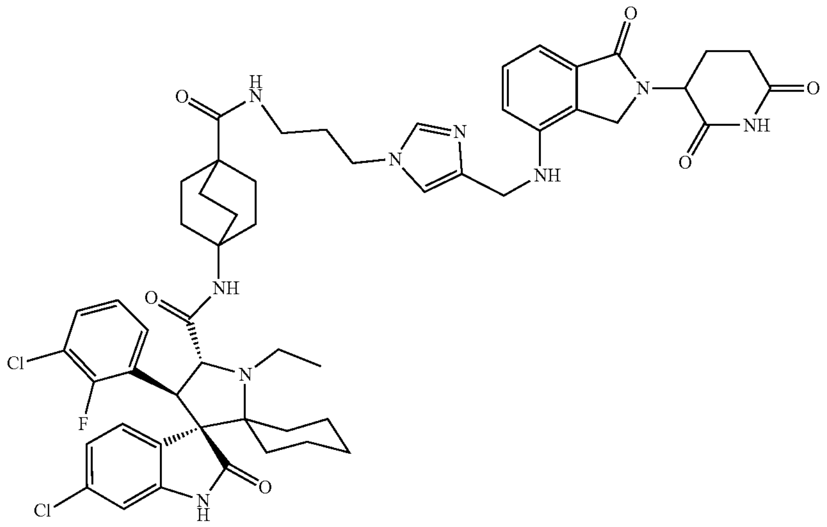 [SMILES: CCN1[C@@H](C(=O)NC23CCC(C(=O)NCCCn4cnc(CNc5cccc6c5CN(C5CCC(=O)NC5=O)C6=O)c4)(CC2)CC3)[C@H](c2cccc(Cl)c2F)[C@]2(C(=O)Nc3cc(Cl)ccc32)C12CCCCC2] |
| 52 | 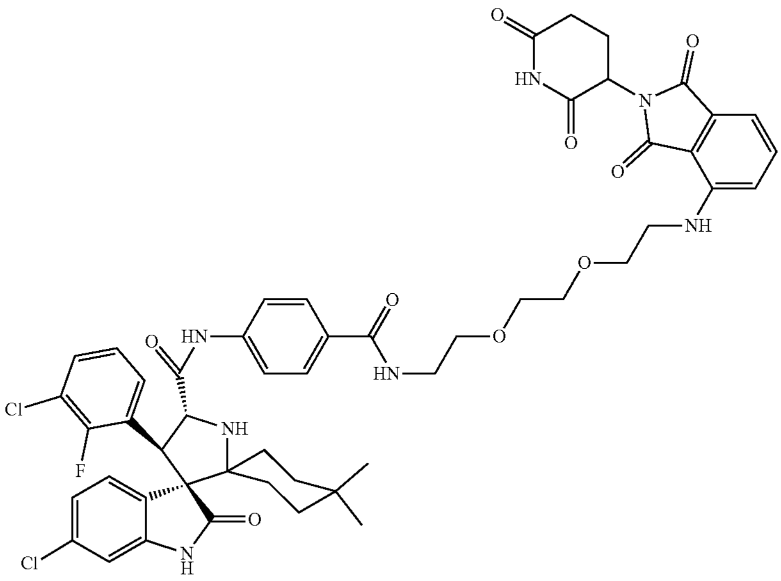 [SMILES: CC1(C)CCC2(CC1)N[C@@H](C(=O)Nc1ccc(C(=O)NCCOCCOCCNc3cccc4c3C(=O)N(C3CCC(=O)NC3=O)C4=O)cc1)[C@H](c1cccc(Cl)c1F)[C@]21C(=O)Nc2cc(Cl)ccc21] |

TABLE 1-continued
| Cpd. No. | Structure |
|---|---|
| 53 | 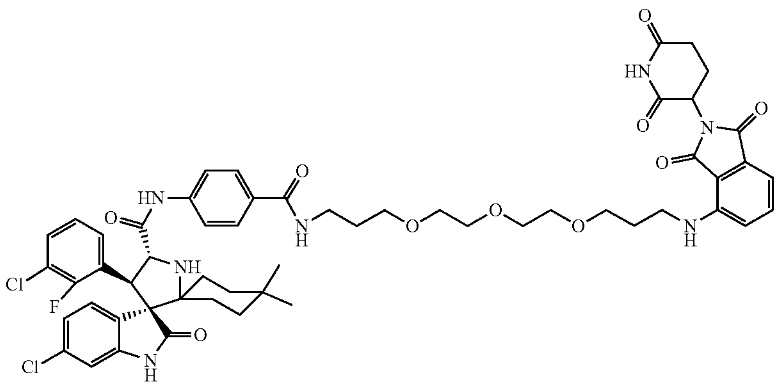 [SMILES: CC1(C)CCC2(CC1)N[C@@H](C(=O)Nc1ccc(C(=O)NCCCOCCOCCOCCCNc3cccc4c3C(=O)N(C3CCC(=O)NC3=O)C4=O)cc1)[C@H](c1cccc(Cl)c1F)[C@]21C(=O)Nc2cc(Cl)ccc21] |
| 54 | 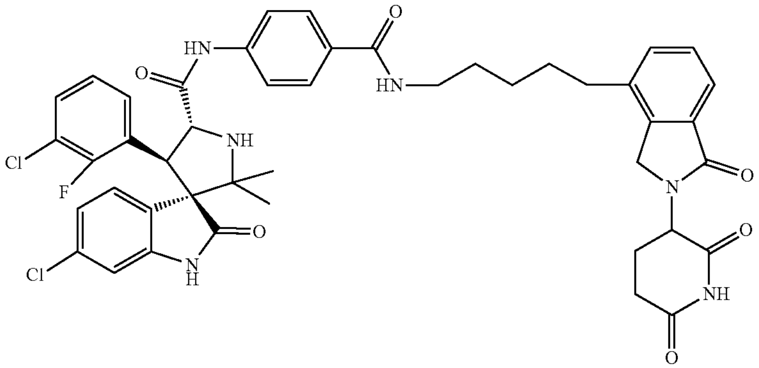 [SMILES: CC1(C)N[C@@H](C(=O)Nc2ccc(C(=O)NCCCCCc3cccc4c3CN(C3CCC(=O)NC3=O)C4=O)cc2)[C@H](c2cccc(Cl)c2F)[C@]12C(=O)Nc1cc(Cl)ccc12] |
| 55 | 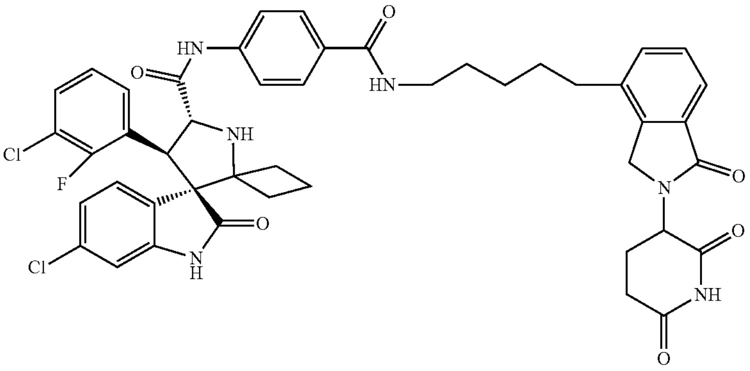 [SMILES: O=C1CCC(N2Cc3c(CCCCCNC(=O)c4ccc(NC(=O)[C@@H]5NC6(CCC6)[C@@]6(C(=O)Nc7cc(Cl)ccc76)[C@H]5c5cccc(Cl)c5F)cc4)cccc3C2=O)C(=O)N1] |
| 56 | 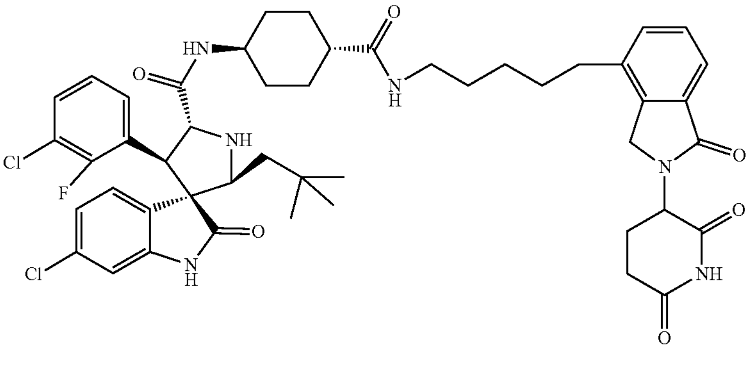 [SMILES: CC(C)(C)C[C@@H]1N[C@@H](C(=O)N[C@H]2CC[C@H](C(=O)NCCCCCc3cccc4c3CN(C3CCC(=O)NC3=O)C4=O)CC2)[C@H](c2cccc(Cl)c2F)[C@]12C(=O)Nc1cc(Cl)ccc12] |

TABLE 1-continued
| Cpd. No. | Structure |
|---|---|
| 57 | 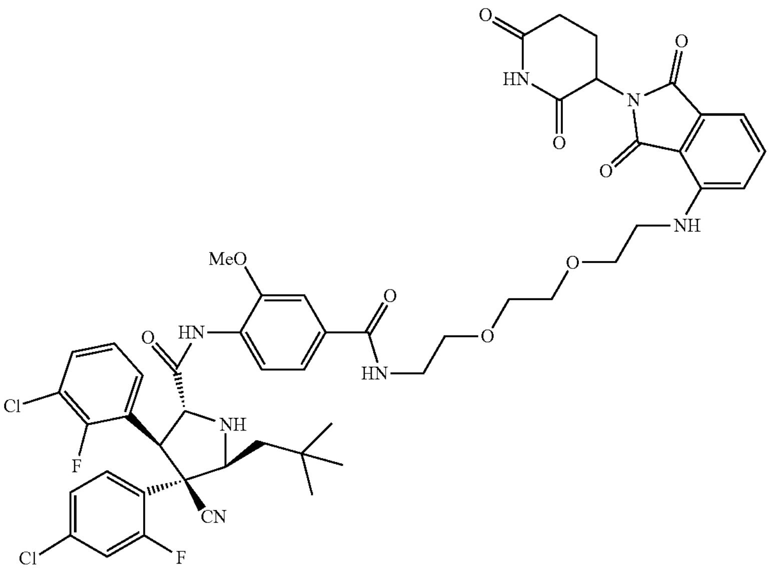 [SMILES: COc1cc(C(=O)NCCOCCOCCNc2cccc3c2C(=O)N(C2CCC(=O)NC2=O)C3=O)ccc1NC(=O)[C@@H]1N[C@@H](CC(C)(C)C)[C@](C#N)(c2ccc(Cl)cc2F)[C@H]1c1cccc(Cl)c1F] |
| 58 | 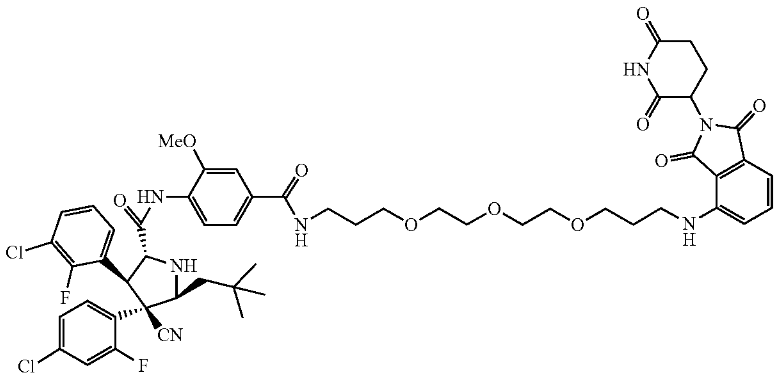 [SMILES: COc1cc(C(=O)NCCCOCCOCCOCCCNc2cccc3c2C(=O)N(C2CCC(=O)NC2=O)C3=O)ccc1NC(=O)[C@@H]1N[C@@H](CC(C)(C)C)[C@](C#N)(c2ccc(Cl)cc2F)[C@H]1c1cccc(Cl)c1F] |
| 59 | 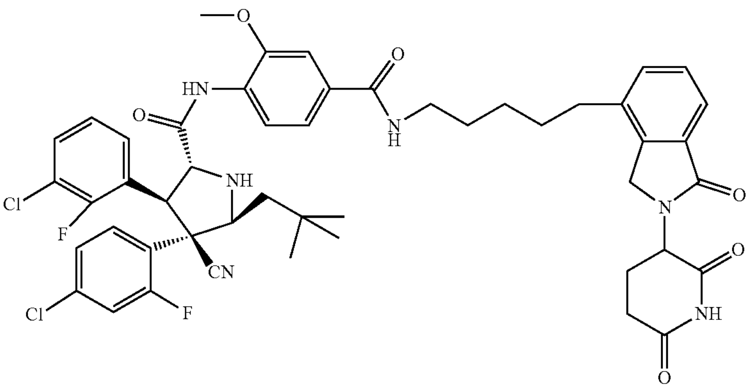 [SMILES: COc1cc(C(=O)NCCCCCc2cccc3c2CN(C2CCC(=O)NC2=O)C3=O)ccc1NC(=O)[C@@H]1N[C@@H](CC(C)(C)C)[C@](C#N)(c2ccc(Cl)cc2F)[C@H]1c1cccc(Cl)c1F] |

TABLE 1-continued
| Cpd. No. | Structure |
|---|---|
| 60 | 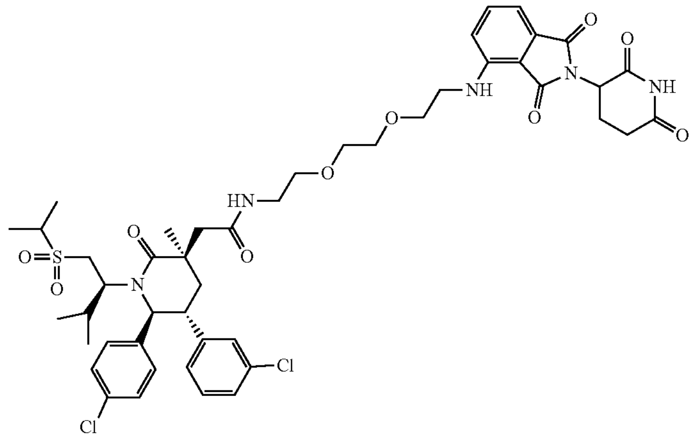 [SMILES: CC(C)[C@@H](CS(=O)(=O)C(C)C)N1C(=O)[C@@](C)(CC(=O)NCCOCCOCCNc2cccc3c2C(=O)N(C2CCC(=O)NC2=O)C3=O)C[C@H](c2cccc(Cl)c2)[C@H]1c1ccc(Cl)cc1] |
| 61 | 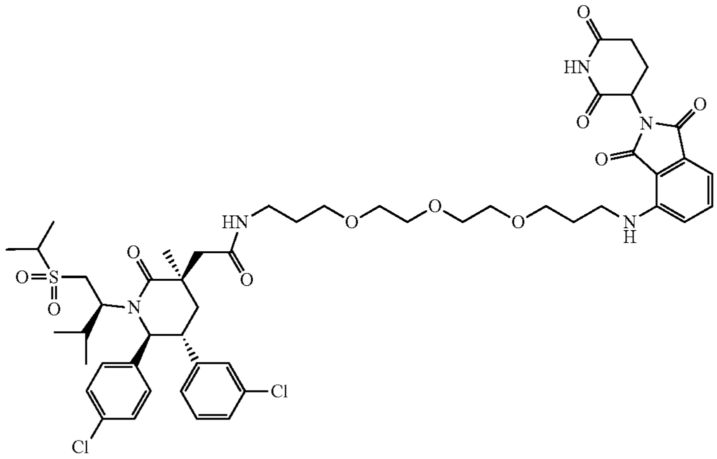 [SMILES: CC(C)[C@@H](CS(=O)(=O)C(C)C)N1C(=O)[C@@](C)(CC(=O)NCCCOCCOCCOCCCNc2cccc3c2C(=O)N(C2CCC(=O)NC2=O)C3=O)C[C@H](c2cccc(Cl)c2)[C@H]1c1ccc(Cl)cc1] |
| 62 | 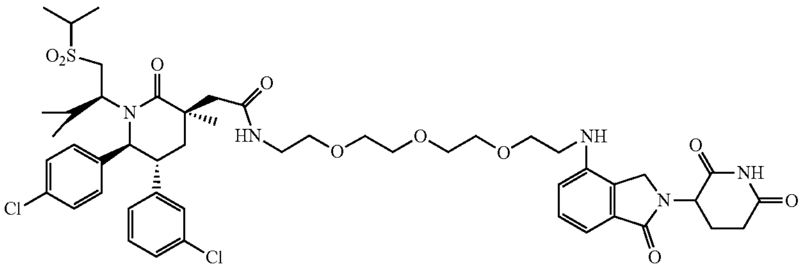 [SMILES: CC(C)[C@@H](CS(=O)(=O)C(C)C)N1C(=O)[C@@](C)(CC(=O)NCCOCCOCCOCCNc2cccc3c2CN(C2CCC(=O)NC2=O)C3=O)C[C@H](c2cccc(Cl)c2)[C@H]1c1ccc(Cl)cc1] |
| 63 | 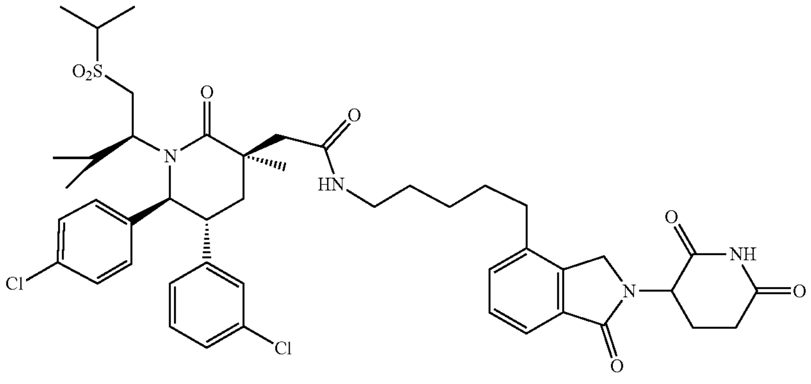 [SMILES: CC(C)[C@@H](CS(=O)(=O)C(C)C)N1C(=O)[C@@](C)(CC(=O)NCCCCCc2cccc3c2CN(C2CCC(=O)NC2=O)C3=O)C[C@H](c2cccc(Cl)c2)[C@H]1c1ccc(Cl)cc1] |

TABLE 1-continued
| Cpd. No. | Structure |
|---|---|
| 64 | 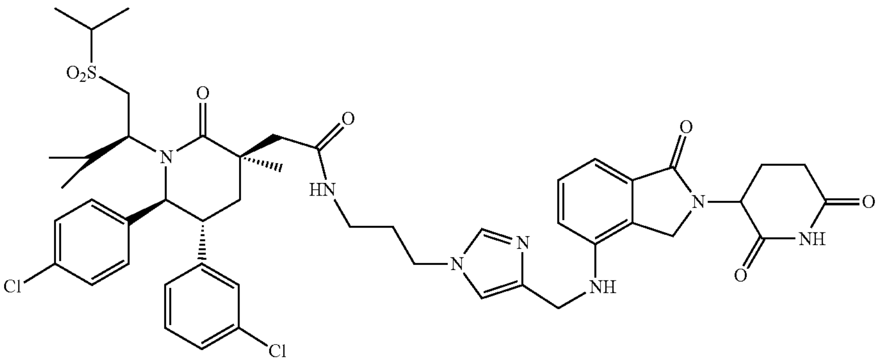 [SMILES: CC(C)[C@@H](CS(=O)(=O)C(C)C)N1C(=O)[C@@](C)(CC(=O)NCCCn2cnc(CNc3cccc4c3CN(C3CCC(=O)NC3=O)C4=O)c2)C[C@H](c2cccc(Cl)c2)[C@H]1c1ccc(Cl)cc1] |
| 65 | 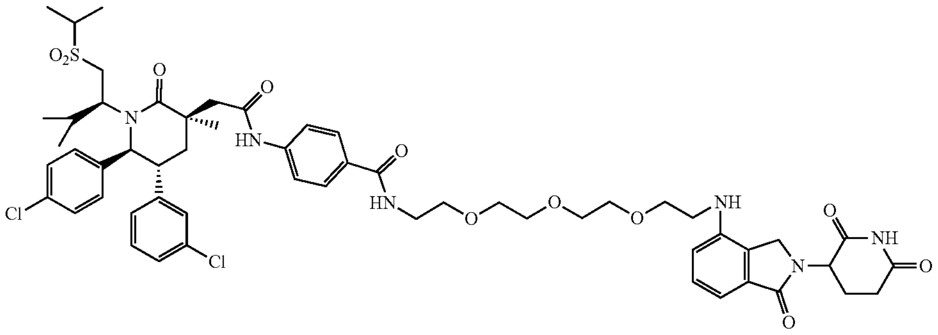 [SMILES: CC(C)[C@@H](CS(=O)(=O)C(C)C)N1C(=O)[C@@](C)(CC(=O)Nc2ccc(C(=O)NCCOCCOCCOCCNc3cccc4c3CN(C3CCC(=O)NC3=O)C4=O)cc2)C[C@H](c2cccc(Cl)c2)[C@H]1c1ccc(Cl)cc1] |
| 66 | 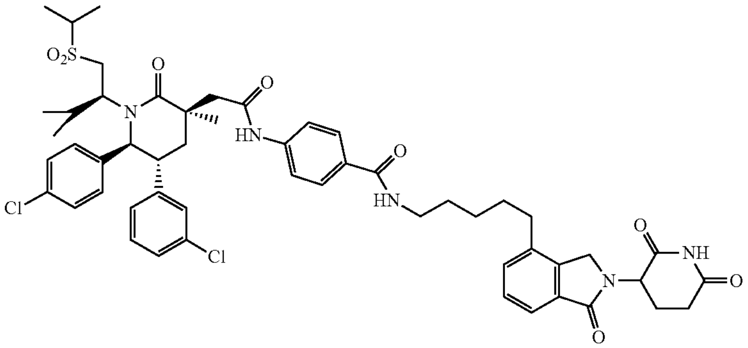 [SMILES: CC(C)[C@@H](CS(=O)(=O)C(C)C)N1C(=O)[C@@](C)(CC(=O)Nc2ccc(C(=O)NCCCCCc3cccc4c3CN(C3CCC(=O)NC3=O)C4=O)cc2)C[C@H](c2cccc(Cl)c2)[C@H]1c1ccc(Cl)cc1] |
| 67 | 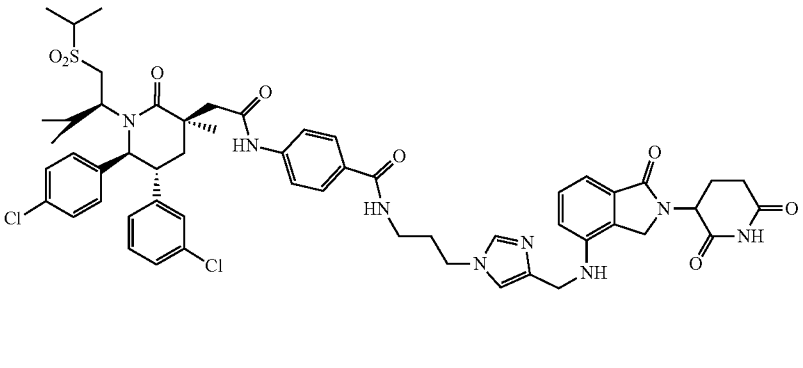 [SMILES: CC(C)[C@@H](CS(=O)(=O)C(C)C)N1C(=O)[C@@](C)(CC(=O)Nc2ccc(C(=O)NCCCn3cnc(CNc4cccc5c4CN(C4CCC(=O)NC4=O)C5=O)c3)cc2)C[C@H](c2cccc(Cl)c2)[C@H]1c1ccc(Cl)cc1] |

TABLE 1-continued
| Cpd. No. | Structure |
|---|---|
| 68 | 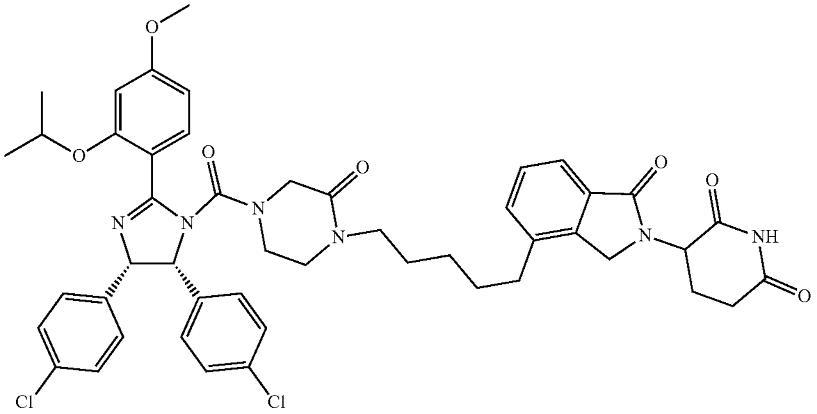 [SMILES: COc1ccc(C2=N[C@@H](c3ccc(Cl)cc3)[C@@H](c3ccc(Cl)cc3)N2C(=O)N2CCN(CCCCCc3cccc4c3CN(C3CCC(=O)NC3=O)C4=O)C(=O)C2)c(OC(C)C)c1] |
| 69 | 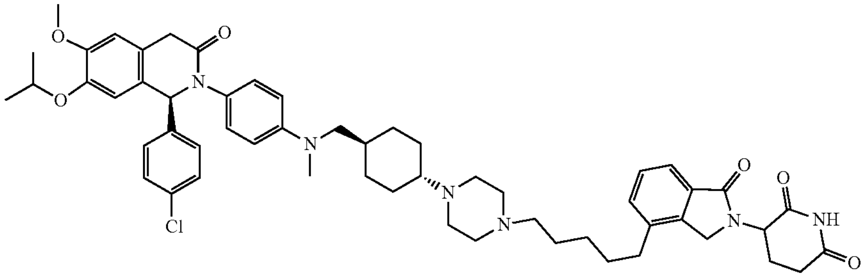 [SMILES: COc1cc2c(cc1OC(C)C)[C@H](c1ccc(Cl)cc1)N(c1ccc(N(C)C[C@H]3CC[C@H](N4CCN(CCCCCc5cccc6c5CN(C5CCC(=O)NC5=O)C6=O)CC4)CC3)cc1)C(=O)C2] |
In another embodiment, Compounds of the Disclosure are any one or more of the compounds of Table 1A. and the pharmaceutically acceptable salts and solvates thereof.
TABLE 1A
| Cpd. No. | Structure |
|---|---|
| 146 | 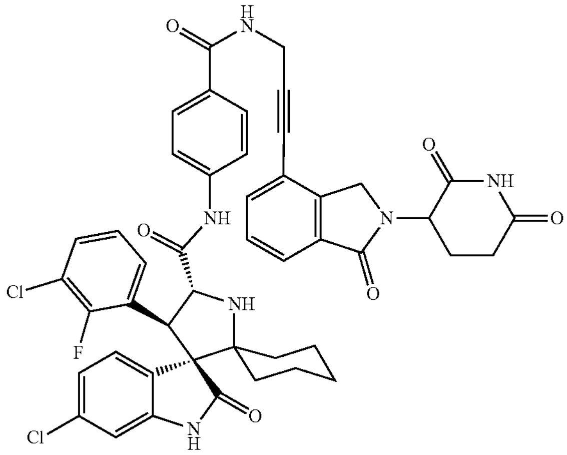 [SMILES: O=C1CCC(N2Cc3c(C#CCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |

TABLE 1A-continued
| Cpd. No. | Structure |
| --- | --- |
| 147 | 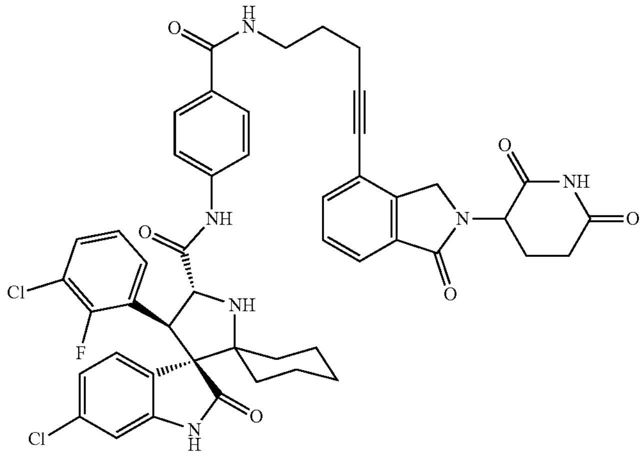 [SMILES: O=C1CCC(N2Cc3c(C#CCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 148 | 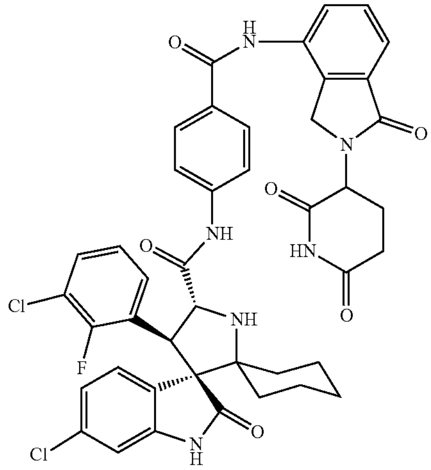 [SMILES: O=C1CCC(N2Cc3c(NC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 149 | 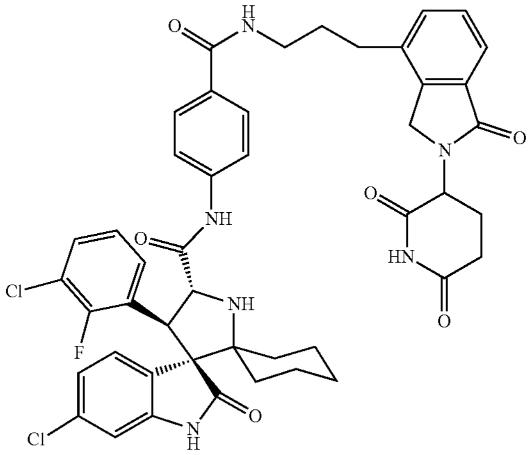 [SMILES: O=C1CCC(N2Cc3c(CCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |

TABLE 1A-continued
| Cpd. No. | Structure |
|---|---|
| 150 | 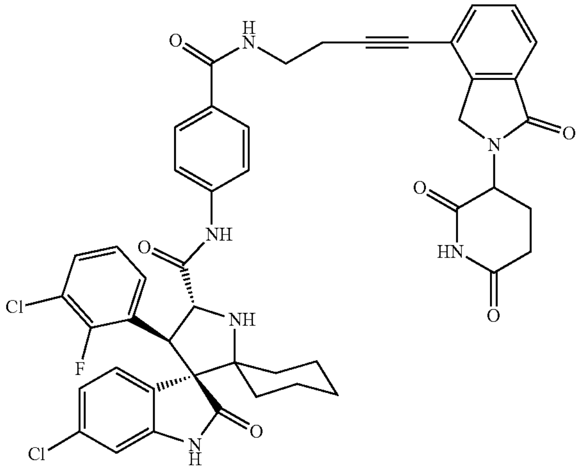 [SMILES: O=C1CCC(N2Cc3c(C#CCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 151 | 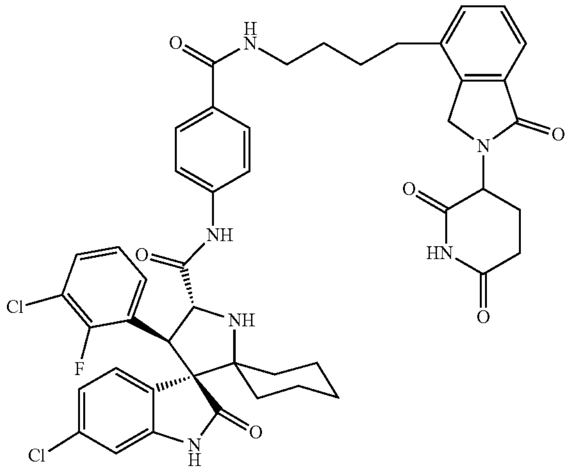 [SMILES: O=C1CCC(N2Cc3c(CCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 152 | 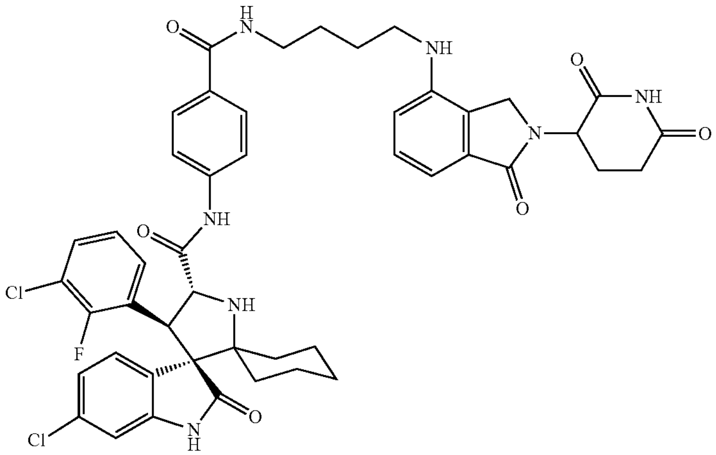 [SMILES: O=C1CCC(N2Cc3c(NCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |

TABLE 1A-continued
| Cpd. No. | Structure |
|---|---|
| 153 | 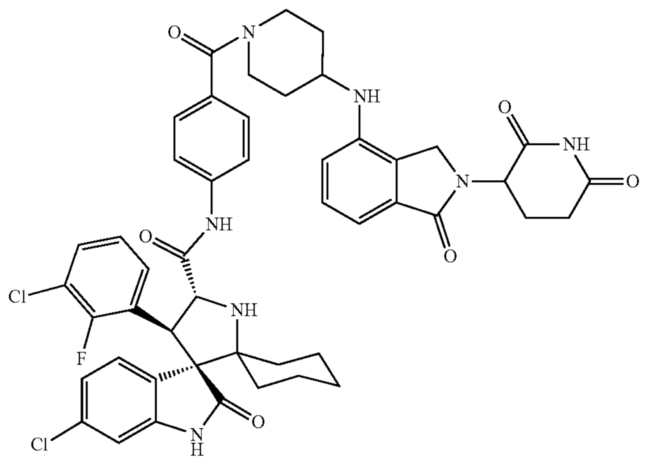 [SMILES: O=C1CCC(N2Cc3c(NC4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |
| 154 | 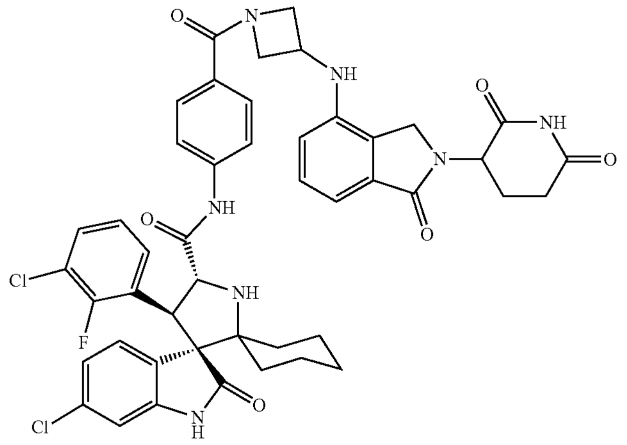 [SMILES: O=C1CCC(N2Cc3c(NC4CN(C(=O)c5ccc(NC(=O)[C@@H]6NC7(CCCCC7)[C@@]7(C(=O)Nc8cc(Cl)ccc87)[C@H]6c6cccc(Cl)c6F)cc5)C4)cccc3C2=O)C(=O)N1] |
| 155 | 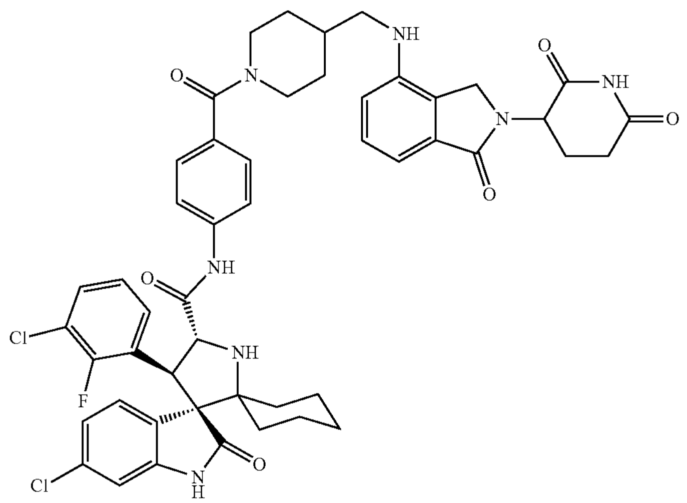 [SMILES: O=C1CCC(N2Cc3c(NCC4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |

TABLE 1A-continued
| Cpd. No. | Structure |
|---|---|
| 156 | 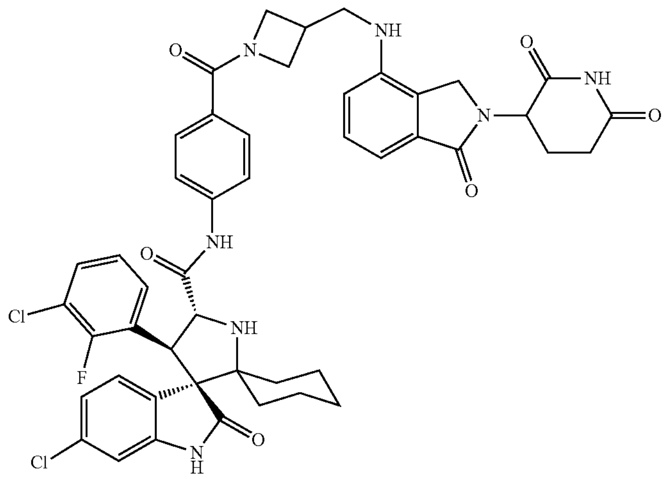 [SMILES: O=C1CCC(N2Cc3c(NCC4CN(C(=O)c5ccc(NC(=O)[C@@H]6NC7(CCCCC7)[C@@]7(C(=O)Nc8cc(Cl)ccc87)[C@H]6c6cccc(Cl)c6F)cc5)C4)cccc3C2=O)C(=O)N1] |
| 157 | 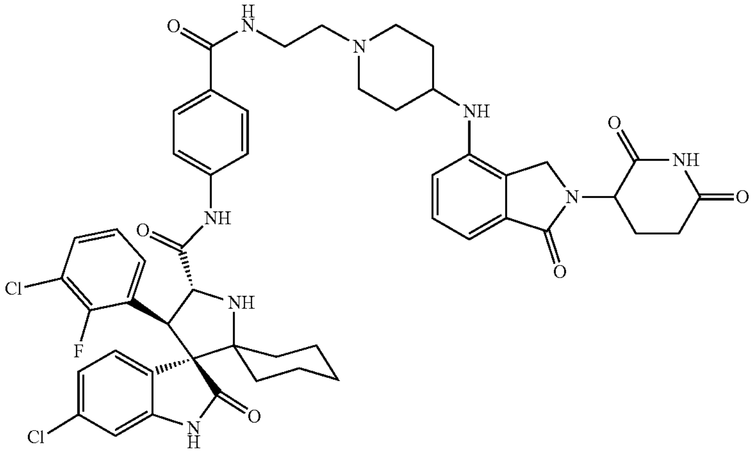 [SMILES: O=C1CCC(N2Cc3c(NC4CCN(CCNC(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |
| 158 | 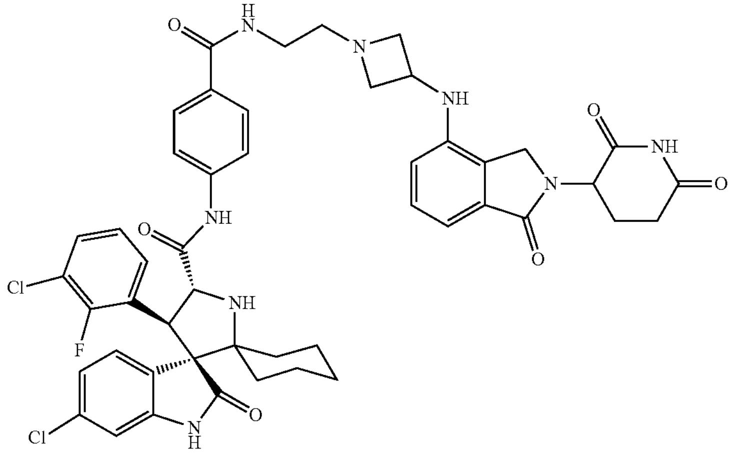 [SMILES: O=C1CCC(N2Cc3c(NC4CN(CCNC(=O)c5ccc(NC(=O)[C@@H]6NC7(CCCCC7)[C@@]7(C(=O)Nc8cc(Cl)ccc87)[C@H]6c6cccc(Cl)c6F)cc5)C4)cccc3C2=O)C(=O)N1] |

TABLE 1A-continued
| Cpd. No. | Structure |
|---|---|
| 159 | 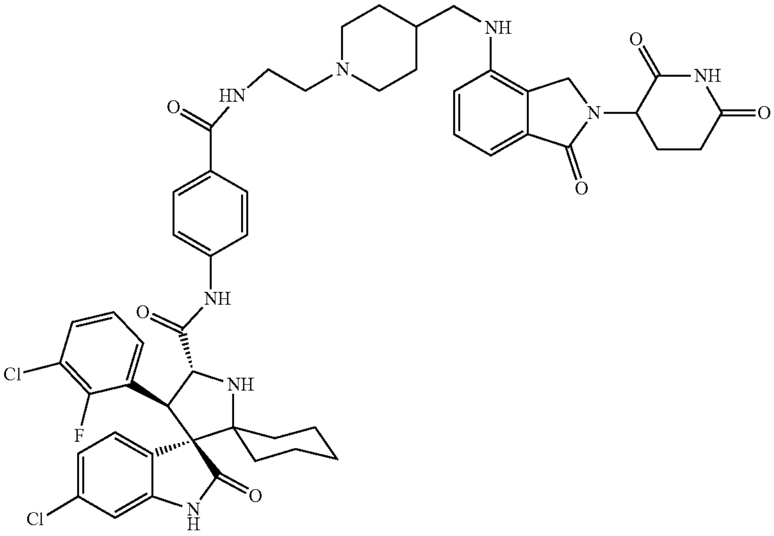 [SMILES: O=C1CCC(N2Cc3c(NCC4CCN(CCNC(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |
| 160 | 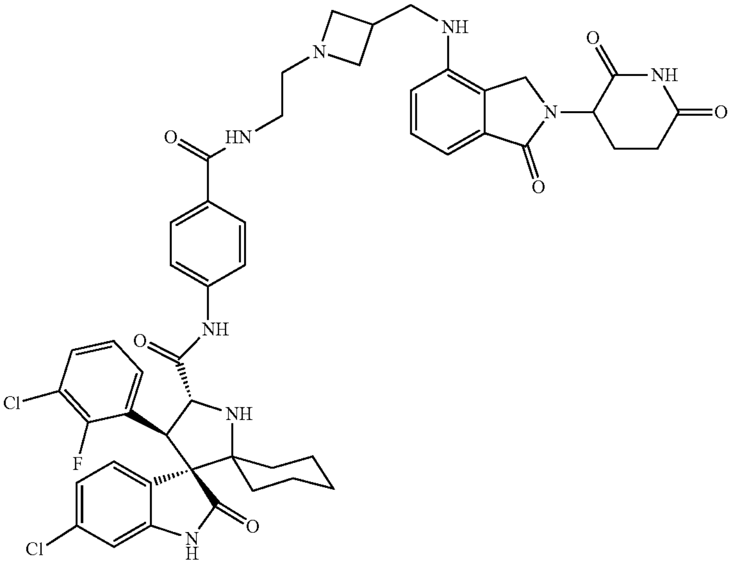 [SMILES: O=C1CCC(N2Cc3c(NCC4CN(CCNC(=O)c5ccc(NC(=O)[C@@H]6NC7(CCCCC7)[C@@]7(C(=O)Nc8cc(Cl)ccc87)[C@H]6c6cccc(Cl)c6F)cc5)C4)cccc3C2=O)C(=O)N1] |
| 161 | 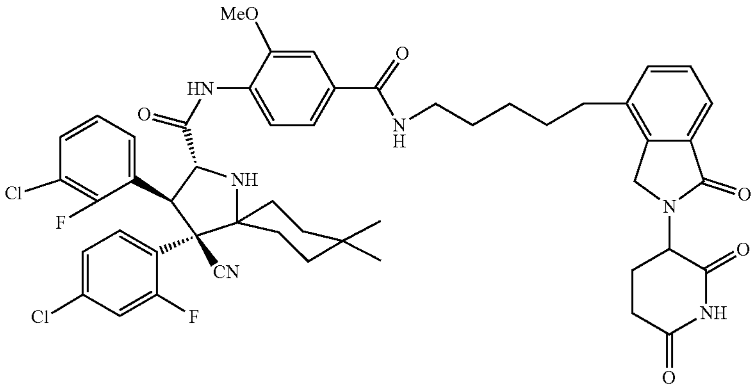 [SMILES: COc1cc(C(=O)NCCCCCc2cccc3c2CN(C2CCC(=O)NC2=O)C3=O)ccc1NC(=O)[C@@H]1NC2(CCC(C)(C)CC2)[C@](C#N)(c2ccc(Cl)cc2F)[C@H]1c1cccc(Cl)c1F] |

TABLE 1A-continued
| Cpd. No. | Structure |
|---|---|
| 162 | 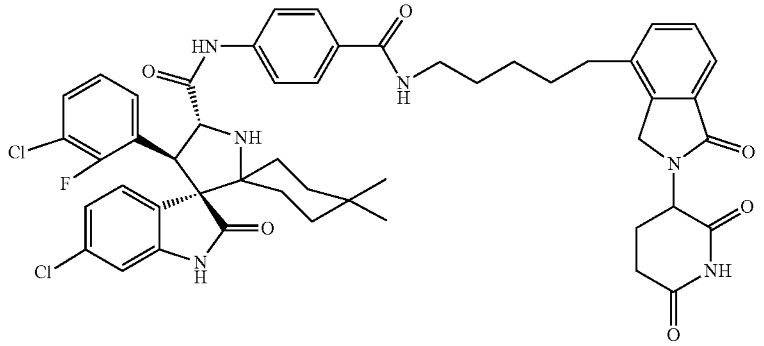 [SMILES: CC1(C)CCC2(CC1)N[C@@H](C(=O)Nc1ccc(C(=O)NCCCCCc3cccc4c3CN(C3CCC(=O)NC3=O)C4=O)cc1)[C@H](c1cccc(Cl)c1F)[C@]21C(=O)Nc2cc(Cl)ccc21] |
| 163 | 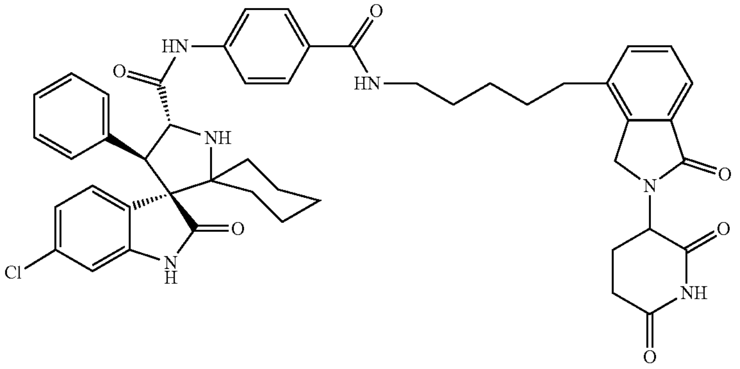 [SMILES: O=C1CCC(N2Cc3c(CCCCCNC(=O)c4ccc(NC(=O)[C@@H]5NC6(CCCCC6)[C@@]6(C(=O)Nc7cc(Cl)ccc76)[C@H]5c5ccccc5)cc4)cccc3C2=O)C(=O)N1] |
| 164 | 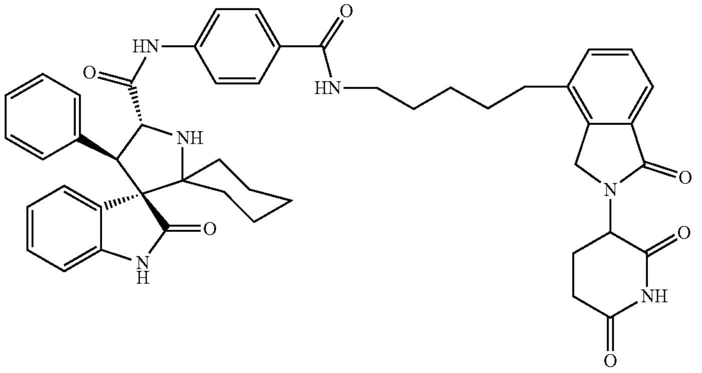 [SMILES: O=C1CCC(N2Cc3c(CCCCCNC(=O)c4ccc(NC(=O)[C@@H]5NC6(CCCCC6)[C@@]6(C(=O)Nc7ccccc76)[C@H]5c5ccccc5)cc4)cccc3C2=O)C(=O)N1] |
| 165 | 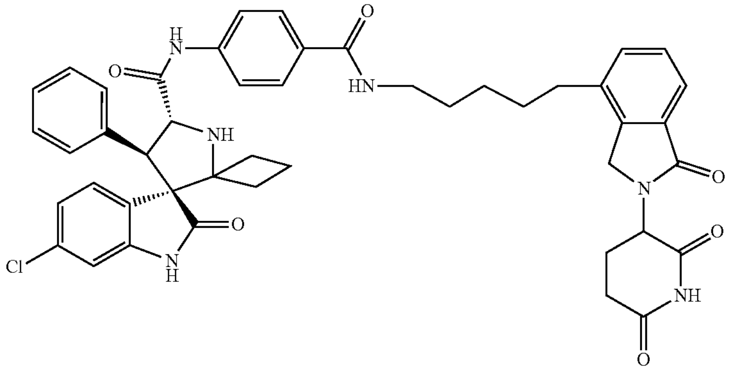 [SMILES: O=C1CCC(N2Cc3c(CCCCCNC(=O)c4ccc(NC(=O)[C@@H]5NC6(CCC6)[C@@]6(C(=O)Nc7cc(Cl)ccc76)[C@H]5c5ccccc5)cc4)cccc3C2=O)C(=O)N1] |

TABLE 1A-continued
| Cpd. No. | Structure |
|---|---|
| 166 | 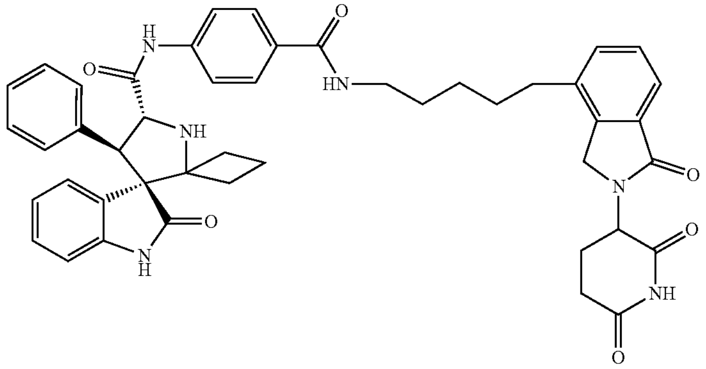 [SMILES: O=C1CCC(N2Cc3c(CCCCCNC(=O)c4ccc(NC(=O)[C@@H]5NC6(CCC6)[C@@]6(C(=O)Nc7ccccc76)[C@H]5c5ccccc5)cc4)cccc3C2=O)C(=O)N1] |
| 167 | 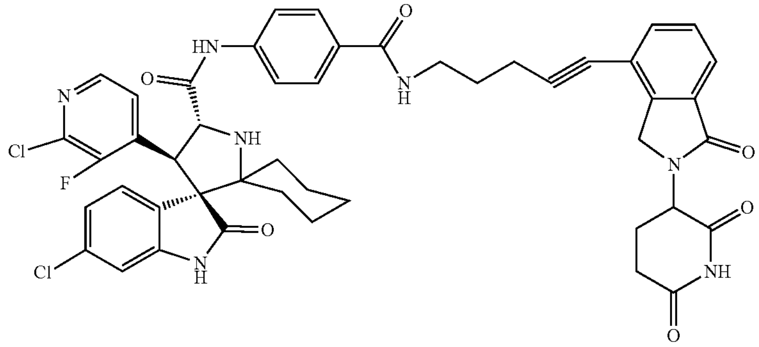 [SMILES: O=C1CCC(N2Cc3c(C#CCCCNC(=O)c4ccc(NC(=O)[C@@H]5NC6(CCCCC6)[C@@]6(C(=O)Nc7cc(Cl)ccc76)[C@H]5c5ccnc(Cl)c5F)cc4)cccc3C2=O)C(=O)N1] |
| 168 | 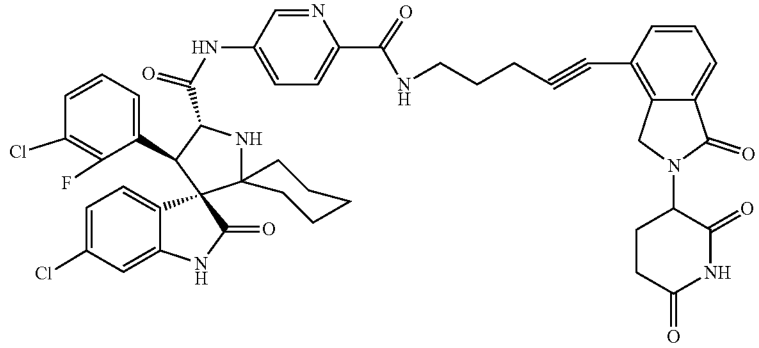 [SMILES: O=C1CCC(N2Cc3c(C#CCCCNC(=O)c4ccc(NC(=O)[C@@H]5NC6(CCCCC6)[C@@]6(C(=O)Nc7cc(Cl)ccc76)[C@H]5c5cccc(Cl)c5F)cn4)cccc3C2=O)C(=O)N1] |
| 169 | 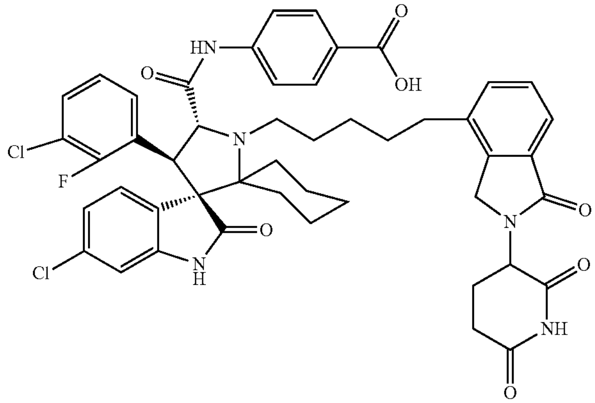 [SMILES: O=C1CCC(N2Cc3c(CCCCCN4[C@@H](C(=O)Nc5ccc(C(=O)O)cc5)[C@H](c5cccc(Cl)c5F)[C@]5(C(=O)Nc6cc(Cl)ccc65)C45CCCCC5)cccc3C2=O)C(=O)N1] |

TABLE 1A-continued
| Cpd. No. | Structure |
| --- | --- |
| 170 | 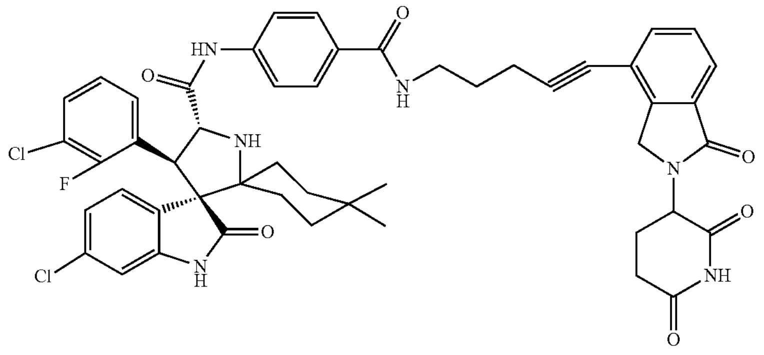 [SMILES: CC1(C)CCC2(CC1)N[C@@H](C(=O)Nc1ccc(C(=O)NCCCC#Cc3cccc4c3CN(C3CCC(=O)NC3=O)C4=O)cc1)[C@H](c1cccc(Cl)c1F)[C@]21C(=O)Nc2cc(Cl)ccc21] |
| 171 | 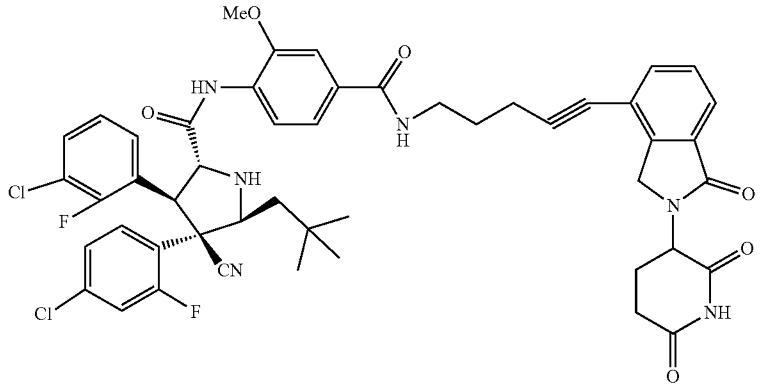 [SMILES: COc1cc(C(=O)NCCCC#Cc2cccc3c2CN(C2CCC(=O)NC2=O)C3=O)ccc1NC(=O)[C@@H]1N[C@@H](CC(C)(C)C)[C@](C#N)(c2ccc(Cl)cc2F)[C@H]1c1cccc(Cl)c1F] |
| 172 | 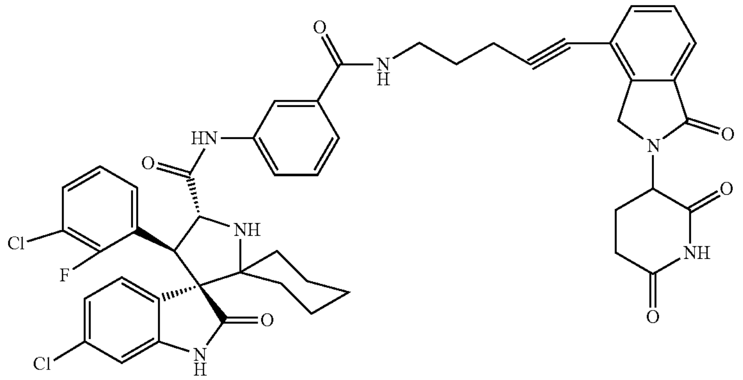 [SMILES: O=C1CCC(N2Cc3c(C#CCCCNC(=O)c4cccc(NC(=O)[C@@H]5NC6(CCCCC6)[C@@]6(C(=O)Nc7cc(Cl)ccc76)[C@H]5c5cccc(Cl)c5F)c4)cccc3C2=O)C(=O)N1] |
| 173 | 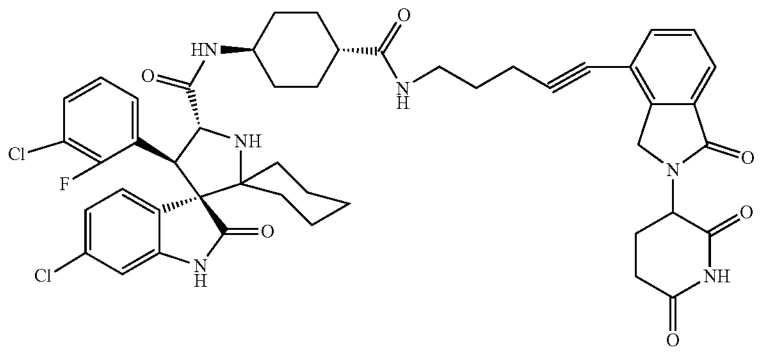 [SMILES: O=C1CCC(N2Cc3c(C#CCCCNC(=O)[C@H]4CC[C@H](NC(=O)[C@@H]5NC6(CCCCC6)[C@@]6(C(=O)Nc7cc(Cl)ccc76)[C@H]5c5cccc(Cl)c5F)CC4)cccc3C2=O)C(=O)N1] |

TABLE 1A-continued
| Cpd. No. | Structure |
|---|---|
| 174 | 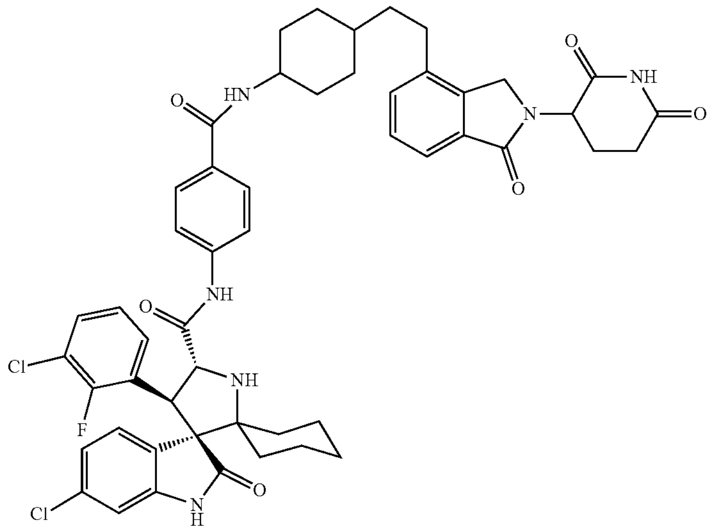 [SMILES: O=C1CCC(N2Cc3c(CCC4CCC(NC(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |
| 175 | 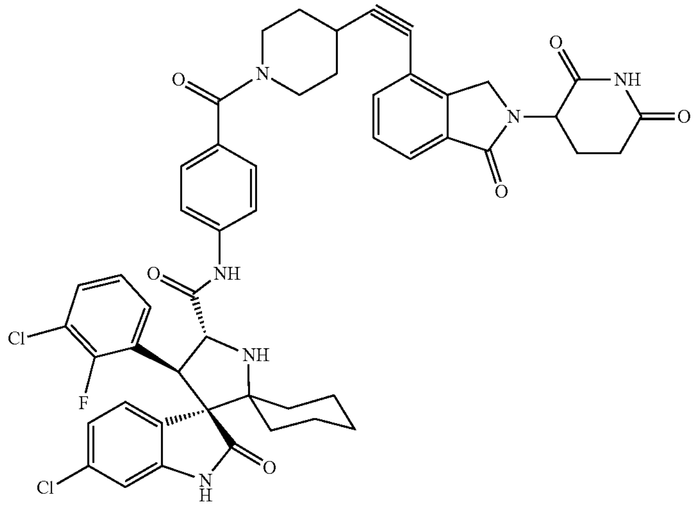 [SMILES: O=C1CCC(N2Cc3c(C#CC4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |
| 176 | 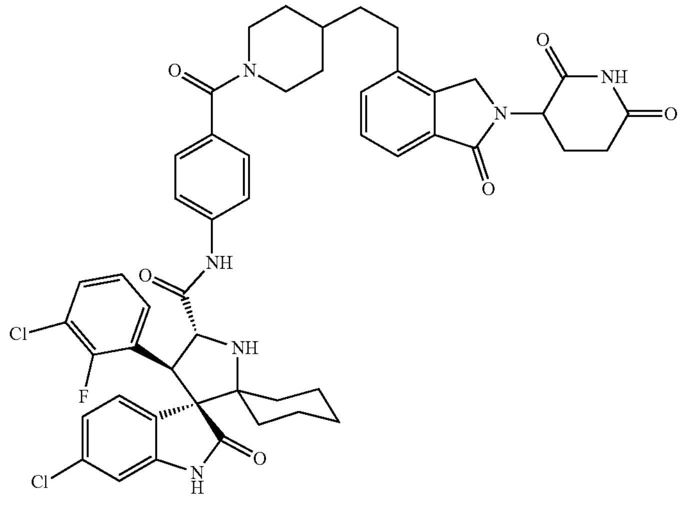 [SMILES: O=C1CCC(N2Cc3c(CCC4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |

TABLE 1A-continued
| Cpd. No. | Structure |
|---|---|
| 177 | 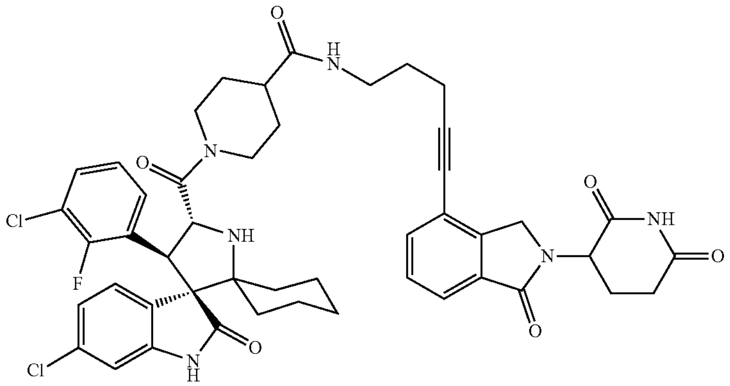 [SMILES: O=C1CCC(N2Cc3c(C#CCCCNC(=O)C4CCN(C(=O)[C@@H]5NC6(CCCCC6)[C@@]6(C(=O)Nc7cc(Cl)ccc76)[C@H]5c5cccc(Cl)c5F)CC4)cccc3C2=O)C(=O)N1] |
| 178 | 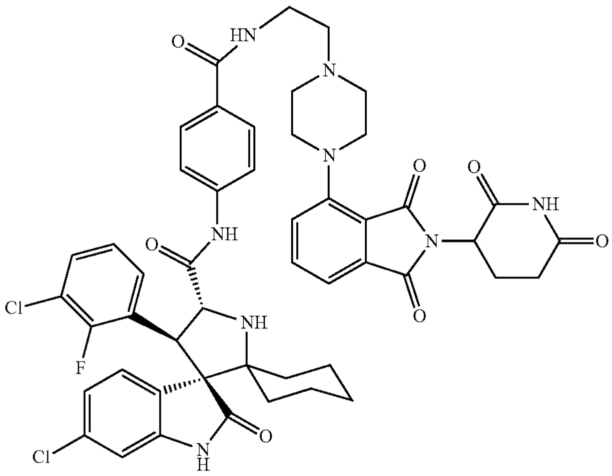 [SMILES: O=C1CCC(N2C(=O)c3cccc(N4CCN(CCNC(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)c3C2=O)C(=O)N1] |
| 179 | 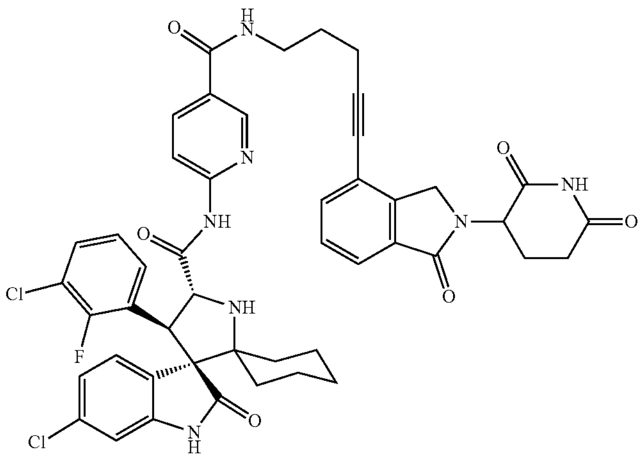 [SMILES: O=C1CCC(N2Cc3c(C#CCCCNC(=O)c4ccc(NC(=O)[C@@H]5NC6(CCCCC6)[C@@]6(C(=O)Nc7cc(Cl)ccc76)[C@H]5c5cccc(Cl)c5F)nc4)cccc3C2=O)C(=O)N1] |

In another embodiment, Compounds of the Disclosure are any one or more of the compounds of Table 1B, and the pharmaceutically acceptable salts and solvates thereof.
TABLE 1B
| Cpd. No. | Structure |
| --- | --- |
| 180 | 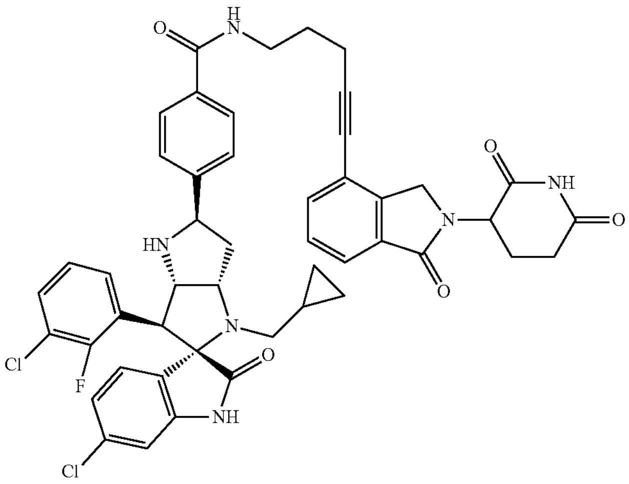 [SMILES: O=C1CCC(N2Cc3c(C#CCCCNC(=O)c4ccc([C@H]5C[C@H]6[C@@H](N5)[C@H](c5cccc(Cl)c5F)[C@]5(C(=O)Nc7cc(Cl)ccc75)N6CC5CC5)cc4)cccc3C2=O)C(=O)N1] |
| 181 | 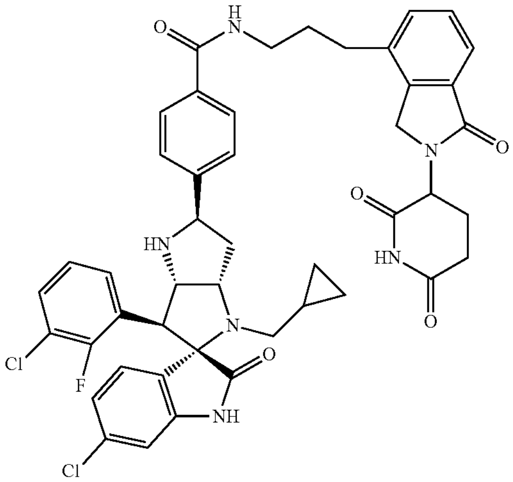 [SMILES: O=C1CCC(N2Cc3c(CCCNC(=O)c4ccc([C@H]5C[C@H]6[C@@H](N5)[C@H](c5cccc(Cl)c5F)[C@]5(C(=O)Nc7cc(Cl)ccc75)N6CC5CC5)cc4)cccc3C2=O)C(=O)N1] |
| 182 | 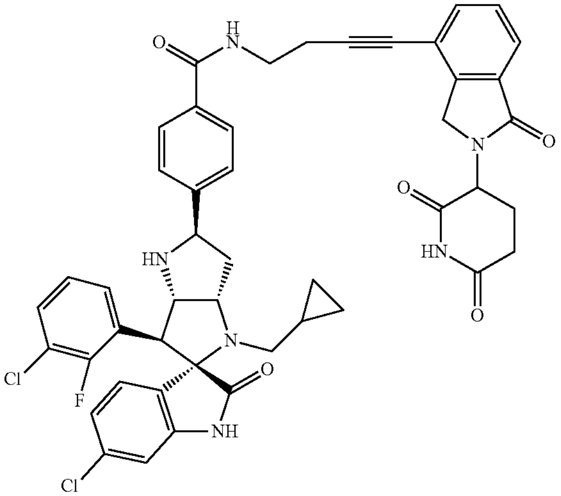 [SMILES: O=C1CCC(N2Cc3c(C#CCCNC(=O)c4ccc([C@H]5C[C@H]6[C@@H](N5)[C@H](c5cccc(Cl)c5F)[C@]5(C(=O)Nc7cc(Cl)ccc75)N6CC5CC5)cc4)cccc3C2=O)C(=O)N1] |

TABLE 1B-continued
| Cpd. No. | Structure |
| --- | --- |
| 183 | 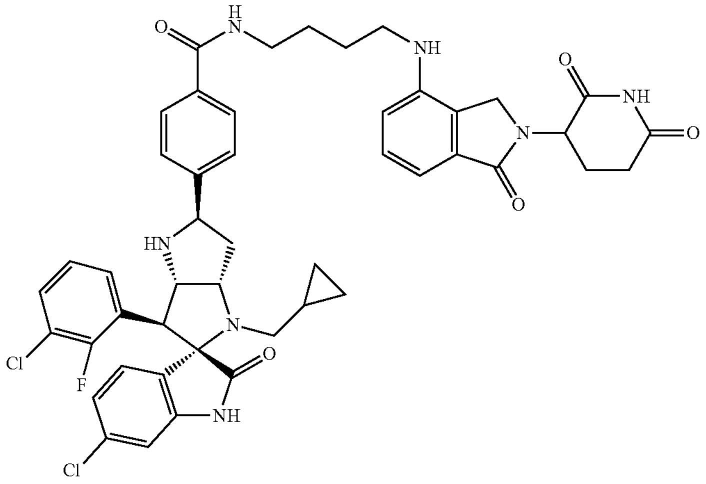 [SMILES: O=C1CCC(N2Cc3c(NCCCCNC(=O)c4ccc([C@H]5C[C@H]6[C@@H](N5)[C@H](c5cccc(Cl)c5F)[C@]5(C(=O)Nc7cc(Cl)ccc75)N6CC5CC5)cc4)cccc3C2=O)C(=O)N1] |
| 184 | 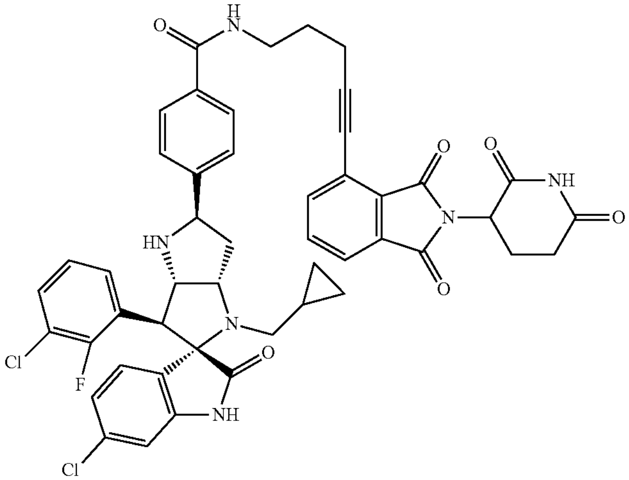 [SMILES: O=C1CCC(N2C(=O)c3cccc(C#CCCCNC(=O)c4ccc([C@H]5C[C@H]6[C@@H](N5)[C@H](c5cccc(Cl)c5F)[C@]5(C(=O)Nc7cc(Cl)ccc75)N6CC5CC5)cc4)c3C2=O)C(=O)N1] |
| 185 | 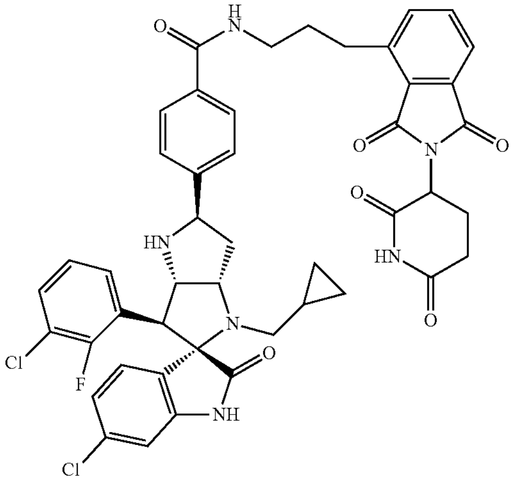 [SMILES: O=C1CCC(N2C(=O)c3cccc(CCCNC(=O)c4ccc([C@H]5C[C@H]6[C@@H](N5)[C@H](c5cccc(Cl)c5F)[C@]5(C(=O)Nc7cc(Cl)ccc75)N6CC5CC5)cc4)c3C2=O)C(=O)N1] |

TABLE 1B-continued
| Cpd. No. | Structure |
| --- | --- |
| 186 | 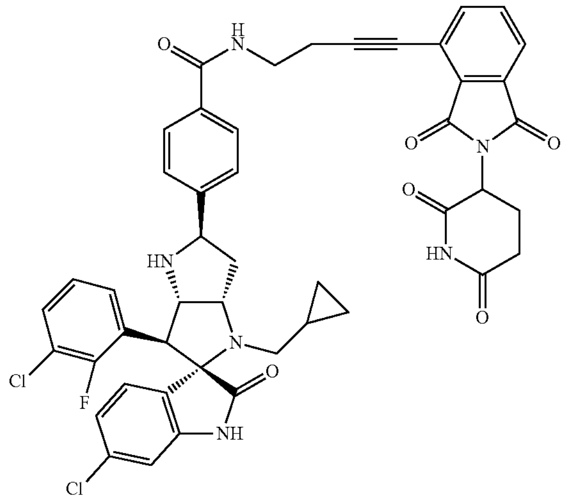 [SMILES: O=C1CCC(N2C(=O)c3cccc(C#CCCNC(=O)c4ccc([C@H]5C[C@H]6[C@@H](N5)[C@H](c5cccc(Cl)c5F)[C@]5(C(=O)Nc7cc(Cl)ccc75)N6CC5CC5)cc4)c3C2=O)C(=O)N1] |
| 187 | 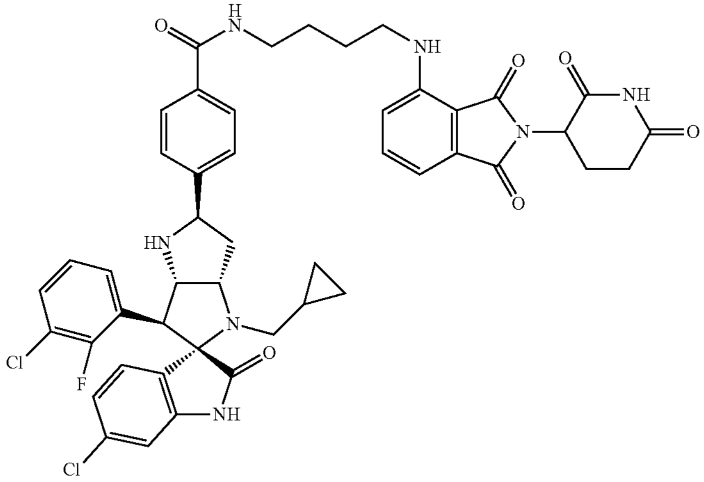 [SMILES: O=C1CCC(N2C(=O)c3cccc(NCCCCNC(=O)c4ccc([C@H]5C[C@H]6[C@@H](N5)[C@H](c5cccc(Cl)c5F)[C@]5(C(=O)Nc7cc(Cl)ccc75)N6CC5CC5)cc4)c3C2=O)C(=O)N1] |

In another embodiment, Compounds of the Disclosure are any one or more of the compounds of Table 1C, and the pharmaceutically acceptable salts and solvates thereof.
TABLE 1C
| Cpd. No. | Structure |
| --- | --- |
| 188 | 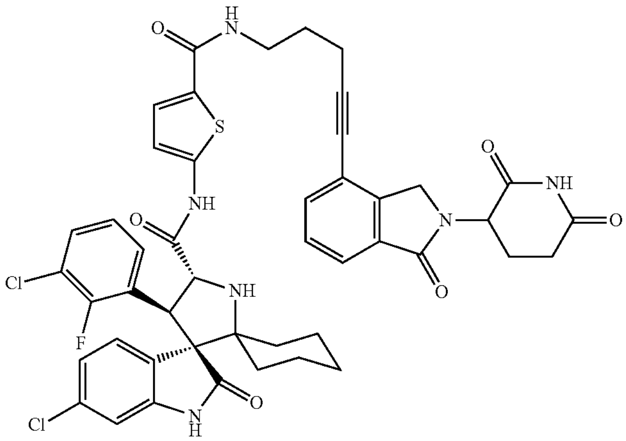 [SMILES: O=C1CCC(N2Cc3c(C#CCCCNC(=O)c4cnc(NC(=O)[C@@H]5NC6(CCCCC6)[C@@]6(C(=O)Nc7cc(Cl)ccc76)[C@H]5c5cccc(Cl)c5F)s4)cccc3C2=O)C(=O)N1] |
| 189 | 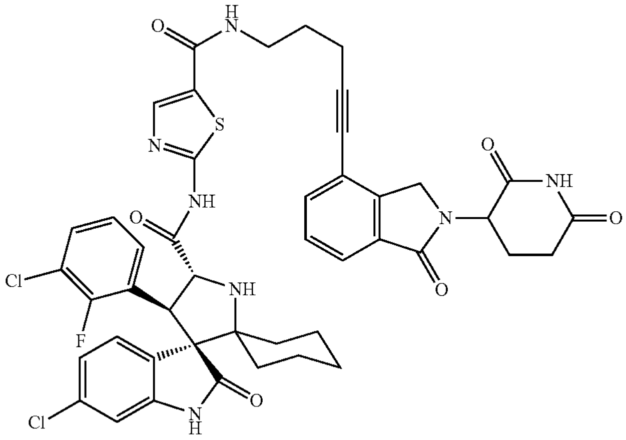 |
| 190 | 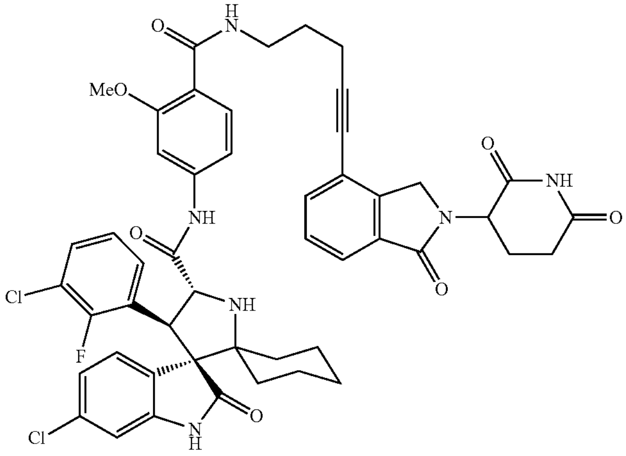 [SMILES: COc1cc(NC(=O)[C@@H]2NC3(CCCCC3)[C@@]3(C(=O)Nc4cc(Cl)ccc43)[C@H]2c2cccc(Cl)c2F)ccc1C(=O)NCCCC#Cc1cccc2c1CN(C1CCC(=O)NC1=O)C2=O] |

TABLE 1C-continued
| Cpd. No. | Structure |
|---|---|
| 191 | 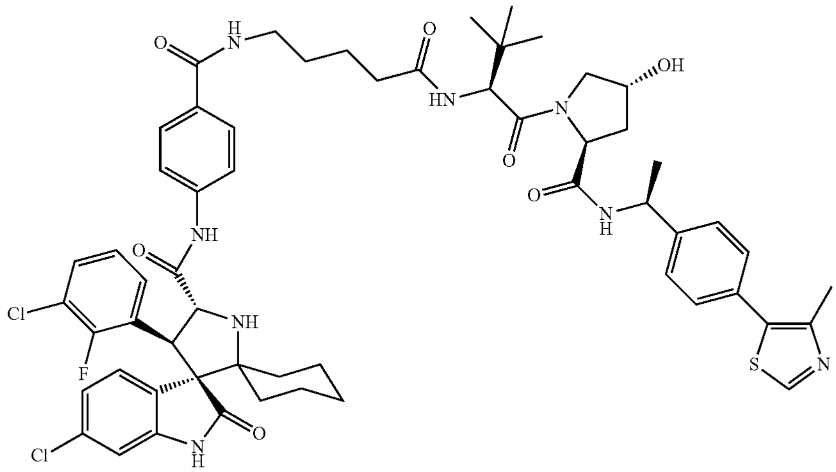 [SMILES: Cc1ncsc1-c1ccc([C@H](C)NC(=O)[C@@H]2C[C@@H](O)CN2C(=O)[C@@H](NC(=O)CCCCNC(=O)c2ccc(NC(=O)[C@@H]3NC4(CCCCC4)[C@@]4(C(=O)Nc5cc(Cl)ccc54)[C@H]3c3cccc(Cl)c3F)cc2)C(C)(C)C)cc1] |
| 192 | 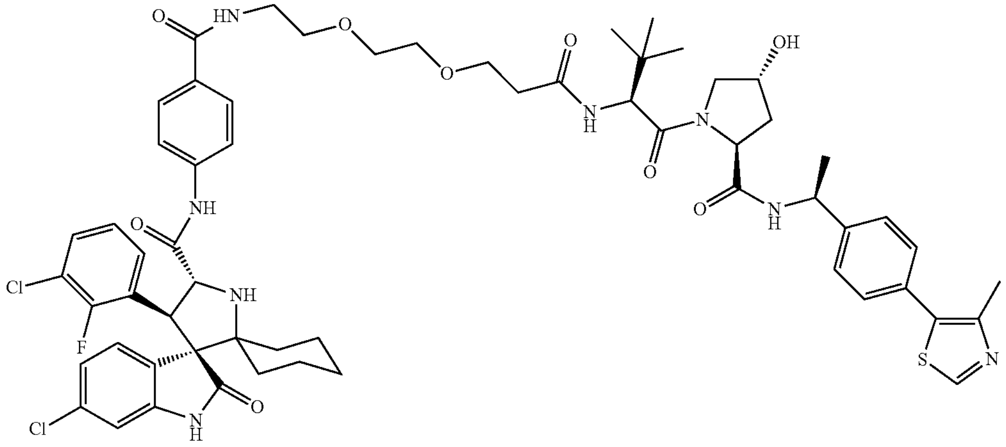 [SMILES: Cc1ncsc1-c1ccc([C@H](C)NC(=O)[C@@H]2C[C@@H](O)CN2C(=O)[C@@H](NC(=O)CCOCCOCCNC(=O)c2ccc(NC(=O)[C@@H]3NC4(CCCCC4)[C@@]4(C(=O)Nc5cc(Cl)ccc54)[C@H]3c3cccc(Cl)c3F)cc2)C(C)(C)C)cc1] |
| 193 | 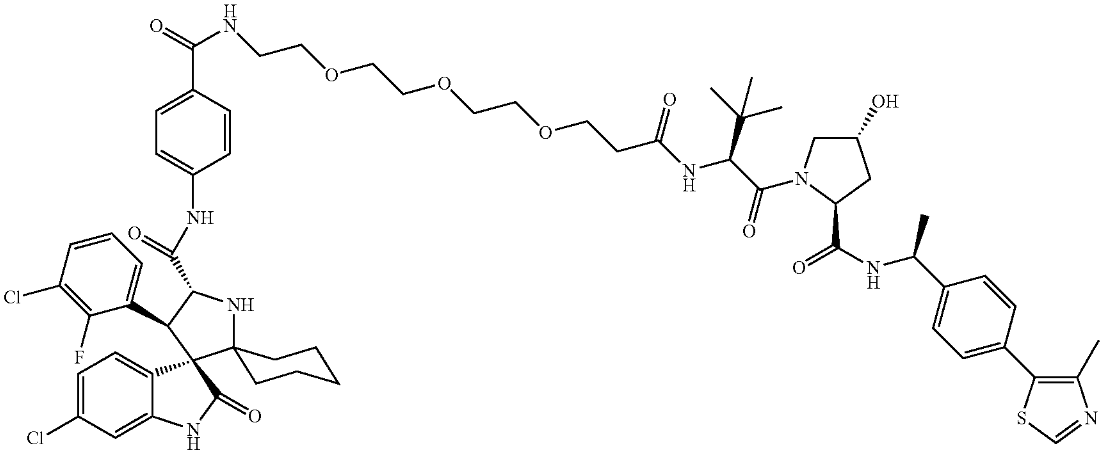 [SMILES: Cc1ncsc1-c1ccc([C@H](C)NC(=O)[C@@H]2C[C@@H](O)CN2C(=O)[C@@H](NC(=O)CCOCCOCCOCCNC(=O)c2ccc(NC(=O)[C@@H]3NC4(CCCCC4)[C@@]4(C(=O)Nc5cc(Cl)ccc54)[C@H]3c3cccc(Cl)c3F)cc2)C(C)(C)C)cc1] |

TABLE 1C-continued
| Cpd. No. | Structure |
|---|---|
| 194 | 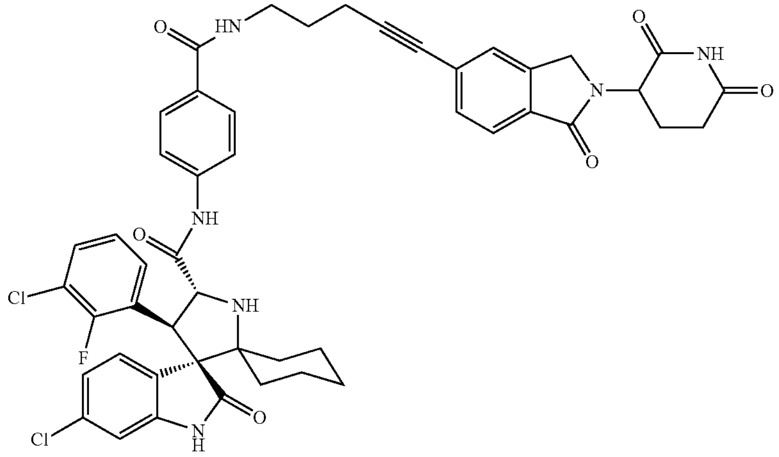 [SMILES: O=C1CCC(N2Cc3cc(C#CCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)ccc3C2=O)C(=O)N1] |
| 195 | 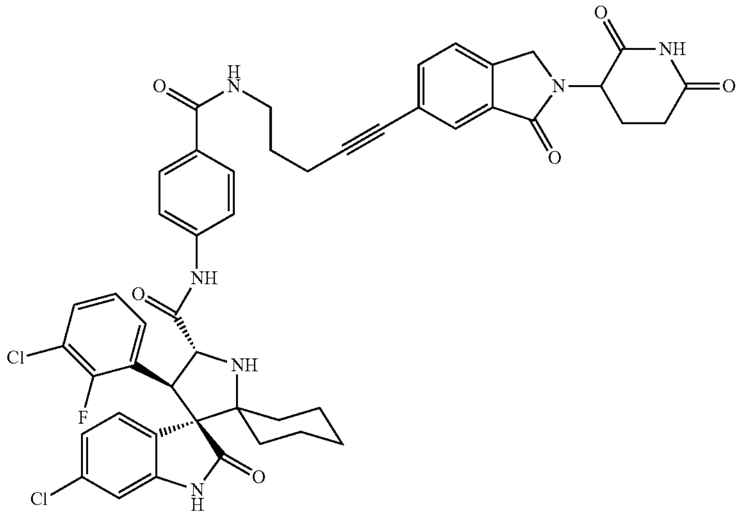 [SMILES: O=C1CCC(N2Cc3ccc(C#CCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cc3C2=O)C(=O)N1] |
| 196 | 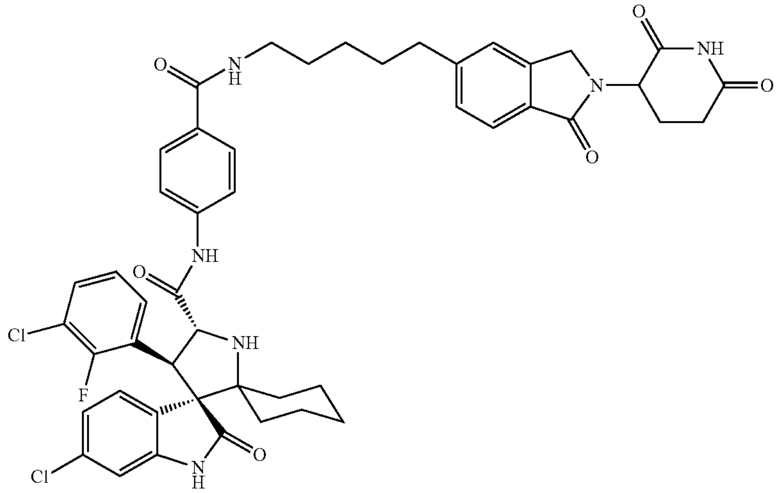 [SMILES: O=C1CCC(N2Cc3cc(CCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)ccc3C2=O)C(=O)N1] |

TABLE 1C-continued
| Cpd. No. | Structure |
| --- | --- |
| 197 | 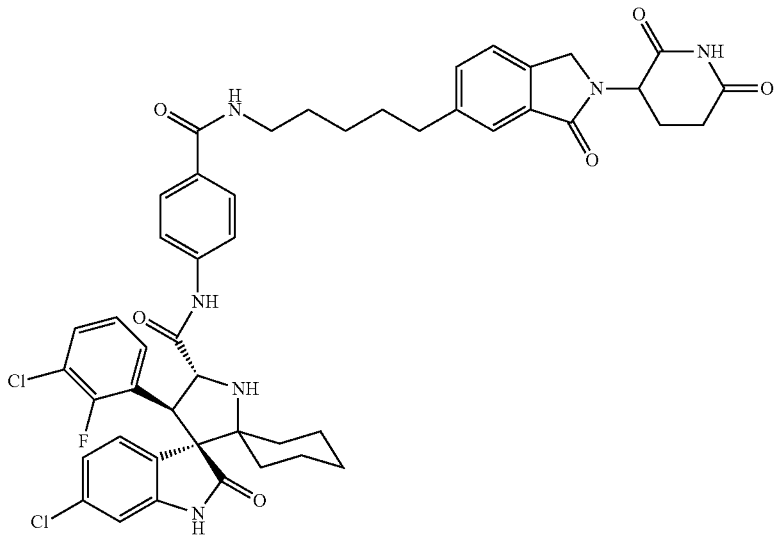 [SMILES: O=C1CCC(N2Cc3ccc(CCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cc3C2=O)C(=O)N1] |
| 198 | 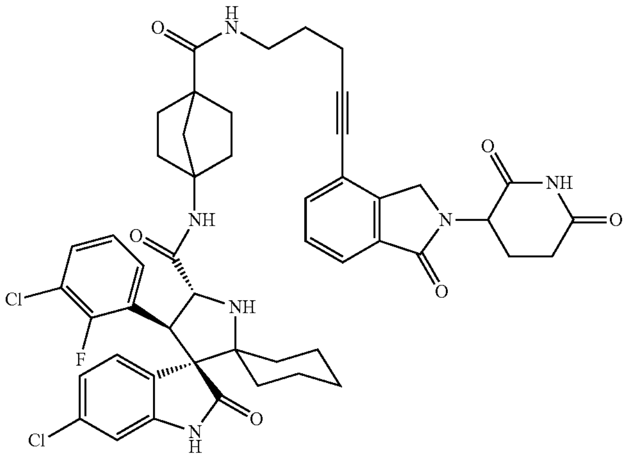 [SMILES: O=C1CCC(N2Cc3c(C#CCCCNC(=O)C45CCC(NC(=O)[C@@H]6NC7(CCCCC7)[C@@]7(C(=O)Nc8cc(Cl)ccc87)[C@H]6c6cccc(Cl)c6F)(CC4)C5)cccc3C2=O)C(=O)N1] |
| 199 | 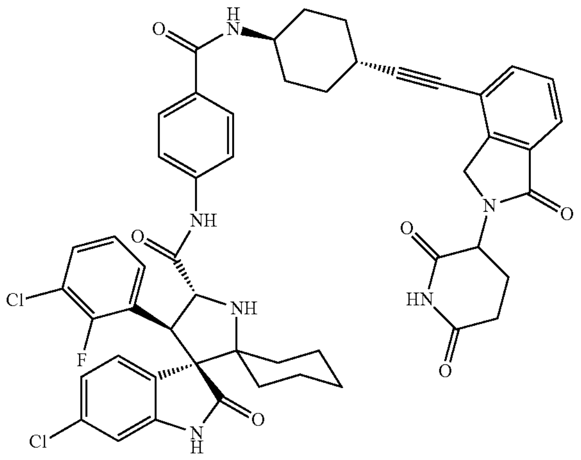 [SMILES: O=C1CCC(N2Cc3c(C#C[C@H]4CC[C@H](NC(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |

TABLE 1C-continued
| Cpd. No. | Structure |
| --- | --- |
| 200 | 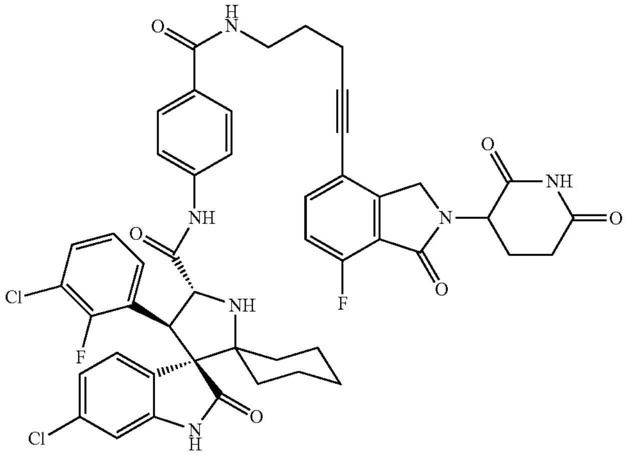 [SMILES: O=C1CCC(N2Cc3c(C#CCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)ccc(F)c3C2=O)C(=O)N1] |
| 201 | 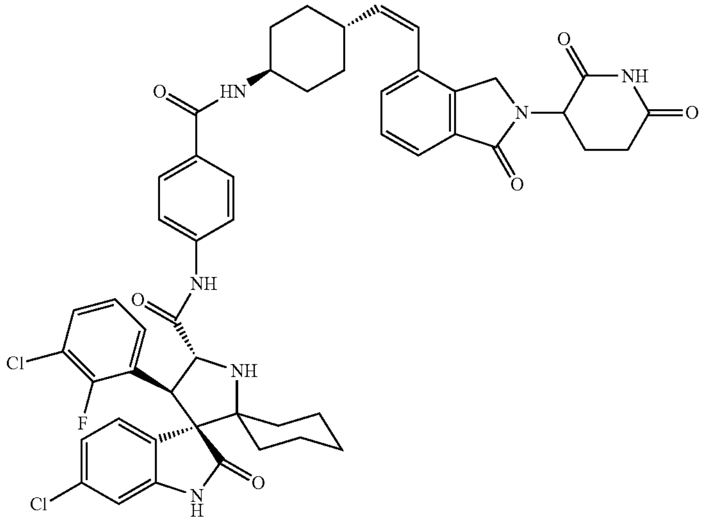 [SMILES: O=C1CCC(N2Cc3c(/C=C\[C@H]4CC[C@H](NC(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |
| 202 | 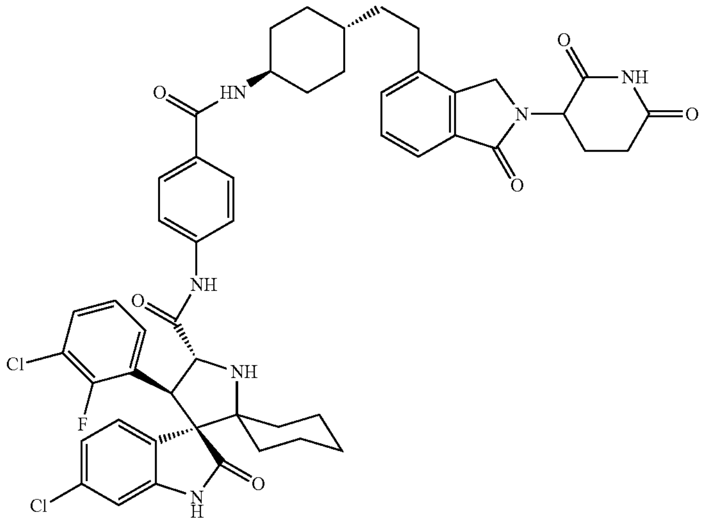 [SMILES: O=C1CCC(N2Cc3c(CC[C@H]4CC[C@H](NC(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |

TABLE 1C-continued
| Cpd. No. | Structure |
|---|---|
| 203 | 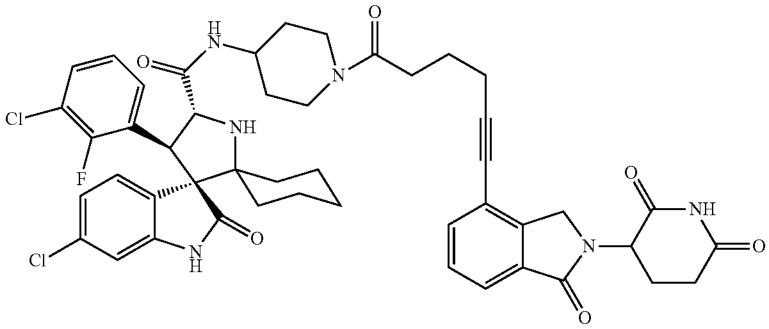 [SMILES: O=C1CCC(N2Cc3c(C#CCCCC(=O)N4CCC(NC(=O)[C@@H]5NC6(CCCCC6)[C@@]6(C(=O)Nc7cc(Cl)ccc76)[C@H]5c5cccc(Cl)c5F)CC4)cccc3C2=O)C(=O)N1] |
| 204 | 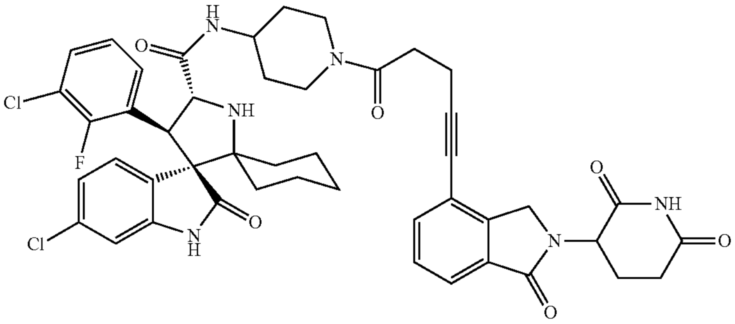 [SMILES: O=C1CCC(N2Cc3c(C#CCCC(=O)N4CCC(NC(=O)[C@@H]5NC6(CCCCC6)[C@@]6(C(=O)Nc7cc(Cl)ccc76)[C@H]5c5cccc(Cl)c5F)CC4)cccc3C2=O)C(=O)N1] |
| 205 | 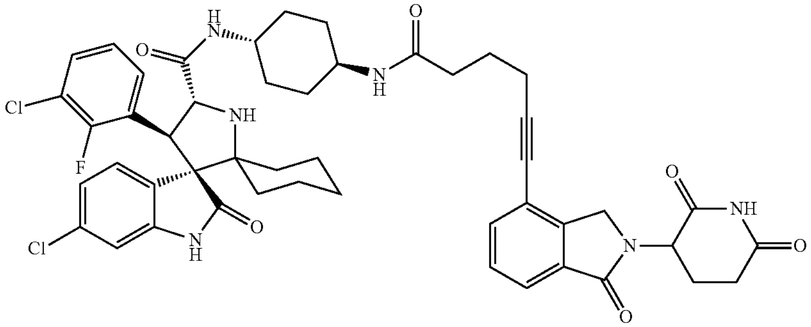 [SMILES: O=C1CCC(N2Cc3c(C#CCCCC(=O)N[C@H]4CC[C@H](NC(=O)[C@@H]5NC6(CCCCC6)[C@@]6(C(=O)Nc7cc(Cl)ccc76)[C@H]5c5cccc(Cl)c5F)CC4)cccc3C2=O)C(=O)N1] |
| 206 | 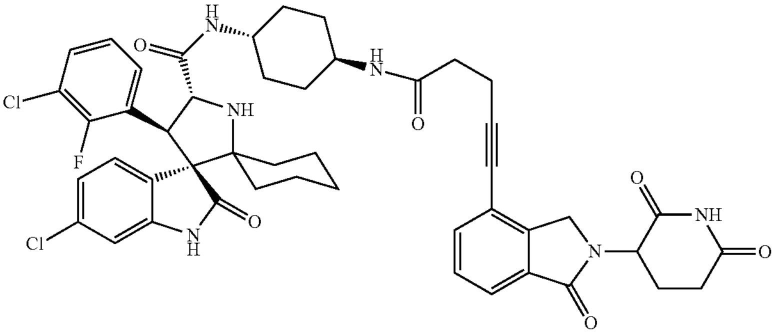 [SMILES: O=C1CCC(N2Cc3c(C#CCCC(=O)N[C@H]4CC[C@H](NC(=O)[C@@H]5NC6(CCCCC6)[C@@]6(C(=O)Nc7cc(Cl)ccc76)[C@H]5c5cccc(Cl)c5F)CC4)cccc3C2=O)C(=O)N1] |

TABLE 1C-continued
| Cpd. No. | Structure |
|---|---|
| 207 | 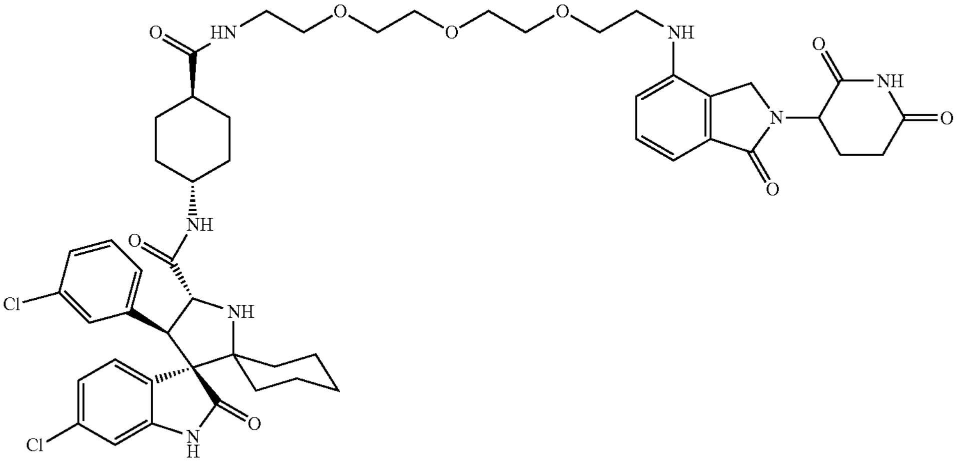 [SMILES: O=C1CCC(N2Cc3c(NCCOCCOCCOCCNC(=O)[C@H]4CC[C@H](NC(=O)[C@@H]5NC6(CCCCC6)[C@@]6(C(=O)Nc7cc(Cl)ccc76)[C@H]5c5cccc(Cl)c5)CC4)cccc3C2=O)C(=O)N1] |
| 208 | 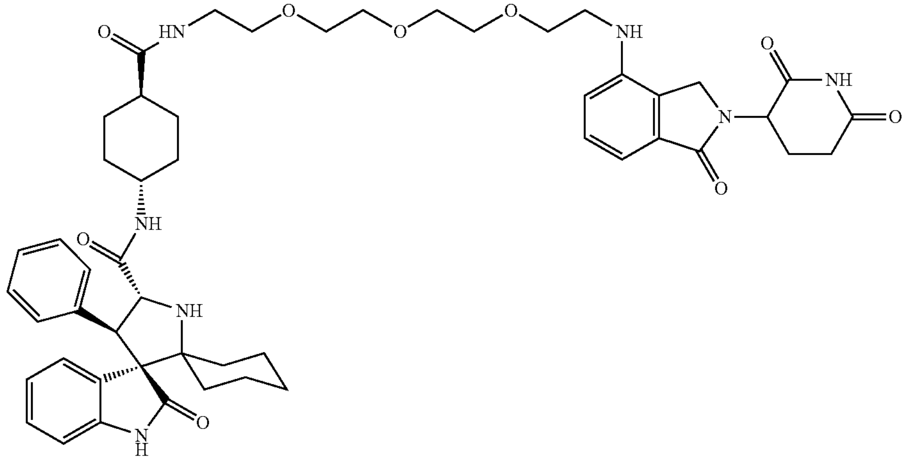 [SMILES: O=C1CCC(N2Cc3c(NCCOCCOCCOCCNC(=O)[C@H]4CC[C@H](NC(=O)[C@@H]5NC6(CCCCC6)[C@@]6(C(=O)Nc7ccccc76)[C@H]5c5ccccc5)CC4)cccc3C2=O)C(=O)N1] |
| 209 | 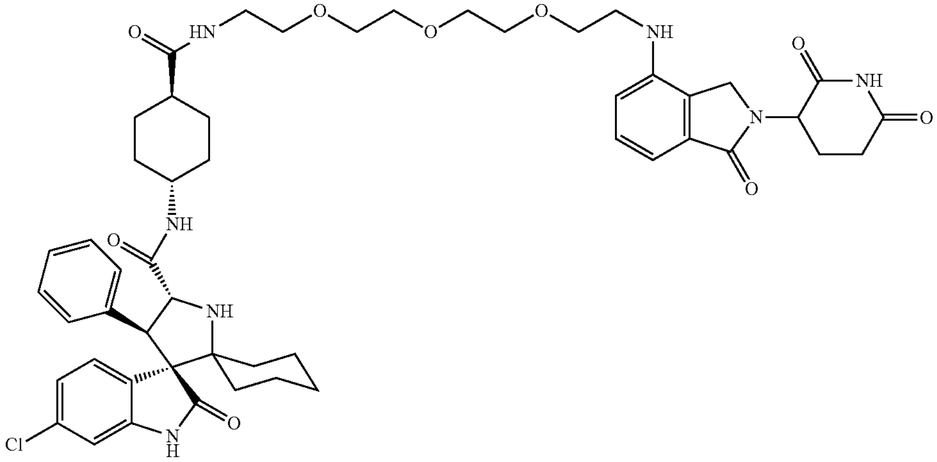 [SMILES: O=C1CCC(N2Cc3c(NCCOCCOCCOCCNC(=O)[C@H]4CC[C@H](NC(=O)[C@@H]5NC6(CCCCC6)[C@@]6(C(=O)Nc7cc(Cl)ccc76)[C@H]5c5ccccc5)CC4)cccc3C2=O)C(=O)N1] |

TABLE 1C-continued
| Cpd. No. | Structure |
| --- | --- |
| 210 | 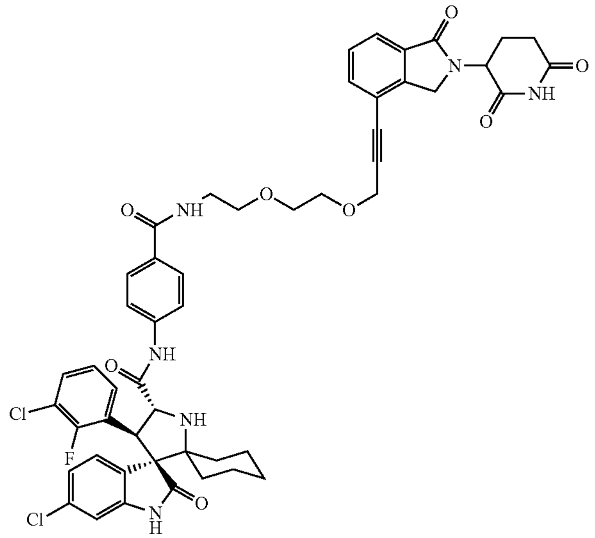 [SMILES: O=C1CCC(N2Cc3c(C#CCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 211 | 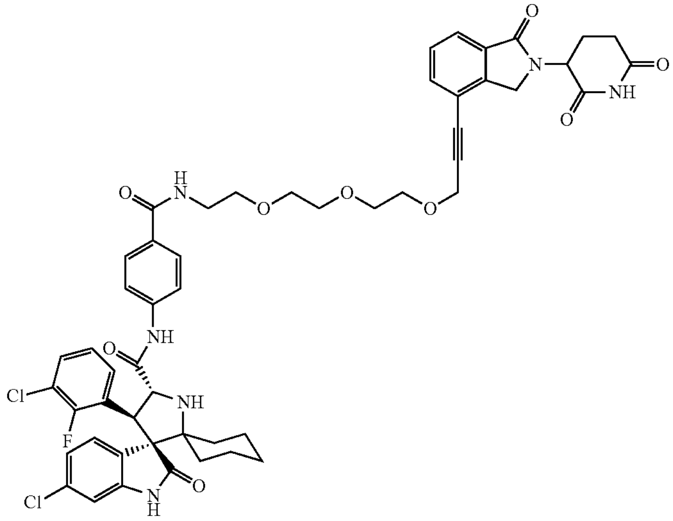 [SMILES: O=C1CCC(N2Cc3c(C#CCOCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 212 | 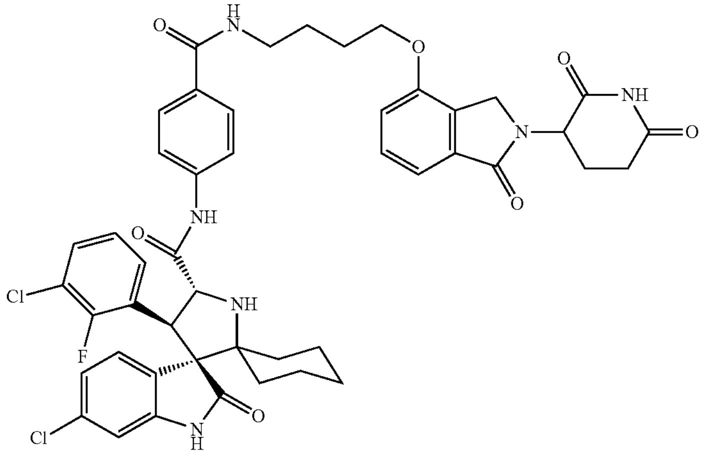 [SMILES: O=C1CCC(N2Cc3c(OCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |

TABLE 1C-continued
| Cpd. No. | Structure |
|---|---|
| 213 | 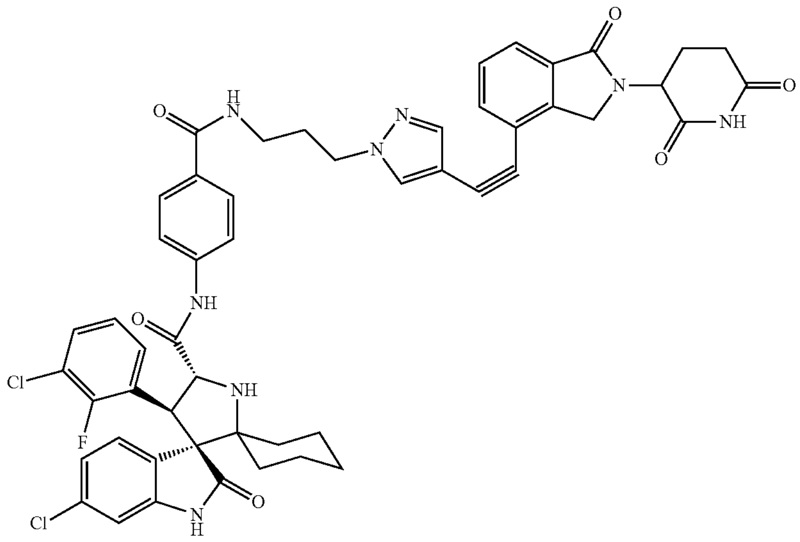 [SMILES: O=C1CCC(N2Cc3c(C#Cc4cnn(CCCNC(=O)c5ccc(NC(=O)[C@@H]6NC7(CCCCC7)[C@@]7(C(=O)Nc8cc(Cl)ccc87)[C@H]6c6cccc(Cl)c6F)cc5)c4)cccc3C2=O)C(=O)N1] |
| 214 | 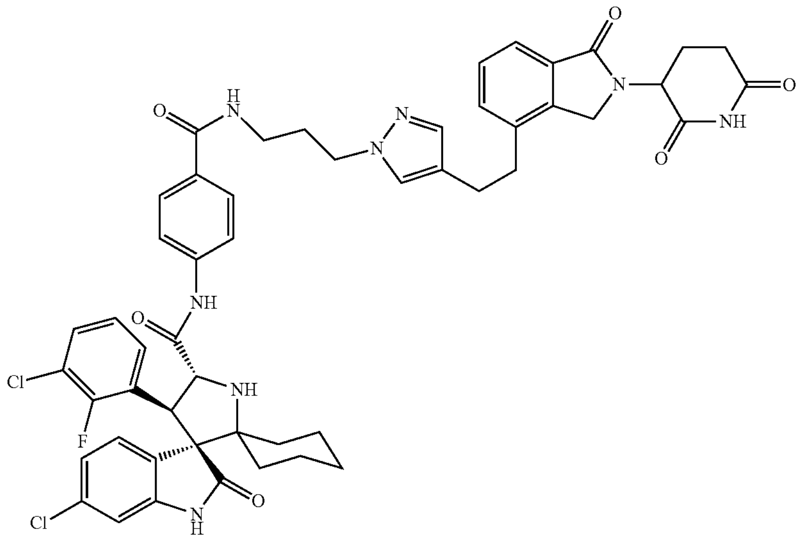 [SMILES: O=C1CCC(N2Cc3c(CCc4cnn(CCCNC(=O)c5ccc(NC(=O)[C@@H]6NC7(CCCCC7)[C@@]7(C(=O)Nc8cc(Cl)ccc87)[C@H]6c6cccc(Cl)c6F)cc5)c4)cccc3C2=O)C(=O)N1] |
| 215 | 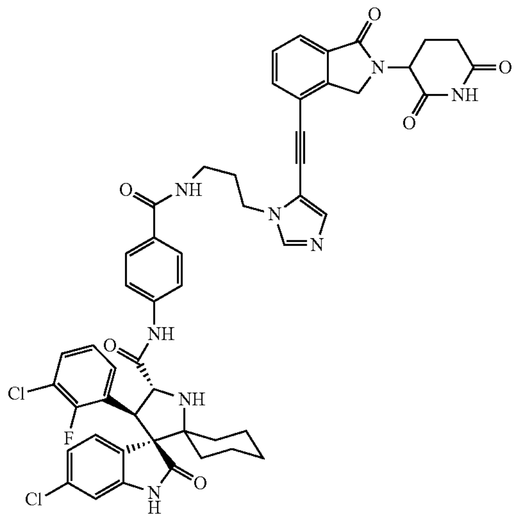 [SMILES: O=C1CCC(N2Cc3c(C#Cc4cncn4CCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |

TABLE 1C-continued
| Cpd. No. | Structure |
|---|---|
| 216 | 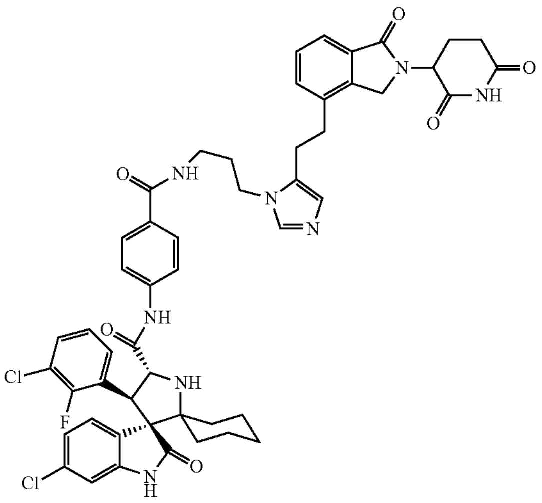 [SMILES: O=C1CCC(N2Cc3c(CCc4cncn4CCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |
| 217 | 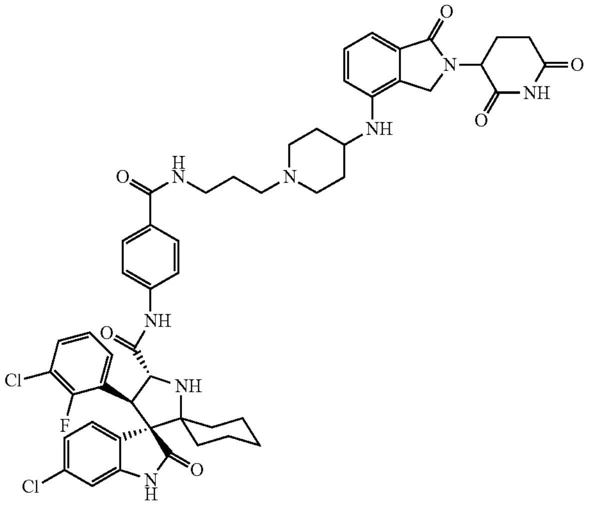 [SMILES: O=C1CCC(N2Cc3c(NC4CCN(CCCNC(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc3C2=O)C(=O)N1] |
| 218 | 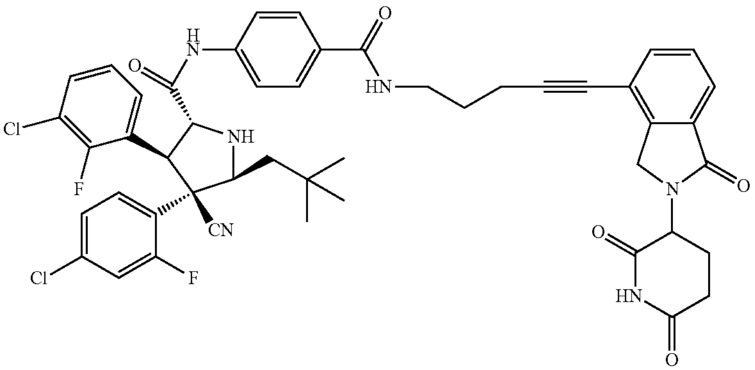 |

TABLE 1C-continued
| Cpd. No. | Structure |
| --- | --- |
| 219 | 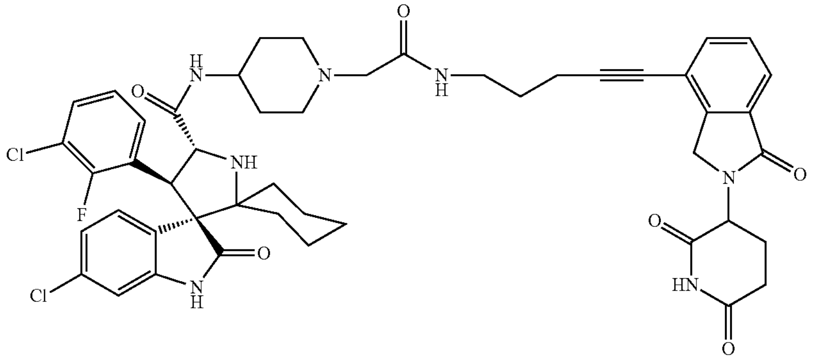 [SMILES: O=C(CN1CCC(NC(=O)[C@@H]2NC3(CCCCC3)[C@@]3(C(=O)Nc4cc(Cl)ccc43)[C@H]2c2cccc(Cl)c2F)CC1)NCCCC#Cc1cccc2c1CN(C1CCC(=O)NC1=O)C2=O] |
| 220 | 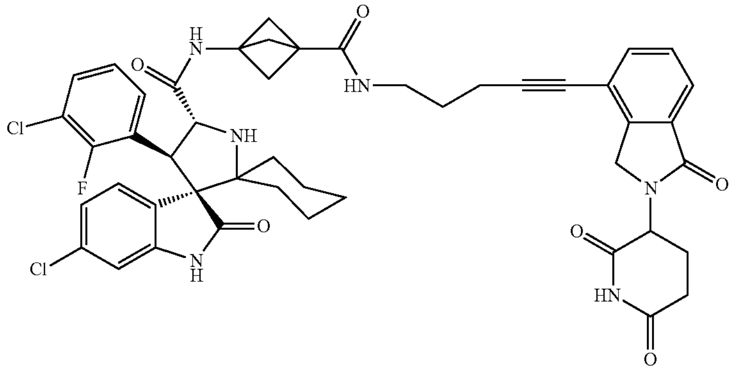 [SMILES: O=C1CCC(N2Cc3c(C#CCCCNC(=O)C45CC(NC(=O)[C@@H]6NC7(CCCCC7)[C@@]7(C(=O)Nc8cc(Cl)ccc87)[C@H]6c6cccc(Cl)c6F)(C4)C5)cccc3C2=O)C(=O)N1] |
| 221 | 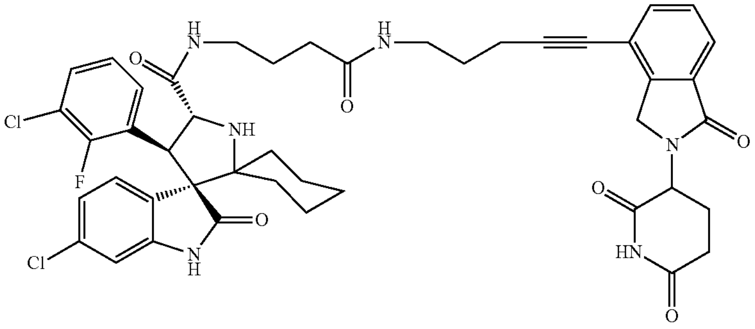 [SMILES: O=C(CCCNC(=O)[C@@H]1NC2(CCCCC2)[C@@]2(C(=O)Nc3cc(Cl)ccc32)[C@H]1c1cccc(Cl)c1F)NCCCC#Cc1cccc2c1CN(C1CCC(=O)NC1=O)C2=O] |
| 222 | 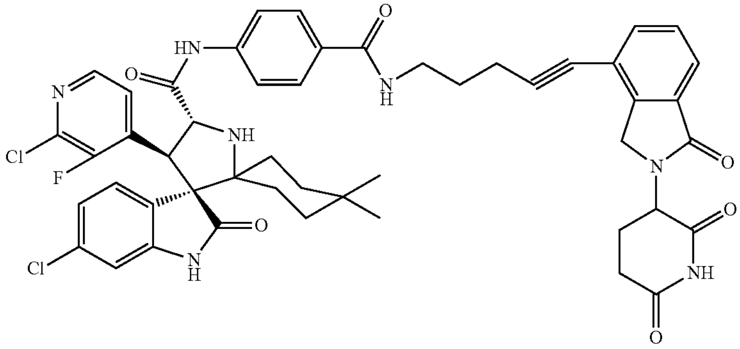 [SMILES: CC1(C)CCC2(CC1)N[C@@H](C(=O)Nc1ccc(C(=O)NCCCC#Cc3cccc4c3CN(C3CCC(=O)NC3=O)C4=O)cc1)[C@H](c1ccnc(Cl)c1F)[C@]21C(=O)Nc2cc(Cl)ccc21] |

TABLE 1C-continued
| Cpd. No. | Structure |
| --- | --- |
| 223 | 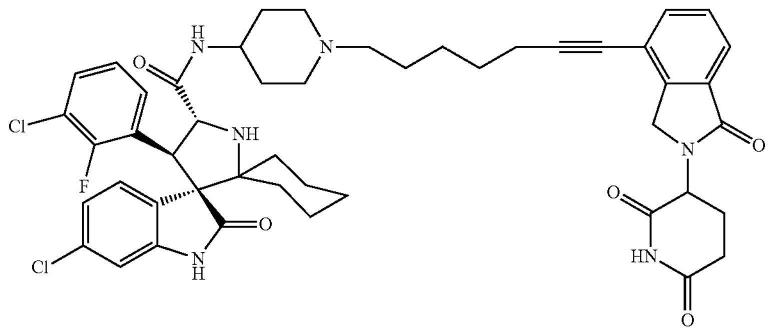 [SMILES: O=C1CCC(N2Cc3c(C#CCCCCCN4CCC(NC(=O)[C@@H]5NC6(CCCCC6)[C@@]6(C(=O)Nc7cc(Cl)ccc76)[C@H]5c5cccc(Cl)c5F)CC4)cccc3C2=O)C(=O)N1] |
| 224 | 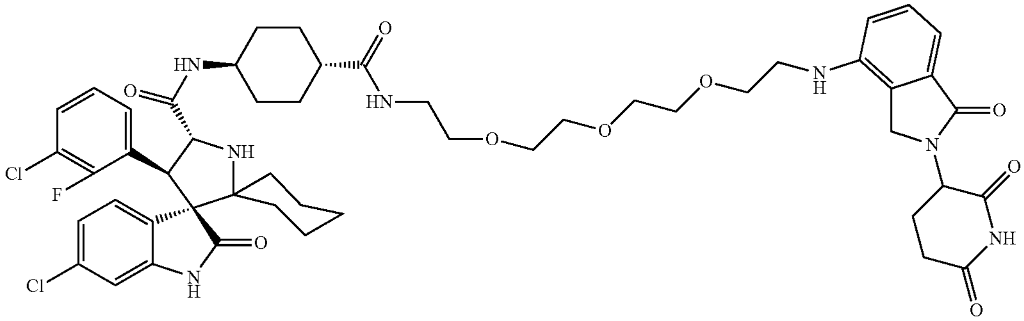 [SMILES: O=C1CCC(N2Cc3c(NCCOCCOCCOCCNC(=O)[C@H]4CC[C@H](NC(=O)[C@@H]5NC6(CCCCC6)[C@@]6(C(=O)Nc7cc(Cl)ccc76)[C@H]5c5cccc(Cl)c5F)CC4)cccc3C2=O)C(=O)N1] |
| 225 | 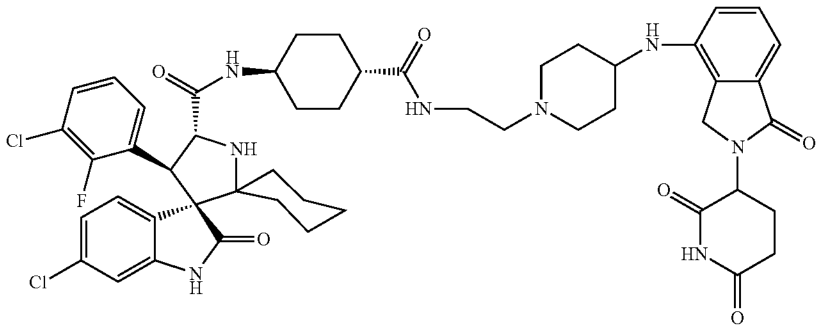 [SMILES: O=C1CCC(N2Cc3c(NC4CCN(CCNC(=O)[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)cccc3C2=O)C(=O)N1] |
| 226 | 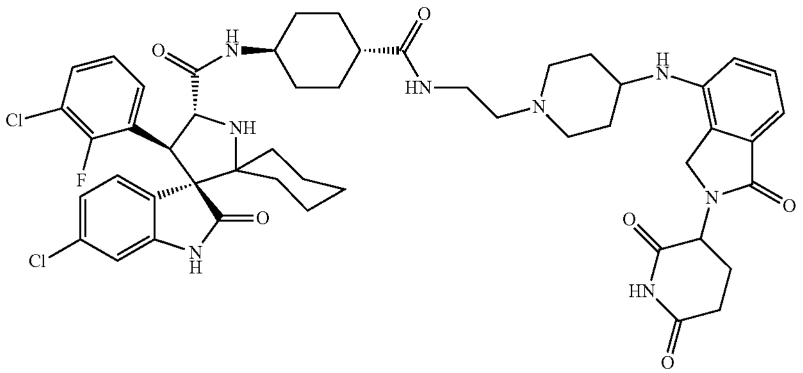 [SMILES: O=C1CCC(N2Cc3c(NC4CCN(CCNC(=O)[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)cccc3C2=O)C(=O)N1] |

TABLE 1C-continued
| Cpd. No. | Structure |
|---|---|
| 227 | 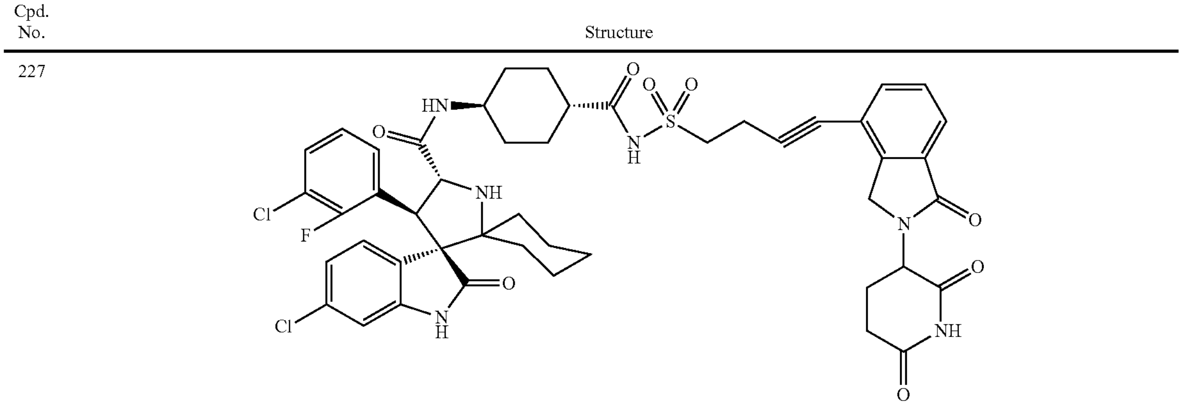 |
| 228 | 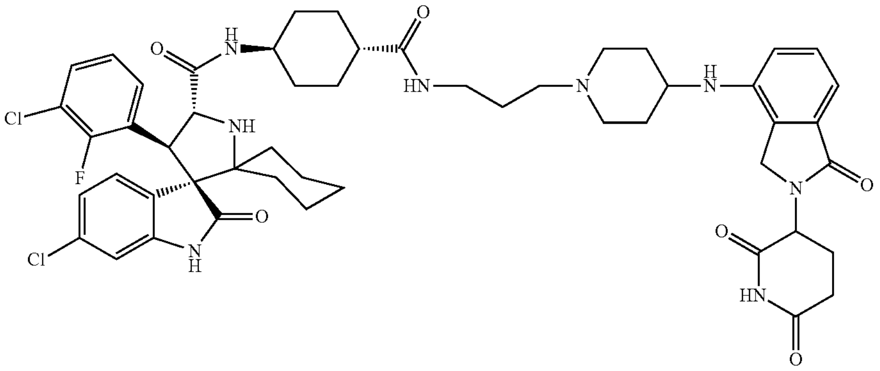 [SMILES: O=C1CCC(N2Cc3c(NC4CCN(CCCNC(=O)[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)cccc3C2=O)C(=O)N1] |
| 229 | 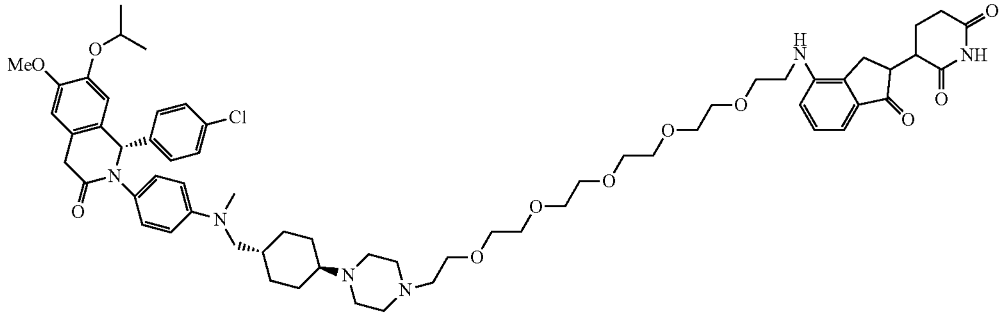 [SMILES: COc1cc2c(cc1OC(C)C)[C@H](c1ccc(Cl)cc1)N(c1ccc(N(C)C[C@H]3CC[C@H](N4CCN(CCOCCOCCOCCOCCOCCNc5cccc6c5CC(C5CCC(=O)NC5=O)C6=O)CC4)CC3)cc1)C(=O)C2] |
| 230 | 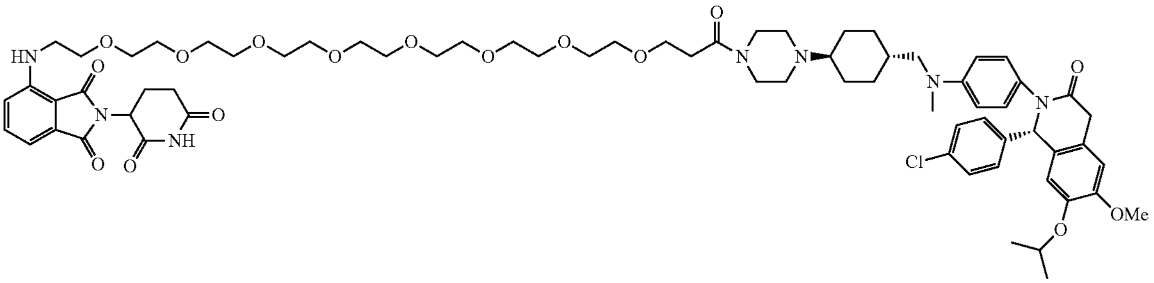 [SMILES: COc1cc2c(cc1OC(C)C)[C@H](c1ccc(Cl)cc1)N(c1ccc(N(C)C[C@H]3CC[C@H](N4CCN(C(=O)CCOCCOCCOCCOCCOCCOCCOCCOCCNc5cccc6c5C(=O)N(C5CCC(=O)NC5=O)C6=O)CC4)CC3)cc1)C(=O)C2] |
| 231 | 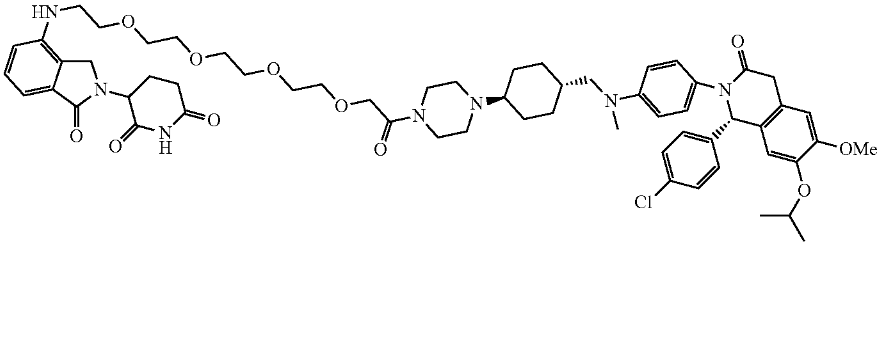 [SMILES: COc1cc2c(cc1OC(C)C)[C@H](c1ccc(Cl)cc1)N(c1ccc(N(C)C[C@H]3CC[C@H](N4CCN(C(=O)COCCOCCOCCOCCNc5cccc6c5CN(C5CCC(=O)NC5=O)C6=O)CC4)CC3)cc1)C(=O)C2] |

TABLE 1C-continued
| Cpd. No. | Structure |
|---|---|
| 232 | 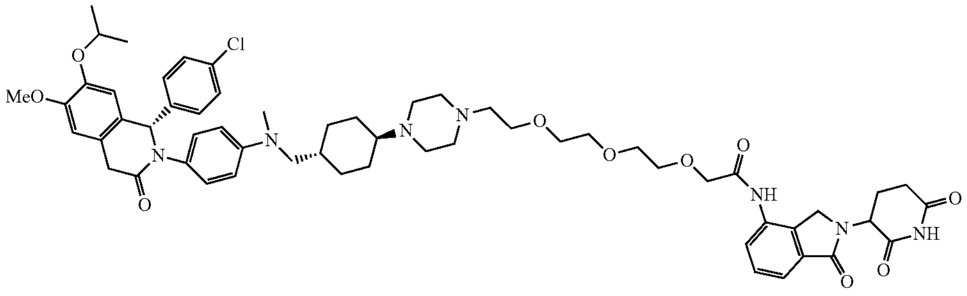 [SMILES: COc1cc2c(cc1OC(C)C)[C@H](c1ccc(Cl)cc1)N(c1ccc(N(C)C[C@H]3CC[C@H](N4CCN(CCOCCOCCOCC(=O)Nc5cccc6c5CN(C5CCC(=O)NC5=O)C6=O)CC4)CC3)cc1)C(=O)C2] |
| 233 | 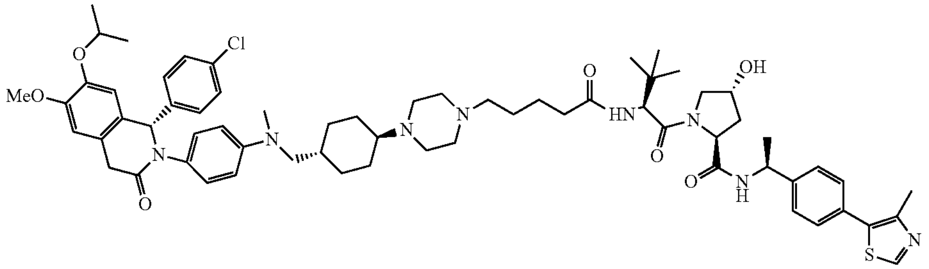 [SMILES: COc1cc2c(cc1OC(C)C)[C@H](c1ccc(Cl)cc1)N(c1ccc(N(C)C[C@H]3CC[C@H](N4CCN(CCCCC(=O)N[C@H](C(=O)N5C[C@H](O)C[C@H]5C(=O)N[C@@H](C)c5ccc(-c6scnc6C)cc5)C(C)(C)C)CC4)CC3)cc1)C(=O)C2] |
| 234 | 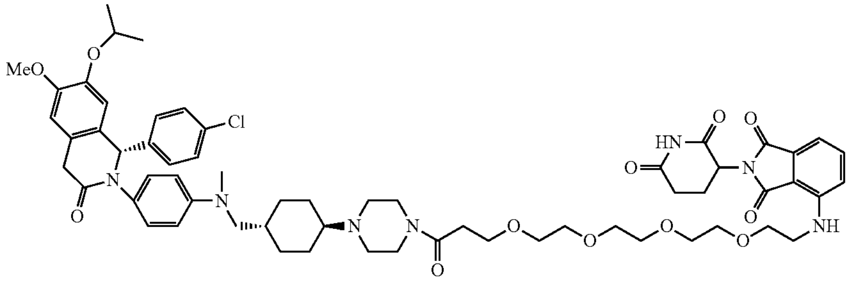 [SMILES: COc1cc2c(cc1OC(C)C)[C@H](c1ccc(Cl)cc1)N(c1ccc(N(C)C[C@H]3CC[C@H](N4CCN(C(=O)CCOCCOCCOCCOCCNc5cccc6c5C(=O)N(C5CCC(=O)NC5=O)C6=O)CC4)CC3)cc1)C(=O)C2] |
| 235 | 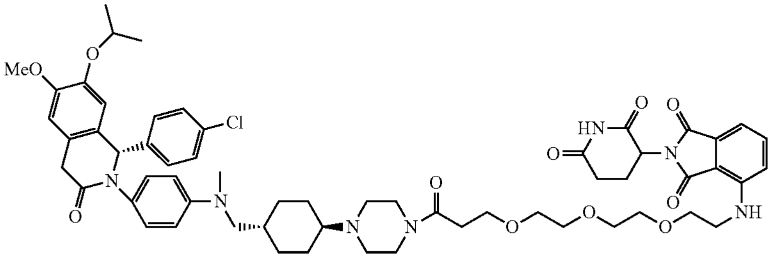 [SMILES: COc1cc2c(cc1OC(C)C)[C@H](c1ccc(Cl)cc1)N(c1ccc(N(C)C[C@H]3CC[C@H](N4CCN(C(=O)CCOCCOCCOCCNc5cccc6c5C(=O)N(C5CCC(=O)NC5=O)C6=O)CC4)CC3)cc1)C(=O)C2] |
| 236 | 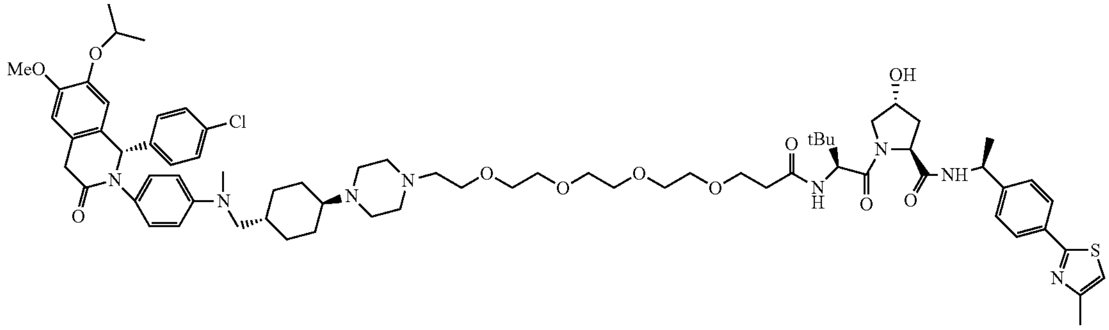 [SMILES: COc1cc2c(cc1OC(C)C)[C@H](c1ccc(Cl)cc1)N(c1ccc(N(C)C[C@H]3CC[C@H](N4CCN(CCOCCOCCOCCOCCC(=O)N[C@H](C(=O)N5C[C@H](O)C[C@H]5C(=O)N[C@@H](C)c5ccc(-c6nc(C)cs6)cc5)C(C)(C)C)CC4)CC3)cc1)C(=O)C2] |

TABLE 1C-continued
| Cpd. No. | Structure |
|---|---|
| 237 | 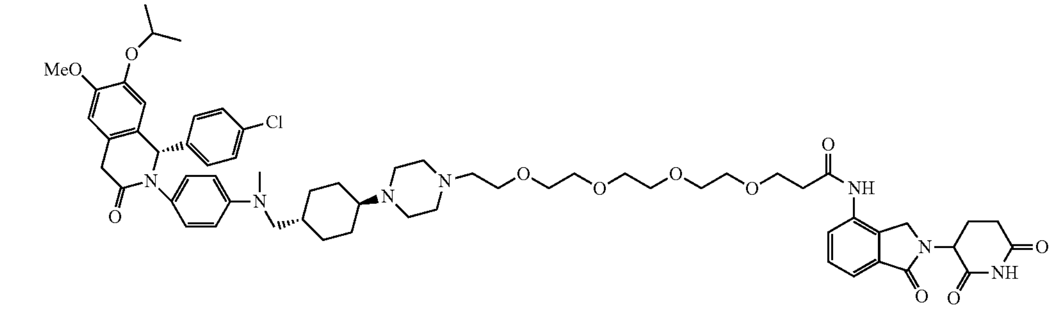 [SMILES: COc1cc2c(cc1OC(C)C)[C@H](c1ccc(Cl)cc1)N(c1ccc(N(C)C[C@H]3CC[C@H](N4CCN(CCOCCOCCOCCOCCC(=O)Nc5cccc6c5CN(C5CCC(=O)NC5=O)C6=O)CC4)CC3)cc1)C(=O)C2] |
| 238 | 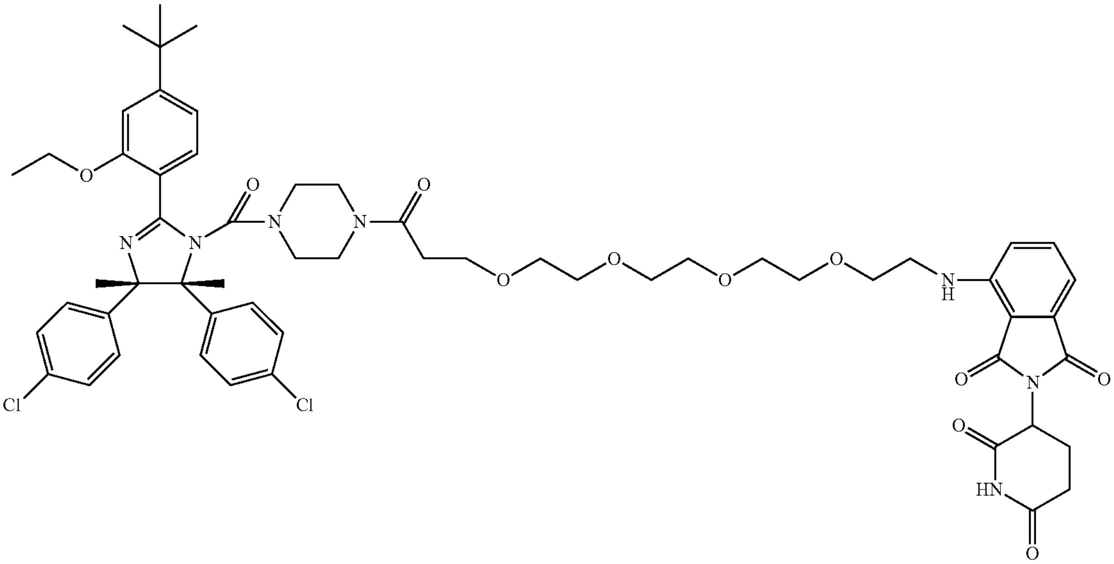 [SMILES: CCOc1cc(C(C)(C)C)ccc1C1=N[C@@](C)(c2ccc(Cl)cc2)[C@@](C)(c2ccc(Cl)cc2)N1C(=O)N1CCN(C(=O)CCOCCOCCOCCOCCNc2cccc3c2C(=O)N(C2CCC(=O)NC2=O)C3=O)CC1] |
| 239 | 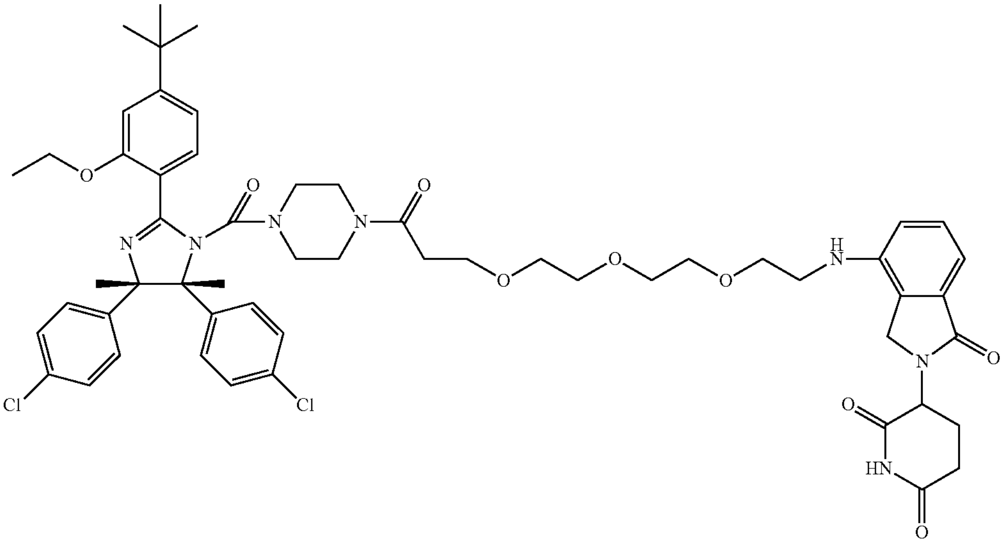 [SMILES: CCOc1cc(C(C)(C)C)ccc1C1=N[C@@](C)(c2ccc(Cl)cc2)[C@@](C)(c2ccc(Cl)cc2)N1C(=O)N1CCN(C(=O)CCOCCOCCOCCNc2cccc3c2CN(C2CCC(=O)NC2=O)C3=O)CC1] |

TABLE 1C-continued
| Cpd. No. | Structure |
|---|---|
| 240 | 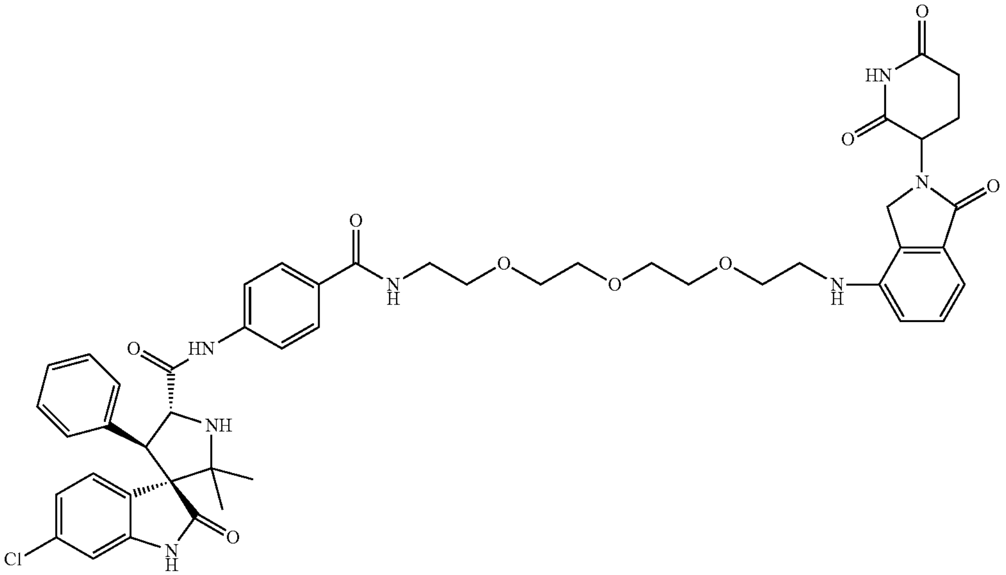 [SMILES: CC1(C)N[C@@H](C(=O)Nc2ccc(C(=O)NCCOCCOCCOCCNc3cccc4c3CN(C3CCC(=O)NC3=O)C4=O)cc2)[C@H](c2ccccc2)[C@]12C(=O)Nc1cc(Cl)ccc12] |
| 241 | 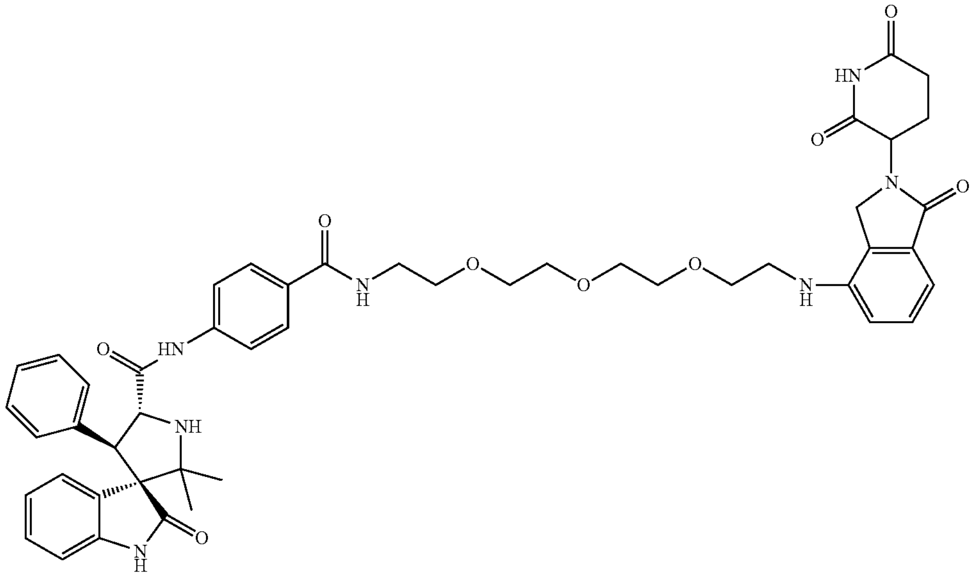 [SMILES: CC1(C)N[C@@H](C(=O)Nc2ccc(C(=O)NCCOCCOCCOCCNc3cccc4c3CN(C3CCC(=O)NC3=O)C4=O)cc2)[C@H](c2ccccc2)[C@]12C(=O)Nc1ccccc12] |

TABLE 1C-continued
| Cpd. No. | Structure |
|---|---|
| 242 | 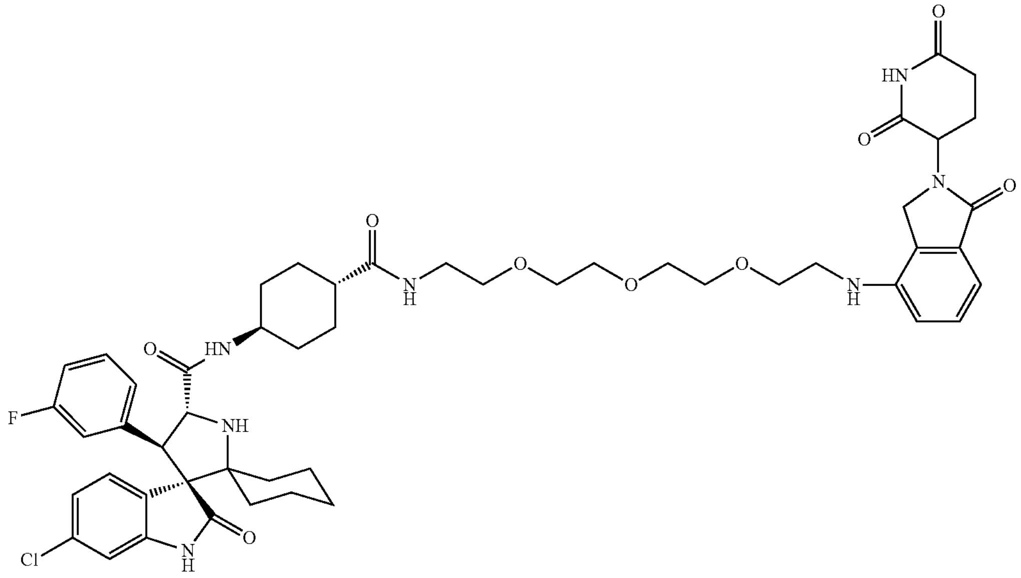 [SMILES: O=C1CCC(N2Cc3c(NCCOCCOCCOCCNC(=O)[C@H]4CC[C@H](NC(=O)[C@@H]5NC6(CCCCC6)[C@@]6(C(=O)Nc7cc(Cl)ccc76)[C@H]5c5cccc(F)c5)CC4)cccc3C2=O)C(=O)N1] |
| 243 | 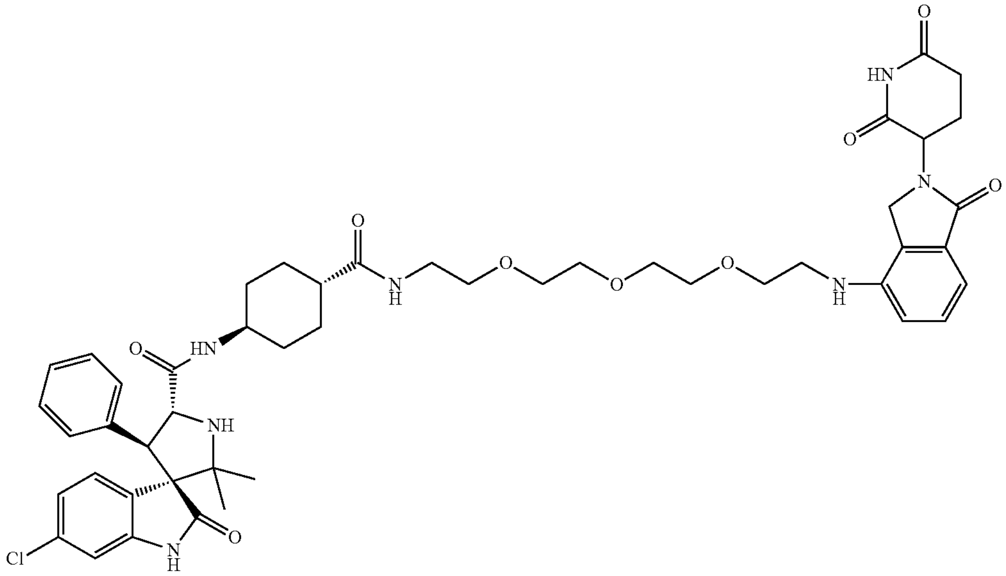 [SMILES: CC1(C)N[C@@H](C(=O)N[C@H]2CC[C@H](C(=O)NCCOCCOCCOCCNc3cccc4c3CN(C3CCC(=O)NC3=O)C4=O)CC2)[C@H](c2ccccc2)[C@]12C(=O)Nc1cc(Cl)ccc12] |

TABLE 1C-continued

| Cpd. No. | Structure |
|---|---|
| 244 | 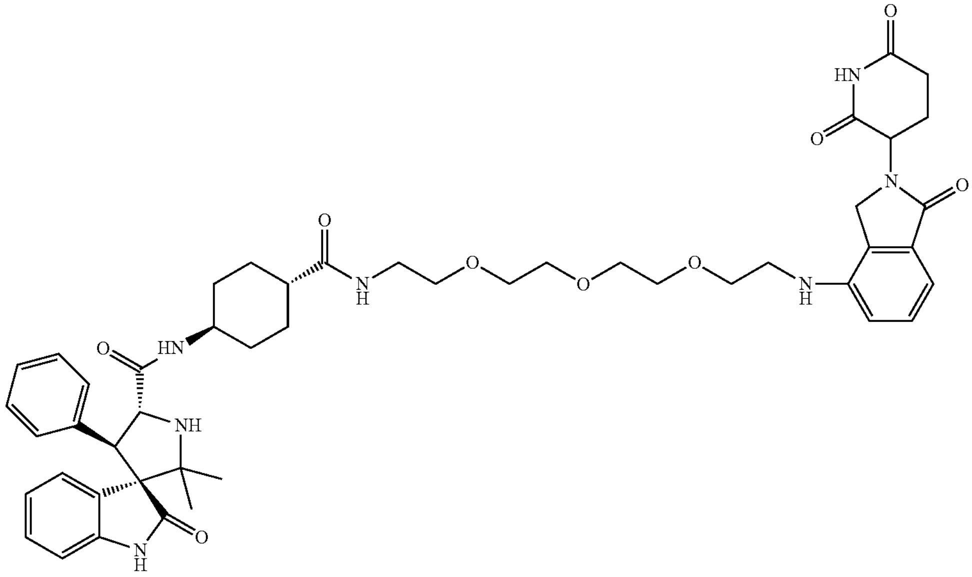 [SMILES: CC1(C)N[C@@H](C(=O)N[C@H]2CC[C@H](C(=O)NCCOCCOCCOCCNc3cccc4c3CN(C3CCC(=O)NC3=O)C4=O)CC2)[C@H](c2ccccc2)[C@]12C(=O)Nc1ccccc12] |

Intermediates of the Disclosure are compounds that can be used as synthetic intermediates to prepare Compounds of the Disclosure. In one embodiment, Intermediates of the Disclosure are compounds represented by Formula IV:

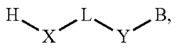

IV and the pharmaceutically acceptable salts or solvates thereof, wherein:

B is selected from the group consisting of:

B-1

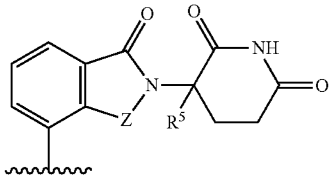

and

B-2

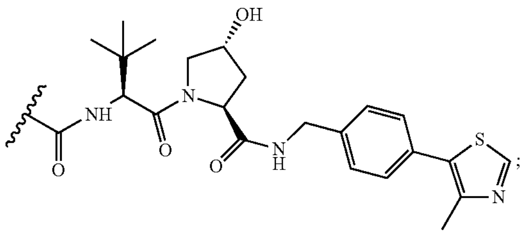

;

X is selected from the group consisting of —N($R^{2a}$)—,

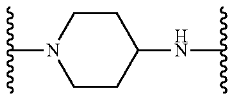 [SMILES: *NC1CCN(*)CC1]

, and

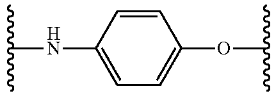 [SMILES: *Nc1ccc(O*)cc1]

;

or

X is absent;

wherein the —N(H)— of

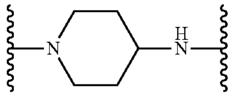

is attached to L and the —O— of

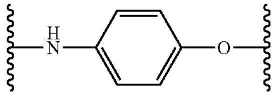

is attached to L;

L is selected from the group consisting of alkylenyl, heteroalkylenyl, and —$(CH_2)_m$—W—$(CH_2)_n$—;

W is selected from the group consisting of optionally substituted phenylenyl, optionally substituted 5-membered heteroarylenyl, and optionally substituted 6-membered heteroarylenyl;

m is 0, 1, 2, 3, 4, 5, 6, or 7;

n is 0, 1, 2, 3, 4, 5, 6, 7, or 8;

Y is selected from the group consisting of —C≡C—, —O—, —N($R^{2b}$)—, —C(═O)N($R^{2c}$)—, —N($R^{2d}$)C(═O)$CH_2$O—, and —N($R^{2e}$)C(═O)$CH_2$N($R^{2f}$)—; or Y is absent;

wherein the carboxamide nitrogen atom of —N($R^{2d}$)C(═O)$CH_2$O— and —N($R^{2e}$)C(═O)$CH_2$N($R^{2f}$)—, and the carbon atom of —C(═O)N($R^{2c}$)— is attached to L;

$R^{2a}$, $R^{2b}$, $R^{2c}$, $R^{2d}$, $R^{2e}$, and $R^{2f}$ are each independently selected from the group consisting of hydrogen and $C_{1-4}$ alkyl;

Z is selected from the group consisting of —$CH_2$ and —C(═O)—; and $R^5$ is selected from the group consisting of hydrogen, methyl, and fluoro, with the proviso that Y is absent when B is B-2.

In another embodiment, Intermediates of the Disclosure are compounds represented by Formula V:

V

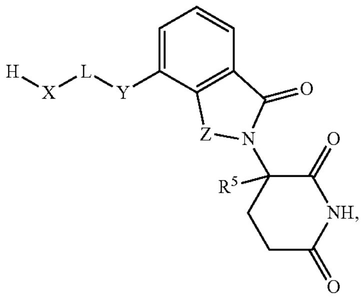

and the pharmaceutically acceptable salts or solvates thereof. In another embodiment, $R^5$ is hydrogen. In another embodiment, Z is —$CH_2$—. In another embodiment, Z is —C(═O)—. In another embodiment, Y is selected from the group consisting of —C≡C—, —O—, —N(H)—, —C(═O)N(H)—, —N(H)C(═O)$CH_2$O—, and —N(H)C(═O)$CH_2$N(H)—. In another embodiment, Y is selected from the group consisting of —C≡C—, —O—, and —N(H)—. In another embodiment, Y is absent.

In another embodiment, Intermediates of the Disclosure are compounds represented by Formula VI:

VI

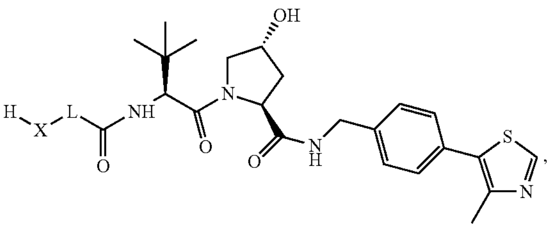

and the pharmaceutically acceptable salts or solvates thereof.

In another embodiment, Intermediates of the Disclosure are compounds represented by any one of Formulae IV-VI, and the pharmaceutically acceptable salts or solvates thereof, wherein X is selected from the group consisting of —N(H)—,

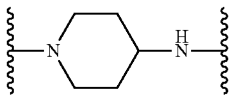

, and

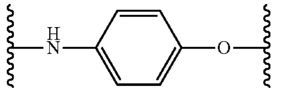

.

In another embodiment, Intermediates of the Disclosure are compounds represented by any one of Formulae IV-VI, and the pharmaceutically acceptable salts or solvates thereof, wherein L is $C_{1-12}$ alkylenyl. In another embodiment, L is selected from the group consisting of —$CH_2$—, —$CH_2CH_2$—, —$CH_2CH_2CH_2$—, —$CH_2(CH_2)_2CH_2$—, —$CH_2(CH_2)_3CH_2$—, —$CH_2(CH_2)_4CH_2$—, —$CH_2(CH_2)_5CH_2$—, and —$CH_2(CH_2)_6CH_2$—.

In another embodiment, Intermediates of the Disclosure are compounds represented by any one of Formulae IV-VI, and the pharmaceutically acceptable salts or solvates thereof, wherein L is 3- to 20-membered heteroalkylenyl. In another embodiment, L is selected from the group consisting of —$(CH_2)_o$O—$(CH_2CH_2O)_p$—$(CH_2)_q$— and —$(CH_2)_r$O—$(CH_2)_s$—O$(CH_2)_t$—; wherein o is 2 or 3; p is 0, 1, 2, 3, 4, 5, 6, or 7; q is 2 or 3; r is 2, 3, or 4; s is 3, 4, or 5; and t is 2 or 3. In another embodiment, L is selected from the group consisting of —$CH_2CH_2OCH_2CH_2$—,
—$CH_2CH_2O(CH_2CH_2O)_2CH_2CH_2$—,
—$CH_2CH_2O(CH_2CH_2O)_3CH_2CH_2$—,
—$CH_2CH_2O(CH_2CH_2O)_4CH_2CH_2$—,
—$CH_2CH_2O(CH_2CH_2O)_6CH_2CH_2$—,
—$CH_2CH_2O(CH_2CH_2O)_6CH_2CH_2$—,
—$CH_2CH_2CH_2OCH_2CH_2OCH_2CH_2CH_2$—,
—$CH_2CH_2CH_2O(CH_2CH_2O)_2CH_2CH_2CH_2$—, and
—$CH_2CH_2CH_2O(CH_2)_4OCH_2CH_2CH_2$—.

In another embodiment, Intermediates of the Disclosure are compounds represented by any one of Formulae IV-VI, and the pharmaceutically acceptable salts or solvates thereof, wherein L is —$(CH_2)_m$—W—$(CH_2)_n$—. In another embodiment, W is phenylenyl. In another embodiment, W is 5-membered heteroarylenyl. In another embodiment, W is 6-membered heteroarylenyl.

In another embodiment, Intermediates of the Disclosure are compounds represented by any one of Formulae IV-VI, and the pharmaceutically acceptable salts or solvates thereof wherein F is selected from the group consisting of:

L-1

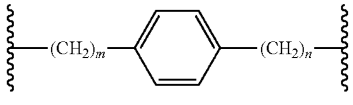

and

L-2

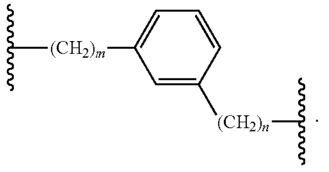

.

In another embodiment, Intermediates of the Disclosure are compounds represented by any one of Formulae IV-VI, and the pharmaceutically acceptable salts or solvates thereof, wherein L is selected from the group consisting of:

L-3

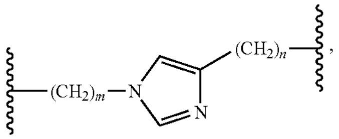

,

L-4

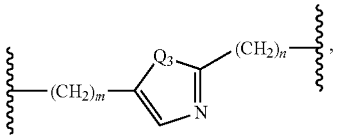

,

L-5

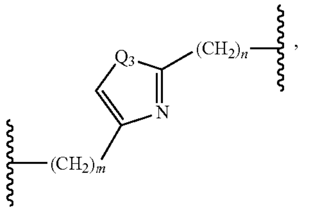

,

L-6

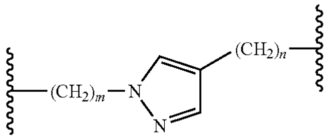

and

L-7

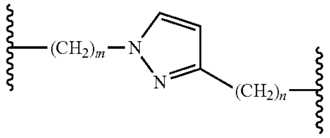

; and $Q^3$ is selected from the group consisting of —O—, —S—, and —N($R^6$)—; and $R^6$ is selected from the group consisting of hydrogen and $C_{1-4}$ alkyl.

In another embodiment, Intermediates of the Disclosure are compounds represented by any one of Formulae IV-VI, and the pharmaceutically acceptable salts or solvates thereof, wherein L is selected from the group consisting of:

L-8

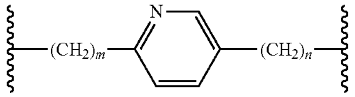

and

L-9

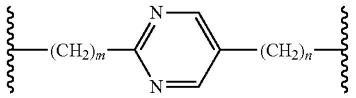

.

In another embodiment, Intermediates of the Disclosure are compounds of Table 2, and the pharmaceutically acceptable salts and solvates thereof.

TABLE 2

| Cpd. No. | Structure |
|---|---|
| 70 | 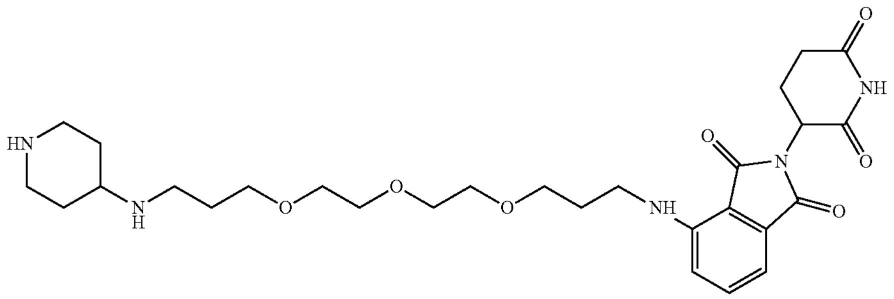 [SMILES: O=C1CCC(N2C(=O)c3cccc(NCCCOCCOCCOCCCNC4CCNCC4)c3C2=O)C(=O)N1] |
| 71 | 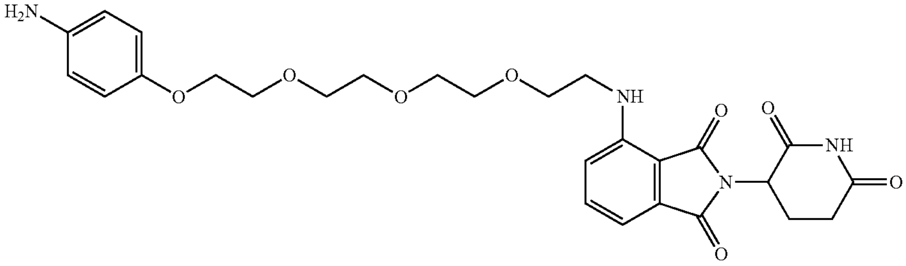 [SMILES: Nc1ccc(OCCOCCOCCOCCNc2cccc3c2C(=O)N(C2CCC(=O)NC2=O)C3=O)cc1] |

TABLE 2-continued
| Cpd. No. | Structure |
|---|---|
| 72 | 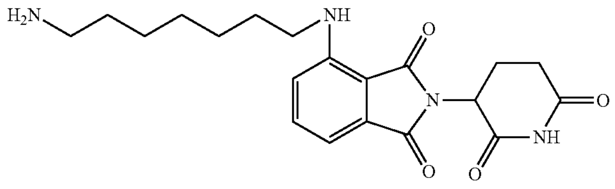 [SMILES: NCCCCCCCNc1cccc2c1C(=O)N(C1CCC(=O)NC1=O)C2=O] |
| 73 | 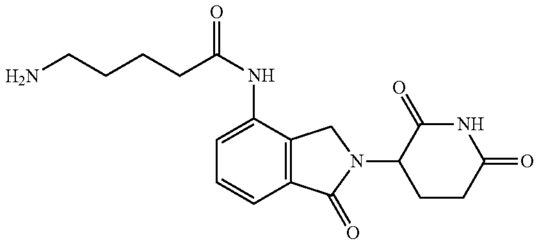 [SMILES: NCCCCC(=O)Nc1cccc2c1CN(C1CCC(=O)NC1=O)C2=O] |
| 74 | 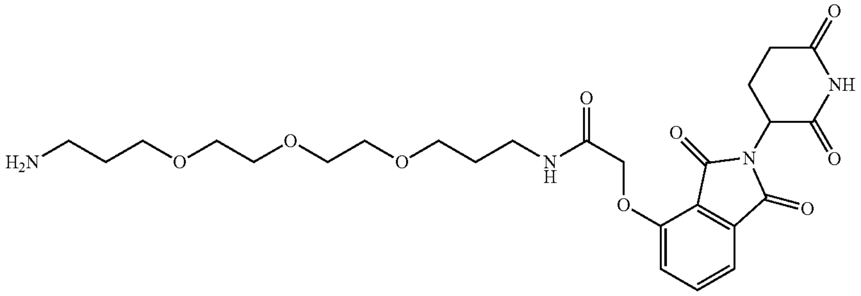 [SMILES: NCCCOCCOCCOCCCNC(=O)COc1cccc2c1C(=O)N(C1CCC(=O)NC1=O)C2=O] |
| 75 | 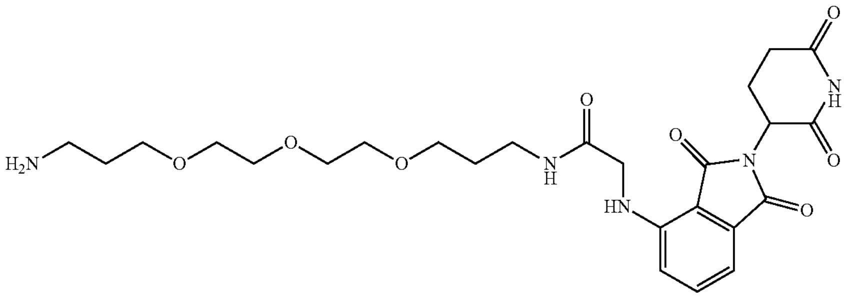 [SMILES: NCCCOCCOCCOCCCNC(=O)CNc1cccc2c1C(=O)N(C1CCC(=O)NC1=O)C2=O] |
| 76 | 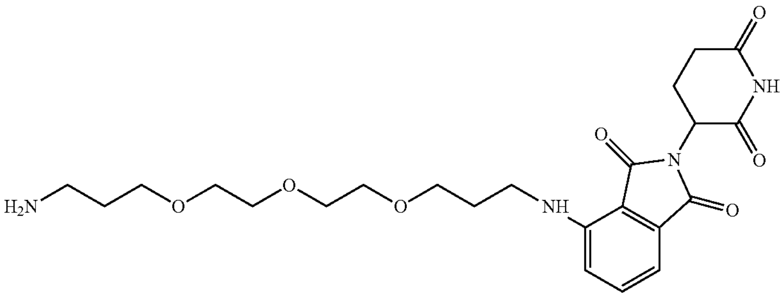 [SMILES: NCCCOCCOCCOCCCNc1cccc2c1C(=O)N(C1CCC(=O)NC1=O)C2=O] |

TABLE 2-continued
| Cpd. No. | Structure |
|---|---|
| 77 | 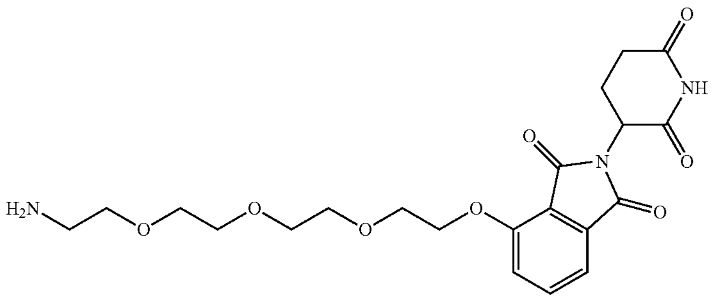 [SMILES: NCCOCCOCCOCCOc1cccc2c1C(=O)N(C1CCC(=O)NC1=O)C2=O] |
| 78 | 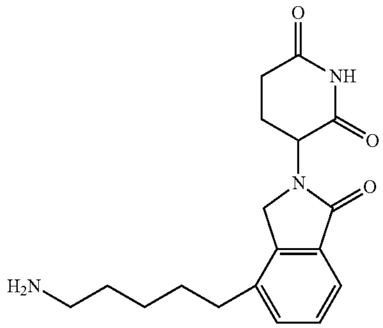 [SMILES: NCCCCCc1cccc2c1CN(C1CCC(=O)NC1=O)C2=O] |
| 79 | 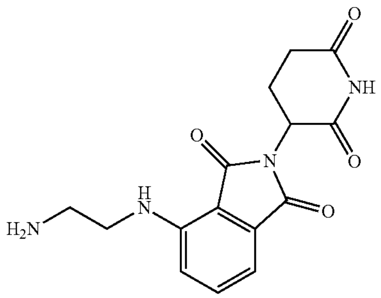 [SMILES: NCCNc1cccc2c1C(=O)N(C1CCC(=O)NC1=O)C2=O] |
| 80 | 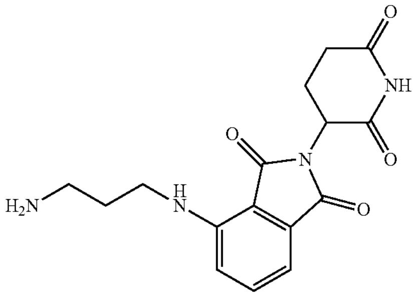 [SMILES: NCCCNc1cccc2c1C(=O)N(C1CCC(=O)NC1=O)C2=O] |
| 81 | 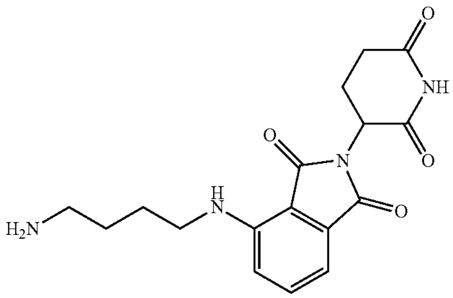 [SMILES: NCCCCNc1cccc2c1C(=O)N(C1CCC(=O)NC1=O)C2=O] |

TABLE 2-continued
| Cpd. No. | Structure |
|---|---|
| 82 | 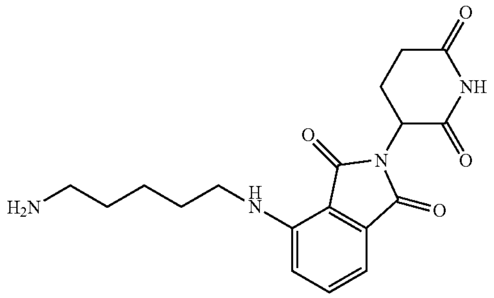 [SMILES: NCCCCCNc1cccc2c1C(=O)N(C1CCC(=O)NC1=O)C2=O] |
| 83 | 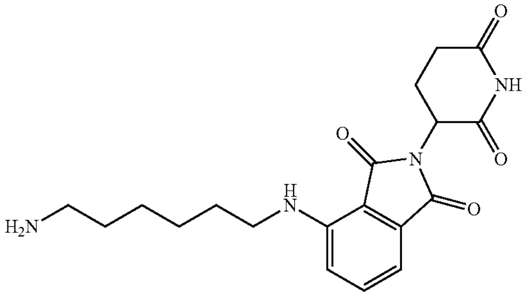 [SMILES: NCCCCCCNc1cccc2c1C(=O)N(C1CCC(=O)NC1=O)C2=O] |
| 84 | 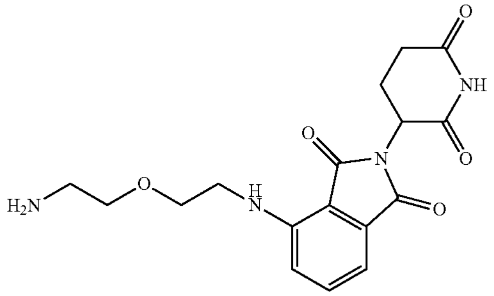 |
| 85 | 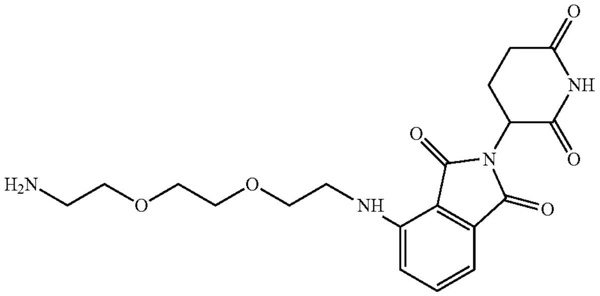 [SMILES: NCCOCCOCCNc1cccc2c1C(=O)N(C1CCC(=O)NC1=O)C2=O] |
| 86 | 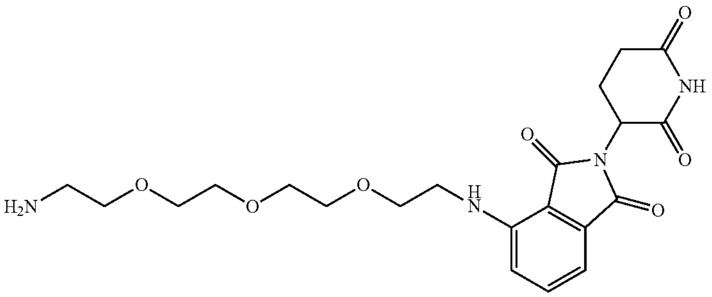 [SMILES: NCCOCCOCCOCCNc1cccc2c1C(=O)N(C1CCC(=O)NC1=O)C2=O] |

TABLE 2-continued
| Cpd. No. | Structure |
|---|---|
| 87 | 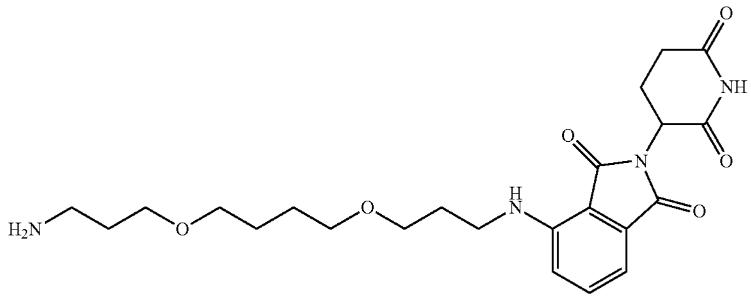 [SMILES: NCCCOCCCCOCCCNc1cccc2c1C(=O)N(C1CCC(=O)NC1=O)C2=O] |
| 88 | 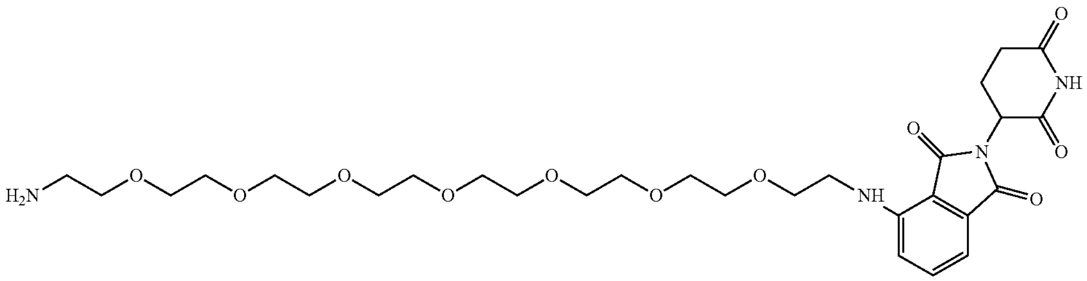 [SMILES: NCCOCCOCCOCCOCCOCCOCCOCCNc1cccc2c1C(=O)N(C1CCC(=O)NC1=O)C2=O] |
| 89 | 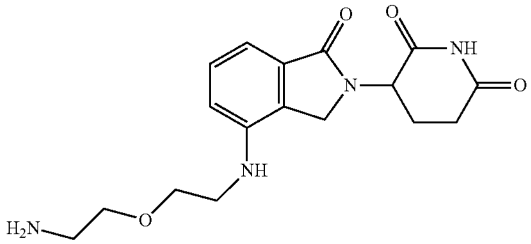 [SMILES: NCCOCCNc1cccc2c1CN(C1CCC(=O)NC1=O)C2=O] |
| 90 | 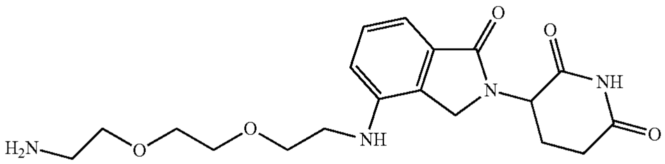 [SMILES: NCCOCCOCCNc1cccc2c1CN(C1CCC(=O)NC1=O)C2=O] |
| 91 | 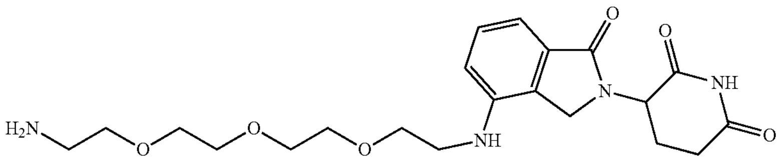 [SMILES: NCCOCCOCCOCCNc1cccc2c1CN(C1CCC(=O)NC1=O)C2=O] |
| 92 | 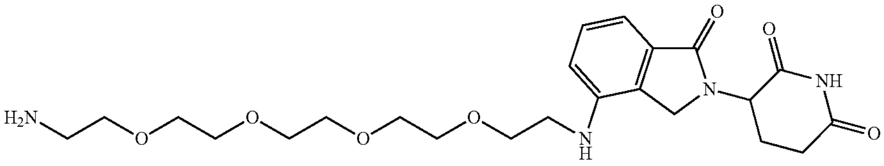 [SMILES: NCCOCCOCCOCCOCCNc1cccc2c1CN(C1CCC(=O)NC1=O)C2=O] |

TABLE 2-continued
| Cpd. No. | Structure |
| --- | --- |
| 93 | 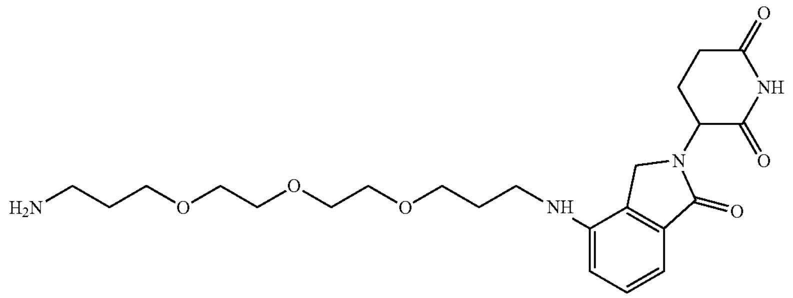 [SMILES: NCCCOCCOCCOCCCNc1cccc2c1CN(C1CCC(=O)NC1=O)C2=O] |
| 94 | 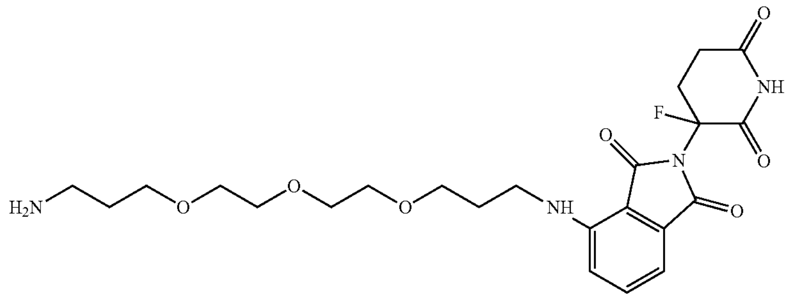 [SMILES: NCCCOCCOCCOCCCNc1cccc2c1C(=O)N(C1(F)CCC(=O)NC1=O)C2=O] |
| 95 | 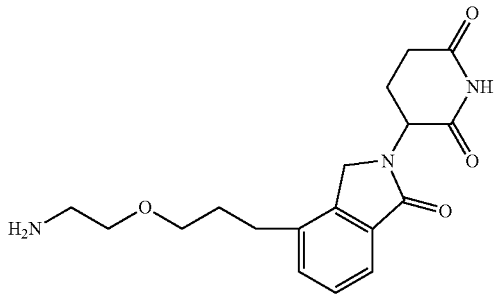 [SMILES: NCCOCCCc1cccc2c1CN(C1CCC(=O)NC1=O)C2=O] |
| 96 | 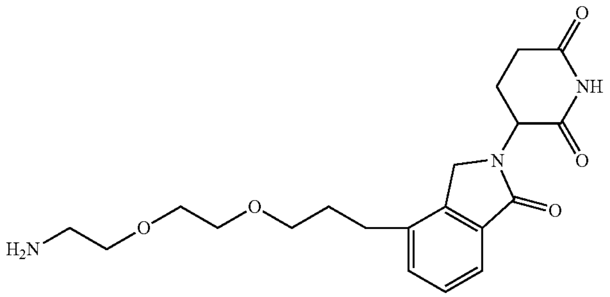 [SMILES: NCCOCCOCCCc1cccc2c1CN(C1CCC(=O)NC1=O)C2=O] |
| 97 | 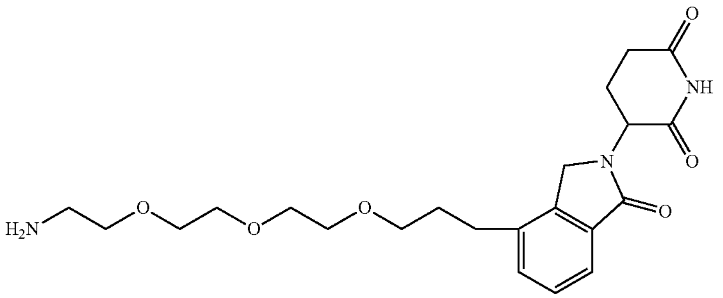 [SMILES: NCCOCCOCCOCCCc1cccc2c1CN(C1CCC(=O)NC1=O)C2=O] |

TABLE 2-continued
| Cpd. No. | Structure |
| --- | --- |
| 98 | 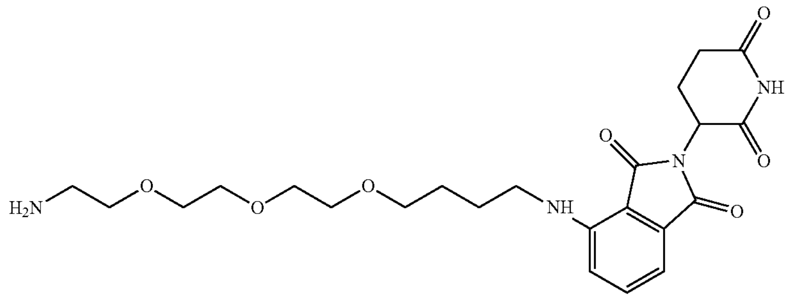 [SMILES: NCCOCCOCCOCCCCNc1cccc2c1C(=O)N(C1CCC(=O)NC1=O)C2=O] |
| 99 | 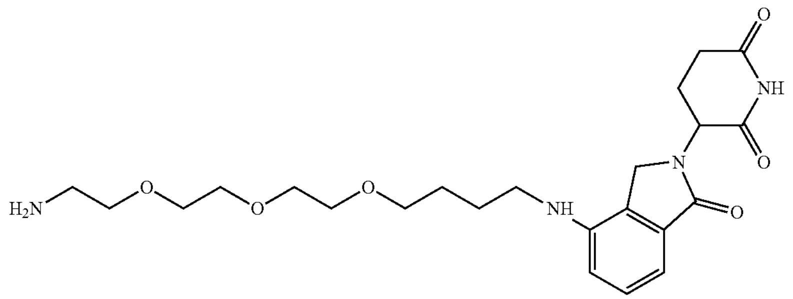 [SMILES: NCCOCCOCCOCCCCNc1cccc2c1CN(C1CCC(=O)NC1=O)C2=O] |
| 100 | 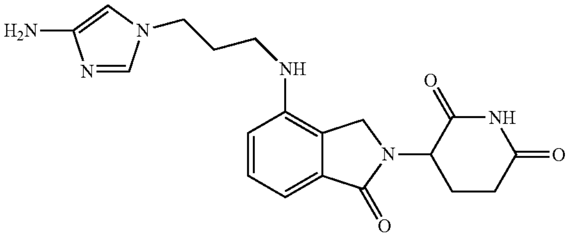 [SMILES: Nc1cn(CCCNc2cccc3c2CN(C2CCC(=O)NC2=O)C3=O)cn1] |
| 101 | 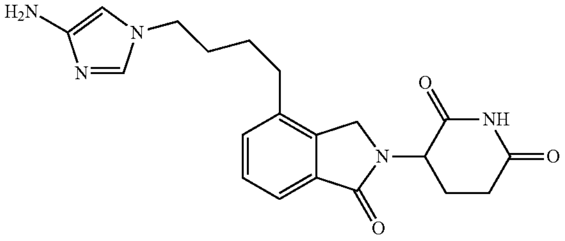 [SMILES: Nc1cn(CCCCc2cccc3c2CN(C2CCC(=O)NC2=O)C3=O)cn1] |
| 102 | 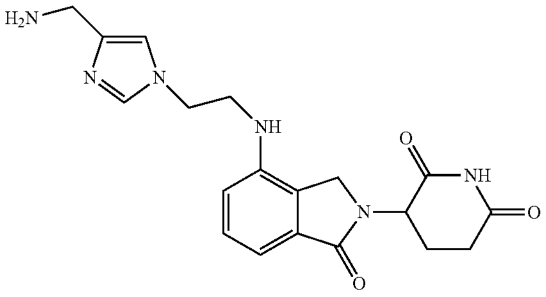 [SMILES: NCc1cn(CCNc2cccc3c2CN(C2CCC(=O)NC2=O)C3=O)cn1] |

TABLE 2-continued
| Cpd. No. | Structure |
| --- | --- |
| 103 | 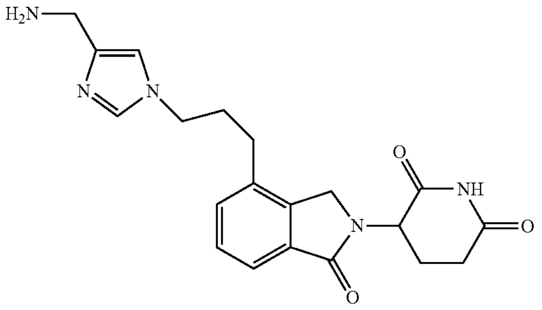 [SMILES: NCc1cn(CCCc2cccc3c2CN(C2CCC(=O)NC2=O)C3=O)cn1] |
| 104 | 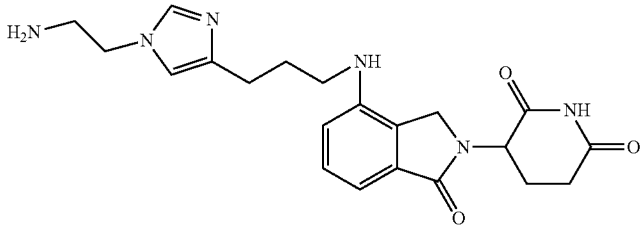 [SMILES: NCCn1cnc(CCCNc2cccc3c2CN(C2CCC(=O)NC2=O)C3=O)c1] |
| 105 | 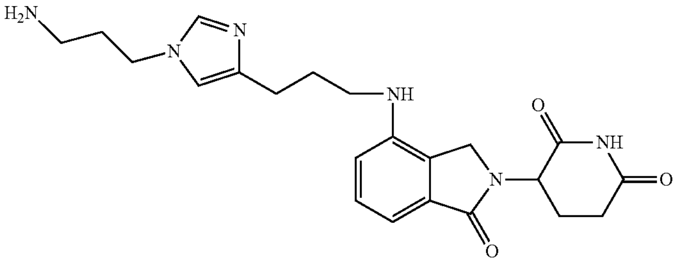 [SMILES: NCCCn1cnc(CCCNc2cccc3c2CN(C2CCC(=O)NC2=O)C3=O)c1] |
| 106 | 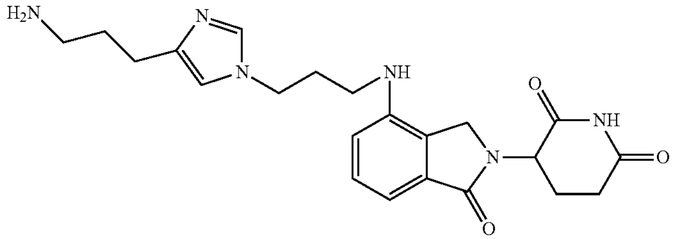 [SMILES: NCCCc1cn(CCCNc2cccc3c2CN(C2CCC(=O)NC2=O)C3=O)cn1] |
| 107 | 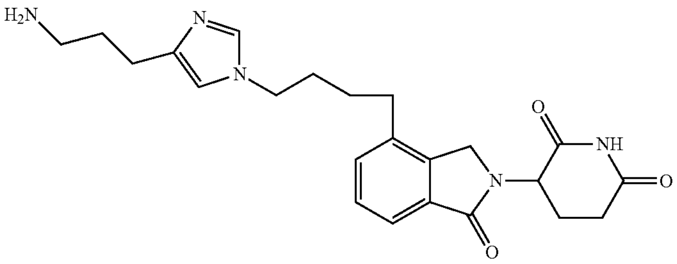 [SMILES: NCCCc1cn(CCCCc2cccc3c2CN(C2CCC(=O)NC2=O)C3=O)cn1] |
| 108 | 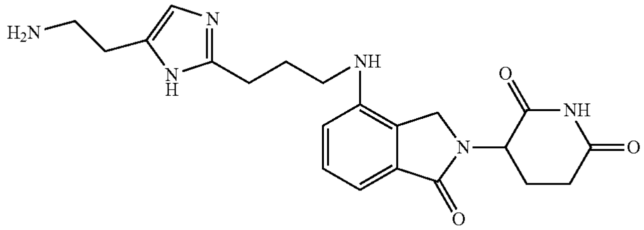 [SMILES: NCCc1cnc(CCCNc2cccc3c2CN(C2CCC(=O)NC2=O)C3=O)[nH]1] |

TABLE 2-continued
| Cpd. No. | Structure |
|---|---|
| 109 | 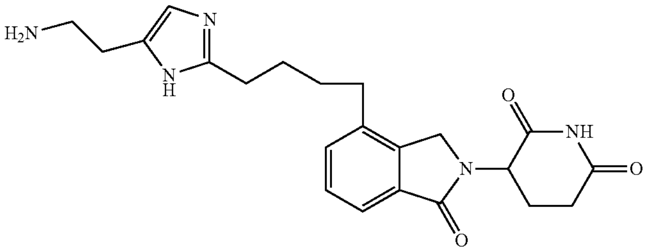 [SMILES: NCCc1cnc(CCCCc2cccc3c2CN(C2CCC(=O)NC2=O)C3=O)[nH]1] |
| 110 | 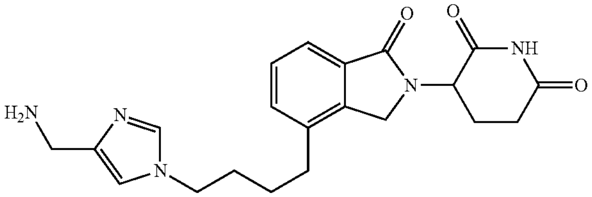 [SMILES: NCc1cn(CCCCc2cccc3c2CN(C2CCC(=O)NC2=O)C3=O)cn1] |
| 111 | 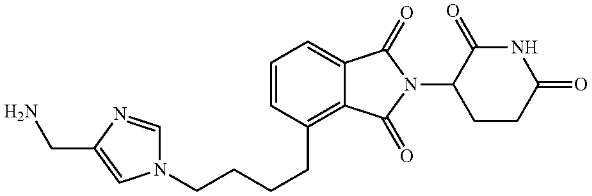 [SMILES: NCc1cn(CCCCc2cccc3c2C(=O)N(C2CCC(=O)NC2=O)C3=O)cn1] |
| 112 | 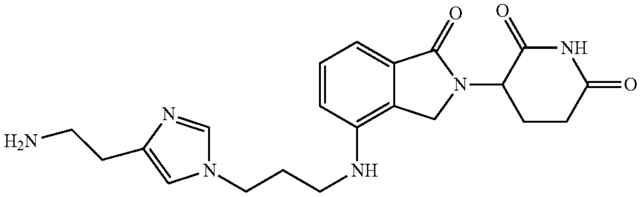 [SMILES: NCCc1cn(CCCNc2cccc3c2CN(C2CCC(=O)NC2=O)C3=O)cn1] |
| 113 | 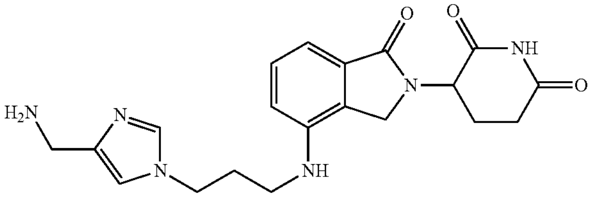 [SMILES: NCc1cn(CCCNc2cccc3c2CN(C2CCC(=O)NC2=O)C3=O)cn1] |
| 114 | 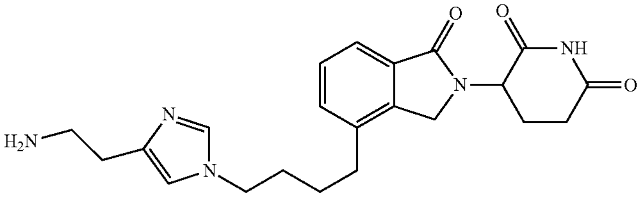 [SMILES: NCCc1cn(CCCCc2cccc3c2CN(C2CCC(=O)NC2=O)C3=O)cn1] |
| 115 | 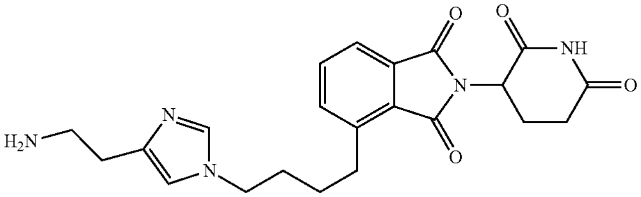 [SMILES: NCCc1cn(CCCCc2cccc3c2C(=O)N(C2CCC(=O)NC2=O)C3=O)cn1] |

TABLE 2-continued
| Cpd. No. | Structure |
|---|---|
| 116 | 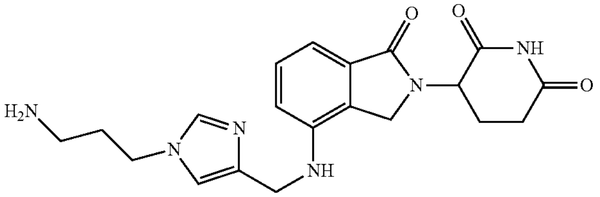 [SMILES: NCCCn1cnc(CNc2cccc3c2CN(C2CCC(=O)NC2=O)C3=O)c1] |
| 117 | 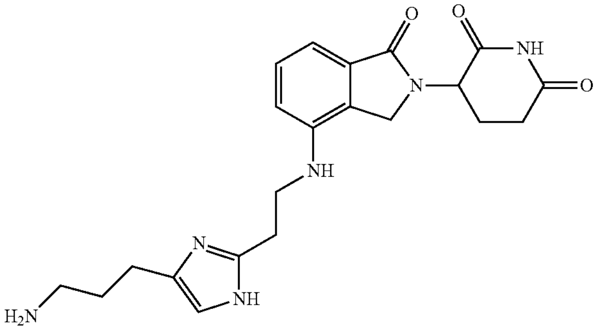 [SMILES: NCCCc1c[nH]c(CCNc2cccc3c2CN(C2CCC(=O)NC2=O)C3=O)n1] |
| 118 | 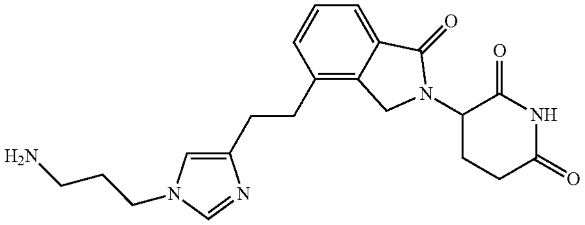 [SMILES: NCCCn1cnc(CCc2cccc3c2CN(C2CCC(=O)NC2=O)C3=O)c1] |
| 119 | 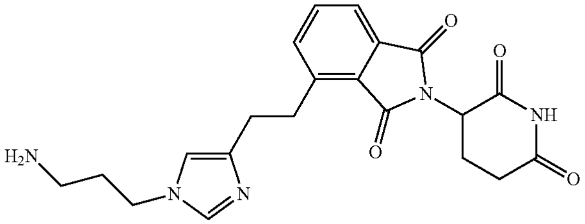 [SMILES: NCCCn1cnc(CCc2cccc3c2C(=O)N(C2CCC(=O)NC2=O)C3=O)c1] |
| 120 | 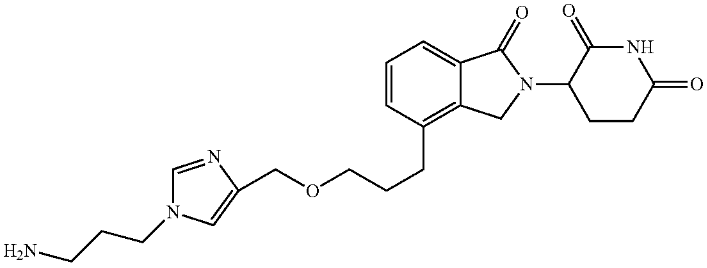 [SMILES: NCCCn1cnc(COCCCc2cccc3c2CN(C2CCC(=O)NC2=O)C3=O)c1] |
| 121 | 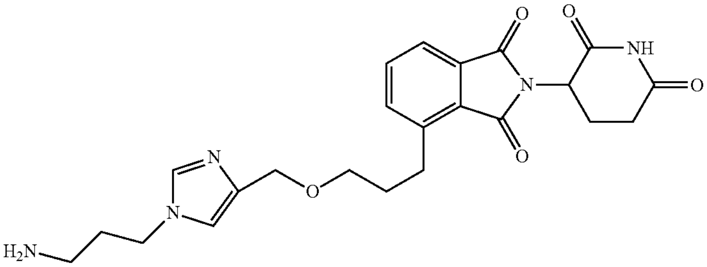 [SMILES: NCCCn1cnc(COCCCc2cccc3c2C(=O)N(C2CCC(=O)NC2=O)C3=O)c1] |

TABLE 2-continued
| Cpd. No. | Structure |
|---|---|
| 122 | 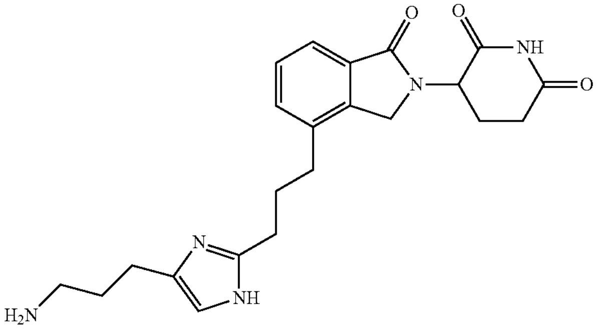 [SMILES: NCCCc1c[nH]c(CCCc2cccc3c2CN(C2CCC(=O)NC2=O)C3=O)n1] |
| 123 | 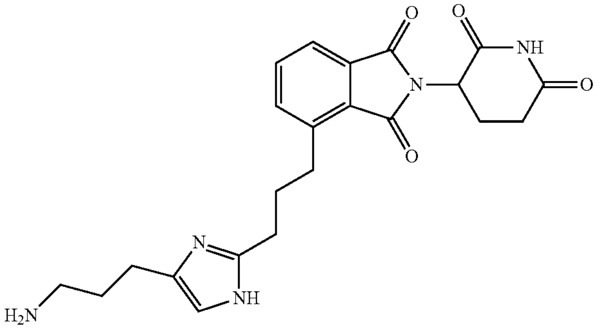 [SMILES: NCCCc1c[nH]c(CCCc2cccc3c2C(=O)N(C2CCC(=O)NC2=O)C3=O)n1] |
| 125 | 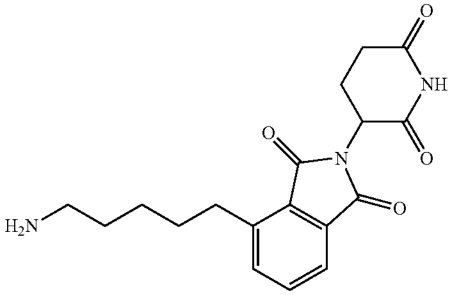 [SMILES: NCCCCCc1cccc2c1C(=O)N(C1CCC(=O)NC1=O)C2=O] |
| 126 | 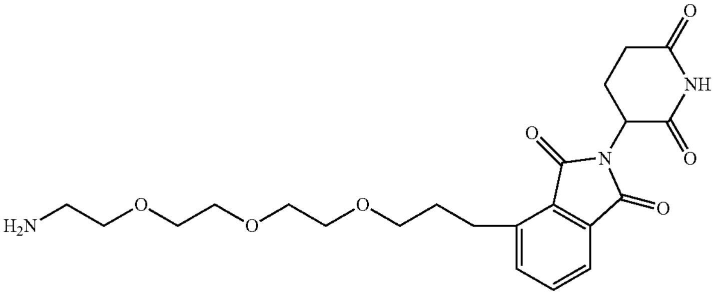 [SMILES: NCCOCCOCCOCCCc1cccc2c1C(=O)N(C1CCC(=O)NC1=O)C2=O] |
| 127 | 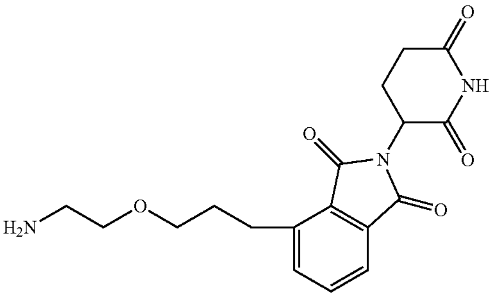 [SMILES: NCCOCCCc1cccc2c1C(=O)N(C1CCC(=O)NC1=O)C2=O] |

TABLE 2-continued
| Cpd. No. | Structure |
| --- | --- |
| 128 | 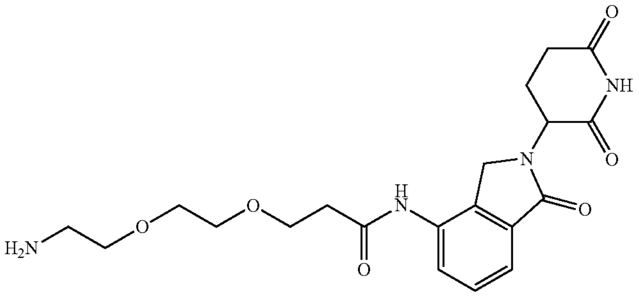 [SMILES: NCCOCCOCCC(=O)Nc1cccc2c1CN(C1CCC(=O)NC1=O)C2=O] |
| 129 | 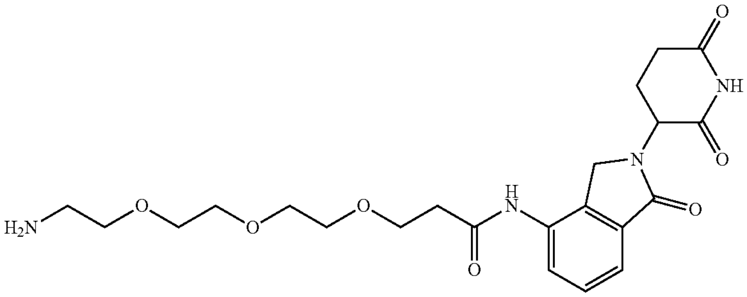 [SMILES: NCCOCCOCCOCCC(=O)Nc1cccc2c1CN(C1CCC(=O)NC1=O)C2=O] |
| 130 | 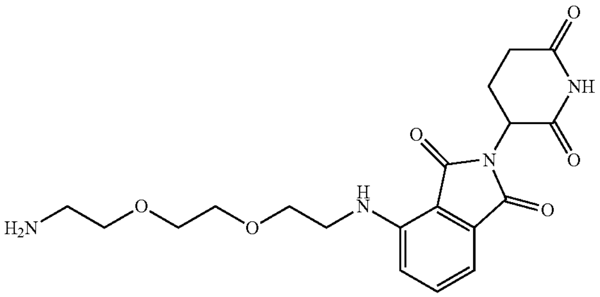 [SMILES: NCCOCCOCCNc1cccc2c1C(=O)N(C1CCC(=O)NC1=O)C2=O] |
| 131 | 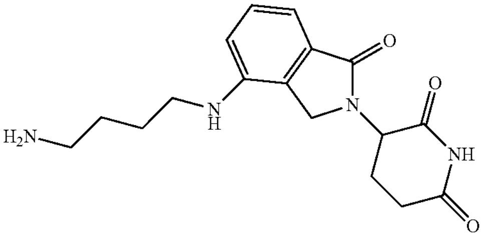 [SMILES: NCCCCNc1cccc2c1CN(C1CCC(=O)NC1=O)C2=O] |
| 132 | 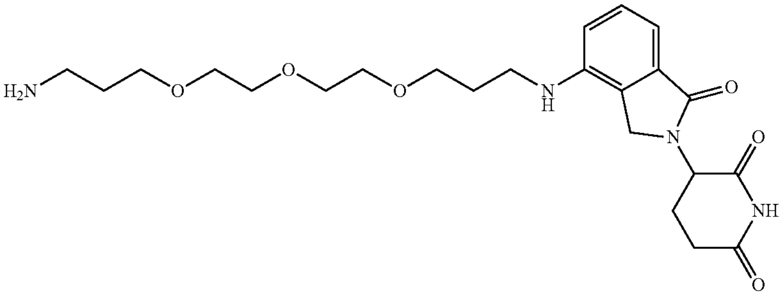 [SMILES: NCCCOCCOCCOCCCNc1cccc2c1CN(C1CCC(=O)NC1=O)C2=O] |

TABLE 2-continued
| Cpd. No. | Structure |
| --- | --- |
| 133 | 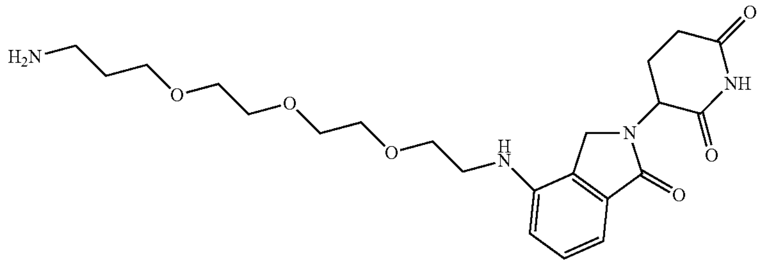 [SMILES: NCCCOCCOCCOCCNc1cccc2c1CN(C1CCC(=O)NC1=O)C2=O] |
| 134 | 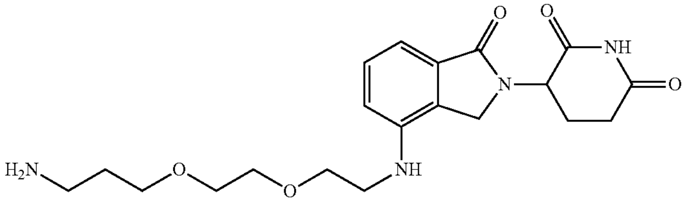 [SMILES: NCCCOCCOCCNc1cccc2c1CN(C1CCC(=O)NC1=O)C2=O] |
| 135 | 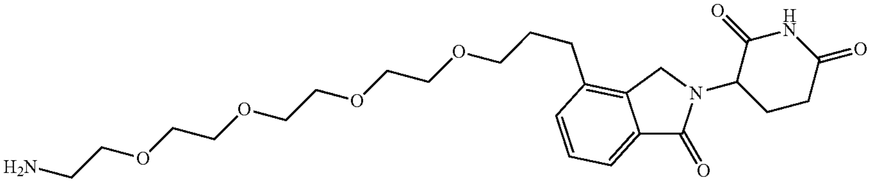 [SMILES: NCCOCCOCCOCCOCCCc1cccc2c1CN(C1CCC(=O)NC1=O)C2=O] |
| 136 | 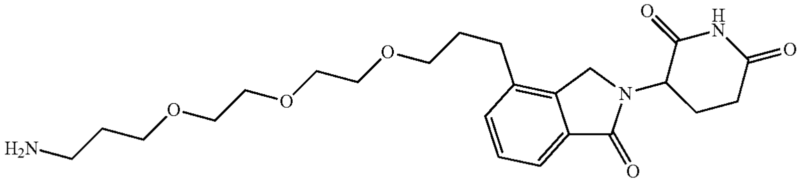 [SMILES: NCCCOCCOCCOCCCc1cccc2c1CN(C1CCC(=O)NC1=O)C2=O] |
| 137 | 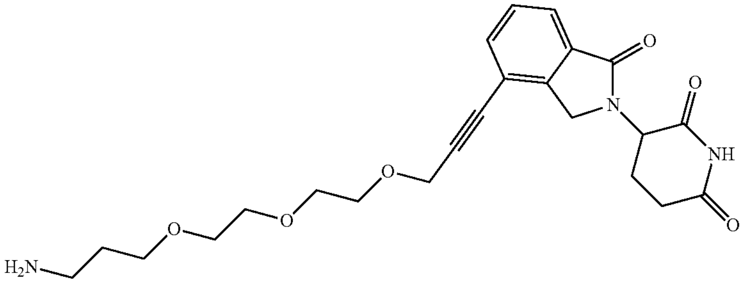 [SMILES: NCCCOCCOCCOCC#Cc1cccc2c1CN(C1CCC(=O)NC1=O)C2=O] |
| 138 | 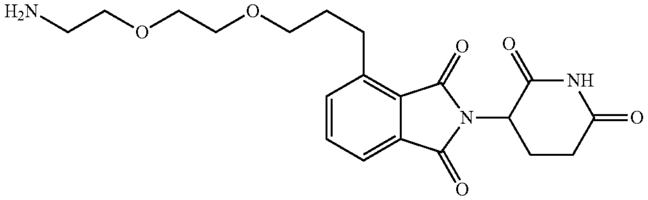 [SMILES: NCCOCCOCCCc1cccc2c1C(=O)N(C1CCC(=O)NC1=O)C2=O] |
| 139 | 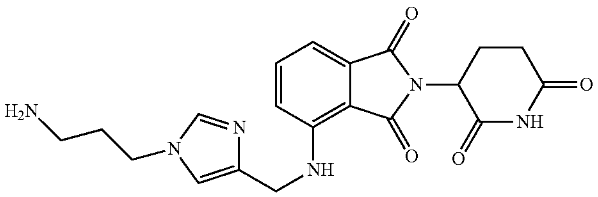 [SMILES: NCCCn1cnc(CNc2cccc3c2C(=O)N(C2CCC(=O)NC2=O)C3=O)c1] |

TABLE 2-continued
| Cpd. No. | Structure |
|---|---|
| 140 | 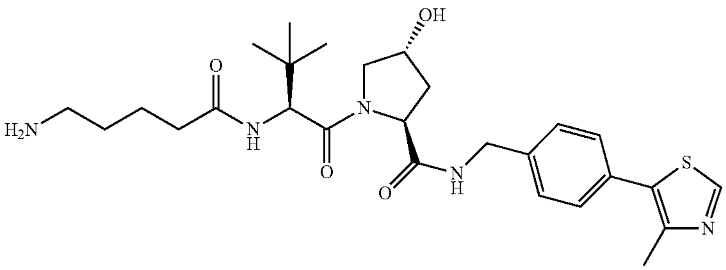 [SMILES: Cc1ncsc1-c1ccc(CNC(=O)[C@@H]2C[C@@H](O)CN2C(=O)[C@@H](NC(=O)CCCCN)C(C)(C)C)cc1] |
| 141 | 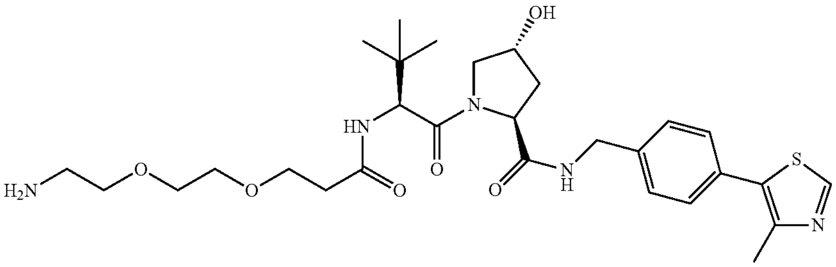 [SMILES: Cc1ncsc1-c1ccc(CNC(=O)[C@@H]2C[C@@H](O)CN2C(=O)[C@@H](NC(=O)CCOCCOCCN)C(C)(C)C)cc1] |
| 142 | 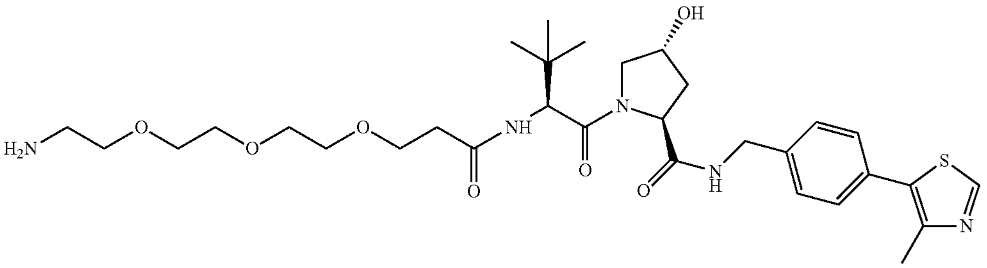 [SMILES: Cc1ncsc1-c1ccc(CNC(=O)[C@@H]2C[C@@H](O)CN2C(=O)[C@@H](NC(=O)CCOCCOCCOCCN)C(C)(C)C)cc1] |
| 143 | 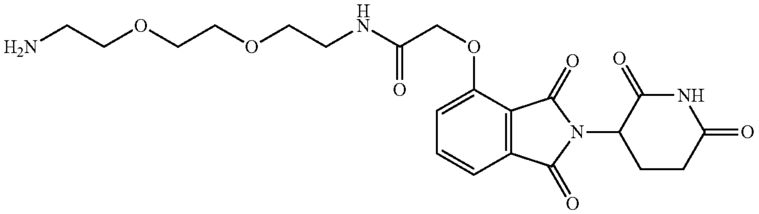 [SMILES: NCCOCCOCCNC(=O)COc1cccc2c1C(=O)N(C1CCC(=O)NC1=O)C2=O] |
| 144 | 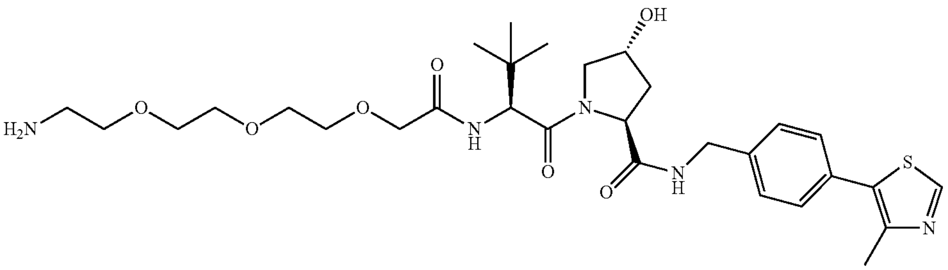 [SMILES: Cc1ncsc1-c1ccc(CNC(=O)[C@@H]2C[C@@H](O)CN2C(=O)[C@@H](NC(=O)COCCOCCOCCN)C(C)(C)C)cc1] |

TABLE 2-continued
| Cpd. No. | Structure |
|---|---|
| 145 | 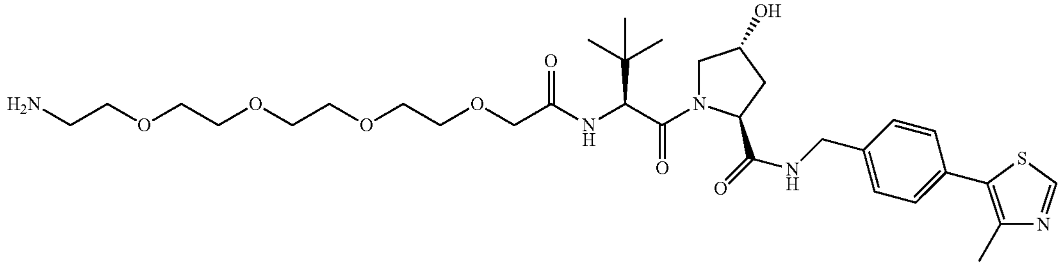 [SMILES: Cc1ncsc1-c1ccc(CNC(=O)[C@@H]2C[C@@H](O)CN2C(=O)[C@@H](NC(=O)COCCOCCOCCOCCN)C(C)(C)C)cc1] |
In another embodiment, the disclosure provides methods of making a compound having Formula II:
II
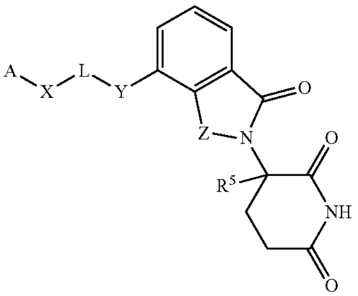
and the pharmaceutically acceptable salts or solvates thereof, wherein:
A is selected from the group consisting of:
A-1
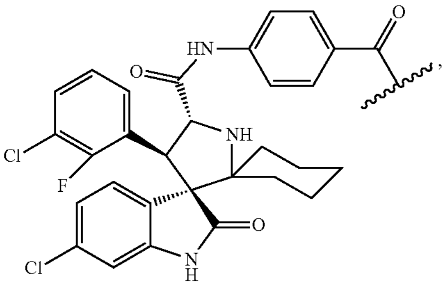
A-2
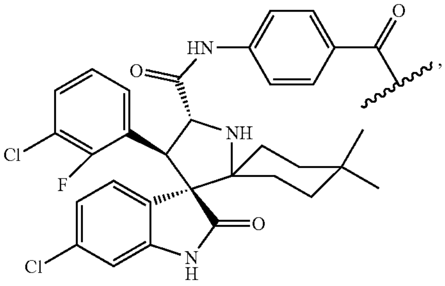
-continued
A-3
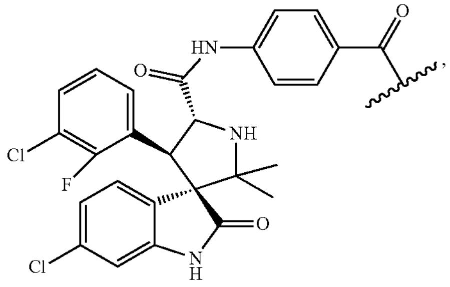
A-4
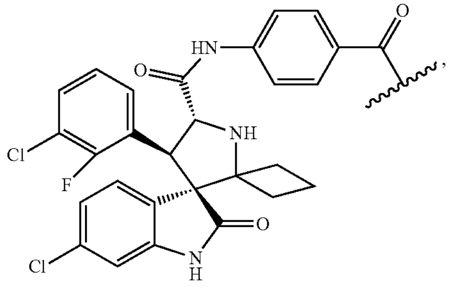
A-5
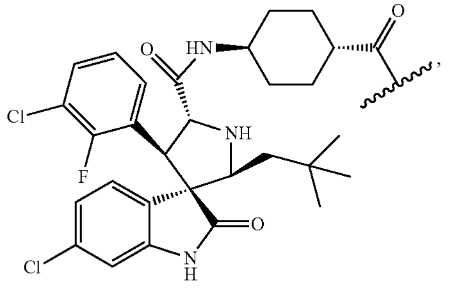
A-6
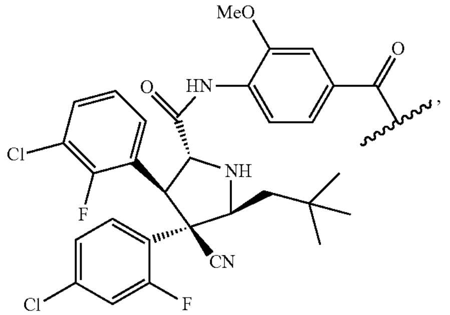

-continued

A-7

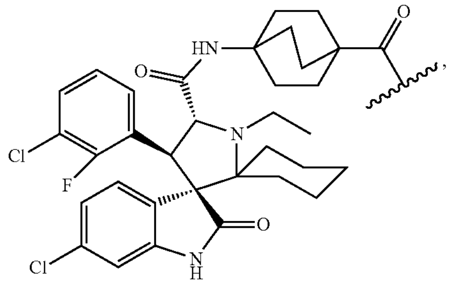

,

A-8

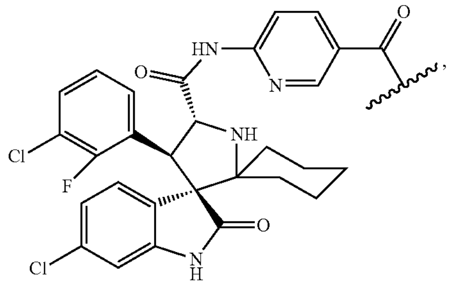

,

A-9

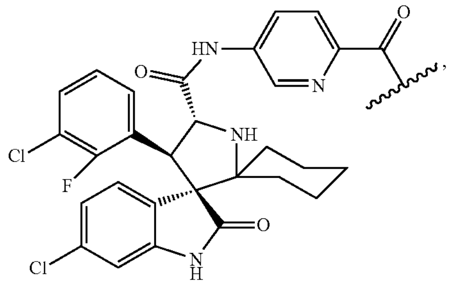

,

A-10

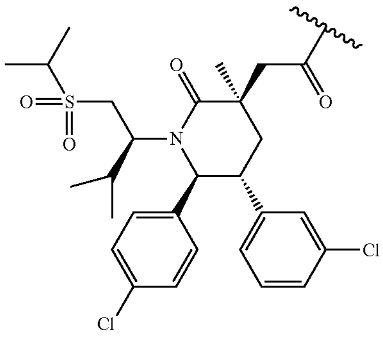

and

A-15

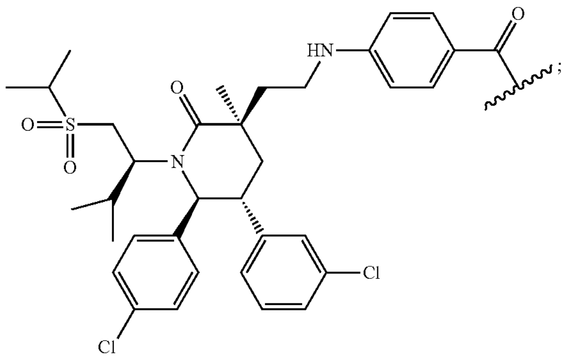

;

X is selected from the group consisting of —N($R^{2a}$)—,

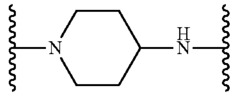

, and

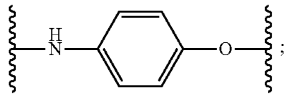

;

wherein the —N(H)— of

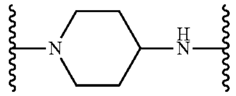 [SMILES: *NC1CCN(*)CC1]

is attached to L and the —O— of

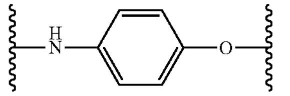 [SMILES: *Nc1ccc(O*)cc1]

is attached to L;

L is selected from the group consisting of alkylenyl, heteroalkylenyl, and —$(CH_2)_m$—W—$(CH_2)_n$—;

W is selected from the group consisting of optionally substituted phenyl, optionally substituted 5-membered heteroaryl, and optionally substituted 6-membered heteroaryl;

m is 0, 1, 2, 3, 4, 5, 6, or 7;

n is 0, 1, 2, 3, 4, 5, 6, 7, or 8;

Y is selected from the group consisting of —C≡C—, —O—, —N($R^{2b}$)—, —C(═O)N($R^{2c}$)—, —N($R^{2d}$)C(═O)$CH_2$O—, and —N($R^{2e}$)C(═O)$CH_2$N($R^{2f}$)—; or Y is absent;

wherein the carboxamide nitrogen atom of —N($R^{2d}$)C(═O)$CH_2$O— and —N($R^{2e}$)C(═O)$CH_2$N($R^{2f}$)—, and the carbon atom of —C(═O)N($R^{2c}$)— is attached to L;

$R^{2a}$, $R^{2b}$, $R^{2c}$, $R^{2d}$, $R^{2e}$, and $R^{2f}$ are each independently selected from the group consisting of hydrogen and $C_{1-4}$ alkyl;

Z is selected from the group consisting of —$CH_2$ and —C(═O)—; and $R^5$ is selected from the group consisting of hydrogen, methyl, and fluoro, the method comprising:

(1) reacting a compound selected from the group consisting of:

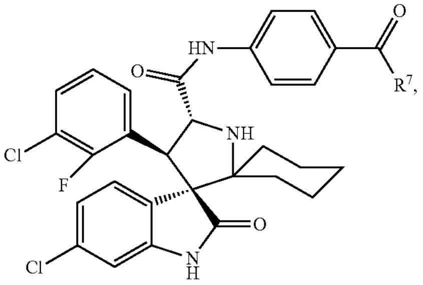

,

-continued
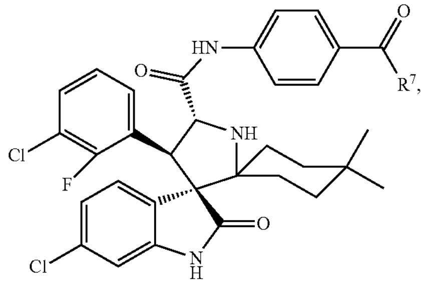
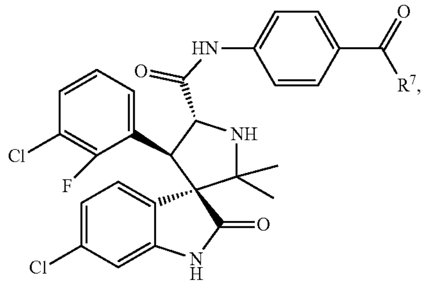
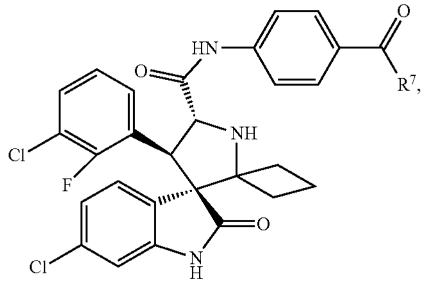
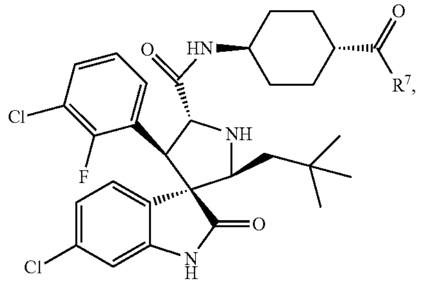
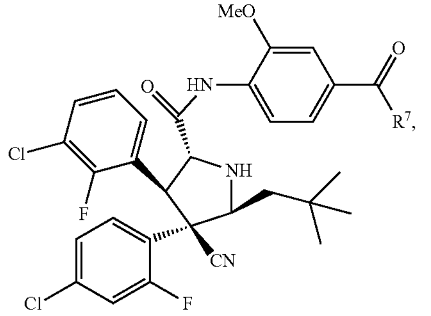
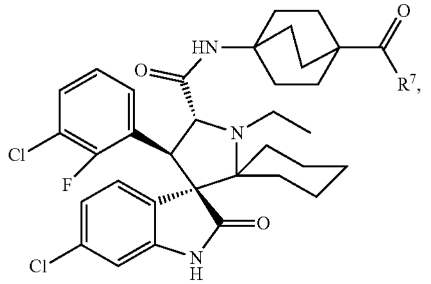
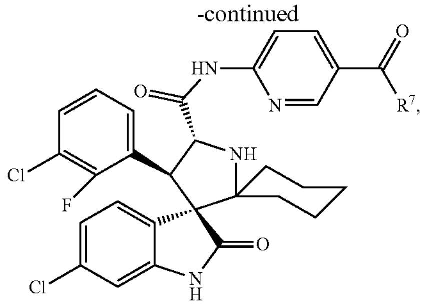
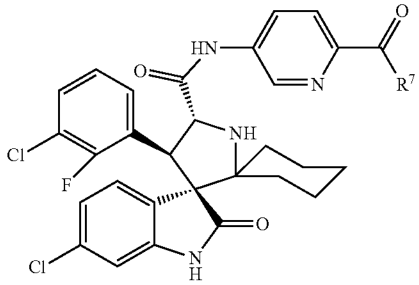
and
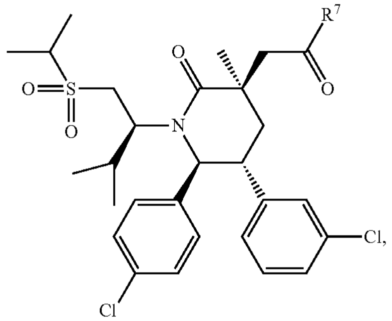
wherein $R^7$ is selected from the group consisting of —Cl and —OH,
with a compound having Formula V:
V
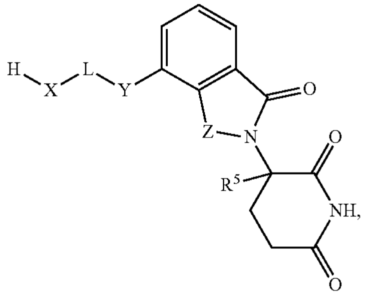
wherein:
X is selected from the group consisting of —$N(R^{2a})$—,
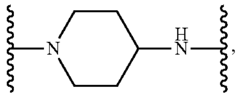
and
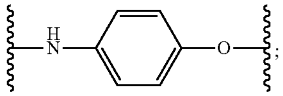

wherein the —N(H)— of

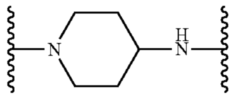 [SMILES: *NC1CCN(*)CC1]

is attached to L and the —O— of

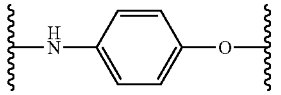 [SMILES: *Nc1ccc(O*)cc1]

is attached to L;

L is selected from the group consisting of alkylenyl, heteroalkylenyl, and $—(CH_2)_m—W—(CH_2)_n—$;

W is selected from the group consisting of optionally substituted phenyl, optionally substituted 5-membered heteroaryl, and optionally substituted 6-membered heteroaryl;

m is 0, 1, 2, 3, 4, 5, 6, or 7;

n is 0, 1, 2, 3, 4, 5, 6, 7, or 8;

Y is selected from the group consisting of —C≡C—, —O—, $—N(R^{2b})—$, $—C(═O)N(R^{2c})—$, $—N(R^{2d})C(═O)CH_2O—$, and $—N(R^{2e})C(═O)CH_2N(R^{2f})—$; or Y is absent;

wherein the carboxamide nitrogen atom of $—N(R^{2d})C(═O)CH_2O—$ and $—N(R^{2e})C(═O)CH_2N(R^{2f})—$, and the carbon atom of $—C(═O)N(R^{2c})—$ is attached to L;

$R^{2a}$, $R^{2b}$, $R^{2c}$, $R^{2d}$, $R^{2e}$, and $R^{2f}$ are each independently selected from the group consisting of hydrogen and $C_{1-4}$ alkyl;

Z is selected from the group consisting of $—CH_2—$ and —C(═O)—; and $R^5$ is selected from the group consisting of hydrogen and fluoro, and (2) isolating the compound having Formula II, and the pharmaceutically acceptable salts or solvates thereof.

In another embodiment, the disclosure provides methods of making a compound having Formula II, and the pharmaceutically acceptable salts or solvates thereof, wherein A is A-16, the method comprising:

(1) reacting a compound having the structure:

A-16

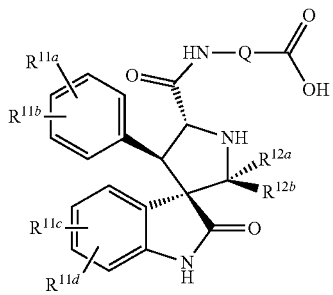

with a compound having Formula V, and (2) isolating the compound having Formula II, and the pharmaceutically acceptable salts or solvates thereof.

In another embodiment, the disclosure provides methods of making a compound having Formula III:

III

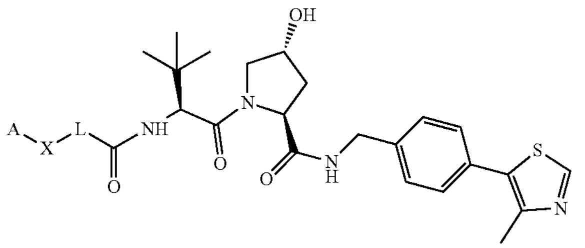

and the pharmaceutically acceptable salts or solvates thereof, wherein:

A is selected from the group consisting of:

A-1

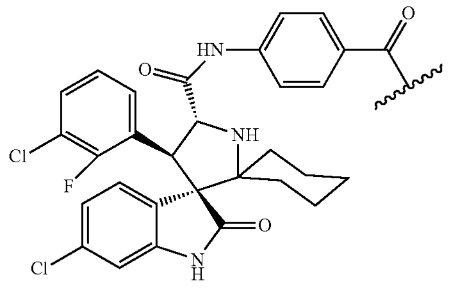

,

A-2

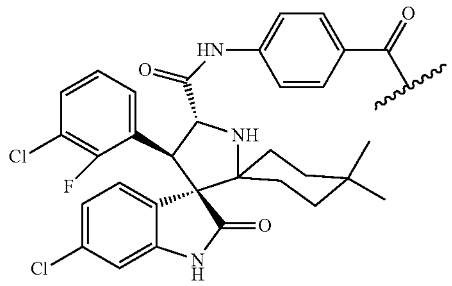

,

A-3

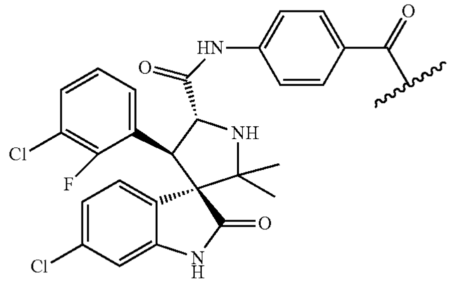

,

A-4

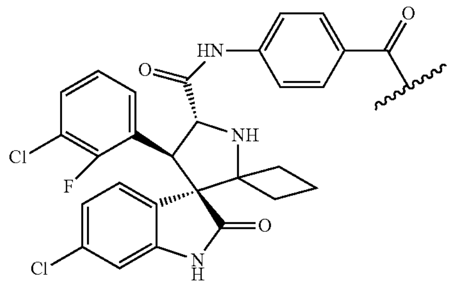

,

-continued

A-5

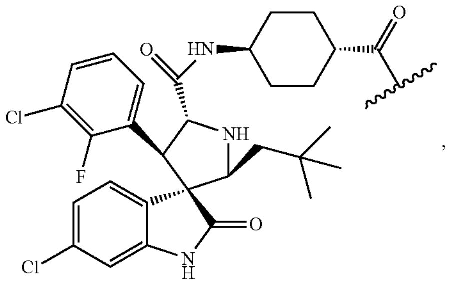

,

A-6

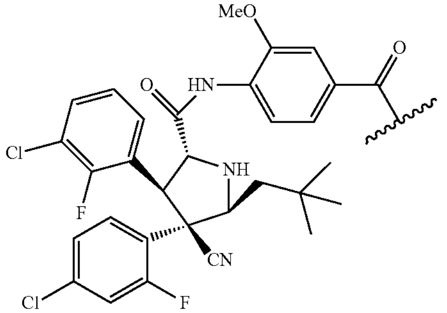

,

A-7

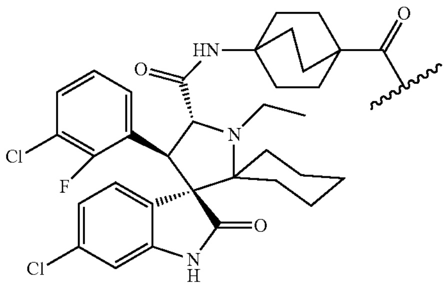

,

A-8

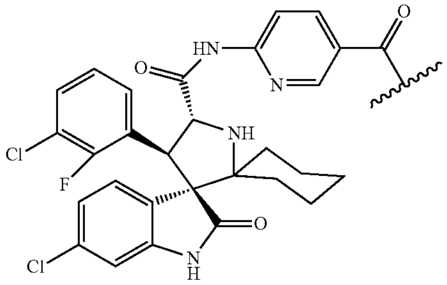

,

A-9

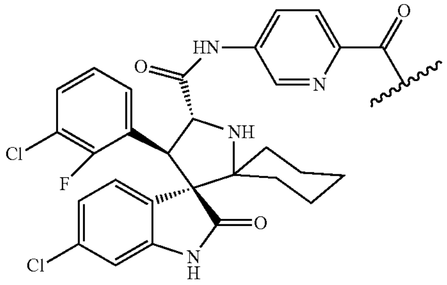

,

-continued

A-10

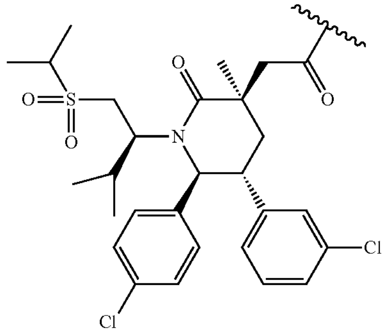

and

A-15

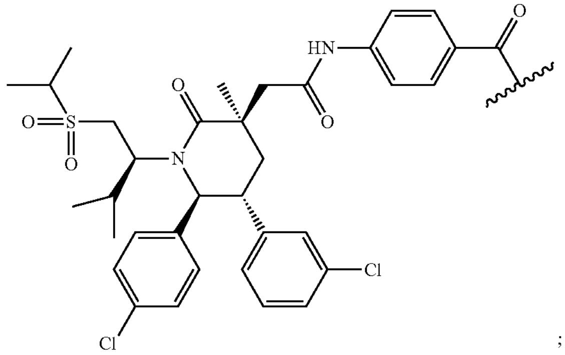

;

X is selected from the group consisting of —$N(R^{2a})$—,

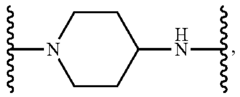

, and

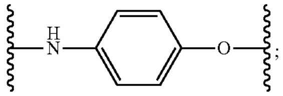

;

wherein the —N(H)— of

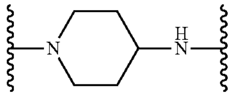 [SMILES: *NC1CCN(*)CC1]

is attached to L and the —O— of

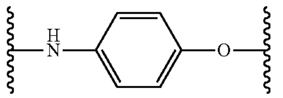 [SMILES: *Nc1ccc(O*)cc1]

is attached to L;

L is selected from the group consisting of alkylenyl, heteroalkylenyl, and —$(CH_2)_m$—W—$(CH_2)_n$—;

W is selected from the group consisting of optionally substituted phenyl, optionally substituted 5-membered heteroaryl, and optionally substituted 6-membered heteroaryl;

m is 0, 1, 2, 3, 4, 5, 6, or 7; and n is 0, 1, 2, 3, 4, 5, 6, 7, or 8;

the method comprising:
(1) reacting a compound selected from the group consisting of:
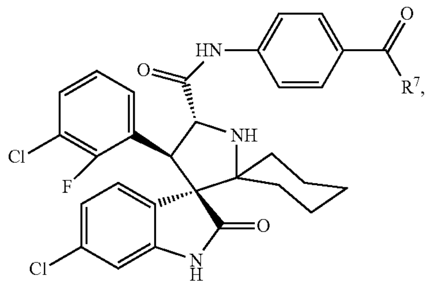
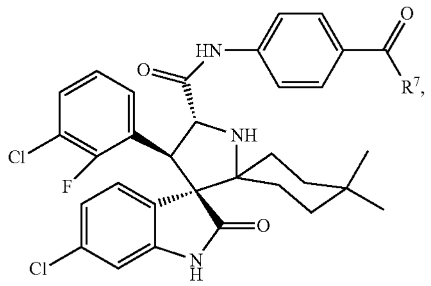
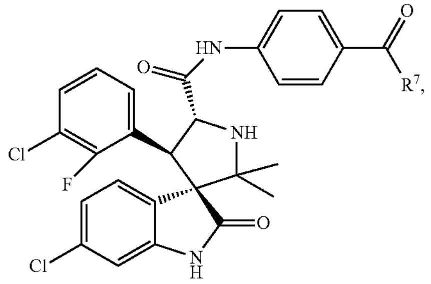
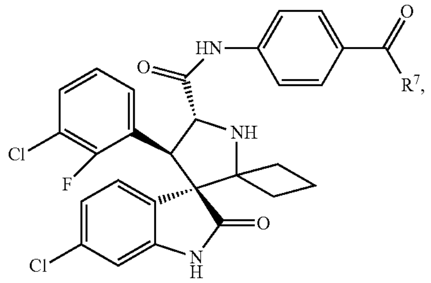
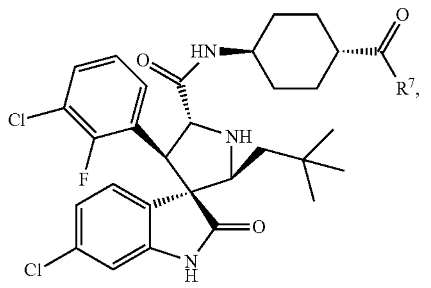
-continued
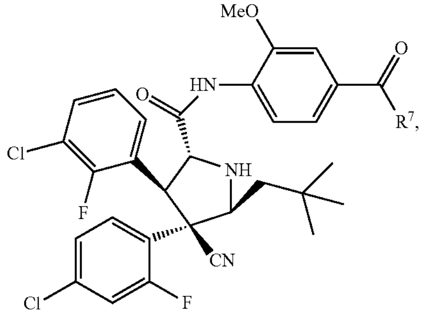
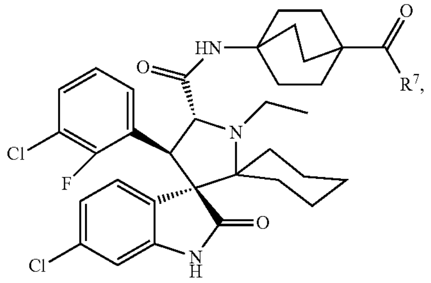
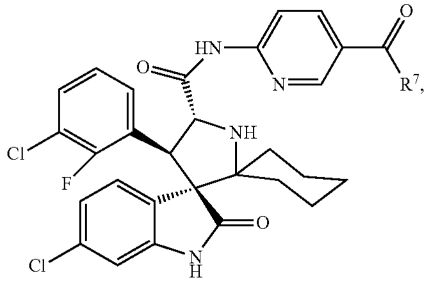
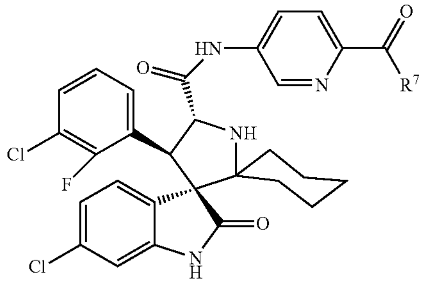
and
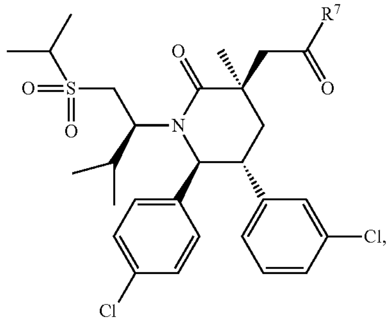
wherein $R^7$ is selected from the group consisting of —Cl and —OH, with a compound having Formula VI:

VI

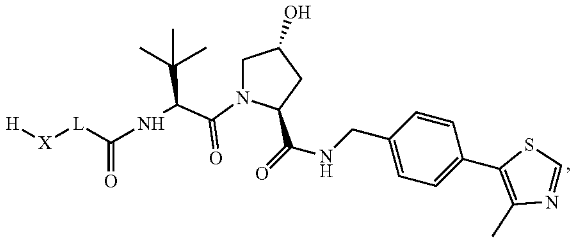

wherein:

X is selected from the group consisting of —$N(R^{2a})$—,

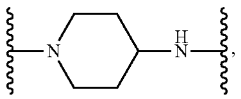

, and

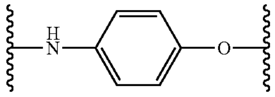

;

wherein the —N(H)— of

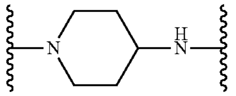 [SMILES: *NC1CCN(*)CC1]

is attached to L and the —O— of

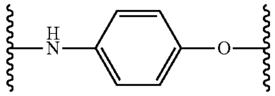 [SMILES: *Nc1ccc(O*)cc1]

is attached to L;

L is selected from the group consisting of alkylenyl, heteroalkylenyl, and —$(CH_2)_m$—W—$(CH_2)_n$—;

W is selected from the group consisting of optionally substituted phenyl, optionally substituted 5-membered heteroaryl, and optionally substituted 6-membered heteroaryl;

m is 0, 1, 2, 3, 4, 5, 6, or 7; and n is 0, 1, 2, 3, 4, 5, 6, 7, or 8, and (2) isolating the compound having Formula III, and the pharmaceutically acceptable salts or solvates thereof.

In another embodiment, the disclosure provides methods of making a compound having Formula III, and the pharmaceutically acceptable salts or solvates thereof, wherein A is A-16, the method comprising:

(1) reacting a compound having the structure:

A-16

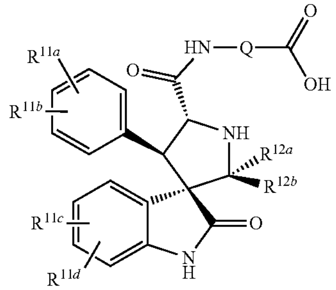

with a compound having Formula VI, and (2) isolating the compound having Formula III, and the pharmaceutically acceptable salts or solvates thereof.

Compounds of the Disclosure degrade MDM2 proteins and are useful in the treatment of a variety of diseases and conditions. In particular, Compounds of the Disclosure are useful in methods of treating a disease or condition wherein degradation MDM2 proteins provides a benefit, for example, cancers and proliferative diseases. The therapeutic methods of the disclosure comprise administering a therapeutically effective amount of a Compound of the Disclosure to an individual in need thereof. The present methods also encompass administering a second therapeutic agent to the individual in addition to the Compound of the Disclosure. The second therapeutic agent is selected from drugs known as useful in treating the disease or condition afflicting the individual in need thereof, e.g., a chemotherapeutic agent and/or radiation known as useful in treating a particular cancer.

Salts, hydrates, and solvates of the Compounds of the Disclosure can also be used in the methods disclosed herein. The present disclosure further includes all possible stereoisomers and geometric isomers of Compounds of the Disclosure to include both racemic compounds and optically active isomers. When a Compound of the Disclosure is desired as a single enantiomer, it can be obtained either by resolution of the final product or by stereospecific synthesis from either isomerically pure starting material or use of a chiral auxiliary reagent, for example, see Z. Ma et ah, *Tetrahedron: Asymmetry,* 8(6), pages 883-888 (1997). Resolution of the final product, an intermediate, or a starting material can be achieved by any suitable method known in the art. Additionally, in situations where tautomers of the Compounds of the Disclosure are possible, the present disclosure is intended to include all tautomeric forms of the compounds.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with a suitable acid. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al. *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5/7): Article 12 (2004), and A. L. Bingham et al, *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

A "monovalent radical of a ligand for an E3 ubiquitin ligase protein" is derived from the removal of a hydrogen or other suitable atom, e.g., Br, I, or group, e.g., —OH, from a parent E3 ubiquitin ligase protein ligand. The removal of a hydrogen atom or other suitable atom or group facilitates the linkage of the parent E3 ubiquitin ligase protein ligand to a target protein inhibitor to give a heterobifunctional compound having any one of Formulae I-A or I-III, as defined above. In one embodiment, a hydrogen atom is removed from any suitable —$NH_2$ group of the parent E3 ubiquitin ligase protein ligand. In another embodiment, a hydrogen atom is removed from any suitable —OH group of the parent E3 ubiquitin ligase protein ligand. In another embodiment, a hydrogen atom is removed from any suitable —N(H)— group of the parent E3 ubiquitin ligase protein ligand. In another embodiment, a hydrogen atom is removed from any suitable —$CH_3$, —$CH_2$—, —CH=group of the parent E3 ubiquitin ligase protein ligand. In another embodiment, a Br or I atom is removed from any suitable aryl or heteroaryl group of the parent E3 ubiquitin ligase protein ligand. Exemplary non-limiting monovalent radicals of E3 ubiquitin ligase protein ligands include:

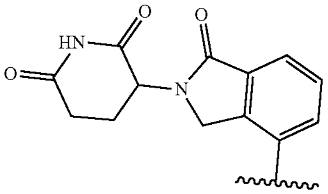
,

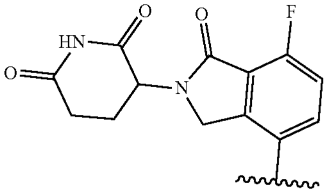
,

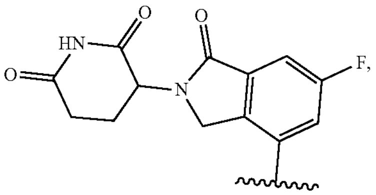

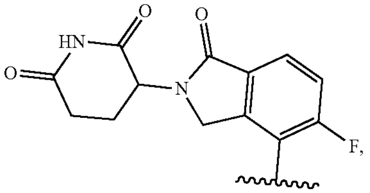

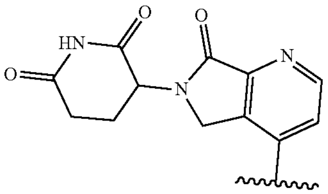
,

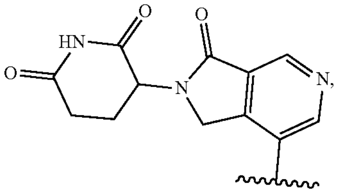

-continued

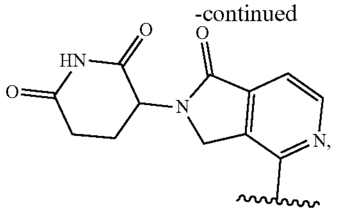

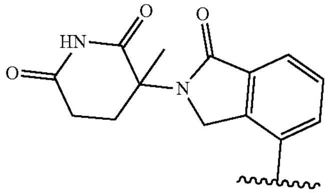

,

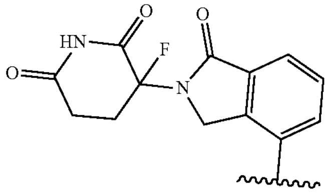

,

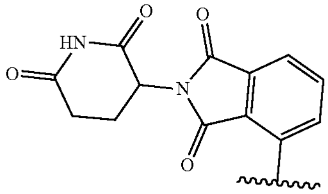

,

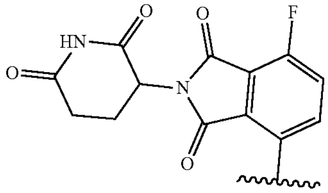

,

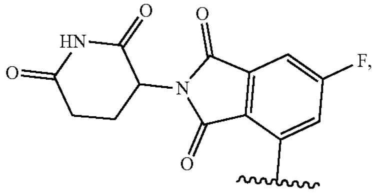

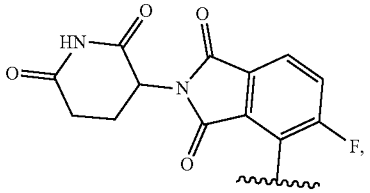

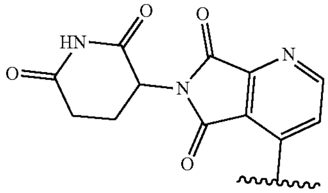

,

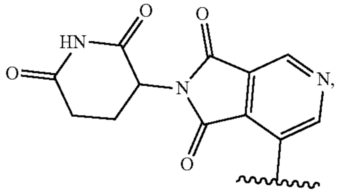

-continued

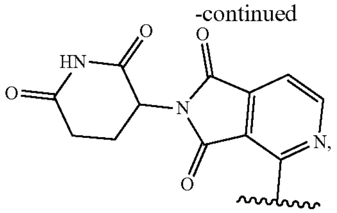

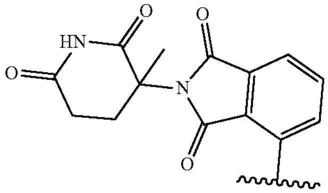

,

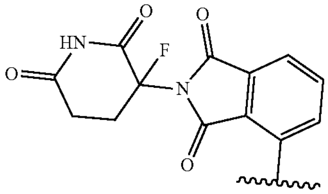

,

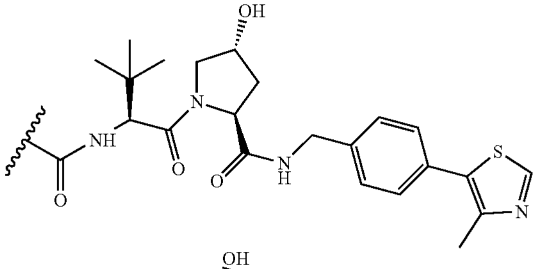

,

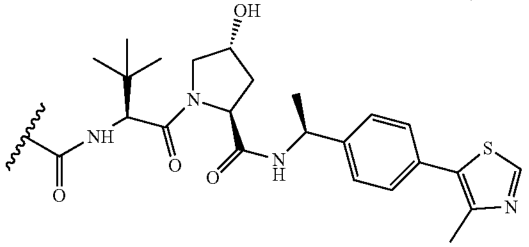

and

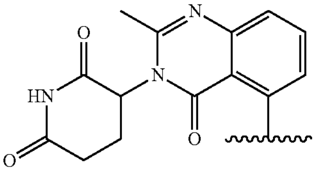

.

A "ligand for an E3 ubiquitin ligase protein" or "parent ligand for an E3 ubiquitin ligase protein" or "E3 ubiquitin ligase protein ligand" and the like refers to a compound that binds, e.g., inhibits, an E3 ubiquitin ligase protein, including the von Hippel-Lindau protein (VHL). Ligands for E3 ubiquitin ligase proteins are known to those of ordinary skill in the art. Exemplary non-limiting ligands for an E3 ubiquitin ligase protein include phthalimide-based drugs such as thalidomide.

A "monovalent radical of a MDM2 inhibitor" is derived from the removal of a hydrogen or other suitable atom, e.g., Br, I, or group, e.g., —OH, from a parent MDM2 inhibitor. The removal of a hydrogen atom or other suitable atom or group facilitates the linkage of the MDM2 inhibitor to an E3 ubiquitin ligase protein ligand to give a heterobifunctional compound having any one of Formulae I-A or I-III, as defined above. In one embodiment, a hydrogen atom is removed from any suitable —$NH_2$ group of the parent MDM2 inhibitor. In another embodiment, a hydrogen atom is removed from any suitable —OH group of the parent MDM2 inhibitor. In another embodiment, a hydrogen atom is removed from any suitable —N(H)— group of the parent MDM2 inhibitor. In another embodiment, a hydrogen atom is removed from any suitable $—CH_3$, $—CH_2—$, —CH═, or —C≡CH group of the parent MDM2 inhibitor. In another embodiment, the hydrogen atom is removed from any suitable —OH group of the parent MDM2 inhibitor. In another embodiment, the —OH group is removed from any suitable —C(═O)OH group of the parent MDM2 inhibitor. In another embodiment, a Br or I atom is removed from any suitable aryl or heteroaryl group of the parent MDM2 inhibitor.

A "linker" is a divalent chemical moiety that joins a monovalent radical of a ligand for an E3 ubiquitin ligase protein and a monovalent radical of a MDM2 inhibitor.

A "MDM2 inhibitor" or "parent MDM2 inhibitor" and the like refer to a compound that disrupts the p53-MDM2 interaction and/or interferes with MDM2 activity. MDM2 inhibitors are known to those of ordinary skill in the art. See, e.g., Shangary. et al., *Annual Review Of Pharmacology and Toxicology* 49: 223-241 (2009); and Weber, *Expert Opinion On Therapeutic Patents* 20: 179-191 (2010).

In one embodiment, the MDM2 inhibitor is a spiro-oxindole compound. As used herein, the term "spiro-oxindole MDM2 inhibitor" refers, for example, to a compound disclosed and/or claimed in U.S. Pat. Nos. 7,759,383; 7,737,174; 8,518,984; 8,680,132; or 8,629,141. In another embodiment, the term "spiro-oxindole MDM2 inhibitor" refers to a compound disclosed and/or claimed in US 2015/0291611, US 2016/0000764, or US 2016/0052938.

In another embodiment, the MDM2 inhibitor is a cis-imidazoline compound As used herein, the term "cis-imidazoline MDM2 inhibitor" refers, for example, to a compound disclosed and/or claimed in U.S. Pat. Nos. 6,617,346; 6,734,302; 7,132,421; 7,425,638; or 7,579,368; or U.S. Patent Application Publication Nos. 2005/0288287 or U.S. 2009/0143364. A cis-imidazoline MDM2 inhibitor is commonly referred to as a "nutlin." In a particular embodiment, the cis-imidazoline is Nutlin-1, Nutlin-2, or Nutlin-3 (Chart 3; see Vassilev, L. T. et al., *Science* 363:844-848 (2004)).

Chart 3 Nutlin MDM2 inhibitors

Nutlin-1

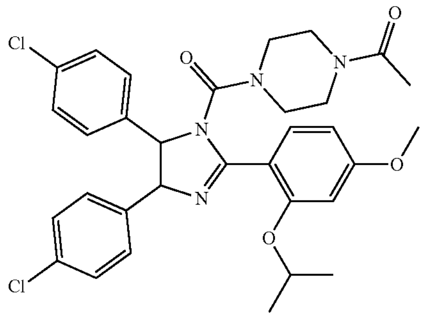

-continued

Nutlin-2

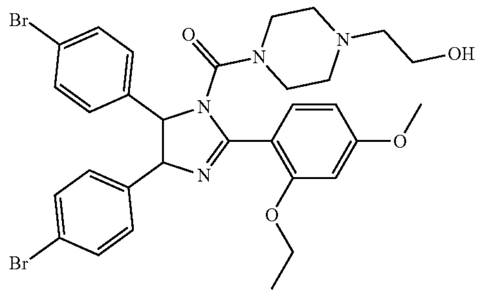

Nutlin-3

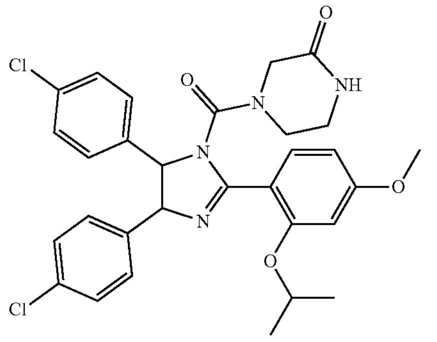

In another particular embodiment, the MDM2 inhibitor is any one of the inhibitors disclosed and/or claimed in U.S. Pat. No. 6,734,302. For example, the MDM2 inhibitor is a compound of Formula III-A:

III-A

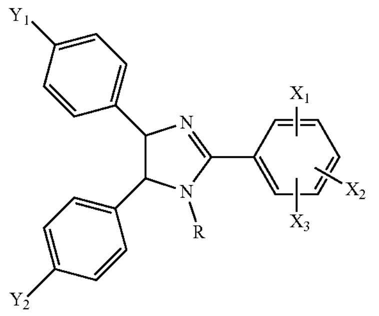

or pharmaceutically acceptable salts or esters thereof, wherein:

R is-$COR^1$;

wherein $R^1$ is selected from $C_1$-$C_4$ alkyl, —C≡CHCOOH, $—NHCH_2CH_2R^2$, $—N(CH_2CH_2OH)CH_2CH_2OH$, $—N(CH_3)CH_2CH_2NHCH_3$, $—N(CH_3)CH_2CH_2N(CH_3)CH_3$, saturated 4-, 5- and 6-membered rings, and saturated and unsaturated 5- and 6-membered rings containing at least one hetero atom wherein the hetero atom is selected from S, N and O and being optionally substituted with a group selected from lower alkyl, —C═O—$R^5$, —OH, lower alkyl substituted with hydroxy, lower alkyl substituted with $—NH_2$, N-lower alkyl, $—SO_2CH_3$, ═O, $—CH_2C{=}OCH_3$, and 5- and 6-membered saturated rings containing at least one hetero atom selected from S, N and O;

wherein $R^5$ is selected from H, lower alkyl, $—NH_2$, —N-lower alkyl, lower alkyl substituted with hydroxy, and lower alkyl substituted with $NH_2$;

wherein $R^2$ is selected from —$N(CH_3)CH_3$, —$NHCH_2CH_2NH_2$, —$NH_2$, morpholinyl and piperazinyl;

$X_1$, $X_2$ and $X_3$ are independently selected from —OH, $C_1$-$C_2$ alkyl, $C_1$-$C_5$ alkoxy, —Cl, —Br, —F, —$CH_2OCH_3$, and —$CH_2OCH_2CH_3$;

or one of $X_1$, $X_2$ or $X_3$ is H and the other two are independently selected from hydroxy, lower alkyl, lower alkoxy, —Cl, —Br, —F, —$CF_3$, —$CH_2OCH_3$, —$CH_2OCH_2CH_3$, —$OCH_2CH_2R^3$, —$OCH_2CF_3$, and —$OR^4$;

or one of $X_1$, $X_2$ or $X_3$ is H and the other two taken together with the two carbon atoms and the bonds between them from the benzene ring to which they are substituted form a 5- or 6-membered saturated ring that contains at least one hetero atom selected from S, N, and O, wherein $R^3$ is selected from —F, —$OCH_3$, —$N(CH_3)CH_3$, unsaturated 5- and 6-membered rings containing at least one hetero atom wherein the hetero atom is selected from S, N and O;

wherein $R^4$ is a 3- to 5-membered saturated ring; and $Y_1$ and $Y_2$ are each independently selected from —Cl, —Br, —$NO_2$, —C≡N, and —C≡CH.

In another embodiment, the MDM2 inhibitor is a substituted piperidine compound. As used herein, the term "substituted piperidine MDM2 inhibitor" refers, for example, to a compound disclosed and/or claimed in U.S. Pat. No. 7,060,713 or 7,553,833.

In another embodiment, the MDM2 inhibitor is a spiroindolinone compound. As used herein, the term "spiroindolinone MDM2 inhibitor" refers, for example, to a compound disclosed and/or claimed in U.S. Pat. Nos. 6,916,833; 7,495,007; or 7,638,548.

In another embodiment, the MDM2 inhibitor is an oxindole compound. As used herein, the term "oxindole MDM2 inhibitor" refers, for example, to a compound disclosed and/or claimed in U.S. Pat. No. 7,576,082.

In another embodiment, the MDM2 inhibitor is a diphenyl-dihydro-imidazopyridinone compound. As used herein, the term "diphenyl-dihydro-imidazopyridinone MDM2 inhibitor" refers, for example, to a compound disclosed and/or claimed in U.S. Pat. No. 7,625,895.

In another embodiment, the MDM2 inhibitor is an imidazothiazole compound. As used herein, the term "imidazothiazole MDM2 inhibitor" refers, for example, to a compound disclosed and/or claimed in U.S. 2009/0312310.

In another embodiment, the MDM2 inhibitor is a deazaflavin compound. As used herein, the term "deazaflavin MDM2 inhibitor" refers, for example, to a compound disclosed and/or claimed in U.S. Patent Application Publication Nos. 2006/0211718 or 2010/0048593.

In another embodiment, the MDM2 inhibitor is a benzodiazapine compound. As used herein, the term "benzodiazapine MDM2 inhibitor" refers, for example, to a compound disclosed and/or claimed in U.S. 2005/0227932.

In another embodiment, the MDM2 inhibitor is a isoindolin-1-one compound. As used herein, the term "isoindolin-1-one MDM2 inhibitor" refers, for example, to a compound disclosed and/or claimed in U.S. 2008/0261917.

In another embodiment, the MDM2 inhibitor is a boronic acid. As used herein, the term "boronic acid MDM2 inhibitor" refers, for example, to a compound disclosed and/or claimed in U.S. Patent Application Publication Nos. 2009/0227542 or 2008/0171723.

In another embodiment, the MDM2 inhibitor is a peptide or polypeptide. As used herein, the term "peptidic MDM2 inhibitor" refers for example, to a compound disclosed and/or claimed in U.S. Pat. No. 7,083,983; U.S. 2006/0211757 A1; U.S. 2005/0137137; U.S. 2002/0132977; U.S. 2009/0030181; or WO 2008/106507.

In another embodiment, the MDM2 inhibitor is a compound disclosed and/or claimed in any of Shangary, S, et al., *Proc. Natl. Acad. Sci. USA.* 105:3933-3938 (2008); Vassilev, L. T., *Trends Mol. Med.* 13:23-31 (2007); Vassilev, L. T. et al., *Science* 363:844-848 (2004); Ding, K. et al, *J. Med. Chem.* 49:3432-3435 2006; Shangary, S. et al., *Clin. Cancer Res.* 34:5318-5324 (2008); Chene, P., *Molecular Cancer Research* 2:20-28 (2004); Pazgier et al., *Proc. Natl. Acad. Sci. USA.* 366:4665-4670 (2009); U.S. 2008/0280769; U.S. 008/0039472; U.S. 2009/0149493; or U.S. 2004/0171035.

In another embodiment, the MDM2 inhibitor is a compound disclosed and/or claimed in any of WO 2009/151069 A1; WO 2009/037343 A1 (U.S. application Ser. No. 12/678,680); WO 2008/125487 A1 (U.S. Pat. No. 7,625,895); WO 2008/119741 A2 (U.S. application Ser. No. 12/593,721); and WO 2009/156735 A2.

In another particular embodiment, the MDM2 inhibitor is any one of the inhibitors disclosed and/or claimed in WO 2009/156735 A2. For example, the MDM2 inhibitor is a compound of Formulae IV-F or V-F:

IV-F

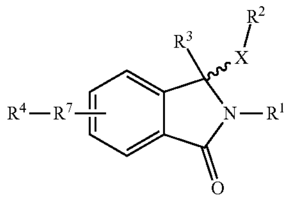

V-F

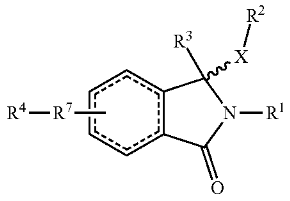

wherein in both Formulae IV-F and V-F:

X is selected from O, N or S;

$R^1$ is selected from hydrogen, substituted or unsubstituted alkyl, substituted or unsubstituted hydroxyalkyl, substituted or unsubstituted alkylamine, substituted or unsubstituted aryl, substituted or unsubstituted heteroaryl, substituted or unsubstituted aralkyl, and substituted or unsubstituted heteroaralkyl;

$R^2$ is selected from hydrogen, substituted or unsubstituted alkenyl, substituted or unsubstituted alkynyl, substituted or unsubstituted branched hydroxyalkyl, substituted or unsubstituted cycloalkyl having 6 ring carbon atoms or greater, substituted or unsubstituted cycloalkenyl, hydroxyalkylaralkyl, hydroxyalkylhetero aralkyl, and a carboxylic acid-containing group;

$R^3$ is selected from hydrogen, substituted or unsubstituted alkyl, substituted or unsubstituted hydroxyalkyl, substituted or unsubstituted alkylamine, substituted or unsubstituted alkoxy, substituted or unsubstituted aryl, substituted or unsubstituted heteroaryl, substituted or unsubstituted aralkyl, and substituted or unsubstituted heteroaralkyl; and $R^4$-$R^7$ represents groups $R^4$, $R^5$, $R^6$ and $R^7$ which are independently selected from hydrogen, halo, hydroxy, substituted or unsubstituted alkyl, substituted or unsubstituted hydroxyalkyl, substituted or unsubstituted alkenyl, substituted or unsubstituted alkynyl, substituted or unsubstituted heteroaryl, substituted or unsubstituted heteroaralkyl, substituted or unsubstituted alkylamine, substituted or unsubstituted alkoxy, trifluoromethyl, amino, nitro, carboxyl, carbonylmethylsulfone, trifluoromethylsulfone, cyano and substituted or unsubstituted sulfonamide;

wherein $R^2$ is substituted or unsubstituted branched hydroxyalkyl, X is O or S; and wherein $R^2$ is hydrogen, at least one of $R^4$-$R^7$ is not hydrogen and $R^3$ is not a benzimidazole derivative or a benzimidazoline derivative; and wherein, in the Formula V, the 6-membered ring may have 0, 1, or 2 C═C double bonds.

In a particular embodiment, the MDM2 inhibitor is any one of the inhibitors disclosed and/or claimed in WO 2009/1511069 A1. For example, the MDM2 inhibitor is a compound of Formula VI-G:

VI-G

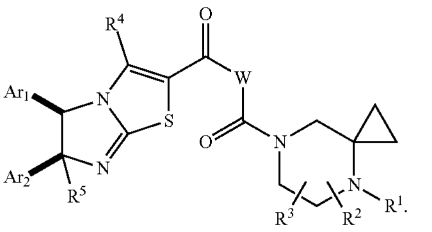

Possible examples of substituent groups include where:

$Ar_1$ and $Ar_2$ are each independently selected from the group consisting of optionally substituted aryl and optionally substituted heteroaryl;

$R^1$ is selected from the group consisting of hydrogen, optionally substituted alkyl, and —$COR^{1a}$;

$R^{1a}$ is selected from the group consisting of hydrogen, optionally substituted alkyl, optionally substituted cycloalkyl, and optionally substituted aryl;

$R^2$ and $R^3$ are each independently selected from the group consisting of hydrogen and optionally substituted alkyl; or $R^2$ and $R^3$ taken together form a 3- to 6-membered optionally substituted cycloalkyl or heterocyclo;

$R^4$ and $R^5$ are each independently selected from the group consisting of hydrogen, optionally substituted alkyl, optionally substituted cycloalkyl, and optionally substituted aryl;

W is selected from the group consisting of:

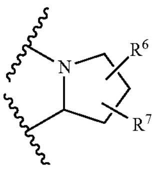

and

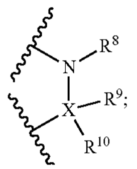

wherein:

$R^6$ and $R^7$ are each independently selected from the group consisting of hydrogen, hydroxy and optionally substituted alkyl; or $R^6$ and $R^7$ taken together form a 3- to 6-membered optionally substituted cycloalkyl or an oxo, i.e., C═O;

$R^8$ is selected from the group consisting of hydrogen or optionally substituted alkyl;

$R^9$ and $R^{10}$ are each independently selected from the group consisting of hydrogen or optionally substituted alkyl; or $R^9$ and $R^{10}$ taken together form a 3- to 6-membered optionally substituted cycloalkyl or heterocyclo; and X is a carbon atom.

In a particular embodiment, MDM2 inhibitor is a compound of Formula VI-G wherein possible examples of substituent groups include where:

An and $Ar_2$ are each independently selected from the group consisting of optionally substituted phenyl and optionally substituted pyridyl;

$R^1$ is selected from the group consisting of hydrogen, optionally substituted $C_1$-$C_6$ alkyl, and —$COR^{1a}$;

$R^{1a}$ is selected from the group consisting of hydrogen and optionally substituted $C_1$-$C_6$ alkyl;

$R^2$ and $R^3$ are each independently selected from the group consisting of hydrogen and optionally substituted $C_1$-$C_6$ alkyl; or $R^2$ and $R^3$ taken together form a 3- to 6-membered optionally substituted cycloalkyl;

$R^4$ and $R^5$ are each independently selected from the group consisting of hydrogen and optionally substituted $C_1$-$C_6$ alkyl;

W is:

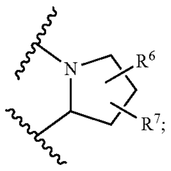

wherein:

$R^6$ and $R^7$ are each independently selected from the group consisting of hydrogen and optionally substituted $C_1$-$C_6$ alkyl; or $R^6$ and $R^7$ taken together form a 3- to 6-membered optionally substituted cycloalkyl or an oxo.

The present disclosure provides Compounds of the Disclosure as MDM2 protein degraders for the treatment of a variety of diseases and conditions wherein degradation of MDM2 proteins has a beneficial effect. Compounds of the Disclosure typically have a binding affinity ($IC_{50}$) to MDM2 of less than 100 μM, e.g., less than 50 μM, less than 25 μM, and less than 5 μM, less than about 1 μM, less than about 0.5 μM, or less than about 0.1 μM. In one embodiment, the present disclosure relates to a method of treating an individual suffering from a disease or condition wherein degradation of MDM2 proteins provides a benefit comprising administering a therapeutically effective amount of a Compound of the Disclosure to an individual in need thereof.

Since Compounds of the Disclosure are degraders of MDM2 protein, a number of diseases and conditions mediated by MDM2 can be treated by employing these compounds. The present disclosure is thus directed generally to a method for treating a condition or disorder responsive to degradation of MDM2, in an animal, e.g., a human, suffering from, or at risk of suffering from, the condition or disorder, the method comprising administering to the animal an effective amount of one or more Compounds of the Disclosure.

The present disclosure is further directed to a method of degrading MDM2 protein in an animal in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent useful in the treatment of diseases and conditions wherein degradation of MDM2 protein provides a benefit, packaged separately or together, and an insert having instructions for using these active agents.

In one embodiment, a Compound of the Disclosure is administered in conjunction with a second therapeutic agent useful in the treatment of a disease or condition wherein degradation of MDM2 protein provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to degrade MDM2 protein in the patient.

In one embodiment, the disease to be treated by the Compound of the Disclosure is cancer. Examples of treatable cancers include, but are not limited to, any one or more of the cancers of Table 9.

TABLE 9

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryoblastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blastoma | bone cancer | Brenner tumor |
| Brown tumor | Burkitt's lymphoma | breast cancer | brain cancer |
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |

TABLE 9-continued

| | | | |
|---|---|---|---|
| glial tumor | glioblastoma multiforme | glioma | gliomatosis cerebri |
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological malignancy | hepatoblastoma |
| hepatosplenic T-cell lymphoma | Hodgkin's lymphoma | non-Hodgkin's lymphoma | invasive lobular carcinoma |
| intestinal cancer | kidney cancer | laryngeal cancer | lentigo maligna |
| lethal midline carcinoma | leukemia | leydig cell tumor | liposarcoma |
| lung cancer | lymphangioma | lymphangiosarcoma | lymphoepithelioma |
| lymphoma | acute lymphocytic leukemia | acute myelogeous leukemia | chronic lymphocytic leukemia |
| liver cancer | small cell lung cancer | non-small cell lung cancer | MALT lymphoma |
| malignant fibrous histiocytoma | malignant peripheral nerve sheath tumor | malignant triton tumor | mantle cell lymphoma |
| marginal zone B-cell lymphoma | mast cell leukemia | mediastinal germ cell tumor | medullary carcinoma of the breast |
| medullary thyroid cancer | medulloblastoma | melanoma | meningioma |
| merkel cell cancer | mesothelioma | metastatic urothelial carcinoma | mixed Mullerian tumor |
| mucinous tumor | multiple myeloma | muscle tissue neoplasm | mycosis fungoides |
| myxoid liposarcoma | myxoma | myxosarcoma | nasopharyngeal carcinoma |
| neurinoma | neuroblastoma | neurofibroma | neuroma |
| nodular melanoma | ocular cancer | oligoastrocytoma | oligodendroglioma |
| oncocytoma | optic nerve sheath meningioma | optic nerve tumor | oral cancer |
| osteosarcoma | ovarian cancer | Pancoast tumor | papillary thyroid cancer |
| paraganglioma | pinealoblastoma | pineocytoma | pituicytoma |
| pituitary adenoma | pituitary tumor | plasmacytoma | polyembryoma |
| precursor T-lymphoblastic lymphoma | primary central nervous system lymphoma | primary effusion lymphoma | preimary peritoneal cancer |
| prostate cancer | pancreatic cancer | pharyngeal cancer | pseudomyxoma periotonei |
| renal cell carcinoma | renal medullary carcinoma | retinoblastoma | rhabdomyoma |
| rhabdomyosarcoma | Richter's transformation | rectal cancer | sarcoma |
| Schwannomatosis | seminoma | Sertoli cell tumor | sex cord-gonadal stromal tumor |
| signet ring cell carcinoma | skin cancer | small blue round cell tumors | small cell carcinoma |
| soft tissue sarcoma | somatostatinoma | soot wart | spinal tumor |
| splenic marginal zone lymphoma | squamous cell carcinoma | synovial sarcoma | Sezary's disease |
| small intestine cancer | squamous carcinoma | stomach cancer | T-cell lymphoma |
| testicular cancer | thecoma | thyroid cancer | transitional cell carcinoma |
| throat cancer | urachal cancer | urogenital cancer | urothelial carcinoma |
| uveal melanoma | uterine cancer | verrucous carcinoma | visual pathway glioma |
| vulvar cancer | vaginal cancer | Waldenstrom's macroglobulinemia | Warthin's tumor |
| Wilms' tumor | | | |

In another embodiment, the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the MDM2 protein degrader that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Compound of the Disclosure, or a composition containing the same, can be from about 1 ng/kg to about 200 mg/kg, about 1 μg/kg to about 100 mg/kg, or about 1 mg/kg to about 50 mg/kg. The dosage of a composition can be at any dosage including, but not limited to, about 1 μg/kg. The dosage of a composition may be at any dosage including, but not limited to, about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Non-limiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Non-limiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary non-limiting alkylating agents include cyclophosphamide, ifosfamide, melphalan, and nitrosoureas, such as carmustine and lomustine.

Exemplary non-limiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary non-limiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary non-limiting mTOR inhibitors include compounds that inhibit the mammalian target of rapamycin (mTOR) and possess antiproliferative activity such as sirolimus, everolimus, CCI-779, and ABT578.

Exemplary non-limiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary non-limiting platin compounds include carboplatin, cis-platin, cisplatinum, and oxaliplatin.

Exemplary non-limiting methionine aminopeptidase inhibitors include bengamide or a derivative thereof and PPI-2458.

Exemplary non-limiting bisphosphonates include etridonic acid, clodronic acid, tiludronic acid, pamidronic acid, alendronic acid, ibandronic acid, risedronic acid, and zoledronic acid.

Exemplary non-limiting antiproliferative antibodies include trastuzumab, trastuzumab-DMl, cetuximab, bevacizumab, rituximab, PR064553, and 2C4. The term "antibody" includes intact monoclonal antibodies, polyclonal antibodies, multispecific antibodies formed from at least two intact antibodies, and antibody fragments, so long as they exhibit the desired biological activity.

Exemplary non-limiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a famesyl transferase inhibitor, such as L-744832, DK8G557, tipifamib, and lonafamib.

Exemplary non-limiting telomerase inhibitors include compounds that target, decrease, or inhibit the activity of telomerase, such as compounds that inhibit the telomerase receptor, such as telomestatin.

Exemplary non-limiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosinc (ara-c), and bisulfan; and ALK inhibitors, which are compounds which target, decrease, or inhibit anaplastic lymphoma kinase.

Exemplary non-limiting Flt-3 inhibitors include PKC412, midostaurin, a staurosporine derivative, SU11248, and MLN518.

Exemplary non-limiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino, 17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SUlOl, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD 180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a famesyl transferase inhibitor; PD 184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, Cl-1033, EKB-569, GW-2016, antibodies ELI, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a present MDM2 degrader, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a present MDM2 degrader also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, Pennsylvania, 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

The term "a disease or condition wherein degradation of MDM2 protein provides a benefit" pertains to a disease or condition in which MDM2 and/or an action of MDM2 is important or necessary, e.g., for the onset, progress, expression of that disease or condition, or a disease or a condition which is known to be treated by a MDM2 inhibitor or degrader. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by MDM2 for any particular cell type, for example, by assays which conveniently can be used to assess the activity of particular compounds.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated in the examples below, a Compound of the Disclosure is a degrader of MDM2 protein and can be used in treating diseases and conditions wherein degradation of MDM2 provides a benefit.

As used herein, the terms "treat," "treating," "treatment," refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce MDM2 signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

In the present disclosure, the term "halo" as used by itself or as part of another group refers to —Cl, —F, —Br, or —I.

In the present disclosure, the term "nitro" as used by itself or as part of another group refers to $—NO_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-10}$ alkyl. In another embodiment, the alkyl is a $C_{1-6}$ alkyl. In another embodiment, the alkyl is a $C_{1-4}$ alkyl. In another embodiment, the alkyl is a straight chain $C_{1-10}$ alkyl. In another embodiment, the alkyl is a branched chain $C_{3-10}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-10}$ alkyl groups include methyl, ethyl, propyl, isopropyl, butyl, sec-butyl, tert-butyl, No-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and No-butyl.

In the present disclosure, the term "heteroalkyl" as used by itself or part of another group refers to unsubstituted straight- or branched-chain aliphatic hydrocarbons containing from three to thirty chain atoms, i.e., 3- to 30-membered heteroalkyl, or the number of chain atoms designated, wherein at least one $—CH_2—$ is replaced with at least one —O—, —N(H)—, or —S—. The —O—, —N(H)—, or —S— can independently be placed at any interior position of the aliphatic hydrocarbon chain so long as each —O—, N(H)—, or —S— group is separated by at least two $—CH_2—$ groups. In one embodiment, one $—CH_2—$ group is replaced with one —O— group. In another embodiment, two $—CH_2—$ groups are replaced with two —O— groups. In another embodiment, three $—CH_2—$ groups are replaced with three —O— groups. In another embodiment, four $—CH_2—$ groups are replaced with four —O— groups. Non-limiting exemplary heteroalkyl groups include:

$—CH_2OCH_3$;

$—CH_2OCH_2CH_2CH_3$;

$—CH_2CH_2CH_2OCH_3$;

$—CH_2OCH_2CH_2OCH_3$; and $—CH_2OCH_2CH_2OCH_2CH_2OCH_3$.

In the present disclosure, the term "alkylenyl" as used herein by itself or part of another group refers to a divalent form of an alkyl group. In one embodiment, the alkylenyl is a divalent form of a $C_{1-12}$ alkyl. In one embodiment, the alkylenyl is a divalent form of a $C_{1-10}$ alkyl. In one embodiment, the alkylenyl is a divalent form of a $C_{1-8}$ alkyl. In one embodiment, the alkylenyl is a divalent form of a $C_{1-6}$ alkyl. In another embodiment, the alkylenyl is a divalent form of a $C_{1-4}$ alkyl. Non-limiting exemplary alkylenyl groups include:

$—CH_2—$, $—CH_2CH_2—$, $—CH_2CH_2CH_2—$, $—CH_2(CH_2)_2CH_2—$, $—CH(CH_2)_3CH_2—$, $—CH_2(CH_2)_4CH_2—$, $—CH_2(CH_2)_5CH_2—$, $—CH_2CH(CH_3)CH_2—$, and $—CH_2C(CH_3)_2CH_2—$.

In the present disclosure, the term "heteroalkylenyl" as used herein by itself or part of another group refers to a divalent form of a heteroalkyl group. In one embodiment, the heteroalkylenyl is a divalent form of a 3- to 12-membered heteroalkyl. In another embodiment, the heteroalkylenyl is a divalent form of a 3- to 10-membered heteroalkyl. In another embodiment, the heteroalkylenyl is a divalent form of a 3- to 8-membered heteroalkyl. In another embodiment, the heteroalkylenyl is a divalent form of a 3- to 6-membered heteroalkyl. In another embodiment, the heteroalkylenyl is a divalent form of a 3- to 4-membered heteroalkyl. In another embodiment, the heteroalkylenyl is a radical of the formula: $—(CH_2)_oO—(CH_2CH_2O)_p—(CH_2)_q—$, wherein o is 2 or 3; p is 0, 1, 2, 3, 4, 5, 6, or 7; and q is 2 or 3. In another embodiment, the heteroalkylenyl is a radical of the formula: $—(CH_2)_rO—(CH_2)_s—O(CH_2)_t—$, wherein r is 2, 3, or 4; s is 3, 4, or 5; and t is 2 or 3. Non-limiting exemplary heteroalkylenyl groups include:

$—CH_2OCH_2—$;

$—CH_2CH_2OCH_2CH_2—$;

$—CH_2OCH_2CH_2CH_2—$;

$—CH_2CH_2OCH_2CH_2CH_2—$;

$—CH_2CH_2OCH_2CH_2OCH_2CH_2—$; and $—CH_2CH_2OCH_2CH_2OCH_2CH_2O—$.

In the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include $—CH_2CH_2NO_2$, $—CH_2SO_2CH_3$ $CH_2CH_2CO_2H$, $—CH_2CH_2SO_2CH_3$, $—CH_2CH_2COPh$, and $—CH_2C_6H_U$.

In the present disclosure, the term "cycloalkyl" as used by itself or as part of another group refers to saturated and partially unsaturated (containing one or two double bonds)

cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbomyl, decalin, adamantyl, cyclohexenyl, cyclopentenyl, and cyclohexenyl.

In the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent.

In the present disclosure, the term "cycloalkylenyl" as used herein by itself or part of another group refers to a divalent form of an optionally substituted cycloalkyl group. Non-limiting examples of a cycloalkylenyl include:

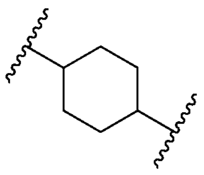

and

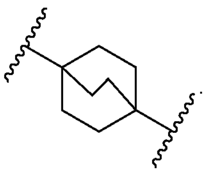

.

Non-limiting examples of a cycloalkylenyl also include:

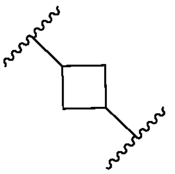

and

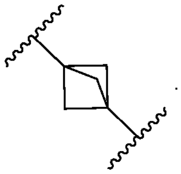

.

In the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

In the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

In the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups, e.g.,

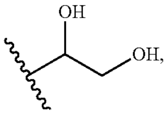

,

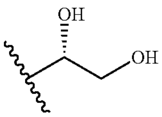

or

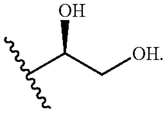

.

In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

In the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

In the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include $—SCH_3$, and $—SCH_2CH_3$.

In the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

In the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Non-limiting examples include:

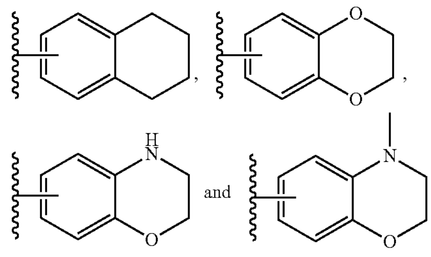

In the present disclosure, the term "arylenyl" as used herein by itself or part of another group refers to a divalent form of an optionally substituted aryl group.

In the present disclosure, the term "phenylenyl" as used herein by itself or part of another group refers to a divalent form of an optionally substituted phenyl group. Non-limiting examples include:

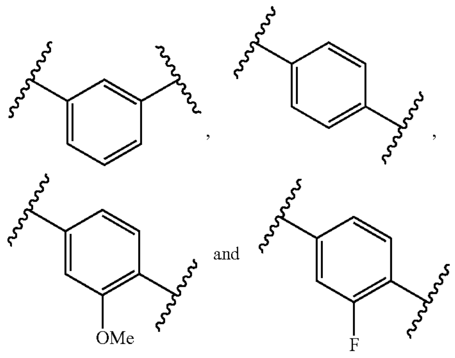

In the present disclosure, the term "aryloxy" as used by itself or as part of another group refers to an optionally substituted aryl attached to a terminal oxygen atom. A non-limiting exemplary aryloxy group is PhO—.

In the present disclosure, the term "aralkyloxy" as used by itself or as part of another group refers to an aralkyl group attached to a terminal oxygen atom. A non-limiting exemplary aralkyloxy group is $PhCH_2O—$.

In the present disclosure, the term "heteroaryl" or "heteroaromatic" refers to monocyclic and bicyclic aromatic ring systems having 5 to 14 ring atoms (i.e., $C_5$-$C_{14}$ heteroaryl), wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. In one embodiment, the optionally substituted heteroaryl has one substituent. Any available carbon or nitrogen atom can be substituted. Non-limiting exemplary optionally substituted 5-membered heteroaryl groups include, but are not limited to:

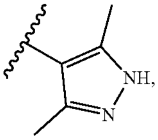 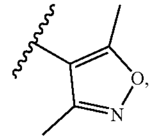 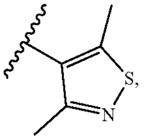

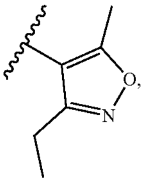 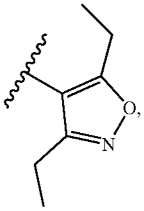 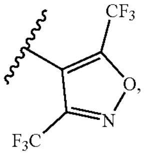

-continued

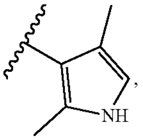 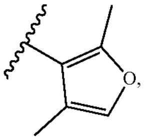 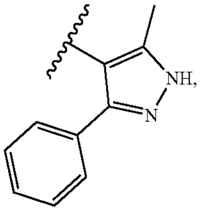

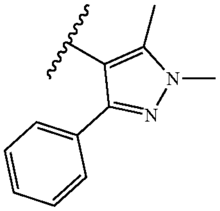, 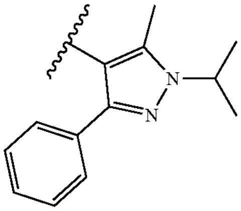,

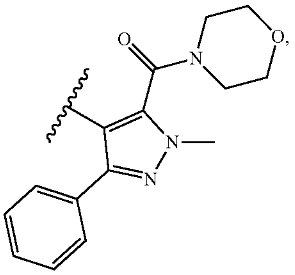

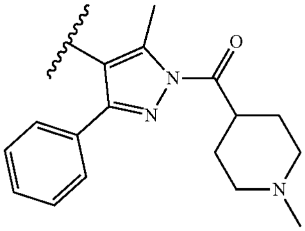

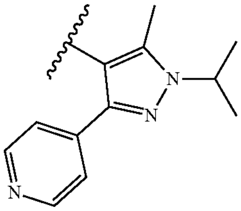,

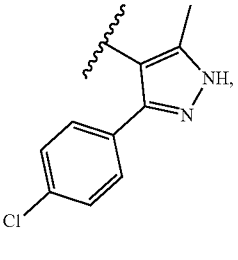 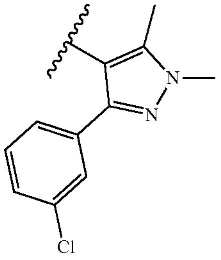

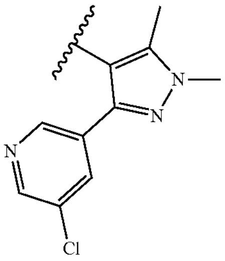, 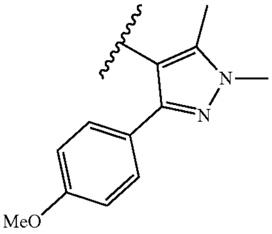,

-continued
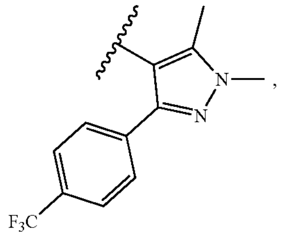
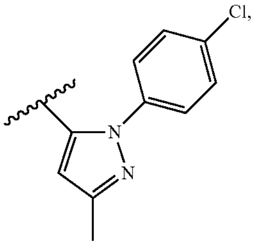
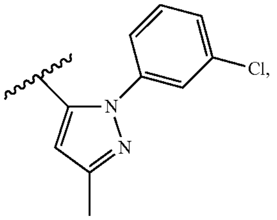
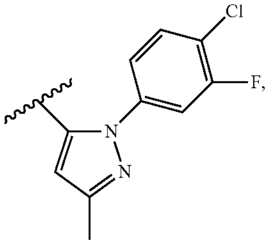
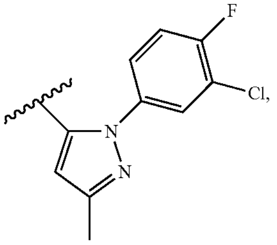
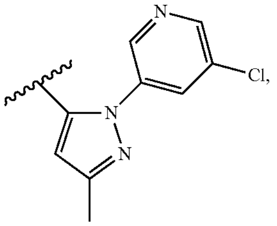
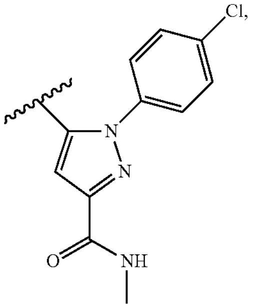
-continued
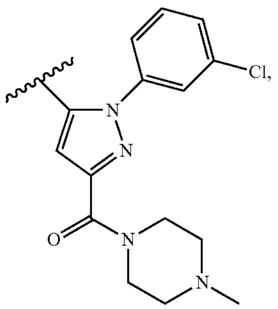
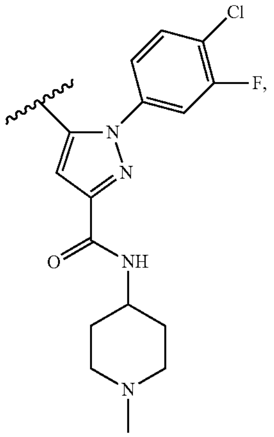
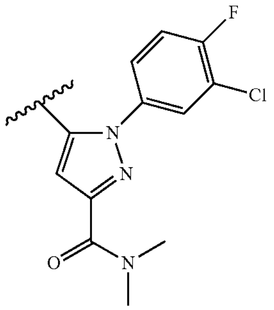
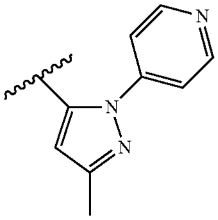
,
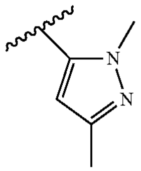
,
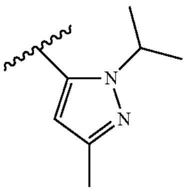
,
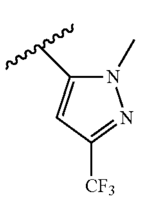
, and
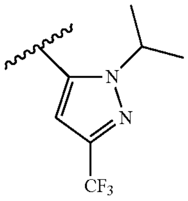
.
The term optionally substituted heteroaryl is also meant to include groups having fused optionally substituted cycloalkyl and fused optionally substituted heterocyclo rings. Non-limiting examples include:

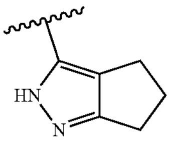, 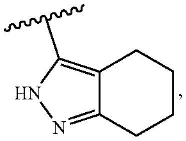,

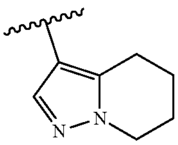 and 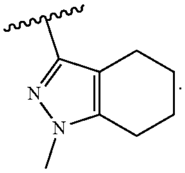.

In the present disclosure, the term "heteroarylenyl" as used herein by itself or part of another group refers to a divalent form of an optionally substituted heteroaryl group. In one embodiment, the heteroarylenyl is a 5-membered heteroarylenyl. Non-limiting examples of a 5-membered heteroarylenyl include:

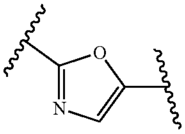, 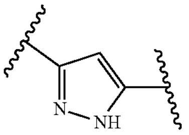,

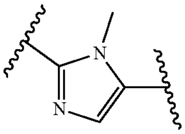 and 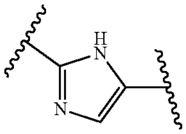.

In one embodiment, the heteroarylenyl is a 6-membered heteroarylenyl. Non-limiting examples of a 6-membered heteroarylenyl include:

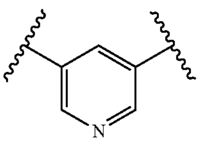, 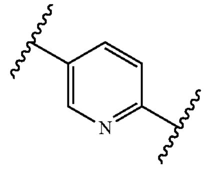,

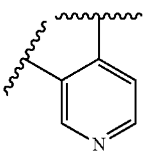 and 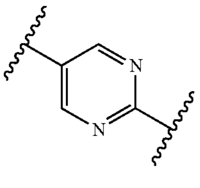

In the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring $—CH_2—$ is replaced with a $—C(═O)—$, for example, cyclic ureido groups such as 2-imidazolidinone and cyclic amide groups such as β-lactam, γ-lactam, δ-lactam, ε-lactam, and piperazin-2-one. The term "heterocyclo" is also meant to include groups having fused optionally substituted aryl groups, e.g., indolinyl, chroman-4-yl. In one embodiment, the heterocyclo group is chosen from a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, alkoxycarbonyl, $CF_3C(═O)—$, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. Substitution may occur on any available carbon or nitrogen atom, or both. Non-limiting exemplary optionally substituted heterocyclo groups include:

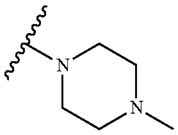 and 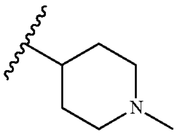

In the present disclosure, the term "heterocyclenyl" as used herein by itself or part of another group refers to a divalent form of an optionally substituted heterocyclo group. Substitution may occur at any available carbon atom or nitrogen atom. In one embodiment, the heterocyclenyl is a 4-membered heterocyclenyl. In another embodiment, the heterocyclenyl is a 5-membered heterocyclenyl. In another embodiment, the heterocyclenyl is a 6-membered heterocyclenyl. Non-limiting exemplary heterocyclenyl groups include:

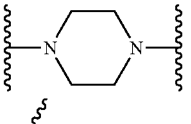, 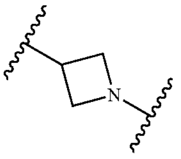 and

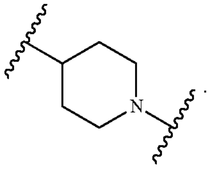.

In the present disclosure, the term "amino" as used by itself or as part of another group refers to $—NR^{10a}R^{10b}$, wherein $R^{10a}$ and $R^{10b}$ are each independently hydrogen, alkyl, hydroxyalkyl, optionally substituted cycloalkyl, optionally substituted aryl, optionally substituted heterocyclo, or optionally substituted heteroaryl, or $R^{10a}$ and $R^{10b}$ are taken together to form a 3- to 8-membered optionally substituted heterocyclo. Non-limiting exemplary amino groups include —$NH_2$ and —N(H)($CH_3$).

In the present disclosure, the term "(amino)alkyl" as used by itself or as part of another group refers to an alkyl group substituted with an amino group. Non-limiting exemplary amino alkyl groups include —$CH_2CH_2NH_2$, and —$CH_2CH_2N(H)CH_3$, —$CH_2CH_2N(CH_3)_2$, and —$CH_2N(H)$ cyclopropyl.

In the present disclosure, the term "carboxamido" as used by itself or as part of another group refers to a radical of formula —C(═O)$NR^{9a}R^{9b}$, wherein $R^{9a}$ and $R^{9b}$ are each independently hydrogen, optionally substituted alkyl, hydroxyalkyl, optionally substituted cycloalkyl, optionally substituted aryl, optionally substituted heterocyclo, or optionally substituted heteroaryl, or $R^{9a}$ and $R^{9b}$ taken together with the nitrogen to which they are attached form a 3- to 8-membered optionally substituted heterocyclo group. In one embodiment, $R^{9a}$ and $R^{9b}$ are each independently hydrogen or optionally substituted alkyl. In one embodiment, $R^{9a}$ and $R^{9b}$ are taken together to taken together with the nitrogen to which they are attached form a 3- to 8-membered optionally substituted heterocyclo group. Non-limiting exemplary carboxamido groups include, but are not limited to, —$CONH_2$, —CON(H)$CH_3$, —CON($CH_3$)$_2$, —CON(H)Ph,

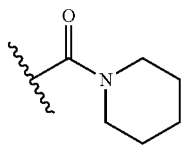,
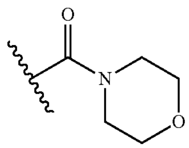,
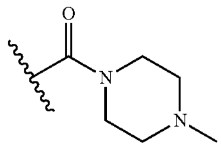
and
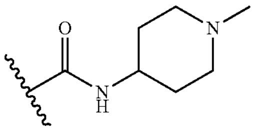

In the present disclosure, the term "sulfonamido" as used by itself or as part of another group refers to a radical of the formula —$SO_2NR^{8a}R^{8b}$, wherein $R^{8a}$ and $R^{8b}$ are each independently hydrogen, optionally substituted alkyl, or optionally substituted aryl, or $R^{8a}$ and $R^{8b}$ taken together with the nitrogen to which they are attached from a 3- to 8-membered heterocyclo group. Non-limiting exemplary sulfonamido groups include —$SO_2NH_2$, —$SO_2N(H)CH_3$, and —$SO_2N(H)Ph$.

In the present disclosure, the term "alkylcarbonyl" as used by itself or as part of another group refers to a carbonyl group, i.e., —C(═O)—, substituted by an alkyl group. A non-limiting exemplary alkylcarbonyl group is —$COCH_3$.

In the present disclosure, the term "arylcarbonyl" as used by itself or as part of another group refers to a carbonyl group, i.e., —C(═O)—, substituted by an optionally substituted aryl group. A non-limiting exemplary arylcarbonyl group is —COPh.

In the present disclosure, the term "alkoxycarbonyl" as used by itself or as part of another group refers to a carbonyl group, i.e., —C(═O)—, substituted by an alkoxy group. Non-limiting exemplary alkoxycarbonyl groups include —C(═O)OMe, —C(═O)OEt, and —C(═O)OtBu.

In the present disclosure, the term "alkylsulfonyl" as used by itself or as part of another group refers to a sulfonyl group, i.e., —$SO_2$—, substituted by any of the above-mentioned optionally substituted alkyl groups. A non-limiting exemplary alkylsulfonyl group is —$SO_2CH_3$.

In the present disclosure, the term "arylsulfonyl" as used by itself or as part of another group refers to a sulfonyl group, i.e., —$SO_2$—, substituted by any of the above-mentioned optionally substituted aryl groups. A non-limiting exemplary arylsulfonyl group is —$SO_2Ph$.

In the present disclosure, the term "mercaptoalkyl" as used by itself or as part of another group refers to any of the above-mentioned alkyl groups substituted by a —SH group.

In the present disclosure, the term "carboxy" as used by itself or as part of another group refers to a radical of the formula —COOH.

In the present disclosure, the term "carboxyalkyl" as used by itself or as part of another group refers to any of the above-mentioned alkyl groups substituted with a —COOH. A non-limiting exemplary carboxyalkyl group is —$CH_2CO_2H$.

In the present disclosure, the terms "aralkyl" or "arylalkyl" as used by themselves or as part of another group refers to an alkyl group substituted with one, two, or three optionally substituted aryl groups. In one embodiment, the optionally substituted aralkyl group is a $C_{1-4}$ alkyl substituted with one optionally substituted aryl group. In one embodiment, the optionally substituted aralkyl group is a $C_1$ or $C_2$ alkyl substituted with one optionally substituted aryl group. In one embodiment, the optionally substituted aralkyl group is a $C_1$ or $C_2$ alkyl substituted with one optionally substituted phenyl group. Non-limiting exemplary optionally substituted aralkyl groups include benzyl, phenethyl, —$CHPh_2$, —$CH_2$(4-F-Ph), —$CH_2$(4-Me-Ph), —$CH_2$(4-$CF_3$-Ph), and —CH(4-F-Ph)$_2$.

In the present disclosure, the terms "(heterocyclo)alkyl" as used by itself or part of another group refers to an alkyl group substituted with an optionally substituted heterocyclo group. In one embodiment, the (heterocyclo)alkyl is a $C_{1-4}$ alkyl substituted with one optionally substituted heterocyclo group. Non-limiting exemplary (heterocyclo)alkyl groups include:

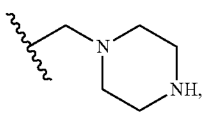
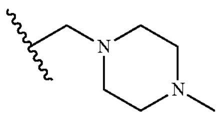
and
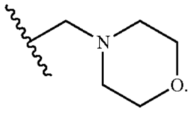

The present disclosure encompasses any of the Compounds of the Disclosure being isotopically-labeled, i.e., radiolabeled, by having one or more atoms replaced by an atom having a different atomic mass or mass number. Examples of isotopes that can be incorporated into Compounds of the Disclosure include isotopes of hydrogen, carbon, nitrogen, sulfur, oxygen, fluorine, and chlorine, such as $^{2}H$ (or deuterium (D)), $^{3}H$, $^{11}C$, $^{13}C$, $^{14}C$, $^{15}N$, $^{18}O$, $^{17}O$, $^{35}S$, $^{18}F$, and $^{36}Cl$, e.g., $^{2}H$, $^{3}H$, and $^{13}C$. In one embodiment, a portion of the atoms at a position within a Compound of the Disclosure are replaced, i.e., the Compound of the Disclosure is enriched at a position with an atom having a different atomic mass or mass number. In one embodiment, at least about 1% of the atoms are replaced with atoms having a different atomic mass or mass number. In another embodiment, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% of the atoms are replaced with atoms having a different atomic mass or mass number. For example, when $B^1$ of Formula I-A, VII, or VIII, is B-1a, B-1b, B-1c, or B-1d, and $R^5$ is hydrogen, the hydrogen at $R^5$ may be replaced entirely or partially with deuterium, e.g., at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the hydrogen atoms at $R^5$ are deuterium atoms. Isotopically-labeled Compounds of the Disclosure can be prepared by methods known in the art.

General Synthesis of Compounds

Compounds of the Disclosure are prepared using methods known to those skilled in the art in view of this disclosure, or by the illustrative methods shown in the General Schemes below. Suitable protecting can be employed in the synthesis, if needed. See Wuts, P. G. M.; Greene, T. W., "Greene's Protective Groups in Organic Synthesis", 4th Ed., J. Wiley & Sons, NY, 2007.

General Scheme 1

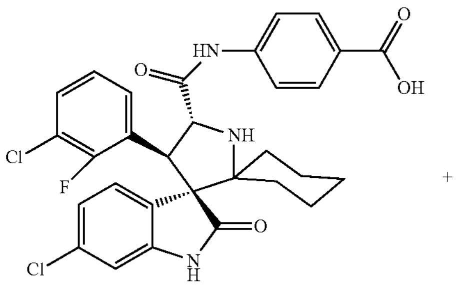

Cpd. A

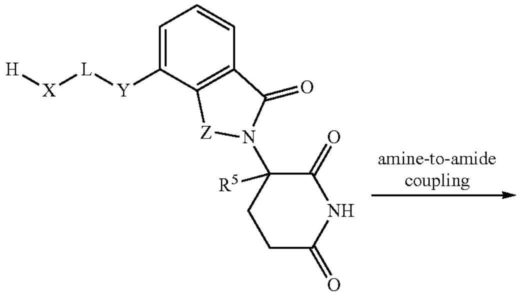

Formula V

-continued

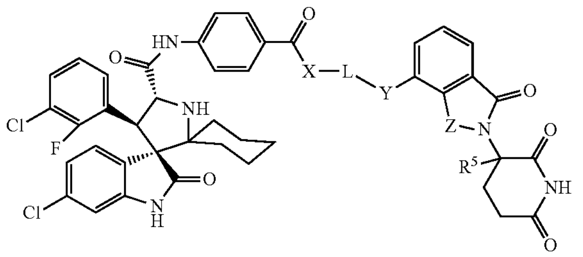

Formula II
(wherein A is A-1)

In General Scheme 1, Cpd. A is reacted with a compound having Formula V in an organic solvent to give a compound having Formula II, wherein A is A-1. Cpd. A is a MDM2 inhibitor. See Compound Example No. 22 of U.S. Pat. No. 8,629,141. Compounds having Formula V may be prepared using methods known in the art and/or as illustrated in the Examples below. Suitable amine-to-amide coupling reagents and conditions, e.g., HATU/base, HBTU/base, or EDCI/HOBt/base, are well known in the art. See Montalbetti and Falque, *Tetrahedron* 67:10827-10852 (2005).

In the alternative, the carboxylic acid of Cpd. A can be converted to the acid chloride, and reacted with a compound having Formula V to give a compound having Formula II, wherein A is A-1 according to General Scheme 2.

General Scheme 2

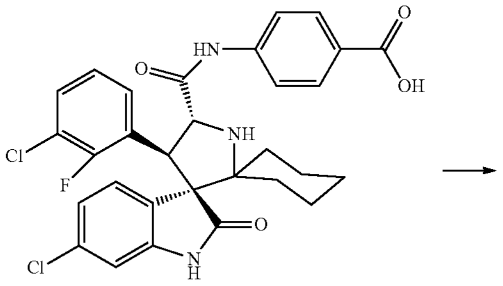

Cpd. A

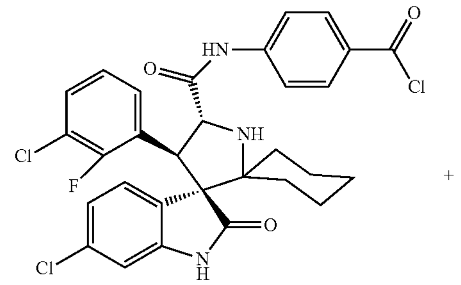

-continued

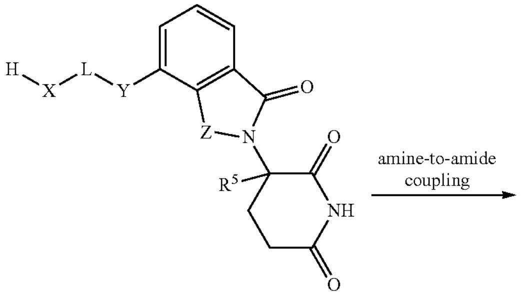

Formula V

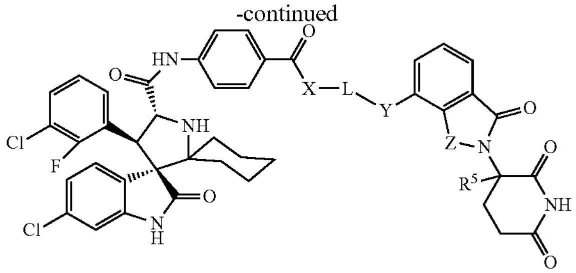

Formula II
(wherein A is A-1)

In General Scheme 3, Cpd. A is reacted with a compound having Formula VI in an organic solvent to give a compound having Formula III, wherein A is A-1. Compounds having Formula V may be prepared using methods known in the art and/or as illustrated in the Examples below. Suitable amine-to-amide coupling reagents and conditions e.g., HATU/base, HBTU/base, or EDCI/HOBt/base, are well known in the art. See Montalbetti and Falque, *Tetrahedron* 61: 10827-10852 (2005).

General Scheme 3

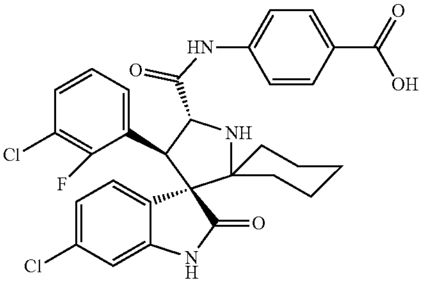

Cpd. A

+

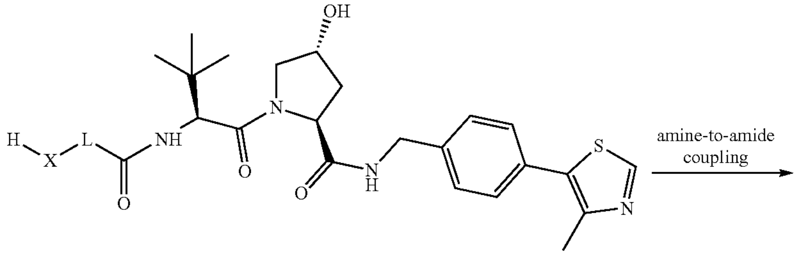

Formula VI

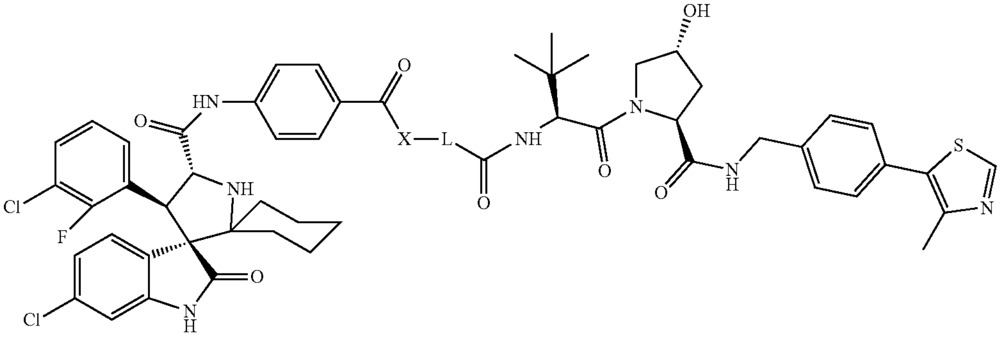

Formula III
(wherein A is A-1)

EXAMPLES

Example 1

Synthesis of (3'R,4'S,5'R)-6"-chloro-4'-(3-chloro-2-fluorophenyl)-N-(4-((4-(2-((2-(2,6-dioxopiperidin-3-yl)-1,3-dioxoisoindolin-4-yl)oxy)acetamido)butyl)carbamoyl)phenyl)-2"-oxodispiro[cyclohexane-1,2'-pyrrolidine-3',3"-indoline]-5'-carboxamide (Cpd. No. 1)

Step 1: Synthesis of S1

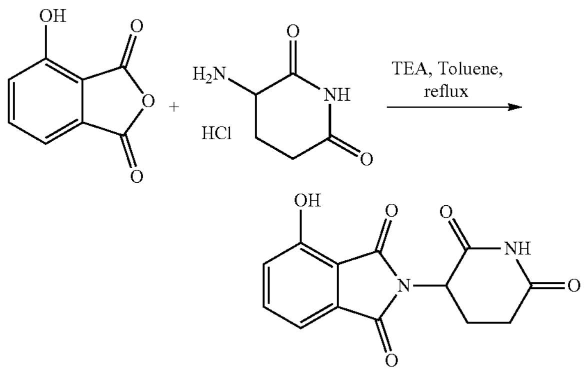

S1

To a round-bottom flask, 3-hydroxyphthalic anhydride (1 g, 6.09 mmol) and 3-aminoperidine-2,6-dione hydrochloride (1.0 g, 6.09 mmol) were mixed in 50 mL of toluene. Triethyl amine (0.93 mL, 6.7 mmol) was added. The resulting reaction mixture was heated to reflux for 12 h with Dean-Stark Trap equipment. After cooling to ambient temperature, evaporation of most of the solvent to give a crude product, which was purified by flash column chromatography with DCM:EA to get the desired product as a slightly yellow solid S1 (1.5 g, 90% yield). $^1$H NMR (400 MHz, DMSO-$d^6$) δ (ppm) 11.16 (s, 1H), 11.08 (s, 1H), 7.65 (t, J=7.6 Hz, 1H), 7.32 (d, J=7.2 Hz, 1H), 7.25 (d, J=8.4 Hz, 1H), 5.07 (dd, J=12.8 Hz, J=5.2 Hz, 1H), 2.93-2.84 (m, 1H), 2.61-2.46 (m, 1H), 2.05-2.01 (m, 1H).

Step 1: Synthesis of S2

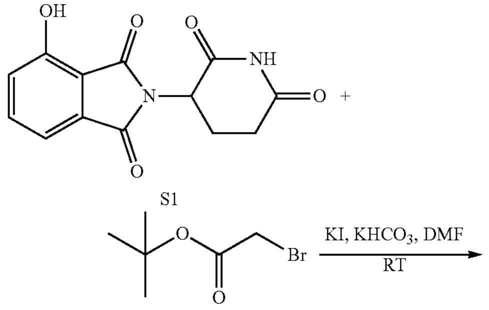

S1

-continued

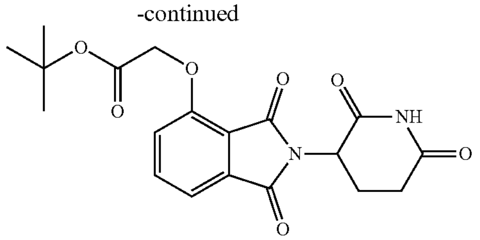

S2

To a round-bottom flask, S1 (1.5 g, 5.5 mmol) was dissolved in 10 mL of DMF. To the stirred solution, KI (91 mg, 0.55 mmol) and $KHCO_3$ (826 mg, 8.25 mmol) were added. Then tert-butyl bromoacetate (0.98 mL, 6.6 mmol) was added dropwise. The resulting mixture was stirred at room temperature for 12 h. After normal workup with EtOAc and saturated brine, the combined organic layer was dried over $Na_2SO_4$. After filtration and evaporation, the residue was purified by flash column chromatography with DCM:EA to get the desired product S2 as a white solid (1.7 g, 80% yield). $^1$H NMR (400 MHz, DMSO-$d^6$) δ (ppm) 11.13 (s, 1H), 7.80 (t, J=8.0 Hz, 1H), 7.48 (d, J=7.2 Hz, 1H), 7.38 (d, J=8.4 Hz, 1H), 5.13 (dd, J=12.8 Hz, J=5.2 Hz, 1H), 4.97 (s, 2H), 2.97-2.85 (m, 1H), 2.65-2.52 (m, 2H), 2.14-2.03 (m, 1H), 1.43 (s, 9H); $^{13}$C NMR (100 MHz, DMSO-$d^6$) δ (ppm) 173.2, 170.3, 167.5, 167.2, 165.6, 155.5, 137.2, 133.7, 120.4, 116.9, 116.3, 66.0, 60.2, 49.3, 31.4, 28.1, 22.5.

Step 3: Synthesis of S3

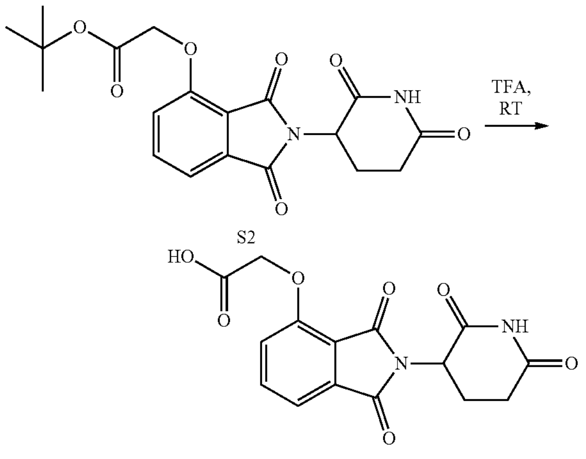

S2

S3

To a round-bottom flask, S2 (1.7 g, 4.4 mmol) was dissolved in 8.0 mL of TFA. The reaction mixture was stirred at room temperature for 2 h. After evaporation of the solvent, the residue was used in the following steps without further purification. ESI-MS calculated for $C_{15}H_{13}N_2O_7$ $[M+H]^+$=333.07, obtained: 333.17. $^1$H NMR (400 MHz, DMSO-$d^6$) δ (ppm) 13.16 (s, 1H), 11.11 (s, 1H), 7.80 (t, J=8.0 Hz, 1H), 7.48 (d, J=7.2 Hz, 1H), 7.40 (d, J=8.8 Hz, 1H), 5.11 (dd, J=12.8 Hz, J=5.2 Hz, 1H), 4.99 (s, 2H), 2.95-2.86 (m, 1H), 2.63-2.48 (m, 2H), 2.08-2.03 (m, 1H).

Step 4: Synthesis of S4

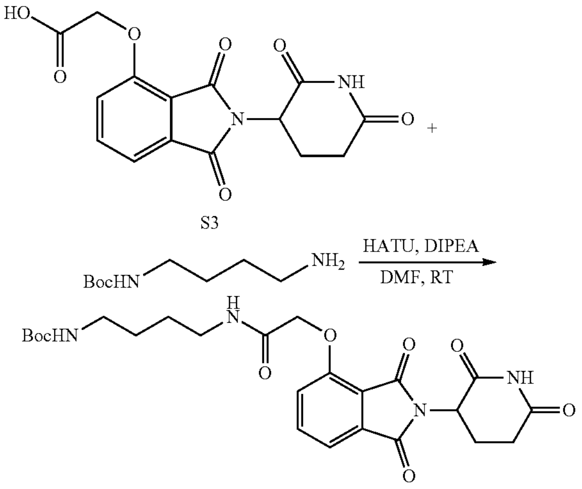

S3

S4

To a round-bottom flask, S3 (99.7 mg, 0.3 mmol) was dissolved in 2 mL of anhydrous DMF. N-Boc-1,4-butanediamine (68 mg, 0.36 mmol), HATU (137 mg, 0.36 mmol) and DIPEA (157 μL, 0.9 mmol) were added sequentially. The reaction mixture was stirred at room temperature for 2 h, and then purified by HPLC to get the desired compound S4 as a slightly yellow solid (128 mg, 85% yield).

Step 5: Synthesis of S5

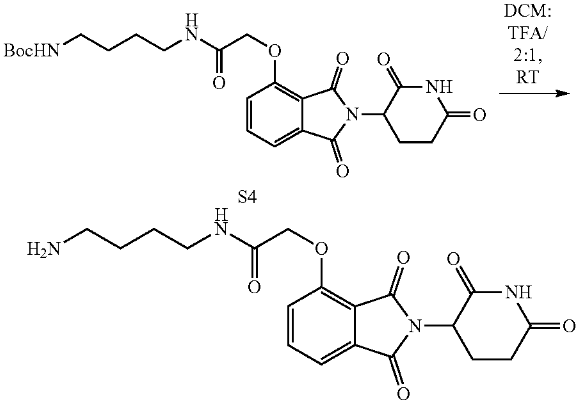

S4

S5

To a round-bottom flask, S4 (15.1 mg, 0.03 mmol) was dissolved in 3 mL of DCM and TFA (2:1). After stirring for 1 h, the solvent was evaporated to give the crude product S5, which was used in the next step without further purification. ESI-MS calculated for $C_{19}H_{23}N_4O_6$ $[M+H]^+$=403.16, obtained: 403.17.

Step 6: Synthesis of Cpd. No. 1

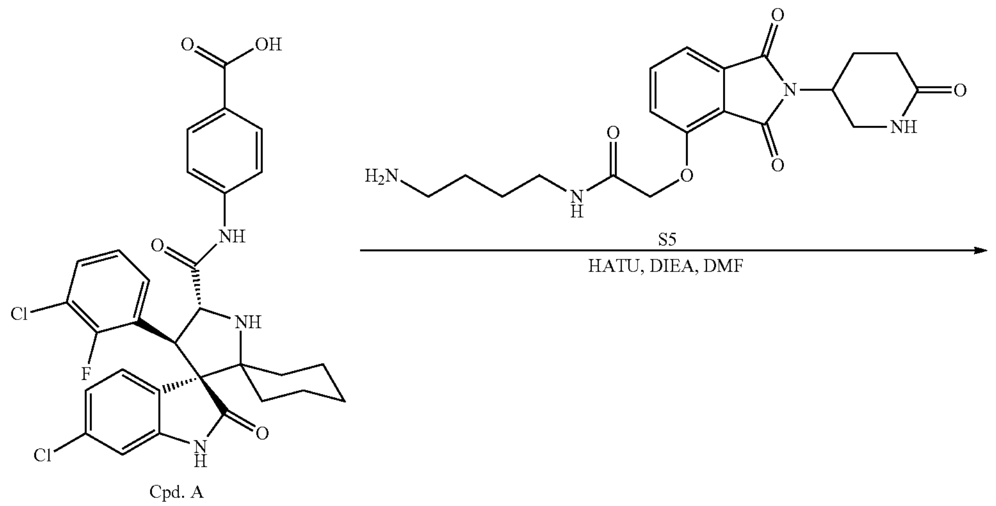

S5

Cpd. A

-continued

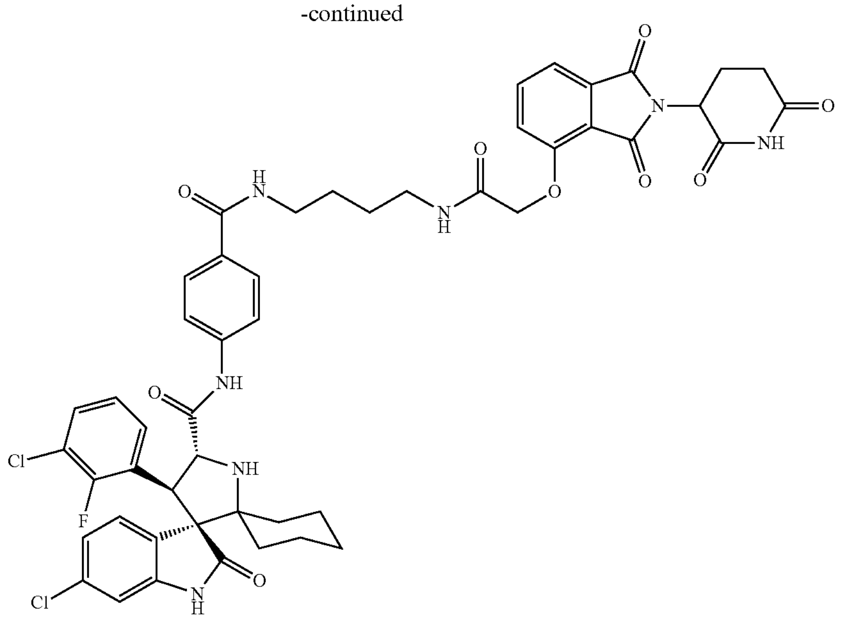

Cpd. No. 1

HATU (13.3 mg, 0.035 mmol) and N,N-diisopropylethylamine (0.026 mL, 0.15 mmol) were added to a solution of Cpd. A (20 mg, 0.029 mmol) in 0.5 mL DMF and stirred. After 10 minutes, S5 (0.35 mL, 0.1 M in DMSO) was added to the reaction. After 30 minutes, the solvent was removed and the crude was dissolved in 3:1 methanol/water, acidified with trifluoroacetic acid and purified by reverse-phase preparative HPLC. The purified fractions were combined, concentrated in vacuo, re-dissolved in $H_2O$, frozen and lyophilized to give Cpd. No. 1 (TFA salt) as a white powder.

LC-MS(ESI) m/z $(M+H)^+$: 966.28, 5.13 min; calcd: 966.28; >98% purity. $^1H$ NMR (400 MHz, MeOD) δ 7.80-7.68 (m, 4H), 7.62-7.56 (m, 2H), 7.54 (dd, J=8.3, 2.5 Hz, 1H), 7.48 (dd, J=7.2, 1.4 Hz, 1H), 7.43-7.32 (m, 2H), 7.18 (t, J=8.1 Hz, 1H), 7.11 (dd, J=8.2, 1.9 Hz, 1H), 6.79 (d, J=1.9 Hz, 1H), 5.31 (d, J=10.8 Hz, 1H), 5.08 (dd, J=12.6, 5.2 Hz, 1H), 4.97 (d, J=10.8 Hz, 1H), 4.75 (s, 2H), 3.36 (dd, J=4.6, 3.0 Hz, 4H), 2.92-2.64 (m, 4H), 2.25-2.13 (m, 1H), 2.13-2.04 (m, 1H), 2.04-1.84 (m, 3H), 1.78 (d, J=11.5 Hz, 2H), 1.72-1.48 (m, 5H), 1.31-1.16 (m, 2H).

Example 2

Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide (Cpd. No. 74)

Step 1: Synthesis of S7

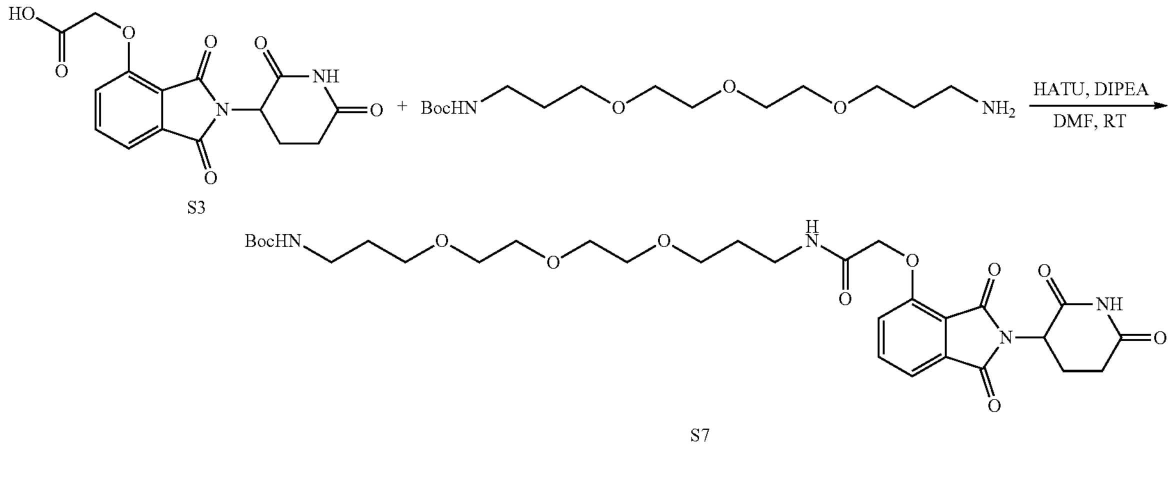

To a round-bottom flask, S3 (99.7 mg, 0.3 mmol) was dissolved in 2 mL of anhydrous DMF. tert-butyl (3-(2-(2-(3-aminopropoxy)ethoxy)ethoxy)propyl)carbamate (68 mg, 0.36 mmol), HATU (137 mg, 0.36 mmol) and DIPEA (157 μL, 0.9 mmol) were added sequentially. The reaction mixture was stirred at room temperature for 2 h, and then purified by HPLC to get the desired compound S7 as a slightly yellow solid (128 mg, 85% yield).

Step 2: Synthesis of Cpd. No. 74

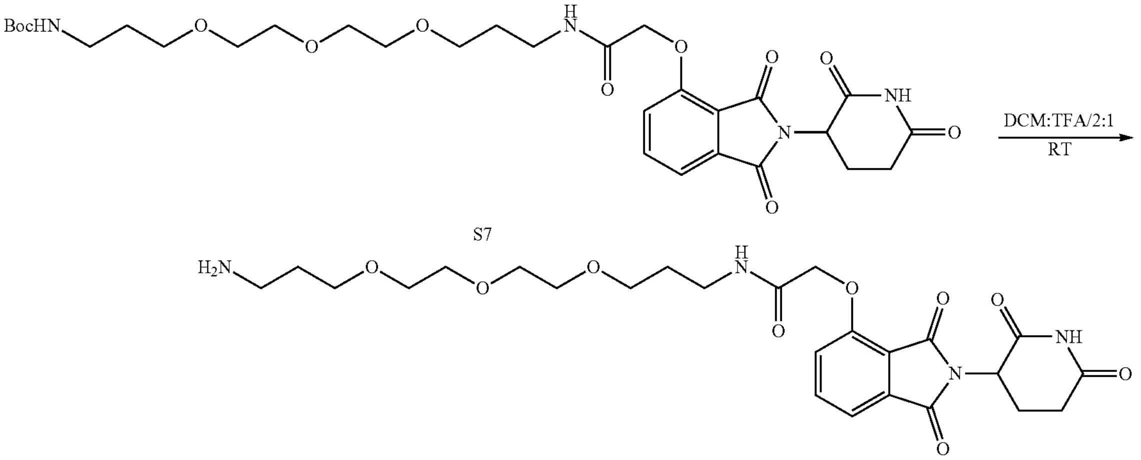

S7

Cpd. No. 74

To a round-bottom flask, S7 (15 mg) was dissolved in 3 mL of DCM and TFA (2:1). After stirring for 1 h, the solvent was evaporated to give the crude product Cpd. No. 74, which was used in the next step without further purification. ESI-MS calculated for $C_{25}H_{35}N_4O_9$ $[M+H]^+$=535.24, obtained: 535.14.

Example 3

Synthesis of N-(3-(2-(2-(3-aminopropoxy)ethoxy)ethoxy)propyl)-2-((2-(2,6-dioxopiperidin-3-yl)-1,3-dioxoisoindolin-4-yl)amino)acetamide (Cpd. No. 75)

Step 1: Synthesis of S16

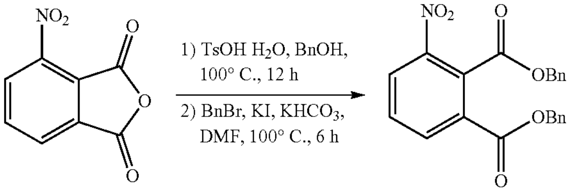

S16

To a round-bottom flask, 3-nitrophthalic anhydride (5.79 g, 30 mmol) and p-toluenesulfonic acid monohydrate (571 mg, 3 mmol) were mixed in 20 mL of benzyl alcohol. The mixture was heat to 100° C. to stir overnight. After cooling to room temperature, benzyl bromide (7.1 mL, 45 mmol), KI (498 mg, 3 mmol), $KHCO_3$ (9.0 g, 90 mmol) and DMF (25 mL) were added. The mixture was heated to 100° C. for 6 h. After the reaction was cooled to room temperature, the solvent was evaporated as much as possible and was poured into larger amount of water. The solution was extracted with ethyl acetate. The combined organic layer was washed with brine and dried over anhydrous $Na_2SO_4$. After filtration and evaporation, the crude residue was purified by flash column chromatography with hexane/ethyl acetate to give S16 as a slightly yellow solid (9.4 g, 80% yield).

Step 2: Synthesis of S17

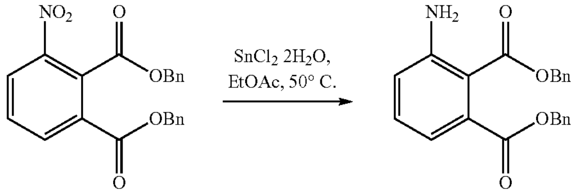

S16 S17

To a round-bottom flask, compound S16 (9.4 g, 24 mmol) was dissolved in 100 mL of ethyl acetate. Then Tin (II) chloride dehydrate (11.3 g, 50 mmol) was added portion wisely to the reaction mixture. The resulting reaction mixture was heated to 50° C. to stir overnight. Aqueous NaOH and $NaHCO_3$ solution were added to the reaction mixture to quench the reaction. The reaction mixture was filtered through celite and washed with ethyl acetate. The filtrate was extracted with ethyl acetate and brine. The combined organic layer was dried over anhydrous $Na_2SO_4$. After filtration and evaporation, the crude residue was purified by flash column chromatography with hexane/ethyl acetate to give compound S17 as a slightly yellow solid (7.8 g, 90% yield).

Step 3: Synthesis of S18

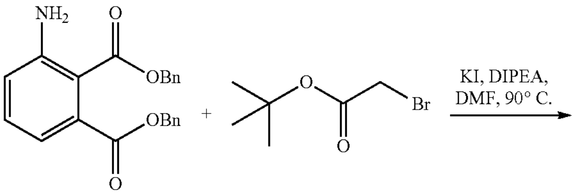

S17

-continued

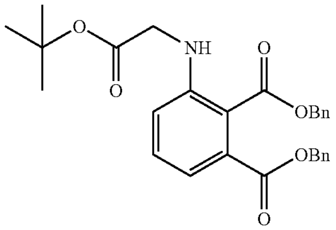

S18

To a round-bottom flask, compound S17 (2.0 g, 5.54 mmol) and KI (100 mg, 0.56 mmol) were added to 10 mL of anhydrous DMF. Tert-butyl bromoacetate (2.4 mL, 16.6 mmol) and DIPEA (4.8 mL, 27.7 mmol) were added to the reaction mixture. The reaction mixture was heated to 90° C. to stir overnight. After cooling to room temperature, most of the solvent was evaporated and the residue was purified by column chromatography with hexane/ethyl acetate to give compound S18 as a slightly yellow solid (1.05 g, 40% yield).

Step 4: Synthesis of S19

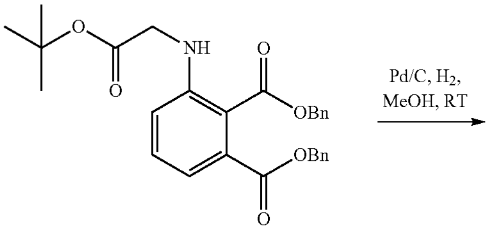

S18

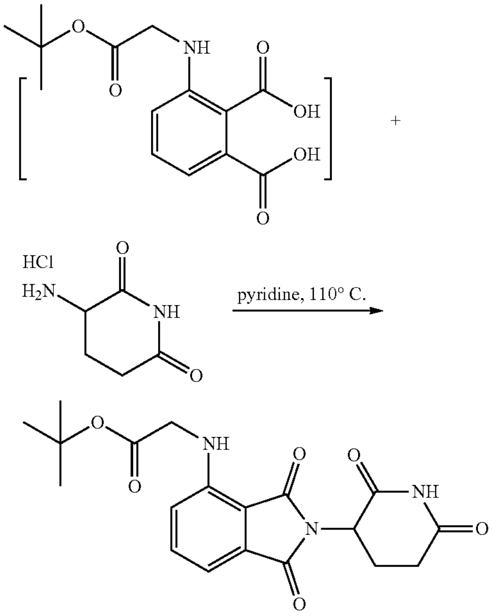

S19

To a round-bottom flask, compound S18 (1.0 g, 2.1 mmol) was dissolved in 20 mL of methanol. 100 mg of Pd/C (10 wt %) was added. The reaction mixture was stirred at room temperature under 1 atm $H_2$ atmosphere. Once the starting material disappeared by TLC, the mixture was filtrated through celite and washed with methanol. After evaporation of the solvent, 3-aminopiperidine-2,6-dione hydrochloride (380 mg, 2.31 mmol) and 20 mL of pyridine were added. The reaction mixture was heated to 110° C. to stir overnight. After cooling to room temperature, the solvent was evaporated as much as possible and the residue was poured into water. After extraction with ethyl acetate for three times, the combined organic layer was washed with brine and dried over anhydrous $Na_2SO_4$. After filtration and evaporation, the crude residue was purified by flash column chromatography with DCM/ethyl acetate to give compound S19 as a yellow solid (325 mg, 40% yield).

Step 5: Synthesis of 520

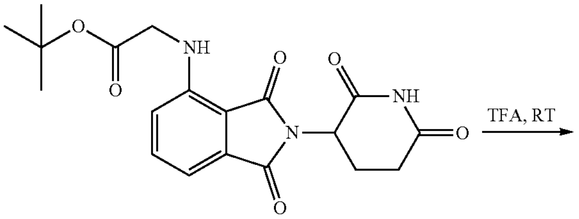

S19

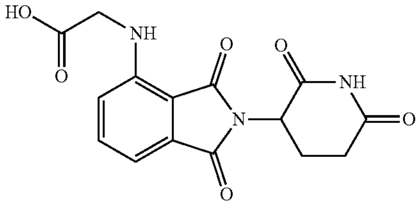

S20

To a round-bottom flask, S19 (1.7 g) was dissolved in 8.0 mL of TFA. The reaction mixture was stirred at room temperature for 2 h. After evaporation of the solvent, the residue was used in the following steps without further purification. $^1H$ NMR (400 MHz, DMSO-$d^6$) δ (ppm) 12.91 (s, 1H), 11.10 (s, 1H), 7.59 (t, J=8.0 Hz, 1H), 7.08 (d, J=6.80 Hz, 1H), 6.99 (d, J=8.4 Hz, 1H), 6.86 (t, J=5.6 Hz, 1H), 5.08 (dd, J=13.2 Hz, J=5.6 Hz, 1H), 4.12 (d, J=5.2 Hz, 2H), 2.94-2.85 (m, 1H), 2.63-2.49 (m, 2H), 2.09-2.07 (m, 1H); $^{13}C$ NMR (100 MHz, DMSO-$d^6$) δ (ppm) 173.3, 171.9, 170.5, 169.3, 167.8, 146.3, 136.6, 132.5, 118.2, 111.5, 110.1, 60.2, 49.1, 31.5, 22.6.

Step 6: Synthesis of S21

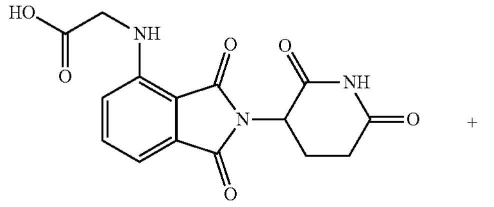

S20

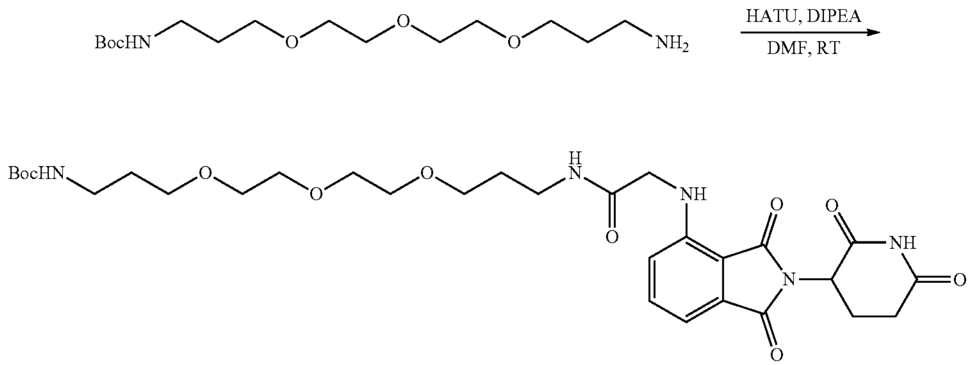

S21

Following the procedure for S4 synthesis, compound S21 was synthesized with S20 (99.7 mg, 0.3 mmol), amine (115 mg, 0.36 mmol), HATU (137 mg, 0.36 mmol) and DIPEA (157 μL, 0.9 mmol). ESI-MS calculated for $C_{30}H_{43}N_5NaO_{10}$ $[M+Na]^+$=656.29, obtained: 656.26.

Step 7: Synthesis of Cpd. No. 75

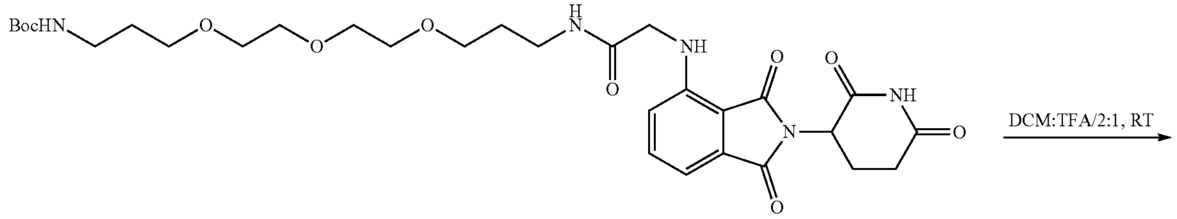

S21

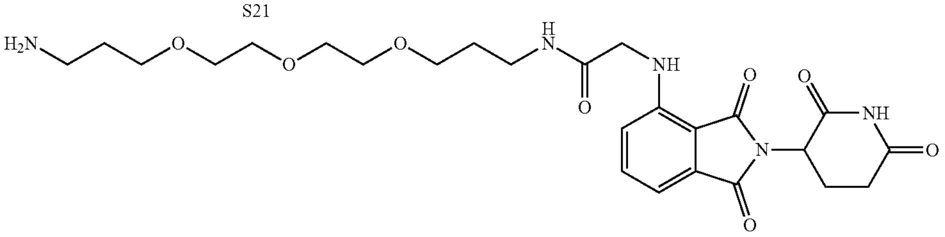

Cpd. No. 75

To a round-bottom flask, S21 (15.1 mg) was dissolved in 3 mL of DCM and TFA (2:1). After stirring for 1 h, the solvent was evaporated to give crude product Cpd. No. 75, which was used in the next step without further purification.

Example 4

Synthesis of 4-((3-(2-(2-(3-aminopropoxy)ethoxy)ethoxy)propyl)amino)-2-(2,6-dioxopiperidin-3-yl)isoindoline-1,3-dione (Cpd. No. 76)

Step 1: Synthesis of S13

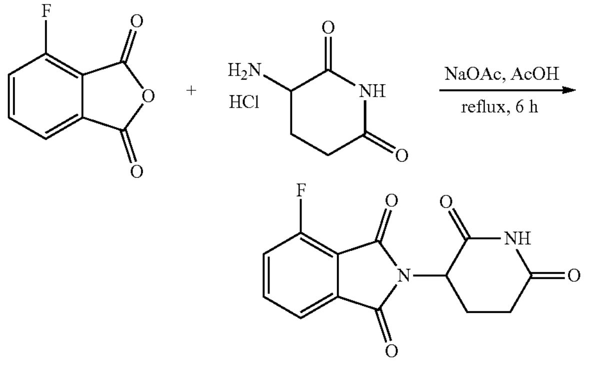

S13

To a round-bottom flask, 3-fluorophthalic anhydride (6.64 g, 40 mmol), 3-aminopiperidine-2,6-dione hydrochloride (6.58 g, 40 mmol) and sodium acetate (3.94 g, 48 mmol) were mixed in 120 mL of acetic acid. The resulting reaction mixture was heated to reflux at 140° C. for 12 h. After cooling to room temperature, most of acetic acid was evaporated and the residue was purified by flash column chromatography with DCM/MeOH to get S13 as a slightly yellow solid (9.7 g, 88% yield). ESI-MS calculated for $C_{13}H_{10}FN_2O_4[M+H]^+$=277.06, obtained: 277.02. $^1H$ NMR (400 MHz, DMSO-$d^6$) δ (ppm) 11.15 (s, 1H), 7.98-7.93 (m, 1H), 7.80-7.72 (m, 2H), 5.17 (dd, J=13.2 Hz, J=5.2 Hz, 1H), 2.95-2.86 (m, 1H), 2.64-2.47 (m, 2H), 2.10-2.06 (m, 1H);

Step 2: Synthesis of S14

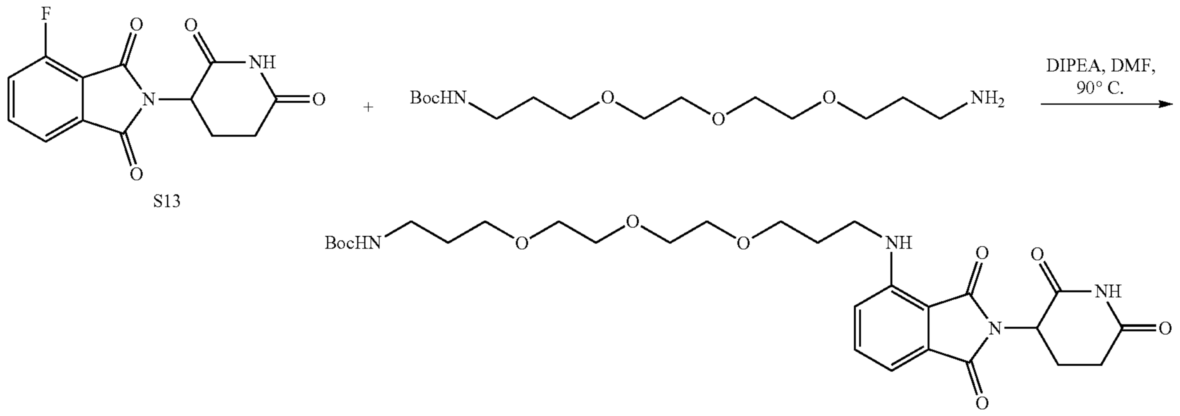

S13

S14

To a round-bottom flask, S13 (276 mg, 1.0 mmol) was dissolved in 3.0 mL of anhydrous DMF. Amine (320 mg, 1.0 mmol) and DIPEA (259 mg, 2.0 mmol) were added. The reaction mixture was stirred at 90° C. for 12 h. The mixture was cooled to room temperature, poured into water and extracted with ethyl acetate for two times. The combined organic layer was washed with brine, dried over anhydrous $Na_2SO_4$. After filtration and evaporation, the crude residue was purified by HPLC with $H_2O$/MeCN to give compound S14 as colorless oil (172 mg, 30% yield). ESI-MS calculated for $C_{28}H_{41}N_4O_9$ $[M+H]^+$=577.2; Observed: 577.3.

Step 3: Synthesis of Cpd. No. 76

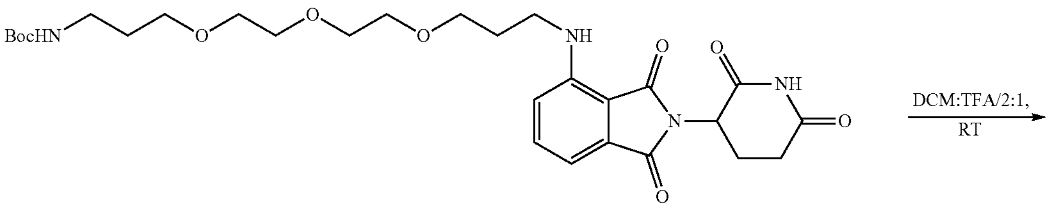

S14

-continued

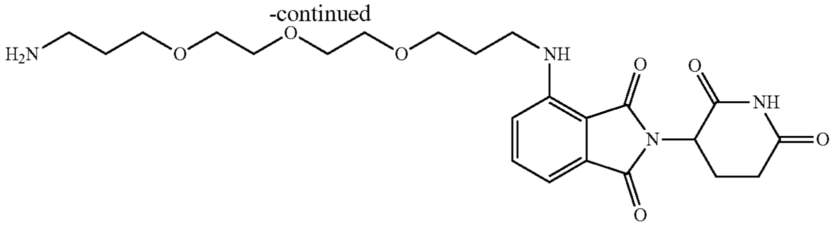

Cpd. No. 76

To a round-bottom flask, S14 (15 mg) was dissolved in 3 mL of DCM and TFA (2:1). After stirring for 1 h, the solvent was evaporated to give crude product Cpd. No. 76, which was used in the next step without further purification.

Example 5

Synthesis of 4-(2-(2-(2-(2-aminoethoxy)ethoxy) ethoxy)ethoxy)-2-(2,6-dioxopiperidin-3-yl)isoindoline-1,3-dione (Cpd. No. 77)

Step 1: Synthesis of S9

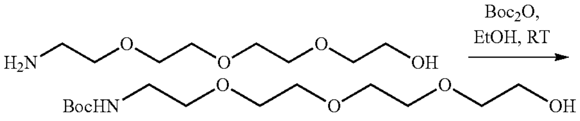

S9

To a round-bottom flask, 2-(2-(2-(2-aminoethoxy)ethoxy) ethoxy)ethanol (2.9 g, 15 mmol) was diluted in 10 mL of ethanol. Di-tert-butyl dicarbonate (3.6 g, 16.5 mmol) was dissolved in 10 mL of ethanol and the solution was added dropwise within a period of 10 min. The resulting reaction mixture was stirred at room temperature for 2 h. After evaporation of the solvent, the residue was purified by column chromatography with DCM/MeOH to obtain S9 as colorless oil (3.69 g, 80% yield). $^1$H NMR (400 MHz, $CDCl_3$) δ (ppm) 5.49 (s, 1H), 3.46-3.25 (m, 14H), 3.02 (s, 2H), 1.18 (s, 9H); ESI-MS calculated for $C_{13}H_{27}NNaO_6$ $[M+Na]^+$=316.17, obtained: 316.18.

Step 2: Synthesis of S10

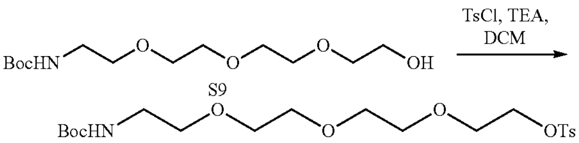

S9

S10

To a round-bottom flask, S9 (3.69 g, 12 mmol) was diluted in 100 mL of DCM. After cooling to 0° C., 4-toluenesulfonyl chloride (2.75 g, 14.4 mmol) and triethyl amine (2.51 mL, 18 mmol) were added sequentially. The resulting reaction mixture was stirred at 0° C. for 30 min and then room temperature for 2 h. After workup with DCM and saturated $NaHCO_3$ solution, the combined organic layer was dried over anhydrous $Na_2SO_4$. After filtration and evaporation, the residue was purified by column chromatography with hexane: ethyl acetate to give S10 as colorless oil (4.98 g, 90% yield). $^1$H NMR (400 MHz, $CDCl_3$) δ (ppm) 7.76 (d, J=8.4 Hz, 2H), 7.31 (d, J=8.4 Hz, 2H), 4.12 (m, 2H), 3.67-3.47 (m, 12H), 3.25-3.23 (m, 2H), 2.40 (s, 3H), 1.39 (s, 9H); ESI-MS calculated for $C_{20}H_{33}NNaO_8S$ $[M+Na]^+$=470.18, obtained: 470.20.

Step 3: Synthesis of S11

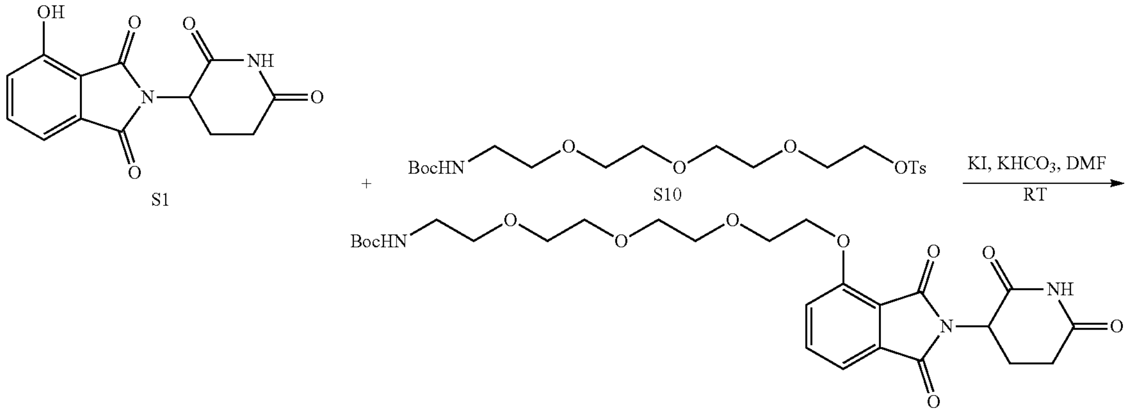

S1

+

S10

S11

To a round-bottom flask, S1 (274 mg, 1.0 mmol) and S10 (492 mg, 1.1 mmol) were mixed in 5.0 mL of anhydrous DMF. KI (17 mg, 0.1 mmol) and $KHCO_3$ (150 mg, 1.5 mmol) were added sequentially. The reaction mixture was stirred at room temperature for 12 h. After evaporation of most of the solvent, the residue was purified by column chromatography with DCM/MeOH to get S1I as colorless oil (453 mg, 82% yield). ESI-MS calculated for $C_{25}H_{36}N_3O_{10}Na$ $[M+Na]^+$=572.22, obtained: 572.13.

Step 4: Synthesis of Cpd. No. 77

To a round-bottom flask, methyl 3-bromo-2-(bromomethyl)benzoate (50 mg) and $Et_3N$ (60 mg) were added to a solution of 3-aminopiperidine-2,6-dione (30 mg) in $CH_3CN$ (5 mL). The mixture was stirred for 10 hours at 60° C. and purified by flash column chromatography to yield S23 in 30 mg. ESI-MS calculated for $C_{13}H_{12}BrN_2O_3$ $[M+H]^+$=323.0; Observed: 323.2.

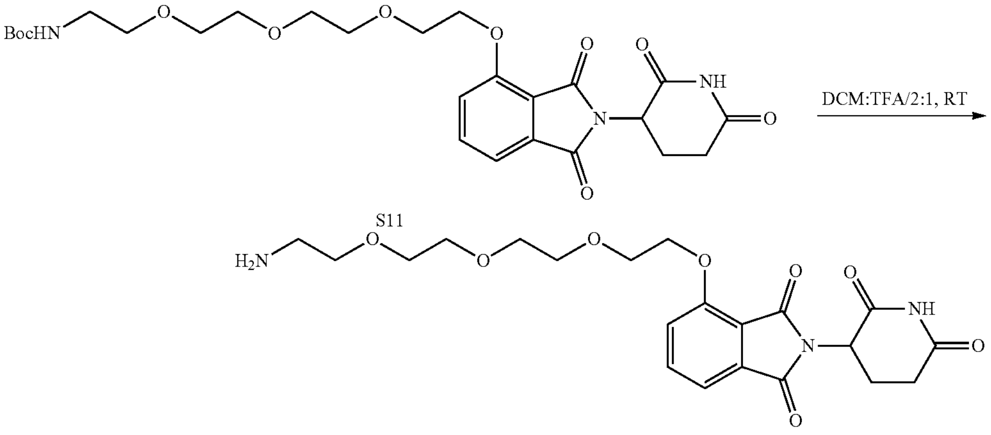

S11

Cpd. No. 77

To a round-bottom flask, S11 (15 mg) was dissolved in 3 mL of DCM and TFA (2:1). After stirring for 1 h, the solvent was evaporated to give crude product Cpd. No. 77, which was used in the next step without further purification. ESI-MS calculated for $C_{21}H_{28}N_3O_8$ $[M+Na]^+$=450.19, obtained: 450.20.

Example 6

Synthesis of 3-(4-(5-aminopentyl)-1-oxoisoindolin-2-yl)piperidine-2,6-dione (Cpd. No. 78)

Step 1: Synthesis of S23

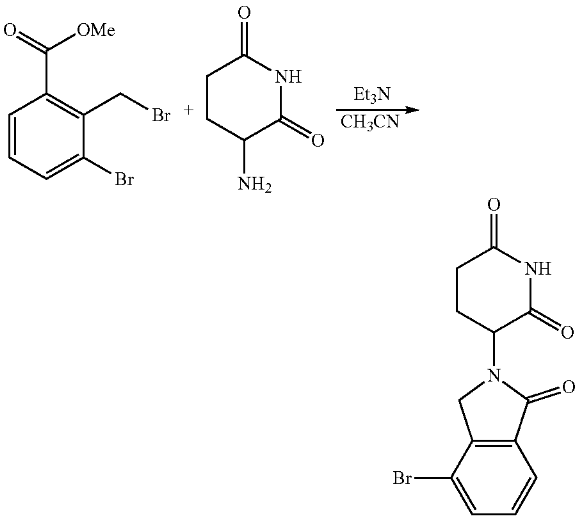

S23

Step 2: Synthesis of S24

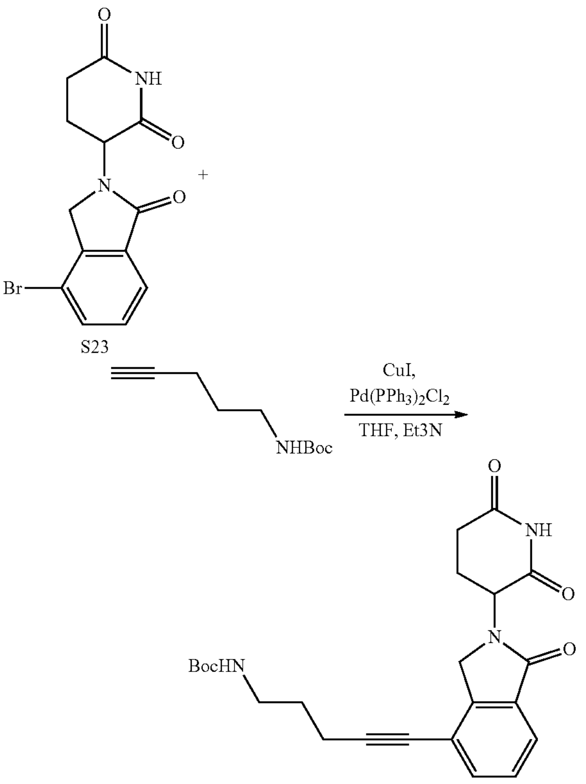

S24

To a round-bottom flask, S23 (50 mg) and tert-butyl pent-4-yn-1-ylcarbamate (50 mg) were added to a solution of CuI (6.3 mg) and $Pd(PPh_3)_2Cl_2$ (11 mg) in THF (5 mL) and $Et_3N$ (2 mL). The mixture was stirred for 10 hours at 70° C. under Ar and purified directly by flash column chromatography to yield S24 in 20 mg. ESI-MS calculated for $C_{23}H_{28}N_3O_5$ $[M+H]^+$=426.2; Observed: 426.4.

Step 3: Synthesis of Cpd. No. 78

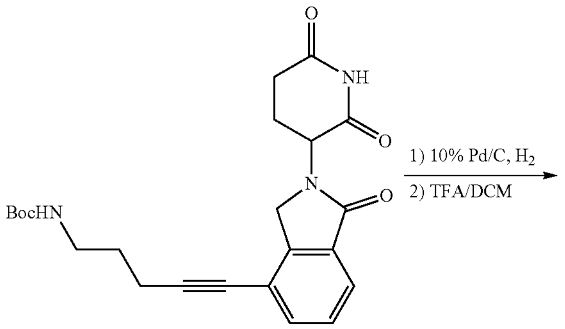

S24

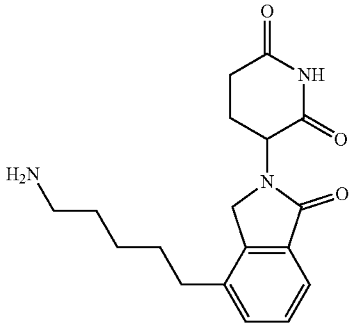

Cpd. No. 78

S24 (30 mg) was dissolved in MeOH (10 mL). 5 mg 10% Pd/C was added. the reaction mixture was degassed 2 times, each time replacing the vacuum with hydrogen, then stirred at room temperature under $H_2$ overnight. The mixture was filtered and concentrated on a rotary evaporator to give the crude which was dissolved in 3 mL of DCM and TFA (2:1). After stirring for 1 h, the solvent was evaporated to give crude product Cpd. No. 78, which was used in the next step without further purification. ESI-MS calculated for $C_{18}H_{24}N_3O_3$ $[M+H]^+$=330.1; Observed: 330.4.

Example 7

Synthesis of 4-((4-aminobutyl)amino)-2-(2,6-dioxopiperidin-3-yl)isoindoline-1,3-dione (Cpd. No. 81)

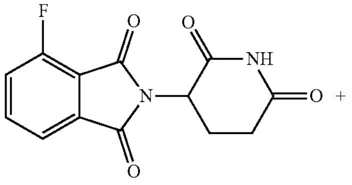

S13

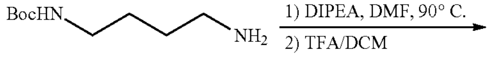

-continued

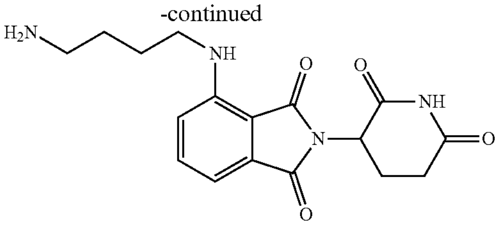

Cpd. No. 81

To a round-bottom flask, S13 (276 mg, 1.0 mmol) was dissolved in 3.0 mL of anhydrous DMF. tert-butyl (4-aminobutyl)carbamate (320 mg) and DIPEA (259 mg, 2.0 mmol) were added. The reaction mixture was stirred at 90° C. for 12 h. The mixture was cooled to room temperature, poured into water and extracted with ethyl acetate for two times. The combined organic layer was washed with brine, dried over anhydrous $Na_2SO_4$. After filtration and evaporation, the crude residue was dissolved in 3 mL of DCM and TFA (2:1). After stirring for 1 h, the solvent was evaporated to give the crude which was purified by HPLC with $H_2O$/MeCN to give compound Cpd. No. 81 as colorless oil (100 mg). ESI-MS calculated for $C_{17}H_{21}N_4O_4$ $[M+H]^+$=345.1; Observed: 345.4.

Example 8

Synthesis of 4-((2-(2-(2-aminoethoxy)ethoxy)ethyl)amino)-2-(2,6-dioxopiperidin-3-yl)isoindoline-1,3-dione (Cpd. No. 85)

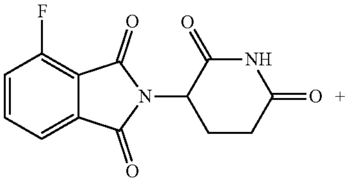

S13

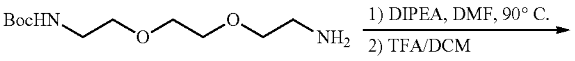

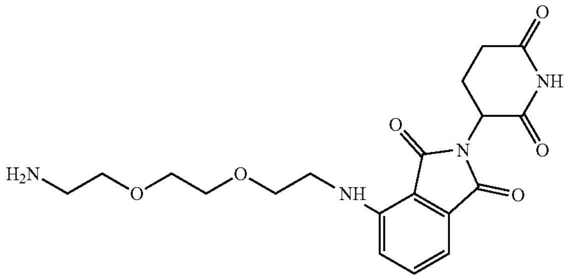

Cpd. No. 85

To a round-bottom flask, S13 (276 mg, 1.0 mmol) was dissolved in 3.0 mL of anhydrous DMF. tert-butyl (2-(2-(2-aminoethoxy)ethoxy)ethyl)carbamate (320 mg) and DIPEA (259 mg, 2.0 mmol) were added. The reaction mixture was stirred at 90° C. for 12 h. The mixture was cooled to room temperature, poured into water and extracted with ethyl acetate for two times. The combined organic layer was washed with brine, dried over anhydrous $Na_2SO_4$. After filtration and evaporation, the crude residue was dissolved in 3 mL of DCM and TFA (2:1). After stirring for 1 h, the solvent was evaporated to give the crude which was purified by HPLC with $H_2O$/MeCN to give Cpd. No. 85 as colorless oil (130 mg). ESI-MS calculated for $C_{19}H_{25}N_4O_6$ $[M+H]^+$=405.1; Observed: 405.4.

Example 9

Synthesis of 3-(4-(3-(2-aminoethoxy)propyl)-1-oxoisoindolin-2-yl)piperidine-2,6-dione (Cpd. No. 95)

Step 1: Synthesis of S28

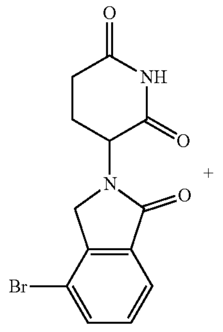

S23

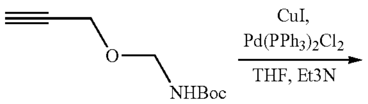

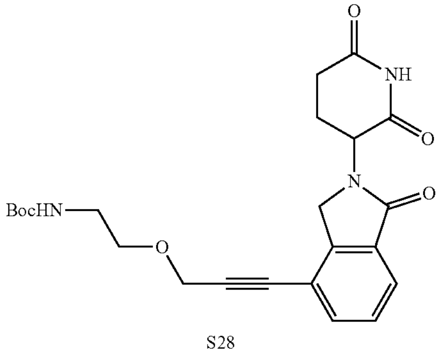

S28

To a round-bottom flask, S23 (50 mg) and tert-butyl (2-(prop-2-yn-1-yloxy)ethyl)carbamate (60 mg) were added to a solution of CuI (6.3 mg) and $Pd(PPh_3)_2Cl_2$ (11 mg) in THF (5 mL) and $Et_3N$ (2 mL). The mixture was stirred for 10 hours at 70° C. under Ar and purified directly by flash column chromatography to yield 22 mg of S28. ESI-MS calculated for $C_{23}H_{28}N_3O_6[M+H]^+$=442.1; Observed: 442.3.

Step 2: Synthesis of Cpd. No. 95

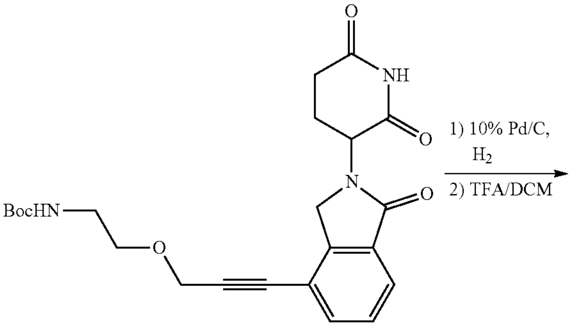

S28

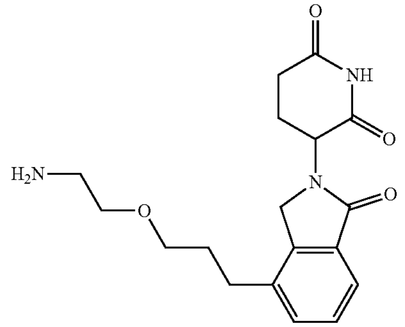

Cpd. No. 95

S28 (30 mg) was dissolved in MeOH (10 mL). 5 mg 10% Pd/C was added. the reaction mixture was degassed 2 times, each time replacing the vacuum with hydrogen, then stirred at room temperature under $H_2$ overnight. The mixture was filtered and concentrated on a rotary evaporator to give the crude which was dissolved in 3 mL of DCM and TFA (2:1). After stirring for 1 h, the solvent was evaporated to give crude product Cpd. No. 95, which was used in the next step without further purification. ESI-MS calculated for $C_{18}H_{24}N_3O_4$ $[M+H]^+$=346.1; Observed: 346.3.

Example 10

Synthesis of 4-(5-aminopentyl)-2-(2,6-dioxopiperidin-3-yl)isoindoline-1,3-dione (Cpd. No. 125)

Step 1: Synthesis of S30

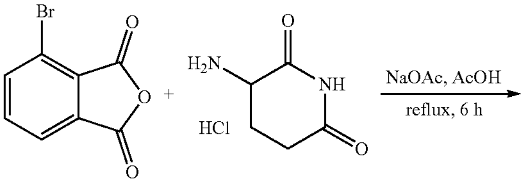

-continued

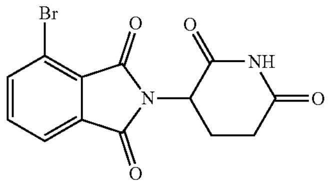

S30

To a round-bottom flask, 3-bromophthalic anhydride (6.64 g), 3-aminopiperidine-2,6-dione hydrochloride (6.58 g, 40 mmol) and sodium acetate (3.94 g, 48 mmol) were mixed in 120 mL of acetic acid. The resulting reaction mixture was heated to reflux at 140° C. for 12 h. After cooling to room temperature, most of acetic acid was evaporated and the residue was purified by flash column chromatography with DCM/MeOH to get S130 as a solid (7 g). ESI-MS calculated for $C_{13}H_{10}BrN_2O_4$ $[M+H]^+$=336.9, obtained: 336.9.

Step 2: Synthesis of S31

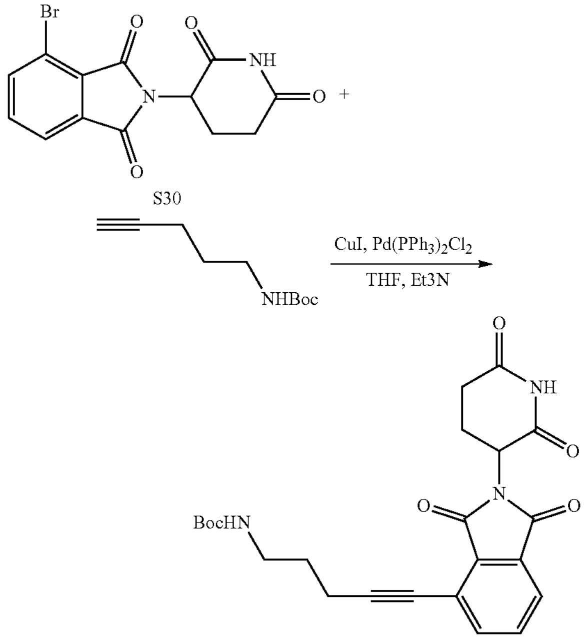

S30

S31

To a round-bottom flask, S30 (50 mg) and tert-butyl pent-4-yn-1-ylcarbamate (50 mg) were added to a solution of CuI (6.3 mg) and $Pd(PPh_3)_2Cl_2$ (11 mg) in THF (5 mL) and $Et_3N$ (2 mL). The mixture was stirred for 10 hours at 70° C. under Ar and purified directly by flash column chromatography to yield 14 mg of S31. ESI-MS calculated for $C_{23}H_{26}N_3O_6$ $[M+H]^+$=440.1; Observed: 440.3.

Step 3: Synthesis of Cpd. No. 125

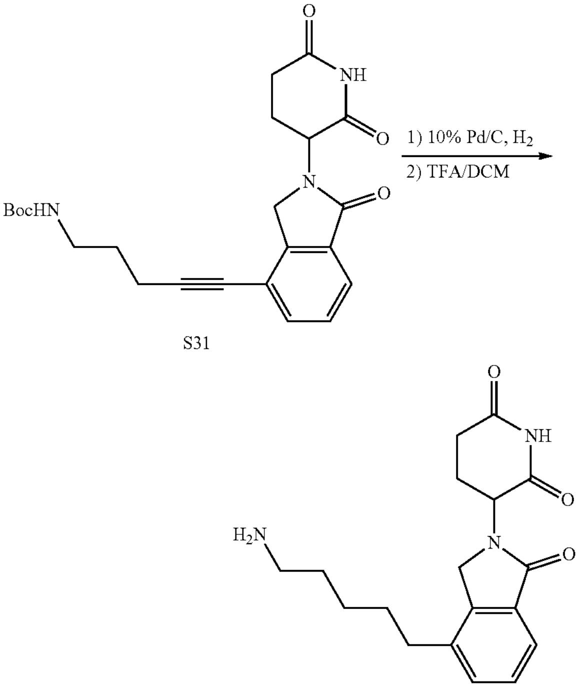

S31

Cpd. No. 125

S31 (30 mg) was dissolved in MeOH (10 mL). 5 mg 10% Pd/C was added. the reaction mixture was degassed 2 times, each time replacing the vacuum with hydrogen, then stirred at room temperature under $H_2$ overnight. The mixture was filtered and concentrated on a rotary evaporator to give the crude which was dissolved in 3 mL of DCM and TFA (2:1). After stirring for 1 h, the solvent was evaporated to give crude product Cpd. No. 125, which was used in the next step without further purification. ESI-MS calculated for $C_{18}H_{22}N_3O_4$ $[M+H]^+$=344.1; Observed: 344.4.

Example 11

Synthesis of 4-(3-(2-(2-(2-aminoethoxy)ethoxy)ethoxy)propyl)-2-(2,6-dioxopiperidin-3-yl)isoindoline-1,3-dione (Cpd. No. 126)

Step 1: Synthesis of S33

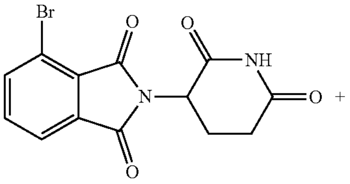

S30

-continued

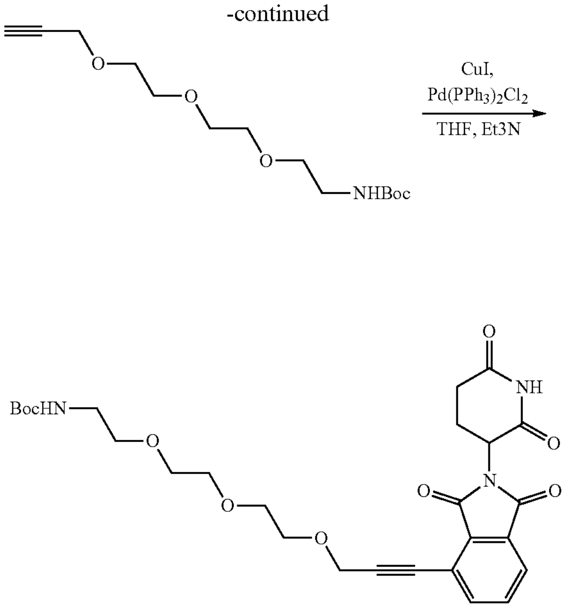

S33

To a round-bottom flask, S30 (50 mg) and tert-butyl (2-(2-(2-(prop-2-yn-1-yloxy)ethoxy)ethoxy)ethyl)carbamate (60 mg) were added to a solution of CuI (6.3 mg) and $Pd(PPh_3)_2Cl_2$ (11 mg) in THF (5 mL) and $Et_3N$ (2 mL). The mixture was stirred for 10 hours at 70° C. under Ar and purified directly by flash column chromatography to yield S33 in 18 mg. ESI-MS calculated for $C_{27}H_{34}N_3O_9$ $[M+H]^+$ =544.2; Observed: 544.4.

Step 2: Synthesis of Cpd. No. 126

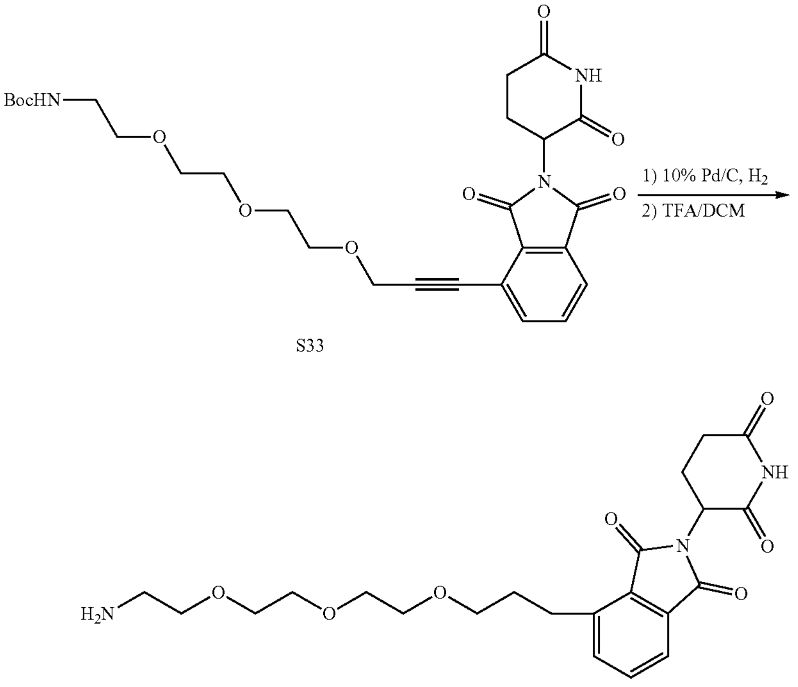

S33

Cpd. No. 126

S33 (30 mg) was dissolved in MeOH (10 mL) and 5 mg 10% Pd/C was added. The reaction mixture was degassed 2 times, each time replacing the vacuum with hydrogen, then stirred at room temperature under $H_2$ overnight. The mixture was filtered and concentrated on a rotary evaporator to give the crude which was dissolved in 3 mL of DCM and TFA (2:1). After stirring for 1 h, the solvent was evaporated to give crude product Cpd. No. 126, which was used in the next step without further purification. ESI-MS calculated for $C_{22}H_{30}N_3O_7$ $[M+H]^+$=448.2; Observed: 448.3.

Example 12

Synthesis of 4-(3-(2-aminoethoxy)propyl)-2-(2,6-dioxopiperidin-3-yl)isoindoline-1,3-dione (Cpd. No. 127)

Step 1: Synthesis of S35

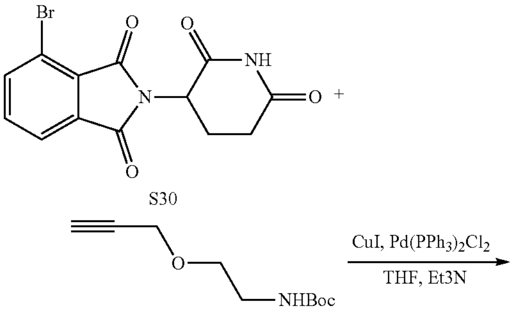

S30

-continued

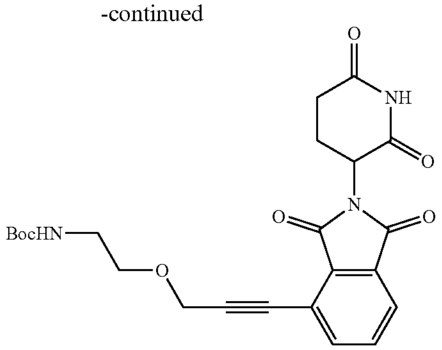

S35

To a round-bottom flask, S30 (50 mg) and tert-butyl (2-(prop-2-yn-1-yloxy)ethyl)carbamate (60 mg) were added to a solution of CuI (6.3 mg) and $Pd(PPh_3)_2Cl_2$ (11 mg) in THF (5 mL) and $Et_3N$ (2 mL). The mixture was stirred for 10 hours at 70° C. under Ar and purified directly by flash column chromatography to yield 19 mg of S35. ESI-MS calculated for $C_{23}H_{26}N_3O_7$ $[M+H]^+$=456.1; Observed: 456.3.

Step 2: Synthesis of Cpd. No. 127

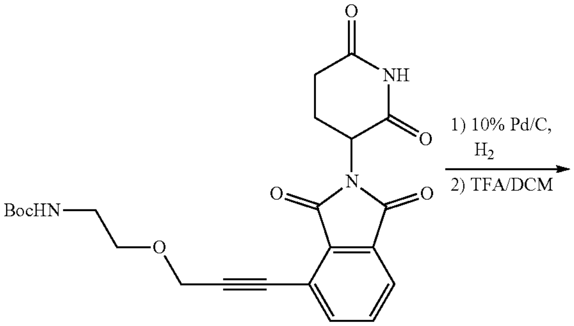

S35

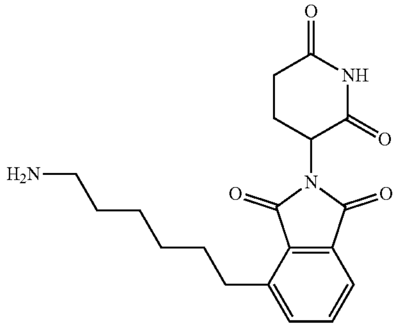

Cpd. No. 127

S35 (30 mg) was dissolved in MeOH (10 mL). 5 mg 10% Pd/C was added. the reaction mixture was degassed 2 times, each time replacing the vacuum with hydrogen, then stirred at room temperature under $H_2$ overnight. The mixture was filtered and concentrated on a rotary evaporator to give the crude which was dissolved in 3 mL of DCM and TFA (2:1). After stirring for 1 h, the solvent was evaporated to give crude product Cpd. No. 127, which was used in the next step without further purification. ESI-MS calculated for $C_{18}H_{22}N_3O_5$ $[M+H]^+$=360.1; Observed: 360.2.

Example 13

Synthesis of 3-(2-(2-aminoethoxy)ethoxy)-N-(2-(2,6-dioxopiperidin-3-yl)-1-oxoisoindolin-4-yl)propanamide (Cpd. No. 128)

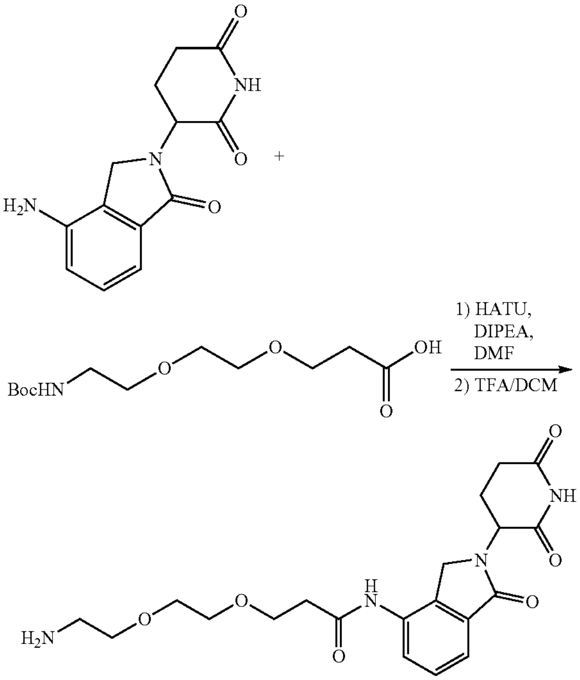

Cpd. No. 128

To a round-bottom flask, N,N-diisopropylethylamine (50 mg) was added to a solution of 3-(4-amino-1-oxoisoindolin-2-yl)piperidine-2,6-dione (20 mg), HATU (30 mg), and 2,2-dimethyl-4-oxo-3,8,11-trioxa-5-azatetradecan-14-oic acid (50 mg) in DMF (1 mL) at room temperature. The mixture was stirred for 30 min and the solvent was evaporated as much as possible and the residue was poured into water. After extraction with ethyl acetate for three times, the combined organic layer was washed with brine and dried over anhydrous $Na_2SO_4$. After filtration and evaporation, the crude residue was dissolved in 3 mL of DCM and TFA (2:1). After stirring for 1 h, the solvent was evaporated to give the crude product which was purified by flash column chromatography to yield Cpd. No. 128. ESI-MS calculated for $C_{20}H_{27}N_4O_6$$[M+H]^+$=419.1; Observed: 419.2.

Example 14

Synthesis of 3-(2-(2-(2-aminoethoxy)ethoxy)ethoxy)-N-(2-(2,6-dioxopiperidin-3-yl)-1-oxoisoindolin-4-yl)propanamide (Cpd. No. 129)

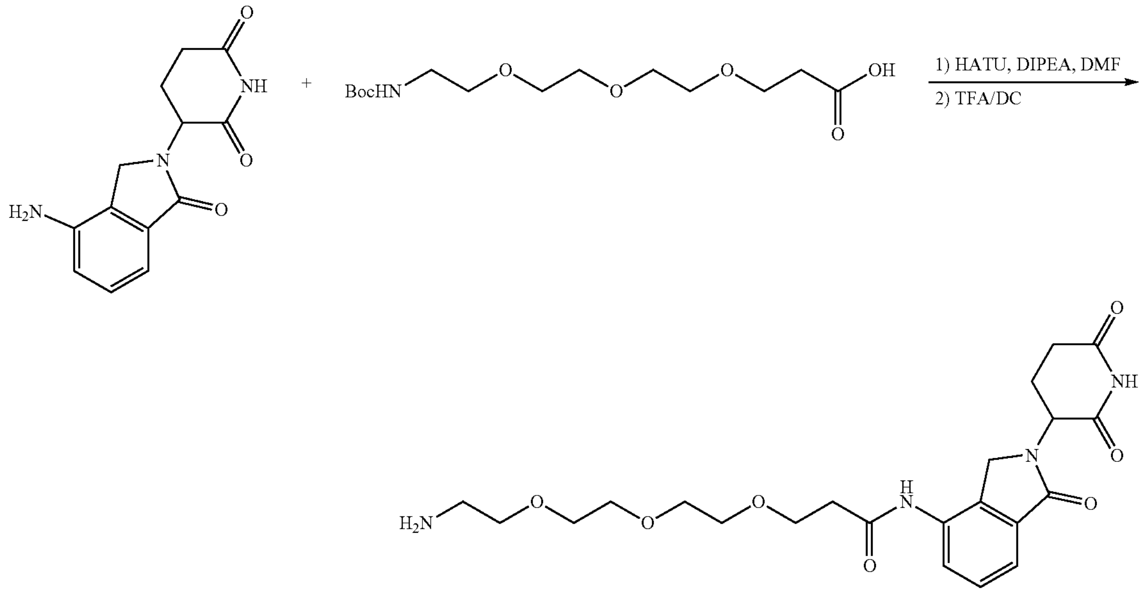

Cpd. No. 129

To a round-bottom flask, N,N-diisopropylethylamine (50 mg) was added to a solution of 3-(4-amino-1-oxoisoindolin-2-yl)piperidine-2,6-dione (20 mg), HATU (30 mg), and 2,2-dimethyl-4-oxo-3,8,11,14-tetraoxa-5-azaheptadecan-17-oic acid (50 mg) in DMF (1 mL) at room temperature. The mixture was stirred for 30 min and the solvent was evaporated as much as possible and the residue was poured into water. After extraction with ethyl acetate for three times, the combined organic layer was washed with brine and dried over anhydrous $Na_2SO_4$. After filtration and evaporation, the crude residue was dissolved in 3 mL of DCM and TFA (2:1). After stirring for 1 h, the solvent was evaporated to give the crude product which was purified by flash column chromatography to yield Cpd. No. 129. ESI-MS calculated for $C_{22}H_{31}N_4O_7[M+H]^+=463.2$; Observed: 463.4.

Example 15

Synthesis of (3'R,4'S,5'R)-6"-chloro-4'-(3-chloro-2-fluorophenyl)-N-(4-((4-((2-(2,6-dioxopiperidin-3-yl)-1-oxoisoindolin-4-yl)amino)butyl)carbamoyl)phenyl)-2"-oxodispiro[cyclohexane-1,2'-pyrrolidine-3',3"-indoline]-5'-carboxamide (Cpd. No. 19)

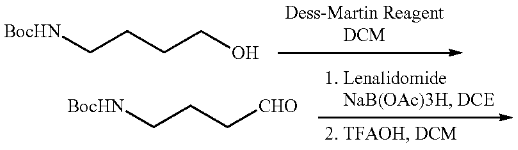

-continued

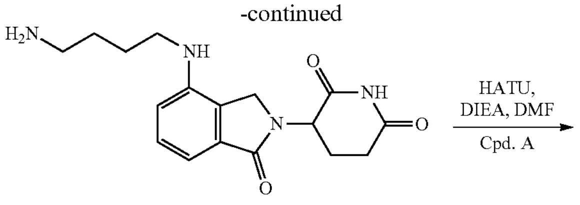

Cpd. No. 131

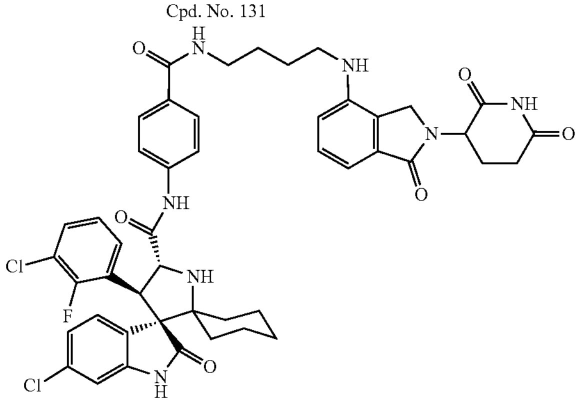

Cpd. No. 19

Step 1: Synthesis of tert-butyl (4-oxobutyl)carbamate

To solution of tert-butyl 4-hydroxybutyl)carbamate (380 mg, 2 mmol) in 15 ml of DCM was added Dess-Martin periodinane reagent (1.7 g, 4 mmol). After stirring at room temperature for 1 h the reaction mixture was filtered by celite. The filtrate was then washed with brine, dried over $Na_2SO_4$, filtered, and the solvent evaporated in vacuo. The residue was purified by chromatography over silica gel, to yield tert-butyl (4-oxobutyl)carbamate as colorless oil.

Step 2: Synthesis of 3-(4-((4-aminobutyl)amino)-1-oxoisoindolin-2-yl)piperidine-2,6-dione (Cpd. No. 131)

To tert-butyl (4-oxobutyl)carbamate (190 mg, 1 mmol) in 1,2-dichloroethane (15 mL) was added Lenalidomide (285 mg, 1.1 mmol), and the resulting solution was stirred at room temperature for 30 min. The solution was treated with $Na(OAc)_3BH$ (0.42 g, 2 mmol), and the resulting suspension was stirred overnight. The solvent was diluted with DCM and washed with sat. $NaHCO_3$, brine, dried ($Na_2SO_4$), filtered, and concentrated. Then residue was diluted in 10 mL DCM then 2 mL trifluoroacetic acid was added to the reaction and stirred for 30 min. The solvent was removed by vacuo and the residue was purified by reverse phase chromatography over C18 column to yield Cpd. No. 131 as colorless oil.

Step 3: Synthesis of Cpd. No. 19

HATU (13.3 mg, 1.2 eq.) and N,N-Diisopropylethylamine (0.026 mL, 0.15 mmol) were added to a solution of Cpd. A (20 mg, 0.029 mmol) in 0.5 mL DMF and stirred. After 10 minutes, Cpd. No. 131 (0.35 mL, 0.1 M in DMSO) was added to the reaction. After 30 minutes, the solvent was removed and the crude was dissolved in 3:1 methanol/water, acidified with trifluoroacetic acid and purified by reverse-phase preparative HPLC. The purified fractions were combined, concentrated in vacuo, re-dissolved in $H_2O$, frozen and lyophilized to give Cpd. No. 19 (TFA salt) as a white powder.

LC-MS(ESI) m/z $(M+H)^+$: 894.25, 4.96 min; calcd: 894.29; >98% purity.

Example 16

Synthesis of (3'R,4'S,5'R)-6"-chloro-4'-(3-chloro-2-fluorophenyl)-N-(4-((5-((2-(2,6-dioxopiperidin-3-yl)-1-oxoisoindolin-4-yl)amino)-5-oxopentyl)carbamoyl)phenyl)-2"-oxodispiro[cyclohexane-1,2'-pyrrolidine-3',3"-indoline]-5'-carboxamide (Cpd. No. 28)

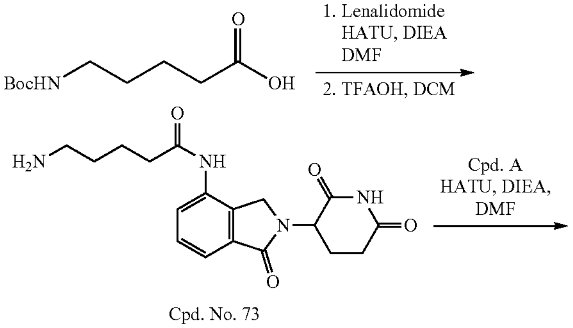

Cpd. No. 73

-continued

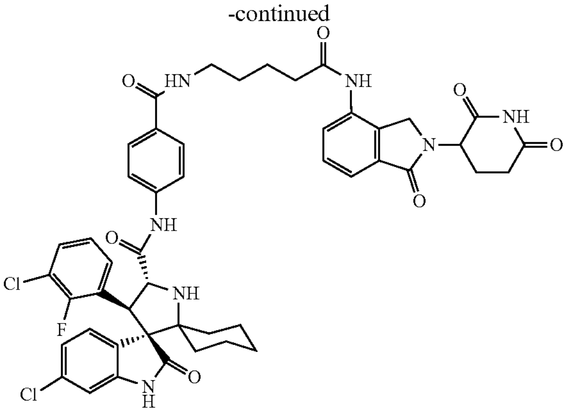

Cpd. No. 28

Step 1: Synthesis of 5-amino-N-(2-(2,6-dioxopiperidin-3-yl)-1-oxoisoindolin-4-yl)pentanamide (Cpd. No. 73)

HATU (380 mg, 1 mmol) and N,N-diisopropylethylamine (0.44 mL, 2.5 mmol) were added to a solution of Boc-5-aminopentanoic acid (110 mg, 0.5 mmol) in 3 mL DMF and stirred. After 10 minutes, Lenalidomide (200 mg, 0.75 mmol) was added to the reaction. After 30 minutes, the solvent was removed and the crude was dissolved in 10 mL DCM and 2 mL trifluoroacetic acid. The reaction was stirred for 30 min and then the solvent was removed by vacuo. The residue was purified by reverse phase chromatography over C18 column to yield 5-amino-N-(2-(2,6-dioxopiperidin-3-yl)-1-oxoisoindolin-4-yl)pentanamide as colorless oil.

Reaction 2: Synthesis of Cpd. No. 28

HATU (13.3 mg, 1.2 eq.) and N,N-diisopropylethylamine (0.026 mL, 0.15 mmol) were added to a solution of Cpd. A (20 mg, 0.029 mmol) in 0.5 mL DMF and stirred. After 10 minutes, 5-amino-N-(2-(2,6-dioxopiperidin-3-yl)-1-oxoisoindolin-4-yl)pentanamide (0.35 mL, 0.1 M in DMSO) was added to the reaction. After 30 minutes, the solvent was removed and the crude was dissolved in 3:1 methanol/water, acidified with trifluoroacetic acid and purified by reverse-phase preparative HPLC. The purified fractions were combined, concentrated in vacuo, re-dissolved in $H_2O$, frozen and lyophilized to give Cpd. No. 28 (TFA salt) as a white powder.

LC-MS(ESI) m/z $(M+H)^+$:922.26, 5.39 min; calcd: 922.29; >98% purity. $^1H$ NMR (400 MHz, MeOD) δ 7.77 (d, J=8.2 Hz, 2H), 7.74-7.67 (m, 2H), 7.63-7.57 (m, 3H), 7.54 (dd, J=8.2, 2.4 Hz, 1H), 7.47 (t, J=7.7 Hz, 1H), 7.39-7.31 (m, 1H), 7.17 (t, J=8.1 Hz, 1H), 7.11 (dd, J=8.2, 1.9 Hz, 1H), 6.79 (d, J=1.9 Hz, 1H), 5.38 (d, J=10.9 Hz, 1H), 5.12 (dd, J=13.3, 5.1 Hz, 1H), 4.98 (d, J=10.9 Hz, 1H), 4.45 (d, J=2.1 Hz, 2H), 3.40 (t, J=6.7 Hz, 2H), 3.02-2.79 (m, 2H), 2.78-2.66 (m, 1H), 2.57-2.30 (m, 3H), 2.21 (d, J=14.0 Hz, 1H), 2.17-2.07 (m, 1H), 2.06-1.88 (m, 3H), 1.81-1.63 (m, 6H), 1.60-1.46 (m, 1H), 1.24 (td, J=13.8, 3.9 Hz, 2H).

Example 17

(3'R,4'S,5'R)-6"-chloro-4'-(3-chloro-2-fluorophenyl)-N-(4-((5-(2-(2,6-dioxopiperidin-3-yl)-1-oxoisoindolin-4-yl)pentyl)carbamoyl)phenyl)-2"-oxodispiro[cyclohexane-1,2'-pyrrolidine-3',3"-indoline]-5'-carboxamide (Cpd. No. 31)

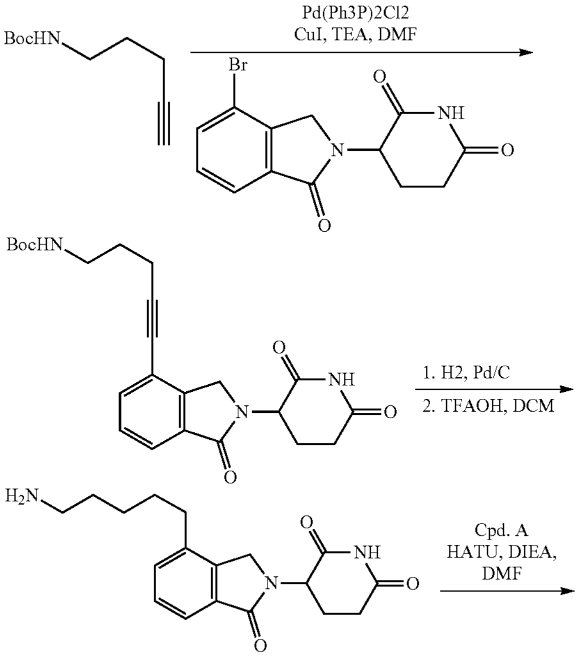

Cpd. No. 78

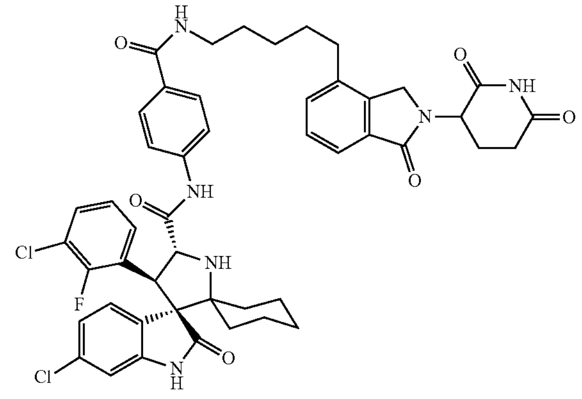

Cpd. No. 31

Step 1: Synthesis of tert-butyl (5-(2-(2,6-dioxopiperidin-3-yl)-1-oxoisoindolin-4-yl)pent-4-yn-1-yl) carbamate To a solution of tert-butyl pent-4-yn-1-ylcarbamate (236 mg, 1.29 mmol) and 3-(4-bromo-1-oxoisoindolin-2-yl)piperidine-2,6-dione (400 mg, 1.29 mmol) in triethylamine (3 mL) and DMF (3 mL), CuI (50 mg, 0.25 mmol) and the $Pd(Ph_3P)_2Cl_2$ (90 mg, 0.13 mmol) were added. The mixture was stirred at 80° C. under $N_2$-atmosphere overnight. The reaction mixture was poured into a saturated aqueous solution of NH4Cl and after separation of the organic layer the aqueous layer was extracted with Ethyl Acetate. The combined organic layers were washed with brine, dried over $Na_2SO_4$ and concentrated in vacuo. The crude product was purified by flash chromatography to afford tert-butyl (5-(2-(2,6-dioxopiperidin-3-yl)-1-oxoisoindolin-4-yl)pent-4-yn-1-yl)carbamate as white solid.

Step 2: Synthesis of 3-(4-(5-aminopentyl)-1-oxoisoindolin-2-yl)piperidine-2,6-dione (Cpd. No. 78)

To a solution of tert-butyl (5-(2-(2,6-dioxopiperidin-3-yl)-1-oxoisoindolin-4-yl)pent-4-yn-1-yl)carbamate (210 mg, 0.5 mmol) in EtOH (5 mL) was added Pd/C (20 mg). The reaction was stirred under H2-atmosphere for 2 hr. Then the mixture was filtered by celite and the solvent was removed by vacuo. The residue was dissolved in 10 mL DCM and 2 mL trifluoroacetic acid. The reaction was stirred for 30 min and then the solvent was removed by vacuo. The residue was purified by reverse phase chromatography over C18 column to 3-(4-(5-aminopentyl)-1-oxoisoindolin-2-yl)piperidine-2,6-dione as colorless oil.

Step 3: Synthesis of Cpd. No. 31

HATU (13.3 mg, 1.2 eq.) and N,N-diisopropylethylamine (0.026 mL, 0.15 mmol) were added to a solution of Cpd. A (20 mg, 0.029 mmol) in 0.5 mL DMF and stirred. After 10 minutes, 3-(4-(5-aminopentyl)-1-oxoisoindolin-2-yl)piperidine-2,6-dione (0.35 mL, 0.1 M in DMSO) was added to the reaction. After 30 minutes, the solvent was removed and the crude was dissolved in 3:1 methanol/water, acidified with trifluoroacetic acid and purified by reverse-phase preparative HPLC. The purified fractions were combined, concentrated in vacuo, re-dissolved in $H_2O$, frozen and lyophilized to give Cpd. No. 31 (TFA salt) as a white powder.

LC-MS(ESI) m/z $(M+H)^+$: 893.19, 6.12 min; calcd $(M+H)^+$: 893.30; >98% purity. $^1H$ NMR (400 MHz, MeOD) δ 7.78-7.66 (m, 3H), 7.66-7.56 (m, 3H), 7.53 (dd, J=8.2, 2.5 Hz, 1H), 7.47-7.38 (m, 2H), 7.38-7.32 (m, 1H), 7.17 (t, J=8.1 Hz, 1H), 7.11 (dd, J=8.2, 2.0 Hz, 1H), 6.79 (d, J=1.9 Hz, 1H), 5.29 (d, J=10.7 Hz, 1H), 5.14 (dd, J=13.3, 5.2 Hz, 1H), 4.97 (d, J=10.8 Hz, 1H), 4.46 (dd, J=5.7, 2.5 Hz, 2H), 3.41-3.33 (m, 2H), 2.96-2.64 (m, 5H), 2.50 (qdd, J=13.3, 4.6, 2.5 Hz, 1H), 2.22-2.09 (m, 2H), 2.02-1.84 (m, 3H), 1.79-1.48 (m, 7H), 1.48-1.35 (m, 2H), 1.22 (td, J=13.7, 4.0 Hz, 2H).

Example 18

The following Compounds of the Disclosure were prepared using the illustrative methods described in the General Schemes, Examples 1-17, and/or methods known to those skilled in the art in view of this disclosure.

Cpd. No. 2: (3'R,4'S,5'R)-6"-chloro-4'-(3-chloro-2-fluorophenyl)-N-(4-((1-((2-(2,6-dioxopiperidin-3-yl)-1,3-dioxoisoindolin-4-yl)oxy)-2-oxo-7,10,13-trioxa-3-azahexadecan-16-yl)carbamoyl)phenyl)-2"-oxodispiro[cyclohexane-1,2'-pyrrolidine-3',3"-indoline]-5'-carboxamide; LC-MS (ESI) m/z $(M+H)^+$: 1098.32, 5.27 min; calcd: 1098.36; >98% purity.

Cpd. No. 3: (3'R,4'S,5'R)-6"-chloro-4'-(3-chloro-2-fluorophenyl)-N-(4-((1-((2-(2,6-dioxopiperidin-3-yl)-1,3-dioxoisoindolin-4-yl)amino)-2-oxo-7,10,13-trioxa-3-azahexadecan-16-yl)carbamoyl)phenyl)-2"-oxodispiro [cyclohexane-1,2'-pyrrolidine-3',3"-indoline]-5'-carboxamide; LC-MS(ESI) m/z $(M+H)^+$: 1097.34, 5.48 min; calcd: 1097.37; >98% purity. $^1H$ NMR (400 MHz, MeOD)

δ 7.78-7.74 (m, 2H), 7.71 (t, J=6.6 Hz, 1H), 7.60 (d, J=8.7 Hz, 2H), 7.52 (dd, J=8.3, 7.4 Hz, 2H), 7.35 (t, J=7.0 Hz, 1H), 7.17 (t, J=8.0 Hz, 1H), 7.10 (dd, J=8.2, 1.8 Hz, 1H), 7.07 (d, J=7.1 Hz, 1H), 6.84 (d, J=8.4 Hz, 1H), 6.79 (d, J=1.9 Hz, 1H), 5.31 (d, J=10.8 Hz, 1H), 5.06 (dd, J=12.5, 5.4 Hz, 1H), 4.96 (d, J=10.8 Hz, 1H), 3.97 (s, 2H), 3.61-3.52 (m, 8H), 3.48-3.40 (m, 6H), 3.30-3.25 (m, 2H), 2.85 (ddd, J=17.7, 14.2, 5.1 Hz, 2H), 2.79-2.67 (m, 2H), 2.17 (d, J=13.5 Hz, 1H), 2.13-2.05 (m, 1H), 1.96-1.68 (m, 9H), 1.55 (dd, J=27.1, 13.6 Hz, 1H), 1.22 (td, J=13.6, 3.7 Hz, 3H).

Cpd. No. 4: (3'R,4'S,5'R)-6"-chloro-4'-(3-chloro-2-fluorophenyl)-N-(4-((2-(2-(2-(2-((2-(2,6-dioxopiperidin-3-yl)-1,3-dioxoisoindolin-4-yl)oxy)ethoxy)ethoxy)ethoxy)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 1013.33, 5.37 min; calcd: 1013.31; >98% purity. $^1H$ NMR (400 MHz, MeOD) δ 7.77 (d, J=8.8 Hz, 2H), 7.74-7.65 (m, 2H), 7.60 (d, J=8.7 Hz, 2H), 7.52 (dd, J=8.2, 2.4 Hz, 1H), 7.42-7.30 (m, 3H), 7.17 (t, J=8.0 Hz, 1H), 7.10 (dd, J=8.2, 1.5 Hz, 1H), 6.79 (d, J=1.8 Hz, 1H), 5.29 (d, J=10.7 Hz, 1H), 5.08 (dd, J=12.4, 5.5 Hz, 1H), 4.95 (d, J=10.8 Hz, 1H), 4.33-4.25 (m, 2H), 3.90-3.82 (m, 2H), 3.75-3.69 (m, 2H), 3.65-3.58 (m, 8H), 3.52 (t, J=5.3 Hz, 2H), 2.89-2.66 (m, 4H), 2.19-2.05 (m, 2H), 1.98-1.84 (m, 3H), 1.77 (d, J=10.9 Hz, 2H), 1.55 (dd, J=27.2, 13.7 Hz, 1H), 1.26-1.14 (m, 2H).

Cpd. No. 5: (3'R,4'S,5'R)-6"-chloro-4'-(3-chloro-2-fluorophenyl)-N-(4-(4-((3-(2-(2-(3-((2-(2,6-dioxopiperidin-3-yl)-1,3-dioxoisoindolin-4-yl)amino)propoxy)ethoxy)ethoxy)propyl)amino)piperidine-1-carbonyl)phenyl)-2"-oxodispiro[cyclohexane-1,2'-pyrrolidine-3',3"-indoline]-5'-carboxamide; LC-MS(ESI) m/z $(M+H)^+$: 1123.37, 4.83 min; calcd: 1123.43; >98% purity. $^1H$ NMR (400 MHz, Methanol-$d_4$) δ 7.71 (t, J=7.2 Hz, 1H), 7.68-7.60 (m, 2H), 7.54-7.45 (m, 2H), 7.42-7.35 (m, 2H), 7.35-7.30 (m, 1H), 7.19-7.12 (m, 1H), 7.09 (ddd, J=8.3, 2.0, 0.8 Hz, 1H), 7.06-6.95 (m, 2H), 6.78 (d, J=1.9 Hz, 1H), 5.17 (d, J=7.4 Hz, 1H), 5.04 (dd, J=12.4, 5.5 Hz, 1H), 4.92 (d, J=10.0 Hz, 1H), 3.80-3.45 (m, 13H), 3.38 (t, J=5.9 Hz, 3H), 3.18 (t, J=6.7 Hz, 2H), 2.97-2.79 (m, 2H), 2.79-2.60 (m, 3H), 2.23-2.02 (m, 4H), 2.02-1.62 (m, 10H), 1.63-1.44 (m, 3H), 1.34-1.04 (m, 3H).

Cpd. No. 6: (3'R,4'S,5'R)-6"-chloro-4'-(3-chloro-2-fluorophenyl)-N-(4-((4-(2-(2-(2-(2-((2-(2,6-dioxopiperidin-3-yl)-1,3-dioxoisoindolin-4-yl)amino)ethoxy)ethoxy) ethoxy)ethoxy)phenyl)carbamoyl)phenyl)-2"-oxodispiro[cyclohexane-1,2'-pyrrolidine-3',3"-indoline]-5'-carboxamide; LC-MS(ESI) m/z $(M+H)^+$: 1104.29, 6.47 min; calcd: 1104.35; >98% purity.

Cpd. No. 7: (3'R,4'S,5'R)-6"-chloro-4'-(3-chloro-2-fluorophenyl)-N-(4-((2-((2-(2,6-dioxopiperidin-3-yl)-1,3-dioxoisoindolin-4-yl)amino)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 880.21, 5.66 min; calcd: 880.24; >98% purity.

Cpd. No. 8: (3'R,4'S,5'R)-6"-chloro-4'-(3-chloro-2-fluorophenyl)-N-(4-((3-((2-(2,6-dioxopiperidin-3-yl)-1,3-dioxoisoindolin-4-yl)amino)propyl)carbamoyl)phenyl)-2"-oxodispiro[cyclohexane-1,2'-pyrrolidine-3',3"-indoline]-5'-carboxamide; LC-MS(ESI) m/z $(M+H)^+$: 894.24, 5.31 min; calcd: 894.26; >98% purity.

Cpd. No. 9: (3'R,4'S,5'R)-6"-chloro-4'-(3-chloro-2-fluorophenyl)-N-(4-((4-((2-(2,6-dioxopiperidin-3-yl)-1,3-dioxoisoindolin-4-yl)amino)butyl)carbamoyl)phenyl)-2"-oxodispiro[cyclohexane-1,2'-pyrrolidine-3',3"-indoline]-5'-carboxamide; LC-MS(ESI) m/z $(M+H)^+$: 908.32, 5.86 min; calcd: 908.27; >98% purity. $^1H$ NMR (400 MHz, MeOD) δ 7.79-7.68 (m, 3H), 7.63-7.58 (m, 2H), 7.53 (dd, J=8.3, 2.4 Hz, 1H), 7.49 (ddd, J=8.5, 7.1, 1.4 Hz, 1H), 7.39-7.32 (m, 1H), 7.17 (t, J=8.1 Hz, 1H), 7.11 (dd, J=8.2, 2.0 Hz, 1H), 7.02 (d, J=8.6 Hz, 1H), 6.98 (dd, J=6.8, 2.8 Hz, 1H), 6.79 (d, J=1.9 Hz, 1H), 5.30 (d, J=10.7 Hz, 1H), 5.03 (dd, J=12.6, 5.5 Hz, 1H), 4.96 (d, J=10.8 Hz, 1H), 3.44-3.34 (m, 4H), 2.92-2.79 (m, 2H), 2.78-2.65 (m, 2H), 2.17 (d, J=14.1 Hz, 1H), 2.13-2.05 (m, 1H), 2.02-1.87 (m, 3H), 1.81-1.69 (m, 6H), 1.62-1.48 (m, 1H), 1.27-1.16 (m, 2H).

Cpd. No. 10: (3'R,4'S,5'R)-6"-chloro-4'-(3-chloro-2-fluorophenyl)-N-(4-((5-((2-(2,6-dioxopiperidin-3-yl)-1,3-dioxoisoindolin-4-yl)amino)pentyl)carbamoyl)phenyl)-2"-oxodispiro[cyclohexane-1,2'-pyrrolidine-3',3"-indoline]-5'-carboxamide; LC-MS(ESI) m/z $(M+H)^+$: 922.30, 6.54 min; calcd: 922.29; >98% purity. $^1H$ NMR (400 MHz, MeOD) δ 7.79-7.67 (m, 3H), 7.63-7.57 (m, 2H), 7.57-7.46 (m, 2H), 7.37-7.30 (m, 1H), 7.16 (t, J=7.9 Hz, 1H), 7.10 (dd, J=8.2, 1.9 Hz, 1H), 7.02 (d, J=8.6 Hz, 1H), 6.98 (dd, J=6.7, 4.1 Hz, 1H), 6.78 (d, J=1.9 Hz, 1H), 5.22 (d, J=9.8 Hz, 1H), 5.04-4.98 (m, 1H), 4.95 (dd, J=10.6, 2.9 Hz, 1H), 3.41-3.33 (m, 4H), 2.90-2.61 (m, 4H), 2.17-2.04 (m, 2H), 1.97-1.82 (m, 3H), 1.78-1.49 (m, 9H), 1.24-1.13 (m, 2H).

Cpd. No. 11: (3'R,4'S,5'R)-6"-chloro-4'-(3-chloro-2-fluorophenyl)-N-(4-((6-((2-(2,6-dioxopiperidin-3-yl)-1,3-dioxoisoindolin-4-yl)amino)hexyl)carbamoyl)phenyl)-2"-oxodispiro[cyclohexane-1,2'-pyrrolidine-3',3"-indoline]-5'-carboxamide; LC-MS(ESI) m/z $(M+H)^+$: 936.27, 6.76 min; calcd: 936.31; >98% purity. $^1H$ NMR (400 MHz, MeOD) δ 7.76 (d, J=8.7 Hz, 2H), 7.71 (t, J=6.7 Hz, 1H), 7.60 (d, J=8.7 Hz, 2H), 7.56-7.47 (m, 2H), 7.36 (t, J=7.0 Hz, 1H), 7.18 (t, J=8.0 Hz, 1H), 7.11 (dd, J=8.2, 1.9 Hz, 1H), 7.02-6.97 (m, 2H), 6.79 (d, J=1.9 Hz, 1H), 5.33 (d, J=10.9 Hz, 1H), 5.03 (dd, J=12.4, 5.3 Hz, 1H), 4.97 (d, J=10.9 Hz, 1H), 3.40-3.27 (m, 4H), 2.93-2.65 (m, 4H), 2.19 (d, J=11.6 Hz, 1H), 2.15-2.06 (m, 1H), 2.04-1.89 (m, 3H), 1.78 (d, J=11.8 Hz, 2H), 1.71-1.59 (m, 4H), 1.55-1.38 (m, 5H), 1.27-1.18 (m, 2H).

Cpd. No. 12: (3'R,4'S,5'R)-6"-chloro-4'-(3-chloro-2-fluorophenyl)-N-(4-((7-((2-(2,6-dioxopiperidin-3-yl)-1,3-dioxoisoindolin-4-yl)amino)heptyl)carbamoyl)phenyl)-2"-oxodispiro[cyclohexane-1,2'-pyrrolidine-3',3"-indoline]-5'-carboxamide; LC-MS(ESI) m/z $(M+H)^+$: 950.29, 7.10 min; calcd: 950.32; >98% purity. $^1H$ NMR (400 MHz, MeOD) δ 7.80-7.74 (m, 2H), 7.74-7.68 (m, 1H), 7.64-7.59 (m, 2H), 7.55-7.47 (m, 2H), 7.37-7.30 (m, 1H), 7.16 (t, J=8.1 Hz, 1H), 7.10 (dd, J=8.2, 1.9 Hz, 1H), 7.01 (s, 1H), 6.99 (d, J=2.2 Hz, 1H), 6.79 (d, J=1.9 Hz, 1H), 5.27 (d, J=10.6 Hz, 1H), 5.03 (dd, J=12.6, 5.4 Hz, 1H), 4.95 (d, J=10.7 Hz, 1H), 3.38-3.27 (m, 4H), 2.90-2.64 (m, 4H), 2.20-2.05 (m, 2H), 2.00-1.84 (m, 3H), 1.83-1.71 (m, 2H), 1.67-1.53 (m, 5H), 1.46-1.35 (m, 6H), 1.25-1.13 (m, 2H).

Cpd. No. 13: (3'R,4'S,5'R)-6"-chloro-4'-(3-chloro-2-fluorophenyl)-N-(4-((2-(2-((2-(2,6-dioxopiperidin-3-yl)-1,3-dioxoisoindolin-4-yl)amino)ethoxy)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 924.20, 5.28 min; calcd: 924.27; >98% purity. $^1H$ NMR (400 MHz, MeOD) δ 7.76-7.68 (m, 3H), 7.61-7.51 (m, 3H), 7.47-7.39 (m, 1H), 7.35 (t, J=7.6 Hz, 1H), 7.19 (t, J=8.1 Hz, 1H), 7.11 (dd, J=8.2, 0.9 Hz, 1H), 7.01 (d, J=8.6 Hz, 1H), 6.91 (t, J=7.2 Hz, 1H), 6.79 (d, J=1.9 Hz, 1H), 5.39 (d, J=10.9 Hz, 1H), 5.03-4.92 (m, 3H), 3.69 (dt, J=10.5, 5.0 Hz, 4H), 3.58-3.50 (m, 2H), 3.45 (t, J=4.9 Hz, 2H), 3.03-2.53 (m, 4H), 2.22 (d, J=13.4 Hz, 1H), 2.09-1.86 (m, 4H), 1.78 (d, J=12.1 Hz, 2H), 1.54 (dd, J=27.2, 13.5 Hz, 1H), 1.29-1.12 (m, 2H).

Cpd. No. 14: (3'R,4'S,5'R)-6"-chloro-4'-(3-chloro-2-fluorophenyl)-N-(4-((2-(2-(2-((2-(2,6-dioxopiperidin-3-yl)-1,3-dioxoisoindolin-4-yl)amino)ethoxy)ethoxy)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 968.35, 5.58 min; calcd: 968.30; >98% purity. $^1$H NMR (400 MHz, MeOD) δ 7.79-7.66 (m, 3H), 7.59-7.47 (m, 3H), 7.40-7.27 (m, 2H), 7.19 (t, J=8.1 Hz, 1H), 7.10 (dd, J=8.2, 1.8 Hz, 1H), 6.95-6.83 (m, 2H), 6.79 (d, J=1.9 Hz, 1H), 5.40 (d, J=10.9 Hz, 1H), 5.03-4.96 (m, 3H), 3.73-3.62 (m, 8H), 3.57-3.50 (m, 2H), 3.42-3.35 (m, 2H), 2.94 (d, J=8.0 Hz, 1H), 2.85-2.57 (m, 3H), 2.21 (d, J=13.6 Hz, 1H), 2.07-1.87 (m, 4H), 1.76 (d, J=11.6 Hz, 2H), 1.53 (dd, J=26.9, 13.3 Hz, 1H), 1.31-1.10 (m, 2H).

Cpd. No. 15: (3'R,4'S,5'R)-6"-chloro-4'-(3-chloro-2-fluorophenyl)-N-(4-((2-(2-(2-(2-((2-(2,6-dioxopiperidin-3-yl)-1,3-dioxoisoindolin-4-yl)amino) ethoxy)ethoxy)ethoxy) ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 1012.30, 5.68 min; calcd: 1012.32; >98% purity. $^1$H NMR (400 MHz, MeOD) δ 7.76 (d, J=8.7 Hz, 2H), 7.72 (t, J=6.6 Hz, 1H), 7.58 (d, J=8.7 Hz, 2H), 7.53 (dd, J=8.2, 2.3 Hz, 1H), 7.49-7.43 (m, 1H), 7.36 (t, J=7.0 Hz, 1H), 7.19 (t, J=8.1 Hz, 1H), 7.11 (dd, J=8.2, 1.8 Hz, 1H), 6.99 (d, J=8.0 Hz, 2H), 6.79 (d, J=1.9 Hz, 1H), 5.37 (d, J=10.9 Hz, 1H), 5.02 (ddd, J=12.3, 5.4, 1.3 Hz, 1H), 4.97 (d, J=11.0 Hz, 1H), 3.68-3.60 (m, 12H), 3.52 (t, J=5.3 Hz, 2H), 3.42 (t, J=5.2 Hz, 2H), 2.95-2.87 (m, 1H), 2.86-2.79 (m, 1H), 2.76-2.61 (m, 2H), 2.21 (d, J=13.4 Hz, 1H), 2.13-2.05 (m, 1H), 2.00-1.88 (m, 3H), 1.77 (d, J=11.7 Hz, 2H), 1.53 (dd, J=27.1, 13.2 Hz, 1H), 1.29-1.19 (m, 2H).

Cpd. No. 16: (3'R,4'S,5'R)-6"-chloro-4'-(3-chloro-2-fluorophenyl)-N-(4-((23-((2-(2,6-dioxopiperidin-3-yl)-1,3-dioxoisoindolin-4-yl)amino)-3,6,9,12,15,18,21-heptaoxatricosyl)carbamoyl) phenyl)-2"-oxodispiro[cyclohexane-1,2'-pyrrolidine-3',3"-indoline]-5'-carboxamide; LC-MS(ESI) m/z $(M+H)^+$: 1188.42, 5.69 min; calcd: 1188.43; >98% purity. $^1$H NMR (400 MHz, MeOD) δ 7.84-7.77 (m, 2H), 7.70 (t, J=6.5 Hz, 1H), 7.66-7.59 (m, 2H), 7.55-7.48 (m, 2H), 7.39-7.31 (m, 1H), 7.16 (t, J=8.0 Hz, 1H), 7.09 (dd, J=8.2, 1.5 Hz, 1H), 7.06 (d, J=8.5 Hz, 1H), 7.03 (d, J=7.1 Hz, 1H), 6.78 (d, J=1.9 Hz, 1H), 5.23 (d, J=10.3 Hz, 1H), 5.04 (dd, J=12.5, 5.5 Hz, 1H), 4.94 (d, J=10.7 Hz, 1H), 3.70 (t, J=5.3 Hz, 2H), 3.64-3.54 (m, 28H), 3.47 (t, J=5.3 Hz, 2H), 2.88-2.65 (m, 4H), 2.18-2.05 (m, 2H), 2.00-1.81 (m, 3H), 1.75 (t, J=11.9 Hz, 2H), 1.56 (dd, J=27.2, 13.5 Hz, 1H), 1.27-1.12 (m, 2H).

Cpd. No. 17: (3'R,4'S,5'R)-6"-chloro-4'-(3-chloro-2-fluorophenyl)-N-(4-((3-(4-(3-((2-(2,6-dioxopiperidin-3-yl)-1,3-dioxoisoindolin-4-yl)amino)propoxy)butoxy)propyl) carbamoyl)phenyl)-2"-oxodispiro[cyclohexane-1,2'-pyrrolidine-3',3"-indoline]-5'-carboxamide; LC-MS(ESI) m/z $(M+H)^+$: 1024.35, 6.54 min; calcd: 1024.36; >98% purity. $^1$H NMR (400 MHz, MeOD) δ 7.76 (d, J=8.7 Hz, 2H), 7.71 (t, J=6.6 Hz, 1H), 7.61 (d, J=8.7 Hz, 2H), 7.54-7.45 (m, 2H), 7.39-7.30 (m, 1H), 7.17 (t, J=8.0 Hz, 1H), 7.10 (dd, J=8.2, 1.8 Hz, 1H), 7.00 (d, J=8.1 Hz, 2H), 6.79 (d, J=1.9 Hz, 1H), 5.29 (d, J=10.7 Hz, 1H), 5.03 (dd, J=12.5, 5.4 Hz, 1H), 4.95 (d, J=10.8 Hz, 1H), 3.52 (dd, J=10.4, 5.8 Hz, 4H), 3.47-3.40 (m, 6H), 3.38 (t, J=6.6 Hz, 2H), 2.92-2.62 (m, 4H), 2.16 (d, J=13.3 Hz, 1H), 2.13-2.04 (m, 1H), 1.99-1.82 (m, 7H), 1.76 (d, J=12.1 Hz, 2H), 1.64 (t, J=2.9 Hz, 4H), 1.54 (dd, J=25.8, 12.1 Hz, 1H), 1.27-1.15 (m, 2H).

Cpd. No. 18: (3'R,4'S,5'R)-6"-chloro-4'-(3-chloro-2-fluorophenyl)-N-(4-((3-(2-(2-(3-((2-(2,6-dioxopiperidin-3-yl)-1,3-dioxoisoindolin-4-yl)amino)propoxy) ethoxy)ethoxy) propyl)carbamoyl)phenyl)-2"-oxodispiro[cyclohexane-1,2'-pyrrolidine-3',3"-indoline]-5'-carboxamide; LC-MS(ESI) m/z $(M+H)^+$: 1040.40, 5.93 min; calcd: 1040.35; >98% purity. $^1$H NMR (400 MHz, MeOD) δ 7.80-7.74 (m, 2H), 7.70 (t, J=7.1 Hz, 1H), 7.61 (d, J=8.6 Hz, 2H), 7.55-7.46 (m, 2H), 7.39-7.31 (m, 1H), 7.17 (t, J=8.1 Hz, 1H), 7.10 (dd, J=8.2, 1.6 Hz, 1H), 7.04-6.96 (m, 2H), 6.79 (d, J=1.9 Hz, 1H), 5.26 (d, J=10.4 Hz, 1H), 5.03 (dd, J=12.4, 5.5 Hz, 1H), 4.94 (d, J=10.7 Hz, 1H), 3.68-3.62 (m, 4H), 3.62-3.54 (m, 8H), 3.45 (t, J=6.6 Hz, 2H), 3.38 (t, J=6.5 Hz, 2H), 2.90-2.67 (m, 4H), 2.20-2.05 (m, 2H), 1.96-1.73 (m, 9H), 1.55 (dd, J=27.1, 13.6 Hz, 1H), 1.27-1.13 (m, 2H).

Cpd. No. 20: (3'R,4'S,5'R)-6"-chloro-4'-(3-chloro-2-fluorophenyl)-N-(4-((2-(2-((2-(2,6-dioxopiperidin-3-yl)-1-oxoisoindolin-4-yl)amino)ethoxy)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 910.19, 5.15 min; calcd: 910.29; >98% purity. $^1$H NMR (400 MHz, MeOD) δ 7.71 (t, J=6.8 Hz, 1H), 7.65-7.55 (m, 3H), 7.50 (d, J=8.7 Hz, 1H), 7.44 (d, J=8.7 Hz, 1H), 7.36 (t, J=7.6 Hz, 1H), 7.26 (td, J=7.8, 2.3 Hz, 1H), 7.18 (t, J=8.0 Hz, 1H), 7.12 (dd, J=8.2, 1.8 Hz, 1H), 7.03 (dd, J=7.3, 3.4 Hz, 1H), 6.83 (dd, J=8.1, 4.5 Hz, 1H), 6.80 (d, J=1.8 Hz, 1H), 5.32 (d, J=10.4 Hz, 1H), 5.12-5.04 (m, 1H), 5.01 (d, J=10.9 Hz, 1H), 4.26-4.05 (m, 2H), 3.73 (t, J=4.8 Hz, 2H), 3.67 (t, J=5.0 Hz, 2H), 3.59-3.51 (m, 2H), 3.41-3.35 (m, 2H), 3.01-2.76 (m, 3H), 2.42-2.29 (m, 1H), 2.24-2.09 (m, 2H), 2.05-1.91 (m, 3H), 1.79 (d, J=12.1 Hz, 2H), 1.57 (dd, J=24.5, 11.9 Hz, 1H), 1.24 (t, J=11.8 Hz, 2H).

Cpd. No. 21: (3'R,4'S,5'R)-6"-chloro-4'-(3-chloro-2-fluorophenyl)-N-(4-((2-(2-(2-((2-(2,6-dioxopiperidin-3-yl)-1-oxoisoindolin-4-yl)amino)ethoxy)ethoxy) ethyl)carbamoyl) phenyl)-2"-oxodispiro[cyclohexane-1,2'-pyrrolidine-3',3"-indoline]-5'-carboxamide; LC-MS(ESI) m/z $(M+H)^+$: 954.24, 4.88 min; calcd: 954.32; >98% purity. $^1$H NMR (400 MHz, MeOD) δ 7.77-7.68 (m, 3H), 7.57-7.49 (m, 2H), 7.45 (d, J=8.8 Hz, 1H), 7.36 (t, J=7.5 Hz, 1H), 7.25 (td, J=7.8, 2.8 Hz, 1H), 7.18 (t, J=8.2 Hz, 1H), 7.12 (ddd, J=8.3, 1.9, 0.9 Hz, 1H), 7.06 (dd, J=7.0, 5.2 Hz, 1H), 6.84-6.74 (m, 2H), 5.28 (d, J=10.6 Hz, 1H), 5.11 (td, J=13.5, 5.2 Hz, 1H), 4.96 (d, J=10.9 Hz, 1H), 4.26-4.10 (m, 2H), 3.77-3.60 (m, 8H), 3.55 (t, J=4.4 Hz, 2H), 3.39-3.35 (m, 2H), 2.93-2.70 (m, 3H), 2.48-2.31 (m, 1H), 2.24-2.05 (m, 2H), 2.04-1.88 (m, 3H), 1.78 (d, J=10.9 Hz, 2H), 1.62-1.52 (m, 1H), 1.28-1.15 (m, 2H).

Cpd. No. 22: (3'R,4'S,5'R)-6"-chloro-4'-(3-chloro-2-fluorophenyl)-N-(4-((2-(2-(2-(2-((2-(2,6-dioxopiperidin-3-yl)-1-oxoisoindolin-4-yl)amino)ethoxy)ethoxy)ethoxy) ethyl) carbamoyl)phenyl)-2"-oxodispiro[cyclohexane-1,2'-pyrrolidine-3',3"-indoline]-5'-carboxamide; LC-MS(ESI) m/z $(M+H)^+$: 998.29, 5.21 min; calcd: 998.34; >98% purity. $^1$H NMR (400 MHz, MeOD) δ 7.76 (dd, J=8.8, 2.8 Hz, 2H), 7.71 (t, J=7.0 Hz, 1H), 7.57 (t, J=8.3 Hz, 2H), 7.51 (dt, J=8.2, 2.7 Hz, 1H), 7.36 (t, J=7.6 Hz, 1H), 7.30-7.23 (m, 1H), 7.18 (t, J=8.1 Hz, 1H), 7.11 (d, J=8.2 Hz, 1H), 7.07 (dd, J=7.3, 2.2 Hz, 1H), 6.84-6.77 (m, 2H), 5.32 (d, J=10.9 Hz, 1H), 5.16-5.10 (m, 1H), 4.95 (dd, J=10.8, 2.7 Hz, 1H), 4.32-4.19 (m, 2H), 3.68-3.60 (m, 12H), 3.52 (t, J=5.3 Hz, 2H), 3.36 (t, J=4.6 Hz, 2H), 2.97-2.86 (m, 2H), 2.80-2.71 (m, 1H), 2.50-2.37 (m, 1H), 2.22-2.12 (m, 2H), 1.94 (dd, J=19.7, 10.4 Hz, 3H), 1.78 (d, J=12.3 Hz, 2H), 1.54 (dd, J=25.6, 13.6 Hz, 1H), 1.28-1.17 (m, 2H).

Cpd. No. 23: (3'R,4'S,5'R)-6"-chloro-4'-(3-chloro-2-fluorophenyl)-N-(4-((14-((2-(2,6-dioxopiperidin-3-yl)-1-oxoisoindolin-4-yl)amino)-3,6,9,12-tetraoxatetradecyl)carbamoyl)phenyl)-2"-oxodispiro[cyclohexane-1,2'-pyrrolidine-3',3"-indoline]-5'-carboxamide; LC-MS(ESI) m/z $(M+H)^+$: 1042.31, 5.22 min; calcd: 1042.37; >98% purity. $^1$H NMR (400 MHz, MeOD) δ 7.79 (dd, J=8.8, 1.9 Hz, 2H), 7.70 (t, J=6.6 Hz, 1H), 7.65-7.58 (m, 2H), 7.50 (dt, J=8.1, 2.2 Hz, 1H), 7.37-7.27 (m, 2H), 7.16 (t, J=7.8 Hz, 1H), 7.12-7.06 (m, 2H), 6.84 (dd, J=8.1, 1.7 Hz, 1H), 6.78 (d, J=1.9 Hz, 1H), 5.23 (d, J=9.0 Hz, 1H), 5.14 (dt, J=13.3, 4.9 Hz, 1H), 4.93 (d, J=10.7 Hz, 1H), 4.28 (d, J=4.4 Hz, 2H), 3.67-3.50 (m, 18H), 3.38 (t, J=4.9 Hz, 2H), 2.93-2.83 (m, 1H), 2.77 (ddd, J=17.6, 4.5, 2.3 Hz, 2H), 2.52-2.37 (m, 1H), 2.20-2.08 (m, 2H), 1.99-1.85 (m, 3H), 1.80-1.72 (m, 2H), 1.56 (dd, J=27.5, 14.1 Hz, 1H), 1.20 (t, J=13.2 Hz, 2H).

Cpd. No. 24: (3'R,4'S,5'R)-6"-chloro-4'-(3-chloro-2-fluorophenyl)-N-(5-((2-(2-(2-((2-(2,6-dioxopiperidin-3-yl)-1,3-dioxoisoindolin-4-yl)amino)ethoxy)ethoxy)ethyl) carbamoyl)pyridin-2-yl)-2"-oxodispiro[cyclohexane-1,2'-pyrrolidine-3',3"-indoline]-5'-carboxamide; LC-MS(ESI) m/z $(M+H)^+$: 969.35, 6.18 min; calcd: 969.29; >98% purity.

Cpd. No. 25: (3'R,4'S,5'R)-6"-chloro-4'-(3-chloro-2-fluorophenyl)-N-(5-((3-(2-(2-(3-((2-(2,6-dioxopiperidin-3-yl)-1,3-dioxoisoindolin-4-yl)amino)propoxy)ethoxy)ethoxy) propyl)carbamoyl)pyridin-2-yl)-2"-oxodispiro[cyclohexane-1,2'-pyrrolidine-3',3"-indoline]-5'-carboxamide; LC-MS(ESI) m/z $(M+H)^+$: 1041.31, 6.52 min; calcd: 1041.35; >98% purity.

Cpd. No. 26: (3'R,4'S,5'R)-6"-chloro-4'-(3-chloro-2-fluorophenyl)-N-(6-((2-(2-(2-((2-(2,6-dioxopiperidin-3-yl)-1,3-dioxoisoindolin-4-yl)amino)ethoxy)ethoxy)ethyl) carbamoyl)pyridin-3-yl)-2"-oxodispiro[cyclohexane-1,2'-pyrrolidine-3',3"-indoline]-5'-carboxamide; LC-MS(ESI) m/z $(M+H)^+$:969.24, 6.20 min; calcd: 969.29; >98% purity.

Cpd. No. 27: (3'R,4'S,5'R)-6"-chloro-4'-(3-chloro-2-fluorophenyl)-N-(6-((3-(2-(2-(3-((2-(2,6-dioxopiperidin-3-yl)-1,3-dioxoisoindolin-4-yl)amino)propoxy)ethoxy)ethoxy) propyl)carbamoyl)pyridin-3-yl)-2"-oxodispiro[cyclohexane-1,2'-pyrrolidine-3',3"-indoline]-5'-carboxamide; LC-MS(ESI) m/z $(M+H)^+$:1041.32, 6.51 min; calcd: 1041.35; >98% purity. $^1$H NMR (400 MHz, MeOD) δ 8.79 (d, J=2.2 Hz, 1H), 8.11 (dt, J=8.6, 2.2 Hz, 1H), 8.00 (d, J=8.5 Hz, 1H), 7.69 (t, J=7.0 Hz, 1H), 7.54-7.45 (m, 2H), 7.34 (t, J=7.3 Hz, 1H), 7.16 (t, J=8.1 Hz, 1H), 7.10 (dd, J=8.2, 1.8 Hz, 1H), 6.99 (dd, J=16.6, 7.9 Hz, 2H), 6.78 (d, J=1.9 Hz, 1H), 5.18 (d, J=9.9 Hz, 1H), 5.03 (ddd, J=12.3, 5.4, 1.5 Hz, 1H), 4.95 (dd, J=10.4, 2.8 Hz, 1H), 3.73-3.65 (m, 4H), 3.64-3.52 (m, 8H), 3.49 (t, J=6.5 Hz, 2H), 3.39 (t, J=6.6 Hz, 2H), 2.83 (ddd, J=14.4, 5.4, 2.7 Hz, 1H), 2.78-2.62 (m, 3H), 2.16-2.04 (m, 2H), 2.00-1.79 (m, 7H), 1.75 (t, J=13.5 Hz, 2H), 1.58 (dd, J=26.7, 13.2 Hz, 1H), 1.23-1.09 (m, 2H).

Cpd. No. 29: (3'R,4'S,5'R)-6"-chloro-4'-(3-chloro-2-fluorophenyl)-N-(4-((2-(2-(3-((2-(2,6-dioxopiperidin-3-yl)-1-oxoisoindolin-4-yl)amino)-3-oxopropoxy)ethoxy)ethyl) carbamoyl)phenyl)-2"-oxodispiro[cyclohexane-1,2'-pyrrolidine-3',3"-indoline]-5'-carboxamide; LC-MS(ESI) m/z $(M+H)^+$:982.27, 4.57 min; calcd: 982.31; >98% purity. $^1$H NMR (400 MHz, MeOD) δ 7.76-7.63 (m, 4H), 7.60-7.47 (m, 4H), 7.43-7.29 (m, 2H), 7.18 (t, J=8.1 Hz, 1H), 7.11 (dd, J=8.2, 2.0 Hz, 1H), 6.80 (d, J=1.9 Hz, 1H), 5.38 (dd, J=10.9, 1.6 Hz, 1H), 5.14 (td, J=13.1, 5.2 Hz, 1H), 4.98 (dd, J=11.0, 2.2 Hz, 1H), 4.44 (d, J=4.2 Hz, 2H), 3.83 (t, J=5.9 Hz, 2H), 3.73-3.57 (m, 6H), 3.54-3.42 (m, 2H), 2.98-2.91 (m, 1H), 2.91-2.82 (m, 1H), 2.82-2.70 (m, 1H), 2.66 (dd, J=6.9, 4.8 Hz, 2H), 2.51-2.36 (m, 1H), 2.28-2.09 (m, 2H), 2.04-1.86 (m, 3H), 1.77 (d, J=11.9 Hz, 2H), 1.64-1.44 (m, 1H), 1.24 (td, J=13.8, 3.6 Hz, 2H).

Cpd. No. 30: (3'R,4'S,5'R)-6"-chloro-4'-(3-chloro-2-fluorophenyl)-N-(4-((2-(2-(2-(3-((2-(2,6-dioxopiperidin-3-yl)-1-oxoisoindolin-4-yl)amino)-3-oxopropoxy)ethoxy) ethoxy)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$:1026.30, 4.54 min; calcd: 1026.34; >98% purity. $^1$H NMR (400 MHz, MeOD) δ 7.80-7.74 (m, 2H), 7.74-7.68 (m, 2H), 7.63-7.56 (m, 3H), 7.53 (dd, J=8.2, 2.5 Hz, 1H), 7.46 (t, J=7.8 Hz, 1H), 7.39-7.31 (m, 1H), 7.17 (t, J=8.1 Hz, 1H), 7.13-7.03 (m, 1H), 6.79 (d, J=1.9 Hz, 1H), 5.35 (d, J=10.9 Hz, 1H), 5.15 (dt, J=13.3, 5.4 Hz, 1H), 4.97 (d, J=10.9 Hz, 1H), 4.45 (t, J=2.6 Hz, 2H), 3.79 (t, J=5.9 Hz, 2H), 3.64-3.51 (m, 10H), 3.48 (t, J=5.2 Hz, 2H), 2.99-2.82 (m, 2H), 2.76 (ddd, J=17.6, 4.5, 2.3 Hz, 1H), 2.65 (dd, J=7.2, 4.7 Hz, 2H), 2.43 (qdd, J=13.2, 4.6, 2.3 Hz, 1H), 2.25-2.10 (m, 2H), 2.04-1.85 (m, 3H), 1.76 (d, J=11.7 Hz, 2H), 1.60-1.44 (m, 1H), 1.23 (td, J=13.7, 3.8 Hz, 2H).

Cpd. No. 32: (3'R,4'S,5'R)-6"-chloro-4'-(3-chloro-2-fluorophenyl)-N-(4-((5-(2-(2,6-dioxopiperidin-3-yl)-1,3-dioxoisoindolin-4-yl)pentyl)carbamoyl)phenyl)-2"-oxodispiro[cyclohexane-1,2'-pyrrolidine-3',3"-indoline]-5'-carboxamide; LC-MS(ESI) m/z $(M+H)^+$: 907.27, 6.37 min; calcd: 907.28; >98% purity. $^1$H NMR (400 MHz, MeOD) δ 7.75-7.68 (m, 3H), 7.66-7.63 (m, 2H), 7.63-7.57 (m, 3H), 7.54 (dd, J=8.2, 2.2 Hz, 1H), 7.37 (t, J=7.4 Hz, 1H), 7.19 (t, J=8.0 Hz, 1H), 7.11 (dd, J=8.2, 1.4 Hz, 1H), 6.80 (d, J=1.5 Hz, 1H), 5.38 (d, J=10.9 Hz, 1H), 5.09 (dd, J=12.6, 5.4 Hz, 1H), 4.99 (d, J=11.0 Hz, 1H), 3.34 (t, J=7.0 Hz, 2H), 3.11 (dd, J=17.7, 10.1 Hz, 2H), 2.98-2.79 (m, 2H), 2.79-2.62 (m, 2H), 2.22 (d, J=13.9 Hz, 1H), 2.10 (dd, J=8.6, 3.5 Hz, 1H), 2.04-1.91 (m, 3H), 1.80-1.51 (m, 7H), 1.44 (dd, J=15.0, 8.0 Hz, 2H), 1.31-1.19 (m, 2H).

Cpd. No. 33: (3'R,4'S,5'R)-6"-chloro-4'-(3-chloro-2-fluorophenyl)-N-(4-((2-(3-(2-(2,6-dioxopiperidin-3-yl)-1-oxoisoindolin-4-yl)propoxy)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 909.27, 5.64 min; calcd: 909.29; >98% purity. $^1$H NMR (400 MHz, MeOD) δ 7.80-7.74 (m, 2H), 7.71 (t, J=6.6 Hz, 1H), 7.63-7.51 (m, 4H), 7.45-7.34 (m, 3H), 7.19 (t, J=8.0 Hz, 1H), 7.12 (dd, J=8.2, 1.9 Hz, 1H), 6.80 (d, J=1.9 Hz, 1H), 5.36 (d, J=11.0 Hz, 1H), 5.12 (dd, J=13.3, 5.1 Hz, 1H), 4.99 (d, J=11.0 Hz, 1H), 4.48-4.33 (m, 2H), 3.61-3.57 (m, 2H), 3.57-3.52 (m, 2H), 3.49 (t, J=5.9 Hz, 2H), 2.99-2.92 (m, 1H), 2.92-2.83 (m, 1H), 2.83-2.72 (m, 3H), 2.46 (ddd, J=26.5, 13.3, 4.8 Hz, 1H), 2.22 (d, J=14.1 Hz, 1H), 2.18-2.10 (m, 1H), 2.03-1.88 (m, 5H), 1.79 (d, J=12.1 Hz, 2H), 1.54 (dd, J=24.9, 13.3 Hz, 1H), 1.30-1.20 (m, 2H).

Cpd. No. 34: (3'R,4'S,5'R)-6"-chloro-4'-(3-chloro-2-fluorophenyl)-N-(4-((2-(3-(2-(2,6-dioxopiperidin-3-yl)-1,3-dioxoisoindolin-4-yl)propoxy)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 923.24, 6.03 min; calcd: 923.27; >98% purity. $^1$H NMR (400 MHz, MeOD) δ 7.83-7.75 (m, 2H), 7.75-7.69 (m, 1H), 7.69-7.49 (m, 6H), 7.36 (t, J=7.5 Hz, 1H), 7.18 (t, J=8.0 Hz, 1H), 7.11 (dd, J=8.2, 1.9 Hz, 1H), 6.79 (d, J=1.9 Hz, 1H), 5.37 (d, J=10.9 Hz, 1H), 5.07 (ddd, J=12.8, 5.5, 1.4 Hz, 1H), 4.98 (d, J=11.0 Hz, 1H), 3.64-3.52 (m, 4H), 3.50 (t, J=6.1 Hz, 2H), 3.23-3.09 (m, 2H), 2.94 (d, J=8.6 Hz, 1H), 2.83 (ddd, J=17.5, 14.0, 5.2 Hz, 1H), 2.77-2.57 (m, 2H), 2.21 (d, J=13.4 Hz, 1H), 2.11-1.90 (m, 6H), 1.78 (d, J=11.9 Hz, 2H), 1.60-1.46 (m, 1H), 1.30-1.17 (m, 2H).

Cpd. No. 35: (3'R,4'S,5'R)-6"-chloro-4'-(3-chloro-2-fluorophenyl)-N-(4-((2-(2-(3-(2-(2,6-dioxopiperidin-3-yl)-1-oxoisoindolin-4-yl)propoxy)ethoxy)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 953.29, 5.01 min; calcd: 953.32; >98% purity. $^1$H NMR (400 MHz, MeOD) δ 7.78-7.66 (m, 3H), 7.64-7.56 (m, 1H), 7.56-7.50 (m, 2H), 7.50-7.44 (m, 1H), 7.42-7.30 (m, 3H), 7.17 (t, J=8.1 Hz, 1H), 7.11 (ddd, J=8.2, 1.9, 0.8 Hz, 1H), 6.79 (d, J=1.5 Hz, 1H), 5.29 (d, J=10.8 Hz, 1H), 5.15 (ddd, J=15.7, 13.3, 5.2 Hz, 1H), 4.95 (dd, J=10.8, 1.3 Hz, 1H), 4.49-4.27 (m, 2H), 3.72-3.61 (m, 4H), 3.61-3.51 (m, 4H), 3.50-3.41 (m, 2H), 2.96-2.73 (m, 3H), 2.67 (dt, J=10.1, 7.9 Hz, 2H), 2.48 (ttd, J=13.4, 8.7, 4.5 Hz, 1H), 2.25-2.10 (m, 2H), 2.07-1.69 (m, 7H), 1.56 (dt, J=23.0, 11.5 Hz, 1H), 1.31-1.14 (m, 2H).

Cpd. No. 36: (3'R,4'S,5'R)-6"-chloro-4'-(3-chloro-2-fluorophenyl)-N-(4-((2-(2-(3-(2-(2,6-dioxopiperidin-3-yl)-1,3-dioxoisoindolin-4-yl)propoxy)ethoxy)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 967.24, 6.00 min; calcd: 967.30; >98% purity. $^1H$ NMR (400 MHz, MeOD) δ 7.81-7.74 (m, 2H), 7.74-7.68 (m, 1H), 7.68-7.58 (m, 2H), 7.58-7.47 (m, 4H), 7.39-7.31 (m, 1H), 7.18 (t, J=8.1 Hz, 1H), 7.11 (ddd, J=8.2, 1.9, 0.6 Hz, 1H), 6.79 (d, J=1.9 Hz, 1H), 5.28 (d, J=10.7 Hz, 1H), 5.10 (dd, J=12.4, 5.5 Hz, 1H), 4.94 (dd, J=10.8, 2.6 Hz, 1H), 3.69-3.61 (m, 4H), 3.61-3.53 (m, 4H), 3.50 (t, J=6.2 Hz, 2H), 3.15-3.03 (m, 2H), 2.92-2.62 (m, 4H), 2.23-2.05 (m, 2H), 2.01-1.82 (m, 5H), 1.77 (d, J=10.8 Hz, 2H), 1.55 (dd, J=27.1, 13.4 Hz, 1H), 1.22 (td, J=13.7, 3.8 Hz, 2H).

Cpd. No. 37: (3'R,4'S,5'R)-6"-chloro-4'-(3-chloro-2-fluorophenyl)-N-(4-((2-(2-(2-(3-(2-(2,6-dioxopiperidin-3-yl)-1-oxoisoindolin-4-yl)propoxy)ethoxy)ethoxy)ethyl) carbamoyl)phenyl)-2"-oxodispiro[cyclohexane-1,2'-pyrrolidine-3',3"-indoline]-5'-carboxamide; LC-MS(ESI) m/z $(M+H)^+$: 997.32, 5.02 min; calcd: 997.35; >98% purity. $^1H$ NMR (400 MHz, MeOD) δ 7.80-7.74 (m, 2H), 7.71 (t, J=7.2 Hz, 1H), 7.63-7.54 (m, 3H), 7.54-7.48 (m, 1H), 7.47-7.29 (m, 3H), 7.18 (t, J=8.1 Hz, 1H), 7.11 (ddd, J=8.3, 1.9, 0.7 Hz, 1H), 6.79 (d, J=1.9 Hz, 1H), 5.34 (d, J=10.9 Hz, 1H), 5.16 (ddd, J=13.4, 9.3, 5.2 Hz, 1H), 4.96 (dd, J=10.9, 3.8 Hz, 1H), 4.43 (t, J=4.9 Hz, 2H), 3.67-3.58 (m, 8H), 3.58-3.47 (m, 4H), 3.47-3.37 (m, 2H), 2.98-2.82 (m, 2H), 2.82-2.63 (m, 3H), 2.50 (qdd, J=13.4, 8.8, 4.7 Hz, 1H), 2.27-2.10 (m, 2H), 2.03-1.81 (m, 5H), 1.77 (d, J=11.9 Hz, 2H), 1.54 (dd, J=26.4, 13.3 Hz, 1H), 1.34-1.12 (m, 2H).

Cpd. No. 38: (3'R,4'S,5'R)-6"-chloro-4'-(3-chloro-2-fluorophenyl)-N-(4-((2-(2-(2-(3-(2-(2,6-dioxopiperidin-3-yl)-1,3-dioxoisoindolin-4-yl)propoxy)ethoxy) ethoxy)ethyl) carbamoyl)phenyl)-2"-oxodispiro[cyclohexane-1,2'-pyrrolidine-3',3"-indoline]-5'-carboxamide; LC-MS(ESI) m/z $(M+H)^+$:1011.31, 5.98 min; calcd: 1011.33; >98% purity. $^1H$ NMR (400 MHz, MeOD) δ 7.77 (d, J=8.1 Hz, 2H), 7.74-7.64 (m, 3H), 7.64-7.56 (m, 3H), 7.53 (dd, J=8.2, 2.4 Hz, 1H), 7.36 (t, J=7.2 Hz, 1H), 7.19 (t, J=8.1 Hz, 1H), 7.14-7.10 (m, 1H), 6.80 (d, J=1.8 Hz, 1H), 5.37 (dd, J=11.0, 1.6 Hz, 1H), 5.11 (dd, J=12.9, 5.0 Hz, 1H), 4.97 (d, J=10.9 Hz, 1H), 3.68-3.57 (m, 8H), 3.57-3.49 (m, 4H), 3.44 (t, J=6.3 Hz, 2H), 3.17-3.06 (m, 2H), 2.98-2.91 (m, 1H), 2.89-2.79 (m, 1H), 2.79-2.65 (m, 2H), 2.22 (d, J=15.2 Hz, 1H), 2.17-2.09 (m, 1H), 2.02-1.84 (m, 5H), 1.84-1.74 (m, 2H), 1.52 (dd, J=27.2, 13.3 Hz, 1H), 1.30-1.19 (m, 2H).

Cpd. No. 39: (3'R,4'S,5'R)-6"-chloro-4'-(3-chloro-2-fluorophenyl)-N-(4-((3-(4-(((2-(2,6-dioxopiperidin-3-yl)-1-oxoisoindolin-4-yl)amino)methyl)-1H-imidazol-1-yl)propyl)carbamoyl)phenyl)-2"-oxodispiro[cyclohexane-1,2'-pyrrolidine-3',3"-indoline]-5'-carboxamide LC-MS(ESI) m/z $(M+H)^+$:960.28, 4.43 min; calcd: 960.32; >98% purity. $^1H$ NMR (400 MHz, MeOD) δ 8.90 (s, 1H), 7.86-7.75 (m, 2H), 7.72 (t, J=7.2 Hz, 1H), 7.67-7.56 (m, 3H), 7.52 (dd, J=8.2, 2.4 Hz, 1H), 7.39-7.32 (m, 1H), 7.29 (t, J=7.8 Hz, 1H), 7.21-7.12 (m, 2H), 7.11 (dd, J=8.2, 1.9 Hz, 1H), 6.89-6.72 (m, 2H), 5.35 (d, J=10.8 Hz, 1H), 5.15 (dt, J=9.2, 4.9 Hz, 1H), 4.96 (dd, J=10.9, 1.7 Hz, 1H), 4.53 (s, 2H), 4.41-4.29 (m, 2H), 4.25 (t, J=6.7 Hz, 2H), 3.39 (t, J=6.1 Hz, 2H), 2.97-2.71 (m, 3H), 2.46 (qd, J=13.2, 4.7 Hz, 1H), 2.25-2.09 (m, 4H), 2.03-1.86 (m, 3H), 1.77 (d, J=11.7 Hz, 2H), 1.66-1.47 (m, 1H), 1.27-1.12 (m, 2H).

Cpd. No. 44: (3'R,4'S,5'R)-6"-chloro-4'-(3-chloro-2-fluorophenyl)-N-(4-((4-(2-((2-(2,6-dioxopiperidin-3-yl)-1,3-dioxoisoindolin-4-yl)oxy)acetamido)butyl)carbamoyl)bicyclo[2.2.2]octan-1-yl)-1'-ethyl-2"-oxodispiro[cyclohexane-1,2'-pyrrolidine-3',3"-indoline]-5'-carboxamide; LC-MS(ESI) m/z $(M+H)^+$: 1026.36, 5.02 min; calcd: 1026.37; >98% purity.

Cpd. No. 45: (3'R,4'S,5'R)-6"-chloro-4'-(3-chloro-2-fluorophenyl)-N-(4-((2-(2-(2-(2-((2-(2,6-dioxopiperidin-3-yl)-1,3-dioxoisoindolin-4-yl)oxy)acetamido)ethoxy) ethoxy) ethyl)carbamoyl)bicyclo[2.2.2]octan-1-yl)-1'-ethyl-2"-oxodispiro[cyclohexane-1,2'-pyrrolidine-3',3"-indoline]-5'-carboxamide; LC-MS(ESI) m/z $(M+H)^+$: 1086.30, 4.93 min; calcd: 1086.39; >98% purity.

Cpd. No. 46: (3'R,4'S,5'R)-6"-chloro-4'-(3-chloro-2-fluorophenyl)-N-(4-((1-((2-(2,6-dioxopiperidin-3-yl)-1,3-dioxoisoindolin-4-yl)oxy)-2-oxo-7,10,13-trioxa-3-azahexadecan-16-yl)carbamoyl)bicyclo[2.2.2]octan-1-yl)-1'-ethyl-2"-oxodispiro[cyclohexane-1,2'-pyrrolidine-3',3"-indoline]-5'-carboxamide; LC-MS(ESI) m/z $(M+H)^+$: 1158.43, 5.16 min; calcd: 1158.45; >98% purity.

Cpd. No. 47: (3'R,4'S,5'R)-6"-chloro-4'-(3-chloro-2-fluorophenyl)-1'-ethyl-N-(4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamoyl)bicyclo[2.2.2]octan-1-yl)-2"-oxodispiro[cyclohexane-1,2'-pyrrolidine-3',3"-indoline]-5'-carboxamide; LC-MS(ESI) m/z $(M+2H)^2$+: 623.13, 5.51 min; calcd: 622.27; >98% purity.

Cpd. No. 48: (3'R,4'S,5'R)-6"-chloro-4'-(3-chloro-2-fluorophenyl)-1'-ethyl-N-(4-(((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)carbamoyl)bicyclo[2.2.2]octan-1-yl)-2"-oxodispiro[cyclohexane-1,2'-pyrrolidine-3',3"-indoline]-5'-carboxamide; LC-MS(ESI) m/z $(M+2H)^2$+: 644.72, 5.49 min; calcd: 644.28; >98% purity.

Cpd. No. 49: (3'R,4'S,5'R)-6"-chloro-4'-(3-chloro-2-fluorophenyl)-N-(4-((2-(2-(2-(2-((2-(2,6-dioxopiperidin-3-yl)-1-oxoisoindolin-4-yl)amino)ethoxy)ethoxy) ethoxy)ethyl) carbamoyl)bicyclo[2.2.2]octan-1-yl)-1'-ethyl-2"-oxodispiro[cyclohexane-1,2'-pyrrolidine-3',3"-indoline]-5'-carboxamide; LC-MS(ESI) m/z $(M+H)^+$: 1058.40, 4.71 min; calcd: 1058.44; >98% purity.

Cpd. No. 50: (3'R,4'S,5'R)-6"-chloro-4'-(3-chloro-2-fluorophenyl)-N-(4-((5-(2-(2,6-dioxopiperidin-3-yl)-1-oxoisoindolin-4-yl)pentyl)carbamoyl)bicyclo[2.2.2]octan-1-yl)-1'-ethyl-2"-oxodispiro[cyclohexane-1,2'-pyrrolidine-3',3"-indoline]-5'-carboxamide. LC-MS(ESI) m/z $(M+H)^+$: 953.35, 5.23 min; calcd: 953.39; >98% purity.

Cpd. No. 51: (3'R,4'S,5'R)-6"-chloro-4'-(3-chloro-2-fluorophenyl)-N-(4-((3-(4-(((2-(2,6-dioxopiperidin-3-yl)-1-oxoisoindolin-4-yl)amino)methyl)-1H-imidazol-1-yl)propyl)carbamoyl)bicyclo[2.2.2]octan-1-yl)-1'-ethyl-2"-oxodispiro[cyclohexane-1,2'-pyrrolidine-3',3"-indoline]-5'-carboxamide; LC-MS(ESI) m/z $(M+H)^+$: 1020.41, 3.65 min; calcd: 1020.41; >98% purity.

Cpd. No. 52: (3'R,4'S,5'R)-6"-chloro-4'-(3-chloro-2-fluorophenyl)-N-(4-((2-(2-(2-((2-(2,6-dioxopiperidin-3-yl)-1,3-dioxoisoindolin-4-yl)amino)ethoxy)ethoxy) ethyl)carbamoyl)phenyl)-4,4-dimethyl-2"-oxodispiro[cyclohexane-1,2'-pyrrolidine-3',3"-indoline]-5'-carboxamide; ESI-MS m/z 997.42 $(M+H)^+$.

Cpd. No. 53: (3'R,4'S,5'R)-6"-chloro-4'-(3-chloro-2-fluorophenyl)-N-(4-((3-(2-(2-(3-((2-(2,6-dioxopiperidin-3-yl)-

1,3-dioxoisoindolin-4-yl)amino)propoxy)ethoxy)ethoxy) propyl)carbamoyl)phenyl)-4,4-dimethyl-2"-oxodispiro[cyclohexane-1,2'-pyrrolidine-3',3"-indoline]-5'-carboxamide; ESI-MS m/z 1070.00 $(M+H)^+$.

Cpd. No. 56: (2'S,3R,4'S,5'R)-6-chloro-4'-(3-chloro-2-fluorophenyl)-N-((1R,4R)-4-((5-(2-(2,6-dioxopiperidin-3-yl)-1-oxoisoindolin-4-yl)pentyl)carbamoyl)cyclohexyl)-2'-neopentyl-2-oxospiro[indoline-3,3'-pyrrolidine]-5'-carboxamide; ESI-MS m/z 902.17 $(M+H)^+$.

Cpd. No. 57: (2R,3S,4R,5S)-3-(3-chloro-2-fluorophenyl)-4-(4-chloro-2-fluorophenyl)-4-cyano-N-(4-((2-(2-(2-((2-(2,6-dioxopiperidin-3-yl)-1,3-dioxoisoindolin-4-yl) amino)ethoxy) ethoxy)ethyl)carbamoyl)-2-methoxyphenyl)-5-neopentylpyrrolidine-2-carboxamide; ESI-MS m/z 1002.75 $(M+H)^+$ and 1024.75 $(M+Na)^+$.

Cpd. No. 58: (2R,3S,4R,5S)-3-(3-chloro-2-fluorophenyl)-4-(4-chloro-2-fluorophenyl)-4-cyano-N-(4-((3-(2-(2-(3-((2-(2,6-dioxopiperidin-3-yl)-1,3-dioxoisoindolin-4-yl) amino)propoxy) ethoxy)ethoxy)propyl)carbamoyl)-2-methoxyphenyl)-5-neopentylpyrrolidine-2-carboxamide; ESI-MS m/z 1075.42 $(M+H)^+$ and 1097.42 $(M+Na)^+$.

Cpd. No. 59: (2R,3S,4R,5S)-3-(3-chloro-2-fluorophenyl)-4-(4-chloro-2-fluorophenyl)-4-cyano-N-(4-((5-(2-(2,6-dioxopiperidin-3-yl)-1-oxoisoindolin-4-yl)pentyl)carbamoyl)-2-methoxyphenyl)-5-neopentylpyrrolidine-2-carboxamide; ESI-MS m/z 928.83 $(M+H)^+$ and 950.17 $(M+Na)^+$.

Cpd. No. 60: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)-N-(2-(2-(2-((2-(2,6-dioxopiperidin-3-yl)-1,3-dioxoisoindolin-4-yl)amino)ethoxy) ethoxy)ethyl)acetamide; ESI-MS m/z 956.42 $(M+H)^+$ and 978.17 $(M+Na)^+$.

Cpd. No. 61: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)-N-(3-(2-(2-(3-((2-(2,6-dioxopiperidin-3-yl)-1,3-dioxoisoindolin-4-yl)amino) propoxy)ethoxy)ethoxy)propyl)acetamide; ESI-MS m/z 1028.67 $(M+H)^+$ and 1049.75 $(M+Na)^+$.

Cpd. No. 62: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)-N-(2-(2-(2-(2-((2-(2,6-dioxopiperidin-3-yl)-1-oxoisoindolin-4-yl)amino)ethoxy) ethoxy)ethoxy)ethyl)acetamide; LC-MS(ESI) m/z $(M+H)^+$: 984.34, 5.49 min; calcd: 984.38; >98% purity.

Cpd. No. 63: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)-N-(5-(2-(2,6-dioxopiperidin-3-yl)-1-oxoisoindolin-4-yl)pentyl)acetamide; LC-MS (ESI) m/z $(M+H)^+$: 879.21, 5.96 min; calcd: 879.33; >98% purity.

Cpd. No. 64: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)-N-(3-(4-(((2-(2,6-dioxopiperidin-3-yl)-1-oxoisoindolin-4-yl)amino)methyl)-1H-imidazol-1-yl)propyl)acetamide; LC-MS(ESI) m/z $(M+H)^+$: 946.31, 3.44 min; calcd: 946.35; >98% purity.

Cpd. No. 65: 4-(2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetamido)-N-(2-(2-(2-(2-((2-(2,6-dioxopiperidin-3-yl)-1-oxoisoindolin-4-yl) amino)ethoxy)ethoxy)ethoxy)ethyl)benzamide; LC-MS (ESI) m/z $(M+H)^+$: 1103.31, 5.09 min; calcd: 1103.41; >98% purity.

Cpd. No. 66: 4-(2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetamido)-N-(5-(2-(2,6-dioxopiperidin-3-yl)-1-oxoisoindolin-4-yl)pentyl) benzamide; LC-MS(ESI) m/z $(M+H)^+$: 998.23, 5.54 min; calcd: 998.37; >98% purity.

Cpd. No. 67: 4-(2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetamido)-N-(3-(4-(((2-(2,6-dioxopiperidin-3-yl)-1-oxoisoindolin-4-yl)amino) methyl)-1H-imidazol-1-yl)propyl)benzamide; LC-MS(ESI) m/z $(M+H)^+$: 1065.32, 3.83 min; calcd: 1065.39; >98% purity.

Cpd. No. 146: (3'R,4'S,5'R)-6"-chloro-4'-(3-chloro-2-fluorophenyl)-N-(4-((3-(2-(2,6-dioxopiperidin-3-yl)-1-oxoisoindolin-4-yl)prop-2-yn-1-yl)carbamoyl)phenyl)-2"-oxodispiro[cyclohexane-1,2'-pyrrolidine-3',3"-indoline]-5'-carboxamide; LC-MS(ESI) m/z $(M+H)^+$: 861.23, 5.78 min; calcd: 861.24; >98% purity.

Cpd. No. 147: (3'R,4'S,5'R)-6"-chloro-4'-(3-chloro-2-fluorophenyl)-N-(4-((5-(2-(2,6-dioxopiperidin-3-yl)-1-oxoisoindolin-4-yl)pent-4-yn-1-yl)carbamoyl)phenyl)-2"-oxodispiro[cyclohexane-1,2'-pyrrolidine-3',3"-indoline]-5'-carboxamide; LC-MS(ESI) m/z $(M+2H)^2$+: 445.28, 5.92 min; calcd: 445.14; >98% purity.

Cpd. No. 148: (3'R,4'S,5'R)-6"-chloro-4'-(3-chloro-2-fluorophenyl)-N-(4-((2-(2,6-dioxopiperidin-3-yl)-1-oxoisoindolin-4-yl)carbamoyl)phenyl)-2"-oxodispiro[cyclohexane-1,2'-pyrrolidine-3',3"-indoline]-5'-carboxamide; LC-MS(ESI) m/z $(M+H)^+$: 823.09, 5.50 min; calcd: 823.22; >98% purity.

Cpd. No. 149: (3'R,4'S,5'R)-6"-chloro-4'-(3-chloro-2-fluorophenyl)-N-(4-((3-(2-(2,6-dioxopiperidin-3-yl)-1-oxoisoindolin-4-yl)propyl)carbamoyl)phenyl)-2"-oxodispiro[cyclohexane-1,2'-pyrrolidine-3',3"-indoline]-5'-carboxamide; LC-MS(ESI) m/z $(M+H)^+$: 865.27, 5.19 min; calcd: 865.30; >98% purity.

Cpd. No. 150: (3'R,4'S,5'R)-6"-chloro-4'-(3-chloro-2-fluorophenyl)-N-(4-((4-(2-(2,6-dioxopiperidin-3-yl)-1-oxoisoindolin-4-yl)but-3-yn-1-yl)carbamoyl)phenyl)-2"-oxodispiro[cyclohexane-1,2'-pyrrolidine-3',3"-indoline]-5'-carboxamide; LC-MS(ESI) m/z $(M+H)^+$: 875.25, 5.38 min; calcd: 875.29; >98% purity.

Cpd. No. 151: (3'R,4'S,5'R)-6"-chloro-4'-(3-chloro-2-fluorophenyl)-N-(4-((4-(2-(2,6-dioxopiperidin-3-yl)-1-oxoisoindolin-4-yl)butyl)carbamoyl)phenyl)-2"-oxodispiro [cyclohexane-1,2'-pyrrolidine-3',3"-indoline]-5'-carboxamide; LC-MS(ESI) m/z $(M+H)^+$: 879.28, 5.42 min; calcd: 879.36; >98% purity.

Cpd. No. 152: (3'R,4'S,5'R)-6"-chloro-4'-(3-chloro-2-fluorophenyl)-N-(4-((4-((2-(2,6-dioxopiperidin-3-yl)-1-oxoisoindolin-4-yl)amino)butyl)carbamoyl)phenyl)-2"-oxodispiro[cyclohexane-1,2'-pyrrolidine-3',3"-indoline]-5'-carboxamide LC-MS(ESI) m/z $(M+2H)^2$+: 894.29, 5.43 min; calcd: 894.30; >98% purity.

Cpd. No. 153: (3'R,4'S,5'R)-6"-chloro-4'-(3-chloro-2-fluorophenyl)-N-(4-(4-((2-(2,6-dioxopiperidin-3-yl)-1-oxoisoindolin-4-yl)amino)piperidine-1-carbonyl)phenyl)-2"-oxodispiro[cyclohexane-1,2'-pyrrolidine-3',3"-indoline]-5'-carboxamide; LC-MS(ESI) m/z $(M+H)^+$: 906.43, 5.26 min; calcd: 906.29; >98% purity.

Cpd. No. 154: (3'R,4'S,5'R)-6"-chloro-4'-(3-chloro-2-fluorophenyl)-N-(4-(3-((2-(2,6-dioxopiperidin-3-yl)-1-oxoisoindolin-4-yl)amino)azetidine-1-carbonyl)phenyl)-2"-oxodispiro[cyclohexane-1,2'-pyrrolidine-3',3"-indoline]-5'-carboxamide; LC-MS(ESI) m/z $(M+H)^+$: 878.38, 5.08 min; calcd: 878.26; >98% purity.

Cpd. No. 155: (3'R,4'S,5'R)-6"-chloro-4'-(3-chloro-2-fluorophenyl)-N-(4-(4-(((2-(2,6-dioxopiperidin-3-yl)-1-oxoisoindolin-4-yl)amino)methyl)piperidine-1-carbonyl)

phenyl)-2"-oxodispiro[cyclohexane-1,2'-pyrrolidine-3',3"-indoline]-5'-carboxamide; LC-MS(ESI) m/z $(M+H)^+$: 920.44, 5.41 min; calcd 920.31; >98% purity.

Cpd. No. 156: (3'R,4'S,5'R)-6"-chloro-4'-(3-chloro-2-fluorophenyl)-N-(4-(3-(((2-(2,6-dioxopiperidin-3-yl)-1-oxoisoindolin-4-yl)amino)methyl)azetidine-1-carbonyl)phenyl)-2"-oxodispiro[cyclohexane-1,2'-pyrrolidine-3',3"-indoline]-5'-carboxamide; LC-MS(ESI) m/z $(M+H)^+$: 892.40, 5.127 min; calcd: 892.28; >98% purity.

Cpd. No. 157: (3'R,4'S,5'R)-6"-chloro-4'-(3-chloro-2-fluorophenyl)-N-(4-((2-(4-((2-(2,6-dioxopiperidin-3-yl)-1-oxoisoindolin-4-yl)amino)piperidin-1-yl)ethyl)carbamoyl)phenyl)-2"-oxodispiro[cyclohexane-1,2'-pyrrolidine-3',3"-indoline]-5'-carboxamide; LC-MS(ESI) m/z $(M+2H)^2$+: 475.46, 4.29 min; calcd: 475.17; >98% purity.

Cpd. No. 158: (3'R,4'S,5'R)-6"-chloro-4'-(3-chloro-2-fluorophenyl)-N-(4-((2-(3-((2-(2,6-dioxopiperidin-3-yl)-1-oxoisoindolin-4-yl)amino)azetidin-1-yl)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 921.41, 4.30 min; calcd: 921.31; >98% purity.

Cpd. No. 159: (3'R,4'S,5'R)-6"-chloro-4'-(3-chloro-2-fluorophenyl)-N-(4-((2-(4-(((2-(2,6-dioxopiperidin-3-yl)-1-oxoisoindolin-4-yl)amino)methyl)piperidin-1-yl)ethyl)carbamoyl)phenyl)-2"-oxodispiro[cyclohexane-1,2'-pyrrolidine-3',3"-indoline]-5'-carboxamide; LC-MS(ESI) m/z $(M+2H)^2$+: 482.47, 4.44 min; calcd: 482.18; >98% purity.

Cpd. No. 160: (3'R,4'S,5'R)-6"-chloro-4'-(3-chloro-2-fluorophenyl)-N-(4-((2-(3-(((2-(2,6-dioxopiperidin-3-yl)-1-oxoisoindolin-4-yl)amino)methyl)azetidin-1-yl)ethyl)carbamoyl)phenyl)-2"-oxodispiro[cyclohexane-1,2'-pyrrolidine-3',3"-indoline]-5'-carboxamide; LC-MS(ESI) m/z $(M+2H)^2$+: 468.38, 4.28 min; calcd: 468.17; >98% purity.

Cpd. No. 161: (2R,3S,4R)-3-(3-chloro-2-fluorophenyl)-4-(4-chloro-2-fluorophenyl)-4-cyano-N-(4-((5-(2-(2,6-dioxopiperidin-3-yl)-1-oxoisoindolin-4-yl)pentyl)carbamoyl)-2-methoxyphenyl)-8,8-dimethyl-1-azaspiro[4.5]decane-2-carboxamide; ESI-MS m/z 953.50 $(M+H)^+$.

Cpd. No. 162: (3'R,4'S,5'R)-6"-chloro-4'-(3-chloro-2-fluorophenyl)-N-(4-((5-(2-(2,6-dioxopiperidin-3-yl)-1-oxoisoindolin-4-yl)pentyl)carbamoyl)phenyl)-4,4-dimethyl-2"-oxodispiro[cyclohexane-1,2'-pyrrolidine-3',3"-indoline]-5'-carboxamide; ESI-MS m/z 921.42 $(M+H)^+$.

Cpd. No. 163: (3'R,4'R,5'R)-6"-chloro-N-(4-((5-(2-(2,6-dioxopiperidin-3-yl)-1-oxoisoindolin-4-yl)pentyl)carbamoyl)phenyl)-2"-oxo-4'-phenyldispiro[cyclohexane-1,2'-pyrrolidine-3',3"-indoline]-5'-carboxamide; ESI-MS m/z 841.33 $(M+H)^+$.

Cpd. No. 164: (3'R,4'R,5'R)—N-(4-((5-(2-(2,6-dioxopiperidin-3-yl)-1-oxoisoindolin-4-yl)pentyl)carbamoyl)phenyl)-2"-oxo-4'-phenyldispiro[cyclohexane-1,2'-pyrrolidine-3',3"-indoline]-5'-carboxamide; ESI-MS m/z 808.00 $(M+H)^+$.

Cpd. No. 165: (3'R,4'R,5'R)-6"-chloro-N-(4-((5-(2-(2,6-dioxopiperidin-3-yl)-1-oxoisoindolin-4-yl)pentyl)carbamoyl)phenyl)-2"-oxo-4'-phenyldispiro[cyclobutane-1,2'-pyrrolidine-3',3"-indoline]-5'-carboxamide; ESI-MS m/z 813.20 $(M+H)^+$.

Cpd. No. 166: (3'R,4'R,5'R)—N-(4-((5-(2-(2,6-dioxopiperidin-3-yl)-1-oxoisoindolin-4-yl)pentyl)carbamoyl)phenyl)-2"-oxo-4'-phenyldispiro[cyclobutane-1,2'-pyrrolidine-3',3"-indoline]-5'-carboxamide; ESI-MS m/z 779.58 $(M+H)^+$.

Cpd. No. 171: (2R,3S,4R,5S)-3-(3-chloro-2-fluorophenyl)-4-(4-chloro-2-fluorophenyl)-4-cyano-N-(4-((5-(2-(2,6-dioxopiperidin-3-yl)-1-oxoisoindolin-4-yl)pent-4-yn-1-yl)carbamoyl)-2-methoxyphenyl)-5-neopentylpyrrolidine-2-carboxamide; ESI-MS m/z 923.36 $(M+H)^+$.

Cpd. No. 173: (3'R,4'S,5'R)-6"-chloro-4'-(3-chloro-2-fluorophenyl)-N-((1R,4R)-4-((5-(2-(2,6-dioxopiperidin-3-yl)-1-oxoisoindolin-4-yl)pent-4-yn-1-yl)carbamoyl)cyclohexyl)-2"-oxodispiro[cyclohexane-1,2'-pyrrolidine-3',3"-indoline]-5'-carboxamide; ESI-MS m/z 895.40 $(M+H)^+$.

Cpd. No. 168: (3'R,4'S,5'R)-6"-chloro-4'-(3-chloro-2-fluorophenyl)-N-(6-((5-(2-(2,6-dioxopiperidin-3-yl)-1-oxoisoindolin-4-yl)pent-4-yn-1-yl)carbamoyl)pyridin-3-yl)-2"-oxodispiro[cyclohexane-1,2'-pyrrolidine-3',3"-indoline]-5'-carboxamide; ESI-MS m/z 890.45 $(M+H)^+$.

Cpd. No. 172: (3'R,4'S,5'R)-6"-chloro-4'-(3-chloro-2-fluorophenyl)-N-(3-((5-(2-(2,6-dioxopiperidin-3-yl)-1-oxoisoindolin-4-yl)pent-4-yn-1-yl)carbamoyl)phenyl)-2"-oxodispiro[cyclohexane-1,2'-pyrrolidine-3',3"-indoline]-5'-carboxamide; ESI-MS m/z 889.36 $(M+H)^+$.

Cpd. No. 170: (3'R,4'S,5'R)-6"-chloro-4'-(3-chloro-2-fluorophenyl)-N-(4-((5-(2-(2,6-dioxopiperidin-3-yl)-1-oxoisoindolin-4-yl)pent-4-yn-1-yl)carbamoyl)phenyl)-4,4-dimethyl-2"-oxodispiro[cyclohexane-1,2'-pyrrolidine-3',3"-indoline]-5'-carboxamide; ESI-MS m/z 917.28 $(M+H)^+$.

Cpd. No. 174: (3'R,4'S,5'R)-6"-chloro-4'-(3-chloro-2-fluorophenyl)-N-(4-((4-(2-(2-(2,6-dioxopiperidin-3-yl)-1-oxoisoindolin-4-yl)ethyl)cyclohexyl)carbamoyl)phenyl)-2"-oxodispiro[cyclohexane-1,2'-pyrrolidine-3',3"-indoline]-5'-carboxamide; LC-MS(ESI) m/z $(M+H)^+$: 933.41, 6.22 min; calcd: 933.33; >98% purity.

Cpd. No. 175: (3'R,4'S,5'R)-6"-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)phenyl)-2"-oxodispiro[cyclohexane-1,2'-pyrrolidine-3',3"-indoline]-5'-carboxamide; LC-MS(ESI) m/z $(M+H)^+$: 915.43, 5.82 min; calcd: 915.28; >98% purity.

Cpd. No. 176: (3'R,4'S,5'R)-6"-chloro-4'-(3-chloro-2-fluorophenyl)-N-(4-(4-(2-(2-(2,6-dioxopiperidin-3-yl)-1-oxoisoindolin-4-yl)ethyl)piperidine-1-carbonyl)phenyl)-2"-oxodispiro[cyclohexane-1,2'-pyrrolidine-3',3"-indoline]-5'-carboxamide; LC-MS(ESI) m/z $(M+H)^+$: 919.48, 5.77 min; calcd: 919.32; >98% purity.

Cpd. No. 177: 1-((3'R,4'S,5'R)-6"-chloro-4'-(3-chloro-2-fluorophenyl)-2"-oxodispiro[cyclohexane-1,2'-pyrrolidine-3',3"-indoline]-5'-carbonyl)-N-(5-(2-(2,6-dioxopiperidin-3-yl)-1-oxoisoindolin-4-yl)pent-4-yn-1-yl)piperidine-4-carboxamide; LC-MS(ESI) m/z $(M+H)^+$: 881.50, 4.38 min; calcd: 881.30; >98% purity.

Cpd. No. 178: (3'R,4'S,5'R)-6"-chloro-4'-(3-chloro-2-fluorophenyl)-N-(4-((2-(4-(2-(2,6-dioxopiperidin-3-yl)-1,3-dioxoisoindolin-4-yl)piperazin-1-yl)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$: 949.40, 4.95 min; calcd: 949.30; >98% purity.

Cpd. No. 179: (3'R,4'S,5'R)-6"-chloro-4'-(3-chloro-2-fluorophenyl)-N-(5-((5-(2-(2,6-dioxopiperidin-3-yl)-1-oxoisoindolin-4-yl)pent-4-yn-1-yl)carbamoyl)pyridin-2-yl)-2"-oxodispiro[cyclohexane-1,2'-pyrrolidine-3',3"-indoline]-5'-carboxamide; LC-MS(ESI) m/z $(M+H)^+$: 890.39, 5.78 min; calcd: 890.26; >98% purity.

Cpd. No. 188: (3'R,4'S,5'R)-6"-chloro-4'-(3-chloro-2-fluorophenyl)-N-(5-((5-(2-(2,6-dioxopiperidin-3-yl)-1-oxoisoindolin-4-yl)pent-4-yn-1-yl)carbamoyl)thiophen-2-yl)-2"-oxodispiro[cyclohexane-1,2'-pyrrolidine-3',3"-indoline]-5'-carboxamide; LC-MS(ESI) m/z $(M+H)^+$: 895.37, 4.812 min; calcd: 895.23; >95% purity.

Cpd. No. 189: 2-((3'R,4'S,5'R)-6"-chloro-4'-(3-chloro-2-fluorophenyl)-2"-oxodispiro[cyclohexane-1,2'-pyrrolidine- 3',3"-indoline]-5'-carboxamido)-N-(5-(2-(2,6-dioxopiperidin-3-yl)-1-oxoisoindolin-4-yl)pent-4-yn-1-yl)thiazole-5-carboxamide; LC-MS(ESI) m/z $(M+H)^+$:896.26, 4.639 min; calcd: 896.22; >95% purity.

Cpd. No. 190: (3'R,4'S,5'R)-6"-chloro-4'-(3-chloro-2-fluorophenyl)-N-(4-((5-(2-(2,6-dioxopiperidin-3-yl)-1-oxoisoindolin-4-yl)pent-4-yn-1-yl)carbamoyl)-3-methoxyphenyl)-2"-oxodispiro[cyclohexane-1,2'-pyrrolidine-3',3"-indoline]-5'-carboxamide; LC-MS(ESI) m/z $(M+H)^+$: 919.24, 5.193 min; calcd: 919.28; >95% purity.

Cpd. No. 191: (3'R,4'S,5'R)-6"-chloro-4'-(3-chloro-2-fluorophenyl)-N-(4-((5-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-5-oxopentyl)carbamoyl)phenyl)-2"-oxodispiro[cyclohexane-1,2'-pyrrolidine-3',3"-indoline]-5'-carboxamide; LC-MS (ESI) m/z (M+2H)2+:553.30, 5.765 min; calcd: 553.20; >95% purity.

Cpd. No. 192: (3'R,4'S,5'R)-6"-chloro-4'-(3-chloro-2-fluorophenyl)-N-(4-((2-(2-(3-(((S)-1-((2S,4R)-4-hydroxy-2-(((S)-1-(4-(4-methylthiazol-5-yl)phenyl)ethyl)carbamoyl) pyrrolidin-1-yl)-3,3-dimethyl-1-oxobutan-2-yl)amino)-3-oxopropoxy)ethoxy)ethyl)carbamoyl)phenyl)-2"-oxodispiro[cyclohexane-1,2'-pyrrolidine-3',3"-indoline]-5'-carboxamide; LC-MS(ESI) m/z $(M+H)^+$:1167.64, 5.656 min; calcd: 1167.44; >95% purity.

Cpd. No. 193: (3'R,4'S,5'R)-6"-chloro-4'-(3-chloro-2-fluorophenyl)-N-(4-(((S)-14-((2S,4R)-4-hydroxy-2-(((S)-1-(4-(4-methylthiazol-5-yl)phenyl)ethyl)carbamoyl)pyrrolidine-1-carbonyl)-15,15-dimethyl-12-oxo-3,6,9-trioxa-13-azahexadecyl)carbamoyl)phenyl)-2"-oxodispiro[cyclohexane-1,2'-pyrrolidine-3',3"-indoline]-5'-carboxamide; LC-MS(ESI) m/z $(M+2H)^2$+:605.31; calcd: 605.22; >95% purity.

Cpd. No. 194: (3'R,4'S,5'R)-6"-chloro-4'-(3-chloro-2-fluorophenyl)-N-(4-((5-(2-(2,6-dioxopiperidin-3-yl)-1-oxoisoindolin-5-yl)pent-4-yn-1-yl)carbamoyl)phenyl)-2"-oxodispiro[cyclohexane-1,2'-pyrrolidine-3',3"-indoline]-5'-carboxamide; LC-MS(ESI) m/z $(M+H)^+$:889.38, 5.552 min; calcd: 889.27; >95% purity.

Cpd. No. 195: (3'R,4'S,5'R)-6"-chloro-4'-(3-chloro-2-fluorophenyl)-N-(4-((5-(2-(2,6-dioxopiperidin-3-yl)-3-oxoisoindolin-5-yl)pent-4-yn-1-yl)carbamoyl)phenyl)-2"-oxodispiro[cyclohexane-1,2'-pyrrolidine-3',3"-indoline]-5'-carboxamide; LC-MS(ESI) m/z $(M+H)^+$:889.32, 5.587 min; calcd: 889.27; >95% purity.

Cpd. No. 196: (3'R,4'S,5'R)-6"-chloro-4'-(3-chloro-2-fluorophenyl)-N-(4-((5-(2-(2,6-dioxopiperidin-3-yl)-1-oxoisoindolin-5-yl)pentyl)carbamoyl)phenyl)-2"-oxodispiro[cyclohexane-1,2'-pyrrolidine-3',3"-indoline]-5'-carboxamide; LC-MS(ESI) m/z $(M+H)^+$:893.28, 5.693 min; calcd: 893.30; >95% purity.

Cpd. No. 197: (3'R,4'S,5'R)-6"-chloro-4'-(3-chloro-2-fluorophenyl)-N-(4-((5-(2-(2,6-dioxopiperidin-3-yl)-3-oxoisoindolin-5-yl)pentyl)carbamoyl)phenyl)-2"-oxodispiro[cyclohexane-1,2'-pyrrolidine-3',3"-indoline]-5'-carboxamide; LC-MS(ESI) m/z $(M+H)^+$:893.27, 5.740 min; calcd: 893.30; >95% purity.

Cpd. No. 198: (3'R,4'S,5'R)-6"-chloro-4'-(3-chloro-2-fluorophenyl)-N-(4-((5-(2-(2,6-dioxopiperidin-3-yl)-1-oxoisoindolin-4-yl)pent-4-yn-1-yl)carbamoyl)bicyclo[2.2.1]heptan-1-yl)-2"-oxodispiro[cyclohexane-1,2'-pyrrolidine-3',3"-indoline]-5'-carboxamide; LC-MS(ESI) m/z $(M+H)^+$:907.34, 4.768 min; calcd: 907.32; >95% purity.

Cpd. No. 199: (3'R,4'S,5'R)-6"-chloro-4'-(3-chloro-2-fluorophenyl)-N-(4-(((1R,4R)-4-((2-(2,6-dioxopiperidin-3-yl)-1-oxoisoindolin-4-yl)ethynyl)cyclohexyl)carbamoyl) phenyl)-2"-oxodispiro[cyclohexane-1,2'-pyrrolidine-3',3"-indoline]-5'-carboxamide; LC-MS(ESI) m/z $(M+H)^+$: 929.43, 5.944 min; calcd: 929.30; >95% purity.

Cpd. No. 200: (3'R,4'S,5'R)-6"-chloro-4'-(3-chloro-2-fluorophenyl)-N-(4-((5-(2-(2,6-dioxopiperidin-3-yl)-7-fluoro-1-oxoisoindolin-4-yl)pent-4-yn-1-yl)carbamoyl)phenyl)-2"-oxodispiro[cyclohexane-1,2'-pyrrolidine-3',3"-indoline]-5'-carboxamide; LC-MS(ESI) m/z $(M+H)^+$: 907.44, 5.379 min; calcd: 907.26; >95% purity.

Cpd. No. 201: (3'R,4'S,5'R)-6"-chloro-4'-(3-chloro-2-fluorophenyl)-N-(4-(((1R,4R)-4-((Z)-2-(2-(2,6-dioxopiperidin-3-yl)-1-oxoisoindolin-4-yl)vinyl)cyclohexyl)carbamoyl)phenyl)-2"-oxodispiro[cyclohexane-1,2'-pyrrolidine-3',3"-indoline]-5'-carboxamide; LC-MS(ESI) m/z $(M+H)^+$: 931.49, 5.786 min; calcd: 931.32; >95% purity.

Cpd. No. 202: (3'R,4'S,5'R)-6"-chloro-4'-(3-chloro-2-fluorophenyl)-N-(4-(((1s,4R)-4-(2-(2-(2,6-dioxopiperidin-3-yl)-1-oxoisoindolin-4-yl)ethyl)cyclohexyl)carbamoyl) phenyl)-2"-oxodispiro[cyclohexane-1,2'-pyrrolidine-3',3"-indoline]-5'-carboxamide; LC-MS(ESI) m/z $(M+H)^+$: 933.36, 5.967 min; calcd: 933.33; >95% purity.

Cpd. No. 203: (3'R,4'S,5'R)-6"-chloro-4'-(3-chloro-2-fluorophenyl)-N-(1-(6-(2-(2,6-dioxopiperidin-3-yl)-1-oxoisoindolin-4-yl)hex-5-ynoyl)piperidin-4-yl)-2"-oxodispiro[cyclohexane-1,2'-pyrrolidine-3',3"-indoline]-5'-carboxamide; LC-MS(ESI) m/z $(M+H)^+$:881.33, 4.509 min; calcd: 881.30; >95% purity.

Cpd. No. 204: (3'R,4'S,5'R)-6"-chloro-4'-(3-chloro-2-fluorophenyl)-N-(1-(5-(2-(2,6-dioxopiperidin-3-yl)-1-oxoisoindolin-4-yl)pent-4-ynoyl)piperidin-4-yl)-2"-oxodispiro[cyclohexane-1,2'-pyrrolidine-3',3"-indoline]-5'-carboxamide; LC-MS(ESI) m/z $(M+H)^+$:867.30, 4.413 min; calcd: 867.29; >95% purity.

Cpd. No. 205: (3'R,4'S,5'R)-6"-chloro-4'-(3-chloro-2-fluorophenyl)-N-((1R,4R)-4-(6-(2-(2,6-dioxopiperidin-3-yl)-1-oxoisoindolin-4-yl)hex-5-ynamido)cyclohexyl)-2"-oxodispiro[cyclohexane-1,2'-pyrrolidine-3',3"-indoline]-5'-carboxamide; LC-MS(ESI) m/z $(M+H)^+$:895.52, 4.545 min; calcd: 895.32; >95% purity.

Cpd. No. 206: (3'R,4'S,5'R)-6"-chloro-4'-(3-chloro-2-fluorophenyl)-N-((1R,4R)-4-(5-(2-(2,6-dioxopiperidin-3-yl)-1-oxoisoindolin-4-yl)pent-4-ynamido)cyclohexyl)-2"-oxodispiro[cyclohexane-1,2'-pyrrolidine-3',3"-indoline]-5'-carboxamide; LC-MS(ESI) m/z $(M+H)^+$:881.35, 4.351 min; calcd: 881.30; >95% purity.

Cpd. No. 207: (3'R,4'R,5'R)-6"-chloro-4'-(3-chlorophenyl)-N-((1R,4R)-4-((2-(2-(2-(2-((2-(2,6-dioxopiperidin-3-yl)-1-oxoisoindolin-4-yl)amino)ethoxy)ethoxy)ethoxy) ethyl)carbamoyl)cyclohexyl)-2"-oxodispiro[cyclohexane-1,2'-pyrrolidine-3',3"-indoline]-5'-carboxamide; LC-MS(ESI) m/z $(M+H)^+$:986.59, 3.954 min; calcd: 986.40; >95% purity.

Cpd. No. 208: (3'R,4'R,5'R)—N-((1R,4R)-4-((2-(2-(2-(2-((2-(2,6-dioxopiperidin-3-yl)-1-oxoisoindolin-4-yl)amino) ethoxy)ethoxy)ethoxy)ethyl)carbamoyl)cyclohexyl)-2"-oxo-4'-phenyldispiro[cyclohexane-1,2'-pyrrolidine-3',3"-indoline]-5'-carboxamide LC-MS(ESI) m/z $(M+H)^+$:918.53, 3.177 min; calcd: 918.48; >95% purity.

Cpd. No. 209: (3'R,4'R,5'R)-6"-chloro-4'-(3-chlorophenyl)-N-((1R,4R)-4-((2-(2-(2-(2-((2-(2,6-dioxopiperidin-3-yl)-1-oxoisoindolin-4-yl)amino)ethoxy)ethoxy)ethoxy) ethyl)carbamoyl)cyclohexyl)-2"-oxodispiro[cyclohexane-1,2'-pyrrolidine-3',3"-indoline]-5'-carboxamide; LC-MS(ESI) m/z $(M+H)^+$:952.58, 3.640 min; calcd: 952.44; >95% purity.

Cpd. No. 210: (3'R,4'S,5'R)-6"-chloro-4'-(3-chloro-2-fluorophenyl)-N-(4-((2-(2-((3-(2-(2,6-dioxopiperidin-3-yl)-1-oxoisoindolin-4-yl)prop-2-yn-1-yl)oxy)ethoxy)ethyl)carbamoyl)phenyl)-2"-oxodispiro[cyclohexane-1,2'- pyrrolidine-3',3"-indoline]-5'-carboxamide; LC-MS(ESI) m/z $(M+H)^+$:949.53, 5.201 min; calcd: 949.29; >95% purity.

Cpd. No. 211: (3'R,4'S,5'R)-6"-chloro-4'-(3-chloro-2-fluorophenyl)-N-(4-((2-(2-(2-((3-(2-(2,6-dioxopiperidin-3-yl)-1-oxoisoindolin-4-yl)prop-2-yn-1-yl)oxy)ethoxy)ethoxy)ethyl)carbamoyl)phenyl)-2"-oxodispiro[cyclohexane-1,2'-pyrrolidine-3',3"-indoline]-5'-carboxamide; LC-MS(ESI) m/z $(M+2H)^2$+:496.68, 5.209 min; calcd: 496.15; >95% purity.

Cpd. No. 212: (3'R,4'S,5'R)-6"-chloro-4'-(3-chloro-2-fluorophenyl)-N-(4-((4-((2-(2,6-dioxopiperidin-3-yl)-1-oxoisoindolin-4-yl)oxy)butyl)carbamoyl)phenyl)-2"-oxodispiro[cyclohexane-1,2'-pyrrolidine-3',3"-indoline]-5'-carboxamide; LC-MS(ESI) m/z $(M+H)^+$:895.26, 5.266 min; calcd: 895.28; >95% purity.

Cpd. No. 213: (3'R,4'S,5'R)-6"-chloro-4'-(3-chloro-2-fluorophenyl)-N-(4-((3-(4-((2-(2,6-dioxopiperidin-3-yl)-1-oxoisoindolin-4-yl)ethynyl)-1H-pyrazol-1-yl)propyl)carbamoyl)phenyl)-2"-oxodispiro[cyclohexane-1,2'-pyrrolidine-3',3"-indoline]-5'-carboxamide; LC-MS(ESI) m/z $(M+H)^+$:955.52, 5.437 min; calcd: 955.29; >95% purity.

Cpd. No. 214: (3'R,4'S,5'R)-6"-chloro-4'-(3-chloro-2-fluorophenyl)-N-(4-((3-(4-(2-(2-(2,6-dioxopiperidin-3-yl)-1-oxoisoindolin-4-yl)ethyl)-1H-pyrazol-1-yl)propyl)carbamoyl)phenyl)-2"-oxodispiro[cyclohexane-1,2'-pyrrolidine-3',3"-indoline]-5'-carboxamide LC-MS(ESI) m/z $(M+H)^+$:479.55, 5.231 min; calcd: 479.16; >95% purity.

Cpd. No. 215: (3'R,4'S,5'R)-6"-chloro-4'-(3-chloro-2-fluorophenyl)-N-(4-((3-(5-((2-(2,6-dioxopiperidin-3-yl)-1-oxoisoindolin-4-yl)ethynyl)-1H-imidazol-1-yl)propyl)carbamoyl)phenyl)-2"-oxodispiro[cyclohexane-1,2'-pyrrolidine-3',3"-indoline]-5'-carboxamide; LC-MS(ESI) m/z $(M+H)^+$:955.62, 4.163 min; calcd: 955.29; >95% purity.

Cpd. No. 216: (3'R,4'S,5'R)-6"-chloro-4'-(3-chloro-2-fluorophenyl)-N-(4-((3-(5-(2-(2-(2,6-dioxopiperidin-3-yl)-1-oxoisoindolin-4-yl)ethyl)-1H-imidazol-1-yl)propyl)carbamoyl)phenyl)-2"-oxodispiro[cyclohexane-1,2'-pyrrolidine-3',3"-indoline]-5'-carboxamide; LC-MS(ESI) m/z $(M+H)^+$:959.42, 4.344 min; calcd: 959.32; >95% purity.

Cpd. No. 217: (3'R,4'S,5'R)-6"-chloro-4'-(3-chloro-2-fluorophenyl)-N-(4-((3-(4-((2-(2,6-dioxopiperidin-3-yl)-1-oxoisoindolin-4-yl)amino)piperidin-1-yl)propyl)carbamoyl)phenyl)-2"-oxodispiro[cyclohexane-1,2'-pyrrolidine-3',3"-indoline]-5'-carboxamide; LC-MS(ESI) m/z $(M+H)^+$: 963.62, 3.957 min; calcd: 963.35; >95% purity.

Cpd. No. 218: (2R,3S,4R,5S)-3-(3-chloro-2-fluorophenyl)-4-(4-chloro-2-fluorophenyl)-4-cyano-N-(4-((5-(2-(2,6-dioxopiperidin-3-yl)-1-oxoisoindolin-4-yl)pent-4-yn-1-yl)carbamoyl)phenyl)-5-neopentylpyrrolidine-2-carboxamide; ESI-MS m/z 893.30 $(M+H)^+$.

Cpd. No. 219: (3'R,4'S,5'R)-6"-chloro-4'-(3-chloro-2-fluorophenyl)-N-(1-(2-((5-(2-(2,6-dioxopiperidin-3-yl)-1-oxoisoindolin-4-yl)pent-4-yn-1-yl)amino)-2-oxoethyl)piperidin-4-yl)-2"-oxodispiro[cyclohexane-1,2'-pyrrolidine-3',3"-indoline]-5'-carboxamide; ESI-MS m/z 910.35 $(M+H)^+$.

Cpd. No. 220: (3'R,4'S,5'R)-6"-chloro-4'-(3-chloro-2-fluorophenyl)-N-(3-((5-(2-(2,6-dioxopiperidin-3-yl)-1-oxoisoindolin-4-yl)pent-4-yn-1-yl)carbamoyl)bicyclo[1.1.1]pentan-1-yl)-2"-oxodispiro[cyclohexane-1,2'-pyrrolidine-3',3"-indoline]-5'-carboxamide; ESI-MS m/z 879.43 $(M+H)^+$.

Cpd. No. 221: (3'R,4'S,5'R)-6"-chloro-4'-(3-chloro-2-fluorophenyl)-N-(4-((5-(2-(2,6-dioxopiperidin-3-yl)-1-oxoisoindolin-4-yl)pent-4-yn-1-yl)amino)-4-oxobutyl)-2"-oxodispiro[cyclohexane-1,2'-pyrrolidine-3',3"-indoline]-5'-carboxamide; ESI-MS m/z 855.34 $(M+H)^+$.

Cpd. No. 222: (3'R,4'S,5'R)-6"-chloro-4'-(2-chloro-3-fluoropyridin-4-yl)-N-(4-((5-(2-(2,6-dioxopiperidin-3-yl)-1-oxoisoindolin-4-yl)pent-4-yn-1-yl)carbamoyl)phenyl)-4,4-dimethyl-2"-oxodispiro[cyclohexane-1,2'-pyrrolidine-3',3"-indoline]-5'-carboxamide; ESI-MS m/z 918.39 $(M+H)^+$.

Cpd. No. 223: (3'R,4'S,5'R)-6"-chloro-4'-(3-chloro-2-fluorophenyl)-N-(1-(7-(2-(2,6-dioxopiperidin-3-yl)-1-oxoisoindolin-4-yl)hept-6-yn-1-yl)piperidin-4-yl)-2"-oxodispiro[cyclohexane-1,2'-pyrrolidine-3',3"-indoline]-5'-carboxamide; ESI-MS m/z 881.43 $(M+H)^+$.

Cpd. No. 224: (3'R,4'S,5'R)-6"-chloro-4'-(3-chloro-2-fluorophenyl)-N-((1R,4R)-4-((2-(2-(2-(2-((2-(2,6-dioxopiperidin-3-yl)-1-oxoisoindolin-4-yl)amino)ethoxy)ethoxy)ethoxy)ethyl)carbamoyl)cyclohexyl)-2"-oxodispiro[cyclohexane-1,2'-pyrrolidine-3',3"-indoline]-5'-carboxamide; ESI-MS m/z 1004.44 $(M+H)^+$.

Cpd. No. 225: (3'R,4'S,5'R)-6"-chloro-4'-(3-chloro-2-fluorophenyl)-N-((1r,4R)-4-((2-(4-((2-(2,6-dioxopiperidin-3-yl)-1-oxoisoindolin-4-yl)amino)piperidin-1-yl)ethyl)carbamoyl)cyclohexyl)-2"-oxodispiro[cyclohexane-1,2'-pyrrolidine-3',3"-indoline]-5'-carboxamide; ESI-MS m/z 955.61 $(M+H)^+$.

Cpd. No. 226: (3'R,4'S,5'R)-6"-chloro-4'-(3-chloro-2-fluorophenyl)-N-((1R,4R)-4-((2-(4-((2-(2,6-dioxopiperidin-3-yl)-1-oxoisoindolin-4-yl)amino)piperidin-1-yl)ethyl)carbamoyl)cyclohexyl)-4,4-dimethyl-2"-oxodispiro[cyclohexane-1,2'-pyrrolidine-3',3"-indoline]-5'-carboxamide; ESI-MS m/z 983.66 $(M+H)^+$.

Cpd. No. 227: (3'R,4'S,5'R)-6"-chloro-4'-(3-chloro-2-fluorophenyl)-N-((1R,4R)-4-(((4-(2-(2,6-dioxopiperidin-3-yl)-1-oxoisoindolin-4-yl)but-3-yn-1-yl)sulfonyl)carbamoyl)cyclohexyl)-2"-oxodispiro[cyclohexane-1,2'-pyrrolidine-3',3"-indoline]-5'-carboxamide; ESI-MS m/z 945.47 $(M+H)^+$.

Cpd. No. 228: (3'R,4'S,5'R)-6"-chloro-4'-(3-chloro-2-fluorophenyl)-N-((1R,4R)-4-((3-(4-((2-(2,6-dioxopiperidin-3-yl)-1-oxoisoindolin-4-yl)amino)piperidin-1-yl)propyl)carbamoyl)cyclohexyl)-2"-oxodispiro[cyclohexane-1,2'-pyrrolidine-3',3"-indoline]-5'-carboxamide; ESI-MS m/z 969.57 $(M+H)^+$.

Cpd. No. 238: 4-((15-(4-((4S,5R)-2-(4-(tert-butyl)-2-ethoxyphenyl)-4,5-bis(4-chlorophenyl)-4,5-dimethyl-4,5-dihydro-1H-imidazole-1-carbonyl)piperazin-1-yl)-15-oxo-3,6,9,12-tetraoxapentadecyl)amino)-2-(2,6-dioxopiperidin-3-yl)isoindoline-1,3-dione; ESI-MS m/z 1112.83 $(M+H)^+$.

Cpd. No. 239: 3-(4-((2-(2-(2-(3-(4-((4S,5R)-2-(4-(tert-butyl)-2-ethoxyphenyl)-4,5-bis(4-chlorophenyl)-4,5-dimethyl-4,5-dihydro-1H-imidazole-1-carbonyl)piperazin-1-yl)-3-oxopropoxy)ethoxy)ethoxy)ethyl)amino)-1-oxoisoindolin-2-yl)piperidine-2,6-dione; ESI-MS m/z 1053.92 $(M+H)^+$.

Cpd. No. 240: (3R,4'R,5'R)-6-chloro-N-(4-((2-(2-(2-(2-((2-(2,6-dioxopiperidin-3-yl)-1-oxoisoindolin-4-yl)amino)ethoxy)ethoxy)ethoxy)ethyl)carbamoyl)phenyl)-2',2'-dimethyl-2-oxo-4'-phenylspiro[indoline-3,3'-pyrrolidine]-5'-carboxamide; ESI-MS m/z 906.31 $(M+H)^+$.

Cpd. No. 241: (3R,4'R,5'R)—N-(4-((2-(2-(2-(2-((2-(2,6-dioxopiperidin-3-yl)-1-oxoisoindolin-4-yl)amino)ethoxy)ethoxy)ethoxy)ethyl)carbamoyl)phenyl)-2',2'-dimethyl-2-oxo-4'-phenylspiro[indoline-3,3'-pyrrolidine]-5'-carboxamide; ESI-MS m/z 872.36 $(M+H)^+$.

Cpd. No. 242: (3'R,4'R,5'R)-6"-chloro-N-((1R,4R)-4-((2-(2-(2-(2-((2-(2,6-dioxopiperidin-3-yl)-1-oxoisoindolin-4-yl)amino)ethoxy)ethoxy)ethoxy)ethyl)carbamoyl)cyclohexyl)-4'-(3-fluorophenyl)-2"-oxodispiro[cyclohexane-1,2'-pyrrolidine-3',3"-indoline]-5'-carboxamide; ESI-MS m/z 970.45 $(M+H)^+$.

Cpd. No. 243: (3R,4'R,5'R)-6-chloro-N-((1R,4R)-4-((2-(2-(2-(2-((2-(2,6-dioxopiperidin-3-yl)-1-oxoisoindolin-4-yl)amino)ethoxy)ethoxy)ethoxy)ethyl)carbamoyl)cyclohexyl)-2',2'-dimethyl-2-oxo-4'-phenylspiro[indoline-3,3'-pyrrolidine]-5'-carboxamide; ESI-MS m/z 912.35 $(M+H)^+$.

Cpd. No. 244: (3R,4'R,5'R)—N-((1R,4R)-4-((2-(2-(2-(2-((2-(2,6-dioxopiperidin-3-yl)-1-oxoisoindolin-4-yl)amino)ethoxy)ethoxy)ethoxy)ethyl)carbamoyl)cyclohexyl)-2',2'-dimethyl-2-oxo-4'-phenylspiro[indoline-3,3'-pyrrolidine]-5'-carboxamide; ESI-MS m/z 878.42 $(M+H)^+$.

Example 19

Synthesis of 3-(4-((17-(4-((1S,4r)-4-(((4-((S)-1-(4-chlorophenyl)-7-isopropoxy-6-methoxy-3-oxo-3,4-dihydroisoquinolin-2(1H)-yl)phenyl)(methyl)amino)methyl) cyclohexyl)piperazin-1-yl)-13,6,9,12,15-pentaoxaheptadecyl)amino)-1-oxoisoindolin-2-yl)piperidine-2,6-dione (Cpd. No. 229)

Scheme 1

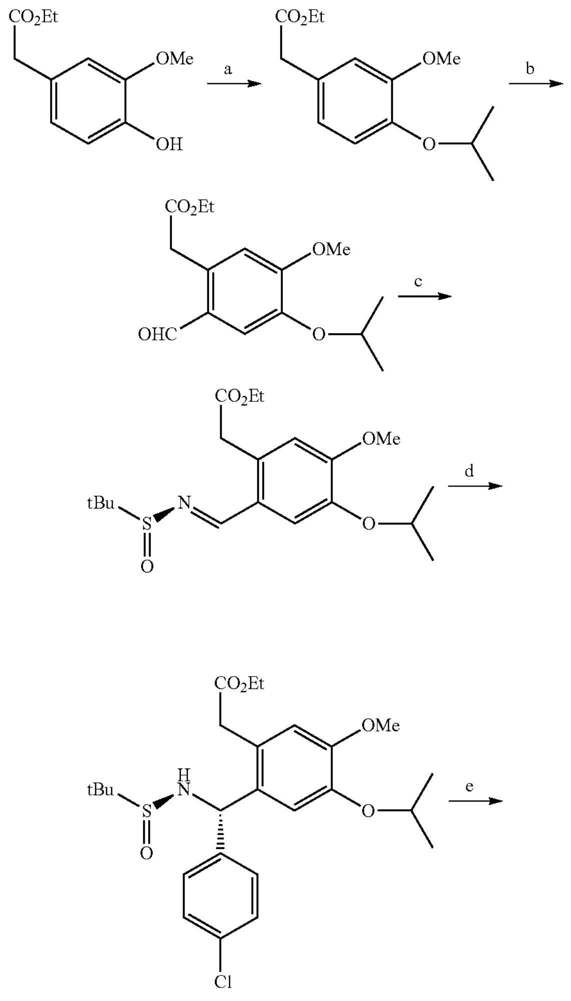

-continued

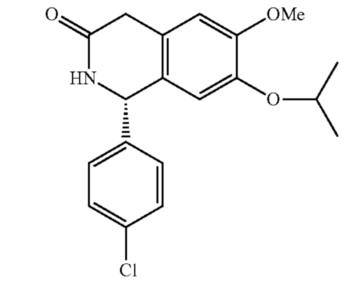

Scheme 2

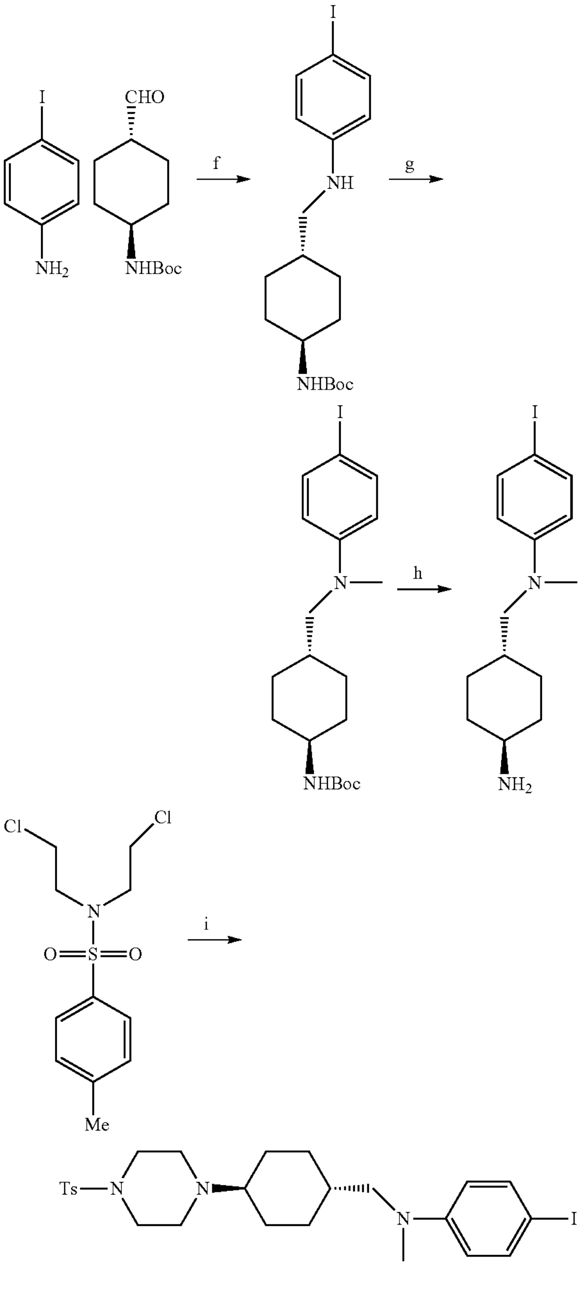

Scheme 3
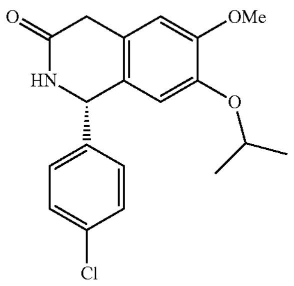
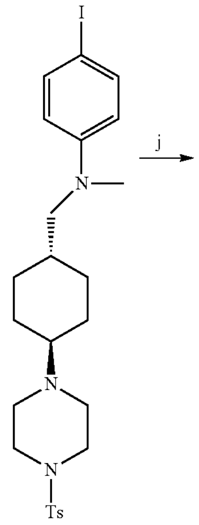
-continued
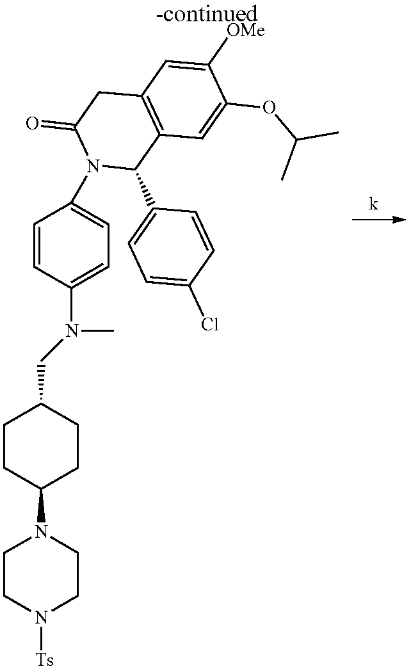
RRM-01-145
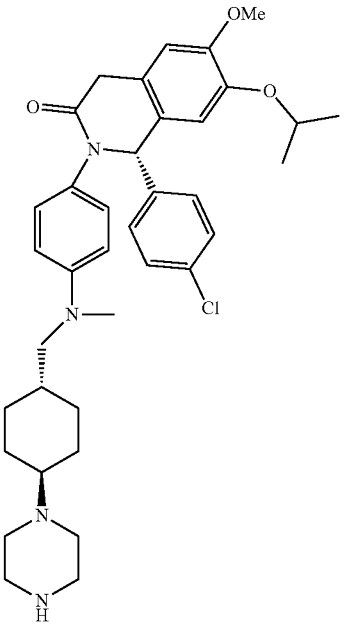
RRM-01-146
Scheme 4
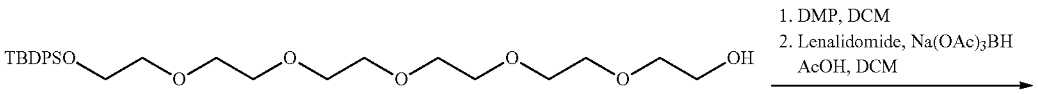

-continued

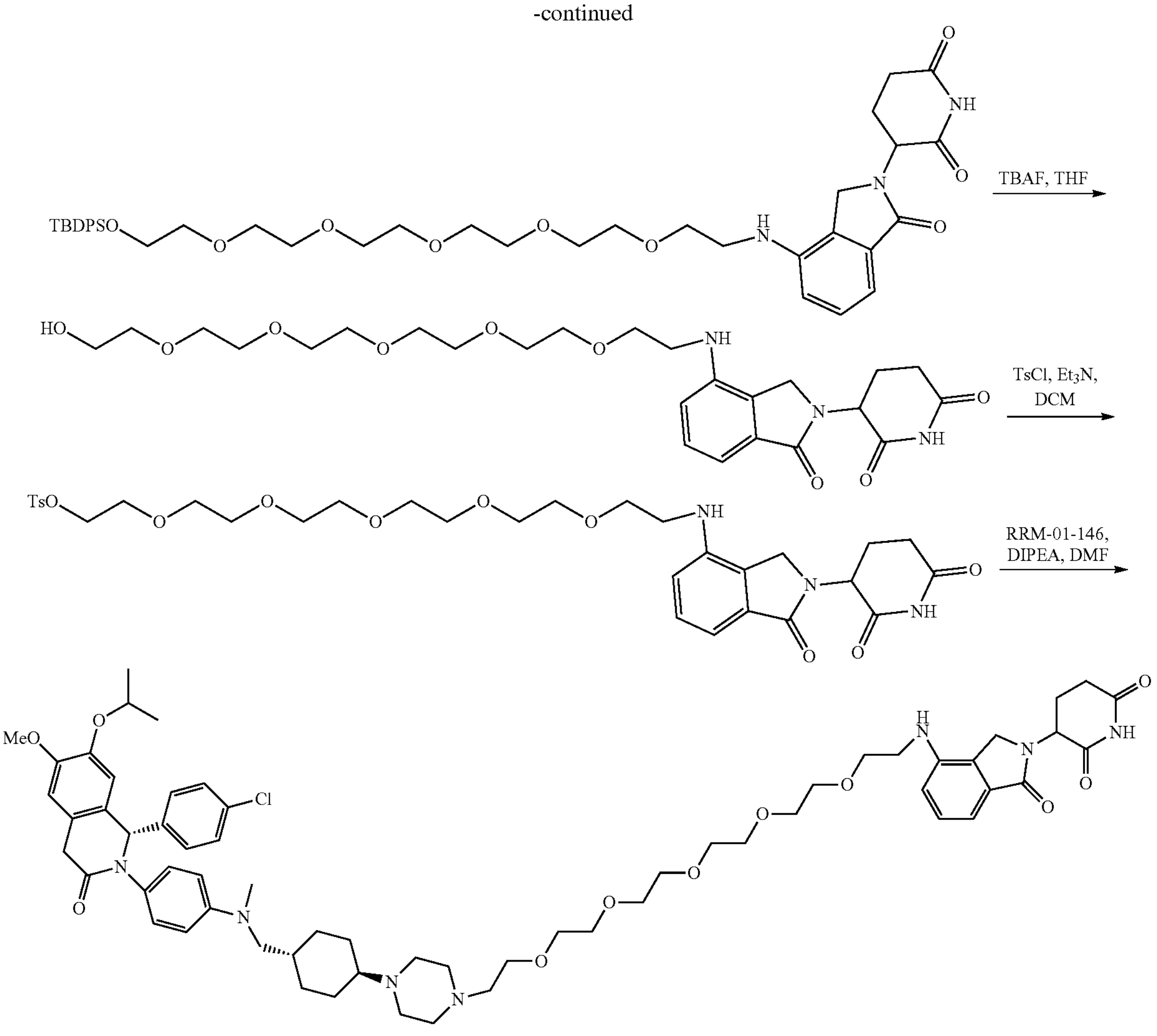

Cpd. No. 229

Reagents and conditions of Schemes 1-3: (a) 2-iodopropane, $K_2CO_3$, DMF, 60° C., 12 h, 95%; (b) $MeOCHCl_2$, $SnCl_4$, DCM, 0° C., 2 h, 84%; (c) (S)-(−)-2-methyl-2-propanesulfinamide, $Ti(OEt)_4$, DCM, reflux, 5 h, 89%; (d) $[Rh(cod)(MeCN)_2]BF_4$, THF, 60° C., 6 h, 35%; (e) HCl, MeOH, RT, 1 h then $Et_3N$, RT, 6 h, 90%; (f) AcOH, $NaBH(OAc)_3$, DCM, RT, 1 h, 79%; (g) AcOH, aq HCHO, $NaBH(OAc)_3$, DCM, RT, 2 h, 76%; (h) TFA, DCM, RT, 30 min, 97%; (i) N,N-bis(2-chloroethyl)-4-methylbenzenesulfonamide, DIPEA, 120° C., 24 h, 50%, (j) $K_3PO_4$, CuI, (±)-trans-1,2-diaminocyclohexane, dioxane, 95° C., 22.5 h, 24%, (k) Mg, MeOH, sonication, Overnight, 40%.

(S)-1-(4-chlorophenyl)-7-isopropoxy-6-methoxy-2-(4-(methyl(((1R,4S)-4-(4-tosylpiperazin-1-yl)cyclohexyl)methyl)amino)phenyl)-1,2-dihydroisoquinolin-3(4H)-one (RRM-01-145): $^1H$ NMR (400 MHz, DMSO-$d_6$) δ 7.72-7.65 (m, 2H), 7.55-7.48 (m, 2H), 7.36 (s, 4H), 7.04 (s, 1H), 6.90 (d, J=8.8 Hz, 2H), 6.84 (s, 1H), 6.63-6.53 (m, 2H), 5.94 (s, 1H), 4.45 (p, J=6.0 Hz, 1H), 3.90 (d, J=19.8 Hz, 1H), 3.78-3.75 (m, 1H), 3.74 (s, 3H), 3.58-3.55 (m, 1H), 3.49-3.46 (m, 2H), 3.18-3.15 (m, 2H), 3.15 (s, 3H), 3.13-3.10 (m, 2H), 2.88 (s, 3H), 2.43 (s, 3H), 1.97 (d, J=11.4 Hz, 2H), 1.77 (d, J=12.9 Hz, 2H), 1.60-1.55 (m, 2H), 1.34-1.30 (m, 2H), 1.24 (d, J=6.0 Hz, 3H), 1.19 (d, J=6.0 Hz, 3H), 1.01 (q, J=12.3 Hz, 2H).

(S)-1-(4-chlorophenyl)-7-isopropoxy-6-methoxy-2-(4-(methyl(((1R,4S)-4-(piperazin-1-yl)cyclohexyl)methyl)amino)phenyl)-1,2-dihydroisoquinolin-3(4H)-one (RRM-01-146): $^1H$ NMR (400 MHz, DMSO-$d_6$) δ 9.24 (s, 1H), 7.36 (s, 4H), 7.04 (s, 1H), 6.91 (d, J=9.0 Hz, 2H), 6.84 (s, 1H), 6.61 (s, 2H), 5.95 (s, 1H), 4.46 (p, J=6.1 Hz, 1H), 3.91 (d, J=19.9 Hz, 1H), 3.74 (s, 3H), 3.58 (d, J=19.9 Hz, 2H), 3.55-3.48 (m, 6H), 3.15 (d, J=7.0 Hz, 2H), 2.90 (s, 3H), 2.02 (d, J=11.3 Hz, 2H), 1.82 (d, J=13.0 Hz, 2H), 1.65 (m, 2H), 1.43 (q, J=11.9 Hz, 3H), 1.24 (d, J=6.0 Hz, 3H), 1.19 (d, J=6.0 Hz, 3H), 1.07-1.05 (m, 2H).

3-(4-((17-(4-((1S,4r)-4-(((4-((S)-1-(4-chlorophenyl)-7-isopropoxy-6-methoxy-3-oxo-3,4-dihydroisoquinolin-2(1H)-yl)phenyl)(methyl)amino)methyl)cyclohexyl)piperazin-1-yl)-3,6,9,12,15-pentaoxaheptadecyl)amino)-1-oxoisoindolin-2-yl)piperidine-2,6-dione (Cpd. No. 229): $^1H$ NMR (400 MHz, DMSO-$d_6$) δ 11.01 (s, 1H), 9.07 (brs, 1H), 7.36 (d, J=1.2 Hz, 3H), 7.30 (dd, J=9.0, 6.4 Hz, 1H), 7.04 (s, 1H), 6.96 (d, J=7.4 Hz, 1H), 6.91 (d, J=8.7 Hz, 2H), 6.86-6.78 (m, 2H), 6.67-6.46 (m, 2H), 5.94 (s, 1H), 5.12 (dd, J=13.2, 5.1 Hz, 1H), 4.45 (p, J=5.9 Hz, 2H), 4.24 (d, J=17.1 Hz, 2H), 4.13 (d, J=17.1 Hz, 2H), 3.91 (d, J=19.9 Hz, 2H), 3.74 (s, 3H), 3.58-3.44 (m, 15H), 3.38-3.24 (m, 7H), 3.19-3.02 (m, 9H), 2.89 (d, J=2.5 Hz, 4H), 2.62 (d, J=17.1 Hz, 2H), 2.37-2.24 (m, 2H), 2.03 (d, J=17.8 Hz, 3H), 1.79 (d, J=11.7 Hz, 2H), 1.24 (d, J=6.0 Hz, 3H), 1.24 (d, J=6.0 Hz, 3H), 1.19 (d, J=6.0 Hz, 3H), 1.05 (q, J=12.3 Hz, 2H).
Example 20
Synthesis of (2S,4R)-1-((S)-2-(5-(4-((1S,4S)-4-(((4-((S)-1-(4-chlorophenyl)-7-isopropoxy-6-methoxy-3-oxo-3,4-dihydroisoquinolin-2(1H)-yl)phenyl)(methyl)amino)methyl)cyclohexyl)piperazin-1-yl)pentanamido)-3,3-dimethylbutanoyl)-4-hydroxy-N—((S)-1-(4-(4-methylthiazol-5-yl)phenyl)ethyl)pyrrolidine-2-carboxamide
(Cpd. No. 233)
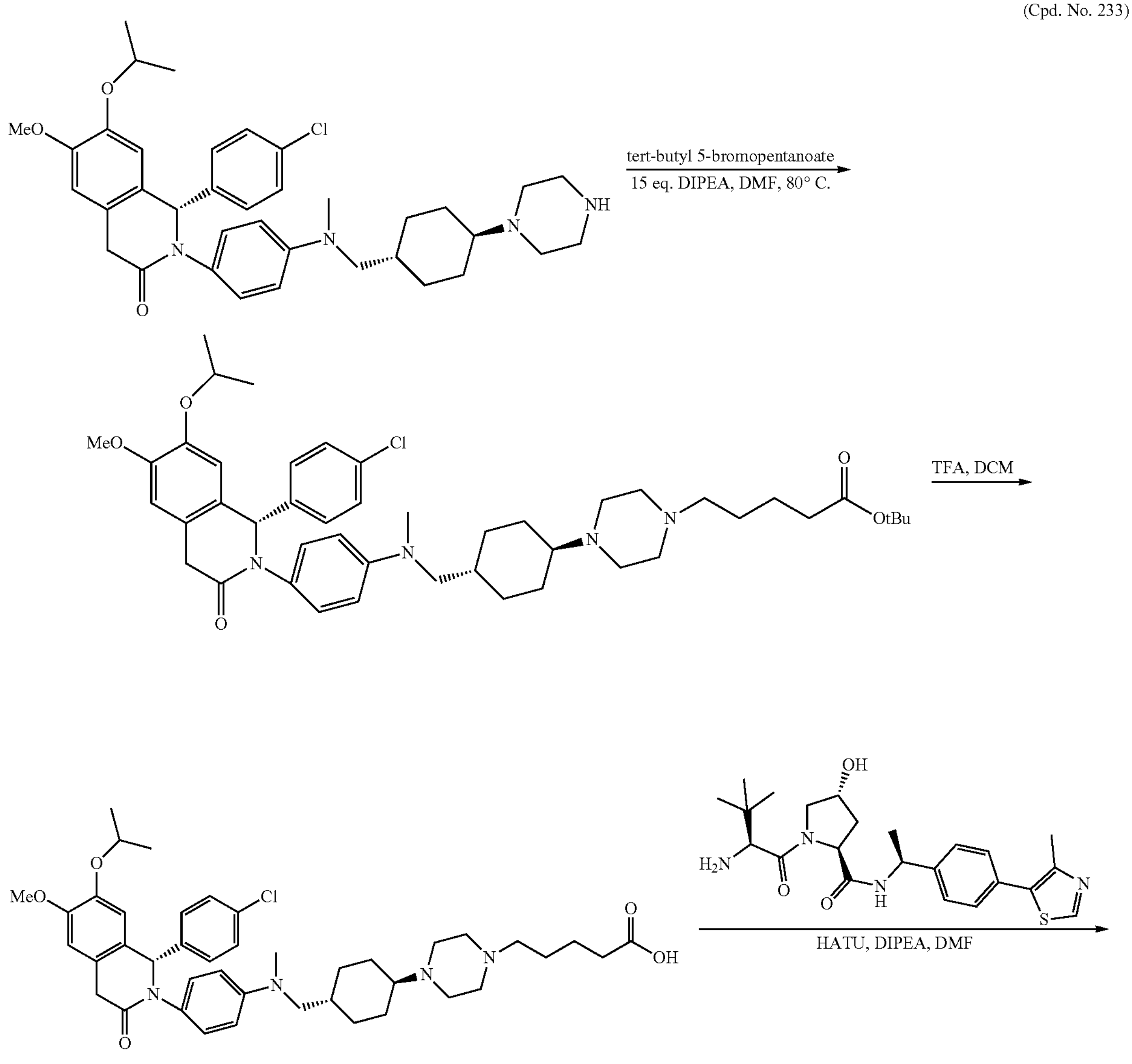

-continued

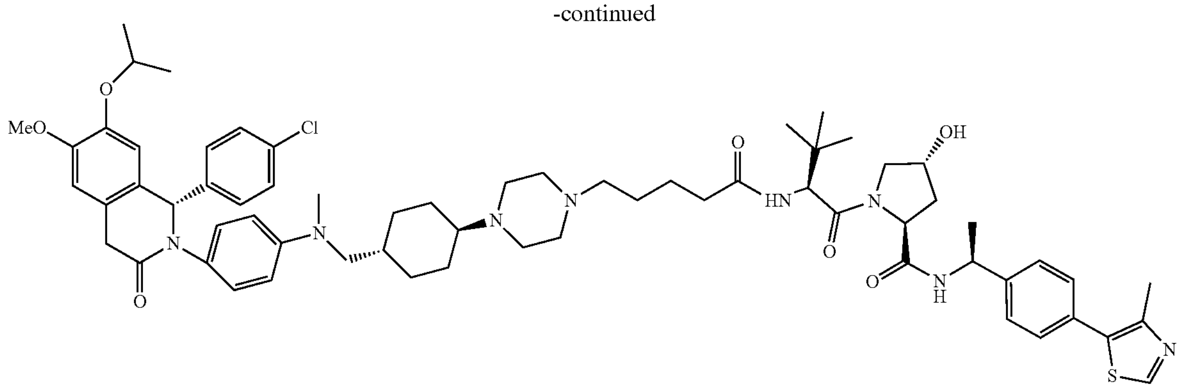

Cpd. No. 233

To a solution of RRM-01-146 (30 mg, 0.047 mmol) and DIPEA (0.12 ml, 0.70 m mol) in DMF (1 ml) was added tert-butyl 5-bromopentanoate (23 mg, 0.95 mmol) and the resulting solution stirred for overnight at 80° C. The solvent was evaporated and purified by silica gel DCM/MeOH (95:5) to give 27 mg (75%) of the desired product.

A solution of tert-butyl 5-(4-((1S,4r)-4-(((4-((S)-1-(4-chlorophenyl)-7-isopropoxy-6-methoxy-3-oxo-3,4-dihydroisoquinolin-2(1I)-yl)phenyl)(methyl)amino) methyl)cyclohexyl)piperazin-1-yl)pentanoate (27 mg) in DCM:TFA (2:1, 3 mL) was stirred at room temperature for 2 h. The solvent was evaporated to give the desired product which was carried to the next step without further purification.

5-(4-((1S,4r)-4-(((4-((S)-1-(4-chlorophenyl)-7-isopropoxy-6-methoxy-3-oxo-3,4-dihydroisoquinolin-2(1H)-yl)phenyl)(methyl)amino)methyl)cyclohexyl)piperazin-1-yl)pentanoic acid was coupled with (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide to give Cpd. No. 233. $^1$H NMR (400 MHz, DMSO-d6) δ 9.00 (s, 1H), 8.35 (d, J=7.8 Hz, 1H), 7.96 (s, 1H), 7.87 (d, J=9.2 Hz, 1H), 7.45 (d, J=8.2 Hz, 2H), 7.38 (d, J=16.1 Hz, 6H), 7.03 (s, 1H), 6.91 (d, J=8.6 Hz, 2H), 6.85 (s, 1H), 6.59 (d, J=9.0 Hz, 2H), 5.94 (s, 1H), 5.10-5.10 (m, 1H), 4.59-4.56 (m, 1H), 4.38-4.35 (m, 2H), 3.91 (m, 1H), 3.74 (s, 3H), 3.69-3.52 (m, 6H), 3.11-2.96 (m, 6H), 2.95-2.90 (m, 4H), 2.77 (m, 2H), 2.74 (d, J=0.6 Hz, 3H), 2.46 (s, 3H), 2.26-2.14 (m, 2H), 2.01 (d, J=9.9 Hz, 3H), 2.10-1.90 (m, 6H), 1.81 (d, J=12.5 Hz, 2H), 1.65-1.61 (m, 1H), 1.39 (d, J=7.0 Hz, 3H), 1.24 (d, J=6.0 Hz, 3H), 1.19 (d, J=6.0 Hz, 3H), 1.05 (q, J=12.3 Hz, 2H), 1.03 (s, 9H).

The following compounds were prepared using the methods described in Examples 19 and 20:

Cpd. No. 230: 4-((27-(4-((1S,4R)-4-(((4-((S)-1-(4-chlorophenyl)-7-isopropoxy-6-methoxy-3-oxo-3,4-dihydroisoquinolin-2(1H)-yl)phenyl)(methyl)amino)methyl)cyclohexyl)piperazin-1-yl)-27-oxo-3,6,9,12,15,18,21,24-octaoxaheptacosyl)amino)-2-(2,6-dioxopiperidin-3-yl) isoindoline-1,3-dione; $^1$H NMR (400 MHz, DMSO-d$_6$) δ 11.09 (s, 1H), 9.69 (s, 1H), 7.59 (dd, J=8.6, 7.1 Hz, 1H), 7.36 (s, 4H), 7.15 (d, J=8.6 Hz, 2H), 7.09-7.01 (m, 2H), 6.91 (d, J=9.0 Hz, 2H), 6.84 (s, 1H), 6.59 (d, J=9.1 Hz, 3H), 5.95 (s, 1H), 5.06 (dd, J=12.9, 5.4 Hz, 1H), 4.46 (dq, J=12.1, 6.2 Hz, 2H), 4.11 (d, J=14.2 Hz, 1H), 3.98-3.85 (m, 1H), 3.74 (s, 3H), 3.65-3.60 (m, 5H), 3.60-3.40 (m, 34H), 3.14 (d, J=6.9 Hz, 4H), 2.89 (s, 3H), 2.71-2.54 (m, 4H), 2.13-1.95 (m, 3H), 1.83-1.79 (m, 2H), 1.64-1.62 (m, 1H), 1.49-1.29 (m, 2H), 1.24 (d, J=6.0 Hz, 3H), 1.19 (d, J=6.0 Hz, 3H), 1.05 (q, J=12.3 Hz, 2H).

Cpd. No. 231: 3-(4-((14-(4-((1S,4r)-4-(((4-((S)-1-(4-chlorophenyl)-7-isopropoxy-6-methoxy-3-oxo-3,4-dihydroisoquinolin-2(1H)-yl)phenyl)(methyl)amino)methyl)cyclohexyl)piperazin-1-yl)-14-oxo-3,6,9,12-tetraoxatetradecyl) amino)-1-oxoisoindolin-2-yl)piperidine-2,6-dione; $^1$H NMR (400 MHz, DMSO-d$_6$) δ 11.01 (s, 1H), 9.76 (s, 1H), 7.36 (s, 4H), 7.29-7.27 (m, 2H), 7.04 (s, 1H), 6.94-6.92 (m, 4H), 6.87-6.78 (m, 3H), 6.66-6.56 (m, 2H), 5.95 (s, 1H), 5.12 (dd, J=13.2, 5.1 Hz, 1H), 4.48-4.44 (m, 2H), 4.29-4.18 (m, 2H), 4.18-4.09 (m, 2H), 3.91 (d, J=19.8 Hz, 1H), 3.74 (s, 3H), 3.65-3.47 (m, 16H), 3.33 (m, 3H), 3.21-3.02 (m, 4H), 2.89-2.83 (m, 6H), 2.67-2.57 (m, 1H), 2.40-2.21 (m, 2H), 2.10-1.95 (m, 3H), 1.81 (d, J=12.5 Hz, 2H), 1.65-1.61 (m, 1H), 1.24 (d, J=6.0 Hz, 3H), 1.19 (d, J=6.0 Hz, 3H), 1.05 (q, J=12.3 Hz, 2H).

Cpd. No. 232: 2-(2-(2-(2-(4-((1S,4R)-4-(((4-((S)-1-(4-chlorophenyl)-7-isopropoxy-6-methoxy-3-oxo-3,4-dihydroisoquinolin-2(1H)-yl)phenyl)(methyl)amino)methyl)cyclohexyl)piperazin-1-yl)ethoxy)ethoxy)ethoxy)-N-(2-(2,6-dioxopiperidin-3-yl)-1-oxoisoindolin-4-yl)acetamide; $^1$H NMR (400 MHz, DMSO-d$_6$) δ 11.02 (s, 1H), 9.78 (brs, 1H), 7.76 (d, J=8.0 Hz, 1H), 7.56-7.36 (m, 2H), 7.36 (s, 4H), 7.04 (s, 1H), 6.95-6.86 (m, 3H), 6.84 (s, 2H), 6.65-6.48 (m, 3H), 5.95 (s, 1H), 5.12 (dd, J=13.2, 5.1 Hz, 1H), 4.51-4.27 (m, 2H), 4.17 (s, 1H), 3.97-3.90 (m, 1H), 3.74 (s, 3H), 3.70-3.50 (m, 16H), 3.30-3.20 (m, 3H), 3.15 (m, 7H), 2.89 (d, J=6.5 Hz, 4H), 2.56 (t, J=5.5 Hz, 1H), 2.10-1.95 (m, 3H), 1.81 (d, J=12.5 Hz, 2H), 1.65-1.61 (m, 1H), 1.24 (d, J=6.0 Hz, 3H), 1.19 (d, J=6.0 Hz, 3H), 1.05 (q, J=12.3 Hz, 2H).

Cpd. No. 234: 4-((15-(4-((1S,4R)-4-(((4-((S)-1-(4-chlorophenyl)-7-isopropoxy-6-methoxy-3-oxo-3,4-dihydroisoquinolin-2(1H)-yl)phenyl)(methyl)amino)methyl)cyclohexyl)piperazin-1-yl)-15-oxo-3,6,9,12-tetraoxapentadecyl) amino)-2-(2,6-dioxopiperidin-3-yl)isoindoline-1,3-dione; $^1$H NMR (400 MHz, DMSO-d$_6$) δ 11.09 (s, 1H), 9.55 (s, 1H), 7.59 (dd, J=8.6, 7.1 Hz, 1H), 7.36 (s, 4H), 7.15 (d, J=8.6 Hz, 1H), 7.09-6.98 (m, 2H), 6.91 (d, J=8.9 Hz, 2H), 6.84 (s, 1H), 6.68-6.51 (m, 3H), 5.94 (s, 1H), 5.06 (dd, J=12.9, 5.4 Hz, 1H), 4.46 (dq, J=12.2, 5.8 Hz, 2H), 4.10 (d, J=14.1 Hz, 2H), 3.91 (d, J=19.8 Hz, 2H), 3.62 (td, J=6.0, 3.8 Hz, 4H), 3.59-3.52 (m, 4H), 3.59-3.40 (m, 15H), 3.13 (d, J=6.8 Hz, 2H), 3.05-3.00 (m, 2H), 2.97 (s, 3H), 3.95-2.82 (m, 2H), 2.55-2.50 (m, 3H), 2.10-1.90 (m, 3H), 1.80 (d, J=12.5 Hz, 2H), 1.64-1.60 (m, 2H), 1.43-1.36 (m, 2H), 1.24 (d, J=6.0 Hz, 3H), 1.19 (d, J=6.0 Hz, 3H), 1.04 (q, J=12.2 Hz, 2H).

Cpd. No. 235: 4-((2-(2-(2-(3-(4-((1S,4R)-4-(((4-((S)-1-(4-chlorophenyl)-7-isopropoxy-6-methoxy-3-oxo-3,4-dihydroisoquinolin-2(1H)-yl)phenyl)(methyl)amino)methyl)cyclohexyl)piperazin-1-yl)-3-oxopropoxy)ethoxy)ethoxy)ethyl)amino)-2-(2,6-dioxopiperidin-3-yl)isoindoline-1,3-dione; $^{1}$H NMR (400 MHz, DMSO-$d_6$) δ 11.09 (s, 1H), 9.57 (s, 1H), 7.59 (dd, J=8.6, 7.1 Hz, 1H), 7.36 (s, 4H), 7.15 (d, J=8.6 Hz, 1H), 7.09-6.98 (m, 2H), 6.95-6.88 (m, 2H), 6.84 (s, 1H), 6.59 (m, 3H), 5.94 (s, 1H), 5.06 (dd, J=12.9, 5.4 Hz, 1H), 4.45 (p, J=6.1 Hz, 2H), 4.16-4.03 (m, 1H), 3.91-3.85 (m, 1H), 3.74 (s, 3H), 3.65-3.60 (m, 4H), 3.59-3.25 (m, 14H), 3.13 (d, J=6.8 Hz, 2H), 3.05-3.00 (m, 2H), 2.97 (s, 3H), 3.95-2.82 (m, 2H), 2.55-2.50 (m, 3H), 2.10-1.90 (m, 3H), 1.80 (d, J=12.5 Hz, 2H), 1.64-1.60 (m, 2H), 1.43-1.36 (m, 2H), 1.24 (d, J=6.0 Hz, 3H), 1.19 (d, J=6.0 Hz, 3H), 1.04 (q, J=12.2 Hz, 2H).

Cpd. No. 236: (2S,4R)-1-((S)-17-(tert-butyl)-1-(4-((1S,4R)-4-(((4-((S)-1-(4-chlorophenyl)-7-isopropoxy-6-methoxy-3-oxo-3,4-dihydroisoquinolin-2(1H)-yl)phenyl)(methyl)amino)methyl)cyclohexyl)piperazin-1-yl)-15-oxo-3,6,9,12-tetraoxa-16-azaoctadecan-18-oyl)-4-hydroxy-N—((S)-1-(4-(4-methylthiazol-2-yl)phenyl)ethyl)pyrrolidine-2-carboxamide; $^{1}$H NMR (400 MHz, DMSO-$d_6$) δ 9.00 (s, 1H), 8.37 (d, J=7.7 Hz, 1H), 7.87 (d, J=9.3 Hz, 1H), 7.51-7.42 (m, 2H), 7.42-7.36 (m, 2H), 7.36 (s, 4H), 7.03 (s, 1H), 6.98-6.88 (m, 2H), 6.84 (s, 1H), 6.59 (d, J=8.9 Hz, 2H), 5.94 (s, 1H), 4.92 (t, J=7.2 Hz, 1H), 4.54 (d, J=9.4 Hz, 1H), 4.50-4.38 (m, 2H), 4.29 (brs, 1H), 3.91 (d, J=19.8 Hz, 1H), 3.74 (s, 3H), 3.69-3.54 (m, 15H), 3.53-3.44 (m, 11H), 3.30-3.22 (m, 3H), 3.18 (s, 3H), 3.15 (d, J=6.9 Hz, 2H), 2.90 (s, 3H), 2.46 (s, 3H), 2.39-2.31 (m, 2H), 2.10-2.00 (m, 3H), 1.87-1.74 (m, 3H), 1.65-1.61 (m, 2H), 1.38 (d, J=6.9 Hz, 3H), 1.24 (d, J=6.0 Hz, 3H), 1.19 (d, J=6.0 Hz, 3H), 1.07 (q, J=12.3 Hz, 2H), 0.94 (s, 9H).

Cpd. No. 237: 1-(4-((1S,4R)-4-(((4-((S)-1-(4-chlorophenyl)-7-isopropoxy-6-methoxy-3-oxo-3,4-dihydroisoquinolin-2(1H)-yl)phenyl)(methyl)amino)methyl)cyclohexyl)piperazin-1-yl)-N-(2-(2,6-dioxopiperidin-3-yl)-1-oxoisoindolin-4-yl)-3,6,9,12-tetraoxapentadecan-15-amide; $^{1}$H NMR (400 MHz, DMSO-$d_6$) δ 11.03 (s, 1H), 9.86 (s, 1H), 7.83 (dd, J=7.4, 1.6 Hz, 1H), 7.59-7.46 (m, 2H), 7.36 (s, 4H), 7.03 (s, 1H), 6.91 (d, J=8.9 Hz, 2H), 6.84 (s, 1H), 6.71-6.50 (m, 2H), 5.94 (s, 2H), 5.16 (dd, J=13.2, 5.1 Hz, 1H), 4.45 (dt, J=12.3, 6.2 Hz, 1H), 4.36 (d, J=10.0 Hz, 1H), 3.91 (d, J=19.8 Hz, 2H), 3.74 (s, 5H), 3.64-3.43 (m, 17H), 3.20-3.10 (m, 9H), 2.90 (d, J=2.2 Hz, 3H), 2.65-2.60 (m, 2H), 2.48-2.42 (m, 2H), 2.39-2.24 (m, 1H), 2.00-1.90 (m, 3H), 1.86-1.76 (m, 2H), 1.65-1.60 (m, 2H), 1.47-1.33 (m, 2H), 1.24 (d, J=6.0 Hz, 3H), 1.19 (d, J=6.0 Hz, 3H), 1.12-0.97 (m, 2H).

Example 21

In Vitro Activity

Cell growth inhibitory activity of representative MDM2 protein degraders was determined using CellTiter-Glo® Luminescent Cell Viability Assay. Cells were seeded in 384-well white opaque cell culture plates at a density of 2,000 cells/well with serially diluted compounds and incubated at 37° C. in an atmosphere of 95% air and 5% $CO_2$ for 4 days. Cell viability was determined using the CellTiter-Glo® Luminescent Cell Viability Assay Kit (Promega, Madison, WI) according to the manufacture's instruction. Briefly, a volume of CellTiter-Glo® Reagent equal to the volume of cell culture medium was added to each well, and then the plates were incubated at room temperature for 10-20 minutes. The luminescent signal was measured using a Tecan Infinite M1000 multimode microplate reader (Tecan, Morrisville, NC). The half maximal inhibitory concentration ($IC_{50}$) was calculated using the GraphPad Prism 5 software (GraphPad Software, La Jolla, CA). Cpd. A (a MDM2 inhibitor; see Compound Example No. 22 of U.S. Pat. No. 8,629,141) has an $IC_{50}$ of 0.086 μM in the RS4; 11 cell line and an $IC_{50}$ of 0.100 μM in the MV4-11 cell line. The structure of Cpd. A is:

Cpd. A

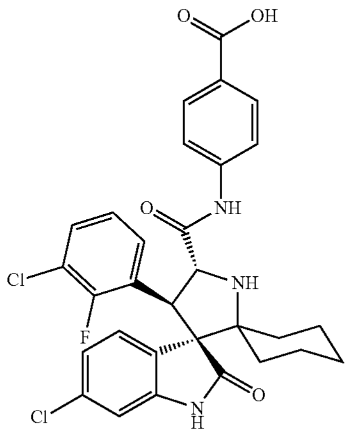

TABLE 3

| | Cell Growth Inhibition $IC_{50}$ (μM) | |
|---|---|---|
| Cpd. No. | RS4; 11 | MV4-11 |
| 1 | 0.233 | 0.416 |
| 2 | 0.085 | 0.157 |
| 3 | 0.022 | 0.0056 |
| 4 | 0.014 | 0.006 |
| 5 | 0.0022 | 0.015 |
| 6 | 0.038 | 0.037 |
| 7 | 0.015 | 0.020 |
| 9 | 0.010 | 0.163 |
| 10 | 0.012 | |
| 11 | 0.030 | 0.042 |
| 12 | 0.10 | |
| 13 | 0.0074 | 0.0052 |
| 14 | 0.0085 | 0.0076 |
| 15 | 0.0044 | 0.002 |
| 16 | 0.0047 | 0.0027 |
| 17 | 0.019 | 0.021 |
| 18 | 0.0074 | 0.0052 |
| 20 | 0.0085 | 0.0076 |
| 21 | 0.0044 | 0.002 |
| 22 | 0.0047 | 0.0027 |
| 23 | 0.019 | 0.021 |
| 24 | 0.007 | 0.005 |
| 25 | 0.0074 | |
| 26 | 0.008 | |
| 27 | 0.0046 | |
| 28 | 0.007 | |
| 29 | 0.015 | |
| 30 | 0.013 | |
| 31 | 0.0018 | |
| 32 | 0.023 | |
| 33 | 0.0029 | |
| 34 | 0.0178 | |
| 35 | 0.0057 | |
| 36 | 0.0374 | |
| 37 | 0.0038 | |
| 38 | 0.046 | |
| 39 | 0.0015 | |
| 41 | 0.991 | |
| 42 | 0.677 | |
| 43 | 0.445 | |

TABLE 3-continued

| Cpd. No. | Cell Growth Inhibition $IC_{50}$ (μM) | |
|---|---|---|
| | RS4; 11 | MV4-11 |
| 45 | 0.035 | |
| 46 | 0.02 | 0.02 |
| 47 | 0.26 | 0.16 |
| 48 | 0.19 | 0.13 |
| 52 | 0.0015 | |
| 53 | 0.0052 | |
| 57 | 0.013 | |
| 58 | 0.014 | |
| 60 | 0.404 | |
| 61 | 0.098 | |

Example 22

MDM2 Degradation and p53 Activation in the RS4; 11 Cell Line

RS4; 11 cells were treated with Cpd. A, Cpd. B, Cpd. No. 15, and Cpd. No. 22 for 2 hours, then harvested and lysed. The cell lysates were subjected to western blotting analysis. See FIG. 1. The protein level of MDM2 was significantly decreased after treatment with Cpd. No. 15 and Cpd. No. 22 as compared to Cpd. A, indicating MDM2 degradation. The structure of Cpd. B is:

Cpd. B

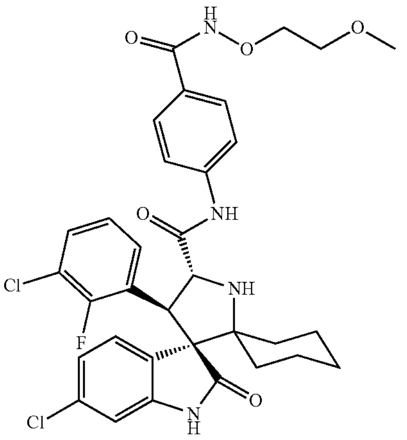

Example 23

MDM2 Degradation and p53 Activation in the MV-4-11 Cell Line

MV-4-11 cells were treated with Cpd. A, Cpd. B, Cpd. No. 15, and Cpd. No. 22 for 2 hours, then harvested and lysed. The cell lysates were subjected to western blotting analysis. See FIG. 2. The protein level of MDM2 was significantly decreased after treatment with Cpd. No. 15 and Cpd. No. 22 as compared to Cpd. A, indicating MDM2 degradation.

Example 24

Activation of p53 Downstream Target Genes by the MDM2 Degraders

RS4; 11 cells were treated with Cpd. A (0.3 μM), Cpd. No. 15 (10 nM), and Cpd. No. 22 (10 nM) for 3, 6, or 12 hours, and then harvested and washed. Cellular mRNA samples were extracted from the cells and then subjected to Reverse Transcription and quantitative real-time PCR for the analysis of the mRNA levels of three representative p53 target genes: p21, that induces cell cycle arrest, and PUMA and BAX that leads to apoptosis. Significant activation of these p53 downstream target genes was detected with Cpd. A, Cpd. No. 15, and Cpd. No. 22. See FIG. 3, FIG. 4, and FIG. 5.

Example 25

MDM2 Degradation by Compounds of the Disclosure

RS4; 11 cells were pre-incubated with the proteasome inhibitor MG-132 (20 μM) or without any pre-incubation for 2 hours. Next, the cells were treated with Cpd. A (0.3 μM), Cpd. No. 14 (0.03 μM), Cpd. No. 15 (0.01 μM), and Cpd. No. 22 (0.01 μM) for 2 hours, then harvested and lysed. The cell lysates were subject to western blotting analysis. See FIG. 6. In the absence of pre-incubation with MG-132, the protein level of MDM2 was significantly decreased after treatment with the Compounds of the Disclosure as compared to Cpd. A. However, in the presence of MG-132, no significant MDM2 degradation was detected with the Compounds of the Disclosure, indicating that the degradation of MDM2 by the Compounds of the Disclosure is proteasome dependent.

Example 26

MDM2 Degradation by Compounds of the Disclosure is Cereblon (CRBN)-Dependent

RS4; 11 cells were pre-incubated with different concentrations of Cpd. C to compete for the binding of phthalimide to CRBN, or DMSO, for 2 hours before adding Cpd. A, Cpd. No. 14, Cpd. No. 15, and Cpd. No. 22. The cells were then co-treated with 10, 20, or 30 μM Cpd. C and increasing concentrations of Cpd. A, Cpd. No. 14, Cpd. No. 15, and Cpd. No. 22 for 4 days, with a starting cell concentration of ~15,000/well. Cell growth inhibition was determined by the WST assay. See Tables 4, 5, and 6. Significant rightward shifts of the dose response curves were observed with Cpd. No. 14, Cpd. No. 15, and Cpd. No. 22 with co-treatment of Cpd. C. The structure of Cpd. C is:

Cpd. C

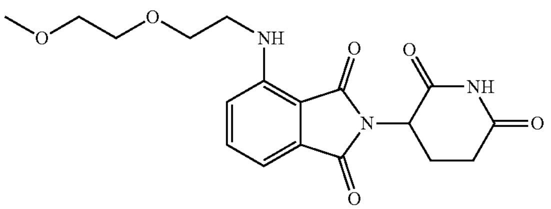

TABLE 4

| | LogIC50 | HillSlope | IC50 |
|---|---|---|---|
| Cpd. A | −1.030 | −1.496 | 0.09329 |
| Cpd. A + 10 uM Cpd. C | −1.317 | −1.569 | 0.04814 |

TABLE 4-continued

| | LogIC50 | HillSlope | IC50 |
|---|---|---|---|
| Cpd. A + 20 uM Cpd. C | −1.409 | −1.406 | 0.03898 |
| Cpd. A + 30 uM Cpd. C | −1.438 | −1.411 | 0.03650 |
| Cpd. No. 14 | −2.147 | −1.996 | 0.007133 |
| Cpd. 14 + 10 uM Cpd. C | −1.244 | −1.705 | 0.05697 |
| Cpd. 14 + 20 uM Cpd. C | −1.091 | −1.667 | 0.08110 |
| Cpd. 14 + 30 uM Cpd. C | −1.111 | −1.600 | 0.07738 |

TABLE 5

| | LogIC50 | HillSlope | IC50 |
|---|---|---|---|
| Cpd. A | −1.030 | −1.496 | 0.09329 |
| Cpd. A + 10 uM Cpd. C | −1.317 | −1.569 | 0.04814 |
| Cpd. A + 20 uM Cpd. C | −1.409 | −1.406 | 0.03898 |
| Cpd. A + 30 uM Cpd. C | −1.438 | −1.411 | 0.03650 |
| Cpd. No. 15 | −2.312 | −1.839 | 0.004871 |
| Cpd. 15 + 10 uM Cpd. C | −1.356 | −1.654 | 0.04401 |
| Cpd. 15 + 20 uM Cpd. C | −1.167 | −1.540 | 0.06815 |
| Cpd. 15 + 30 uM Cpd. C | −1.205 | −1.416 | 0.06236 |

TABLE 6

| | LogIC50 | HillSlope | IC50 |
|---|---|---|---|
| Cpd. A | −1.030 | −1.496 | 0.09329 |
| Cpd. A + 10 uM Cpd. C | −1.317 | −1.569 | 0.04814 |
| Cpd. A + 20 uM Cpd. C | −1.409 | −1.406 | 0.03898 |
| Cpd. A + 30 uM Cpd. C | −1.438 | −1.411 | 0.03650 |
| Cpd. No. 22 | −2.242 | −1.803 | 0.005727 |
| Cpd. 22 + 10 uM Cpd. C | −1.209 | −1.701 | 0.06174 |
| Cpd. 22 + 20 uM Cpd. C | −1.048 | −1.530 | 0.08960 |
| Cpd. 22 + 30 uM Cpd. C | −1.080 | −1.341 | 0.08324 |

Example 27

MDM2 Degradation by Compounds of the Disclosure is Cereblon (CRBN)-Dependent RS4; 11 cells were pre-incubated with 30 μM Cpd. C to compete for the binding of phthalimide to CRBN, or DMSO, for 2 hours before adding Cpd. A, Cpd. No. 14, Cpd. No. 15, and Cpd. No. 22. In the Western blot RS4; 11 cells were then co-treated with the indicated compounds at the indicated concentrations after pre-incubation. See FIG. 7. These data suggest that both MDM2 degradation and p53 activation by Cpd. No. 14, Cpd. No. 15, and Cpd. No. 22 were significantly competed by Cpd. C, indicating that they are CRBN binding-dependent.

Example 28

Cell Growth Inhibitory Activity of Compounds of the Disclosure is p53-Dependent RS4; 11 cells with stable shRNA knockdown of p53 or those transfected shRNA control vector were treated with Cpd. A, Cpd. B, Cpd. No. 14, Cpd. No. 21, Cpd. No. 15, and Cpd. No. 22 for 4 days, with a cell concentration of ~15,000/well. Cell growth inhibition was determined by WST assay. See Table 7 (p53) and Table 8 (control). Significant increases in $IC_{50}$ of the Compounds of the Disclosure in the p53 knockdown RS4; 11 cells were observed compared with that in the sh control cells. These result show that activities of the Compounds of the Disclosure are largely p53-dependent. The p53 knockdown efficiency was determined by western blot for p53 protein levels with or without treatment of Cpd. A (1 μM) for 2 hours. See FIG. 8.

TABLE 7

| | RS4;11 sh p53 | | | | | |
|---|---|---|---|---|---|---|
| | Cpd. A | Cpd. B | Cpd. 14 | Cpd. 21 | Cpd. 15 | Cpd. 22 |
| LogIC50 | 0.9926 | 0.7537 | −0.3000 | 0.6196 | −0.9565 | −0.8628 |
| HiliSlope | −0.4240 | −0.7973 | −0.4731 | −0.4410 | −0.8905 | −0.8833 |
| IC50 | 9.832 | 5.671 | 0.5012 | 4.165 | 0.1105 | 0.1371 |

TABLE 8

| | RS4;11 sh Control | | | | | |
|---|---|---|---|---|---|---|
| | Cpd. A | Cpd. B | Cpd. 14 | Cpd. 21 | Cpd. 15 | Cpd. 22 |
| LogIC50 | −1.011 | −1.069 | −2.014 | −1.882 | −2.127 | −2.025 |
| HiliSlope | −1.155 | −0.9620 | −1.475 | −1.448 | −1.626 | −1.567 |
| IC50 | 0.09748 | 0.08528 | 0.009674 | 0.01311 | 0.007469 | 0.009445 |

It is to be understood that the foregoing embodiments and exemplifications are not intended to be limiting in any respect to the scope of the disclosure, and that the claims presented herein are intended to encompass all embodiments and exemplifications whether or not explicitly presented herein All patents and publications cited herein are fully incorporated by reference in their entirety.

What is claimed is:

1. A compound having Formula I-A:

$A^1$-$L^1$-$B^1$ I-A or a pharmaceutically acceptable salt or solvate thereof, wherein:

$A^1$ is:

A-28

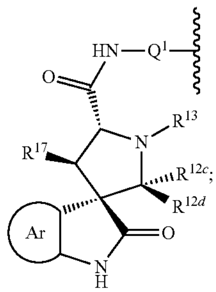

$R^{12c}$ and $R^{12d}$ taken together with the carbon atom to which they are attached form a 4- to 8-membered optionally substituted cycloalkyl or a 4- to 8-membered optionally substituted heterocyclo;

$R^{13}$ is selected from the group consisting of hydrogen, optionally substituted $C_{1-6}$ alkyl, and heteroalkyl;

$R^{17}$ is selected from the group consisting of optionally substituted aryl and optionally substituted heteroaryl;

$Q^1$ is selected from the group consisting of phenylenyl;

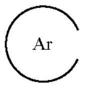

is a fused optionally substituted phenyl, fused optionally substituted thienyl, fused optionally substituted pyridyl, or fused optionally substituted pyrimidyl group;

$L^1$ is —$X^1$-$L^2$-$Y^1$—;

$X^1$ is $X^2$; or $X^1$ is absent;

$X^2$ is selected from the group consisting of —N(H)C(═O)—, —C(═O)N(H)—, —C(═O)N(H)S(O)$_2$—, —N(H)C(═O)N(H)—, —N(H)C(═O)O—, —OC(═O)N(H)—, —SO$_2$—, —O—, —N(H)—, —SO$_2$N(H)—, —N(H)SO$_2$—, —CH$_2$—, and —CH═CH;

$L^2$ is selected from the group consisting of alkylenyl, and heteroalkylenyl; or $L^2$ is absent;

$Y^1$ is selected from the group consisting of —C≡C—, —CH═CH—, —CH$_2$—, —O—, —N($R^{2b}$)—, —C(═O)N($R^{2c}$)—, —N($R^{2d}$)C(═O)CH$_2$O—, and —N($R^{2e}$)C(═O)CH$_2$N($R^{2f}$)—; or $Y^1$ is absent;

wherein the carboxamide nitrogen atom of —N($R^{2d}$)C(═O)CH$_2$O— and —N($R^{2e}$)C(═O)CH$_2$N($R^{2f}$)—, and the carbon atom of —C(═O)N($R^{2c}$)— is attached to $L^2$;

$R^{2b}$, $R^{2c}$, $R^{2d}$, $R^{2e}$, and $R^{2f}$ are each independently selected from the group consisting of hydrogen and $C_{1-4}$ alkyl;

$B^1$ is selected from the group consisting of:

B-1a

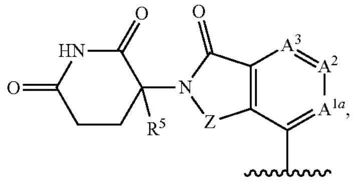

B-1b

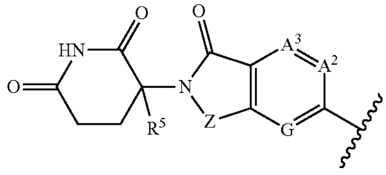

B-1c

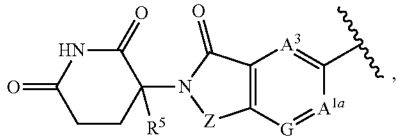

, and

B-1d

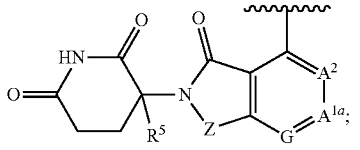

$A^{1a}$ is selected from the group consisting of —C($R^{16a}$)═ and —N═;

$A^2$ is selected from the group consisting of —C($R^{16b}$)═ and —N═;

$A^3$ is selected from the group consisting of —C($R^{16c}$)═ and —N═;

G is selected from the group consisting of —C($R^{16d}$)═ and —N═;

Z is selected from the group consisting of —CH$_2$ and —C(═O)—;

$R^5$ is selected from the group consisting of hydrogen, methyl, and fluoro;

$R^{16a}$ is selected from the group consisting of hydrogen, halo, and $C_{1-4}$ alkyl;

$R^{16b}$ is selected from the group consisting of hydrogen, halo, and $C_{1-4}$ alkyl;

$R^{16c}$ is selected from the group consisting of hydrogen, halo, and $C_{1-4}$ alkyl; and $R^{16d}$ is selected from the group consisting of hydrogen, halo, and $C_{1-4}$ alkyl.

2. The compound of claim 1, or a pharmaceutically acceptable salt or solvate thereof, wherein $A^1$ is:

A-35

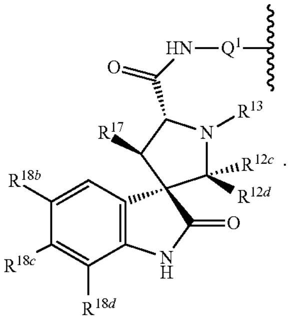

3. The compound of claim 2, or a pharmaceutically acceptable salt or solvate thereof, wherein:

$A^1$ is:

A-100

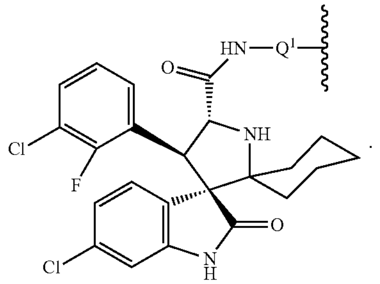

4. The compound of claim 2, or a pharmaceutically acceptable salt or solvate thereof, having Formula VII:

VII

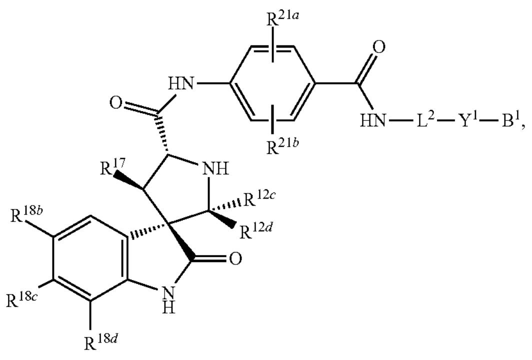

wherein:

$R^{12c}$ and $R^{12d}$ taken together with the carbon atom to which they are attached form a 4-membered cycloalkyl or 6-membered optionally substituted cycloalkyl;

$R^{17}$ is:

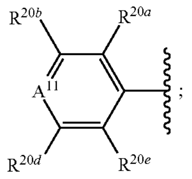

$A^{11}$ is —C($R^{20c}$)=;

$R^{20a}$, $R^{20b}$, and $R^{20c}$ are each hydrogen;

$R^{20d}$ and $R^{20e}$ are independently selected from the group consisting of hydrogen and halo;

$R^{18b}$, $R^{18c}$, and $R^{18d}$ are each independently selected from the group consisting of hydrogen and halo; and $R^{21a}$ and $R^{21b}$ are each independently selected from the group consisting of hydrogen, halo, $C_{1-4}$ alkyl, haloalkyl, alkoxy, and haloalkoxy.

5. The compound of claim 2, or a pharmaceutically acceptable salt or solvate thereof, wherein $L^2$ is $C_{1-12}$ alkylenyl.

6. The compound of claim 2, or a pharmaceutically acceptable salt or solvate thereof, wherein $L^2$ is 3- to 12-membered heteroalkylenyl.

7. The compound of claim 1, or a pharmaceutically acceptable salt or solvate thereof, wherein $Y^1$ is —CH=CH—$CH_2$—, —O—, and —N(H)—; or Y is absent.

8. The compound of claim 2, or a pharmaceutically acceptable salt or solvate thereof, wherein $B^1$ is selected from the group consisting of:

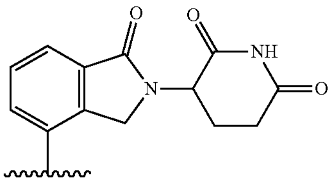

and

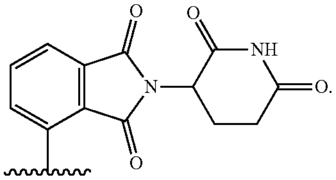

9. The compound of claim 1, or a pharmaceutically acceptable salt or solvate thereof, selected from the group consisting of:

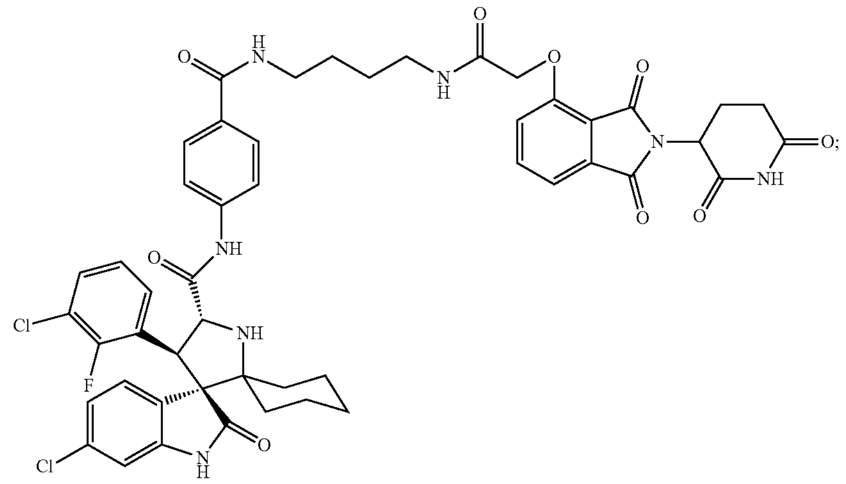
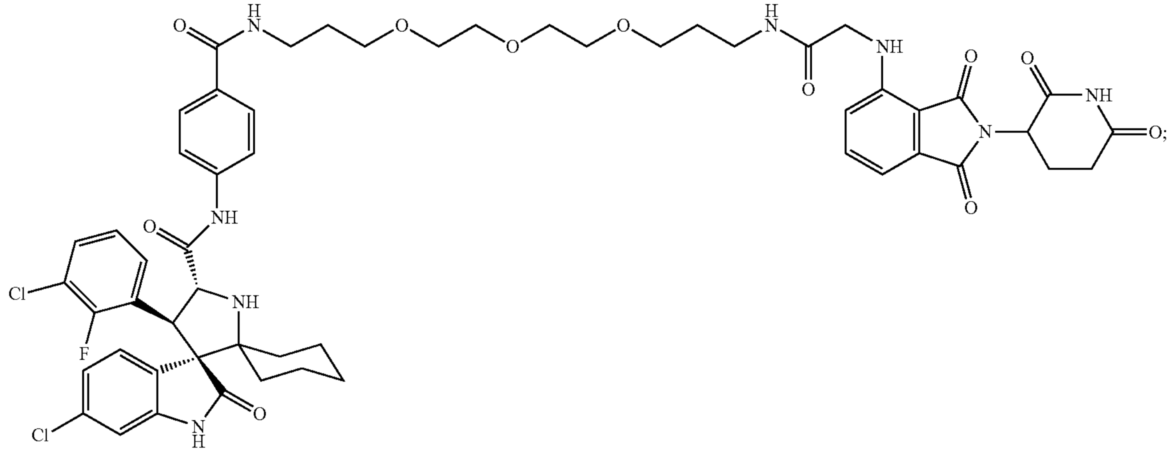
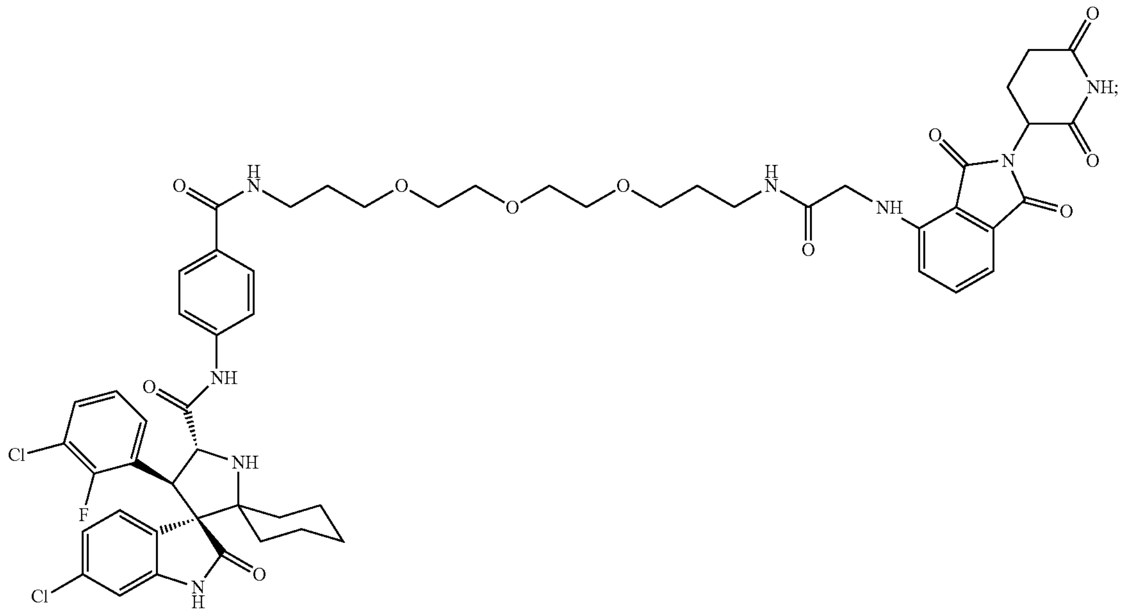

-continued
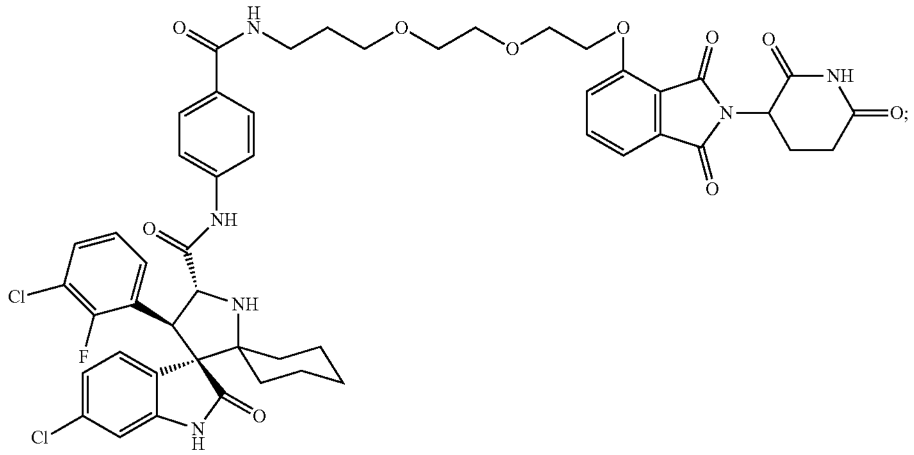
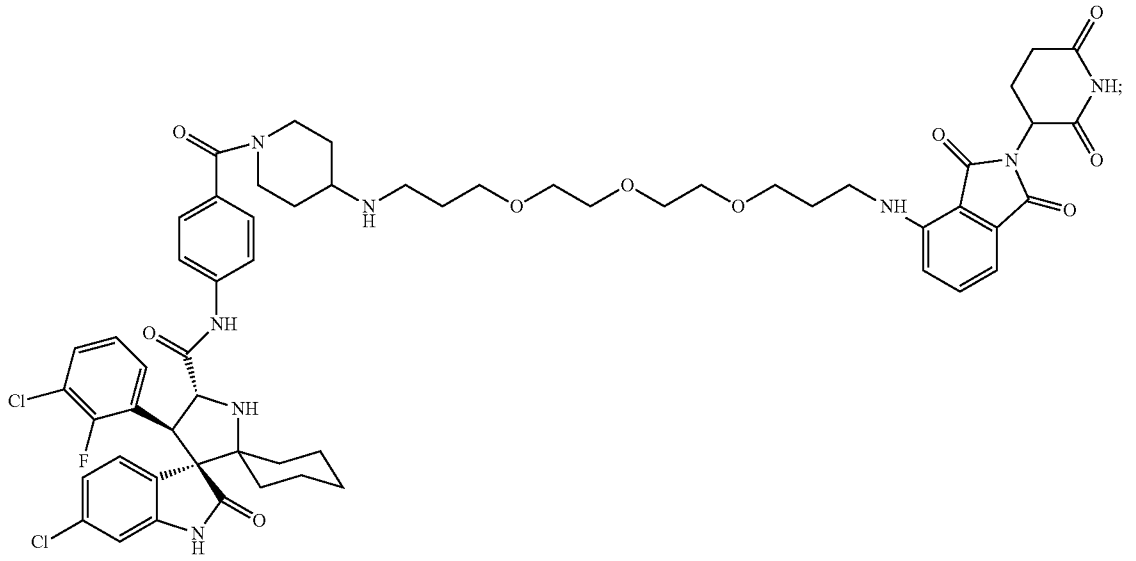
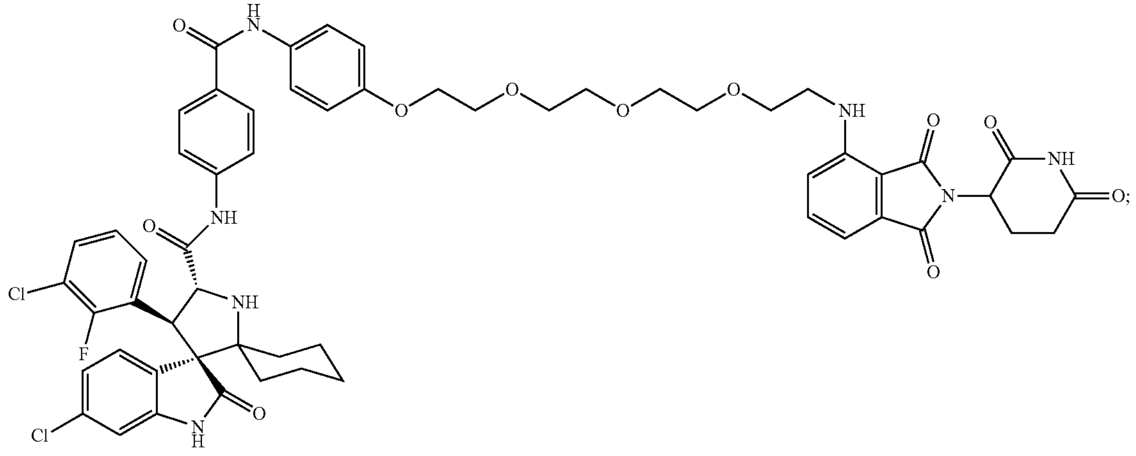

-continued
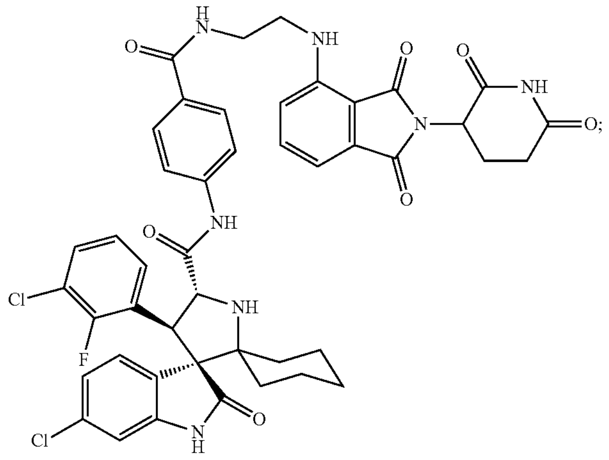
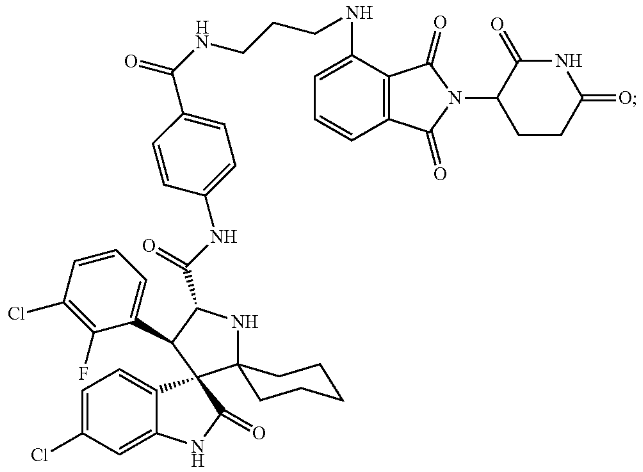
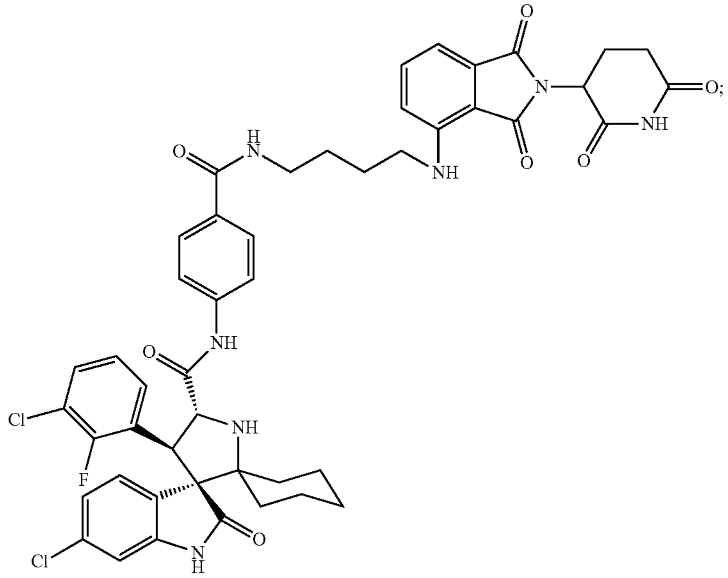

-continued
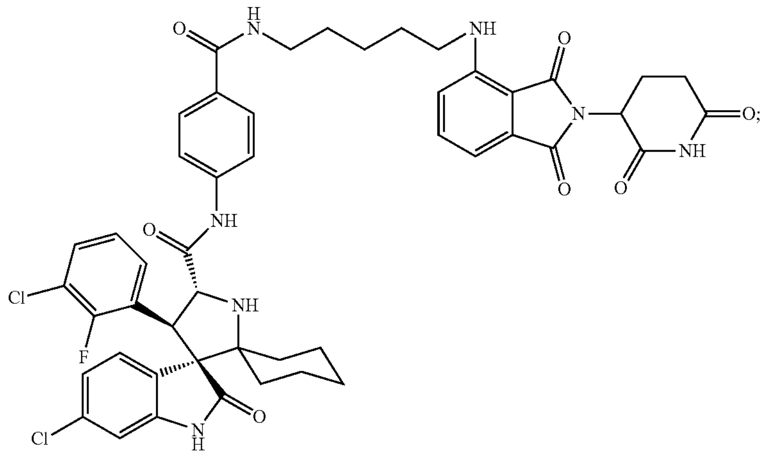
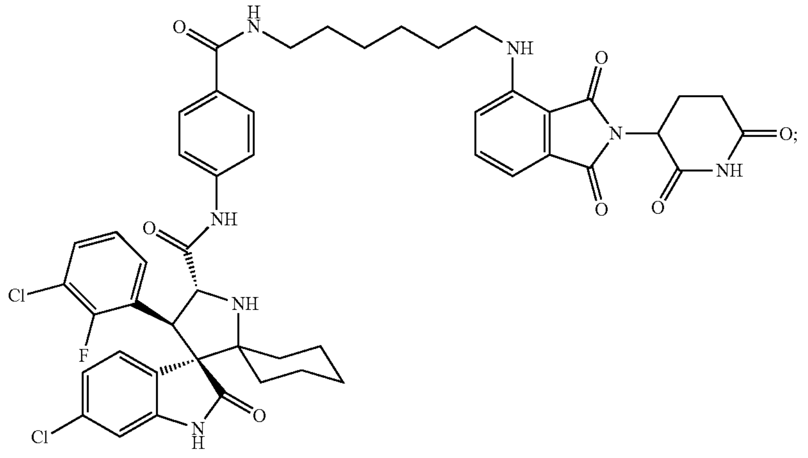
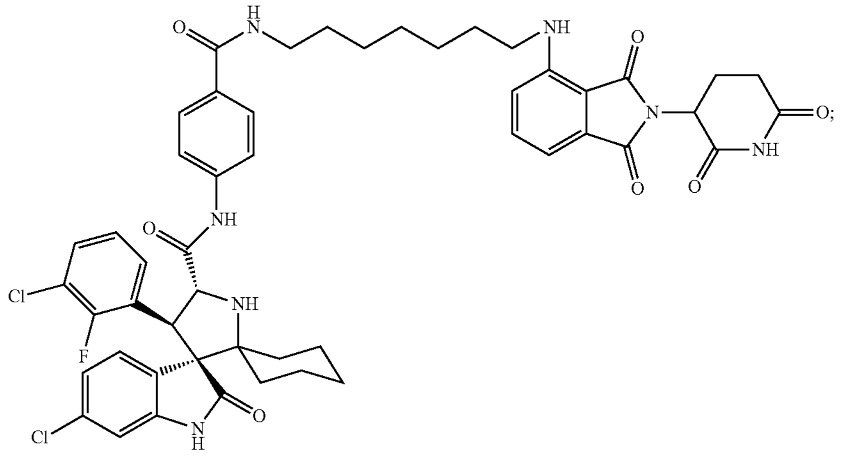

-continued
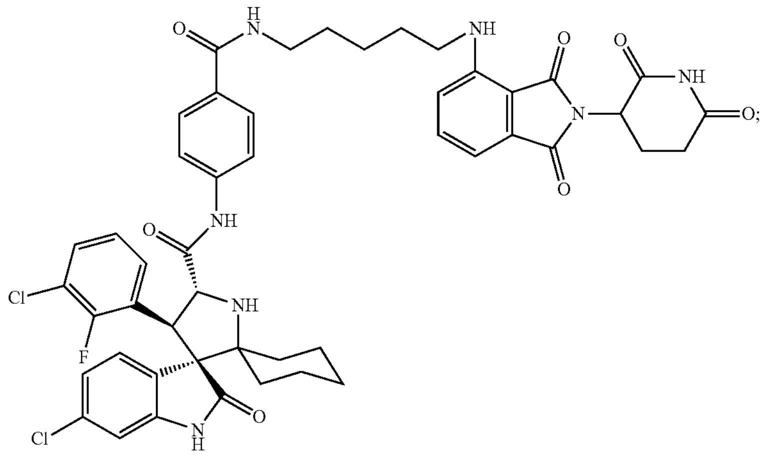
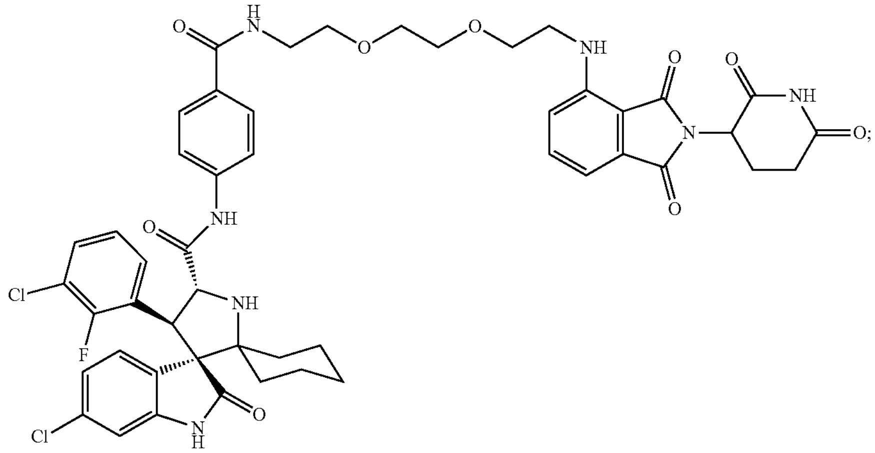
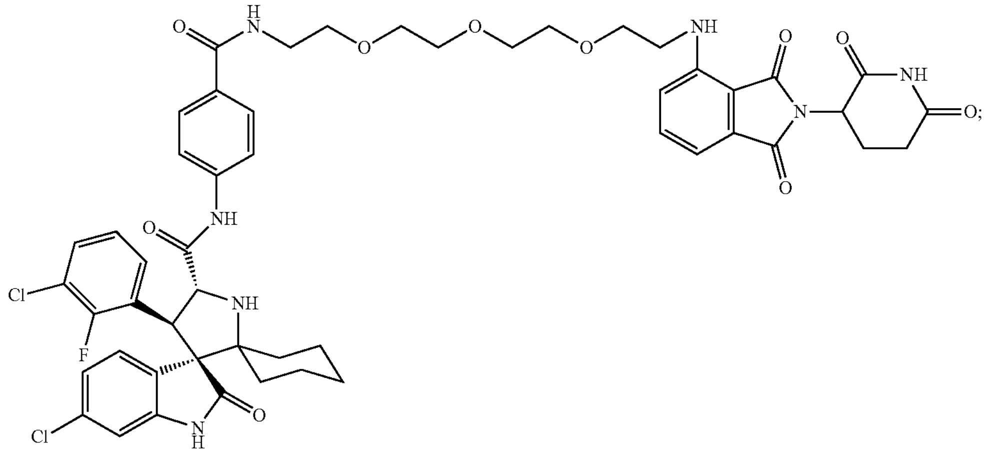

-continued
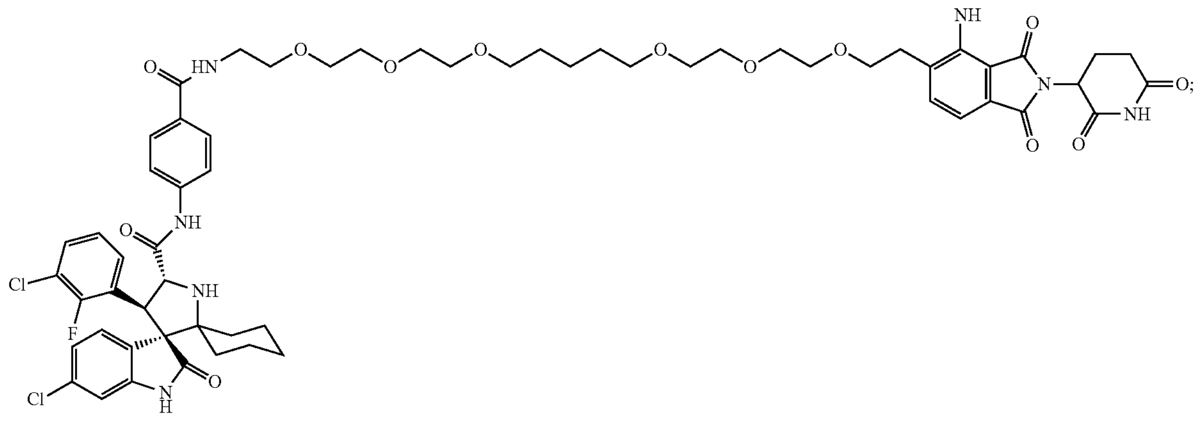
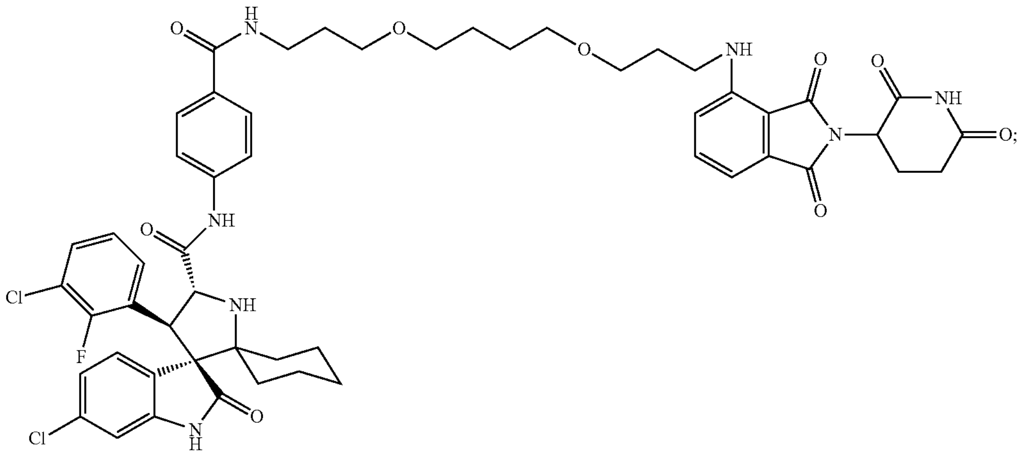
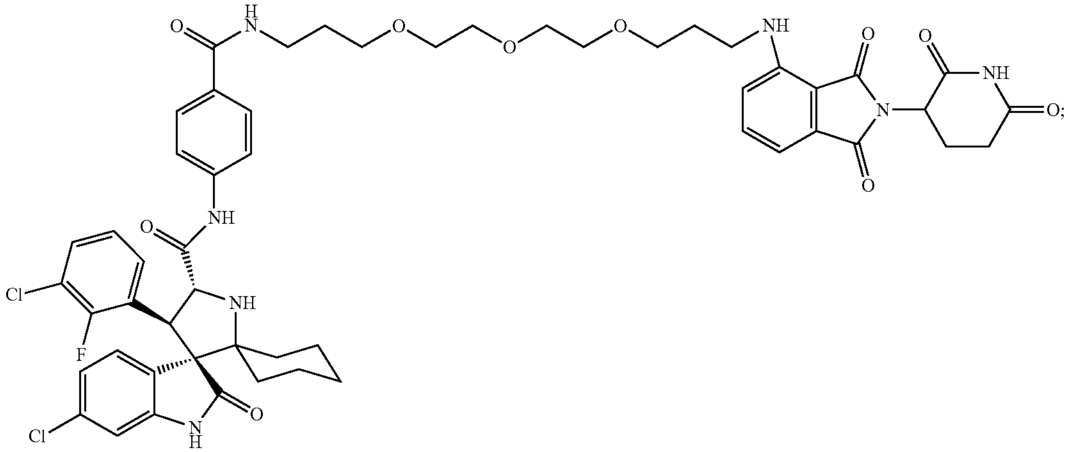

-continued
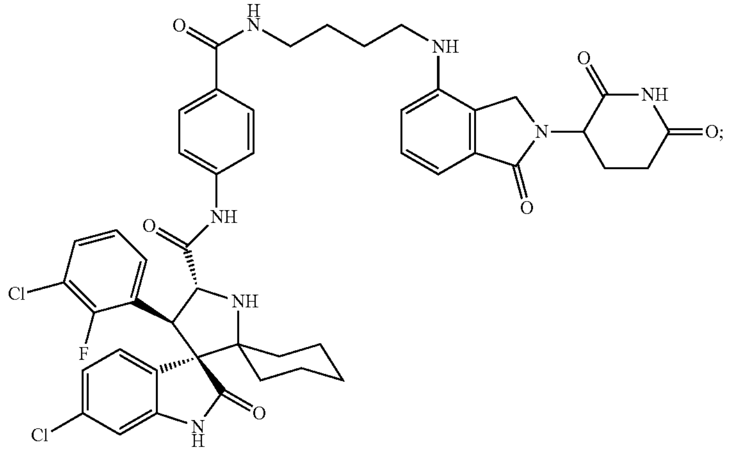
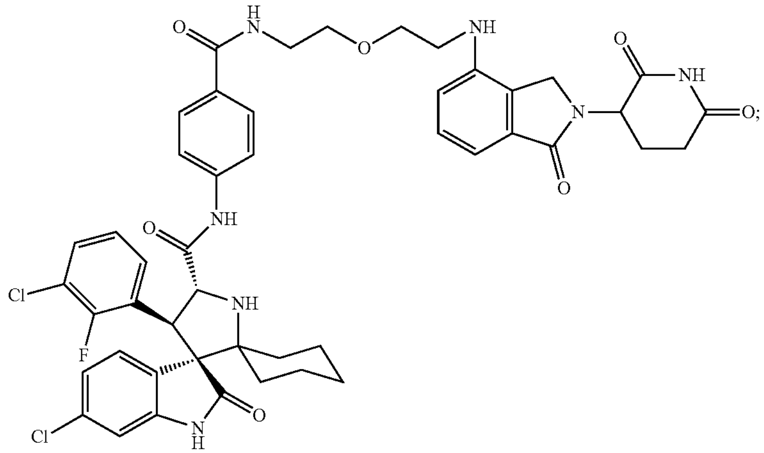
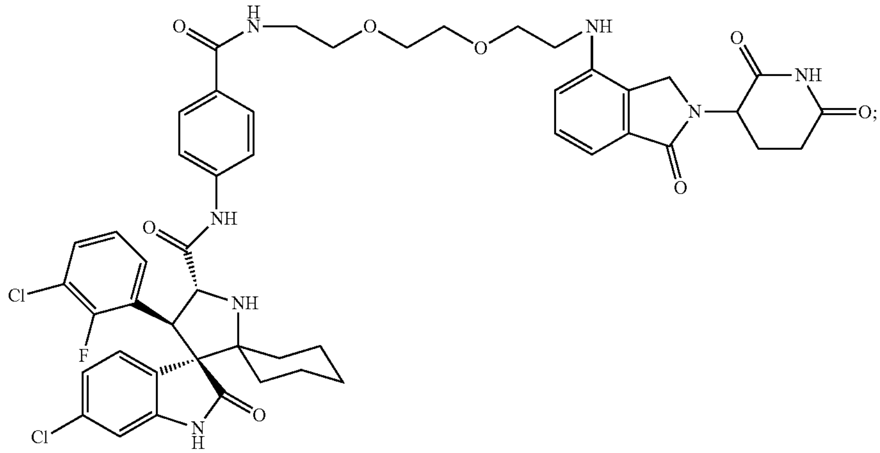

-continued
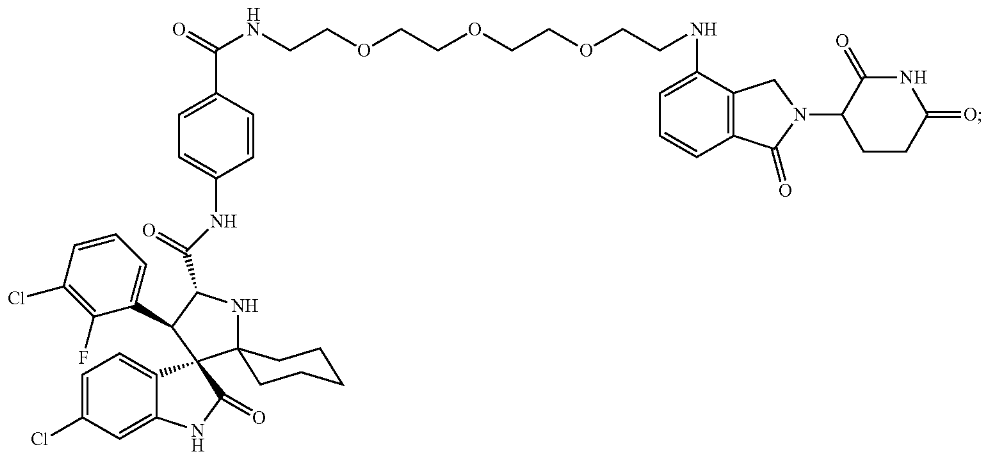
;
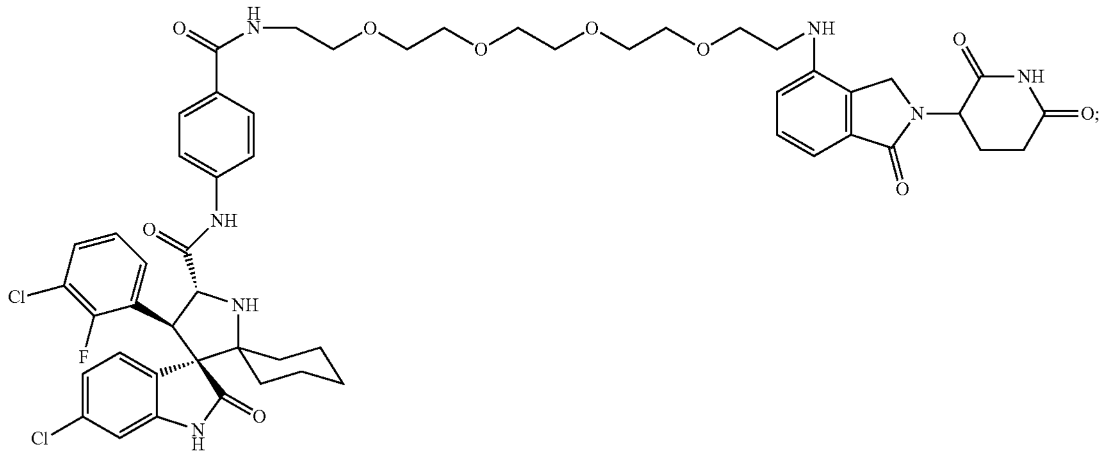
;
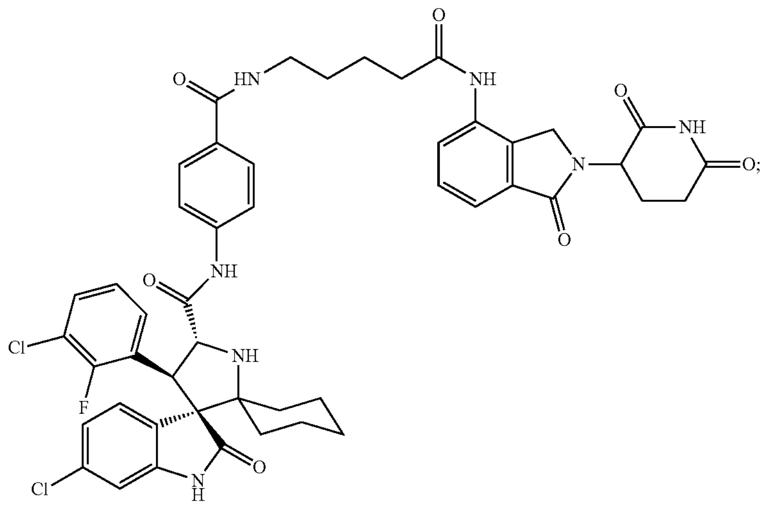
;

-continued
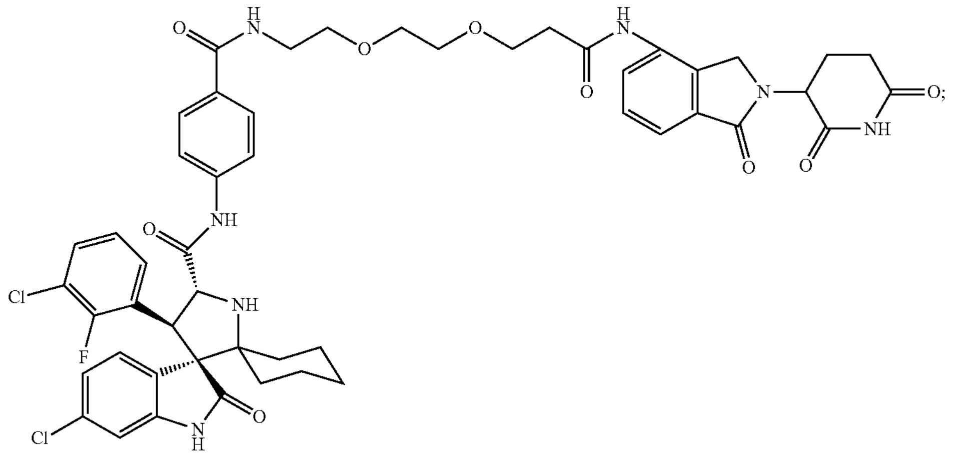
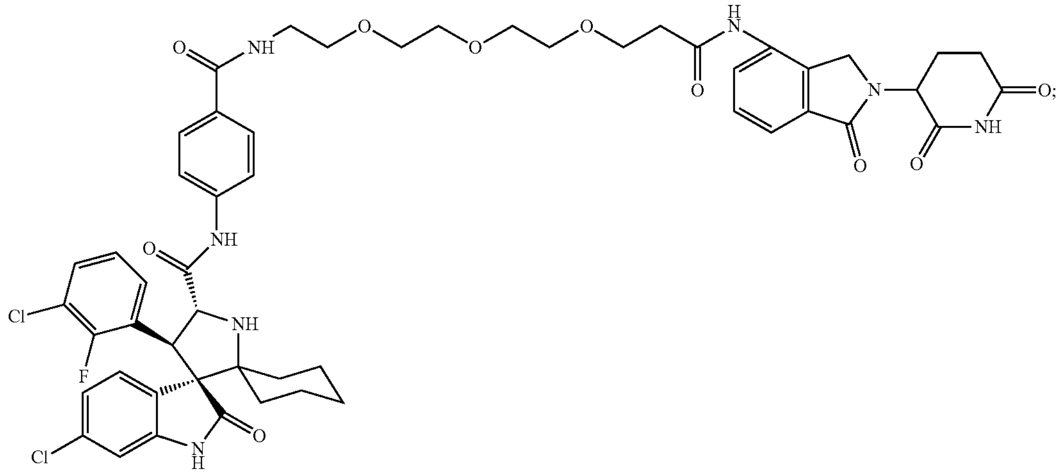
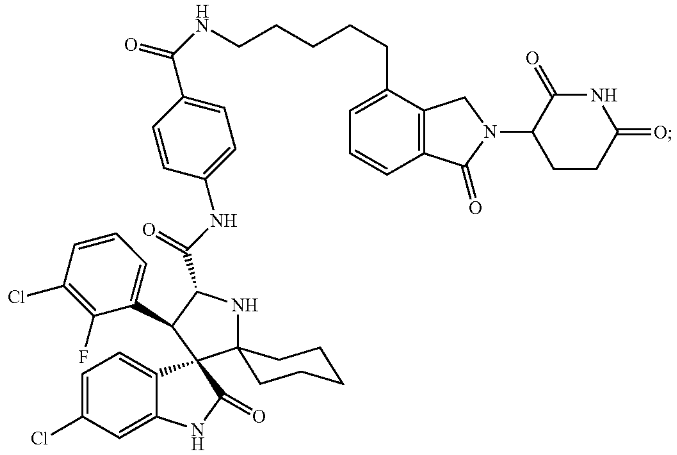

-continued
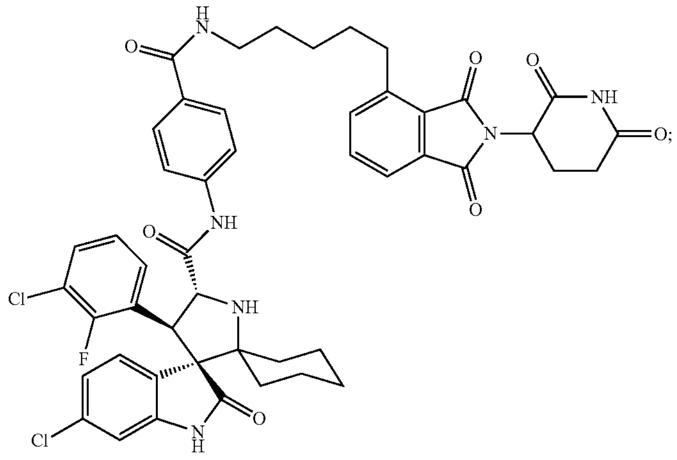
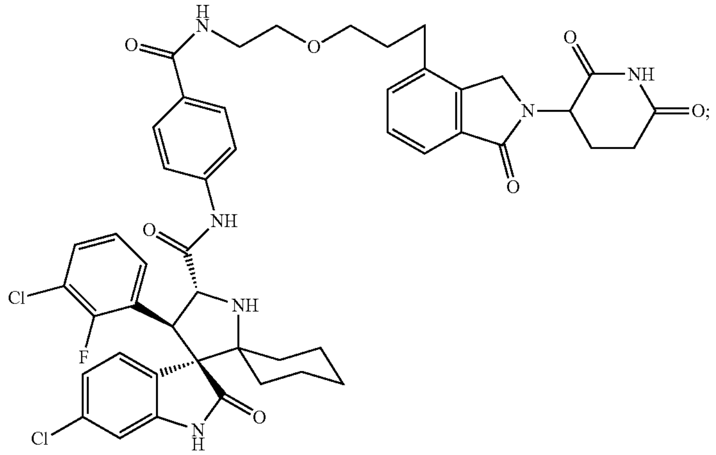
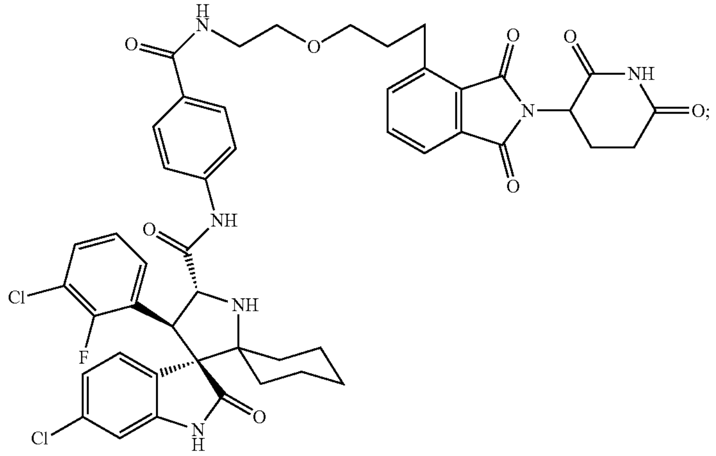

-continued
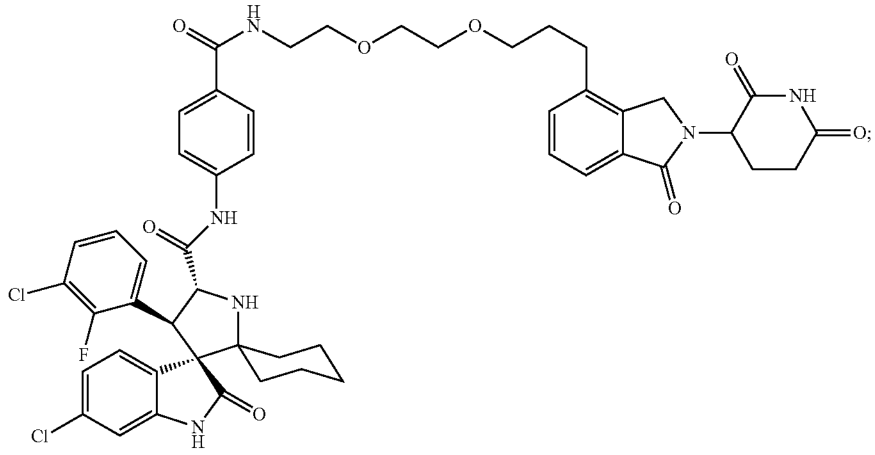
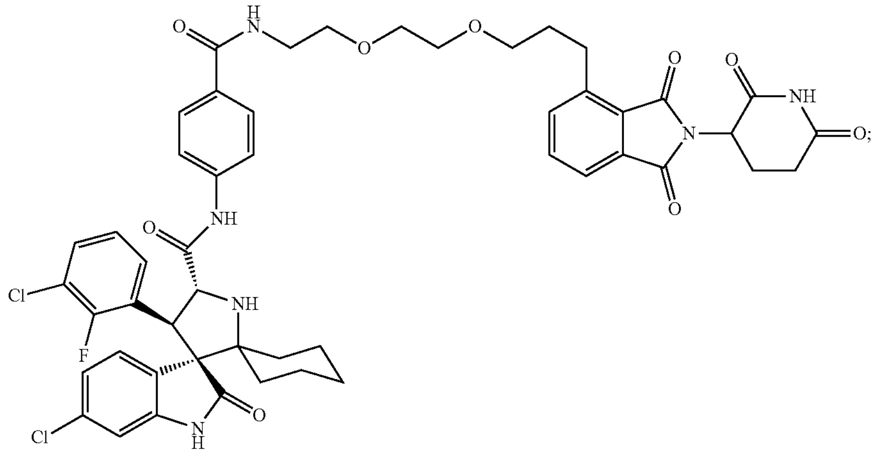
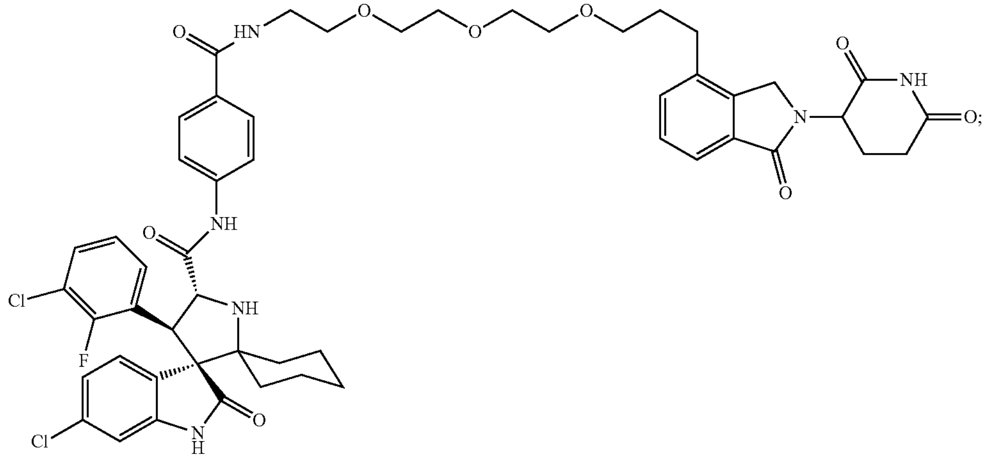

-continued
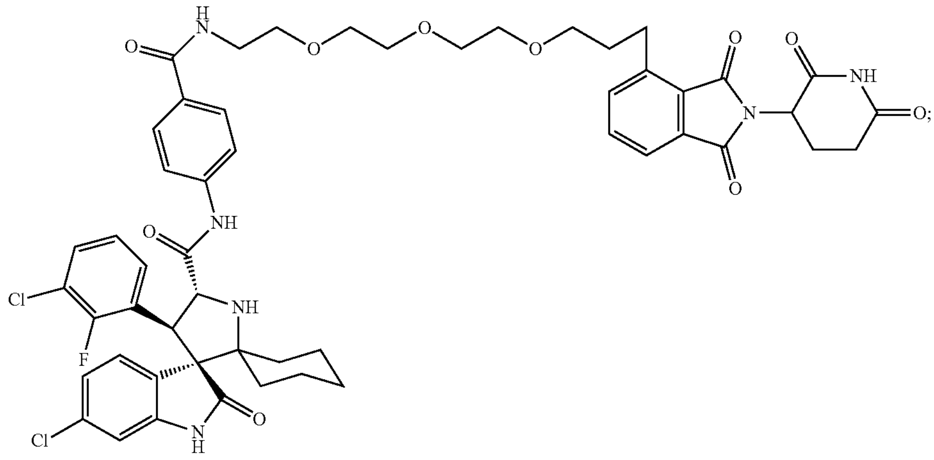
;
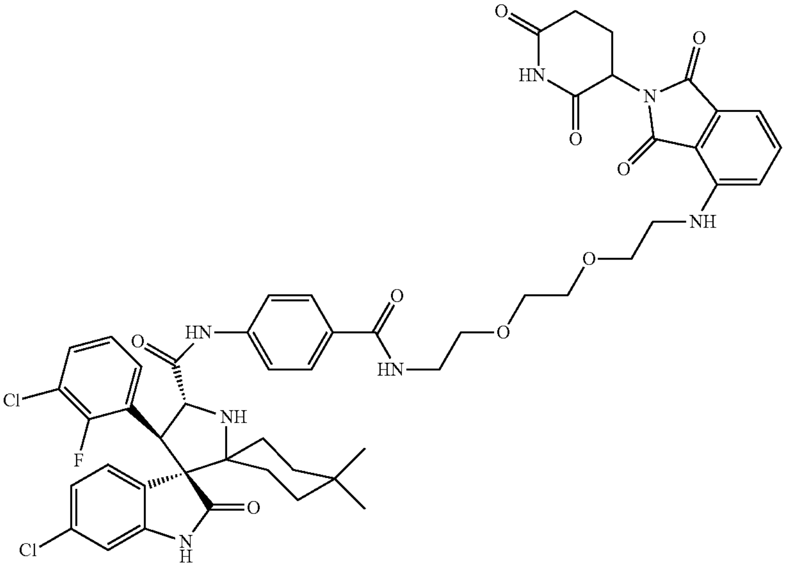
;
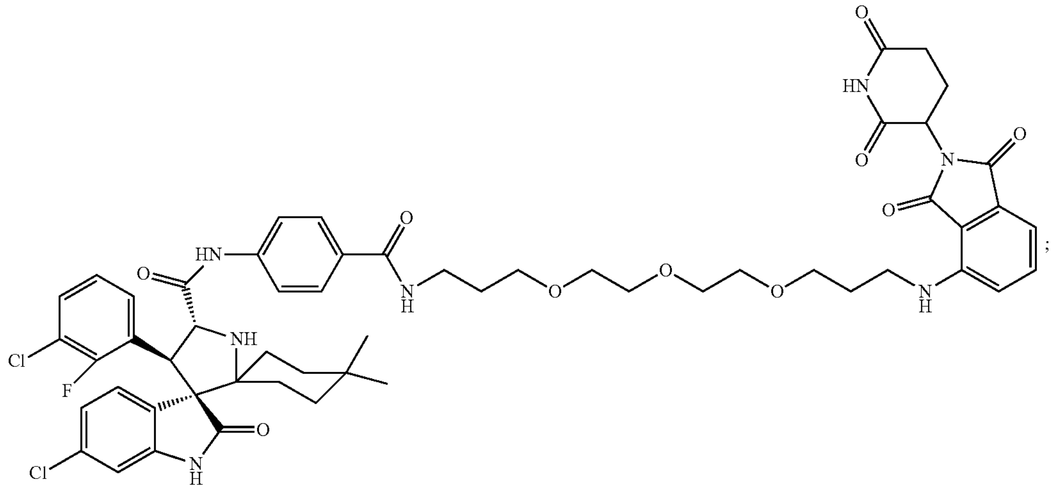
;

-continued
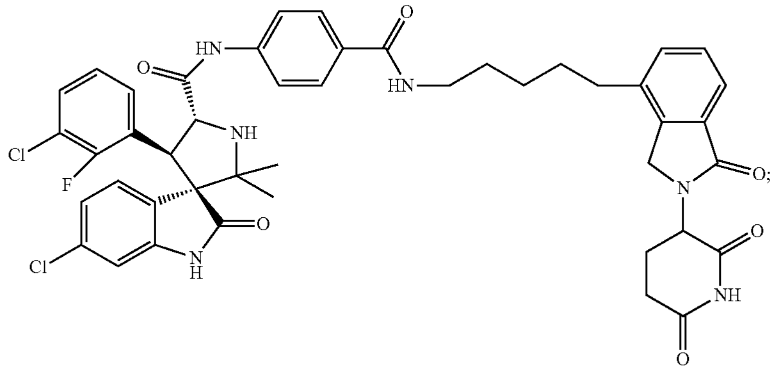
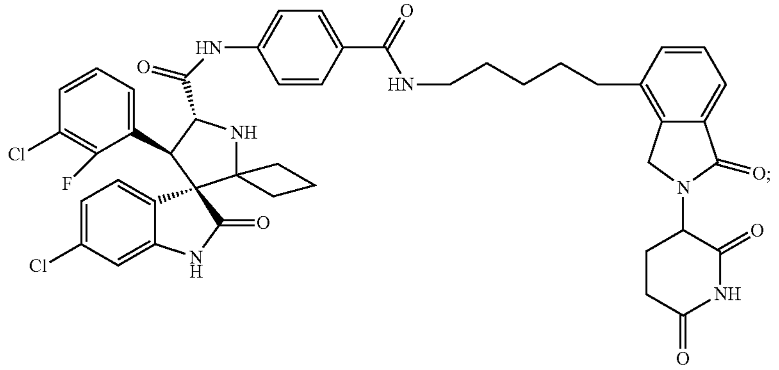 [SMILES: O=C1CCC(N2Cc3c(CCCCCNC(=O)c4ccc(NC(=O)[C@@H]5NC6(CCC6)[C@@]6(C(=O)Nc7cc(Cl)ccc76)[C@H]5c5cccc(Cl)c5F)cc4)cccc3C2=O)C(=O)N1]
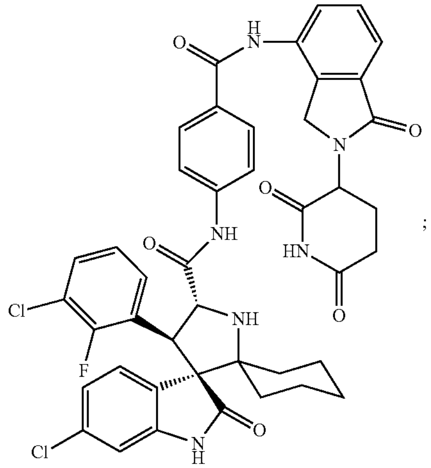
;
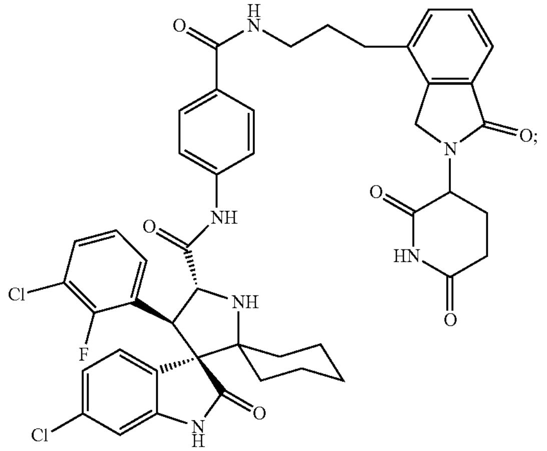

-continued
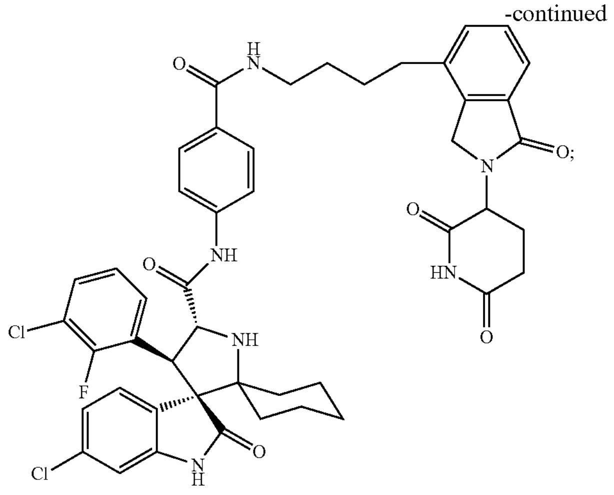
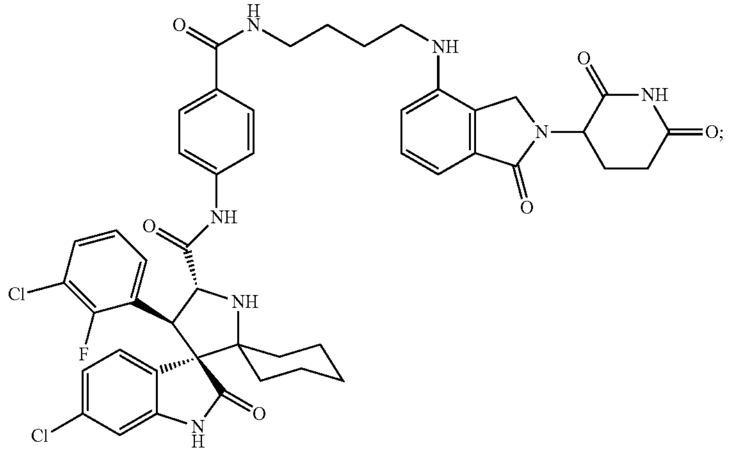
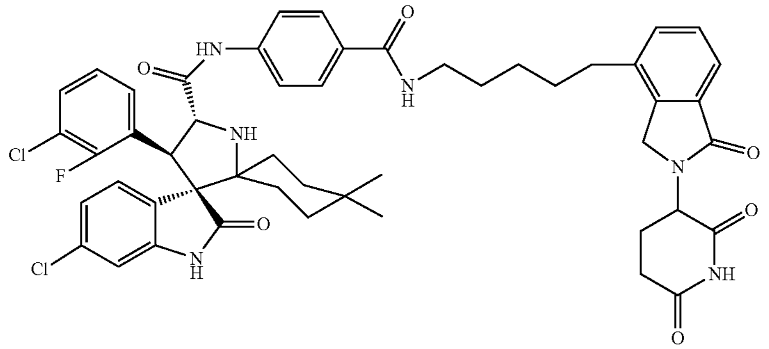

-continued
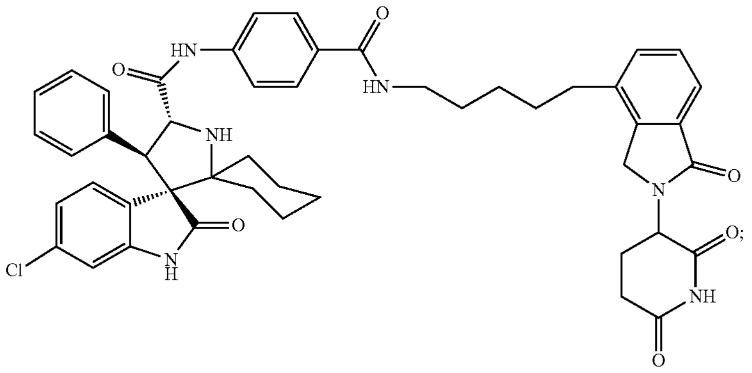
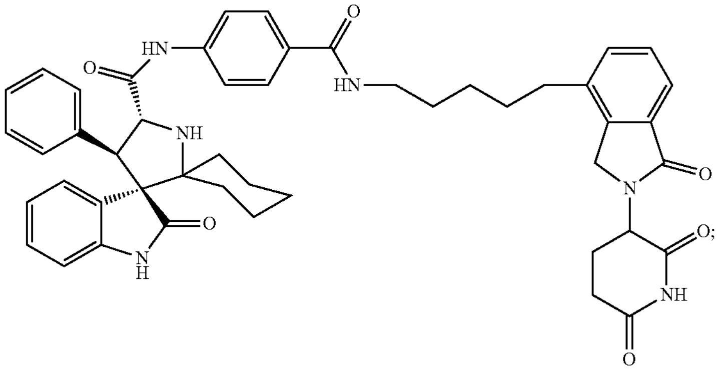
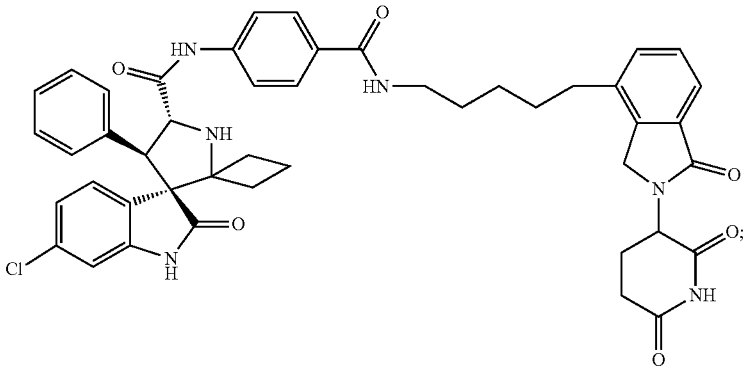
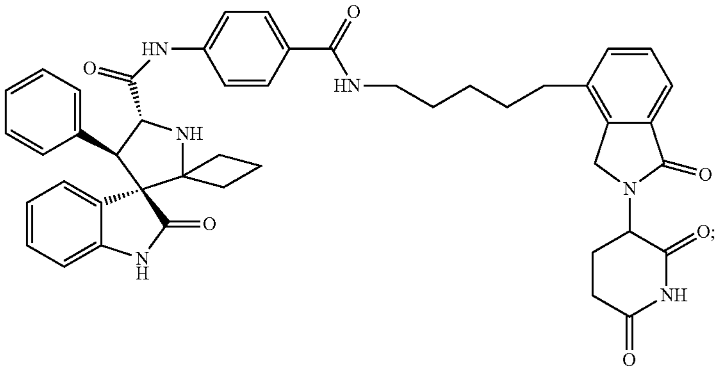

-continued
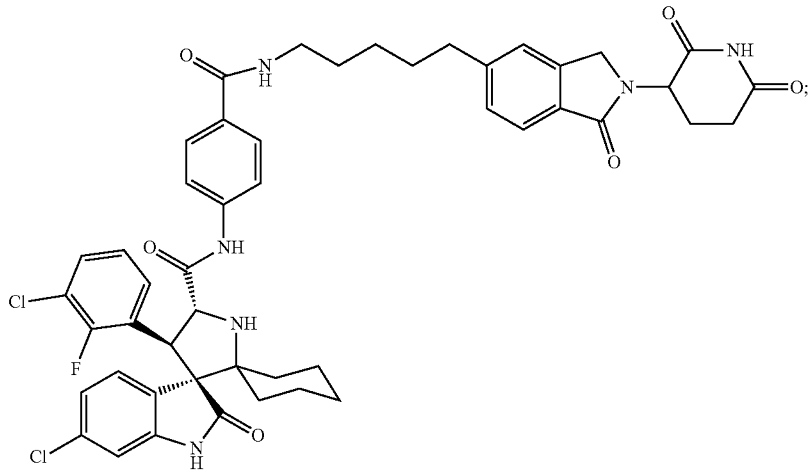
;
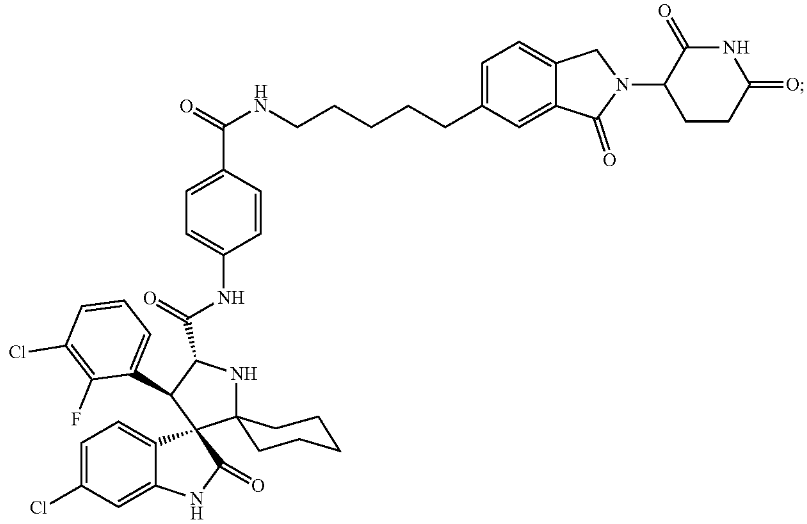
;
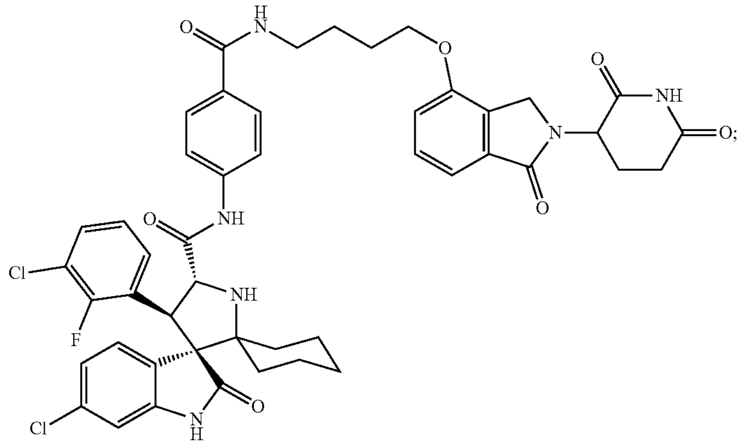
;

-continued

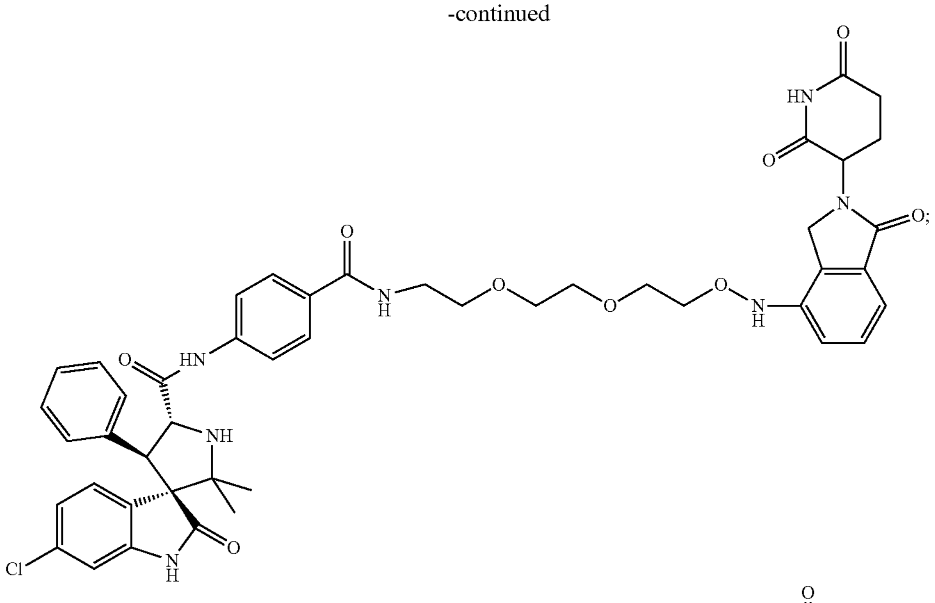

and

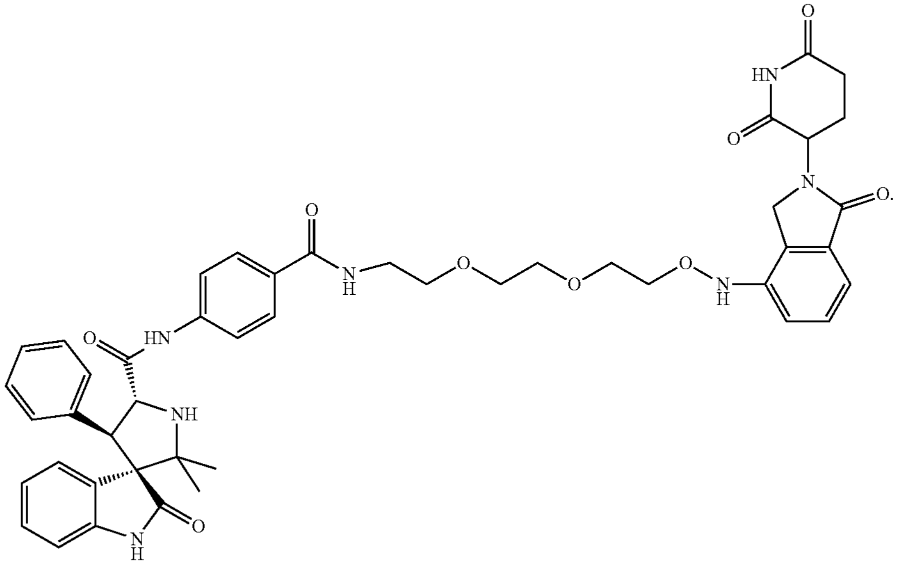

10. A pharmaceutical composition comprising the compound of claim 1, or a pharmaceutically acceptable salt or solvate thereof, and a pharmaceutically acceptable carrier.

11. A method of treating a patient, the method comprising administering to the patient a therapeutically effective amount of the compound of claim 1, or a pharmaceutically acceptable salt or solvate thereof, wherein the patient has cancer.

12. The method of claim 11, wherein the cancer is selected from the group consisting of adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

13. A kit comprising the compound of claim 1, or a pharmaceutically acceptable salt or solvate thereof, and instructions for administering the compound, or a pharmaceutically acceptable salt or solvate thereof, to a patient having cancer.

* * * * *